US006656709B1

(12) United States Patent
Blanche et al.

(10) Patent No.: US 6,656,709 B1
(45) Date of Patent: Dec. 2, 2003

(54) METHODS OF INCREASING THE PRODUCTION OF COBALAMINS USING COB GENE EXPRESSION

(75) Inventors: Francis Blanche, Paris (FR); Beatrice Cameron, Paris (FR); Joel Crouzet, Paris (FR); Laurent Debussche, Paris (FR); Sophie Levy Schil, Paris (FR); Denis Thibaut, Paris (FR)

(73) Assignee: Rhone-Poulenc Biochimie, et al., Antony (FR)

( * ) Notice: Subject to any disclaimer, the term of this patent is extended or adjusted under 35 U.S.C. 154(b) by 0 days.

(21) Appl. No.: 08/426,630

(22) Filed: Apr. 21, 1995

Related U.S. Application Data

(63) Continuation of application No. 07/916,151, filed as application No. PCT/FR91/00054 on Jan. 30, 1991, now abandoned.

(30) Foreign Application Priority Data

Jan. 31, 1990 (FR) ........................................ 90 01137

(51) Int. Cl.[7] ........................................ C12P 19/42
(52) U.S. Cl. ........................................ 435/86
(58) Field of Search ........................................ 536/232, 23.7; 435/320.1, 240.2, 252.3, 69.1, 86, 232

(56) References Cited

U.S. PATENT DOCUMENTS 3,018,225 A * 1/1962 Long ........................ 435/86

FOREIGN PATENT DOCUMENTS

WO WO A 8701391 12/1987

OTHER PUBLICATIONS

Sasarman, Rev. Can. Biol. Exp. 42(3): 308–309 (1983).*
Brey et al., J. Bacteriol. 167: 623–630 (1986).*
Crouzet et al., J. Bacteriol. 172: 5968–5979 (Oct. 1990).*
Crouzet et al., J. Bacteriol. 172: 5980–5990 (Oct. 1990).*
Cameron et al., J. Bacteriol, 173: 6058–6065 (1991).*
Cameron et al., J. Bacteriol. 173: 6066–6073 (1991).*
Crouzet et al., J. Bacteriol. 173: 6074–6087 (1991).*
Cameron, et al.; "Cloning and analysis of genes involved in coenzyme B12 biosynthesis in Pseudomonas denitrificans", pps. 547–557; Journal of Bacteriology, vol. 171, No. 1, Jan. 1989; American Society for Microbiology (Washington, D.C. US).
Blanche, et al.; "Purification and characterization of S–adenosyl–L–methionine: Uroporphyrinogen III methyl–transferase from Pseudomonas denitrificans", pps. 4222–4231; Journal of Bacteriology, vol. 171, No. 8, Aug. 1989; American Society for Microbiology, (Wash. D.C. ).

* cited by examiner

*Primary Examiner*—Ponnathapu Achutamurthy
*Assistant Examiner*—Kathleen Kerr
(74) *Attorney, Agent, or Firm*—Finnegan, Henderson, Farabow, Garrett, & Dunner LLP

(57) ABSTRACT

Novel polypeptides involved in the biosynthesis of cobalamines and/or cobamides, in particular coenzyme $B_{12}$, genetic material responsible for expressing these polypeptides, and a method for preparing them, are described. A method for amplifying the production of cobalamines, and particularly coenzyme $B_{12}$, using recombinant DNA techniques, are also described.

58 Claims, 189 Drawing Sheets

ADENOSYLCOBALAMIN R = $CH_2COHN_2$, R' = $CH_2CH_2CONH_2$

ADENOSYLCOBALAMIN R = $CH_2COHN_2$, R' = $CH_2CH_2CONH_2$

SUCCINYL CoA
GLYCINE
UROPORPHYRINOGEN III
HAEMS
SIROHAEM
COBYRINIC ACID
COBINAMIDE
COBALAMIN

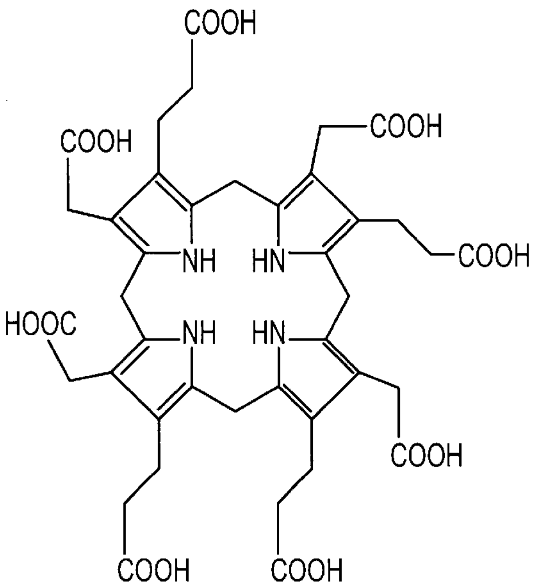
uro'gen III
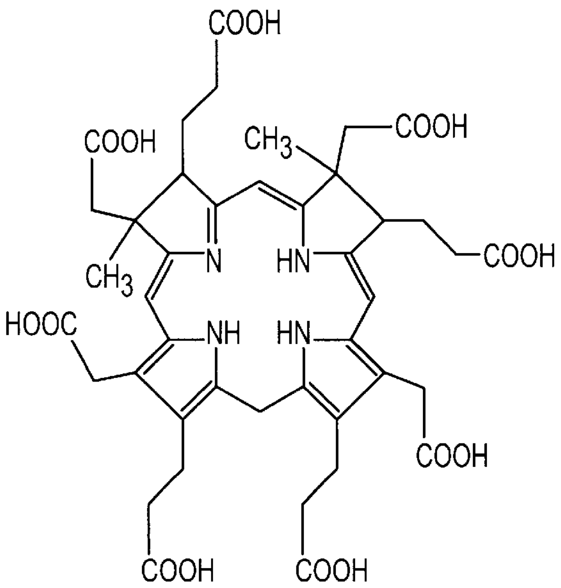
precorrin-2
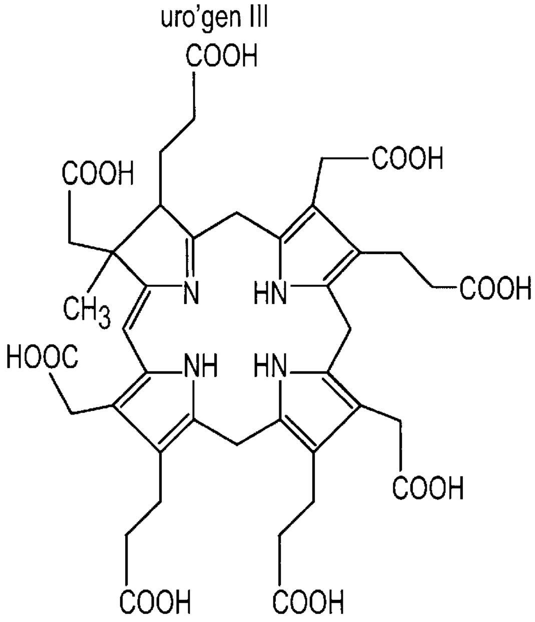
precorrin-1
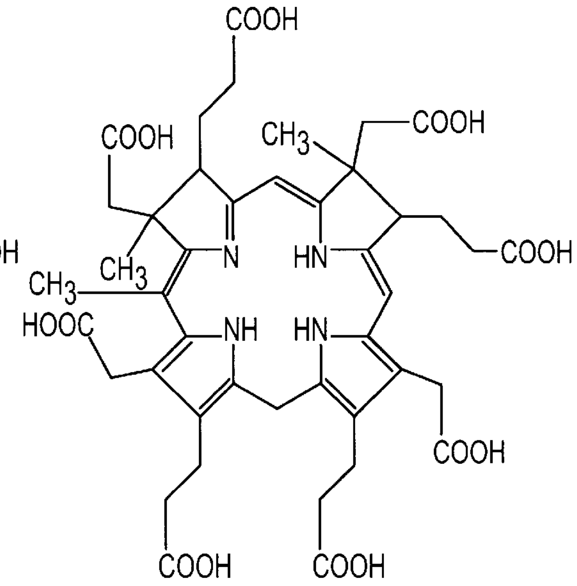
precorrin-3
FIG. 3

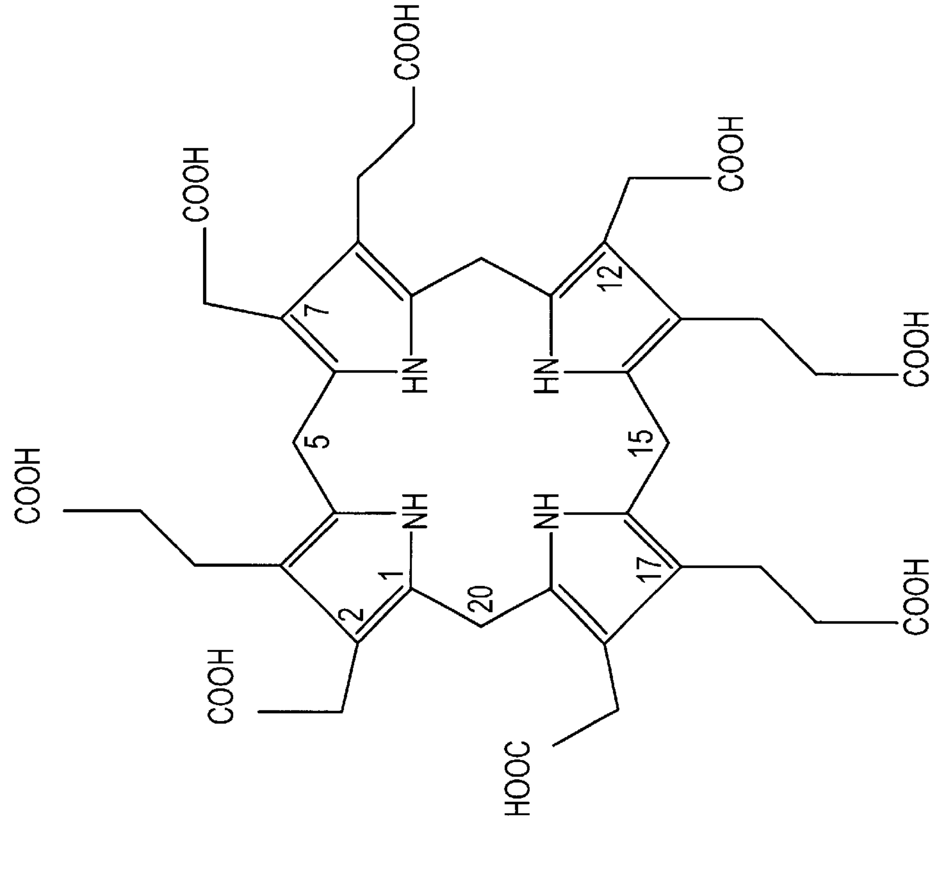
URO'GEN III
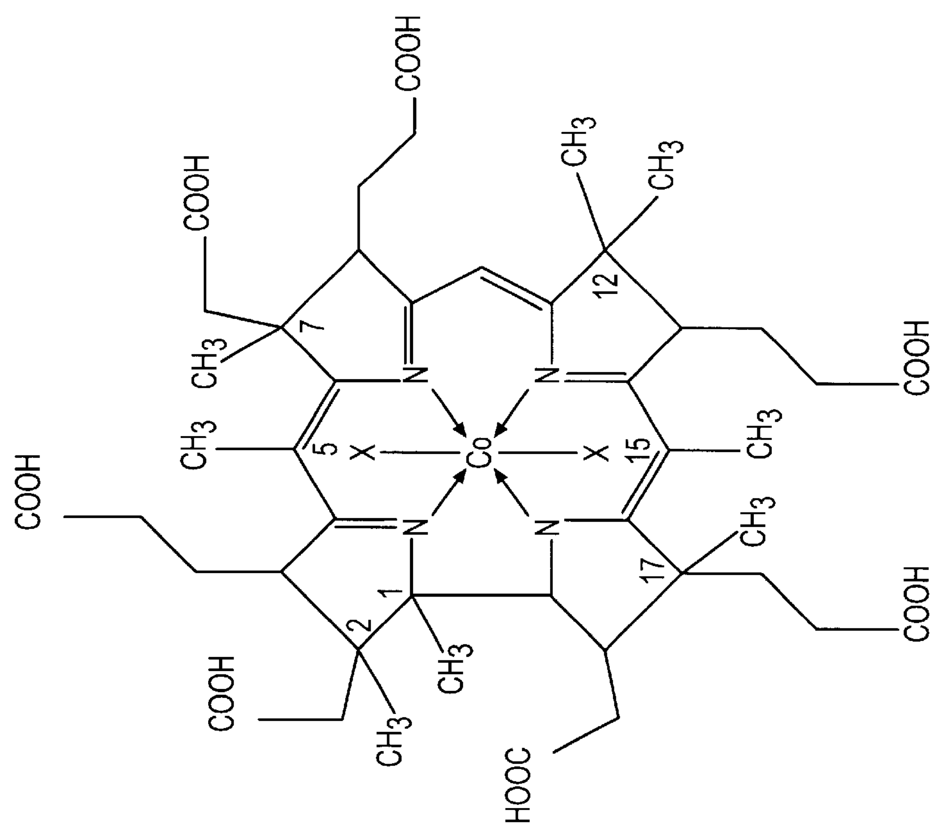
COBYRINIC ACID
FIG. 4

RESTRICTION MAP OF THE 4748-BP SalI-SalI-SalI-SalI-SalI-BglI FRAGMENT

RESTRICTION MAP OF THE 3855-BP SatI-SatI-BamHI FRAGMENT

```
        10         20         30         40         50         60
GGGCTGCAGG TCGACTCTAG AATCGATGAA GCCTGCGATG AAGGCGGCGA CGAACAGGAA
CCCGACGTCC AGCTGAGATC TTAGCTACTT CGGACGCTAC TTCCGCCGCT GCTTGTCCTT

        70         80         90        100        110        120
GGCGAGCAGG TGGAAGGCGA GATCTTGCAC GGCGGGGACT CGAGAGGAGA GCTGTCAGGC
CCGCTCGTCC ACCTTCCGCT CTAGAACGTG CCGCCCCTGA GCTCTCCTCT CGACAGTCCG

       130        140        150        160        170        180
GGGATTTTCC GCCTTGTGTC AGAGCCCGGC GCGATTTGCA AAGCCTTCTG TCGCGGTGTT
CCCTAAAAGG CGGAACACAG TCTCGGGCCG CGCTAAACGT TTCGGAAGAC AGCGCCACAA

       190        200        210        220        230        240
GCTGTCCATG CAGGTGTCGA AATTGAAAAA CCGACAAAGA TTCAAAGCCT TGTTCCAGCT
CGACAGGTAC GTCCACAGCT TTAACTTTTT GGCTGTTTCT AAGTTTCGGA ACAAGGTCGA

       250        260        270        280        290        300
CGCTGTCTTT CTGGATGGAG GCGCTCTCGC CCGCATGGTG CCGAAGAAGG GCTGTCCTTG
GCGACAGAAA GACCTACCTC CGCGAGAGCG GGCGTACCAC GGCTTCTTCC CGACAGGAAC

       310        320        330        340        350        360
CGATACGGTA GGCGGATGAC GATCTTCCTC AAACGCGACA TGGCGATGGC GCAATCCGGT
GCTATGCCAT CCGCCTACTG CTAGAAGGAG TTTGCGCTGT ACCGCTACCG CGTTAGGCCA

       370        380        390        400        410        420
TTGACCGGCC TTCCGCGCTC CGGTAAAAAT GAAGGATATG CGACGGCGTC CGCTTTGGCG
AACTGGCCGG AAGGCGCGAG GCCATTTTTA CTTCCTATAC GCTGCCGCAG GCGAAACCGC

       430        440        450        460        470        480
GACTGAAAGA GCGTCCGGTG CGGCCGACCC AGTCAGGGGG GCATCAGCCG GTGCTGTCCA
CTGACTTTCT CGCAGGCCAC GCCGGCTGGG TCAGTCCCCC CGTAGTCGGC CACGACAGGT

       490        500        510        520        530        540
GATCGGCCGG GACGGATCGT CCCAGCCGGC GCTTCGTTAA GGAGAACAAC GAAGGGAGCC
CTAGCCGGCC CTGCCTAGCA GGGTCGGCCG CGAAGCAATT CCTCTTGTTG CTTCCCTCGG

       550        560        570        580        590        600
GGCCGCCGAT GCCATCGGGC CAACACTCTG CACAGACGAC GAAAGCAGGA GCCGGGCTGG
CCGGCGGCTA CGGTAGCCCG GTTGTGAGAC GTGTCTGCTG CTTTCGTCCT CGGCCCGACC
```

FIG. 7A

```
       610        620        630        640        650        660
TGCTCGGGCT CGGCTGCGAG CGTCGCACGC CGGCCGAAGA GGTGATCGCC CTTGCCGAGC
ACGAGCCCGA GCCGACGCTC GCAGCGTGCG GCCGGCTTCT CCACTAGCGG GAACGGCTCG

       670        680        690        700        710        720
GTGCGCTTGC CGATGCCGGT GTTGCGCCCG GCGATCTGCG GCTGGTCGCC TCGCTCGATG
CACGCGAACG GCTACGGCCA CAACGCGGGC CGCTAGACGC CGACCAGCGG AGCGAGCTAC

       730        740        750        760        770        780
CTCGCGCCGA GGAGCCGGCG ATCCTGGCGG CCGCTCAGCA TTTCGCGGTT CCGGCCGCGT
GAGCGCGGCT CCTCGGCCGC TAGGACCGCC GGCGAGTCGT AAAGCGCCAA GGCCGGCGCA

       790        800        810        820        830        840
TCTACGATGC CGCCACGCTC GAAGCCGAAG CTTCCCGGCT CGCCAACCCG TCCGAGATCG
AGATGCTACG GCGGTGCGAG CTTCGGCTTC GAAGGGCCGA GCGGTTGGGC AGGCTCTAGC

       850        860        870        880        890        900
TCTTTGCCTA CACGGGTTGT CATGGCGTTG CCGAGGGTGC AGCGCTCGTC GGCGCCGGTC
AGAAACGGAT GTGCCCAACA GTACCGCAAC GGCTCCCACG TCGCGAGCAG CCGCGGCCAG

       910        920        930        940        950        960
GCGAAGCCGT GCTGATTGTG CAGAAGATCG TCTCCGCCCA TGCGACGGCC GCACTTGCCG
CGCTTCGGCA CGACTAACAC GTCTTCTAGC AGAGGCGGGT ACGCTGCCGG CGTGAACGGC

       970        980        990       1000       1010       1020
GGCCGGCGAC CTTGCGCGCC GAAAAGCGCA TCCAGGCGGC GGAGGCTGTC TGATGCATTC
CCGGCCGCTG GAACGCGCGG CTTTTCGCGT AGGTCCGCCG CCTCCGACAG ACTACGTAAG

      1030       1040       1050       1060       1070       1080
TTATGTTGTT GAATTGAATC AATCTTTTGC CCGGGGTTTC TCTCAAGTGG AATCCGGTTC
AATACAACAA CTTAACTTAG TTAGAAAACG GGCCCCAAAG AGAGTTCACC TTAGGCCAAG

      1090       1100       1110       1120       1130       1140
TTTAGAGAGC GCGTCAGGCG TGCCGTTGGG TGGCGCCGAA ATACAGGTGG GACAGCACGC
AAATCTCTCG CGCAGTCCGC ACGGCAACCC ACCGCGGCTT TATGTCCACC CTGTCGTGCG

      1150       1160       1170       1180       1190       1200
ATGATCGACG ACCTCTTTGC CGGATTGCCG GCGCTCGAAA AAGGTTCGGT CTGGCTGGTC
TACTAGCTGC TGGAGAAACG GCCTAACGGC CGCGAGCTTT TTCCAAGCCA GACCGACCAG
```

FIG. 7B

```
      1210       1220       1230       1240       1250       1260
GGCGCCGGCC CCGGCGATCC CGGCCTGTTG ACGCTGCATG CGGCCAATGC GCTGCGCCAG
CCGCGGCCGG GGCCGCTAGG GCCGGACAAC TGCGACGTAC GCCGGTTACG CGACGCGGTC

      1270       1280       1290       1300       1310       1320
GCGGATGTGA TCGTGCATGA TGCGCTGGTC AACGAGGATT GCCTGAAGCT CGCGCGGCCG
CGCCTACACT AGCACGTACT ACGCGACCAG TTGCTCCTAA CGGACTTCGA GCGCGCCGGC

      1330       1340       1350       1360       1370       1380
GGCGCCGTGC TGGAGTTTGC GGGCAAGCGT GGCGGCAAGC CGTCGCCGAA GCAGCGCGAC
CCGCGGCACG ACCTCAAACG CCCGTTCGCA CCGCCGTTCG GCAGCGGCTT CGTCGCGCTG

      1390       1400       1410       1420       1430       1440
ATCTCGCTTC GCCTCGTCGA ACTCGCGCGC GCCGGCAACC GGGTGCTGCG CCTCAAAGGC
TAGAGCGAAG CGGAGCAGCT TGAGCGCGCG CGGCCGTTGG CCCACGACGC GGAGTTTCCG

      1450       1460       1470       1480       1490       1500
GGCGATCCCT TCGTCTTCGG TCGCGGTGGC GAGGAGGCGC TGACGCTGGT CGAACACCAG
CCGCTAGGGA AGCAGAAGCC AGCGCCACCG CTCCTCCGCG ACTGCGACCA GCTTGTGGTC

      1510       1520       1530       1540       1550       1560
GTGCCGTTCC GAATCGTGCC CGGCATCACC GCCGGTATCG GCGGGCTTGC CTATGCCGGC
CACGGCAAGG CTTAGCACGG GCCGTAGTGG CGGCCATAGC CGCCCGAACG GATACGGCCG

      1570       1580       1590       1600       1610       1620
ATTCCCGTGA CCCATCGCGA GGTCAACCAC GCGGTCACTT TCCTGACTGG CCATGATTCC
TAAGGGCACT GGGTAGCGCT CCAGTTGGTG CGCCAGTGAA AGGACTGACC GGTACTAAGG

      1630       1640       1650       1660       1670       1680
TCCGGCCTGG TGCCGGATCG CATCAACTGG CAGGGCATCG CCAGCGGCTC GCCTGTCATC
AGGCCGGACC ACGGCCTAGC GTAGTTGACC GTCCCGTAGC GGTCGCCGAG CGGACAGTAG

      1690       1700       1710       1720       1730       1740
GTCATGTACA TGGCGATGAA ACATATCGGC GCGATCACCG CCAACCTCAT TGCCGGCGGC
CAGTACATGT ACCGCTACTT TGTATAGCCG CGCTAGTGGC GGTTGGAGTA ACGGCCGCCG

      1750       1760       1770       1780       1790       1800
CGCTCGCCGG ACGAACCGGT CGCCTTCGTC TGCAACGCCG CGACGCCGCA GCAGGCGGTG
GCGAGCGGCC TGCTTGGCCA GCGGAAGCAG ACGTTGCGGC GCTGCGGCGT CGTCCGCCAC
```

FIG. 7C

```
      1810       1820       1830       1840       1850       1860
CTGGAAACGA CGCTTGCGCG TGCAGAGGCC GATGTTGCGG CGGCAGGGCT GGAGCCGCCG
GACCTTTGCT GCGAACGCGC ACGTCTCCGG CTACAACGCC GCCGTCCCGA CCTCGGCGGC

      1870       1880       1890       1900       1910       1920
GCGATCGTCG TCGTCGGCGA GGTGGTGCGG CTGCGCGCAG CGCTCGACTG GATCGGCGCG
CGCTAGCAGC AGCAGCCGCT CCACCACGCC GACGCGCGTC GCGAGCTGAC CTAGCCGCGC

      1930       1940       1950       1960       1970       1980
CTGGACGGGC GCAAGCTTGC CGCCGACCCG TTCGCCAATC GCATTCTCAG GAACCCGGCA
GACCTGCCCG CGTTCGAACG GCGGCTGGGC AAGCGGTTAG CGTAAGAGTC CTTGGGCCGT

      1990       2000       2010       2020       2030       2040
TGAGCGGATT GCTGATTGCC GCACCCGCGT CCGGCTCCGG CAAGACGACG GTGACGCTCG
ACTCGCCTAA CGACTAACGG CGTGGGCGCA GGCCGAGGCC GTTCTGCTGC CACTGCGAGC

      2050       2060       2070       2080       2090       2100
GGCTGATGCG CGCCCTGAAG AGGCGCGGCG TGGCGATCGC GCCCGGCAAG GCGGGGCCGG
CCGACTACGC GCGGGACTTC TCCGCGCCGC ACCGCTAGCG CGGGCCGTTC CGCCCCGGCC

      2110       2120       2130       2140       2150       2160
ACTATATCGA TCCCGCTTTC CACGCGGCAG CGACCGGCGA GCCCTGCTTC AACTACGACC
TGATATAGCT AGGGCGAAAG GTGCGCCGTC GCTGGCCGCT CGGGACGAAG TTGATGCTGG

      2170       2180       2190       2200       2210       2220
CCTGGGCGAT GCGCCCGGAA CTGCTGCTTG CCAATGCGTC GCATGTGGCC TCCGGCGGGC
GGACCCGCTA CGCGGGCCTT GACGACGAAC GGTTACGCAG CGTACACCGG AGGCCGCCCG

      2230       2240       2250       2260       2270       2280
GCACATTGAT CGTCGAGGCG ATGATGGGAC TGCATGACGG TGCTGCCGAC GGCTCGGGAA
CGTGTAACTA GCAGCTCCGC TACTACCCTG ACGTACTGCC ACGACGGCTG CCGAGCCCTT

      2290       2300       2310       2320       2330       2340
CGCCAGCGGA CCTCGCCGCG ACGCTGAACC TTGCGGTCAT TCTGGTGGTC GATTGCGCCC
GCGGTCGCCT GGAGCGGCGC TGCGACTTGG AACGCCAGTA AGACCACCAG CTAACGCGGG

      2350       2360       2370       2380       2390       2400
GCATGTCCCA GTCGGTTGCC GCCCTCGTGC GCGGCTATGC GGATCATCGC GACGATATCC
CGTACAGGGT CAGCCAACGG CGGGAGCACG CGCCGATACG CCTAGTAGCG CTGCTATAGG
```

FIG. 7D

```
      2410       2420       2430       2440       2450       2460
GGGTGGTTGG CGTCATCCTC AACAAGGTCG GCAGCGATCG GCATGAAATG ATGCTGCGCG
CCCACCAACC GCAGTAGGAG TTGTTCCAGC CGTCGCTAGC CGTACTTTAC TACGACGCGC

      2470       2480       2490       2500       2510       2520
ATGCGCTCGG CAAGGTGCGC ATGCCTGTCT TCGGCGTGCT CCGGCAGGAC AGCGCATTGC
TACGCGAGCC GTTCCACGCG TACGGACAGA AGCCGCACGA GGCCGTCCTG TCGCGTAACG

      2530       2540       2550       2560       2570       2580
AACTGCCGGA GCGCCATCTC GGGCTCGTGC AGGCGGGCGA ACACTCAGCG CTTGAGGGCT
TTGACGGCCT CGCGGTAGAG CCCGAGCACG TCCGCCCGCT TGTGAGTCGC GAACTCCCGA

      2590       2600       2610       2620       2630       2640
TCATCGAGGC GGCGGCCGCG CGGGTCGAGG CTGCCTGCGA TCTCGACGCC ATCCGCCTGA
AGTAGCTCCG CCGCCGGCGC GCCCAGCTCC GACGGACGCT AGAGCTGCGG TAGGCGGACT

      2650       2660       2670       2680       2690       2700
TCGCGACGAT TTTCCCGCAG GTGCCCGCGG CGGCCGATGC CGAGCGTTTG CGGCCGCTCG
AGCGCTGCTA AAAGGGCGTC CACGGGCGCC GCCGGCTACG GCTCGCAAAC GCCGGCGAGC

      2710       2720       2730       2740       2750       2760
GTCAGCGCAT CGCGGTCGCG CGCGATATCG CCTTTGCCTT CTGCTACGAG CACCTGCTTT
CAGTCGCGTA GCGCCAGCGC GCGCTATAGC GGAAACGGAA GACGATGCTC GTGGACGAAA

      2770       2780       2790       2800       2810       2820
ACGGCTGGCG GCAAGGCGGC GCGGAGATTT CCTTCTTCTC GCCGCTCGCC GACGAGGGGC
TGCCGACCGC CGTTCCGCCG CGCCTCTAAA GGAAGAAGAG CGGCGAGCGG CTGCTCCCCG

      2830       2840       2850       2860       2870       2880
CGGATGCGGC AGCCGATGCC GTCTATCTTC CGGGGGGTTA TCCGGAGCTG CATGCGGGGC
GCCTACGCCG TCGGCTACGG CAGATAGAAG GCCCCCCAAT AGGCCTCGAC GTACGCCCCG

      2890       2900       2910       2920       2930       2940
AGCTGAGCGC CGCCGCCCGA TTCCGTTCCG GCATGCATTC CGCGGCGGAA CGCGGCGCCC
TCGACTCGCG GCGGCGGGCT AAGGCAAGGC CGTACGTAAG GCGCCGCCTT GCGCCGCGGG

      2950       2960       2970       2980       2990       3000
GCATCTTCGG CGAGTGCGGC GGCTATATGG TGCTCGGCGA AGGGCTTGTC GCTGCCGATG
CGTAGAAGCC GCTCACGCCG CCGATATACC ACGAGCCGCT TCCCGAACAG CGACGGCTAC
```

FIG. 7E

```
      3010       3020       3030       3040       3050       3060
GCACACGCTA CGACATGCTC GGCCTGCTGC CGCTCGTAAC CAGTTTTGCC GAGCGCAGGC
CGTGTGCGAT GCTGTACGAG CCGGACGACG GCGAGCATTG GTCAAAACGG CTCGCGTCCG

      3070       3080       3090       3100       3110       3120
GGCACCTCGG CTATCGCCGC GTCGTGCCTG TCGACAACGC CTTCTTCGAT GGACCCATGA
CCGTGGAGCC GATAGCGGCG CAGCACGGAC AGCTGTTGCG GAAGAAGCTA CCTGGGTACT

      3130       3140       3150       3160       3170       3180
CGGCGCACGA ATTCCACTAT GCGACCATCG TCGCCGAAGG GGCGGCCGAT CGGCTGTTTG
GCCGCGTGCT TAAGGTGATA CGCTGGTAGC AGCGGCTTCC CCGCCGGCTA GCCGACAAAC

      3190       3200       3210       3220       3230       3240
CGGTCAGCGA CGCCGCCGGC GAGGATCTCG GCCAGGCGGG CCTCCGGCGC GGCCCTGTCG
GCCAGTCGCT GCGGCGGCCG CTCCTAGAGC CGGTCCGCCC GGAGGCCGCG CCGGGACAGC

      3250       3260       3270       3280       3290       3300
CCGGTTCCTT CATGCATCTG ATCGACGTCG CAGGTGCTGC ATGAGCGCAC CGATCGTTCA
GGCCAAGGAA GTACGTAGAC TAGCTGCAGC GTCCACGACG TACTCGCGTG GCTAGCAAGT

      3310       3320       3330       3340       3350       3360
TGGTGGCGGC ATCACCGAGG CCGCAGCGCG CTATGGCGGC CGGCCTGAAG ACTGGCTCGA
ACCACCGCCG TAGTGGCTCC GGCGTCGCGC GATACCGCCG GCCGGACTTC TGACCGAGCT

      3370       3380       3390       3400       3410       3420
TCTGTCGACC GGCATCAATC CATGCCCCGT CGCCTTGCCC GCGGTCCCTG AGCGCGCCTG
AGACAGCTGG CCGTAGTTAG GTACGGGGCA GCGGAACGGG CGCCAGGGAC TCGCGCGGAC

      3430       3440       3450       3460       3470       3480
GCACCGGCTG CCGGATCGGC AGACGGTAGA TGATGCGCGG AGCGCCGCCG CCGACTACTA
CGTGGCCGAC GGCCTAGCCG TCTGCCATCT ACTACGCGCC TCGCGGCGGC GGCTGATGAT

      3490       3500       3510       3520       3530       3540
CCGCACCAAC GGCGTGCTGC CTTTGCCGGT GCCGGGCACC CAGTCGGTGA TCCAGCTCCT
GGCGTGGTTG CCGCACGACG GAAACGGCCA CGGCCCGTGG GTCAGCCACT AGGTCGAGGA

      3550       3560       3570       3580       3590       3600
GCCACGTCTT GCTCCGGCCA ACAGGCACGT CGCGATTTTC GGGCCGACCT ATGGCGAGTA
CGGTGCAGAA CGAGGCCGGT TGTCCGTGCA GCGCTAAAAG CCCGGCTGGA TACCGCTCAT
```

FIG. 7F

```
      3610       3620       3630       3640       3650       3660
TGCCCGCGTG CTTGAAGCGG CCGGCTTTGC TGTCGATCGC GTCGCGGATG CCGACGCGCT
ACGGGCGCAC GAACTTCGCC GGCCGAAACG ACAGCTAGCG CAGCGCCTAC GGCTGCGCGA

      3670       3680       3690       3700       3710       3720
CACGGCCGAA CATGGGCTTG TCATCGTCGT CAACCCCAAC AACCCGACCG GCCGCGCCTT
GTGCCGGCTT GTACCCGAAC AGTAGCAGCA GTTGGGGTTG TTGGGCTGGC CGGCGCGGAA

      3730       3740       3750       3760       3770       3780
GGCGCCGGCG GAGCTTCTGG CGATCGCCGC AAGGCAGAAG GCGAGCGGCG GACTGCTGCT
CCGCGGCCGC CTCGAAGACC GCTAGCGGCG TTCCGTCTTC CGCTCGCCGC CTGACGACGA

      3790       3800       3810       3820       3830       3840
GGTCGATGAG GCCTTCGGCG ATCTTGAGCC GCAACTGAGT GTCGCTGGTC ACGCGTCAGG
CCAGCTACTC CGGAAGCCGC TAGAACTCGG CGTTGACTCA CAGCGACCAG TGCGCAGTCC

      3850       3860       3870       3880       3890       3900
GCAAGGCAAC CTCATCGTCT TCCGCTCCTT CGGCAAGTTC TTCGGCCTTG CGGGCCTGCG
CGTTCCGTTG GAGTAGCAGA AGGCGAGGAA GCCGTTCAAG AAGCCGGAAC GCCCGGACGC

      3910       3920       3930       3940       3950       3960
CCTCGGCTTC GTCGTTGCGA CCGAGCCAGT GCTTGCATCC TTTGCCGATT GGCTCGGTCC
GGAGCCGAAG CAGCAACGCT GGCTCGGTCA CGAACGTAGG AAACGGCTAA CCGAGCCAGG

      3970       3980       3990       4000       4010       4020
CTGGGCTGTC TCCGGCCCGG CGTTGACGAT CTCGAAAGCG CTGATGCAGG GCGATACGAA
GACCCGACAG AGGCCGGGCC GCAACTGCTA GAGCTTTCGC GACTACGTCC CGCTATGCTT

      4030       4040       4050       4060       4070       4080
GGCGATCGCG GCGGGCATCC TCGAGCGTCG CGCCGGCCTC GATGCGGCTC TCGATGGGGC
CCGCTAGCGC CGCCCGTAGG AGCTCGCAGC GCGGCCGGAG CTACGCCGAG AGCTACCCCG

      4090       4100       4110       4120       4130       4140
AGGGCTCAAC CGTATCGGCG GCACGGGGCT ATTCGTGCTG GTCGAGCATC CCAGGGCAGC
TCCCGAGTTG GCATAGCCGC CGTGCCCCGA TAAGCACGAC CAGCTCGTAG GGTCCCGTCG

      4150       4160       4170       4180       4190       4200
TCTGCTGCAG GAGCGGCTCT GCGAGGCCCA TATTCTCACG CGCAAGTTCG ACTATGCCCC
AGACGACGTC CTCGCCGAGA CGCTCCGGGT ATAAGAGTGC GCGTTCAAGC TGATACGGGG
```

FIG. 7G

```
       4210       4220       4230       4240       4250       4260
GACCTGGCTC AGGGTCGGTC TTGCGCCTGA CGCGGCTGGT GACCGACGGC TGGCGGACGC
CTGGACCGAG TCCCAGCCAG AACGCGGACT GCGCCGACCA CTGGCTGCCG ACCGCCTGCG

       4270       4280       4290       4300       4310       4320
GCTTGCCCGC ATGGAGCTCT GAGGTGTCGG AGACGATCCT GCTCATTCTC GCGCTGGCGC
CGAACGGGCG TACCTCGAGA CTCCACAGCC TCTGCTAGGA CGAGTAAGAG CGCGACCGCG

       4330       4340       4350       4360       4370       4380
TGGTGATCGA CCGCGTTGTC GGCGATCCGG ACTGGCTCTG GGCGCGCGTG CCGCATCCGG
ACCACTAGCT GGCGCAACAG CCGCTAGGCC TGACCGAGAC CCGCGCGCAC GGCGTAGGCC

       4390       4400       4410       4420       4430       4440
TCGTGTTTTT CGGCAAGGCC ATCGGCTTTT TCGACGCGCG GCTGAACCGG GAGGACCTCG
AGCACAAAAA GCCGTTCCGG TAGCCGAAAA AGCTGCGCGC CGACTTGGCC CTCCTGGAGC

       4450       4460       4470       4480       4490       4500
AGGATAGCGC GCGCAAATTT CGTGGCGTCG TCGCGATCCT TTTGTTGCTT GGCATCAGCG
TCCTATCGCG CGCGTTTAAA GCACCGCAGC AGCGCTAGGA AAACAACGAA CCGTAGTCGC

       4510       4520       4530       4540       4550       4560
CCTGGTTCGG CCATCTGCTG CATCGCCTGT TCGCCGTCCT CGGACCGCTC GGCTTTCTGC
GGACCAAGCC GGTAGACGAC GTAGCGGACA AGCGGCAGGA GCCTGGCGAG CCGAAAGACG

       4570       4580       4590       4600       4610       4620
TCGAGGCGGT TCTGGTCGCG GTCTTCCTGG CACAGAAGAG CCTCGCCGAT CACGTGCGTC
AGCTCCGCCA AGACCAGCGC CAGAAGGACC GTGTCTTCTC GGAGCGGCTA GTGCACGCAG

       4630       4640       4650       4660       4670       4680
GCGTGGCCGG GGGCTTGCGA CAGGGCGGGC TGGAAGGCGG GCGTGCCGCC GTGTCGATGA
CGCACCGGCC CCCGAACGCT GTCCCGCCCG ACCTTCCGCC CGCACGGCGG CACAGCTACT

       4690       4700       4710       4720       4730       4740
TCGTTGGTCG CGATCCAAAG ACGCTCGACG AGCCGGCGGT CTGCCGTGCC GCGATCGAAA
AGCAACCAGC GCTAGGTTTC TGCGAGCTGC TCGGCCGCCA GACGGCACGG CGCTAGCTTT

       4750       4760       4770       4780       4790       4800
GCCTTGCCGA GAATTTCTCC GACGGCGTCG TGGCGCCGGC CTTCTGGTAC GCGGTTGCCG
CGGAACGGCT CTTAAAGAGG CTGCCGCAGC ACCGCGGCCG GAAGACCATG CGCCAACGGC
```

FIG. 7H

```
      4810       4820       4830       4840       4850       4860
GCCTGCCGGG GCTTCTTGCC TACAAGATGC TGAACACCGC CGATTCGATG ATCGGCCACA
CGGACGGCCC CGAAGAACGG ATGTTCTACG ACTTGTGGCG GCTAAGCTAC TAGCCGGTGT

      4870       4880       4890       4900       4910       4920
AGTCGCCGAA ATATCTGCAC TTCGGCTGGG CCTCGGCCCG ACTCGACGAT CTCGCCAACC
TCAGCGGCTT TATAGACGTG AAGCCGACCC GGAGCCGGGC TGAGCTGCTA GAGCGGTTGG

      4930       4940       4950       4960       4970       4980
TGCCGGCAGC GAGGCTCTCG ATCCTTTTGA TCTCAGCCGG TGCGCTGATC CATCGTGGCG
ACGGCCGTCG CTCCGAGAGC TAGGAAAACT AGAGTCGGCC ACGCGACTAG GTAGCACCGC

      4990       5000       5010       5020       5030       5040
CCAGCGCCGC CAAGGATGCG CTGACCGTGG CCCTTCGCGA CCATGGCCTG CACCGCTCGC
GGTCGCGGCG GTTCCTACGC GACTGGCACC GGGAAGCGCT GGTACCGGAC GTGGCGAGCG

      5050       5060       5070       5080       5090       5100
CGAACTCCGG CTGGCCGGAA GCGGCCATGG CCGGCGCGCT CGATCTGCAG CTTGCCGGTC
GCTTGAGGCC GACCGGCCTT CGCCGGTACC GGCCGCGCGA GCTAGACGTC GAACGGCCAG

      5110       5120       5130       5140       5150       5160
CGCGGATCTA TGGCGGCGTC AAGGTCAGCG AACCTATGAT CAACGGTCCG GGCCGAGCGG
GCGCCTAGAT ACCGCCGCAG TTCCAGTCGC TTGGATACTA GTTGCCAGGC CCGGCTCGCC

      5170       5180       5190       5200       5210       5220
TTGCAACAAG CGAAGACATC GACGCCGGTA TTGCTGTATT TTATGGCGCC TGTACGGTCA
AACGTTGTTC GCTTCTGTAG CTGCGGCCAT AACGACATAA AATACCGCGG ACATGCCAGT

      5230       5240       5250       5260       5270       5280
TGGCCGGGTT TGTTCTTGCA ATCGCAATGA TTTGATCGCG GAAGTTGACC TTCGCATTAA
ACCGGCCCAA ACAAGAACGT TAGCGTTACT AAACTAGCGC CTTCAACTGG AAGCGTAATT

      5290       5300       5310       5320       5330       5340
GACTCTGCTT TCCATATGTA TTAAGATCGT ATCATATTCG ATCAGTTATT CTCCTGGAAC
CTGAGACGAA AGGTATACAT AATTCTAGCA TAGTATAAGC TAGTCAATAA GAGGACCTTG

      5350       5360       5370       5380       5390       5400
GTTTGGTTCC ACCGGTACGT GTTCGTCTTC CCGGAGAGAG AAGCATGCGC AAAAGCTT
CAAACCAAGG TGGCCATGCA CAAGCAGAAG GGCCTCTCTC TTCGTACGCG TTTTCGAA
```

FIG. 7I

```
        10         20         30         40         50         60
GAATTCGCCA GCGCCTACAT GGCTGACCTC AAGCAGTTCC TCGTGGCCCA GAAGAACGAG
CTTAAGCGGT CGCGGATGTA CCGACTGGAG TTCGTCAAGG AGCACCGGGT CTTCTTGCTC

        70         80         90        100        110        120
GGCCGGCAGA TTTTCCCTCG CGGGCCTGAG TATTTTCGCG CGCTCGACCT GACGCCGCTC
CCGGCCGTCT AAAAGGGAGC GCCCGGACTC ATAAAAGCGC GCGAGCTGGA CTGCGGCGAG

       130        140        150        160        170        180
GACAAGGTGC GCGTGGTCAT TCTCGGCCAG GATCCCTATC ACGGTGACGG CCAGGCGCAT
CTGTTCCACG CGCACCAGTA AGAGCCGGTC CTAGGGATAG TGCCACTGCC GGTCCGCGTA

       190        200        210        220        230        240
GGGCTCTGCT TCAGCGTTCG CCCCGGTGTC CGGACGCCGC CGTCGCTGGT CAACATCTAC
CCCGAGACGA AGTCGCAAGC GGGGCCACAG GCCTGCGGCG GCAGCGACCA GTTGTAGATG

       250        260        270        280        290        300
AAGGAACTGA ATACCGATCT CGGTATTCCG CCGGCGCGTC ACGGTTTTCT CGAAAGCTGG
TTCCTTGACT TATGGCTAGA GCCATAAGGC GGCCGCGCAG TGCCAAAAGA GCTTTCGACC

       310        320        330        340        350        360
GCAAGGCAGG GCGTGCTGCT TTTGAACAGC GTGCTGACGG TAGAGCGCGG GAACGTGCGT
CGTTCCGTCC CGCACGACGA AAACTTGTCG CACGACTGCC ATCTCGCGCC CTTGCACGCA

       370        380        390        400        410        420
CACACCAGGG TCACGGTTGG GAAAAGTTCA CGGATGCGAT CATCCGTGCG GTCAACGAGG
GTGTGGTCCC AGTGCCAACC CTTTTCAAGT GCCTACGCTA GTAGGCACGC CAGTTGCTCC

       430        440        450        460        470        480
CCGAGCATCC CGTCGTCTTC ATGCTTTGGG GCTCCTATGC GCAGAAGAAG GCGGCCTTCG
GGCTCGTAGG GCAGCAGAAG TACGAAACCC CGAGGATACG CGTCTTCTTC CGCCGGAAGC

       490        500        510        520        530        540
TCGACCGCTC GCGCCATCTT GTCCTGAGGG CACCACATCC GTCGCCGCTC TCAGCCCATT
AGCTGGCGAG CGCGGTAGAA CAGGACTCCC GTGGTGTAGG CAGCGGCGAG AGTCGGGTAA

       550        560        570        580        590        600
CCGGCTTTCT CGGCTGCCGG CATTTTTCCC AGGCCAATGC CTTCCTCGAA AGCAAAGGCT
GGCCGAAAGA GCCGACGGCC GTAAAAAGGG TCCGGTTACG GAAGGAGCTT TCGTTTCCGA
```

*FIG. 8A*

```
       610        620        630        640        650        660
TCGATCCGAT CGACTGGCGG CTGCCGGAAA ATCCGGCTGC GGACATCAAC TGAAGGCTTG
AGCTAGGCTA GCTGACCGCC GACGGCCTTT TAGGCCGACG CCTGTAGTTG ACTTCCGAAC

       670        680        690        700        710        720
GCGCGAATGA CGGCTTTGTC GTCGCCCTGA GGTCTTGCCT TGGCGGCGGC GATCCGCCTA
CGCGCTTACT GCCGAAACAG CAGCGGGACT CCAGAACGGA ACCGCCGCCG CTAGGCGGAT

       730        740        750        760        770        780
AGACGCCCGA ACGAAATGGC GGAGGCGGGC ATGCGCAAAA TTCTGATCAT CGGCATCGGT
TCTGCGGGCT TGCTTTACCG CCTCCGCCCG TACGCGTTTT AAGACTAGTA GCCGTAGCCA

       790        800        810        820        830        840
TCGGGCAATC CCGAACACAT GACCGTGCAG GCGATCAACG CGCTGAACTG CGCCGACGTG
AGCCCGTTAG GGCTTGTGTA CTGGCACGTC CGCTAGTTGC GCGACTTGAC GCGGCTGCAC

       850        860        870        880        890        900
CTCTTTATCC CGACCAAGGG AGCGAAGAAG ACCGAGCTTG CCGAAGTGCG CCGCGACATC
GAGAAATAGG GCTGGTTCCC TCGCTTCTTC TGGCTCGAAC GGCTTCACGC GGCGCTGTAG

       910        920        930        940        950        960
TGCGCCCGCT ACGTCACGCG CAAGGACAGC CGCACCGTCG AGTTCGCGGT GCCCGTGCGG
ACGCGGGCGA TGCAGTGCGC GTTCCTGTCG GCGTGGCAGC TCAAGCGCCA CGGGCACGCC

       970        980        990       1000       1010       1020
CGCACCGAAG GCGTCAGCTA TGACGGCAGC GTCGATGACT GGCACGCCCA GATCGCTGGG
GCGTGGCTTC CGCAGTCGAT ACTGCCGTCG CAGCTACTGA CCGTGCGGGT CTAGCGACCC

      1030       1040       1050       1060       1070       1080
ATTTACGAAG CGCTTCTATC GAAGGAGTTG GGCGAAGAGG GAACTGGCGC GTTTCTCGTC
TAAATGCTTC GCGAAGATAG CTTCCTCAAC CCGCTTCTCC CTTGACCGCG CAAAGAGCAG

      1090       1100       1110       1120       1130       1140
TGGGGCGACC CGATGCTCTA TGACAGCACC ATTCGCATCG TCGAGCGGGT CAAGGCACGC
ACCCCGCTGG GCTACGAGAT ACTGTCGTGG TAAGCGTAGC AGCTCGCCCA GTTCCGTGCG

      1150       1160       1170       1180       1190       1200
GGTGAGGTCG CCTTCGCCTA CGACGTCATT CCCGGGATCA CCAGTCTGCA GGCGCTTTGC
CCACTCCAGC GGAAGCGGAT GCTGCAGTAA GGGCCCTAGT GGTCAGACGT CCGCGAAACG
```

FIG. 8B

```
      1210       1220       1230       1240       1250       1260
GCCAGCCACC GCATTCCGCT GAACCTCGTC GGCAAGCCGG TGGAGATCAC CACGGGGCGT
CGGTCGGTGG CGTAAGGCGA CTTGGAGCAG CCGTTCGGCC ACCTCTAGTG GTGCCCCGCA

      1270       1280       1290       1300       1310       1320
CGGCTGCACG AAAGCTTTCC CGAGAAGAGC CAGACCTCGG TCGTCATGCT CGATGGCGAA
GCCGACGTGC TTTCGAAAGG GCTCTTCTCG GTCTGGAGCC AGCAGTACGA GCTACCGCTT

      1330       1340       1350       1360       1370       1380
CAGGCGTTTC AGCGGGTCGA GGACCCGGAG GCGGAGATCT ATTGGGGCGC CTATCTCGGC
GTCCGCAAAG TCGCCCAGCT CCTGGGCCTC CGCCTCTAGA TAACCCCGCG GATAGAGCCG

      1390       1400       1410       1420       1430       1440
ACGCGGGATG AGATCGTCAT TTCCGGCCGC GTGGCTGAGG TGAAGGACCG GATCCTTGAA
TGCGCCCTAC TCTAGCAGTA AAGGCCGGCG CACCGACTCC ACTTCCTGGC CTAGGAACTT

      1450       1460       1470       1480       1490       1500
ACGCGGGCGG CGGCGCGCGC GAAGATGGGA TGGATCATGG ACATCTATCT CCTGCGCAAG
TGCGCCCGCC GCCGCGCGCG CTTCTACCCT ACCTAGTACC TGTAGATAGA GGACGCGTTC

      1510       1520       1530       1540       1550       1560
GGCGCCGACT TCGACGAGTG ACGGGGAGGG CCGATCTGCG TCGTGTTTGA TCTCACTCAA
CCGCGGCTGA AGCTGCTCAC TGCCCCTCCC GGCTAGACGC AGCACAAACT AGAGTGAGTT

      1570       1580       1590       1600       1610       1620
GGTTTGCGGC TGTGTTATAG CGTCTTAAGA GGCTTCTTCA GGGAGGAGAA CCTCAAGTGA
CCAAACGCCG ACACAATATC GCAGAATTCT CCGAAGAAGT CCCTCCTCTT GGAGTTCACT

      1630       1640       1650       1660       1670       1680
TGACGGATTT GATGACCAGC TGCGCCCTTC CATTGACCGG AGATGCCGGC ACCGTCGCTT
ACTGCCTAAA CTACTGGTCG ACGCGGGAAG GTAACTGGCC TCTACGGCCG TGGCAGCGAA

      1690       1700       1710       1720       1730       1740
CGATGCGCCG CGGCGCCTGC CCGTCCTTGG CAGAGCCGAT GCAGACCGGC GACGGCCTGC
GCTACGCGGC GCCGCGGACG GGCAGGAACC GTCTCGGCTA CGTCTGGCCG CTGCCGGACG

      1750       1760       1770       1780       1790       1800
TCGTGAGGGT GAGGCCAACG GATGACAGCC TGACGCTGCC GAAGGTCATT GCCCTTGCCA
AGCACTCCCA CTCCGGTTGC CTACTGTCGG ACTGCGACGG CTTCCAGTAA CGGGAACGGT
```

FIG. 8C

```
      1810       1820       1830       1840       1850       1860
CGGCTGCCGA GCGCTTCGGC AATGGCATCA TCGAGATTAC CGCGCGCGGA AACCTGCAGC
GCCGACGGCT CGCGAAGCCG TTACCGTAGT AGCTCTAATG GCGCGCGCCT TTGGACGTCG

      1870       1880       1890       1900       1910       1920
TTCGCGGCCT GAGCGCGGCT TCGGTGCCAA GGCTGGCGCA GGCGATCGGC GATGCGGAGA
AAGCGCCGGA CTCGCGCCGA AGCCACGGTT CCGACCGCGT CCGCTAGCCG CTACGCCTCT

      1930       1940       1950       1960       1970       1980
TCGCCATTGC CGAGGGGCTC GCGATCGAGG TGCCGCCCCT GGCCGGCATC GACCCGGACG
AGCGGTAACG GCTCCCCGAG CGCTAGCTCC ACGGCGGGGA CCGGCCGTAG CTGGGCCTGC

      1990       2000       2010       2020       2030       2040
AGATCGCCGA TCCGCGGCCG ATTGCCACTG AGCTTCGTGA AGCGTTGGAT GTGCGCCAGG
TCTAGCGGCT AGGCGCCGGC TAACGGTGAC TCGAAGCACT TCGCAACCTA CACGCGGTCC

      2050       2060       2070       2080       2090       2100
TGCCGTTGAA GCTTGCACCC AAATTATCCG TCGTCATCGA TAGCGGTGGC CGGTTTGGTC
ACGGCAACTT CGAACGTGGG TTTAATAGGC AGCAGTAGCT ATCGCCACCG GCCAAACCAG

      2110       2120       2130       2140       2150       2160
TCGGCGCTGT CGTCGCCGAC ATTCGCCTTC AGGCGGTTTC GACTGTCGCG GGGGTGGCCT
AGCCGCGACA GCAGCGGCTG TAAGCGGAAG TCCGCCAAAG CTGACAGCGC CCCCACCGGA

      2170       2180       2190       2200       2210       2220
GGGTGCTGTC GCTTGGCGGC ACGTCAACGA AGGCATCGAG CGTCGGGACG TTGGCCGGCA
CCCACGACAG CGAACCGCCG TGCAGTTGCT TCCGTAGCTC GCAGCCCTGC AACCGGCCGT

      2230       2240       2250       2260       2270       2280
ACGCGGTCGT GCCGGCCCTG ATCACCATTC TCGAGAAACT GGCGAGCCTG GGCACGACGA
TGCGCCAGCA CGGCCGGGAC TAGTGGTAAG AGCTCTTTGA CCGCTCGGAC CCGTGCTGCT

      2290       2300       2310       2320       2330       2340
TGCGCGGGCG CGATCTGGAC CCGTCGGAAA TCCGCGCGCT CTGTCGCTGT GAGACATCGT
ACGCGCCCGC GCTAGACCTG GGCAGCCTTT AGGCGCGCGA GACAGCGACA CTCTGTAGCA

      2350       2360       2370       2380       2390       2400
CCGAACGCCC GGCCGCTCCG CGTTCGGCCG CAATACCCGG CATTCATGCG CTGGGTAACG
GGCTTGCGGG CCGGCGAGGC GCAAGCCGGC GTTATGGGCC GTAAGTACGC GACCCATTGC
```

*FIG. 8D*

```
      2410       2420       2430       2440       2450       2460
CCGACACCGT TCTCGGCCTC GGTCTGGCCT TTGCTCAGGT GGAGGCCGCC GCGCTGGCAT
GGCTGTGGCA AGAGCCGGAG CCAGACCGGA AACGAGTCCA CCTCCGGCGG CGCGACCGTA

      2470       2480       2490       2500       2510       2520
CCTACCTGCA TCAGGTCCAG GCGCTTGGCG CCAATGCGAT CCGGCTTGCG CCCGGGCACG
GGATGGACGT AGTCCAGGTC CGCGAACCGC GGTTACGCTA GGCCGAACGC GGGCCCGTGC

      2530       2540       2550       2560       2570       2580
CCTTCTTCGT CCTCGGCCTT TGCCCCGAGA CCGCGGCTGT GGCGCAGAGC CTGGCAGCGT
GGAAGAAGCA GGAGCCGGAA ACGGGGCTCT GGCGCCGACA CCGCGTCTCG GACCGTCGCA

      2590       2600       2610       2620       2630       2640
CACACGGTTT TCGCATTGCC GAGCAGGATC CGCGCAATGC GATCGCCACC TGCGCCGGCA
GTGTGCCAAA AGCGTAACGG CTCGTCCTAG GCGCGTTACG CTAGCGGTGG ACGCGGCCGT

      2650       2660       2670       2680       2690       2700
GCAAGGGTTG CGCCTCGGCG TGGATGGAAA CCAAGGGCAT GGCCGAGCGC CTCGTCGAGA
CGTTCCCAAC GCGGAGCCGC ACCTACCTTT GGTTCCCGTA CCGGCTCGCG GAGCAGCTCT

      2710       2720       2730       2740       2750       2760
CGGCGCCGGA ATTGCTCGAC GGGTCGCTCA CCGTGCATCT CTCCGGCTGC GCCAAGGGCT
GCCGCGGCCT TAACGAGCTG CCCAGCGAGT GGCACGTAGA GAGGCCGACG CGGTTCCCGA

      2770       2780       2790       2800       2810       2820
GCGCCCGGCC GAAGCCGTCC GAACTGACGC TTGTCGGTGC GCCATCAGGA TACGGGCTTG
CGCGGGCCGG CTTCGGCAGG CTTGACTGCG AACAGCCACG CGGTAGTCCT ATGCCCGAAC

      2830       2840       2850       2860       2870       2880
TCGTAAATGG GGCTGCCAAT GGCTTGCCAA GCGCCTACAC CGATGAGAAT GGAATGGGAT
AGCATTTACC CCGACGGTTA CCGAACGGTT CGCGGATGTG GCTACTCTTA CCTTACCCTA

      2890       2900       2910       2920       2930       2940
CCGCCCTTGC CCGGCTCGGC CGGCTGGTGC GGCAAAACAA AGACGCTGGC GAATCGGCGC
GGCGGGAACG GGCCGAGCCG GCCGACCACG CCGTTTTGTT TCTGCGACCG CTTAGCCGCG

      2950       2960       2970       2980       2990       3000
AGTCCTGTCT TACACGGCTC GGAGCTGCGC GCGTCTCGGC AGCGTTCGAA CAGGGATAGA
TCAGGACAGA ATGTGCCGAG CCTCGACGCG CGCAGAGCCG TCGCAAGCTT GTCCCTATCT
```

FIG. 8E

```
      3010       3020       3030       3040       3050       3060
CATGCCTGAG TATGATTACA TTCGCGATGG CAACGCCATC TACGAGCGTT CCTTCGCCAT
GTACGGACTC ATACTAATGT AAGCGCTACC GTTGCGGTAG ATGCTCGCAA GGAAGCGGTA

      3070       3080       3090       3100       3110       3120
CATCCGCGCC GAGGCCGATC TGTCGCGCTT CTCCGAAGAG GAAGCGGATC TGGCTGTGCG
GTAGGCGCGG CTCCGGCTAG ACAGCGCGAA GAGGCTTCTC CTTCGCCTAG ACCGACACGC

      3130       3140       3150       3160       3170       3180
CATGGTGCAC GCCTGCGGTT CCGTCGAGGC GACCAGGCAG TTCGTGTTTT CTCCCGATTT
GTACCACGTG CGGACGCCAA GGCAGCTCCG CTGGTCCGTC AAGCACAAAA GAGGGCTAAA

      3190       3200       3210       3220       3230       3240
CGTAAGCTCG GCCCGTGCGG CGCTGAAAGC CGGTGCGCCG ATCCTCTGCG ATGCCGAGAT
GCATTCGAGC CGGGCACGCC GCGACTTTCG GCCACGCGGC TAGGAGACGC TACGGCTCTA

      3250       3260       3270       3280       3290       3300
GGTTGCGCAC GGTGTCACCC GCGCCCGTCT GCCGGCCGGC AACGAGGTGA TCTGCACGCT
CCAACGCGTG CCACAGTGGG CGCGGGCAGA CGGCCGGCCG TTGCTCCACT AGACGTGCGA

      3310       3320       3330       3340       3350       3360
GCGCGATCCT CGCACGCCCG CACTTGCGGC CGAGATCGGC AACACCCGCT CCGCCGCAGC
CGCGCTAGGA GCGTGCGGGC GTGAACGCCG GCTCTAGCCG TTGTGGGCGA GGCGGCGTCG

      3370       3380       3390       3400       3410       3420
CCTGAAGCTC TGGAGCGAGC GGCTGGCCGG TTCGGTGGTC GCGATCGGCA ACGCGCCGAC
GGACTTCGAG ACCTCGCTCG CCGACCGGCC AAGCCACCAG CGCTAGCCGT TGCGCGGCTG

      3430       3440       3450       3460       3470       3480
GGCGTTGTTC TTCCTCTTGG AAATGCTGCG CGACGGCGCG CCGAAGCCGG CGGCAATCCT
CCGCAACAAG AAGGAGAACC TTTACGACGC GCTGCCGCGC GGCTTCGGCC GCCGTTAGGA

      3490       3500       3510       3520       3530       3540
CGGCATGCCC GTCGGTTTCG TCGGTGCGGC GGAATCGAAG GATGCGCTGG CCGAGAACTC
GCCGTACGGG CAGCCAAAGC AGCCACGCCG CCTTAGCTTC CTACGCGACC GGCTCTTGAG

      3550       3560       3570       3580       3590       3600
CTATGGCGTT CCCTTCGCCA TCGTGCGCGG CCGCCTCGGC GGGAGTGCCA TGACGGCGGC
GATACCGCAA GGGAAGCGGT AGCACGCGCC GGCGGAGCCG CCCTCACGGT ACTGCCGCCG
```

FIG. 8F

```
       3610       3620       3630       3640       3650       3660
AGCGCTTAAC TCGCTCGCGA GGCCGGGCCT GTGAGCGGCG TCGGCGTGGG GCGCCTGATC
TCGCGAATTG AGCGAGCGCT CCGGCCCGGA CACTCGCCGC AGCCGCACCC CGCGGACTAG

       3670       3680       3690       3700       3710       3720
GGTGTTGGGA CCGGCCCCGG TGATCCGGAA CTTTTGACGG TCAAGGCGGT GAAGGCGCTC
CCACAACCCT GGCCGGGGCC ACTAGGCCTT GAAAACTGCC AGTTCCGCCA CTTCCGCGAG

       3730       3740       3750       3760       3770       3780
GGGCAAGCCG ATGTGCTTGC CTATTTCGCC AAGGCCGGGC GAAGCGGTAA CGGCCGCGCG
CCCGTTCGGC TACACGAACG GATAAAGCGG TTCCGGCCCG CTTCGCCATT GCCGGCGCGC

       3790       3800       3810       3820       3830       3840
GTGGTCGAGG GTCTGCTGAA GCCCGATCTT GTCGAGCTGC CGCTATACTA TCCGGTGACG
CACCAGCTCC CAGACGACTT CGGGCTAGAA CAGCTCGACG GCGATATGAT AGGCCACTGC

       3850       3860       3870       3880       3890       3900
ACCGAAATCG ACAAGGACGA TGGCGCCTAC AAGACCCAGA TCACCGACTT CTACAATGCG
TGGCTTTAGC TGTTCCTGCT ACCGCGGATG TTCTGGGTCT AGTGGCTGAA GATGTTACGC

       3910       3920       3930       3940       3950       3960
TCGGCCGAAG CGGTAGCGGC GCATCTTGCC GCCGGGCGCA CGGTCGCCGT GCTCAGTGAA
AGCCGGCTTC GCCATCGCCG CGTAGAACGG CGGCCCGCGT GCCAGCGGCA CGAGTCACTT

       3970       3980       3990       4000       4010       4020
GGCGACCCGC TGTTCTATGG TTCCTACATG CATCTGCATG TGCGGCTCGC CAATCGTTTC
CCGCTGGGCG ACAAGATACC AAGGATGTAC GTAGACGTAC ACGCCGAGCG GTTAGCAAAG

       4030       4040       4050       4060       4070       4080
CCGGTCGAGG TGATCCCCGG CATTACCGCC ATGTCCGGCT GTTGGTCGCT TGCCGGCCTG
GGCCAGCTCC ACTAGGGGCC GTAATGGCGG TACAGGCCGA CAACCAGCGA ACGGCCGGAC

       4090       4100       4110       4120       4130       4140
CCGCTGGTGC AGGGCGACGA CGTGCTCTCG GTGCTTCCGG GCACCATGGC CGAGGCCGAG
GGCGACCACG TCCCGCTGCT GCACGAGAGC CACGAAGGCC CGTGGTACCG GCTCCGGCTC

       4150       4160       4170       4180       4190       4200
CTCGGCCGCA GGCTTGCGGA TACCGAAGCC GCCGTGATCA TGAAGGTCGG GCGCAATTTG
GAGCCGGCGT CCGAACGCCT ATGGCTTCGG CGGCACTAGT ACTTCCAGCC CGCGTTAAAC
```

*FIG. 8G*

```
      4210       4220       4230       4240       4250       4260
CCGAAGATCC GTCGGGCGCT CGCTGCCTCC GGCCGTCTCG ACCAGGCCGT CTATGTCGAA
GGCTTCTAGG CAGCCCGCGA GCGACGGAGG CCGGCAGAGC TGGTCCGGCA GATACAGCTT

      4270       4280       4290       4300       4310       4320
CGCGGCACGA TGAAGAACGC GGCGATGACG GCTCTTGCGG AAAAGGCCGA CGACGAGGCG
GCGCCGTGCT ACTTCTTGCG CCGCTACTGC CGAGAACGCC TTTTCCGGCT GCTGCTCCGC

      4330       4340       4350       4360       4370       4380
CCCTATTTCT CGCTGGTGCT CGTTCCCGGC TGGAAGGACC GACCATGACC GGTACGCTCT
GGGATAAAGA GCGACCACGA GCAAGGGCCG ACCTTCCTGG CTGGTACTGG CCATGCGAGA

      4390       4400       4410       4420       4430       4440
ATGTCGTCGG TACCGGACCG GGCAGCGCCA AGCAGATGAC GCCGGAAACG GCGGAAGCCG
TACAGCAGCC ATGGCCTGGC CCGTCGCGGT TCGTCTACTG CGGCCTTTGC CGCCTTCGGC

      4450       4460       4470       4480       4490       4500
TTGCGGCCGC TCAGGAGTTT TACGGCTACT TTCCCTATCT CGACCGGCTG AACCTCAGAC
AACGCCGGCG AGTCCTCAAA ATGCCGATGA AAGGGATAGA GCTGGCCGAC TTGGAGTCTG

      4510       4520       4530       4540       4550       4560
CGGATCAGAT CCGTGTCGCC TCGGACAACC GCGAGGAGCT CGATCGGGCA CAGGTCGCGC
GCCTAGTCTA GGCACAGCGG AGCCTGTTGG CGCTCCTCGA GCTAGCCCGT GTCCAGCGCG

      4570       4580       4590       4600       4610       4620
TGACGCGGGC TGCGGCAGGC GTGAAGGTCT GCATGGTCTC CGGTGGCGAT CCCGGTGTCT
ACTGCGCCCG ACGCCGTCCG CACTTCCAGA CGTACCAGAG GCCACCGCTA GGGCCACAGA

      4630       4640       4650       4660       4670       4680
TTGCCATGGC GGCCGCCGTC TGCGAGGCGA TCGACAAGGG ACCGGCGGAA TGGAAGTCGG
AACGGTACCG CCGGCGGCAG ACGCTCCGCT AGCTGTTCCC TGGCCGCCTT ACCTTCAGCC

      4690       4700       4710       4720       4730       4740
TTGAACTGGT GATCACGCCC GGCGTGACCG CGATGCTCGC CGTTGCCGCC CGCATCGGCG
AACTTGACCA CTAGTGCGGG CCGCACTGGC GCTACGAGCG GCAACGGCGG GCGTAGCCGC

      4750       4760       4770       4780       4790       4800
CGCCGCTCGG TCATGATTTC TGTGCGATCT CGCTTTCCGA CAATCTGAAG CCCTGGGAAG
GCGGCGAGCC AGTACTAAAG ACACGCTAGA GCGAAAGGCT GTTAGACTTC GGGACCCTTC
```

FIG. 8H

```
      4810       4820       4830       4840       4850       4860
TCATCACCCG GCGTCTCAGG CTGGCGGCGG AAGCGGGCTT CGTCATTGCC CTCTACAATC
AGTAGTGGGC CGCAGAGTCC GACCGCCGCC TTCGCCCGAA GCAGTAACGG GAGATGTTAG

      4870       4880       4890       4900       4910       4920
CGATCAGCAA GGCGCGGCCC TGGCAGCTCG GTGAGGCCTT CGAGCTTCTG CGCAGCGTTC
GCTAGTCGTT CCGCGCCGGG ACCGTCGAGC CACTCCGGAA GCTCGAAGAC GCGTCGCAAG

      4930       4940       4950       4960       4970       4980
TGCCGGCAAG CGTTCCGGTC ATCTTCGGCC GTGCGGCCGG GCGGCCGGAC GAACGGATCG
ACGGCCGTTC GCAAGGCCAG TAGAAGCCGG CACGCCGGCC CGCCGGCCTG CTTGCCTAGC

      4990       5000       5010       5020       5030       5040
CGGTGATGCC GCTCGGCGAG GCCGATGCCA ACCGCGCCGA CATGGCGACC TGCGTCATCA
GCCACTACGG CGAGCCGCTC CGGCTACGGT TGGCGCGGCT GTACCGCTGG ACGCAGTAGT

      5050       5060       5070       5080       5090       5100
TCGGCTCGCC GGAGACGCGC ATCGTCGAGC GCGACGGCCA ACCCGATCTC GTCTACACAC
AGCCGAGCGG CCTCTGCGCG TAGCAGCTCG CGCTGCCGGT TGGGCTAGAG CAGATGTGTG

      5110       5120       5130       5140       5150       5160
CGCGCTTCTA TGCAGGGGCG AGCCAGTGAG CGATGCGGTT GAGTGCCTCG TCGCAACTGC
GCGCGAAGAT ACGTCCCCGC TCGGTCACTC GCTACGCCAA CTCACGGAGC AGCGTTGACG

      5170       5180       5190       5200       5210       5220
CGACCGTCGG CACGTCCGCG GGCTTGCGCC GCTCGACCAT GATCACCTCG ATGCCGAGCC
GCTGGCAGCC GTGCAGGCGC CCGAACGCGG CGAGCTGGTA CTAGTGGAGC TACGGCTCGG

      5230       5240       5250       5260       5270       5280
GGCGCGCTGC GGCAATCTTG CCGTAGGTGG CGCTGCCACC GCTGTTCTTG GCGACGATCA
CCGCGCGACG CCGTTAGAAC GGCATCCACC GCGACGGTGG CGACAAGAAC CGCTGCTAGT

      5290       5300       5310       5320       5330       5340
CATCGATCTG CCGACTCCTG AGCAACGCGG CTTCGTCGGC TTCCGCAAAG GGACCGGTCG
GTAGCTAGAC GGCTGAGGAC TCGTTGCGCC GAAGCAGCCG AAGGCGTTTC CCTGGCCAGC

      5350       5360       5370       5380       5390       5400
CCAGGATCGC CTCCTGGTCG GGCAGATTAA GCGGCGGCGT CACCGGATCG ACGCTGCGGA
GGTCCTAGCG GAGGACCAGC CCGTCTAATT CGCCGCCGCA GTGGCCTAGC TGCGACGCCT
```

FIG. 8I

```
      5410       5420       5430       5440       5450       5460
TGACGTAGCT GTGCTGCGGC GCGACCTCGA AGTGGAAAGC TTCCTGTCGA CCTATCGCCA
ACTGCATCGA CACGACGCCG CGCTGGAGCT TCACCTTTCG AAGGACAGCT GGATAGCGGT

      5470       5480       5490       5500       5510       5520
GGAAGACGCG GCGTCGCCGA TCACCGAGCG CGCTGACGGC CTCGACAACG CTATCGACAG
CCTTCTGCGC CGCAGCGGCT AGTGGCTCGC GCGACTGCCG GAGCTGTTGC GATAGCTGTC

      5530       5540       5550       5560       5570       5580
CAGTCCAGCG GTCGCCAGGC AGGGGCACCC ATTCCGGTCG GCGGAGGGCG ATAAGCGCAA
GTCAGGTCGC CAGCGGTCCG TCCCCGTGGG TAAGGCCAGC CGCCTCCCGC TATTCGCGTT

      5590       5600       5610       5620       5630       5640
CGCCGGTTCT TTGCGCTGCG TCCGCGGCGT TGTGCGAAAT GCGTGCGGCA AAGGGGTGCG
GCGGCCAAGA AACGCGACGC AGGCGCCGCA ACACGCTTTA CGCACGCCGT TTCCCCACGC

      5650       5660       5670       5680       5690       5700
TCGCATCGAC CAGCAGCGCG ATGTTTTCGT CATGCACGAA ATGCGCCAGC CCATCGGCGC
AGCGTAGCTG GTCGTCGCGC TACAAAAGCA GTACGTGCTT TACGCGGTCG GGTAGCCGCG

      5710       5720       5730       5740       5750       5760
CGCCAAAGCC GCCGATGCGC GTCTTGACCG GCTGCGGCCG CGGGTCCGCG GTGCGGCCGG
GCGGTTTCGG CGGCTACGCG CAGAACTGGC CGACGCCGGC GCCCAGGCGC CACGCCGGCC

      5770       5780       5790       5800       5810       5820
CCAGCGAGAT GGCGGTGTCG TAGCGGACAT CTTCGGCCAA GCGGCGCGCG AGTTCGCGTG
GGTCGCTCTA CCGCCACAGC ATCGCCTGTA GAAGCCGGTT CGCCGCGCGC TCAAGCGCAC

      5830       5840       5850       5860       5870       5880
CCTCGGTGGT GCCACCCAGA ATCAGAATAC GAGGTTTTTC CATGGCTGAC GTGTCGAACA
GGAGCCACCA CGGTGGGTCT TAGTCTTATG CTCCAAAAAG GTACCGACTG CACAGCTTGT

      5890       5900       5910       5920       5930       5940
GCGAACCCGC CATAGTCTCC CCCTGGCTGA CCGTCATCGG TATCGGTGAG GATGGTGTAG
CGCTTGGGCG GTATCAGAGG GGGACCGACT GGCAGTAGCC ATAGCCACTC CTACCACATC

      5950       5960       5970       5980       5990       6000
CGGGTCTCGG CGACGAGGCC AAGCGGCTGA TCGCCGAAGC GCCGGTCGTC TACGGCGGCC
GCCCAGAGCC GCTGCTCCGG TTCGCCGACT AGCGGCTTCG CGGCCAGCAG ATGCCGCCGG
```

*FIG. 8J*

```
      6010       6020       6030       6040       6050       6060
ATCGTCATCT GGAGCTCGCC GCCTCCCTCA TCACCGGCGA AGCGCACAAT TGGCTAAGCC
TAGCAGTAGA CCTCGAGCGG CGGAGGGAGT AGTGGCCGCT TCGCGTGTTA ACCGATTCGG

      6070       6080       6090       6100       6110       6120
CCCTCGAACG CTCGGTCGTC GAGATCGTCG CGCGTCGCGG CAGCCCGGTG GTGGTGCTTG
GGGAGCTTGC GAGCCAGCAG CTCTAGCAGC GCGCAGCGCC GTCGGGCCAC CACCACGAAC

      6130       6140       6150       6160       6170       6180
CCTCGGGCGA CCCGTTCTTC TTCGGCGTCG GCGTGACGCT GGCGCGCCGC ATCGCCTCGG
GGAGCCCGCT GGGCAAGAAG AAGCCGCAGC CGCACTGCGA CCGCGCGGCG TAGCGGAGCC

      6190       6200       6210       6220       6230       6240
CCGAAATACG CACGCTTCCG GCGCCGTCGT CGATCAGTCT TGCCGCCTCG CGCCTCGGCT
GGCTTTATGC GTGCGAAGGC CGCGGCAGCA GCTAGTCAGA ACGGCGGAGC GCGGAGCCGA

      6250       6260       6270       6280       6290       6300
GGGCGCTGCA GGATGCGACG CTCGTCTCCG TACATGGGCG GCCGCTGGAT CTGGTGCGAC
CCCGCGACGT CCTACGCTGC GAGCAGAGGC ATGTACCCGC CGGCGACCTA GACCACGCTG

      6310       6320       6330       6340       6350       6360
CGCATTTGCA TCCGGGGGCG CGTGTGCTTA CGCTCACGTC GGACGGTGCG GGTCCGCGAG
GCGTAAACGT AGGCCCCCGC GCACACGAAT GCGAGTGCAG CCTGCCACGC CCAGGCGCTC

      6370       6380       6390       6400       6410       6420
ACCTTGCCGA GCTTCTGGTT TCAAGCGGCT TCGGTCAGTC GCGACTGACC GTGCTCGAAG
TGGAACGGCT CGAAGACCAA AGTTCGCCGA AGCCAGTCAG CGCTGACTGG CACGAGCTTC

      6430       6440       6450       6460       6470       6480
CGCTGGGCGG CGCCGGCGAA CGGGTGACGA CGCAGATCGC CGCGCGCTTC ATGCTCGGCC
GCGACCCGCC GCGGCCGCTT GCCCACTGCT GCGTCTAGCG GCGCGCGAAG TACGAGCCGG

      6490       6500       6510       6520       6530       6540
TCGTGCATCC TTTGAACGTC TGCGCCATTG AGGTGGCGGC CGACGAGGGC GCGCGCATCC
AGCACGTAGG AAACTTGCAG ACGCGGTAAC TCCACCGCCG GCTGCTCCCG CGCGCGTAGG

      6550       6560       6570       6580       6590       6600
TGCCGCTTGC CGCCGGCCGC GACGATGCGC TGTTCGAACA TGACGGGCAG ATCACCAAGC
ACGGCGAACG GCGGCCGGCG CTGCTACGCG ACAAGCTTGT ACTGCCCGTC TAGTGGTTCG
```

FIG. 8K

```
      6610       6620       6630       6640       6650       6660
GCGAGGTGCG GGCGCTGACG CTGTCGGCAC TCGCACCGCG CAAGGGCGAA CTGCTATGGG
CGCTCCACGC CCGCGACTGC GACAGCCGTG AGCGTGGCGC GTTCCCGCTT GACGATACCC

      6670       6680       6690       6700       6710       6720
ACATCGGCGG CGGCTCCGGC TCGATCGGCA TCGAATGGAT GCTCGCCGAT CCGACCATGC
TGTAGCCGCC GCCGAGGCCG AGCTAGCCGT AGCTTACCTA CGAGCGGCTA GGCTGGTACG

      6730       6740       6750       6760       6770       6780
AGGCGATCAC CATCGAGGTT GAGCCGGAGC GGGCAGCGCG CATCGGCCGC AACGCGACGA
TCCGCTAGTG GTAGCTCCAA CTCGGCCTCG CCCGTCGCGC GTAGCCGGCG TTGCGCTGCT

      6790       6800       6810       6820       6830       6840
TGTTCGGCGT GCCCGGGCTG ACGGTTGTCG AAGGCGAGGC GCCGGCGGCG CTTGCCGGCC
ACAAGCCGCA CGGGCCCGAC TGCCAACAGC TTCCGCTCCG CGGCCGCCGC GAACGGCCGG

      6850       6860       6870       6880       6890       6900
TGCCACAACC GGACGCGATC TTCATCGGCG GCGGCGGCAG CGAAGACGGC GTCATGGAAG
ACGGTGTTGG CCTGCGCTAG AAGTAGCCGC CGCCGCCGTC GCTTCTGCCG CAGTACCTTC

      6910       6920       6930       6940       6950       6960
CAGCGATCGA GGCGCTCAAG TCAGGCGGAC GGCTGGTTGC CAACGCGGTG ACGACGGACA
GTCGCTAGCT CCGCGAGTTC AGTCCGCCTG CCGACCAACG GTTGCGCCAC TGCTGCCTGT

      6970       6980       6990       7000       7010       7020
TGGAAGCGGT GCTGCTCGAT CATCACGCGC GGCTCGGCGG TTCGCTGATC CGCATCGATA
ACCTTCGCCA CGACGAGCTA GTAGTGCGCG CCGAGCCGCC AAGCGACTAG GCGTAGCTAT

      7030       7040       7050       7060       7070       7080
TCGCGCGTGC AGGACCCATC GGCGGCATGA CCGGCTGGAA GCCGGCCATG CCGGTCACCC
AGCGCGCACG TCCTGGGTAG CCGCCGTACT GGCCGACCTT CGGCCGGTAC GGCCAGTGGG

      7090       7100       7110       7120       7130       7140
AATGGTCGTG GACGAAGGGC TAAAGCAGTT CCAGCGAAAG TGTGACGCGG TTTTGCGTCC
TTACCAGCAC CTGCTTCCCG ATTTCGTCAA GGTCGCTTTC ACACTGCGCC AAAACGCAGG

      7150       7160       7170       7180       7190       7200
GGAACTGCGC AAGAAAAAGA AAGAGTAACC TATGACGGTA CATTTCATCG GCGCCGGCCC
CCTTGACGCG TTCTTTTTCT TTCTCATTGG ATACTGCCAT GTAAAGTAGC CGCGGCCGGG
```

*FIG. 8L*

```
      7210       7220       7230       7240       7250       7260
GGGAGCCGCA GACCTGATCA CGGTGCGTGG TCGCGACCTG ATCGGGCGCT GCCCGGTCTG
CCCTCGGCGT CTGGACTAGT GCCACGCACC AGCGCTGGAC TAGCCCGCGA CGGGCCAGAC

      7270       7280       7290       7300       7310       7320
CCTTTACGCC GGCTCGATCG TCTCGCCGGA GCTGCTGCGA TATTGCCCGC CGGGCGCCCG
GGAAATGCGG CCGAGCTAGC AGAGCGGCCT CGACGACGCT ATAACGGGCG GCCCGCGGGC

      7330       7340       7350       7360       7370       7380
CATTGTCGAT ACGGCGCCGA TGTCCCTCGA CGAGATCGAG GCGGAGTATG TGAAGGCCGA
GTAACAGCTA TGCCGCGGCT ACAGGGAGCT GCTCTAGCTC CGCCTCATAC ACTTCCGGCT

      7390       7400       7410       7420       7430       7440
AGCCGAAGGG CTCGACGTGG CGCGGCTTCA TTCGGGCGAC CTTTCGGTCT GGAGTGCTGT
TCGGCTTCCC GAGCTGCACC GCGCCGAAGT AAGCCCGCTG GAAAGCCAGA CCTCACGACA

      7450       7460       7470       7480       7490       7500
GGCCGAACAG ATCCGCCGGC TCGAGAAGCA TGGCATCGCC TATACGATGA CGCCGGGCGT
CCGGCTTGTC TAGGCGGCCG AGCTCTTCGT ACCGTAGCGG ATATGCTACT GCGGCCCGCA

      7510       7520       7530       7540       7550       7560
TCCTTCCTTT GCGGCGGCGG CTTCAGCGCT CGGTCGCGAA TTGACCATTC CGGCCGTGGC
AGGAAGGAAA CGCCGCCGCC GAAGTCGCGA GCCAGCGCTT AACTGGTAAG GCCGGCACCG

      7570       7580       7590       7600       7610       7620
CCAGAGCCTG GTGCTGACCC GCGTTTCGGG CCGCGCCTCG CCGATGCCGA ACTCAGAAAC
GGTCTCGGAC CACGACTGGG CGCAAAGCCC GGCGCGGAGC GGCTACGGCT TGAGTCTTTG

      7630       7640       7650       7660       7670       7680
GCTTTCCGCT TTCGGCGCTA CGGGATCGAC GCTGGCAATC CACCTTGCGA TCCATGCGCT
CGAAAGGCGA AAGCCGCGAT GCCCTAGCTG CGACCGTTAG GTGGAACGCT AGGTACGCGA

      7690       7700       7710       7720       7730       7740
TCAGCAGGTG GTCGAGGAAC TGACGCCGCT CTACGGTGCC GACTGCCCGG TCGCCATCGT
AGTCGTCCAC CAGCTCCTTG ACTGCGGCGA GATGCCACGG CTGACGGGCC AGCGGTAGCA

      7750       7760       7770       7780       7790       7800
CGTCAAGGCC TCCTGGCCGG ACGAACGCGT GGTGCGCGGC ACGCTCGGTG ACATCGCCGC
GCAGTTCCGG AGGACCGGCC TGCTTGCGCA CCACGCGCCG TGCGAGCCAC TGTAGCGGCG
```

FIG. 8M

```
      7810       7820       7830       7840       7850       7860
CAAGGTGGCG GAAGAGCCGA TCGAGCGCAC GGCGCTGATC TTCGTCGGTC CGGGGCTCGA
GTTCCACCGC CTTCTCGGCT AGCTCGCGTG CCGCGACTAG AAGCAGCCAG GCCCCGAGCT

      7870       7880       7890       7900       7910       7920
AGCCTCCGAT TTCCGTGAAA GCTCGCTCTA CGATCCCGCC TATCAGCGGC GCTTCAGAGG
TCGGAGGCTA AAGGCACTTT CGAGCGAGAT GCTAGGGCGG ATAGTCGCCG CGAAGTCTCC

      7930       7940       7950       7960       7970       7980
GCGCGGCGAA TAGGCCGCAC TCCCTCGGGG GTCGGCCTAA GTTTCCCGCT GAGAGGGTTT
CGCGCCGCTT ATCCGGCGTG AGGGAGCCCC CAGCCGGATT CAAAGGGCGA CTCTCCCAAA

      7990       8000       8010       8020       8030       8040
TGAAACCTAT TCTGCCGGTT CTTCGCGCGG CGGCCGCTGC TTGAGCGGGA CGCCGCGCTT
ACTTTGGATA AGACGGCCAA GAAGCGCGCC GCCGGCGACG AACTCGCCCT GCGGCGCGAA

      8050       8060       8070       8080       8090       8100
TTCCTCGACG CGGTCGCGGT AGAGCGCTGC CTGTCCAAGC AGCATCAGCG TCACCGGCGT
AAGGAGCTGC GCCAGCGCCA TCTCGCGACG GACAGGTTCG TCGTAGTCGC AGTGGCCGCA

      8110       8120       8130       8140       8150       8160
GGTGGCGACG ACGAAGACGA TGATCAGGAT TTCGTGGAAT ACCCAGCGGC TCTGCAGCAC
CCACCGCTGC TGCTTCTGCT ACTAGTCCTA AAGCACCTTA TGGGTCGCCG AGACGTCGTG

      8170       8180       8190       8200       8210       8220
GGCAAAGCAG ATGATAGAGG CGGCGCAGAT CATCAGTACG CCGCCGCTGG TCGCCAGCGT
CCGTTTCGTC TACTATCTCC GCCGCGTCTA GTAGTCATGC GGCGGCGACC AGCGGTCGCA

      8230       8240       8250       8260       8270       8280
CGGTGCGTGC AGGCGCTCGT AGAAGCTGGT GAACCGGAGC AAGCCGACGG AGCCGATCAG
GCCACGCACG TCCGCGAGCA TCTTCGACCA CTTGGCCTCG TTCGGCTGCC TCGGCTAGTC

      8290       8300       8310       8320       8330       8340
CGCCACTGCG GCGCCGAGGA CGGTGAGCCC GCAGACGAGA ACGGCTGCCC AGACGGGAAG
GCGGTGACGC CGCGGCTCCT GCCACTCGGG CGTCTGCTCT TGCCGACGGG TCTGCCCTTC

      8350       8360       8370       8380       8390       8400
GTCGGTGAGG TGGCTCATTC GATGATCTCC CCGCGCATCA GGAACTTGCC GAAGGCGATC
CAGCCACTCC ACCGAGTAAG CTACTAGAGG GGCGCGTAGT CCTTGAACGG CTTCCGCTAG
```

*FIG. 8N*

```
      8410       8420       8430       8440       8450       8460
GACGAGACGA AGCCGATCAA AGCCACGATC AGGGCGGACT CGAAATAGAG CGAGTTGGCC
CTGCTCTGCT TCGGCTAGTT TCGGTGCTAG TCCCGCCTGA GCTTTATCTC GCTCAACCGG

      8470       8480       8490       8500       8510       8520
GTGCGGATGC CGAAGGTCAA GAGCATCAGC ATGGCGTTGA TATAGAGCGT GTCGAGGCCG
CACGCCTACG GCTTCCAGTT CTCGTAGTCG TACCGCAACT ATATCTCGCA CAGCTCCGGC

      8530       8540       8550       8560       8570       8580
AGGATACGGT CCTGGGCGCG CGGTCCCCTC ACCATGCGAT AGAAGGCAAA AGCCATCGCC
TCCTATGCCA GGACCCGCGC GCCAGGGGAG TGGTACGCTA TCTTCCGTTT TCGGTAGCGG

      8590       8600       8610       8620       8630       8640
AGGCCGAGCA TGATCTGGGC AATCAGGATC GACCAGATGA TTGAAAGTTC CATCATCCGA
TCCGGCTCGT ACTAGACCCG TTAGTCCTAG CTGGTCTACT AACTTTCAAG GTAGTAGGCT

      8650       8660       8670       8680       8690       8700
ATATCTCCTT CAGGGCGGTC TCATAGCGCT TGACCGTATC GAGCCAGATG TCCTCGTTCT
TATAGAGGAA GTCCCGCCAG AGTATCGCGA ACTGGCATAG CTCGGTCTAC AGGAGCAAGA

      8710       8720       8730       8740       8750       8760
CCATGTCGAG CACGTGGAAG AGCAGGGACT TGCGGCCGCG ATCCGGGGAA TTC
GGTACAGCTC GTGCACCTTC TCGTCCCTGA ACGCCGGCGC TAGGCCCCTT AAG
```

FIG. 8O

A = ATG

*: STOP

CS: COMPLEMENTARY STRAND

OPEN READING FRAME 7

A = ATG

*: STOP

CS: COMPLEMENTARY STRAND

OPEN READING FRAME 8

A = ATG

*: STOP

CS: COMPLEMENTARY STRAND

SEQUENCE: 8753-BP FRAGMENT FROM 4150 TO 5150 LENGTH = 1001

OPEN READING FRAME 10

A = ATG

*: STOP

CS: COMPLEMENTARY STRAND cobA GENE (SEQ ID NO: 3) AND COBA PROTEIN (SEQ ID NO: 4)
SEQUENCE OF THE 5396-BP ClaI-HindIII-HindIII-HindIII FRAGMENT
FROM 1141 TO 1980

```
MetIleAspAspLeuPheAlaGlyLeuProAlaLeuGluLysGlySerValTrpLeuValGlyAlaGlyProGly
ATGATCGACGACCTCTTTGCCGGATTGCCGGCGCTCGAAAAAGGTTCGGTCTGGCTGGTCGGCGCCGGCCCCGGC
    1141      1151      1161      1171      1181      1191      1201
AspProGlyLeuLeuThrLeuHisAlaAlaAsnAlaLeuArgGlnAlaAspValIleValHisAspAlaLeuVal
GATCCCGGCCTGTTGACGCTGCATGCGGCCAATGCGCTGCGCCAGGCGGATGTGATCGTGCATGATGCGCTGGTC
    1216      1226      1236      1246      1256      1266      1276
AsnGluAspCysLeuLysLeuAlaArgProGlyAlaValLeuGluPheAlaGlyLysArgGlyGlyLysProSer
AACGAGGATTGCCTGAAGCTCGCGCGGCCGGGCGCCGTGCTGGAGTTTGCGGGCAAGCGTGGCGGCAAGCCGTCG
    1291      1301      1311      1321      1331      1341      1351
ProLysGlnArgAspIleSerLeuArgLeuValGluLeuAlaArgAlaGlyAsnArgValLeuArgLeuLysGly
CCGAAGCAGCGCGACATCTCGCTTCGCCTCGTCGAACTCGCGCGCGCCGGCAACCGGGTGCTGCGCCTCAAAGGC
    1366      1376      1386      1396      1406      1416      1426
GlyAspProPheValPheGlyArgGlyGlyGluGluAlaLeuThrLeuValGluHisGlnValProPheArgIle
GGCGATCCCTTCGTCTTCGGTCGCGGTGGCGAGGAGGCGCTGACGCTGGTCGAACACCAGGTGCCGTTCCGAATC
    1441      1451      1461      1471      1481      1491      1501
ValProGlyIleThrAlaGlyIleGlyGlyLeuAlaTyrAlaGlyIleProValThrHisArgGluValAsnHis
GTGCCCGGCATCACCGCCGGTATCGGCGGGCTTGCCTATGCCGGCATTCCCGTGACCCATCGCGAGGTCAACCAC
    1516      1526      1536      1546      1556      1566      1576
AlaValThrPheLeuThrGlyHisAspSerSerGlyLeuValProAspArgIleAsnTrpGlnGlyIleAlaSer
GCGGTCACTTTCCTGACTGGCCATGATTCCTCCGGCCTGGTGCCGGATCGCATCAACTGGCAGGGCATCGCCAGC
    1591      1601      1611      1621      1631      1641      1651
GlySerProValIleValMetTyrMetAlaMetLysHisIleGlyAlaIleThrAlaAsnLeuIleAlaGlyGly
GGCTCGCCTGTCATCGTCATGTACATGGCGATGAAACATATCGGCGCGATCACCGCCAACCTCATTGCCGGCGGC
    1666      1676      1686      1696      1706      1716      1726
ArgSerProAspGluProValAlaPheValCysAsnAlaAlaThrProGlnGlnAlaValLeuGluThrThrLeu
CGCTCGCCGGACGAACCGGTCGCCTTCGTCTGCAACGCCGCGACGCCGCAGCAGGCGGTGCTGGAAACGACGCTT
    1741      1751      1761      1771      1781      1791      1801
AlaArgAlaGluAlaAspValAlaAlaAlaGlyLeuGluProProAlaIleValValValGlyGluValValArg
GCGCGTGCAGAGGCCGATGTTGCGGCGGCAGGGCTGGAGCCGCCGGCGATCGTCGTCGTCGGCGAGGTGGTGCGG
    1816      1826      1836      1846      1856      1866      1876
LeuArgAlaAlaLeuAspTrpIleGlyAlaLeuAspGlyArgLysLeuAlaAlaAspProPheAlaAsnArgIle
CTGCGCGCAGCGCTCGACTGGATCGGCGCGCTGGACGGGCGCAAGCTTGCCGCCGACCCGTTCGCCAATCGCATT
    1891      1901      1911      1921      1931      1941      1951
                                        LeuArgAsnProAla***
                                        CTCAGGAACCCGGCATGA
    1966      1976      1986      1996      2006      2016      2026
```

FIG. 15A

NAME = COBA

FIRST RESIDUE = 1
LAST RESIDUE = 280

| | | | NUMBER | NO. % | WEIGHT | WEIGHT % |
|---|---|---|---|---|---|---|
| 1 | PHE | F | 8 | 2.86 | 1176.56 | 4.02 |
| 2 | LEU | L | 31 | 11.07 | 3505.48 | 11.99 |
| 3 | ILE | I | 16 | 5.71 | 1809.28 | 6.19 |
| 4 | MET | M | 4 | 1.43 | 524.16 | 1.79 |
| 5 | VAL | V | 27 | 9.64 | 2674.89 | 9.15 |
| 6 | SER | S | 8 | 2.86 | 696.24 | 2.38 |
| 7 | PRO | P | 19 | 6.79 | 1843.95 | 6.31 |
| 8 | THR | T | 10 | 3.57 | 1010.50 | 3.46 |
| 9 | ALA | A | 41 | 14.64 | 2912.64 | 9.96 |
| 10 | TYR | Y | 2 | 0.71 | 326.12 | 1.12 |
| 11 | * | * | 0 | 0.00 | 0.00 | 0.00 |
| 12 | HIS | H | 7 | 2.50 | 959.42 | 3.28 |
| 13 | GLN | Q | 6 | 2.14 | 768.36 | 2.63 |
| 14 | ASN | N | 9 | 3.21 | 1026.36 | 3.51 |
| 15 | LYS | K | 8 | 2.86 | 1024.72 | 3.51 |
| 16 | ASP | D | 15 | 5.36 | 1725.45 | 5.90 |
| 17 | GLU | E | 13 | 4.64 | 1677.52 | 5.74 |
| 18 | CYS | C | 2 | 0.71 | 206.02 | 0.70 |
| 19 | TRP | W | 3 | 1.07 | 558.24 | 1.91 |
| 20 | ARG | R | 19 | 6.79 | 2965.90 | 10.15 |
| 21 | GLY | G | 32 | 11.43 | 1824.64 | 6.24 |
| 22 | - | - | 0 | 0.00 | 0.00 | 0.00 |

RESIDUES = 280
MOLECULAR WEIGHT = 29234.
INDEX OF POLARITY (%) = 34.
ISOELECTRIC POINT = 7.51
OD 260 (1mg/ml) = 0.464 OD 280 (1mg/ml) = 0.652

HYDROPHILICITY PROFILE OF THE COBA PROTEIN
COBA FROM 1 TO 280 cobB GENE (SEQ ID NO: 5) AND COBB PROTEIN (SEQ ID NO: 6)
SEQUENCE OF THE 5396-BP ClaI-HindIII-HindIII-HindIII FRAGMENT
FROM 1980 TO 3281

```
   MetSerGlyLeuLeuIleAlaAlaProAlaSerGlySerGlyLysThrThrValThrLeuGlyLeuMetArgAla
   ATGAGCGGATTGCTGATTGCCGCACCCGCGTCCGGCTCCGGCAAGACGACGGTGACGCTCGGGCTGATGCGCGCC
1980      1990      2000      2010      2020      2030      2040
   LeuLysArgArgGlyValAlaIleAlaProGlyLysAlaGlyProAspTyrIleAspProAlaPheHisAlaAla
   CTGAAGAGGCGCGGCGTGGCGATCGCGCCCGGCAAGGCGGGGCCGGACTATATCGATCCCGCTTTCCACGCGGCA
2055      2065      2075      2085      2095      2105      2115
   AlaThrGlyGluProCysPheAsnTyrAspProTrpAlaMetArgProGluLeuLeuLeuAlaAsnAlaSerHis
   GCGACCGGCGAGCCCTGCTTCAACTACGACCCCTGGGCGATGCGCCCGGAACTGCTGCTTGCCAATGCGTCGCAT
2130      2140      2150      2160      2170      2180      2190
   ValAlaSerGlyGlyArgThrLeuIleValGluAlaMetMetGlyLeuHisAspGlyAlaAlaAspGlySerGly
   GTGGCCTCCGGCGGGCGCACATTGATCGTCGAGGCGATGATGGGACTGCATGACGGTGCTGCCGACGGCTCGGGA
2205      2215      2225      2235      2245      2255      2265
   ThrProAlaAspLeuAlaAlaThrLeuAsnLeuAlaValIleLeuValValAspCysAlaArgMetSerGlnSer
   ACGCCAGCGGACCTCGCCGCGACGCTGAACCTTGCGGTCATTCTGGTGGTCGATTGCGCCCGCATGTCCCAGTCG
2280      2290      2300      2310      2320      2330      2340
   ValAlaAlaLeuValArgGlyTyrAlaAspHisArgAspAspIleArgValValGlyValIleLeuAsnLysVal
   GTTGCCGCCCTCGTGCGCGGCTATGCGGATCATCGCGACGATATCCGGGTGGTTGGCGTCATCCTCAACAAGGTC
2355      2365      2375      2385      2395     2405      2415
   GlySerAspArgHisGluMetMetLeuArgAspAlaLeuGlyLysValArgMetProValPheGlyValLeuArg
   GGCAGCGATCGGCATGAAATGATGCTGCGCGATGCGCTCGGCAAGGTGCGCATGCCTGTCTTCGGCGTGCTCCGG
2430      2440      2450      2460      2470      2480      2490
   GlnAspSerAlaLeuGlnLeuProGluArgHisLeuGlyLeuValGlnAlaGlyGluHisSerAlaLeuGluGly
   CAGGACAGCGCATTGCAACTGCCGGAGCGCCATCTCGGGCTCGTGCAGGCGGGCGAACACTCAGCGCTTGAGGGC
2505      2515      2525      2535      2545      2555      2565
   PheIleGluAlaAlaAlaAlaArgValGluAlaAlaCysAspLeuAspAlaIleArgLeuIleAlaThrIlePhe
   TTCATCGAGGCGGCGGCCGCGCGGGTCGAGGCTGCCTGCGATCTCGACGCCATCCGCCTGATCGCGACGATTTTC
2580      2590      2600      2610      2620      2630      2640
   ProGlnValProAlaAlaAlaAspAlaGluArgLeuArgProLeuGlyGlnArgIleAlaValAlaArgAspIle
   CCGCAGGTGCCCGCGGCGGCCGATGCCGAGCGTTTGCGGCCGCTCGGTCAGCGCATCGCGGTCGCGCGCGATATC
2655      2665      2675      2685      2695      2705      2715
   AlaPheAlaPheCysTyrGluHisLeuLeuTyrGlyTrpArgGlnGlyGlyAlaGluIleSerPhePheSerPro
   GCCTTTGCCTTCTGCTACGAGCACCTGCTTTACGGCTGGCGGCAAGGCGGCGCGGAGATTTCCTTCTTCTCGCCG
2730      2740      2750      2760      2770      2780      2790
   LeuAlaAspGluGlyProAspAlaAlaAlaAspAlaValTyrLeuProGlyGlyTyrProGluLeuHisAlaGly
   CTCGCCGACGAGGGGCCGGATGCGGCAGCCGATGCCGTCTATCTTCCGGGGGGTTATCCGGAGCTGCATGCGGGG
2805      2815      2825      2835      2845      2855      2865
```

FIG. 15C

```
    GlnLeuSerAlaAlaAlaArgPheArgSerGlyMetHisSerAlaAlaGluArgGlyAlaArgIlePheGlyGlu
    CAGCTGAGCGCCGCCGCCCGATTCCGTTCCGGCATGCATTCCGCGGCGGAACGCGGCGCCCGCATCTTCGGCGAG
2880      2890      2900      2910      2920      2930      2940
    CysGlyGlyTyrMetValLeuGlyGluGlyLeuValAlaAlaAspGlyThrArgTyrAspMetLeuGlyLeuLeu
    TGCGGCGGCTATATGGTGCTCGGCGAAGGGCTTGTCGCTGCCGATGGCACACGCTACGACATGCTCGGCCTGCTG
2955      2965      2975      2985      2995      3005      3015
    ProLeuValThrSerPheAlaGluArgArgArgHisLeuGlyTyrArgArgValValProValAspAsnAlaPhe
    CCGCTCGTAACCAGTTTTGCCGAGCGCAGGCGGCACCTCGGCTATCGCCGCGTCGTGCCTGTCGACAACGCCTTC
3030      3040      3050      3060      3070      3080      3090
    PheAspGlyProMetThrAlaHisGluPheHisTyrAlaThrIleValAlaGluGlyAlaAlaAspArgLeuPhe
    TTCGATGGACCCATGACGGCGCACGAATTCCACTATGCGACCATCGTCGCCGAAGGGGCGGCCGATCGGCTGTTT
3105      3115      3125      3135      3145      3155      3165
    AlaValSerAspAlaAlaGlyGluAspLeuGlyGlnAlaGlyLeuArgArgGlyProValAlaGlySerPheMet
    GCGGTCAGCGACGCCGCCGGCGAGGATCTCGGCCAGGCGGGCCTCCGGCGCGGCCCTGTCGCCGGTTCCTTCATG
3180      3190      3200      3210      3220      3230      3240
    HisLeuIleAspValAlaGlyAlaAla***
    CATCTGATCGACGTCGCAGGTGCTGCATGA
3255      3265      3275      3285      3295      3305      3315
```

FIG. 15D

NAME = COBB FIRST RESIDUE = 1
LAST RESIDUE = 434

| | | | NUMBER | NO. % | WEIGHT | WEIGHT % |
|---|---|---|---|---|---|---|
| 1 | PHE | F | 17 | 3.92 | 2500.19 | 5.47 |
| 2 | LEU | L | 45 | 10.37 | 5088.60 | 11.14 |
| 3 | ILE | I | 17 | 3.92 | 1922.36 | 4.21 |
| 4 | MET | M | 14 | 3.23 | 1834.56 | 4.02 |
| 5 | VAL | V | 31 | 7.14 | 3071.17 | 6.72 |
| 6 | SER | S | 19 | 4.38 | 1653.57 | 3.62 |
| 7 | PRO | P | 21 | 4.84 | 2038.05 | 4.46 |
| 8 | THR | T | 12 | 2.76 | 1212.60 | 2.65 |
| 9 | ALA | A | 76 | 17.51 | 5399.04 | 11.82 |
| 10 | TYR | Y | 11 | 2.53 | 1793.66 | 3.93 |
| 11 | * | * | 0 | 0.00 | 0.00 | 0.00 |
| 12 | HIS | H | 14 | 3.23 | 1918.84 | 4.20 |
| 13 | GLN | Q | 9 | 2.07 | 1152.54 | 2.52 |
| 14 | ASN | N | 5 | 1.15 | 570.20 | 1.25 |
| 15 | LYS | K | 5 | 1.15 | 640.45 | 1.40 |
| 16 | ASP | D | 28 | 6.45 | 3220.84 | 7.05 |
| 17 | GLU | E | 21 | 4.84 | 2709.84 | 5.93 |
| 18 | CYS | C | 5 | 1.15 | 515.05 | 1.13 |
| 19 | TRP | W | 2 | 0.46 | 372.16 | 0.81 |
| 20 | ARG | R | 34 | 7.83 | 5307.40 | 11.62 |
| 21 | GLY | G | 48 | 11.06 | 2736.96 | 5.99 |
| 22 | - | - | 0 | 0.00 | 0.00 | 0.00 |

RESIDUES 434
MOLECULAR WEIGHT = 45676.
INDEX OF POLARITY (%) = 34.
ISOELECTRIC POINT = 6.47
OD 260 (1mg/ml) = 0.351 OD 280 (1mg/ml) = 0.529

HYDROPHILICITY PROFILE OF THE COBB PROTEIN
COBB FROM 1 TO 434 cobC GENE (SEQ ID NO: 7) AND COBC PROTEIN (SEQ ID NO: 8)
SEQUENCE OF THE 5396-BP ClaI-HindIII-HindIII-HindIII FRAGMENT
FROM 3281 TO 4279

```
    MetSerAlaProIleValHisGlyGlyGlyIleThrGluAlaAlaAlaArgTyrGlyGlyArgProGluAspTrp
    ATGAGCGCACCGATCGTTCATGGTGGCGGCATCACCGAGGCCGCAGCGCGCTATGGCGGCCGGCCTGAAGACTGG
3281      3291      3301      3311      3321      3331      3341
    LeuAspLeuSerThrGlyIleAsnProCysProValAlaLeuProAlaValProGluArgAlaTrpHisArgLeu
    CTCGATCTGTCGACCGGCATCAATCCATGCCCCGTCGCCTTGCCCGCGGTCCCTGAGCGCGCCTGGCACCGGCTG
3356      3366      3376      3386      3396      3406      3416
    ProAspArgGlnThrValAspAspAlaArgSerAlaAlaAlaAspTyrTyrArgThrAsnGlyValLeuProLeu
    CCGGATCGGCAGACGGTAGATGATGCGCGGAGCGCCGCCGCCGACTACTACCGCACCAACGGCGTGCTGCCTTTG
3431      3441      3451      3461      3471      3481      3491
    ProValProGlyThrGlnSerValIleGlnLeuLeuProArgLeuAlaProAlaAsnArgHisValAlaIlePhe
    CCGGTGCCGGGCACCCAGTCGGTGATCCAGCTCCTGCCACGTCTTGCTCCGGCCAACAGGCACGTCGCGATTTTC
3506      3516      3526      3536      3546      3556      3566
    GlyProThrTyrGlyGluTyrAlaArgValLeuGluAlaAlaGlyPheAlaValAspArgValAlaAspAlaAsp
    GGGCCGACCTATGGCGAGTATGCCCGCGTGCTTGAAGCGGCCGGCTTTGCTGTCGATCGCGTCGCGGATGCCGAC
3581      3591      3601      3611      3621      3631      3641
    AlaLeuThrAlaGluHisGlyLeuValIleValValAsnProAsnAsnProThrGlyArgAlaLeuAlaProAla
    GCGCTCACGGCCGAACATGGGCTTGTCATCGTCGTCAACCCCAACAACCCGACCGGCCGCGCCTTGGCGCCGGCG
3656      3666      3676      3686      3696      3706      3716
    GluLeuLeuAlaIleAlaAlaArgGlnLysAlaSerGlyGlyLeuLeuLeuValAspGluAlaPheGlyAspLeu
    GAGCTTCTGGCGATCGCCGCAAGGCAGAAGGCGAGCGGCGGACTGCTGCTGGTCGATGAGGCCTTCGGCGATCTT
3731      3741      3751      3761      3771      3781      3791
    GluProGlnLeuSerValAlaGlyHisAlaSerGlyGlnGlyAsnLeuIleValPheArgSerPheGlyLysPhe
    GAGCCGCAACTGAGTGTCGCTGGTCACGCGTCAGGGCAAGGCAACCTCATCGTCTTCCGCTCCTTCGGCAAGTTC
3806      3816      3826      3836      3846      3856      3866
    PheGlyLeuAlaGlyLeuArgLeuGlyPheValValAlaThrGluProValLeuAlaSerPheAlaAspTrpLeu
    TTCGGCCTTGCGGGCCTGCGCCTCGGCTTCGTCGTTGCGACCGAGCCAGTGCTTGCATCCTTTGCCGATTGGCTC
3881      3891      3901      3911      3921      3931      3941
    GlyProTrpAlaValSerGlyProAlaLeuThrIleSerLysAlaLeuMetGlnGlyAspThrLysAlaIleAla
    GGTCCCTGGGCTGTCTCCGGCCCGGCGTTGACGATCTCGAAAGCGCTGATGCAGGGCGATACGAAGGCGATCGCG
3956      3966      3976      3986      3996      4006      4016
    AlaGlyIleLeuGluArgArgAlaGlyLeuAspAlaAlaLeuAspGlyAlaGlyLeuAsnArgIleGlyGlyThr
    GCGGGCATCCTCGAGCGTCGCGCCGGCCTCGATGCGGCTCTCGATGGGGCAGGGCTCAACCGTATCGGCGGCACG
4031      4041      4051      4061      4071      4081      4091
    GlyLeuPheValLeuValGluHisProArgAlaAlaLeuLeuGlnGluArgLeuCysGluAlaHisIleLeuThr
    GGGCTATTCGTGCTGGTCGAGCATCCCAGGGCAGCTCTGCTGCAGGAGCGGCTCTGCGAGGCCCATATTCTCACG
4106      4116      4126      4136      4146      4156      4166
    ArgLysPheAspTyrAlaProThrTrpLeuArgValGlyLeuAlaProAspAlaAlaGlyAspArgArgLeuAla
    CGCAAGTTCGACTATGCCCCGACCTGGCTCAGGGTCGGTCTTGCGCCTGACGCGGCTGGTGACCGACGGCTGGCG
4181      4191      4201      4211      4221      4231      4241
    AspAlaLeuAlaArgMetGluLeu***
    GACGCGCTTGCCCGCATGGAGCTCTGA
4256      4266      4276      4286      4296      4306      4316
```

FIG. 15F

NAME = COBC

FIRST RESIDUE = 1
LAST RESIDUE = 333

| | | | NUMBER | NO. % | WEIGHT | WEIGHT % |
|---|---|---|---|---|---|---|
| 1 | PHE | F | 11 | 3.30 | 1617.77 | 4.62 |
| 2 | LEU | L | 43 | 12.91 | 4862.44 | 13.90 |
| 3 | ILE | I | 13 | 3.90 | 1470.04 | 4.20 |
| 4 | MET | M | 3 | 0.90 | 393.12 | 1.12 |
| 5 | VAL | V | 24 | 7.21 | 2377.68 | 6.79 |
| 6 | SER | S | 11 | 3.30 | 957.33 | 2.74 |
| 7 | PRO | P | 23 | 6.91 | 2232.15 | 6.38 |
| 8 | THR | T | 14 | 4.20 | 1414.70 | 4.04 |
| 9 | ALA | A | 56 | 16.82 | 3978.24 | 11.37 |
| 10 | TYR | Y | 6 | 1.80 | 978.36 | 2.80 |
| 11 | * | * | 0 | 0.00 | 0.00 | 0.00 |
| 12 | HIS | H | 7 | 2.10 | 959.42 | 2.74 |
| 13 | GLN | Q | 8 | 2.40 | 1024.48 | 2.93 |
| 14 | ASN | N | 8 | 2.40 | 912.32 | 2.61 |
| 15 | LYS | K | 5 | 1.50 | 640.45 | 1.83 |
| 16 | ASP | D | 19 | 5.71 | 2185.57 | 6.25 |
| 17 | GLU | E | 15 | 4.50 | 1935.60 | 5.53 |
| 18 | CYS | C | 2 | 0.60 | 206.02 | 0.59 |
| 19 | TRP | W | 5 | 1.50 | 930.40 | 2.66 |
| 20 | ARG | R | 25 | 7.51 | 3902.50 | 11.15 |
| 21 | GLY | G | 35 | 10.51 | 1995.70 | 5.70 |
| 22 | - | - | 0 | 0.00 | 0.00 | 0.00 |

RESIDUES = 333
MOLECULAR WEIGHT = 34992.
INDEX OF POLARITY (%) = 34.
ISOELECTRIC POINT = 6.72
OD 260 (1mg/ml) = 0.670 OD 280 (1mg/ml) = 0.998

HYDROPHILICITY PROFILE OF THE COBC PROTEIN
FROM 1 TO 333 cobD GENE (SEQ ID NO: 9) AND COBD PROTEIN (SEQ ID NO: 10)
SEQUENCE OF THE 5396-BP ClaI-HindIII-HindIII-HindIII FRAGMENT
FROM 4284 TO 5252

```
    MetSerGluThrIleLeuLeuIleLeuAlaLeuAlaLeuValIleAspArgValValGlyAspProAspTrpLeu
    GTGTCGGAGACGATCCTGCTCATTCTCGCGCTGGCGCTGGTGATCGACCGCGTTGTCGGCGATCCGGACTGGCTC
4284      4294      4304      4314      4324      4334      4344
    TrpAlaArgValProHisProValValPhePheGlyLysAlaIleGlyPhePheAspAlaArgLeuAsnArgGlu
    TGGGCGCGCGTGCCGCATCCGGTCGTGTTTTTCGGCAAGGCCATCGGCTTTTTCGACGCGCGGCTGAACCGGGAG
4359      4369      4379      4389      4399      4409      4419
    AspLeuGluAspSerAlaArgLysPheArgGlyValValAlaIleLeuLeuLeuLeuGlyIleSerAlaTrpPhe
    GACCTCGAGGATAGCGCGCGCAAATTTCGTGGCGTCGTCGCGATCCTTTTGTTGCTTGGCATCAGCGCCTGGTTC
4434      4444      4454      4464      4474      4484      4494
    GlyHisLeuLeuHisArgLeuPheAlaValLeuGlyProLeuGlyPheLeuLeuGluAlaValLeuValAlaVal
    GGCCATCTGCTGCATCGCCTGTTCGCCGTCCTCGGACCGCTCGGCTTTCTGCTCGAGGCGGTTCTGGTCGCGGTC
4509      4519      4529      4539      4549      4559      4569
    PheLeuAlaGlnLysSerLeuAlaAspHisValArgArgValAlaGlyGlyLeuArgGlnGlyGlyLeuGluGly
    TTCCTGGCACAGAAGAGCCTCGCCGATCACGTGCGTCGCGTGGCCGGGGGCTTGCGACAGGGCGGGCTGGAAGGC
4584      4594      4604      4614      4624      4634      4644
    GlyArgAlaAlaValSerMetIleValGlyArgAspProLysThrLeuAspGluProAlaValCysArgAlaAla
    GGGCGTGCCGCCGTGTCGATGATCGTTGGTCGCGATCCAAAGACGCTCGACGAGCCGGCGGTCTGCCGTGCCGCG
4659      4669      4679      4689      4699      4709      4719
    IleGluSerLeuAlaGluAsnPheSerAspGlyValValAlaProAlaPheTrpTyrAlaValAlaGlyLeuPro
    ATCGAAAGCCTTGCCGAGAATTTCTCCGACGGCGTCGTGGCGCCGGCCTTCTGGTACGCGGTTGCCGGCCTGCCG
4734      4744      4754      4764      4774      4784      4794
    GlyLeuLeuAlaTyrLysMetLeuAsnThrAlaAspSerMetIleGlyHisLysSerProLysTyrLeuHisPhe
    GGGCTTCTTGCCTACAAGATGCTGAACACCGCCGATTCGATGATCGGCCACAAGTCGCCGAAATATCTGCACTTC
4809      4819      4829      4839      4849      4859      4869
    GlyTrpAlaSerAlaArgLeuAspAspLeuAlaAsnLeuProAlaAlaArgLeuSerIleLeuLeuIleSerAla
    GGCTGGGCCTCGGCCCGACTCGACGATCTCGCCAACCTGCCGGCAGCGAGGCTCTCGATCCTTTTGATCTCAGCC
4884      4894      4904      4914      4924      4934      4944
    GlyAlaLeuIleHisArgGlyAlaSerAlaAlaLysAspAlaLeuThrValAlaLeuArgAspHisGlyLeuHis
    GGTGCGCTGATCCATCGTGGCGCCAGCGCCGCCAAGGATGCGCTGACCGTGGCCCTTCGCGACCATGGCCTGCAC
4959      4969      4979      4989      4999      5009      5019
    ArgSerProAsnSerGlyTrpProGluAlaAlaMetAlaGlyAlaLeuAspLeuGlnLeuAlaGlyProArgIle
    CGCTCGCCGAACTCCGGCTGGCCGGAAGCGGCCATGGCCGGCGCGCTCGATCTGCAGCTTGCCGGTCCGCGGATC
5034      5044      5054      5064      5074      5084      5094
    TyrGlyGlyValLysValSerGluProMetIleAsnGlyProGlyArgAlaValAlaThrSerGluAspIleAsp
    TATGGCGGCGTCAAGGTCAGCGAACCTATGATCAACGGTCCGGGCCGAGCGGTTGCAACAAGCGAAGACATCGAC
5109      5119      5129      5139      5149      5159      5169
    AlaGlyIleAlaValPheTyrGlyAlaCysThrValMetAlaGlyPheValLeuAlaIleAlaMetIle***
    GCCGGTATTGCTGTATTTTATGGCGCCTGTACGGTCATGGCCGGGTTTGTTCTTGCAATCGCAATGATTTGA
5184      5194      5204      5214      5224      5234      5244
```

FIG. 15H

NAME = COBD

FIRST RESIDUE = 1
LAST RESIDUE = 323

| | | | NUMBER | NO. % | WEIGHT | WEIGHT % |
|---|---|---|---|---|---|---|
| 1 | PHE | F | 14 | 4.33 | 2058.98 | 6.02 |
| 2 | LEU | L | 45 | 13.93 | 5088.60 | 14.89 |
| 3 | ILE | I | 18 | 5.57 | 2035.44 | 5.96 |
| 4 | MET | M | 8 | 2.48 | 1048.32 | 3.07 |
| 5 | VAL | V | 27 | 8.36 | 2674.89 | 7.83 |
| 6 | SER | S | 17 | 5.26 | 1479.51 | 4.33 |
| 7 | PRO | P | 15 | 4.64 | 1455.75 | 4.26 |
| 8 | THR | T | 6 | 1.86 | 606.30 | 1.77 |
| 9 | ALA | A | 51 | 15.79 | 3623.04 | 10.60 |
| 10 | TYR | Y | 5 | 1.55 | 815.30 | 2.39 |
| 11 | * | * | 0 | 0.00 | 0.00 | 0.00 |
| 12 | HIS | H | 9 | 2.79 | 1233.54 | 3.61 |
| 13 | GLN | Q | 3 | 0.93 | 384.18 | 1.12 |
| 14 | ASN | N | 6 | 1.86 | 684.24 | 2.00 |
| 15 | LYS | K | 9 | 2.79 | 1152.81 | 3.37 |
| 16 | ASP | D | 18 | 5.57 | 2070.54 | 6.06 |
| 17 | GLU | E | 11 | 3.41 | 1419.44 | 4.15 |
| 18 | CYS | C | 2 | 0.62 | 206.02 | 0.60 |
| 19 | TRP | W | 6 | 1.86 | 1116.48 | 3.27 |
| 20 | ARG | R | 20 | 6.19 | 3122.00 | 9.14 |
| 21 | GLY | G | 33 | 10.22 | 1881.66 | 5.51 |
| 22 | - | - | 0 | 0.00 | 0.00 | 0.00 |

RESIDUES = 323
MOLECULAR WEIGHT = 34175.
INDEX OF POLARITY (%) = 31.
ISOELECTRIC POINT = 8.00
OD 260 (1mg/ml) = 0.789 OD 280 (1mg/ml) = 1.150

HYDROPHILICITY PROFILE OF THE COBD PROTEIN cobE GENE (SEQ ID NO: 11) AND COBE PROTEIN (SEQ ID NO: 12)
SEQUENCE OF THE 5396-BP ClaI-HindIII-HindIII-HindIII FRAGMENT
FROM 549 TO 1010

```
 MetProSerGlyGlnHisSerAlaGlnThrThrLysAlaGlyAlaGlyLeuValLeuGlyLeuGlyCysGluArg
 ATGCCATCGGGCCAACACTCTGCACAGACGACGAAAGCAGGAGCCGGGCTGGTGCTCGGGCTCGGCTGCGAGCGT
549       559       569       579       589       599       609
 ArgThrProAlaGluGluValIleAlaLeuAlaGluArgAlaLeuAlaAspAlaGlyValAlaProGlyAspLeu
 CGCACGCCGGCCGAAGAGGTGATCGCCCTTGCCGAGCGTGCGCTTGCCGATGCCGGTGTTGCGCCCGGCGATCTG
624       634       644       654       664       674       684
 ArgLeuValAlaSerLeuAspAlaArgAlaGluGluProAlaIleLeuAlaAlaAlaGlnHisPheAlaValPro
 CGGCTGGTCGCCTCGCTCGATGCTCGCGCCGAGGAGCCGGCGATCCTGGCGGCCGCTCAGCATTTCGCGGTTCCG
699       709       719       729       739       749       759
 AlaAlaPheTyrAspAlaAlaThrLeuGluAlaGluAlaSerArgLeuAlaAsnProSerGluIleValPheAla
 GCCGCGTTCTACGATGCCGCCACGCTCGAAGCCGAAGCTTCCCGGCTCGCCAACCCGTCCGAGATCGTCTTTGCC
774       784       794       804       814       824       834
 TyrThrGlyCysHisGlyValAlaGluGlyAlaAlaLeuValGlyAlaGlyArgGluAlaValLeuIleValGln
 TACACGGGTTGTCATGGCGTTGCCGAGGGTGCAGCGCTCGTCGGCGCCGGTCGCGAAGCCGTGCTGATTGTGCAG
849       859       869       879       889       899       909
 LysIleValSerAlaHisAlaThrAlaAlaLeuAlaGlyProAlaThrLeuArgAlaGluLysArgIleGlnAla
 AAGATCGTCTCCGCCCATGCGACGGCCGCACTTGCCGGGCCGGCGACCTTGCGCGCCGAAAAGCGCATCCAGGCG
924       934       944       954       964       974       984
 AlaGluAlaVal***
 GCGGAGGCTGTCTGA
999      1009      1019      1029      1039      1049      1059
```

FIG. 15J

NAME = COBE

FIRST RESIDUE = 1
LAST RESIDUE = 154

| | | | NUMBER | NO. % | WEIGHT | WEIGHT % |
|---|---|---|---|---|---|---|
| 1 | PHE | F | 3 | 1.95 | 441.21 | 2.85 |
| 2 | LEU | L | 15 | 9.74 | 1696.20 | 10.96 |
| 3 | ILE | I | 6 | 3.90 | 678.48 | 4.38 |
| 4 | MET | M | 1 | 0.65 | 131.04 | 0.85 |
| 5 | VAL | V | 12 | 7.79 | 1188.84 | 7.68 |
| 6 | SER | S | 6 | 3.90 | 522.18 | 3.37 |
| 7 | PRO | P | 7 | 4.55 | 679.35 | 4.39 |
| 8 | THR | T | 7 | 4.55 | 707.35 | 4.57 |
| 9 | ALA | A | 41 | 26.62 | 2912.64 | 18.82 |
| 10 | TYR | Y | 2 | 1.30 | 326.12 | 2.11 |
| 11 | * | * | 0 | 0.00 | 0.00 | 0.00 |
| 12 | HIS | H | 4 | 2.60 | 548.24 | 3.54 |
| 13 | GLN | Q | 5 | 3.25 | 640.30 | 4.14 |
| 14 | ASN | N | 1 | 0.65 | 114.04 | 0.74 |
| 15 | LYS | K | 3 | 1.95 | 384.27 | 2.48 |
| 16 | ASP | D | 4 | 2.60 | 460.12 | 2.97 |
| 17 | GLU | E | 13 | 8.44 | 1677.52 | 10.84 |
| 18 | CYS | C | 2 | 1.30 | 206.02 | 1.33 |
| 19 | TRP | W | 0 | 0.00 | 0.00 | 0.00 |
| 20 | ARG | R | 9 | 5.84 | 1404.90 | 9.08 |
| 21 | GLY | G | 13 | 8.44 | 741.26 | 4.79 |
| 22 | - | - | 0 | 0.00 | 0.00 | 0.00 |

RESIDUES = 154
MOLECULAR WEIGHT = 15478.
INDEX OF POLARITY (%) = 34.
ISOELECTRIC POINT = 5.61
OD 260 (1mg/ml) = 0.113 OD 280 (1mg/ml) = 0.154

HYDROPHILICITY PROFILE OF THE COBE PROTEIN
FROM 1 TO 154 cobF GENE (SEQ ID NO: 13) AND COBF PROTEIN (SEQ ID NO: 14)
SEQUENCE OF THE 8753-BP FRAGMENT FROM 736 TO 1521

```
 MetAlaGluAlaGlyMetArgLysIleLeuIleIleGlyIleGlySerGlyAsnProGluHisMetThrValGln
 ATGGCGGAGGCGGGCATGCGCAAAATTCTGATCATCGGCATCGGTTCGGGCAATCCCGAACACATGACCGTGCAG
736       746       756       766       776       786       796
 AlaIleAsnAlaLeuAsnCysAlaAspValLeuPheIleProThrLysGlyAlaLysLysThrGluLeuAlaGlu
 GCGATCAACGCGCTGAACTGCGCCGACGTGCTCTTTATCCCGACCAAGGGAGCGAAGAAGACCGAGCTTGCCGAA
811       821       831       841       851       861       871
 ValArgArgAspIleCysAlaArgTyrValThrArgLysAspSerArgThrValGluPheAlaValProValArg
 GTGCGCCGCGACATCTGCGCCCGCTACGTCACGCGCAAGGACAGCCGCACCGTCGAGTTCGCGGTGCCCGTGCGG
886       896       906       916       926       936       946
 ArgThrGluGlyValSerTyrAspGlySerValAspAspTrpHisAlaGlnIleAlaGlyIleTyrGluAlaLeu
 CGCACCGAAGGCGTCAGCTATGACGGCAGCGTCGATGACTGGCACGCCCAGATCGCTGGGATTTACGAAGCGCTT
961       971       981       991       1001      1011      1021
 LeuSerLysGluLeuGlyGluGluGlyThrGlyAlaPheLeuValTrpGlyAspProMetLeuTyrAspSerThr
 CTATCGAAGGAGTTGGGCGAAGAGGGAACTGGCGCGTTTCTCGTCTGGGGCGACCCGATGCTCTATGACAGCACC
1036      1046      1056      1066      1076      1086      1096
 IleArgIleValGluArgValLysAlaArgGlyGluValAlaPheAlaTyrAspValIleProGlyIleThrSer
 ATTCGCATCGTCGAGCGGGTCAAGGCACGCGGTGAGGTCGCCTTCGCCTACGACGTCATTCCCGGGATCACCAGT
1111      1121      1131      1141      1151      1161      1171
 LeuGlnAlaLeuCysAlaSerHisArgIleProLeuAsnLeuValGlyLysProValGluIleThrThrGlyArg
 CTGCAGGCGCTTTGCGCCAGCCACCGCATTCCGCTGAACCTCGTCGGCAAGCCGGTGGAGATCACCACGGGGCGT
1186      1196      1206      1216      1226      1236      1246
 ArgLeuHisGluSerPheProGluLysSerGlnThrSerValValMetLeuAspGlyGluGlnAlaPheGlnArg
 CGGCTGCACGAAAGCTTTCCCGAGAAGAGCCAGACCTCGGTCGTCATGCTCGATGGCGAACAGGCGTTTCAGCGG
1261      1271      1281      1291      1301      1311      1321
 ValGluAspProGluAlaGluIleTyrTrpGlyAlaTyrLeuGlyThrArgAspGluIleValIleSerGlyArg
 GTCGAGGACCCGGAGGCGGAGATCTATTGGGGCGCCTATCTCGGCACGCGGGATGAGATCGTCATTTCCGGCCGC
1336      1346      1356      1366      1376      1386      1396
 ValAlaGluValLysAspArgIleLeuGluThrArgAlaAlaAlaArgAlaLysMetGlyTrpIleMetAspIle
 GTGGCTGAGGTGAAGGACCGGATCCTTGAAACGCGGGCGGCGGCGCGCGCGAAGATGGGATGGATCATGGACATC
1411      1421      1431      1441      1451      1461      1471
 TyrLeuLeuArgLysGlyAlaAspPheAspGlu***
 TATCTCCTGCGCAAGGGCGCCGACTTCGACGAGTGA
1486      1496      1506      1516
```

FIG. 16A

COBF PROTEIN

FIRST RESIDUE = 1
LAST RESIDUE = 261

| | | | NUMBER | NO. % | WEIGHT | WEIGHT % |
|---|---|---|---|---|---|---|
| 1 | PHE | F | 7 | 2.68 | 1029.49 | 3.56 |
| 2 | LEU | L | 19 | 7.28 | 2148.52 | 7.43 |
| 3 | ILE | I | 21 | 8.05 | 2374.68 | 8.21 |
| 4 | MET | M | 7 | 2.68 | 917.28 | 3.17 |
| 5 | VAL | V | 22 | 8.43 | 2179.54 | 7.53 |
| 6 | SER | S | 12 | 4.60 | 1044.36 | 3.61 |
| 7 | PRO | P | 9 | 3.45 | 873.45 | 3.02 |
| 8 | THR | T | 14 | 5.36 | 1414.70 | 4.89 |
| 9 | ALA | A | 27 | 10.34 | 1918.08 | 6.63 |
| 10 | TYR | Y | 8 | 3.07 | 1304.48 | 4.51 |
| 11 | * | * | 0 | 0.00 | 0.00 | 0.00 |
| 12 | HIS | H | 4 | 1.53 | 548.24 | 1.90 |
| 13 | GLN | Q | 6 | 2.30 | 768.36 | 2.66 |
| 14 | ASN | N | 4 | 1.53 | 456.16 | 1.58 |
| 15 | LYS | K | 12 | 4.60 | 1537.08 | 5.31 |
| 16 | ASP | D | 16 | 6.13 | 1840.48 | 6.36 |
| 17 | GLU | E | 23 | 8.81 | 2967.92 | 10.26 |
| 18 | CYS | C | 3 | 1.15 | 309.03 | 1.07 |
| 19 | TRP | W | 4 | 1.53 | 744.32 | 2.57 |
| 20 | ARG | R | 21 | 8.05 | 3278.10 | 11.33 |
| 21 | GLY | G | 22 | 8.43 | 1254.44 | 4.34 |

RESIDUES = 261
MOLECULAR WEIGHT = 28927.
INDEX OF POLARITY (%) = 43.
ISOELECTRIC POINT = 5.70
OD 260 (1mg/ml) = 0.705 OD 280 (1mg/ml) = 1.097 cobG GENE (SEQ ID NO: 15) AND COBG PROTEIN (SEQ ID NO: 16)
SEQUENCE OF THE 8753-BP FRAGMENT FROM 1620 TO 2999

```
    MetThrAspLeuMetThrSerCysAlaLeuProLeuThrGlyAspAlaGlyThrValAlaSerMetArgArgGly
    ATGACGGATTTGATGACCAGCTGCGCCCTTCCATTGACCGGAGATGCCGGCACCGTCGCTTCGATGCGCCGCGGC
1620      1630      1640      1650      1660      1670      1680
    AlaCysProSerLeuAlaGluProMetGlnThrGlyAspGlyLeuLeuValArgValArgProThrAspAspSer
    GCCTGCCCGTCCTTGGCAGAGCCGATGCAGACCGGCGACGGCCTGCTCGTGAGGGTGAGGCCAACGGATGACAGC
1695      1705      1715      1725      1735      1745      1755
    LeuThrLeuProLysValIleAlaLeuAlaThrAlaAlaGluArgPheGlyAsnGlyIleIleGluIleThrAla
    CTGACGCTGCCGAAGGTCATTGCCCTTGCCACGGCTGCCGAGCGCTTCGGCAATGGCATCATCGAGATTACCGCG
1770      1780      1790      1800      1810      1820      1830
    ArgGlyAsnLeuGlnLeuArgGlyLeuSerAlaAlaSerValProArgLeuAlaGlnAlaIleGlyAspAlaGlu
    CGCGGAAACCTGCAGCTTCGCGGCCTGAGCGCGGCTTCGGTGCCAAGGCTGGCGCAGGCGATCGGCGATGCGGAG
1845      1855      1865      1875      1885      1895      1905
    IleAlaIleAlaGluGlyLeuAlaIleGluValProProLeuAlaGlyIleAspProAspGluIleAlaAspPro
    ATCGCCATTGCCGAGGGGCTCGCGATCGAGGTGCCGCCCCTGGCCGGCATCGACCCGGACGAGATCGCCGATCCG
1920      1930      1940      1950      1960      1970      1980
    ArgProIleAlaThrGluLeuArgGluAlaLeuAspValArgGlnValProLeuLysLeuAlaProLysLeuSer
    CGGCCGATTGCCACTGAGCTTCGTGAAGCGTTGGATGTGCGCCAGGTGCCGTTGAAGCTTGCACCCAAATTATCC
1995      2005      2015      2025      2035      2045      2055
    ValValIleAspSerGlyGlyArgPheGlyLeuGlyAlaValValAlaAspIleArgLeuGlnAlaValSerThr
    GTCGTCATCGATAGCGGTGGCCGGTTTGGTCTCGGCGCTGTCGTCGCCGACATTCGCCTTCAGGCGGTTTCGACT
2070      2080      2090      2100      2110      2120      2130
    ValAlaGlyValAlaTrpValLeuSerLeuGlyGlyThrSerThrLysAlaSerSerValGlyThrLeuAlaGly
    GTCGCGGGGGTGGCCTGGGTGCTGTCGCTTGGCGGCACGTCAACGAAGGCATCGAGCGTCGGGACGTTGGCCGGC
2145      2155      2165      2175      2185      2195      2205
    AsnAlaValValProAlaLeuIleThrIleLeuGluLysLeuAlaSerLeuGlyThrThrMetArgGlyArgAsp
    AACGCGGTCGTGCCGGCCCTGATCACCATTCTCGAGAAACTGGCGAGCCTGGGCACGACGATGCGCGGGCGCGAT
2220      2230      2240      2250      2260      2270      2280
    LeuAspProSerGluIleArgAlaLeuCysArgCysGluThrSerSerGluArgProAlaAlaProArgSerAla
    CTGGACCCGTCGGAAATCCGCGCGCTCTGTCGCTGTGAGACATCGTCCGAACGCCCGGCCGCTCCGCGTTCGGCC
2295      2305      2315      2325      2335      2345      2355
    AlaIleProGlyIleHisAlaLeuGlyAsnAlaAspThrValLeuGlyLeuGlyLeuAlaPheAlaGlnValGlu
    GCAATACCCGGCATTCATGCGCTGGGTAACGCCGACACCGTTCTCGGCCTCGGTCTGGCCTTTGCTCAGGTGGAG
2370      2380      2390      2400      2410      2420      2430
    AlaAlaAlaLeuAlaSerTyrLeuHisGlnValGlnAlaLeuGlyAlaAsnAlaIleArgLeuAlaProGlyHis
    GCCGCCGCGCTGGCATCCTACCTGCATCAGGTCCAGGCGCTTGGCGCCAATGCGATCCGGCTTGCGCCCGGGCAC
2445      2455      2465      2475      2485      2495      2505
```

*FIG. 16C*

```
    AlaPhePheValLeuGlyLeuCysProGluThrAlaAlaValAlaGlnSerLeuAlaAlaSerHisGlyPheArg
    GCCTTCTTCGTCCTCGGCCTTTGCCCCGAGACCGCGGCTGTGGCGCAGAGCCTGGCAGCGTCACACGGTTTTCGC
2520      2530      2540      2550      2560      2570      2580
    IleAlaGluGlnAspProArgAsnAlaIleAlaThrCysAlaGlySerLysGlyCysAlaSerAlaTrpMetGlu
    ATTGCCGAGCAGGATCCGCGCAATGCGATCGCCACCTGCGCCGGCAGCAAGGGTTGCGCCTCGGCGTGGATGGAA
2595      2605      2615      2625      2635      2645      2655
    ThrLysGlyMetAlaGluArgLeuValGluThrAlaProGluLeuLeuAspGlySerLeuThrValHisLeuSer
    ACCAAGGGCATGGCCGAGCGCCTCGTCGAGACGGCGCCGGAATTGCTCGACGGGTCGCTCACCGTGCATCTCTCC
2670      2680      2690      2700      2710      2720      2730
    GlyCysAlaLysGlyCysAlaArgProLysProSerGluLeuThrLeuValGlyAlaProSerGlyTyrGlyLeu
    GGCTGCGCCAAGGGCTGCGCCCGGCCGAAGCCGTCCGAACTGACGCTTGTCGGTGCGCCATCAGGATACGGGCTT
2745      2755      2765      2775      2785      2795      2805
    ValValAsnGlyAlaAlaAsnGlyLeuProSerAlaTyrThrAspGluAsnGlyMetGlySerAlaLeuAlaArg
    GTCGTAAATGGGGCTGCCAATGGCTTGCCAAGCGCCTACACCGATGAGAATGGAATGGGATCCGCCCTTGCCCGG
2820      2830      2840      2850      2860      2870      2880
    LeuGlyArgLeuValArgGlnAsnLysAspAlaGlyGluSerAlaGlnSerCysLeuThrArgLeuGlyAlaAla
    CTCGGCCGGCTGGTGCGGCAAAACAAAGACGCTGGCGAATCGGCGCAGTCCTGTCTTACACGGCTCGGAGCTGCG
2895      2905      2915      2925      2935      2945      2955
    ArgValSerAlaAlaPheGluGlnGly***
    CGCGTCTCGGCAGCGTTCGAACAGGGATAG
2970      2980      2990      3000
```

*FIG. 16D*

COBG PROTEIN

FIRST RESIDUE = 1
LAST RESIDUE = 459

| | | | NUMBER | NO. % | WEIGHT | WEIGHT % |
|---|---|---|---|---|---|---|
| 1 | PHE | F | 7 | 1.53 | 1029.49 | 2.21 |
| 2 | LEU | L | 56 | 12.20 | 6332.48 | 13.57 |
| 3 | ILE | I | 21 | 4.58 | 2374.68 | 5.09 |
| 4 | MET | M | 8 | 1.74 | 1048.32 | 2.25 |
| 5 | VAL | V | 31 | 6.75 | 3071.17 | 6.58 |
| 6 | SER | S | 32 | 6.97 | 2784.96 | 5.97 |
| 7 | PRO | P | 26 | 5.66 | 2523.30 | 5.41 |
| 8 | THR | T | 27 | 5.88 | 2728.35 | 5.85 |
| 9 | ALA | A | 78 | 16.99 | 5541.12 | 11.88 |
| 10 | TYR | Y | 3 | 0.65 | 489.18 | 1.05 |
| 11 | * | * | 0 | 0.00 | 0.00 | 0.00 |
| 12 | HIS | H | 5 | 1.09 | 685.30 | 1.47 |
| 13 | GLN | Q | 13 | 2.83 | 1664.78 | 3.57 |
| 14 | ASN | N | 10 | 2.18 | 1140.40 | 2.44 |
| 15 | LYS | K | 10 | 2.18 | 1280.90 | 2.75 |
| 16 | ASP | D | 19 | 4.14 | 2185.57 | 4.68 |
| 17 | GLU | E | 24 | 5.23 | 3096.96 | 6.64 |
| 18 | CYS | C | 10 | 2.18 | 1030.10 | 2.21 |
| 19 | TRP | W | 2 | 0.44 | 372.16 | 0.80 |
| 20 | ARG | R | 29 | 6.32 | 4526.90 | 9.70 |
| 21 | GLY | G | 48 | 10.46 | 2736.96 | 5.87 |
| 22 | - | - | 0 | 0.00 | 0.00 | 0.00 |

RESIDUES = 459
MOLECULAR WEIGHT = 46661.
INDEX OF POLARITY (%) = 37.
ISOELECTRIC POINT = 6.41
OD 260 (1mg/ml) = 0.215 OD 280 (1mg/ml) = 0.315 cobH GENE (SEQ ID NO: 17) AND COBH PROTEIN (SEQ ID NO: 18)
SEQUENCE OF THE 8753-BP FRAGMENT FROM 3002 TO 3634

```
 MetProGluTyrAspTyrIleArgAspGlyAsnAlaIleTyrGluArgSerPheAlaIleIleArgAlaGluAla
 ATGCCTGAGTATGATTACATTCGCGATGGCAACGCCATCTACGAGCGTTCCTTCGCCATCATCCGCGCCGAGGCC
3002      3012      3022      3032      3042      3052      3062
 AspLeuSerArgPheSerGluGluGluAlaAspLeuAlaValArgMetValHisAlaCysGlySerValGluAla
 GATCTGTCGCGCTTCTCCGAAGAGGAAGCGGATCTGGCTGTGCGCATGGTGCACGCCTGCGGTTCCGTCGAGGCG
3077      3087      3097      3107      3117      3127      3137
 ThrArgGlnPheValPheSerProAspPheValSerSerAlaArgAlaAlaLeuLysAlaGlyAlaProIleLeu
 ACCAGGCAGTTCGTGTTTTCTCCCGATTTCGTAAGCTCGGCCCGTGCGGCGCTGAAAGCCGGTGCGCCGATCCTC
3152      3162      3172      3182      3192      3202      3212
 CysAspAlaGluMetValAlaHisGlyValThrArgAlaArgLeuProAlaGlyAsnGluValIleCysThrLeu
 TGCGATGCCGAGATGGTTGCGCACGGTGTCACCCGCGCCCGTCTGCCGGCCGGCAACGAGGTGATCTGCACGCTG
3227      3237      3247      3257      3267      3277      3287
 ArgAspProArgThrProAlaLeuAlaAlaGluIleGlyAsnThrArgSerAlaAlaAlaLeuLysLeuTrpSer
 CGCGATCCTCGCACGCCCGCACTTGCGGCCGAGATCGGCAACACCCGCTCCGCCGCAGCCCTGAAGCTCTGGAGC
3302      3312      3322      3332      3342      3352      3362
 GluArgLeuAlaGlySerValValAlaIleGlyAsnAlaProThrAlaLeuPhePheLeuLeuGluMetLeuArg
 GAGCGGCTGGCCGGTTCGGTGGTCGCGATCGGCAACGCGCCGACGGCGTTGTTCTTCCTCTTGGAAATGCTGCGC
3377      3387      3397      3407      3417      3427      3437
 AspGlyAlaProLysProAlaAlaIleLeuGlyMetProValGlyPheValGlyAlaAlaGluSerLysAspAla
 GACGGCGCGCCGAAGCCGGCGGCAATCCTCGGCATGCCCGTCGGTTTCGTCGGTGCGGCGGAATCGAAGGATGCG
3452      3462      3472      3482      3492      3502      3512
 LeuAlaGluAsnSerTyrGlyValProPheAlaIleValArgGlyArgLeuGlyGlySerAlaMetThrAlaAla
 CTGGCCGAGAACTCCTATGGCGTTCCCTTCGCCATCGTGCGCGGCCGCCTCGGCGGGAGTGCCATGACGGCGGCA
3527      3537      3547      3557      3567      3577      3587
 AlaLeuAsnSerLeuAlaArgProGlyLeu***
 GCGCTTAACTCGCTCGCGAGGCCGGGCCTGTGA
3602      3612      3622      3632
```

FIG. 16F

COBH PROTEIN    FIRST RESIDUE = 1
LAST RESIDUE = 210

| | | | NUMBER | NO. % | WEIGHT | WEIGHT % |
|---|---|---|---|---|---|---|
| 1 | PHE | F | 9 | 4.29 | 1323.63 | 6.00 |
| 2 | LEU | L | 20 | 9.52 | 2261.60 | 10.26 |
| 3 | ILE | I | 10 | 4.76 | 1130.80 | 5.13 |
| 4 | MET | M | 6 | 2.86 | 786.24 | 3.57 |
| 5 | VAL | V | 14 | 6.67 | 1386.98 | 6.29 |
| 6 | SER | S | 14 | 6.67 | 1218.42 | 5.53 |
| 7 | PRO | P | 12 | 5.71 | 1164.60 | 5.28 |
| 8 | THR | T | 7 | 3.33 | 707.35 | 3.21 |
| 9 | ALA | A | 40 | 19.05 | 2841.60 | 12.89 |
| 10 | TYR | Y | 4 | 1.90 | 652.24 | 2.96 |
| 11 | * | * | 0 | 0.00 | 0.00 | 0.00 |
| 12 | HIS | H | 2 | 0.95 | 274.12 | 1.24 |
| 13 | GLN | Q | 1 | 0.48 | 128.06 | 0.58 |
| 14 | ASN | N | 6 | 2.86 | 684.24 | 3.10 |
| 15 | LYS | K | 4 | 1.90 | 512.36 | 2.32 |
| 16 | ASP | D | 9 | 4.29 | 1035.27 | 4.70 |
| 17 | GLU | E | 14 | 6.67 | 1806.56 | 8.19 |
| 18 | CYS | C | 3 | 1.43 | 309.03 | 1.40 |
| 19 | TRP | W | 1 | 0.48 | 186.08 | 0.84 |
| 20 | ARG | R | 17 | 8.10 | 2653.70 | 12.03 |
| 21 | GLY | G | 17 | 8.10 | 969.34 | 4.40 |
| 22 | - | - | 0 | 0.00 | 0.00 | 0.00 |

RESIDUES = 210
MOLECULAR WEIGHT = 22050.
INDEX OF POLARITY (%) = 35.
ISOELECTRIC POINT = 6.22
OD 260 (1mg/ml) = 0.291  OD 280 (1mg/ml) = 0.467

<u>cobI</u> GENE (SEQ ID NO: 19) AND COBI PROTEIN (SEQ ID NO: 20)
SEQUENCE OF THE 8753-BP FRAGMENT FROM 3631 TO 4368

```
    MetSerGlyValGlyValGlyArgLeuIleGlyValGlyThrGlyProGlyAspProGluLeuLeuThrValLys
    GTGAGCGGCGTCGGCGTGGGGCGCCTGATCGGTGTTGGGACCGGCCCCGGTGATCCGGAACTTTTGACGGTCAAG
3631      3641      3651      3661      3671      3681      3691
    AlaValLysAlaLeuGlyGlnAlaAspValLeuAlaTyrPheAlaLysAlaGlyArgSerGlyAsnGlyArgAla
    GCGGTGAAGGCGCTCGGGCAAGCCGATGTGCTTGCCTATTTCGCCAAGGCCGGGCGAAGCGGTAACGGCCGCGCG
3706      3716      3726      3736      3746      3756      3766
    ValValGluGlyLeuLeuLysProAspLeuValGluLeuProLeuTyrTyrProValThrThrGluIleAspLys
    GTGGTCGAGGGTCTGCTGAAGCCCGATCTTGTCGAGCTGCCGCTATACTATCCGGTGACGACCGAAATCGACAAG
3781      3791      3801      3811      3821      3831      3841
    AspAspGlyAlaTyrLysThrGlnIleThrAspPheTyrAsnAlaSerAlaGluAlaValAlaAlaHisLeuAla
    GACGATGGCGCCTACAAGACCCAGATCACCGACTTCTACAATGCGTCGGCCGAAGCGGTAGCGGCGCATCTTGCC
3856      3866      3876      3886      3896      3906      3916
    AlaGlyArgThrValAlaValLeuSerGluGlyAspProLeuPheTyrGlySerTyrMetHisLeuHisValArg
    GCCGGGCGCACGGTCGCCGTGCTCAGTGAAGGCGACCCGCTGTTCTATGGTTCCTACATGCATCTGCATGTGCGG
3931      3941      3951      3961      3971      3981      3991
    LeuAlaAsnArgPheProValGluValIleProGlyIleThrAlaMetSerGlyCysTrpSerLeuAlaGlyLeu
    CTCGCCAATCGTTTCCCGGTCGAGGTGATCCCCGGCATTACCGCCATGTCCGGCTGTTGGTCGCTTGCCGGCCTG
4006      4016      4026      4036      4046      4056      4066
    ProLeuValGlnGlyAspAspValLeuSerValLeuProGlyThrMetAlaGluAlaGluLeuGlyArgArgLeu
    CCGCTGGTGCAGGGCGACGACGTGCTCTCGGTGCTTCCGGGCACCATGGCCGAGGCCGAGCTCGGCCGCAGGCTT
4081      4091      4101      4111      4121      4131      4141
    AlaAspThrGluAlaAlaValIleMetLysValGlyArgAsnLeuProLysIleArgArgAlaLeuAlaAlaSer
    GCGGATACCGAAGCCGCCGTGATCATGAAGGTCGGGCGCAATTTGCCGAAGATCCGTCGGGCGCTCGCTGCCTCC
4156      4166      4176      4186      4196      4206      4216
    GlyArgLeuAspGlnAlaValTyrValGluArgGlyThrMetLysAsnAlaAlaMetThrAlaLeuAlaGluLys
    GGCCGTCTCGACCAGGCCGTCTATGTCGAACGCGGCACGATGAAGAACGCGGCGATGACGGCTCTTGCGGAAAAG
4231      4241      4251      4261      4271      4281      4291
    AlaAspAspGluAlaProTyrPheSerLeuValLeuValProGlyTrpLysAspArgPro***
    GCCGACGACGAGGCGCCCTATTTCTCGCTGGTGCTCGTTCCCGGCTGGAAGGACCGACCATGA
4306      4316      4326      4336      4346      4356      4366
```

FIG. 16H

COBI PROTEIN

FIRST RESIDUE = 1
LAST RESIDUE = 245

| | | | NUMBER | NO. % | WEIGHT | WEIGHT % |
|---|---|---|---|---|---|---|
| 1 | PHE | F | 5 | 2.04 | 735.35 | 2.84 |
| 2 | LEU | L | 28 | 11.43 | 3166.24 | 12.24 |
| 3 | ILE | I | 7 | 2.86 | 791.56 | 3.06 |
| 4 | MET | M | 7 | 2.86 | 917.28 | 3.54 |
| 5 | VAL | V | 25 | 10.20 | 2476.75 | 9.57 |
| 6 | SER | S | 10 | 4.08 | 870.30 | 3.36 |
| 7 | PRO | P | 14 | 5.71 | 1358.70 | 5.25 |
| 8 | THR | T | 12 | 4.90 | 1212.60 | 4.69 |
| 9 | ALA | A | 34 | 13.88 | 2415.36 | 9.33 |
| 10 | TYR | Y | 9 | 3.67 | 1467.54 | 5.67 |
| 11 | * | * | 0 | 0.00 | 0.00 | 0.00 |
| 12 | HIS | H | 3 | 1.22 | 411.18 | 1.59 |
| 13 | GLN | Q | 4 | 1.63 | 512.24 | 1.98 |
| 14 | ASN | N | 5 | 2.04 | 570.20 | 2.20 |
| 15 | LYS | K | 11 | 4.49 | 1408.99 | 5.44 |
| 16 | ASP | D | 15 | 6.12 | 1725.45 | 6.67 |
| 17 | GLU | E | 13 | 5.31 | 1677.52 | 6.48 |
| 18 | CYS | C | 1 | 0.41 | 103.01 | 0.40 |
| 19 | TRP | W | 2 | 0.82 | 372.16 | 1.44 |
| 20 | ARG | R | 14 | 5.71 | 2185.40 | 8.44 |
| 21 | GLY | G | 26 | 10.61 | 1482.52 | 5.73 |
| 22 | - | - | 0 | 0.00 | 0.00 | 0.00 |

RESIDUES = 245
MOLECULAR WEIGHT = 25878.
INDEX OF POLARITY (%) = 36.
ISOELECTRIC POINT = 6.17
OD 260 (1 mg/ml) = 0.512 OD 280 (1 mg/ml) = 0.843

COBI FROM 1 TO 245 cobJ GENE (SEQ ID NO: 21) AND COBJ PROTEIN (SEQ ID NO: 22)
SEQUENCE OF THE 8753-BP FRAGMENT FROM 4365 TO 5129

```
   MetThrGlyThrLeuTyrValValGlyThrGlyProGlySerAlaLysGlnMetThrProGluThrAlaGluAla
   ATGACCGGTACGCTCTATGTCGTCGGTACCGGACCGGGCAGCGCCAAGCAGATGACGCCGGAAACGGCGGAAGCC
4365      4375      4385      4395      4405      4415      4425
   ValAlaAlaAlaGlnGluPheTyrGlyTyrPheProTyrLeuAspArgLeuAsnLeuArgProAspGlnIleArg
   GTTGCGGCCGCTCAGGAGTTTTACGGCTACTTTCCCTATCTCGACCGGCTGAACCTCAGACCGGATCAGATCCGT
4440      4450      4460      4470      4480      4490      4500
   ValAlaSerAspAsnArgGluGluLeuAspArgAlaGlnValAlaLeuThrArgAlaAlaAlaGlyValLysVal
   GTCGCCTCGGACAACCGCGAGGAGCTCGATCGGGCACAGGTCGCGCTGACGCGGGCTGCGGCAGGCGTGAAGGTC
4515      4525      4535      4545      4555      4565      4575
   CysMetValSerGlyGlyAspProGlyValPheAlaMetAlaAlaAlaValCysGluAlaIleAspLysGlyPro
   TGCATGGTCTCCGGTGGCGATCCCGGTGTCTTTGCCATGGCGGCCGCCGTCTGCGAGGCGATCGACAAGGGACCG
4590      4600      4610      4620      4630      4640      4650
   AlaGluTrpLysSerValGluLeuValIleThrProGlyValThrAlaMetLeuAlaValAlaAlaArgIleGly
   GCGGAATGGAAGTCGGTTGAACTGGTGATCACGCCCGGCGTGACCGCGATGCTCGCCGTTGCCGCCCGCATCGGC
4665      4675      4685      4695      4705      4715      4725
   AlaProLeuGlyHisAspPheCysAlaIleSerLeuSerAspAsnLeuLysProTrpGluValIleThrArgArg
   GCGCCGCTCGGTCATGATTTCTGTGCGATCTCGCTTTCCGACAATCTGAAGCCCTGGGAAGTCATCACCCGGCGT
4740      4750      4760      4770      4780      4790      4800
   LeuArgLeuAlaAlaGluAlaGlyPheValIleAlaLeuTyrAsnProIleSerLysAlaArgProTrpGlnLeu
   CTCAGGCTGGCGGCGGAAGCGGGCTTCGTCATTGCCCTCTACAATCCGATCAGCAAGGCGCGGCCCTGGCAGCTC
4815      4825      4835      4845      4855      4865      4875
   GlyGluAlaPheGluLeuLeuArgSerValLeuProAlaSerValProValIlePheGlyArgAlaAlaGlyArg
   GGTGAGGCCTTCGAGCTTCTGCGCAGCGTTCTGCCGGCAAGCGTTCCGGTCATCTTCGGCCGTGCGGCCGGGCGG
4890      4900      4910      4920      4930      4940      4950
   ProAspGluArgIleAlaValMetProLeuGlyGluAlaAspAlaAsnArgAlaAspMetAlaThrCysValIle
   CCGGACGAACGGATCGCGGTGATGCCGCTCGGCGAGGCCGATGCCAACCGCGCCGACATGGCGACCTGCGTCATC
4965      4975      4985      4995      5005      5015      5025
   IleGlySerProGluThrArgIleValGluArgAspGlyGlnProAspLeuValTyrThrProArgPheTyrAla
   ATCGGCTCGCCGGAGACGCGCATCGTCGAGCGCGACGGCCAACCCGATCTCGTCTACACACCGCGCTTCTATGCA
5040      5050      5060      5070      5080      5090      5100
   GlyAlaSerGln***
   GGGGCGAGCCAGTGA
5115      5125
```

FIG. 16J

COBJ PROTEIN

FIRST RESIDUE = 1
LAST RESIDUE = 254

| | | | NUMBER | NO. % | WEIGHT | WEIGHT % |
|---|---|---|---|---|---|---|
| 1 | PHE | F | 8 | 3.15 | 1176.56 | 4.34 |
| 2 | LEU | L | 20 | 7.87 | 2261.60 | 8.35 |
| 3 | ILE | I | 13 | 5.12 | 1470.04 | 5.43 |
| 4 | MET | M | 7 | 2.76 | 917.28 | 3.39 |
| 5 | VAL | V | 23 | 9.06 | 2278.61 | 8.41 |
| 6 | SER | S | 11 | 4.33 | 957.33 | 3.53 |
| 7 | PRO | P | 18 | 7.09 | 1746.90 | 6.45 |
| 8 | THR | T | 12 | 4.72 | 1212.60 | 4.48 |
| 9 | ALA | A | 40 | 15.75 | 2841.60 | 10.49 |
| 10 | TYR | Y | 7 | 2.76 | 1141.42 | 4.21 |
| 11 | * | * | 0 | 0.00 | 0.00 | 0.00 |
| 12 | HIS | H | 1 | 0.39 | 137.06 | 0.51 |
| 13 | GLN | Q | 7 | 2.76 | 896.42 | 3.31 |
| 14 | ASN | N | 5 | 1.97 | 570.20 | 2.11 |
| 15 | LYS | K | 6 | 2.36 | 768.54 | 2.84 |
| 16 | ASP | D | 13 | 5.12 | 1495.39 | 5.52 |
| 17 | GLU | E | 16 | 6.30 | 2064.64 | 7.62 |
| 18 | CYS | C | 4 | 1.57 | 412.04 | 1.52 |
| 19 | TRP | W | 3 | 1.18 | 558.24 | 2.06 |
| 20 | ARG | R | 19 | 7.48 | 2965.90 | 10.95 |
| 21 | GLY | G | 21 | 8.27 | 1197.42 | 4.42 |
| 22 | - | - | 0 | 0.00 | 0.00 | 0.00 |

RESIDUES = 254
MOLECULAR WEIGHT = 27088.
INDEX OF POLARITY (%) = 35.
ISOELECTRIC POINT = 5.43
OD 260 (1 mg/ml) = 0.575 OD 260 (1 mg/ml) = 0.922 cobK GENE (SEQ ID NO: 23) AND COBK PROTEIN (SEQ ID NO: 24)
SEQUENCE OF THE 8753-BP ECORI-ECORI FRAGMENT FROM 2861 TO 3646 ON
THE COMPLEMENTARY STRAND

```
  M  A  G  S  L  F  D  T  S  A  M  E  K  P  R  I  L  I  L  G  G  T  T  E  A
 ATGGCGGGTTCGCTGTTCGACACGTCAGCCATGGAAAAACCTCGTATTCTGATTCTGGGTGGCACCACCGAGGCA
2861      2871      2881      2891      2901      2911      2921      2931
  R  E  L  A  R  R  L  A  E  D  V  R  Y  D  T  A  I  S  L  A  G  R  T  A  D
 CGCGAACTCGCGCGCCGCTTGGCCGAAGATGTCCGCTACGACACCGCCATCTCGCTGGCCGGCCGCACCGCGGAC
2936      2946      2956      2966      2976      2986      2996      3006
  P  R  P  Q  P  V  K  T  R  I  G  G  F  G  G  A  D  G  L  A  H  F  V  H  D
 CCGCGGCCGCAGCCGGTCAAGACGCGCATCGGCGGCTTTGGCGGCGCCGATGGGCTGGCGCATTTCGTGCATGAC
3011      3021      3031      3041      3051      3061      3071      3081
  E  N  I  A  L  L  V  D  A  T  H  P  F  A  A  R  I  S  H  N  A  A  D  A  A
 GAAAACATCGCGCTGCTGGTCGATGCGACGCACCCCTTTGCCGCACGCATTTCGCACAACGCCGCGGACGCAGCG
3086      3096      3106      3116      3126      3136      3146      3156
  Q  R  T  G  V  A  L  I  A  L  R  R  P  E  W  V  P  L  P  G  D  R  W  T  A
 CAAAGAACCGGCGTTGCGCTTATCGCCCTCCGCCGACCGGAATGGGTGCCCCTGCCTGGCGACCGCTGGACTGCT
3161      3171      3181      3191      3201      3211      3221      3231
  V  D  S  V  V  E  A  V  S  A  L  G  D  R  R  R  R  V  F  L  A  I  G  R  Q
 GTCGATAGCGTTGTCGAGGCCGTCAGCGCGCTCGGTGATCGGCGACGCCGCGTCTTCCTGGCGATAGGTCGACAG
3236      3246      3256      3266      3276      3286      3296      3306
  E  A  F  H  F  E  V  A  P  Q  H  S  Y  V  I  R  S  V  D  P  V  T  P  P  L
 GAAGCTTTCCACTTCGAGGTCGCGCCGCAGCACAGCTACGTCATCCGCAGCGTCGATCCGGTGACGCCGCCGCTT
3311      3321      3331      3341      3351      3361      3371      3381
  N  L  P  D  Q  E  A  I  L  A  T  G  P  F  A  E  A  D  E  A  A  L  L  R  S
 AATCTGCCCGACCAGGAGGCGATCCTGGCGACCGGTCCCTTTGCGGAAGCCGACGAAGCCGCGTTGCTCAGGAGT
3386      3396      3406      3416      3426      3436      3446      3456
  R  Q  I  D  V  I  V  A  K  N  S  G  G  S  A  T  Y  G  K  I  A  A  A  R  R
 CGGCAGATCGATGTGATCGTCGCCAAGAACAGCGGTGGCAGCGCCACCTACGGCAAGATTGCCGCAGCGCGCCGG
3461      3471      3481      3491      3501      3511      3521      3531
  L  G  I  E  V  I  M  V  E  R  R  K  P  A  D  V  P  T  V  G  S  C  D  E  A
 CTCGGCATCGAGGTGATCATGGTCGAGCGGCGCAAGCCCGCGGACGTGCCGACGGTCGGCAGTTGCGACGAGGCA
3536      3546      3556      3566      3576      3586      3596      3606
  L  N  R  I  A  H  W  L  A  P  A
 CTCAACCGCATCGCTCACTGGCTCGCCCCTGCATGA
3611      3621      3631      3641
```

FIG. 16L

NAME = COBK

FIRST RESIDUE = 1
LAST RESIDUE = 261

| | | | NUMBER | NO. % | WEIGHT | WEIGHT % |
|---|---|---|---|---|---|---|
| 1 | PHE | F | 8 | 3.07 | 1176.55 | 4.19 |
| 2 | LEU | L | 22 | 8.43 | 2487.85 | 8.86 |
| 3 | ILE | I | 16 | 6.13 | 1809.34 | 6.44 |
| 4 | MET | M | 3 | 1.15 | 393.12 | 1.40 |
| 5 | VAL | V | 21 | 8.05 | 2080.44 | 7.41 |
| 6 | SER | S | 12 | 4.60 | 1044.38 | 3.72 |
| 7 | PRO | P | 17 | 6.51 | 1649.90 | 5.88 |
| 8 | THR | T | 13 | 4.98 | 1313.62 | 4.68 |
| 9 | ALA | A | 42 | 16.09 | 2983.56 | 10.63 |
| 10 | TYR | Y | 3 | 1.15 | 489.19 | 1.74 |
| 11 | * | * | 0 | 0.00 | 0.00 | 0.00 |
| 12 | HIS | H | 7 | 2.68 | 959.41 | 3.42 |
| 13 | GLN | Q | 6 | 2.30 | 768.35 | 2.74 |
| 14 | ASN | N | 5 | 1.92 | 570.21 | 2.03 |
| 15 | LYS | K | 5 | 1.92 | 640.47 | 2.28 |
| 16 | ASP | D | 17 | 6.51 | 1955.46 | 6.96 |
| 17 | GLU | E | 15 | 5.75 | 1935.64 | 6.89 |
| 18 | CYS | C | 1 | 0.38 | 103.01 | 0.37 |
| 19 | TRP | W | 3 | 1.15 | 558.24 | 1.99 |
| 20 | ARG | R | 26 | 9.96 | 4058.63 | 14.45 |
| 21 | GLY | G | 19 | 7.28 | 1083.41 | 3.86 |
| 22 | - | - | 0 | 0.00 | 0.00 | 0.00 |

RESIDUES = 261
MOLECULAR WEIGHT (MONOISOTOPIC) = 28078.7988
MOLECULAR WEIGHT (AVERAGE) = 28096.0195
INDEX OF POLARITY (%) = 40.64
ISOELECTRIC POINT = 7.54
OD 260 (1mg/ml) = 0.509 OD 280 (1mg/ml) = 0.721

HYDROPHILICITY PROFILE OF THE COBK PROTIEN
FROM 1 TO 261 cobL GENE (SEQ ID NO: 25) AND COBL PROTEIN (SEQ ID NO: 26)
SEQUENCE OF THE 8753-BP FRAGMENT FROM 5862 TO 7103

```
     MetAlaAspValSerAsnSerGluProAlaIleValSerProTrpLeuThrValIleGlyIleGlyGluAspGly
     ATGGCTGACGTGTCGAACAGCGAACCCGCCATAGTCTCCCCCTGGCTGACCGTCATCGGTATCGGTGAGGATGGT
5862      5872      5882      5892      5902      5912      5922
     ValAlaGlyLeuGlyAspGluAlaLysArgLeuIleAlaGluAlaProValValTyrGlyGlyHisArgHisLeu
     GTAGCGGGTCTCGGCGACGAGGCCAAGCGGCTGATCGCCGAAGCGCCGGTCGTCTACGGCGGCCATCGTCATCTG
5937      5947      5957      5967      5977      5987      5997
     GluLeuAlaAlaSerLeuIleThrGlyGluAlaHisAsnTrpLeuSerProLeuGluArgSerValValGluIle
     GAGCTCGCCGCCTCCCTCATCACCGGCGAAGCGCACAATTGGCTAAGCCCCCTCGAACGCTCGGTCGTCGAGATC
6012      6022      6032      6042      6052      6062      6072
     ValAlaArgArgGlySerProValValValLeuAlaSerGlyAspProPhePhePheGlyValGlyValThrLeu
     GTCGCGCGTCGCGGCAGCCCGGTGGTGGTGCTTGCCTCGGGCGACCCGTTCTTCTTCGGCGTCGGCGTGACGCTG
6087      6097      6107      6117      6127      6137      6147
     AlaArgArgIleAlaSerAlaGluIleArgThrLeuProAlaProSerSerIleSerLeuAlaAlaSerArgLeu
     GCGCGCCGCATCGCCTCGGCCGAAATACGCACGCTTCCGGCGCCGTCGTCGATCAGTCTTGCCGCCTCGCGCCTC
6162      6172      6182      6192      6202      6212      6222
     GlyTrpAlaLeuGlnAspAlaThrLeuValSerValHisGlyArgProLeuAspLeuValArgProHisLeuHis
     GGCTGGGCGCTGCAGGATGCGACGCTCGTCTCCGTACATGGGCGGCCGCTGGATCTGGTGCGACCGCATTTGCAT
6237      6247      6257      6267      6277      6287      6297
     ProGlyAlaArgValLeuThrLeuThrSerAspGlyAlaGlyProArgAspLeuAlaGluLeuLeuValSerSer
     CCGGGGGCGCGTGTGCTTACGCTCACGTCGGACGGTGCGGGTCCGCGAGACCTTGCCGAGCTTCTGGTTTCAAGC
6312      6322      6332      6342      6352      6362      6372
     GlyPheGlyGlnSerArgLeuThrValLeuGluAlaLeuGlyGlyAlaGlyGluArgValThrThrGlnIleAla
     GGCTTCGGTCAGTCGCGACTGACCGTGCTCGAAGCGCTGGGCGGCGCCGGCGAACGGGTGACGACGCAGATCGCC
6387      6397      6407      6417      6427      6437      6447
     AlaArgPheMetLeuGlyLeuValHisProLeuAsnValCysAlaIleGluValAlaAlaAspGluGlyAlaArg
     GCGCGCTTCATGCTCGGCCTCGTGCATCCTTTGAACGTCTGCGCCATTGAGGTGGCGGCCGACGAGGGCGCGCGC
6462      6472      6482      6492      6502      6512      6522
     IleLeuProLeuAlaAlaGlyArgAspAspAlaLeuPheGluHisAspGlyGlnIleThrLysArgGluValArg
     ATCCTGCCGCTTGCCGCCGGCCGCGACGATGCGCTGTTCGAACATGACGGGCAGATCACCAAGCGCGAGGTGCGG
6537      6547      6557      6567      6577      6587      6597
     AlaLeuThrLeuSerAlaLeuAlaProArgLysGlyGluLeuLeuTrpAspIleGlyGlyGlySerGlySerIle
     GCGCTGACGCTGTCGGCACTCGCACCGCGCAAGGGCGAACTGCTATGGGACATCGGCGGCGGCTCCGGCTCGATC
6612      6622      6632      6642      6652      6662      6672
     GlyIleGluTrpMetLeuAlaAspProThrMetGlnAlaIleThrIleGluValGluProGluArgAlaAlaArg
     GGCATCGAATGGATGCTCGCCGATCCGACCATGCAGGCGATCACCATCGAGGTTGAGCCGGAGCGGGCAGCGCGC
6687      6697      6707      6717      6727      6737      6747
```

FIG. 16N

```
   IleGlyArgAsnAlaThrMetPheGlyValProGlyLeuThrValValGluGlyGluAlaProAlaAlaLeuAla
   ATCGGCCGCAACGCGACGATGTTCGGCGTGCCCGGGCTGACGGTTGTCGAAGGCGAGGCGCCGGCGGCGCTTGCC
6762      6772      6782      6792      6802      6812      6822
   GlyLeuProGlnProAspAlaIlePheIleGlyGlyGlyGlySerGluAspGlyValMetGluAlaAlaIleGlu
   GGCCTGCCACAACCGGACGCGATCTTCATCGGCGGCGGCGGCAGCGAAGACGGCGTCATGGAAGCAGCGATCGAG
6837      6847      6857      6867      6877      6887      6897
   AlaLeuLysSerGlyGlyArgLeuValAlaAsnAlaValThrThrAspMetGluAlaValLeuLeuAspHisHis
   GCGCTCAAGTCAGGCGGACGGCTGGTTGCCAACGCGGTGACGACGGACATGGAAGCGGTGCTGCTCGATCATCAC
6912      6922      6932      6942      6952      6962      6972
   AlaArgLeuGlyGlySerLeuIleArgIleAspIleAlaArgAlaGlyProIleGlyGlyMetThrGlyTrpLys
   GCGCGGCTCGGCGGTTCGCTGATCCGCATCGATATCGCGCGTGCAGGACCCATCGGCGGCATGACCGGCTGGAAG
6987      6997      7007      7017      7027      7037      7047
   ProAlaMetProValThrGlnTrpSerTrpThrLysGly***
   CCGGCCATGCCGGTCACCCAATGGTCGTGGACGAAGGGCTAA
7062      7072      7082      7092      7102
```

FIG. 16O

COBL PROTEIN

FIRST RESIDUE = 1
LAST RESIDUE = 413

| | | | NUMBER | NO. % | WEIGHT | WEIGHT % |
|---|---|---|---|---|---|---|
| 1 | PHE | F | 8 | 1.94 | 1176.56 | 2.74 |
| 2 | LEU | L | 47 | 11.38 | 5314.76 | 12.39 |
| 3 | ILE | I | 26 | 6.30 | 2940.08 | 6.85 |
| 4 | MET | M | 9 | 2.18 | 1179.36 | 2.75 |
| 5 | VAL | V | 34 | 8.23 | 3368.38 | 7.85 |
| 6 | SER | S | 25 | 6.05 | 2175.75 | 5.07 |
| 7 | PRO | P | 24 | 5.81 | 2329.20 | 5.43 |
| 8 | THR | T | 21 | 5.08 | 2122.05 | 4.95 |
| 9 | ALA | A | 56 | 13.56 | 3978.24 | 9.27 |
| 10 | TYR | Y | 1 | 0.24 | 163.06 | 0.38 |
| 11 | * | * | 0 | 0.00 | 0.00 | 0.00 |
| 12 | HIS | H | 10 | 2.42 | 1370.60 | 3.19 |
| 13 | GLN | Q | 7 | 1.69 | 896.42 | 2.09 |
| 14 | ASN | N | 5 | 1.21 | 570.20 | 1.33 |
| 15 | LYS | K | 6 | 1.45 | 768.54 | 1.79 |
| 16 | ASP | D | 19 | 4.60 | 2185.57 | 5.09 |
| 17 | GLU | E | 27 | 6.54 | 3484.08 | 8.12 |
| 18 | CYS | C | 1 | 0.24 | 103.01 | 0.24 |
| 19 | TRP | W | 8 | 1.94 | 1488.64 | 3.47 |
| 20 | ARG | R | 28 | 6.78 | 4370.80 | 10.19 |
| 21 | GLY | G | 51 | 12.35 | 2908.02 | 6.78 |
| 22 | - | - | 0 | 0.00 | 0.00 | 0.00 |

RESIDUES = 413
MOLECULAR WEIGHT = 42911.
INDEX OF POLARITY (%) = 36.
ISOELECTRIC POINT = 5.70
OD 260 (1mg/ml) = 0.754 OD 280 (1mg/ml) = 1.064 cobM GENE (SEQ ID NO: 27) AND COBM PROTEIN (SEQ ID NO: 28)
SEQUENCE OF THE 8753-BP FRAGMENT FROM 7172 TO 7930

```
    MetThrValHisPheIleGlyAlaGlyProGlyAlaAlaAspLeuIleThrValArgGlyArgAspLeuIleGly
    ATGACGGTACATTTCATCGGCGCCGGCCCGGGAGCCGCAGACCTGATCACGGTGCGTGGTCGCGACCTGATCGGG
7172      7182      7192      7202      7212      7222      7232
    ArgCysProValCysLeuTyrAlaGlySerIleValSerProGluLeuLeuArgTyrCysProProGlyAlaArg
    CGCTGCCCGGTCTGCCTTTACGCCGGCTCGATCGTCTCGCCGGAGCTGCTGCGATATTGCCCGCCGGGCGCCCGC
7247      7257      7267      7277      7287      7297      7307
    IleValAspThrAlaProMetSerLeuAspGluIleGluAlaGluTyrValLysAlaGluAlaGluGlyLeuAsp
    ATTGTCGATACGGCGCCGATGTCCCTCGACGAGATCGAGGCGGAGTATGTGAAGGCCGAAGCCGAAGGGCTCGAC
7322      7332      7342      7352      7362      7372      7382
    ValAlaArgLeuHisSerGlyAspLeuSerValTrpSerAlaValAlaGluGlnIleArgArgLeuGluLysHis
    GTGGCGCGGCTTCATTCGGGCGACCTTTCGGTCTGGAGTGCTGTGGCCGAACAGATCCGCCGGCTCGAGAAGCAT
7397      7407      7417      7427      7437      7447      7457
    GlyIleAlaTyrThrMetThrProGlyValProSerPheAlaAlaAlaAlaSerAlaLeuGlyArgGluLeuThr
    GGCATCGCCTATACGATGACGCCGGGCGTTCCTTCCTTTGCGGCGGCGGCTTCAGCGCTCGGTCGCGAATTGACC
7472      7482      7492      7502      7512      7522      7532
    IleProAlaValAlaGlnSerLeuValLeuThrArgValSerGlyArgAlaSerProMetProAsnSerGluThr
    ATTCCGGCCGTGGCCCAGAGCCTGGTGCTGACCCGCGTTTCGGGCCGCGCCTCGCCGATGCCGAACTCAGAAACG
7547      7557      7567      7577      7587      7597      7607
    LeuSerAlaPheGlyAlaThrGlySerThrLeuAlaIleHisLeuAlaIleHisAlaLeuGlnGlnValValGlu
    CTTTCCGCTTTCGGCGCTACGGGATCGACGCTGGCAATCCACCTTGCGATCCATGCGCTTCAGCAGGTGGTCGAG
7622      7632      7642      7652      7662      7672      7682
    GluLeuThrProLeuTyrGlyAlaAspCysProValAlaIleValValLysAlaSerTrpProAspGluArgVal
    GAACTGACGCCGCTCTACGGTGCCGACTGCCCGGTCGCCATCGTCGTCAAGGCCTCCTGGCCGGACGAACGCGTG
7697      7707      7717      7727      7737      7747      7757
    ValArgGlyThrLeuGlyAspIleAlaAlaLysValAlaGluGluProIleGluArgThrAlaLeuIlePheVal
    GTGCGCGGCACGCTCGGTGACATCGCCGCCAAGGTGGCGGAAGAGCCGATCGAGCGCACGGCGCTGATCTTCGTC
7772      7782      7792      7802      7812      7822      7832
    GlyProGlyLeuGluAlaSerAspPheArgGluSerSerLeuTyrAspProAlaTyrGlnArgArgPheArgGly
    GGTCCGGGGCTCGAAGCCTCCGATTTCCGTGAAAGCTCGCTCTACGATCCCGCCTATCAGCGGCGCTTCAGAGGG
7847      7857      7867      7877      7887      7897      7907
    ArgGlyGlu
    CGCGGCGAA
7922      7932      7942      7952      7962      7972      7982
```

FIG. 16Q

COBM PROTEIN

FIRST RESIDUE = 1
LAST RESIDUE = 253

| | | | NUMBER | NO. % | WEIGHT | WEIGHT % |
|---|---|---|---|---|---|---|
| 1 | PHE | F | 6 | 2.37 | 882.42 | 3.29 |
| 2 | LEU | L | 24 | 9.49 | 2713.92 | 10.11 |
| 3 | ILE | I | 15 | 5.93 | 1696.20 | 6.32 |
| 4 | MET | M | 4 | 1.58 | 524.16 | 1.95 |
| 5 | VAL | V | 22 | 8.70 | 2179.54 | 8.12 |
| 6 | SER | S | 18 | 7.11 | 1566.54 | 5.84 |
| 7 | PRO | P | 17 | 6.72 | 1649.85 | 6.15 |
| 8 | THR | T | 13 | 5.14 | 1313.65 | 4.89 |
| 9 | ALA | A | 35 | 13.83 | 2486.40 | 9.26 |
| 10 | TYR | Y | 7 | 2.77 | 1141.42 | 4.25 |
| 11 | * | * | 0 | 0.00 | 0.00 | 0.00 |
| 12 | HIS | H | 5 | 1.98 | 685.30 | 2.55 |
| 13 | GLN | Q | 5 | 1.98 | 640.30 | 2.39 |
| 14 | ASN | N | 1 | 0.40 | 114.04 | 0.42 |
| 15 | LYS | K | 4 | 1.58 | 512.36 | 1.91 |
| 16 | ASP | D | 11 | 4.35 | 1265.33 | 4.71 |
| 17 | GLU | E | 19 | 7.51 | 2451.76 | 9.13 |
| 18 | CYS | C | 4 | 1.58 | 412.04 | 1.53 |
| 19 | TRP | W | 2 | 0.79 | 372.16 | 1.39 |
| 20 | ARG | R | 19 | 7.51 | 2965.90 | 11.05 |
| 21 | GLY | G | 22 | 8.70 | 1254.44 | 4.67 |
| 22 | - | - | 0 | 0.00 | 0.00 | 0.00 |

RESIDUES = 253
MOLECULAR WEIGHT = 26846.
INDEX OF POLARITY (%) = 38.
ISOELECTRIC POINT = 5.58
OD 260 (1mg/ml) = 0.461 OD 280 (1mg/ml) = 0.724

COBYRINIC ACID

COBYRINIC ACID DIAMIDE

PRECORRIN-2

PRECORRIN-3

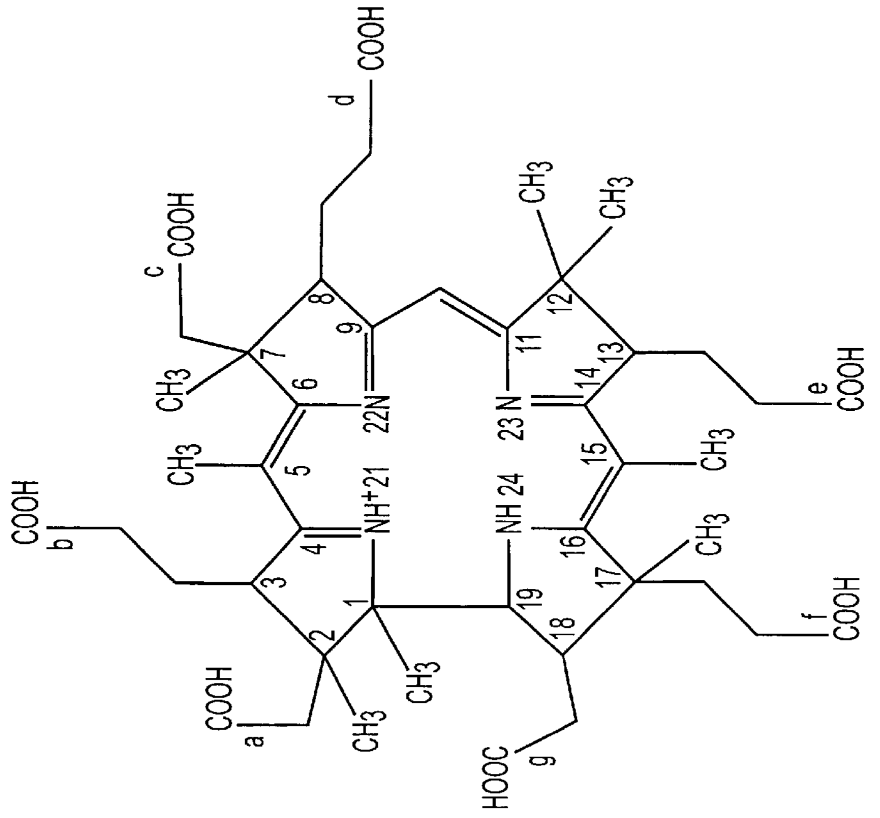
HYDROGENOBYRINIC ACID
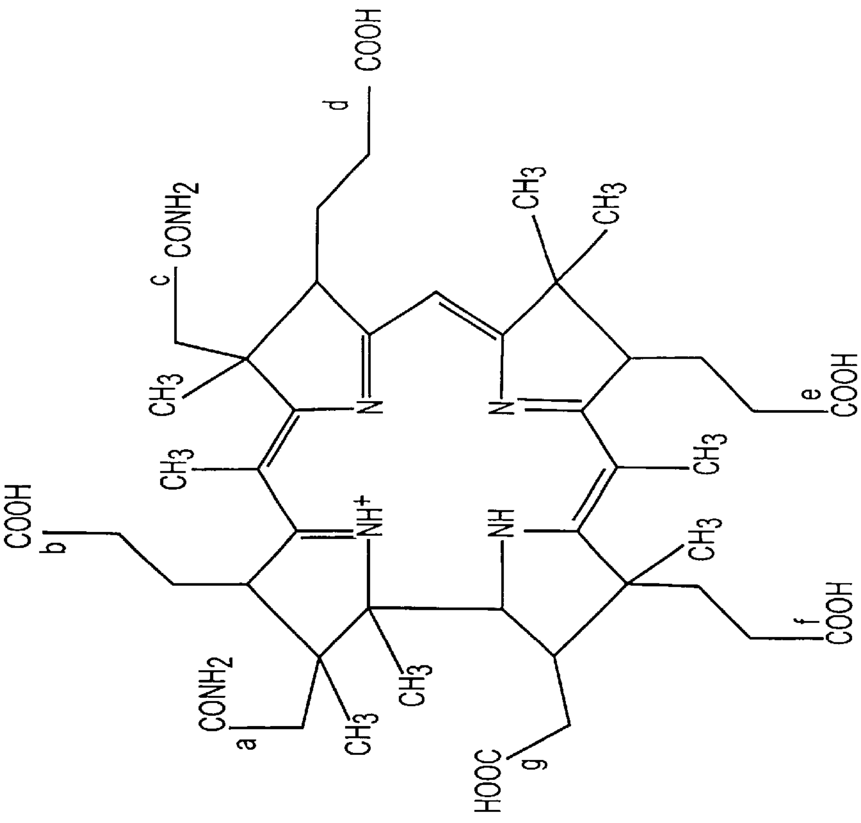
HYDROGENOBYRINIC ACID DIAMIDE
FIG. 19

```
      10         20         30         40
COBA  LPALEKGSVWL-VGAGPGDPGLLTLHAANALRQADVIVH -(AMINO ACIDS 10-46 AND 88-157 OF SEQ ID NO:4)
      - --  = - - ==-===== ===- =  == ====-
COBI  VSGVGVGRL-IGVGTGPGDPELLTVKAVKALGQADVLAY -(AMINO ACIDS 6-44 AND 99-164 OF SEQ ID NO:20)
         10         20         30         40
      ______________________________________
                   REGION 1

     90        100       110       120       130       140       150
COBA LARAGNRVLRLKGGDPFVFGRGGEEALTLVEHQVPFRIVPGITAGIGGLAYAGIPVTHREVNHAVTFLTG
     == ==  =  =  ===  -=      - = -   =  --=====  =  - ==-=-      -  -- = =
COBI LA-AGRTVAVLSEGDPLFYGSYMHLHVRLANR-FPVEVIPGITAMSGCWSLAGLPLVQ-G-DDVLSVLPG
              110       120        130       140       150         160
     ____________________                 __________________
            REGION 2                       REGION 3
```

FIG. 21

ALIGNMENT BETWEEN THE PROTEINS COBA OF PSEUDOMONAS DENITRIFICANS
AND CYSG OF ESCHERICHIA COLI
COBA SEQUENCE
CYSG SEQUENCE

```
                                    1
       10        20        30        40        50        60        70
  DDLFAGLPALEKGSVWLVGAGPGDPGLLTLHAANALRQADVIVHDALVNEDCLKLARPGAVLEFAGKRGG
  --=    =    -= = ======== ===== - - - ====-= = == -= - = =  =   = ===-=
  EQLINE-PLDHRGEVVLVGAGPGDAGLLTLKGLQQIQQADVVVYDRLVSDDIMNLVRRDADRVFVGKRAG
      210       220       230       240       250       260       270
       80        90       100    2  110       120       130       140
  KPSPKQRDISLRLVELARAGNRVLRLKGGDPFVFGRGGEEALTLVEHQVPFRIVPGITAGIGGLAYAGIP
      = -=   =-  =    = ==-========-=======  == -  -== -======- =  ==-===     3
  YHCVPQEEINQILLREAQKGKRVVRLKGGDPFIFGRGGEELETLCNAGIPFSVVPGITAASGCSAYSGIP
      280       290       300       310       320       330       340
      150       160       170       180       190       200       210
  VTHREVNHAVTFLTGHDSSGLVPDRINWQGIASGSPVIVMYMAMKHIGAITANLIAGGRSPDEPVAFVCN
3 -===-    -=   -===  -=   - --=- -=-    -= ===-   --=   ==  =   - === = =
  LTHRDYAQSVRLITGHLKTG-G-E-LDWENLAAEKQTLVFYMGLNQAATIQQKLIEHGMPGEMPVAIVEN
      350       360          370       380       390       400
      220       230       240       250
  AATPQQAVLETTLARAEADVAAAGLEPPAIVVVGEVVRLRAALDWIG
  ---  = =---==-   ---=   -- =-----= == ==  =-= -
  GTAVTQRVIDGTLTQL-GELAQQ-MNSPSLIIIGRVVGLRDKLNWFS
        420        430        440       450
```

COBA SEQUENCE FROM 3 TO 259 -(AMINO ACIDS 3-259 OF SEQ ID NO:4)
CYSG SEQUENCE FROM 204 TO 460 -(SEQ ID NO:55)
STRICT HOMOLOGY OF AMINO ACIDS; 41.6%

FIG. 22

REGION 1

```
CYSG(209-248) EPLDHRGEVVLVGAGPGDAGLLTLKGLQQIQQADVVVYDR
COBA(9-48)    LPALEKGSVWLVGAGPGDPGLLTLHAANALRQADVIVHDA
COBI(1-40)    VSGVGVGRLIGVGTGPGDPELLTVKAVKALGQADVLAYFA
COBF(1-40)    MAEAGMRKILIIGIGSGNPEHMTVQAINALNCADVLFIPT
COBJ(1-40)    MTGTLYVVGTGPGSAKQMTPETAEAVAAAQEFYGYFPYLD
COBL(6-45)    NSEPAIVSPWLTVIGIGEDGVAGLGDEAKALIAEAPVVYG
COBM(1-34)          MTVHFIGAGPGAADLITVRGRDLIGRCPVCLYAG
```

REGION 2

```
CYSG(288-310) EAQKGKRVVRLKGGDPFIFGRGG-(CYSG IS SEQ ID NO:55)
COBA(88-110)  LARAGNRVLRLKGGDPFVFGRGG-(COBA IS SEQ ID NO:4)
COBI(98-120)  HLAAGRTVAVLSEGDPLFYGSYM-(COBI IS SEQ ID NO:20)
COBF(60-83)   VTRKDSRTVEFAVPVRRTEGVSY-(COBF IS SEQ ID NO:14)
COBJ(68-80)   RAAAGVXVCMVSGGDPGVFAMAA-(COBJ IS SEQ ID NO:22)
COBL(76-98)   VARRGSPVVVLASGDPFFFGVGV-(COBL IS SEQ ID NO:26)
COBM(69-91)   AEAEGLDVARLHSGDLSVWSAVA-(COBM IS SEQ ID NO:28)
```

REGION 3

```
CYSG(325-342) VVPGITAASGCSAYSGIP
COBA(125-142) IVPGITAGIGGLAYAGIP
COBI(134-151) VIPGITAMSGCWSLAGLP
COBF(85-102)  SVDDWHAQIAGIYEALLS
COBJ(110-127) ITPGVTAMLAVAARIGAP
COBL(154-171) RVLTLTSDGAGPRDLAEL
COBM(102-119) IAYTMTPGVPSFAAAASA
```

(AMINO ACID NOS. LISTED CORRESPOND TO IDENTIFIED AMINO ACIDS OF SEQ ID NOS.)

*FIG. 23*

```
        10         20         30         40         50         60
GTCGACGAGT ATGGTCAGGT TCAGGGTCTG GTGACGCTGG AGGACATTCT GGAGGAGATC
CAGCTGCTCA TACCAGTCCA AGTCCCAGAC CACTGCGACC TCCTGTAAGA CCTCCTCTAG

        70         80         90        100        110        120
GTCGGCGATA TCGCCGATGA GCACGACCTC GACATTCAGG GCGTGCGCCA GGAAGCCGAT
CAGCCGCTAT AGCGGCTACT CGTGCTGGAG CTGTAAGTCC CGCACGCGGT CCTTCGGCTA

       130        140        150        160        170        180
GGCTCGATCG TCGTCGATGG CTCGGTGCCG ATCCGCGATC TCAACCGCGC GCTCGACTGG
CCGAGCTAGC AGCAGCTACC GAGCCACGGC TAGGCGCTAG AGTTGGCGCG CGAGCTGACC

       190        200        210        220        230        240
TCGCTGCCGG ACGAGGAGGC GACGACGGTG GCCGGTCTGG TCATCCACGA GTCCAAGAGC
AGCGACGGCC TGCTCCTCCG CTGCTGCCAC CGGCCAGACC AGTAGGTGCT CAGGTTCTCG

       250        260        270        280        290        300
ATTCCGGAGG AGCGCCAGGC CTTCACCTTC CACGGCAAAC GCTTCATCGT GATGAAGCGG
TAAGGCCTCC TCGCGGTCCG GAAGTGGAAG GTGCCGTTTG CGAAGTAGCA CTACTTCGCC

       310        320        330        340        350        360
GTGAAGAACC GCATTACCAA GCTGCGCATC CGTCCGGCGG AAGAGGGTGC TCCGCCGGCG
CACTTCTTGG CGTAATGGTT CGACGCGTAG GCAGGCCGCC TTCTCCCACG AGGCGGCCGC

       370        380        390        400        410        420
TGATGGCCGC GATTGCCTCT ACCAGCGGGT CGGCTCGCCG GGGGCTGCCG GCTCGACGGC
ACTACCGGCG CTAACGGAGA TGGTCGCCCA GCCGAGCGGC CCCCGACGGC CGAGCTGCCG

       430        440        450        460        470        480
GAGCGCATGC AGGCCGGCGT CGAGTTCTGG CTTCAGGAGA TCATTGATGG CGCGGTGGCG
CTCGCGTACG TCCGGCCGCA GCTCAAGACC GAAGTCCTCT AGTAACTACC GCGCCACCGC

       490        500        510        520        530        540
GGCGACACGG CTCATGCCGG CAAAGGCGCT AGAAACGATA CGCACCCGCA TGTGGGACTC
CCGCTGTGCC GAGTACGGCC GTTTCCGCGA TCTTTGCTAT GCGTGGGCGT ACACCCTGAG

       550        560        570        580        590        600
GCCGGTACCA TCGAAGCCCG GCTGATGGCC GGTATGCTGA TGGCTCTCGT TGATGACCTC
CGGCCATGGT AGCTTCGGGC CGACTACCGG CCATACGACT ACCGAGAGCA ACTACTGGAG
```

FIG. 32A

```
       610        620        630        640        650        660
GAGCCGTTCA GGGTGGAAGG CCTCGATCAG CTTCTTTTCG ATGGTCTCGG TGAGCGACAT
CTCGGCAAGT CCCACCTTCC GGAGCTAGTC GAAGAAAAGC TACCAGAGCC ACTCGCTGTA

       670        680        690        700        710        720
TCTTCCGTCC CATTTTGCTG TTTGCTTGGC GCCCCCTCGC AGTTAAGAAC CCGGTAATCG
AGAAGGCAGG GTAAAACGAC AAACGAACCG CGGGGGAGCG TCAATTCTTG GGCCATTAGC

       730        740        750        760        770        780
CTGGCACGGC GGCGCAAAAT GCCCGCACAA AGCCAGCAAC ATTCCGCTTT GTCAATTCTT
GACCGTGCCG CCGCGTTTTA CGGGCGTGTT TCGGTCGTTG TAAGGCGAAA CAGTTAAGAA

       790        800        810        820        830        840
GTTGTGACTC CCGCCAAACC CCATAATGAG CGCCATGAGA CTCGATTCAA AATACTTCGA
CAACACTGAG GGCGGTTTGG GGTATTACTC GCGGTACTCT GAGCTAAGTT TTATGAAGCT

       850        860        870        880        890        900
TCGCATTCGA ACCCGGCGCA AGGTCGAGCC GCAGCAGAGC CGGCGGCTCC CGTCTGTCAG
AGCGTAAGCT TGGGCCGCGT TCCAGCTCGG CGTCGTCTCG GCCGCCGAGG GCAGACAGTC

       910        920        930        940        950        960
TGGGACGGCT GCGATCAGAA GGGTGTGCAC CGGGCGCCCG TCGGTCGCAA CGCCGAGGGG
ACCCTGCCGA CGCTAGTCTT CCCACACGTG GCCCGCGGGC AGCCAGCGTT GCGGCTCCCC

       970        980        990       1000       1010       1020
CAGTACTTCA TGTTCTGCTT CGAGCACGTG AAGGAATACA ACAAGGGCTA CAACTTCTTC
GTCATGAAGT ACAAGACGAA GCTCGTGCAC TTCCTTATGT TGTTCCCGAT GTTGAAGAAG

      1030       1040       1050       1060       1070       1080
TCCGGCCTCT CCGACAGCGA GGTCGCCCGC TACCAGAAGG AAGCGATCAC CGGTCATCGG
AGGCCGGAGA GGCTGTCGCT CCAGCGGGCG ATGGTCTTCC TTCGCTAGTG GCCAGTAGCC

      1090       1100       1110       1120       1130       1140
CCCACCTGGA CCGTCGGCGT CAACAAGAAC GCCAAGAACG GCCCGACCCA GTCGCAGACG
GGGTGGACCT GGCAGCCGCA GTTGTTCTTG CGGTTCTTGC CGGGCTGGGT CAGCGTCTGC

      1150       1160       1170       1180       1190       1200
CGGTCTGGCT CTGCCGGCGC CCAGGCCCGC ATGCGCGATC CCTTCGGCTT TGTCAGCGAG
GCCAGACCGA GACGGCCGCG GGTCCGGGCG TACGCGCTAG GGAAGCCGAA ACAGTCGCTC
```

FIG. 32B

```
      1210       1220       1230       1240       1250       1260
GCGCGGGCGC GATCCGGTCG TCCCGAGCCA CGCCAGCGCA AGCTGAAGAC GCTCGAGGCG
CGCGCCCGCG CTAGGCCAGC AGGGCTCGGT GCGGTCGCGT TCGACTTCTG CGAGCTCCGC

      1270       1280       1290       1300       1310       1320
AAGGCCTTCG AAACGCTTGG TCTCGGAGCC TCGGCGACCA CTGCCGACAT CAAGGCGGCC
TTCCGGAAGC TTTGCGAACC AGAGCCTCGG AGCCGCTGGT GACGGCTGTA GTTCCGCCGG

      1330       1340       1350       1360       1370       1380
TACAAGGACC TCGTCAAGAA GCATCACCCC GATGCCAATG GCGGAGATAG AGGATCGGAA
ATGTTCCTGG AGCAGTTCTT CGTAGTGGGG CTACGGTTAC CGCCTCTATC TCCTAGCCTT

      1390       1400       1410       1420       1430       1440
GAGCGTTTTC GCGCGGTTAT TCAGGCCTAC CAATTGTTAA AACAGGCTGG TTTCTGCTAA
CTCGCAAAAG CGCGCCAATA AGTCCGGATG GTTAACAATT TTGTCCGACC AAAGACGATT

      1450       1460       1470       1480       1490       1500
CAACCCGGAT TAATACAGAA GCACTTTTGC AGGCGAATGC GCGGGTGCCG TCCGGTGGCC
GTTGGGCCTA ATTATGTCTT CGTGAAAACG TCCGCTTACG CGCCCACGGC AGGCCACCGG

      1510       1520       1530       1540       1550       1560
GCTCTGGAGA CATGATGAGC AAGATTGACC TCGACATTTC CAACCTCCCC GACACCACGA
CGAGACCTCT GTACTACTCG TTCTAACTGG AGCTGTAAAG GTTGGAGGGG CTGTGGTGCT

      1570       1580       1590       1600       1610       1620
TTTCCGTCCG GGAGGTTTTC GGTATTGATA CGGATTTGCG CGTTCCTGCC TATTCGAAGG
AAAGGCAGGC CCTCCAAAAG CCATAACTAT GCCTAAACGC GCAAGGACGG ATAAGCTTCC

      1630       1640       1650       1660       1670       1680
GCGACGCCTA TGTCCCGGAT CTGGATCCGG ACTACCTCTT CGACCGCGAA ACGACGCTCG
CGCTGCGGAT ACAGGGCCTA GACCTAGGCC TGATGGAGAA GCTGGCGCTT TGCTGCGAGC

      1690       1700       1710       1720       1730       1740
CCATTCTCGC AGGCTTCGCC CACAACCGAC GCGTGATGGT GTCGGGCTAT CACGGCACCG
GGTAAGAGCG TCCGAAGCGG GTGTTGGCTG CGCACTACCA CAGCCCGATA GTGCCGTGGC

      1750       1760       1770       1780       1790       1800
GCAAGTCCAC CCATATCGAG CAGGTCGCCG CGCGCCTCAA CTGGCCGTGC GTGCGCGTCA
CGTTCAGGTG GGTATAGCTC GTCCAGCGGC GCGCGGAGTT GACCGGCACG CACGCGCAGT
```

*FIG. 32C*

```
      1810       1820       1830       1840       1850       1860
ACCTCGATAG CCATGTCAGC CGTATCGACC TCGTCGGCAA GGACGCGATC GTCGTCAAGG
TGGAGCTATC GGTACAGTCG GCATAGCTGG AGCAGCCGTT CCTGCGCTAG CAGCAGTTCC

      1870       1880       1890       1900       1910       1920
ACGGCCTGCA GGTCACCGAA TTCAAGGACG GCATCCTGCC CTGGGCCTAC CAGCACAATG
TGCCGGACGT CCAGTGGCTT AAGTTCCTGC CGTAGGACGG GACCCGGATG GTCGTGTTAC

      1930       1940       1950       1960       1970       1980
TCGCGCTCGT CTTCGACGAA TACGATGCCG GCCGCCCGGA CGTCATGTTC GTCATCCAGC
AGCGCGAGCA GAAGCTGCTT ATGCTACGGC CGGCGGGCCT GCAGTACAAG CAGTAGGTCG

      1990       2000       2010       2020       2030       2040
GCGTGCTGGA ATCCTCCGGC CGCCTGACGC TGCTCGACCA GAGCCGTGTC ATCCGTCCGC
CGCACGACCT TAGGAGGCCG GCGGACTGCG ACGAGCTGGT CTCGGCACAG TAGGCAGGCG

      2050       2060       2070       2080       2090       2100
ACCCGGCCTT CCGCCTGTTT GCGACCGCCA ACACCGTCGG CCTCGGCGAC ACGACCGGCC
TGGGCCGGAA GGCGGACAAA CGCTGGCGGT TGTGGCAGCC GGAGCCGCTG TGCTGGCCGG

      2110       2120       2130       2140       2150       2160
TCTATCACGG CACGCAGCAG ATCAACCAGG CGCAGATGGA CCGCTGGTCG ATCGTCACCA
AGATAGTGCC GTGCGTCGTC TAGTTGGTCC GCGTCTACCT GGCGACCAGC TAGCAGTGGT

      2170       2180       2190       2200       2210       2220
CGCTGAACTA CCTGCCGCAC GACAAGGAAG TCGACATCGT CGCCGCCAAG GTCAAGGGCT
GCGACTTGAT GGACGGCGTG CTGTTCCTTC AGCTGTAGCA GCGGCGGTTC CAGTTCCCGA

      2230       2240       2250       2260       2270       2280
TCACCGCCGA CAAGGGCCGC GAGACCGTCT CCAAGATGGT ACGTGTCGCC GACCTCACGC
AGTGGCGGCT GTTCCCGGCG CTCTGGCAGA GGTTCTACCA TGCACAGCGG CTGGAGTGCG

      2290       2300       2310       2320       2330       2340
GCGCAGCCTT CATCAATGGC GATCTCTCGA CTGTCATGAG CCCGCGTACG GTCATCACCT
CGCGTCGGAA GTAGTTACCG CTAGAGAGCT GACAGTACTC GGGCGCATGC CAGTAGTGGA

      2350       2360       2370       2380       2390       2400
GGGCCGAGAA CGCCCACATC TTCGGCGACA TCGCTTTCGC CTTCCGCGTG ACCTTCCTCA
CCCGGCTCTT GCGGGTGTAG AAGCCGCTGT AGCGAAAGCG GAAGGCGCAC TGGAAGGAGT
```

*FIG. 32D*

```
      2410       2420       2430       2440       2450       2460
ACAAGTGCGA CGAGCTGGAG CGGGCGCTGG TCGCCGAGCA CTACCAGCGC GCCTTCGGCA
TGTTCACGCT GCTCGACCTC GCCCGCGACC AGCGGCTCGT GATGGTCGCG CGGAAGCCGT

      2470       2480       2490       2500       2510       2520
TCGAGCTGAA GGAATGCGCT GCCAACATCG TGCTCGAAGC CACCGCCTGA TCCCACGGCC
AGCTCGACTT CCTTACGCGA CGGTTGTAGC ACGAGCTTCG GTGGCGGACT AGGGTGCCGG

      2530       2540       2550       2560       2570       2580
TGCCGTCCCC TTTGGGAGGG CGGGTCATGA CGCTGTGGCA AACCGGATGA CGCCCCACTG
ACGGCAGGGG AAACCCTCCC GCCCAGTACT GCGACACCGT TTGGCCTACT GCGGGGTGAC

      2590       2600       2610       2620       2630       2640
GGGCGCCGTC GCCTCTGGCT GAAGAAGGAA CTGTCGTGAG CTCGAATTCG AAGGCAAAGC
CCCGCGGCAG CGGAGACCGA CTTCTTCCTT GACAGCACTC GAGCTTAAGC TTCCGTTTCG

      2650       2660       2670       2680       2690       2700
CAACCACGCG CGAGAATGCT GCGGAACCGT TCAAGCGGGC GCTTTCCGGC TGCATCCGAT
GTTGGTGCGC GCTCTTACGA CGCCTTGGCA AGTTCGCCCG CGAAAGGCCG ACGTAGGCTA

      2710       2720       2730       2740       2750       2760
CGATCGCGGG CGATGCCGAG GTGGAAGTCG CCTTCGCCAA CGAGCGGCCG GGCATGACCG
GCTAGCGCCC GCTACGGCTC CACCTTCAGC GGAAGCGGTT GCTCGCCGGC CCGTACTGGC

      2770       2780       2790       2800       2810       2820
GCGAACGCAT CCGTCTGCCG GAACTTTCCA AGCGCCCGAC CCTGCAGGAA CTTGCCGTGA
CGCTTGCGTA GGCAGACGGC CTTGAAAGGT TCGCGGGCTG GGACGTCCTT GAACGGCACT

      2830       2840       2850       2860       2870       2880
CCCGCGGGCT CGGTGACAGC ATGGCGCTGC GCAAGGCCTG TACGCATGCG CGGATCCAGC
GGGCGCCCGA GCCACTGTCG TACCGCGACG CGTTCCGGAC ATGCGTACGC GCCTAGGTCG

      2890       2900       2910       2920       2930       2940
GCACCATGTC GCCGCAAGGG GCGGACGCCC GCGCGATCTT CGATGCGGTG GAGCAGGCTC
CGTGGTACAG CGGCGTTCCC CGCCTGCGGG CGCGCTAGAA GCTACGCCAC CTCGTCCGAG

      2950       2960       2970       2980       2990       3000
GTGTCGAGGC GATCGGGTCG TTGCGCATGG CGGGTGTCGC CAAGAACCTC AACGTCATGC
CACAGCTCCG CTAGCCCAGC AACGCGTACC GCCCACAGCG GTTCTTGGAG TTGCAGTACG
```

FIG. 32E

```
      3010       3020       3030       3040       3050       3060
TCGAAGAGAA ATACGCCAAG GCGAATTTCG CAACGATCGA GCGCCAGGCG GACGCGCCGC
AGCTTCTCTT TATGCGGTTC CGCTTAAAGC GTTGCTAGCT CGCGGTCCGC CTGCGCGGCG

      3070       3080       3090       3100       3110       3120
TCGGCGAGGC CGTAGCGCTG CTGGTGCGCG AGAAGCTGAC GGGCCAGAAG CCGCCGGCGT
AGCCGCTCCG GCATCGCGAC GACCACGCGC TCTTCGACTG CCCGGTCTTC GGCGGCCGCA

      3130       3140       3150       3160       3170       3180
CTGCCGGCAA GGTGCTCGAC CTCTGGCGCG AGTTCATCGA GGGCAAGGCT GCCGGCGACA
GACGGCCGTT CCACGAGCTG GAGACCGCGC TCAAGTAGCT CCCGTTCCGA CGGCCGCTGT

      3190       3200       3210       3220       3230       3240
TTGAGCACCT GTCGTCGACG ATCAACAACC AGCAGGCCTT TGCCCGGGTC GTTCGCGACA
AACTCGTGGA CAGCAGCTGC TAGTTGTTGG TCGTCCGGAA ACGGGCCCAG CAAGCGCTGT

      3250       3260       3270       3280       3290       3300
TGCTGACCTC GATGGAAGTC GCCGAGAAAT ACGGTGACGA CGACAACGAG CCGGACGAGC
ACGACTGGAG CTACCTTCAG CGGCTCTTTA TGCCACTGCT GCTGTTGCTC GGCCTGCTCG

      3310       3320       3330       3340       3350       3360
AGGAAAGCGA GACCGACGAA GACCAGCCGC GCAGCCAGGA GCAGGACGAG AACGCCAGCG
TCCTTTCGCT CTGGCTGCTT CTGGTCGGCG CGTCGGTCCT CGTCCTGCTC TTGCGGTCGC

      3370       3380       3390       3400       3410       3420
ACGAGGAAGC CGGCGACGAT GCCGCACCCG CCGACGAGAA CCAGGCTGCC GAAGAGCAGA
TGCTCCTTCG GCCGCTGCTA CGGCGTGGGC GGCTGCTCTT GGTCCGACGG CTTCTCGTCT

      3430       3440       3450       3460       3470       3480
TGGAAGAAGG CGAGATGGAC GGCGCGGAGA TCTCCGACGA CGATCTCCAG GACGAAGGCG
ACCTTCTTCC GCTCTACCTG CCGCGCCTCT AGAGGCTGCT GCTAGAGGTC CTGCTTCCGC

      3490       3500       3510       3520       3530       3540
ACGAGGACAG CGAAACGCCC GGCGAGGTCA AGCGTCCGAA CCAGCCCTTC GCCGACTTCA
TGCTCCTGTC GCTTTGCGGG CCGCTCCAGT TCGCAGGCTT GGTCGGGAAG CGGCTGAAGT

      3550       3560       3570       3580       3590       3600
ACGAGAAGGT CGACTACGCC GTCTTCACCC GCGAGTTCGA CGAGACGATT GCCTCGGAAG
TGCTCTTCCA GCTGATGCGG CAGAAGTGGG CGCTCAAGCT GCTCTGCTAA CGGAGCCTTC
```

FIG. 32F

```
      3610       3620       3630       3640       3650       3660
AGCTTTGCGA CGAGGCCGAG CTCGACCGGC TGCGCGCCTT CCTCGACAAG CAGCTTGCCC
TCGAAACGCT GCTCCGGCTC GAGCTGGCCG ACGCGCGGAA GGAGCTGTTC GTCGAACGGG

      3670       3680       3690       3700       3710       3720
ATCTTCAAGG CGCGGTCGGC CGCCTTGCCA ACCGGCTGCA GCGCCGCCTG ATGGCGCAGC
TAGAAGTTCC GCGCCAGCCG GCGGAACGGT TGGCCGACGT CGCGGCGGAC TACCGCGTCG

      3730       3740       3750       3760       3770       3780
AGAACCGCTC CTGGGAGTTC GATCTCGAAG AGGGGTATCT CGATTCGGCG CGGCTTCAGC
TCTTGGCGAG GACCCTCAAG CTAGAGCTTC TCCCCATAGA GCTAAGCCGC GCCGAAGTCG

      3790       3800       3810       3820       3830       3840
GCATCATCAT CGATCCGATG CAGCCGCTTT CCTTCAAGCG CGAAAAGGAC ACCAACTTCC
CGTAGTAGTA GCTAGGCTAC GTCGGCGAAA GGAAGTTCGC GCTTTTCCTG TGGTTGAAGG

      3850       3860       3870       3880       3890       3900
GCGATACCGT CGTGACGCTG CTGATCGACA ATTCCGGCTC GATGCGCGGC CGTCCGATCA
CGCTATGGCA GCACTGCGAC GACTAGCTGT TAAGGCCGAG CTACGCGCCG GCAGGCTAGT

      3910       3920       3930       3940       3950       3960
CGGTTGCCGC CACCTGCGCC GATATCCTGG CGCGCACGCT CGAGCGCTGC GGCGTCAAGG
GCCAACGGCG GTGGACGCGG CTATAGGACC GCGCGTGCGA GCTCGCGACG CCGCAGTTCC

      3970       3980       3990       4000       4010       4020
TCGAGATCCT CGGTTTTACC ACCAAGGCGT GGAAGGGTGG GCAGTCACGC GAGAAGTGGC
AGCTCTAGGA GCCAAAATGG TGGTTCCGCA CCTTCCCACC CGTCAGTGCG CTCTTCACCG

      4030       4040       4050       4060       4070       4080
TGGCCGGCGG CAAGCCACAG GCCCCGGGTC GCCTCAACGA CCTGCGACAC ATCGTCTACA
ACCGGCCGCC GTTCGGTGTC CGGGGCCCAG CGGAGTTGCT GGACGCTGTG TAGCAGATGT

      4090       4100       4110       4120       4130       4140
AGTCTGCCGA CGCTCCGTGG CGCCGGGCAC GACGCAATCT CGGCCTGATG ATGCGGGAAG
TCAGACGGCT GCGAGGCACC GCGGCCCGTG CTGCGTTAGA GCCGGACTAC TACGCCCTTC

      4150       4160       4170       4180       4190       4200
GCCTGCTCAA GGAAAACATC GACGGCGAGG CGTTGATTTG GGCGCATGAG CGGCTGATGG
CGGACGAGTT CCTTTTGTAG CTGCCGCTCC GCAACTAAAC CCGCGTACTC GCCGACTACC
```

*FIG. 32G*

```
      4210       4220       4230       4240       4250       4260
CGCGGCGCGA ACAGCGGCGC ATCCTGATGA TGATTTCGGA CGGCGCGCCG GTCGACGACT
GCGCCGCGCT TGTCGCCGCG TAGGACTACT ACTAAAGCCT GCCGCGCGGC CAGCTGCTGA

      4270       4280       4290       4300       4310       4320
CGACGCTGTC GGTCAATCCA GGAAACTATC TGGAGCGTCA CCTGCGCGCG GTCATCGAGC
GCTGCGACAG CCAGTTAGGT CCTTTGATAG ACCTCGCAGT GGACGCGCGC CAGTAGCTCG

      4330       4340       4350       4360       4370       4380
AGATCGAAAC GCGCTCGCCG GTGGAACTGC TGGCGATCGG TATCGGCCAC GACGTGACGC
TCTAGCTTTG CGCGAGCGGC CACCTTGACG ACCGCTAGCC ATAGCCGGTG CTGCACTGCG

      4390       4400       4410       4420       4430       4440
GCTACTATCG CCGTGCCGTC ACCATCGTCG ATGCCGATGA GCTTGCCGGC GCGATGACCG
CGATGATAGC GGCACGGCAG TGGTAGCAGC TACGGCTACT CGAACGGCCG CGCTACTGGC

      4450       4460       4470       4480       4490       4500
AACAGCTGGC CGCACTCTTC GAGGACGAAA GCCAGCGCCG CGGTTCTTCG CGTCTTCGCC
TTGTCGACCG GCGTGAGAAG CTCCTGCTTT CGGTCGCGGC GCCAAGAAGC GCAGAAGCGG

      4510       4520       4530       4540       4550       4560
GCGCCGGGTG ATGCTTCCCC CTTGGGGGCG GTGGAACATC GCCTCCGAGC TGCCAATCGG
CGCGGCCCAC TACGAAGGGG GAACCCCCGC CACCTTGTAG CGGAGGCTCG ACGGTTAGCC

      4570       4580       4590       4600       4610       4620
CACCTGCACG CATCGCTGGC GGCCGAAGTC AATTTACGGA CATAGTTTTA CAGTCTACCA
GTGGACGTGC GTAGCGACCG CCGGCTTCAG TTAAATGCCT GTATCAAAAT GTCAGATGGT

      4630       4640       4650       4660       4670       4680
AGCTACCATG CGTGGCGGGC TCACTTTGAG CGCACGCCGC GTCATTCCCG ATGCCCCCTG
TCGATGGTAC GCACCGCCCG AGTGAAACTC GCGTGCGGCG CAGTAAGGGC TACGGGGGAC

      4690       4700       4710       4720       4730       4740
AAGGTACTTC TCTTGATGCT TGGCCGCGGT CTCCTAGCCC TTTTCCTCCT GGCTTCGGCC
TTCCATGAAG AGAACTACGA ACCGGCGCCA GAGGATCGGG AAAAGGAGGA CCGAAGCCGG

      4750       4760       4770       4780       4790       4800
TGCCCGGC
ACGGGCCG
```

FIG. 32H

```
        10         20         30         40         50         60
GAGCTCATAG AGCAGTTCCT CGATCGACTT CAGCAGTCGC ATGAAATCCA TGCCGTGCTC
CTCGAGTATC TCGTCAAGGA GCTAGCTGAA GTCGTCAGCG TACTTTAGGT ACGGCACGAG

        70         80         90        100        110        120
CCCTTGCTTC TATGCGTGGC ACGACCGCGC GCCGGGGCCG ATGCCGGTCA GTCGCGCAGA
GGGAACGAAG ATACGCACCG TGCTGGCGCG CGGCCCCGGC TACGGCCAGT CAGCGCGTCT

       130        140        150        160        170        180
CGCAGCTCGT CGGTACGCAT CTGCAGCATC TCCAGCGTCG ACAGGAAGCT CATGCCGAGC
GCGTCGAGCA GCCATGCGTA GACGTCGTAG AGGTCGCAGC TGTCCTTCGA GTACGGCTCG

       190        200        210        220        230        240
AGGCTCTGAT CGAGCTTGCC CTTGGCTGCG ACCGTTGCGC CGATGTTGCG GCGGGTGATC
TCCGAGACTA GCTCGAACGG GAACCGACGC TGGCAACGCG GCTACAACGC CGCCCACTAG

       250        260        270        280        290        300
GGGCCGATCG AGATCTCCTG AAGCATCACG GGGGCTGCCT GGGCCCGGCC ATTGGCTGTC
CCCGGCTAGC TCTAGAGGAC TTCGTAGTGC CCCCGACGGA CCCGGGCCGG TAACCGACAG

       310        320        330        340        350        360
ATGACCGTGA CGATAAAGTT GAGGTTGGCC GGGTCGAGGC CGATCTTTTC CGCATCTTCA
TACTGGCACT GCTATTTCAA CTCCAACCGG CCCAGCTCCG GCTAGAAAAG GCGTAGAAGT

       370        380        390        400        410        420
TAGGTGAGCG CGATGTTGCT GGCGCCGGTA TCGACCAGCA TGCTGATGTC CTTGCCGTCG
ATCCACTCGC GCTACAACGA CCGCGGCCAT AGCTGGTCGT ACGACTACAG GAACGGCAGC

       430        440        450        460        470        480
ACCGTCGCAG TGGTCTCGAA ATGACCGTTC AGCATCTTCT GCAGCACCAC TTCCTGCTGT
TGGCAGCGTC ACCAGAGCTT TACTGGCAAG TCGTAGAAGA CGTCGTGGTG AAGGACGACA

       490        500        510        520        530        540
CCCTCGCTGT CAGTGATGAT GGTGGCGCGG CCGGGGATGA GGCCGGCGAG CAGGCGGTTA
GGGAGCGACA GTCACTACTA CCACCGCGCC GGCCCCTACT CCGGCCGCTC GTCCGCCAAT

       550        560        570        580        590        600
CCGAAGCCCT CCAACTCGAA GCGGTAGACA TAGGCCGAGA CCAGCGCCAG AACGACGAAG
GGCTTCGGGA GGTTGAGCTT CGCCATCTGT ATCCGGCTCT GGTCGCGGTC TTGCTGCTTC
```

*FIG. 33A*

```
       610        620        630        640        650        660
AGCCAGATGG CGATCTGACG CAGGCCTTCG CCGAAGCGGT GGCGGCTCTG CAGGATGCCG
TCGGTCTACC GCTAGACTGC GTCCGGAAGC GGCTTCGCCA CCGCCGAGAC GTCCTACGGC

       670        680        690        700        710        720
GCGCCGATCA GCGTGGCGAT GGCGCCGAGC GAGACCAGTT GCCCGAACTG GTCATTGGCA
CGCGGCTAGT CGCACCGCTA CCGCGGCTCG CTCTGGTCAA CGGGCTTGAC CAGTAACCGT

       730        740        750        760        770        780
AGCCCCATGG TGCGGCCGGT GTCGTGGTTG ATGATCAGCA GGATGAGGCC GATGGCCAGG
TCGGGGTACC ACGCCGGCCA CAGCACCAAC TACTAGTCGT CCTACTCCGG CTACCGGTCC

       790        800        810        820        830        840
ATCGAGAGCA GGATGGCAAG ACGGGTCATG CTTCGCCGCG TTCCCTCGCC ATGCGCGTGC
TAGCTCTCGT CCTACCGTTC TGCCCAGTAC GAAGCGGCGC AAGGGAGCGG TACGCGCACG

       850        860        870        880        890        900
GTCGGGTTTC GCGCCGCGGC TTGCGTTCGA CGGTCTCAAG CCGTGCAGGC AACGCGCTCA
CAGCCCAAAG CGCGGCGCCG AACGCAAGCT GCCAGAGTTC GGCACGTCCG TTGCGCGAGT

       910        920        930        940        950        960
TGATCGCGCG GCGTTCGGCA TCGGTATAGA GCGTCCAGCG TCCGACTTCG TCGCGGGTAC
ACTAGCGCGC CGCAAGCCGT AGCCATATCT CGCAGGTCGC AGGCTGAAGC AGCGCCCATG

       970        980        990       1000       1010       1020
GGCCGCAGCC GAAACAGTAG CCGGTCTTGT CATCGATCGA ACAGACGAGA ATGCAGGGAG
CCGGCGTCGG CTTTGTCATC GGCCAGAACA GTAGCTAGCT TGTCTGCTCT TACGTCCCTC

      1030       1040       1050       1060       1070       1080
ATTCCATGGG CGTGCTCAGT TTTCCCTTGA TATATCGATG TTTCAAACCG TCAGCGCAAG
TAAGGTACCC GCACGAGTCA AAAGGGAACT ATATAGCTAC AAAGTTTGGC AGTCGCGTTC

      1090       1100       1110       1120       1130       1140
GGCACCGAGC ACGGCGATTT CGGTCAGTTG CTGCGTCGCC CCGATCGTGT CGCCCGTTTG
CCGTGGCTCG TGCCGCTAAA GCCAGTCAAC GACGCAGCGG GGCTAGCACA GCGGGCAAAC

      1150       1160       1170       1180       1190       1200
TCCGCCGATC TTGCGCATCG CCAGCCGAGC GAAGCCCTTG ACCGTGGCAA GGAATGCGAC
AGGCGGCTAG AACGCGTAGC GGTCGGCTCG CTTCGGGAAC TGGCACCGTT CCTTACGCTG
```

*FIG. 33B*

```
      1210       1220       1230       1240       1250       1260
GAGCGCCGCG ATGACGCCGA GCGCCGGGAC CTGCGCGAGA TAGAAGAGCA GCATTGCGAC
CTCGCGGCGC TACTGCGGCT CGCGGCCCTG GACGCGCTCT ATCTTCTCGT CGTAACGCTG

      1270       1280       1290       1300       1310       1320
AAGAAGTCCG AAGGCAAGCG CGAAGCGCGT GGCCGCCGGT TCCGGCTCGC CAGCCGAGGC
TTCTTCAGGC TTCCGTTCGC GCTTCGCGCA CCGGCGGCCA AGGCCGAGCG GTCGGCTCCG

      1330       1340       1350       1360       1370       1380
CGCGACGCCG CTGCTGCGCG CCGGCGGAAG CGACGACCAG TGCCAGACCA TGGCGGCGCG
GCGCTGCGGC GACGACGCGC GGCCGCCTTC GCTGCTGGTC ACGGTCTGGT ACCGCCGCGC

      1390       1400       1410       1420       1430       1440
GCTGAGGCAC GCTGCGCCAA GGATCGCCAT GGCGGCGCCC AGCGGCGAAA AGAGCGGCAG
CGACTCCGTG CGACGCGGTT CCTAGCGGTA CCGCCGCGGG TCGCCGCTTT TCTCGCCGTC

      1450       1460       1470       1480       1490       1500
GATCGAGGCG AACGCCGAGA CGCGCAGGCC GAAGGAGAGG ATGAGGGCGA CGGCCGCATA
CTAGCTCCGC TTGCGGCTCT GCGCGTCCGG CTTCCTCTCC TACTCCCGCT GCCGGCGTAT

      1510       1520       1530       1540       1550       1560
GGTGCCGATG CGGCTGTCCT TCATGATCGC AAGCGCCGCT TCGCGGTCGC GACCGCCGCC
CCACGGCTAC GCCGACAGGA AGTACTAGCG TTCGCGGCGA AGCGCCAGCG CTGGCGGCGG

      1570       1580       1590       1600       1610       1620
AAAGCCATCG GCCGTGTCGC CAAGCCCGTC TTCGTGCAGT GCGCCGGTGA CAAGCGCCTG
TTTCGGTAGC CGGCACAGCG GTTCGGGCAG AAGCACGTCA CGCGGCCACT GTTCGCGGAC

      1630       1640       1650       1660       1670       1680
GATGGCGACG ACGACAAAGG CGGCAAAGAG CGAGCTCACC TGCAGCGCCA TGAGGGCCAT
CTACCGCTGC TGCTGTTTCC GCCGTTTCTC GCTCGAGTGG ACGTCGCGGT ACTCCCGGTA

      1690       1700       1710       1720       1730       1740
GGCGACGGCC GCCGATGGCA GTGCGATCGC CAGGCCGGCG AACGGGAAGG CGCGCACGGC
CCGCTGCCGG CGGCTACCGT CACGCTAGCG GTCCGGCCGC TTGCCCTTCC GCGCGTGCCG

      1750       1760       1770       1780       1790       1800
ACGGCTCAAG CGCCCGTCAT AACCTTCGAA ATGACGCGCA GGCATCGGGA TGCGGCTGAG
TGCCGAGTTC GCGGGCAGTA TTGGAAGCTT TACTGCGCGT CCGTAGCCCT ACGCCGACTC
```

*FIG. 33C*

```
      1810       1820       1830       1840       1850       1860
AAAGCCGATC GACCGCGCCA CATCGTCACA GAAATCGCCA ACGAAGCCCA TGGCTCCTCC
TTTCGGCTAG CTGGCGCGGT GTAGCAGTGT CTTTAGCGGT TGCTTCGGGT ACCGAGGAGG

      1870       1880       1890       1900       1910       1920
AAGGTTGCGG CCATTGACCC GGCCGCTGCC AAACTCGCCG ACTGCGGCGA GTCTCGCAAG
TTCCAACGCC GGTAACTGGG CCGGCGACGG TTTGAGCGGC TGACGCCGCT CAGAGCGTTC

      1930       1940       1950       1960       1970       1980
CCGGGCGGGC GCACCCGCGA GGGCCGCGCA CACTTTTCCC AGACCTTTCA TAGGCCGTCT
GGCCCGCCCG CGTGGGCGCT CCCGGCGCGT GTGAAAAGGG TCTGGAAAGT ATCCGGCAGA

      1990       2000       2010       2020       2030       2040
GCGACCGCTC GCGGATCGAG ACGGCGACGC CGATTGGCGC AAATGTCGTT GCCCGAATTT
CGCTGGCGAG CGCCTAGCTC TGCCGCTGCG GCTAACCGCG TTTACAGCAA CGGGCTTAAA

      2050       2060       2070       2080       2090       2100
TCGGCGCCCT CTATGAGGGG CGTAGATAGA GCTTCACGAT GATGCAAGGA TTCCTCCCAT
AGCCGCGGGA GATACTCCCC GCATCTATCT CGAAGTGCTA CTACGTTCCT AAGGAGGGTA

      2110       2120       2130       2140       2150       2160
GAGTGCCAGC GGCCTGCCGT TTGATGATTT TCGCGAATTG TTGCGCAACC TGCCGGGCCC
CTCACGGTCG CCGGACGGCA AACTACTAAA AGCGCTTAAC AACGCGTTGG ACGGCCCGGG

      2170       2180       2190       2200       2210       2220
GGATGCGGCA GCCCTCGTTG CCGCGCGGGA GCGGGACGCC CAGCTGACGA AGCCGCCGGG
CCTACGCCGT CGGGAGCAAC GGCGCGCCCT CGCCCTGCGG GTCGACTGCT TCGGCGGCCC

      2230       2240       2250       2260       2270       2280
CGCGCTCGGC CGCCTCGAGG AAATCGCCTT CTGGCTCGCC GCCTGGACGG GCAAGGCGCC
GCGCGAGCCG GCGGAGCTCC TTTAGCGGAA GACCGAGCGG CGGACCTGCC CGTTCCGCGG

      2290       2300       2310       2320       2330       2340
GGTGGTCAAC CGGCCGCTGG TGGCGATCTT TGCCGGCAAC CACGGCGTCA CCCGCCAGGG
CCACCAGTTG GCCGGCGACC ACCGCTAGAA ACGGCCGTTG GTGCCGCAGT GGGCGGTCCC

      2350       2360       2370       2380       2390       2400
GGTGACCCCG TTCCCGTCAT CCGTCACCGC ACAGATGGTC GAGAATTTTG CCGCCGGTGG
CCACTGGGGC AAGGGCAGTA GGCAGTGGCG TGTCTACCAG CTCTTAAAAC GGCGGCCACC
```

*FIG. 33D*

```
       2410       2420       2430       2440       2450       2460
CGCTGCGATC AACCAGATCT GCGTCAGCCA CGACCTCGGG CTGAAGGTCT TCGACCTCGC
GCGACGCTAG TTGGTCTAGA CGCAGTCGGT GCTGGAGCCC GACTTCCAGA AGCTGGAGCG

       2470       2480       2490       2500       2510       2520
ACTCGAATAC CCGACCGGTG ATATCACCGA GGAAGCCGCG CTGTCCGAGC GCGATTGCGC
TGAGCTTATG GGCTGGCCAC TATAGTGGCT CCTTCGGCGC GACAGGCTCG CGCTAACGCG

       2530       2540       2550       2560       2570       2580
CGCGACCATG GCCTTTGGCA TGGAGGCGAT TGCCGGCGGC ACGGATCTTC TGTGCATCGG
GCGCTGGTAC CGGAAACCGT ACCTCCGCTA ACGGCCGCCG TGCCTAGAAG ACACGTAGCC

       2590       2600       2610       2620       2630       2640
CGAAATGGGC ATCGGCAACA CCACGATCGC GGCCGCGATC AATCTCGGCC TTTATGGTGG
GCTTTACCCG TAGCCGTTGT GGTGCTAGCG CCGGCGCTAG TTAGAGCCGG AAATACCACC

       2650       2660       2670       2680       2690       2700
CACGGCCGAA GAATGGGTCG GTCCGGGTAC CGGCTCCGAG GGCGAGGTGC TGAAGCGCAA
GTGCCGGCTT CTTACCCAGC CAGGCCCATG GCCGAGGCTC CCGCTCCACG ACTTCGCGTT

       2710       2720       2730       2740       2750       2760
GATCGCCGCG GTCGAAAAGG CCGTGGCGCT GCATCGCGAT CACCTGTCCG ATCCGCTCGA
CTAGCGGCGC CAGCTTTTCC GGCACCGCGA CGTAGCGCTA GTGGACAGGC TAGGCGAGCT

       2770       2780       2790       2800       2810       2820
ACTGATGCGT CGCCTCGGCG GTCGTGAGAT CGCGGCCATG GCTGGCGCCA TCCTGGCCGC
TGACTACGCA GCGGAGCCGC CAGCACTCTA GCGCCGGTAC CGACCGCGGT AGGACCGGCG

       2830       2840       2850       2860       2870       2880
CCGCGTCCAG AAGGTACCTG TCATCATCGA CGGCTACGTG GCGACCGCTG CGGCTTCGAT
GGCGCAGGTC TTCCATGGAC AGTAGTAGCT GCCGATGCAC CGCTGGCGAC GCCGAAGCTA

       2890       2900       2910       2920       2930       2940
CCTGAAGGCG GCCAACCCGT CGGCCCTCGA CCATTGCCTG ATCGGCCATG TTTCGGGCGA
GGACTTCCGC CGGTTGGGCA GCCGGGAGCT GGTAACGGAC TAGCCGGTAC AAAGCCCGCT

       2950       2960       2970       2980       2990       3000
ACCGGGGCAT CTGCGCGCGA TCGAGAAGCT CGGCAAGACG CCGCTGCTGG CACTCGGCAT
TGGCCCCGTA GACGCGCGCT AGCTCTTCGA GCCGTTCTGC GGCGACGACC GTGAGCCGTA
```

*FIG. 33E*

```
      3010       3020       3030       3040       3050       3060
GCGGCTTGGC GAAGGCACGG GCGCGGCCCT TGCCGCCGGT ATCGTCAAGG CGGCGGCCGC
CGCCGAACCG CTTCCGTGCC CGCGCCGGGA ACGGCGGCCA TAGCAGTTCC GCCGCCGGCG

      3070       3080       3090       3100       3110       3120
TTGCCACAGC GGCATGGCGA CCTTTGCCCA GGCCGGCGTC AGCAACAAGG AATAGTGAAG
AACGGTGTCG CCGTACCGCT GGAAACGGGT CCGGCCGCAG TCGTTGTTCC TTATCACTTC

      3130       3140       3150       3160       3170       3180
TTCCGGCCGG GCTTTGCAGG AAGGCCGGCC GGTTTCTGTC CAAGGCCTGT CACGGGCGCG
AAGGCCGGCC CGAAACGTCC TTCCGGCCGG CCAAAGACAG GTTCCGGACA GTGCCCGCGC

      3190       3200       3210       3220       3230       3240
AAGCTGTCGC GTGCCGGGCC TTGATGGATG CGTCCTTCTC GCCTATCCAA AGCGCAAATG
TTCGACAGCG CACGGCCCGG AACTACCTAC GCAGGAAGAG CGGATAGGTT TCGCGTTTAC

      3250       3260       3270       3280       3290       3300
CGCGCCCTAG CTATAGTCTT GGGTGCCTGC AACCGAGACC GCCTTGCATT CGCCTCAATC
GCGCGGGATC GATATCAGAA CCCACGGACG TTGGCTCTGG CGGAACGTAA GCGGAGTTAG

      3310       3320       3330       3340       3350       3360
ACGATGTCGA AGCAAGCACA GTTTCAAGCC CTGTCGAGAC GAAATGGACG CCAAGAACAC
TGCTACAGCT TCGTTCGTGT CAAAGTTCGG GACAGCTCTG CTTTACCTGC GGTTCTTGTG

      3370       3380       3390       3400       3410       3420
CACGCACCGC ATTGGACAGA CGGGTCCTGT CGAGAAGCAG ACCGGCATTC GGCATCTCTT
GTGCGTGGCG TAACCTGTCT GCCCAGGACA GCTCTTCGTC TGGCCGTAAG CCGTAGAGAA

      3430       3440       3450       3460       3470       3480
TGCCGCTGCG AGCTATTCGC TCGGCGGCGC CAAGCGGCTG ATCGGCGAGG CTGCCTTTCG
ACGGCGACGC TCGATAAGCG AGCCGCCGCG GTTCGCCGAC TAGCCGCTCC GACGGAAAGC

      3490       3500       3510       3520       3530       3540
CCACGAGCTG ATCGCCTTTG CCGCCGCGAT GATCGCTTTC ATCATCGTCG GCGCAACCTT
GGTGCTCGAC TAGCGGAAAC GGCGGCGCTA CTAGCGAAAG TAGTAGCAGC CGCGTTGGAA

      3550       3560       3570       3580       3590       3600
CTTCCAATAT GTGGCGATGG CGATCCTGTT CCTGCTGATG ATGGCCTTCG AGGCGATCAA
GAAGGTTATA CACCGCTACC GCTAGGACAA GGACGACTAC TACCGGAAGC TCCGCTAGTT
```

FIG. 33F

```
      3610       3620       3630       3640       3650       3660
CACGGCAATC GAGGAAATTG TCGATCGCGT TTCTCCCGAA ATCTCGGAAA TGGGTAAGAA
GTGCCGTTAG CTCCTTTAAC AGCTAGCGCA AAGAGGGCTT TAGAGCCTTT ACCCATTCTT

      3670       3680       3690       3700       3710       3720
CGCCAAGGAT CTCGGCTCCT TCGCCTGCCT CTGCCTGATT GTCGCCAACG GTGTCTATGC
GCGGTTCCTA GAGCCGAGGA AGCGGACGGA GACGGACTAA CAGCGGTTGC CACAGATACG

      3730       3740       3750       3760       3770       3780
CGCCTATGTC GTGATCTTCG ACGGCTTCAT GAACTGACCG GCTAGCGGGC CGGCGCCTTC
GCGGATACAG CACTAGAAGC TGCCGAAGTA CTTGACTGGC CGATCGCCCG GCCGCGGAAG

      3790       3800       3810       3820       3830       3840
ACCCGATAAA GCACATGCGG ACGCAGCGGG TTGCCCCCGG GTACCGTGAC GTCGTCGAAA
TGGGCTATTT CGTGTACGCC TGCGTCGCCC AACGGGGGCC CATGGCACTG CAGCAGCTTT

      3850       3860       3870       3880       3890       3900
TCATCAGCCG GATCC
AGTAGTCGGC CTAGG
```

*FIG. 33G*

A = ATG

*: STOP

CS: COMPLEMENTARY STRAND

NAME = COBS

FIRST RESIDUE = 1
LAST RESIDUE = 332

| | | | NUMBER | NO. % | WEIGHT | WEIGHT % |
|---|---|---|---|---|---|---|
| 1 | PHE | F | 15 | 4.52 | 2206.03 | 5.97 |
| 2 | LEU | L | 29 | 8.73 | 3279.44 | 8.87 |
| 3 | ILE | I | 20 | 6.02 | 2261.68 | 6.12 |
| 4 | MET | M | 7 | 2.11 | 917.28 | 2.48 |
| 5 | VAL | V | 33 | 9.94 | 3269.26 | 8.85 |
| 6 | SER | S | 15 | 4.52 | 1305.48 | 3.53 |
| 7 | PRO | P | 11 | 3.31 | 1067.58 | 2.89 |
| 8 | THR | T | 24 | 7.23 | 2425.14 | 6.56 |
| 9 | ALA | A | 32 | 9.64 | 2273.19 | 6.15 |
| 10 | TYR | Y | 9 | 2.71 | 1467.57 | 3.97 |
| 11 | * | * | 0 | 0.00 | 0.00 | 0.00 |
| 12 | HIS | H | 10 | 3.01 | 1370.59 | 3.71 |
| 13 | GLN | Q | 10 | 3.01 | 1280.59 | 3.46 |
| 14 | ASN | N | 12 | 3.61 | 1368.52 | 3.70 |
| 15 | LYS | K | 13 | 3.92 | 1665.23 | 4.51 |
| 16 | ASP | D | 28 | 8.43 | 3220.75 | 8.71 |
| 17 | GLU | E | 15 | 4.52 | 1935.64 | 5.24 |
| 18 | CYS | C | 3 | 0.90 | 309.03 | 0.84 |
| 19 | TRP | W | 4 | 1.20 | 744.32 | 2.01 |
| 20 | ARG | R | 22 | 6.63 | 3434.22 | 9.29 |
| 21 | GLY | G | 20 | 6.02 | 1140.43 | 3.09 |
| 22 | - | - | 0 | 0.00 | 0.00 | 0.00 |

RESIDUES = 332
MOLECULAR WEIGHT (MONOISOTOPIC) = 36960.0000
MOLECULAR WEIGHT (AVERAGE) = 36983.1797
INDEX OF POLARITY (%) = 44.88
ISOELECTRIC POINT = 6.34
OD 260 (1 mg/ml) = 0.611 OD 280 (1 mg/ml) = 0.891

HYDROPHILICITY
COBS FROM 1 TO 332 cobS GENE (SEQ ID NO: 31) AND COBS PROTEIN (SEQ ID NO: 32)
SEQUENCE OF THE 4749-BP SalI-SalI-SalI-SalI-SalI-BglI FRAGMENT
FROM 1512 TO 2510

```
MetMetSerLysIleAspLeuAspIleSerAsnLeuProAspThrThrIleSerValArgGluValPheGlyIle
ATGATGAGCAAGATTGACCTCGACATTTCCAACCTCCCCGACACCACGATTTCCGTCCGGGAGGTTTTCGGTATT
  1521      1531      1541      1551      1561      1571      1581
AspThrAspLeuArgValProAlaTyrSerLysGlyAspAlaTyrValProAspLeuAspProAspTyrLeuPhe
GATACGGATTTGCGCGTTCCTGCCTATTCGAAGGGCGACGCCTATGTCCCGGATCTGGATCCGGACTACCTCTTC
  1596      1606      1616      1626      1636      1646      1656
AspArgGluThrThrLeuAlaIleLeuAlaGlyPheAlaHisAsnArgArgValMetValSerGlyTyrHisGly
GACCGCGAAACGACGCTCGCCATTCTCGCAGGCTTCGCCCACAACCGACGCGTGATGGTGTCGGGCTATCACGGC
  1671      1681      1691      1701      1711      1721      1731
ThrGlyLysSerThrHisIleGluGlnValAlaAlaArgLeuAsnTrpProCysValArgValAsnLeuAspSer
ACCGGCAAGTCCACCCATATCGAGCAGGTCGCCGCGCGCCTCAACTGGCCGTGCGTGCGCGTCAACCTCGATAGC
  1746      1756      1766      1776      1786      1796      1806
HisValSerArgIleAspLeuValGlyLysAspAlaIleValValLysAspGlyLeuGlnValThrGluPheLys
CATGTCAGCCGTATCGACCTCGTCGGCAAGGACGCGATCGTCGTCAAGGACGGCCTGCAGGTCACCGAATTCAAG
  1821      1831      1841      1851      1861      1871      1881
AspGlyIleLeuProTrpAlaTyrGlnHisAsnValAlaLeuValPheAspGluTyrAspAlaGlyArgProAsp
GACGGCATCCTGCCCTGGGCCTACCAGCACAATGTCGCGCTCGTCTTCGACGAATACGATGCCGGCCGCCCGGAC
  1896      1906      1916      1926      1936      1946      1956
ValMetPheValIleGlnArgValLeuGluSerSerGlyArgLeuThrLeuLeuAspGlnSerArgValIleArg
GTCATGTTCGTCATCCAGCGCGTGCTGGAATCCTCCGGCCGCCTGACGCTGCTCGACCAGAGCCGTGTCATCCGT
  1971      1981      1991      2001      2011      2021      2031
ProHisProAlaPheArgLeuPheAlaThrAlaAsnThrValGlyLeuGlyAspThrThrGlyLeuTyrHisGly
CCGCACCCGGCCTTCCGCCTGTTTGCGACCGCCAACACCGTCGGCCTCGGCGACACGACCGGCCTCTATCACGGC
  2046      2056      2066      2076      2086      2096      2106
ThrGlnGlnIleAsnGlnAlaGlnMetAspArgTrpSerIleValThrThrLeuAsnTyrLeuProHisAspLys
ACGCAGCAGATCAACCAGGCGCAGATGGACCGCTGGTCGATCGTCACCACGCTGAACTACCTGCCGCACGACAAG
  2121      2131      2141      2151      2161      2171      2181
GluValAspIleValAlaAlaLysValLysGlyPheThrAlaAspLysGlyArgGluThrValSerLysMetVal
GAAGTCGACATCGTCGCCGCCAAGGTCAAGGGCTTCACCGCCGACAAGGGCCGCGAGACCGTCTCCAAGATGGTA
  2196      2206      2216      2226      2236      2246      2256
ArgValAlaAspLeuThrArgAlaAlaPheIleAsnGlyAspLeuSerThrValMetSerProArgThrValIle
CGTGTCGCCGACCTCACGCGCGCAGCCTTCATCAATGGCGATCTCTCGACTGTCATGAGCCCGCGTACGGTCATC
  2271      2281      2291      2301      2311      2321      2331
ThrTrpAlaGluAsnAlaHisIlePheGlyAspIleAlaPheAlaPheArgValThrPheLeuAsnLysCysAsp
ACCTGGGCCGAGAACGCCCACATCTTCGGCGACATCGCTTTCGCCTTCCGCGTGACCTTCCTCAACAAGTGCGAC
  2346      2356      2366      2376      2386      2396      2406
GluLeuGluArgAlaLeuValAlaGluHisTyrGlnArgAlaPheGlyIleGluLeuLysGluCysAlaAlaAsn
GAGCTGGAGCGGGCGCTGGTCGCCGAGCACTACCAGCGCGCCTTCGGCATCGAGCTGAAGGAATGCGCTGCCAAC
  2421      2431      2441      2451      2461      2471      2481
IleValLeuGluAlaThrAla***
ATCGTGCTCGAAGCCACCGCCTGA
  2496      2506
```

FIG. 40B

NAME = COBT

FIRST RESIDUE = 1
LAST RESIDUE = 631

| | | | NUMBER | NO. % | WEIGHT | WEIGHT % |
|---|---|---|---|---|---|---|
| 1 | PHE | F | 16 | 2.54 | 2353.09 | 3.35 |
| 2 | LEU | L | 56 | 8.87 | 6332.71 | 9.01 |
| 3 | ILE | I | 29 | 4.60 | 3279.44 | 4.67 |
| 4 | MET | M | 18 | 2.85 | 2358.73 | 3.36 |
| 5 | VAL | V | 31 | 4.91 | 3071.12 | 4.37 |
| 6 | SER | S | 33 | 5.23 | 2872.06 | 4.09 |
| 7 | PRO | P | 24 | 3.80 | 2329.27 | 3.31 |
| 8 | THR | T | 28 | 4.44 | 2829.34 | 4.03 |
| 9 | ALA | A | 75 | 11.89 | 5327.78 | 7.58 |
| 10 | TYR | Y | 8 | 1.27 | 1304.51 | 1.86 |
| 11 | * | * | 0 | 0.00 | 0.00 | 0.00 |
| 12 | HIS | H | 7 | 1.11 | 959.41 | 1.36 |
| 13 | GLN | Q | 29 | 4.60 | 3713.70 | 5.28 |
| 14 | ASN | N | 22 | 3.49 | 2508.94 | 3.57 |
| 15 | LYS | K | 25 | 3.96 | 3202.37 | 4.56 |
| 16 | ASP | D | 49 | 7.77 | 5636.32 | 8.02 |
| 17 | GLU | E | 67 | 10.62 | 8645.85 | 12.30 |
| 18 | CYS | C | 5 | 0.79 | 515.05 | 0.73 |
| 19 | TRP | W | 6 | 0.95 | 1116.48 | 1.59 |
| 20 | ARG | R | 61 | 9.67 | 9522.17 | 13.55 |
| 21 | GLY | G | 42 | 6.66 | 2394.90 | 3.41 |
| 22 | - | - | 0 | 0.00 | 0.00 | 0.00 |

RESIDUES = 631
MOLECULAR WEIGHT (MONOISOTOPIC) = 70291.3984
MOLECULAR WEIGHT (AVERAGE) = 70334.7656
INDEX OF POLARITY (%) = 50.87
ISOELECTRIC POINT = 5.10
OD 260 (1mg/ml) = 0.423 OD 280 (1mg/ml) = 0.610 cobT GENE (SEQ ID NO: 33) AND COBT PROTEIN (SEQ ID NO: 44)
SEQUENCE OF THE 4749-BP SalI-SalI-SalI-SalI-SalI-BglI FRAGMENT
FROM 2616 TO 4511

```
ValSerSerAsnSerLysAlaLysProThrThrArgGluAsnAlaAlaGluProPheLysArgAlaLeuSerGly
GTGAGCTCGAATTCGAAGGCAAAGCCAACCACGCGCGAGAATGCTGCGGAACCGTTCAAGCGGGCGCTTTCCGGC
      2625      2635      2645      2655      2665      2675      2685
CysIleArgSerIleAlaGlyAspAlaGluValGluValAlaPheAlaAsnGluArgProGlyMetThrGlyGlu
TGCATCCGATCGATCGCGGGCGATGCCGAGGTGGAAGTCGCCTTCGCCAACGAGCGGCCGGGCATGACCGGCGAA
      2700      2710      2720      2730      2740      2750      2760
ArgIleArgLeuProGluLeuSerLysArgProThrLeuGlnGluLeuAlaValThrArgGlyLeuGlyAspSer
CGCATCCGTCTGCCGGAACTTTCCAAGCGCCCGACCCTGCAGGAACTTGCCGTGACCCGCGGGCTCGGTGACAGC
      2775      2785      2795      2805      2815      2825      2835
MetAlaLeuArgLysAlaCysThrHisAlaArgIleGlnArgThrMetSerProGlnGlyAlaAspAlaArgAla
ATGGCGCTGCGCAAGGCCTGTACGCATGCGCGGATCCAGCGCACCATGTCGCCGCAAGGGGCGGACGCCCGCGCG
      2850      2860      2870      2880      2890      2900      2910
IlePheAspAlaValGluGlnAlaArgValGluAlaIleGlySerLeuArgMetAlaGlyValAlaLysAsnLeu
ATCTTCGATGCGGTGGAGCAGGCTCGTGTCGAGGCGATCGGGTCGTTGCGCATGGCGGGTGTCGCCAAGAACCTC
      2925      2935      2945      2955      2965      2975      2985
AsnValMetLeuGluGluLysTyrAlaLysAlaAsnPheAlaThrIleGluArgGlnAlaAspAlaProLeuGly
AACGTCATGCTCGAAGAGAAATACGCCAAGGCGAATTTCGCAACGATCGAGCGCCAGGCGGACGCGCCGCTCGGC
      3000      3010      3020      3030      3040      3050      3060
GluAlaValAlaLeuLeuValArgGluLysLeuThrGlyGlnLysProProAlaSerAlaGlyLysValLeuAsp
GAGGCCGTAGCGCTGCTGGTGCGCGAGAAGCTGACGGGCCAGAAGCCGCCGGCGTCTGCCGGCAAGGTGCTCGAC
      3075      3085      3095      3105      3115      3125      3135
LeuTrpArgGluPheIleGluGlyLysAlaAlaGlyAspIleGluHisLeuSerSerThrIleAsnAsnGlnGln
CTCTGGCGCGAGTTCATCGAGGGCAAGGCTGCCGGCGACATTGAGCACCTGTCGTCGACGATCAACAACCAGCAG
      3150      3160      3170      3180      3190      3200      3210
AlaPheAlaArgValValArgAspMetLeuThrSerMetGluValAlaGluLysTyrGlyAspAspAspAsnGlu
GCCTTTGCCCGGGTCGTTCGCGACATGCTGACCTCGATGGAAGTCGCCGAGAAATACGGTGACGACGACAACGAG
      3225      3235      3245      3255      3265      3275      3285
ProAspGluGlnGluSerGluThrAspGluAspGlnProArgSerGlnGluGlnAspGluAsnAlaSerAspGlu
CCGGACGAGCAGGAAAGCGAGACCGACGAAGACCAGCCGCGCAGCCAGGAGCAGGACGAGAACGCCAGCGACGAG
      3300      3310      3320      3330      3340      3350      3360
GluAlaGlyAspAspAlaAlaProAlaAspGluAsnGlnAlaAlaGluGluGlnMetGluGluGlyGluMetAsp
GAAGCCGGCGACGATGCCGCACCCGCCGACGAGAACCAGGCTGCCGAAGAGCAGATGGAAGAAGGCGAGATGGAC
      3375      3385      3395      3405      3415      3425      3435
GlyAlaGluIleSerAspAspAspLeuGlnAspGluGlyAspGluAspSerGluThrProGlyGluValLysArg
GGCGCGGAGATCTCCGACGACGATCTCCAGGACGAAGGCGACGAGGACAGCGAAACGCCCGGCGAGGTCAAGCGT
      3450      3460      3470      3480      3490      3500      3510
```

FIG. 40D

ProAsnGlnProPheAlaAspPheAsnGluLysValAspTyrAlaValPheThrArgGluPheAspGluThrIle
CCGAACCAGCCCTTCGCCGACTTCAACGAGAAGGTCGACTACGCCGTCTTCACCCGCGAGTTCGACGAGACGATT
3525 3535 3545 3555 3565 3575 3585

AlaSerGluGluLeuCysAspGluAlaGluLeuAspArgLeuArgAlaPheLeuAspLysGlnLeuAlaHisLeu
GCCTCGGAAGAGCTTTGCGACGAGGCCGAGCTCGACCGGCTGCGCGCCTTCCTCGACAAGCAGCTTGCCCATCTT
3600 3610 3620 3630 3640 3650 3660

GlnGlyAlaValGlyArgLeuAlaAsnArgLeuGlnArgArgLeuMetAlaGlnGlnAsnArgSerTrpGluPhe
CAAGGCGCGGTCGGCCGCCTTGCCAACCGGCTGCAGCGCCGCCTGATGGCGCAGCAGAACCGCTCCTGGGAGTTC
3675 3685 3695 3705 3715 3725 3735

AspLeuGluGluGlyTyrLeuAspSerAlaArgLeuGlnArgIleIleIleAspProMetGlnProLeuSerPhe
GATCTCGAAGAGGGGTATCTCGATTCGGCGCGGCTTCAGCGCATCATCATCGATCCGATGCAGCCGCTTTCCTTC
3750 3760 3770 3780 3790 3800 3810

LysArgGluLysAspThrAsnPheArgAspThrValValThrLeuLeuIleAspAsnSerGlySerMetArgGly
AAGCGCGAAAAGGACACCAACTTCCGCGATACCGTCGTGACGCTGCTGATCGACAATTCCGGCTCGATGCGCGGC
3825 3835 3845 3855 3865 3875 3885

ArgProIleThrValAlaAlaThrCysAlaAspIleLeuAlaArgThrLeuGluArgCysGlyValLysValGlu
CGTCCGATCACGGTTGCCGCCACCTGCGCCGATATCCTGGCGCGCACGCTCGAGCGCTGCGGCGTCAAGGTCGAG
3900 3910 3920 3930 3940 3950 3960

IleLeuGlyPheThrThrLysAlaTrpLysGlyGlyGlnSerArgGluLysTrpLeuAlaGlyGlyLysProGln
ATCCTCGGTTTTACCACCAAGGCGTGGAAGGGTGGGCAGTCACGCGAGAAGTGGCTGGCCGGCGGCAAGCCACAG
3975 3985 3995 4005 4015 4025 4035

AlaProGlyArgLeuAsnAspLeuArgHisIleValTyrLysSerAlaAspAlaProTrpArgArgAlaArgArg
GCCCCGGGTCGCCTCAACGACCTGCGACACATCGTCTACAAGTCTGCCGACGCTCCGTGGCGCCGGGCACGACGC
4050 4060 4070 4080 4090 4100 4110

AsnLeuGlyLeuMetMetArgGluGlyLeuLeuLysGluAsnIleAspGlyGluAlaLeuIleTrpAlaHisGlu
AATCTCGGCCTGATGATGCGGGAAGGCCTGCTCAAGGAAAACATCGACGGCGAGGCGTTGATTTGGGCGCATGAG
4125 4135 4145 4155 4165 4175 4185

ArgLeuMetAlaArgArgGluGlnArgArgIleLeuMetMetIleSerAspGlyAlaProValAspAspSerThr
CGGCTGATGGCGCGGCGCGAACAGCGGCGCATCCTGATGATGATTTCGGACGGCGCGCCGGTCGACGACTCGACG
4200 4210 4220 4230 4240 4250 4260

LeuSerValAsnProGlyAsnTyrLeuGluArgHisLeuArgAlaValIleGluGlnIleGluThrArgSerPro
CTGTCGGTCAATCCAGGAAACTATCTGGAGCGTCACCTGCGCGCGGTCATCGAGCAGATCGAAACGCGCTCGCCG
4275 4285 4295 4305 4315 4325 4335

ValGluLeuLeuAlaIleGlyIleGlyHisAspValThrArgTyrTyrArgArgAlaValThrIleValAspAla
GTGGAACTGCTGGCGATCGGTATCGGCCACGACGTGACGCGCTACTATCGCCGTGCCGTCACCATCGTCGATGCC
4350 4360 4370 4380 4390 4400 4410

AspGluLeuAlaGlyAlaMetThrGluGlnLeuAlaAlaLeuPheGluAspGluSerGlnArgArgGlySerSer
GATGAGCTTGCCGGCGCGATGACCGAACAGCTGGCCGCACTCTTCGAGGACGAAAGCCAGCGCCGCGGTTCTTCG
4425 4435 4445 4455 4465 4475 4485

ArgLeuArgArgAlaGly***
CGTCTTCGCCGCGCCGGGTGA
4500 4510

FIG. 40E

NAME = COBX FIRST RESIDUE = 1
LAST RESIDUE = 93

| | | | NUMBER | NO. % | WEIGHT | WEIGHT % |
|---|---|---|---|---|---|---|
| 1 | PHE | F | 3 | 3.23 | 441.21 | 4.29 |
| 2 | LEU | L | 8 | 8.60 | 904.67 | 8.80 |
| 3 | ILE | I | 5 | 5.38 | 565.42 | 5.50 |
| 4 | MET | M | 3 | 3.23 | 393.12 | 3.82 |
| 5 | VAL | V | 5 | 5.38 | 495.34 | 4.82 |
| 6 | SER | S | 6 | 6.45 | 522.19 | 5.08 |
| 7 | PRO | P | 6 | 6.45 | 582.32 | 5.66 |
| 8 | THR | T | 5 | 5.38 | 505.24 | 4.92 |
| 9 | ALA | A | 10 | 10.75 | 710.37 | 6.91 |
| 10 | TYR | Y | 0 | 0.00 | 0.00 | 0.00 |
| 11 | * | * | 0 | 0.00 | 0.00 | 0.00 |
| 12 | HIS | H | 7 | 7.53 | 959.41 | 9.33 |
| 13 | GLN | Q | 2 | 2.15 | 256.12 | 2.49 |
| 14 | ASN | N | 2 | 2.15 | 228.09 | 2.22 |
| 15 | LYS | K | 3 | 3.23 | 384.28 | 3.74 |
| 16 | ASP | D | 3 | 3.23 | 345.08 | 3.36 |
| 17 | GLU | E | 10 | 10.75 | 1290.43 | 12.55 |
| 18 | CYS | C | 0 | 0.00 | 0.00 | 0.00 |
| 19 | TRP | W | 1 | 1.08 | 186.08 | 1.81 |
| 20 | ARG | R | 7 | 7.53 | 1092.71 | 10.63 |
| 21 | GLY | G | 7 | 7.53 | 399.15 | 3.88 |
| 22 | - | - | 0 | 0.00 | 0.00 | 0.00 |

RESIDUES = 93
MOLECULAR WEIGHT (MONOISOTOPIC) = 10279.2354
MOLECULAR WEIGHT (AVERAGE) = 10285.6309
INDEX OF POLARITY (%) = 48.39
ISOELECTRIC POINT = 6.94
OD 260 (1mg/ml) = 0.411 OD 280 (1mg/ml) = 0.541

HYDROPHILICITY
COBX FROM 1 TO 93 cobX GENE (SEQ ID NO: 35) AND COBX PROTEIN (SEQ ID NO: 36)
SEQUENCE OF THE 4749-BP BglI-SalI-SalI-SalI-SalI-SalI FRAGMENT
FROM 4089 TO 4370

```
MetSerLeuThrGluThrIleGluLysLysLeuIleGluAlaPheHisProGluArgLeuGluValIleAsnGlu
ATGTCGCTCACCGAGACCATCGAAAAGAAGCTGATCGAGGCCTTCCACCCTGAACGGCTCGAGGTCATCAACGAG
        4098        4108        4118        4128        4138        4148        4158
SerHisGlnHisThrGlyHisGlnProGlyPheAspGlyThrGlyGluSerHisMetArgValArgIleValSer
AGCCATCAGCATACCGGCCATCAGCCGGGCTTCGATGGTACCGGCGAGTCCCACATGCGGGTGCGTATCGTTTCT
        4173        4183        4193        4203        4213        4223        4233
SerAlaPheAlaGlyMetSerArgValAlaArgHisArgAlaIleAsnAspLeuLeuLysProGluLeuAspAla
AGCGCCTTTGCCGGCATGAGCCGTGTCGCCCGCCACCGCGCCATCAATGATCTCCTGAAGCCAGAACTCGACGCC
        4248        4258        4268        4278        4288        4298        4308
GlyLeuHisAlaLeuAlaValGluProAlaAlaProGlyGluProThrArgTrp**
GGCCTGCATGCGCTCGCCGTCGAGCCGGCAGCCCCCGGCGAGCCGACCCGCTGGTAG
        4323        4333        4343        4353        4363
```

FIG. 40G

NAME = COBU

FIRST RESIDUE = 1
LAST RESIDUE = 338

| | | | NUMBER | NO. % | WEIGHT | WEIGHT % |
|---|---|---|---|---|---|---|
| 1 | PHE | F | 9 | 2.66 | 1323.62 | 3.82 |
| 2 | LEU | L | 36 | 10.65 | 4071.03 | 11.75 |
| 3 | ILE | I | 19 | 5.62 | 2148.60 | 6.20 |
| 4 | MET | M | 9 | 2.66 | 1179.36 | 3.40 |
| 5 | VAL | V | 21 | 6.21 | 2080.44 | 6.00 |
| 6 | SER | S | 13 | 3.85 | 1131.42 | 3.26 |
| 7 | PRO | P | 16 | 4.73 | 1552.84 | 4.48 |
| 8 | THR | T | 17 | 5.03 | 1717.81 | 4.96 |
| 9 | ALA | A | 61 | 18.05 | 4333.26 | 12.50 |
| 10 | TYR | Y | 3 | 0.89 | 489.19 | 1.41 |
| 11 | * | * | 0 | 0.00 | 0.00 | 0.00 |
| 12 | HIS | H | 8 | 2.37 | 1096.47 | 3.16 |
| 13 | GLN | Q | 6 | 1.78 | 768.35 | 2.22 |
| 14 | ASN | N | 9 | 2.66 | 1026.39 | 2.96 |
| 15 | LYS | K | 12 | 3.55 | 1537.14 | 4.43 |
| 16 | ASP | D | 13 | 3.85 | 1495.35 | 4.31 |
| 17 | GLU | E | 22 | 6.51 | 2838.94 | 8.19 |
| 18 | CYS | C | 5 | 1.48 | 515.05 | 1.49 |
| 19 | TRP | W | 3 | 0.89 | 558.24 | 1.61 |
| 20 | ARG | R | 16 | 4.73 | 2497.62 | 7.21 |
| 21 | GLY | G | 40 | 11.83 | 2280.86 | 6.58 |
| 22 | - | - | 0 | 0.00 | 0.00 | 0.00 |

RESIDUES = 338
MOLECULAR WEIGHT (MONOISOTOPIC) = 34659.9844
MOLECULAR WEIGHT (AVERAGE) = 34681.9609
INDEX OF POLARITY (%) = 34.32
ISOELECTRIC POINT = 6.21
OD 260 (1mg/ml) = 0.416 OD 280 (1mg/ml) = 0.584

HYDROPHILICITY
COBU FROM 1 TO 338 cobU GENE (SEQ ID NO: 37) AND COBU PROTEIN (SEQ ID NO: 38)
SEQUENCE OF THE 3855-BP SstI-SstI-BamHI FRAGMENT
FROM 2099 TO 3115

```
MetSerAlaSerGlyLeuProPheAspAspPheArgGluLeuLeuArgAsnLeuProGlyProAspAlaAlaAla
ATGAGTGCCAGCGGCCTGCCGTTTGATGATTTTCGCGAATTGTTGCGCAACCTGCCGGGCCCGGATGCGGCAGCC
       2108      2118      2128      2138      2148      2158      2168
LeuValAlaAlaArgGluArgAspAlaGlnLeuThrLysProProGlyAlaLeuGlyArgLeuGluGluIleAla
CTCGTTGCCGCGCGGGAGCGGGACGCCCAGCTGACGAAGCCGCCGGGCGCGCTCGGCCGCCTCGAGGAAATCGCC
       2183      2193      2203      2213      2223      2233      2243
PheTrpLeuAlaAlaTrpThrGlyLysAlaProValValAsnArgProLeuValAlaIlePheAlaGlyAsnHis
TTCTGGCTCGCCGCCTGGACGGGCAAGGCGCCGGTGGTCAACCGGCCGCTGGTGGCGATCTTTGCCGGCAACCAC
       2258      2268      2278      2288      2298      2308      2318
GlyValThrArgGlnGlyValThrProPheProSerSerValThrAlaGlnMetValGluAsnPheAlaAlaGly
GGCGTCACCCGCCAGGGGGTGACCCCGTTCCCGTCATCCGTCACCGCACAGATGGTCGAGAATTTTGCCGCCGGT
       2333      2343      2353      2363      2373      2383      2393
GlyAlaAlaIleAsnGlnIleCysValSerHisAspLeuGlyLeuLysValPheAspLeuAlaLeuGluTyrPro
GGCGCTGCGATCAACCAGATCTGCGTCAGCCACGACCTCGGGCTGAAGGTCTTCGACCTCGCACTCGAATACCCG
       2408      2418      2428      2438      2448      2458      2468
ThrGlyAspIleThrGluGluAlaAlaLeuSerGluArgAspCysAlaAlaThrMetAlaPheGlyMetGluAla
ACCGGTGATATCACCGAGGAAGCCGCGCTGTCCGAGCGCGATTGCGCCGCGACCATGGCCTTTGGCATGGAGGCG
       2483      2493      2503      2513      2523      2533      2543
IleAlaGlyGlyThrAspLeuLeuCysIleGlyGluMetGlyIleGlyAsnThrThrIleAlaAlaAlaIleAsn
ATTGCCGGCGGCACGGATCTTCTGTGCATCGGCGAAATGGGCATCGGCAACACCACGATCGCGGCCGCGATCAAT
       2558      2568      2578      2588      2598      2608      2618
LeuGlyLeuTyrGlyGlyThrAlaGluGluTrpValGlyProGlyThrGlySerGluGlyGluValLeuLysArg
CTCGGCCTTTATGGTGGCACGGCCGAAGAATGGGTCGGTCCGGGTACCGGCTCCGAGGGCGAGGTGCTGAAGCGC
       2633      2643      2653      2663      2673      2683      2693
LysIleAlaAlaValGluLysAlaValAlaLeuHisArgAspHisLeuSerAspProLeuGluLeuMetArgArg
AAGATCGCCGCGGTCGAAAAGGCCGTGGCGCTGCATCGCGATCACCTGTCCGATCCGCTCGAACTGATGCGTCGC
       2708      2718      2728      2738      2748      2758      2768
LeuGlyGlyArgGluIleAlaAlaMetAlaGlyAlaIleLeuAlaAlaArgValGlnLysValProValIleIle
CTCGGCGGTCGTGAGATCGCGGCCATGGCTGGCGCCATCCTGGCCGCCCGCGTCCAGAAGGTACCTGTCATCATC
       2783      2793      2803      2813      2823      2833      2843
AspGlyTyrValAlaThrAlaAlaAlaSerIleLeuLysAlaAlaAsnProSerAlaLeuAspHisCysLeuIle
GACGGCTACGTGGCGACCGCTGCGGCTTCGATCCTGAAGGCGGCCAACCCGTCGGCCCTCGACCATTGCCTGATC
       2858      2868      2878      2888      2898      2908      2918
GlyHisValSerGlyGluProGlyHisLeuArgAlaIleGluLysLeuGlyLysThrProLeuLeuAlaLeuGly
GGCCATGTTTCGGGCGAACCGGGGCATCTGCGCGCGATCGAGAAGCTCGGCAAGACGCCGCTGCTGGCACTCGGC
       2933      2943      2953      2963      2973      2983      2993
MetArgLeuGlyGluGlyThrGlyAlaAlaLeuAlaAlaGlyIleValLysAlaAlaAlaAlaCysHisSerGly
ATGCGGCTTGGCGAAGGCACGGGCGCGGCCCTTGCCGCCGGTATCGTCAAGGCGGCGGCCGCTTGCCACAGCGGC
       3008      3018      3028      3038      3048      3058      3068
MetAlaThrPheAlaGlnAlaGlyValSerAsnLysGlu***
ATGGCGACCTTTGCCCAGGCCGGCGTCAGCAACAAGGAATAG
       3083      3093      3103      3113
```

FIG. 41B

NAME = COBV

FIRST RESIDUE = 1
LAST RESIDUE = 302

| | | | NUMBER | NO. % | WEIGHT | WEIGHT % |
|---|---|---|---|---|---|---|
| 1 | PHE | F | 18 | 5.96 | 2647.23 | 8.64 |
| 2 | LEU | L | 39 | 12.91 | 4410.28 | 14.39 |
| 3 | ILE | I | 13 | 4.30 | 1470.09 | 4.80 |
| 4 | MET | M | 10 | 3.31 | 1310.41 | 4.28 |
| 5 | VAL | V | 23 | 7.62 | 2278.57 | 7.44 |
| 6 | SER | S | 18 | 5.96 | 1566.58 | 5.11 |
| 7 | PRO | P | 12 | 3.97 | 1164.63 | 3.80 |
| 8 | THR | T | 10 | 3.31 | 1010.48 | 3.30 |
| 9 | ALA | A | 63 | 20.86 | 4475.34 | 14.61 |
| 10 | TYR | Y | 3 | 0.99 | 489.19 | 1.60 |
| 11 | * | * | 0 | 0.00 | 0.00 | 0.00 |
| 12 | HIS | H | 3 | 0.99 | 411.18 | 1.34 |
| 13 | GLN | Q | 6 | 1.99 | 768.35 | 2.51 |
| 14 | ASN | N | 2 | 0.66 | 228.09 | 0.74 |
| 15 | LYS | K | 5 | 1.66 | 640.47 | 2.09 |
| 16 | ASP | D | 10 | 3.31 | 1150.27 | 3.75 |
| 17 | GLU | E | 7 | 2.32 | 903.30 | 2.95 |
| 18 | CYS | C | 3 | 0.99 | 309.03 | 1.01 |
| 19 | TRP | W | 2 | 0.66 | 372.16 | 1.21 |
| 20 | ARG | R | 19 | 6.29 | 2965.92 | 9.68 |
| 21 | GLY | G | 36 | 11.92 | 2052.77 | 6.70 |
| 22 | - | - | 0 | 0.00 | 0.00 | 0.00 |

RESIDUES = 302
MOLECULAR WEIGHT (MONOISOTOPIC) = 30642.3359
MOLECULAR WEIGHT (AVERAGE) = 30662.0820
INDEX OF POLARITY (%) = 26.49
ISOELECTRIC POINT = 9.97
OD 260 (1mg/ml) = 0.391 OD 280 (1mg/ml) = 0.479

HYDROPHILICITY
COBV FROM 1 TO 302 cobV GENE (SEQ ID NO: 39) AND COBV PROTEIN (SEQ ID NO: 40)
SEQUENCE OF THE 3855-BP BamHI-SstI-SstI FRAGMENT
FROM 1885 TO 2793

```
MetLysGlyLeuGlyLysValCysAlaAlaLeuAlaGlyAlaProAlaArgLeuAlaArgLeuAlaAlaValGly
ATGAAAGGTCTGGGAAAAGTGTGCGCGGCCCTCGCGGGTGCGCCCGCCCGGCTTGCGAGACTCGCCGCAGTCGGC
      1894      1904      1914      1924      1934      1944      1954
GluPheGlySerGlyArgValAsnGlyArgAsnLeuGlyGlyAlaMetGlyPheValGlyAspPheCysAspAsp
GAGTTTGGCAGCGGCCGGGTCAATGGCCGCAACCTTGGAGGAGCCATGGGCTTCGTTGGCGATTTCTGTGACGAT
      1969      1979      1989      1999      2009      2019      2029
ValAlaArgSerIleGlyPheLeuSerArgIleProMetProAlaArgHisPheGluGlyTyrAspGlyArgLeu
GTGGCGCGGTCGATCGGCTTTCTCAGCCGCATCCCGATGCCTGCGCGTCATTTCGAAGGTTATGACGGGCGCTTG
      2044      2054      2064      2074      2084      2094      2104
SerArgAlaValArgAlaPheProPheAlaGlyLeuAlaIleAlaLeuProSerAlaAlaValAlaMetAlaLeu
AGCCGTGCCGTGCGCGCCTTCCCGTTCGCCGGCCTGGCGATCGCACTGCCATCGGCGGCCGTCGCCATGGCCCTC
      2119      2129      2139      2149      2159      2169      2179
MetAlaLeuGlnValSerSerLeuPheAlaAlaPheValValValAlaIleGlnAlaLeuValThrGlyAlaLeu
ATGGCGCTGCAGGTGAGCTCGCTCTTTGCCGCCTTTGTCGTCGTCGCCATCCAGGCGCTTGTCACCGGCGCACTG
      2194      2204      2214      2224      2234      2244      2254
HisGluAspGlyLeuGlyAspThrAlaAspGlyPheGlyGlyGlyArgAspArgGluAlaAlaLeuAlaIleMet
CACGAAGACGGGCTTGGCGACACGGCCGATGGCTTTGGCGGCGGTCGCGACCGCGAAGCGGCGCTTGCGATCATG
      2269      2279      2289      2299      2309      2319      2329
LysAspSerArgIleGlyThrTyrAlaAlaValAlaLeuIleLeuSerPheGlyLeuArgValSerAlaPheAla
AAGGACAGCCGCATCGGCACCTATGCGGCCGTCGCCCTCATCCTCTCCTTCGGCCTGCGCGTCTCGGCGTTCGCC
      2344      2354      2364      2374      2384      2394      2404
SerIleLeuProLeuPheSerProLeuGlyAlaAlaMetAlaIleLeuGlyAlaAlaCysLeuSerArgAlaAla
TCGATCCTGCCGCTCTTTTCGCCGCTGGGCGCCGCCATGGCGATCCTTGGCGCAGCGTGCCTCAGCCGCGCCGCC
      2419      2429      2439      2449      2459      2469      2479
MetValTrpHisTrpSerSerLeuProProAlaArgSerSerGlyValAlaAlaSerAlaGlyGluProGluPro
ATGGTCTGGCACTGGTCGTCGCTTCCGCCGGCGCGCAGCAGCGGCGTCGCGGCCTCGGCTGGCGAGCCGGAACCG
      2494      2504      2514      2524      2534      2544      2554
AlaAlaThrArgPheAlaLeuAlaPheGlyLeuLeuValAlaMetLeuLeuPheTyrLeuAlaGlnValProAla
GCGGCCACGCGCTTCGCGCTTGCCTTCGGACTTCTTGTCGCAATGCTGCTCTTCTATCTCGCGCAGGTCCCGGCG
      2569      2579      2589      2599      2609      2619      2629
LeuGlyValIleAlaAlaLeuValAlaPheLeuAlaThrValLysGlyPheAlaArgLeuAlaMetArgLysIle
CTCGGCGTCATCGCGGCGCTCGTCGCATTCCTTGCCACGGTCAAGGGCTTCGCTCGGCTGGCGATGCGCAAGATC
      2644      2654      2664      2674      2684      2694      2704
GlyGlyGlnThrGlyAspThrIleGlyAlaThrGlnGlnLeuThrGluIleAlaValLeuGlyAlaLeuAlaLeu
GGCGGACAAACGGGCGACACGATCGGGGCGACGCAGCAACTGACCGAAATCGCCGTGCTCGGTGCCCTTGCGCTG
      2719      2729      2739      2749      2759      2769      2779
ThrVal***
ACGGTTTGA
```

FIG. 41D

```
SEQUENCE      LENGTH = 13144 FROM      1 TO 13144
        10         20         30         40         50         60
GAGCTCGAAG GGGCTTCCGC CCCGATCGCT GGCGTTAGCC GACGTTCGAC GTGCGGATGA
CTCGAGCTTC CCCGAAGGCG GGGCTAGCGA CCGCAATCGG CTGCAAGCTG CACGCCTACT

        70         80         90        100        110        120
CGCCGAGCGG GCCGAAGGGC GCGTCGACGA CGAGGTTGCG TACGCGCGAC TGGCTGGACG
GCGGCTCGCC CGGCTTCCCG CGCAGCTGCT GCTCCAACGC ATGCGCGCTG ACCGACCTGC

       130        140        150        160        170        180
GAACCTTCGA GTTCCAGGCG ATCTGAACGA AATTGGGCTT GCTGAAAATA TACAGCATGG
CTTGGAAGCT CAAGGTCCGC TAGACTTGCT TTAACCCGAA CGACTTTTAT ATGTCGTACC

       190        200        210        220        230        240
ACATGAACCT TGAGAGGCCG GAGGCCTATC CTCCGGGGCG TGTTGCTATG CCGCTGATAT
TGTACTTGGA ACTCTCCGGC CTCCGGATAG GAGGCCCCGC ACAACGATAC GGCGACTATA

       250        260        270        280        290        300
AGGTGTGCGC TGCAAAAAAT TGAATGCCAA ACTCGCCACG CCATGTCGCA TTCTGGCTAT
TCCACACGCG ACGTTTTTTA ACTTACGGTT TGAGCGGTGC GGTACAGCGT AAGACCGATA

       310        320        330        340        350        360
CGGCCGCGAC ATTTTCGACA AGCCTTGCGA AAGCGCGAAA CAATGCGTGA AAGGGCTTTG
GCCGGCGCTG TAAAAGCTGT TCGGAACGCT TTCGCGCTTT GTTACGCACT TTCCCGAAAC

       370        380        390        400        410        420
TCAATTGCGG CGAAATCGTG TCGAAACAGA CCTTTGCCGC TGCCCGTTTC AGTGTTACCG
AGTTAACGCC GCTTTAGCAC AGCTTTGTCT GGAAACGGCG ACGGGCAAAG TCACAATGGC

       430        440        450        460        470        480
ATGGCCGCAT GACACGCAGG ATCATGTTGC AGGGAACCGG CTCGGATGTC GGAAAATCGG
TACCGGCGTA CTGTGCGTCC TAGTACAACG TCCCTTGGCC GAGCCTACAG CCTTTTAGCC

       490        500        510        520        530        540
TATTGGTGGC GGGGCTCTGC CGGCTTGCCG CCAATCAGGG CCTGAAGGTC CGGCCGTTCA
ATAACCACCG CCCCGAGACG GCCGAACGGC GGTTAGTCCC GGACTTCCAG GCCGGCAAGT

       550        560        570        580        590        600
AGCCGCAGAA CATGTCGAAC AACGCCGCCG TTTCCGACGA CGGCGGCGAC ATCGGCCGCG
TCGGCGTCTT GTACAGCTTG TTGCGGCGGC AAAGGCTGCT GCCGCCGCTC TAGCCGGCGC
```

FIG. 43A

```
       610        620        630        640        650        660
CGCAATGGCT GCAGGCGCTG GCCGCGCGCG TGCCGTCGTC GGTGCACATG AACCCGGTGC
GCGTTACCGA CGTCCGCGAC CGGCGCGCGC ACGGCAGCAG CCACGTGTAC TTGGGCCACG

       670        680        690        700        710        720
TCCTGAAGCC GCAGTCGGAC GTGGGCAGCC AGATCGTCGT TCAGGGCAAG GTCGCCGGGC
AGGACTTCGG CGTCAGCCTG CACCCGTCGG TCTAGCAGCA AGTCCCGTTC CAGCGGCCCG

       730        740        750        760        770        780
AGGCCAGGGG GCGGGAATAT CAGGCGCTCA AGCCCAAGCT GCTGGGCGCC GTCATGGAGA
TCCGGTCCCC CGCCCTTATA GTCCGCGAGT TCGGGTTCGA CGACCCGCGG CAGTACCTCT

       790        800        810        820        830        840
GTTTCGAACA AATATCGGCC GGTGCCGATC TCGTGGTGGT CGAAGGCGCC GGCTCGCCGG
CAAAGCTTGT TTATAGCCGG CCACGGCTAG AGCACCACCA GCTTCCGCGG CCGAGCGGCC

       850        860        870        880        890        900
CCGAAATCAA CCTCAGGCCC GGCGACATCG CCAATATGGG CTTTGCGACA CGGGCCAATG
GGCTTTAGTT GGAGTCCGGG CCGCTGTAGC GGTTATACCC GAAACGCTGT GCCCGGTTAC

       910        920        930        940        950        960
TGCCGGTCGT GCTGGTCGGC GACATCGACC GCGGGGGGGT GATCGCCTCG CTGGTCGGCA
ACGGCCAGCA CGACCAGCCG CTGTAGCTGG CGCCCCCCCA CTAGCGGAGC GACCAGCCGT

       970        980        990       1000       1010       1020
CGCATGCGAT CCTGCCCGAG GAAGACCGGC GCATGGTGAC CGGCTATCTC ATCAACAAGT
GCGTACGCTA GGACGGGCTC CTTCTGGCCG CGTACCACTG GCCGATAGAG TAGTTGTTCA

      1030       1040       1050       1060       1070       1080
TCCGCGGCGA CGTCACGCTG TTCGACGACG GCATTGCTGC CGTCAACCGC TACACCGGCT
AGGCGCCGCT GCAGTGCGAC AAGCTGCTGC CGTAACGACG GCAGTTGGCG ATGTGGCCGA

      1090       1100       1110       1120       1130       1140
GGCCCTGCTT CGGCGTCGTG CCGTGGCTGA AGGCGGCGGC ACGCCTGCCG GCGGAAGATT
CCGGGACGAA GCCGCAGCAC GGCACCGACT TCCGCCGCCG TGCGGACGGC CGCCTTCTAA

      1150       1160       1170       1180       1190       1200
CCGTCGTGCT GGAGAAGCTG ACGCGCGGCG AGGGGCGGGC GCTGAAGGTT GCCGTCCCGG
GGCAGCACGA CCTCTTCGAC TGCGCGCCGC TCCCCGCCCG CGACTTCCAA CGGCAGGGCC
```

FIG. 43B

```
      1210       1220       1230       1240       1250       1260
TACTGTCGCG CATCGCCAAT TTCGACGACC TCGATCCGCT CGCCGCCGAA CCGGAGATTG
ATGACAGCGC GTAGCGGTTA AAGCTGCTGG AGCTAGGCGA GCGGCGGCTT GGCCTCTAAC

      1270       1280       1290       1300       1310       1320
ATCTCGTCTT CGTGCGGCCT GGCAGTCCCA TTCCGGTCGA CGCTGGCCTC GTCGTCATTC
TAGAGCAGAA GCACGCCGGA CCGTCAGGGT AAGGCCAGCT GCGACCGGAG CAGCAGTAAG

      1330       1340       1350       1360       1370       1380
CCGGGTCGAA ATCGACCATC GGCGACCTCA TCGATTTCCG TGCGCAAGGG TGGGACCGTG
GGCCCAGCTT TAGCTGGTAG CCGCTGGAGT AGCTAAAGGC ACGCGTTCCC ACCCTGGCAC

      1390       1400       1410       1420       1430       1440
ACCTCGAACG TCATGTGCGC CGGGGCGGCC GGGTCATCGG CATCTGCGGC GGCTACCAGA
TGGAGCTTGC AGTACACGCG GCCCCGCCGG CCCAGTAGCC GTAGACGCCG CCGATGGTCT

      1450       1460       1470       1480       1490       1500
TGCTCGGCCG GCGCGTCACC GATCCGCTCG GCATCGAGGG CGGCGAACGT GCGGTCGAGG
ACGAGCCGGC CGCGCAGTGG CTAGGCGAGC CGTAGCTCCC GCCGCTTGCA CGCCAGCTCC

      1510       1520       1530       1540       1550       1560
GCCTCGGGCT GCTCGAGGTC GAGACCGAGA TGGCGCCGGA AAAGACGGTG CGCAACAGCC
CGGAGCCCGA CGAGCTCCAG CTCTGGCTCT ACCGCGGCCT TTTCTGCCAC GCGTTGTCGG

      1570       1580       1590       1600       1610       1620
GCGCCTGGTC GCTGGAGCAT GATGTGGTGC TCGAAGGCTA CGAAATCCAT CTTGGCAAGA
CGCGGACCAG CGACCTCGTA CTACACCACG AGCTTCCGAT GCTTTAGGTA GAACCGTTCT

      1630       1640       1650       1660       1670       1680
CGCAAGGTGC GGACTGTGGC CGGCCGTCGG TGCGCATCGA CAATCGCGCC GACGGCGCCC
GCGTTCCACG CCTGACACCG GCCGGCAGCC ACGCGTAGCT GTTAGCGCGG CTGCCGCGGG

      1690       1700       1710       1720       1730       1740
TTTCGGCCGA TGGCCGCGTG ATGGGCACCT ACCTGCATGG GCTCTTCACC AGCGACGCCT
AAAGCCGGCT ACCGGCGCAC TACCCGTGGA TGGACGTACC CGAGAAGTGG TCGCTGCGGA

      1750       1760       1770       1780       1790       1800
ATCGCGGCGC GCTGCTCAAG AGTTTCGGCA TCGAAGGCGG CGCCAACAAC TACCGCCAAT
TAGCGCCGCG CGACGAGTTC TCAAAGCCGT AGCTTCCGCC GCGGTTGTTG ATGGCGGTTA
```

FIG. 43C

```
      1810       1820       1830       1840       1850       1860
CGGTCGATGC GGCGCTCGAC GATGTCGCGA ACGAACTGGA GGCTGTGCTC GATCGTCGCT
GCCAGCTACG CCGCGAGCTG CTACAGCGCT TGCTTGACCT CCGACACGAG CTAGCAGCGA

      1870       1880       1890       1900       1910       1920
GGCTGGACGA GTTGCTCAGG CACTAGGGAC GCGGCAACGG TCAGCCAGCA GGTCCGGTAC
CCGACCTGCT CAACGAGTCC GTGATCCCTG CGCCGTTGCC AGTCGGTCGT CCAGGCCATG

      1930       1940       1950       1960       1970       1980
GTCGGGCCCA ACAGGAGCAA CGAGCTTATC CGACGGAACT ACGCTGCGAC ATCGTGCTCC
CAGCCCGGGT TGTCCTCGTT GCTCGAATAG GCTGCCTTGA TGCGACGCTG TAGCACGAGG

      1990       2000       2010       2020       2030       2040
TCGCTTGCGG CTTCCCAGAC TTCCCGCGCG GCATCCAGGT TCATCAGGGC AATCCCCAGG
AGCGAACGCC GAAGGGTCTG AAGGGCGCGC CGTAGGTCCA AGTAGTCCCG TTAGGGGTCC

      2050       2060       2070       2080       2090       2100
CCGACGATCA GGTCCGGCCA GGCCGACTGC CACAGATAGG CTGTCGCCAG ACCCGCGGCG
GGCTGCTAGT CCAGGCCGGT CCGGCTGACG GTGTCTATCC GACAGCGGTC TGGGCGCCGC

      2110       2120       2130       2140       2150       2160
ATGATGGCCA CATTGGCGAA GGCATCGTTG CGGGCCGAGA GAAATGCTGC CCGCGTGAGC
TACTACCGGT GTAACCGCTT CCGTAGCAAC GCCCGGCTCT CTTTACGACG GGCGCACTCG

      2170       2180       2190       2200       2210       2220
GTGCCGCTCG TGTGACGGTA GGCGACGAGC AGATAGGCGC AGAAGAGGTT GACCACCAGC
CACGGCGAGC ACACTGCCAT CCGCTGCTCG TCTATCCGCG TCTTCTCCAA CTGGTGGTCG

      2230       2240       2250       2260       2270       2280
GCCCCAAGTC CGGTCAGGGA CAGGGCAAAG GGCTCTGGCG GGACCGGATC CATGAACTTC
CGGGGTTCAG GCCAGTCCCT GTCCCGTTTC CCGAGACCGC CCTGGCCTAG GTACTTGAAG

      2290       2300       2310       2320       2330       2340
GCCCAGGCCG TCCAAAGGAA GGCCAGCGCC GGTACCAGTA GAATGAACGC CATCGCCATG
CGGGTCCGGC AGGTTTCCTT CCGGTCGCGG CCATGGTCAT CTTACTTGCG GTAGCGGTAC

      2350       2360       2370       2380       2390       2400
CCGACCCGCG CGCGGGTTCG CGCCGTCCAG GCCAGAGCAA AGAAAATCAG CATGTTGACG
GGCTGGGCGC GCGCCCAAGC GCGGCAGGTC CGGTCTCGTT TCTTTTAGTC GTACAACTGG
```

*FIG. 43D*

```
      2410       2420       2430       2440       2450       2460
GAGGCGTCTT CGAGGAAGTC GACGCTGTCG GCCATGAGGG ACACCGAGCC GATCGAAAGC
CTCCGCAGAA GCTCCTTCAG CTGCGACAGC CGGTACTCCC TGTGGCTCGG CTAGCTTTCG

      2470       2480       2490       2500       2510       2520
GCGACAAGGA GTTCGACCCC GAAATAGCCA AGGTTCAACA GGGAGACGAT GAGGACGACG
CGCTGTTCCT CAAGCTGGGG CTTTATCGGT TCCAAGTTGT CCCTCTGCTA CTCCTGCTGC

      2530       2540       2550       2560       2570       2580
CGGCGCAGGT CGGTATCCAC TCGAAAGGTT CCCTTTCTGG CGAGATTCGC CCTCGGCACT
GCCGCGTCCA GCCATAGGTG AGCTTTCCAA GGGAAAGACC GCTCTAAGCG GGAGCCGTGA

      2590       2600       2610       2620       2630       2640
TTTTTTGGCG AGATTCGCCC TCGGCACTTT GGCACAGGTG TTAGCAGCAG TTTGCTATCC
AAAAAACCGC TCTAAGCGGG AGCCGTGAAA CCGTGTCCAC AATCGTCGTC AAACGATAGG

      2650       2660       2670       2680       2690       2700
ATAGCACTAG GTTTCGACAT CGGTTCCGTT CACACTGCCG TCGTGCCTGA CGCCCGACAA
TATCGTGATC CAAAGCTGTA GCCAAGGCAA GTGTGACGGC AGCACGGACT GCGGGCTGTT

      2710       2720       2730       2740       2750       2760
ATCGTCGCGT GGCGCAACTC GGCCGGGGAG GCGTCGCATG CGTCGATTGA CTTTGGGCTG
TAGCAGCGCA CCGCGTTGAG CCGGCCCCTC CGCAGCGTAC GCAGCTAACT GAAACCCGAC

      2770       2780       2790       2800       2810       2820
CCCGCTTCCT AATCATCAGG TGTTGGATGG TTCCCCCTTG TCGTGGCGAT CTGGGGGAAT
GGGCGAAGGA TTAGTAGTCC ACAACCTACC AAGGGGGAAC AGCACCGCTA GACCCCCTTA

      2830       2840       2850       2860       2870       2880
AATTGGGAAT GTGACGGATG GACCCAAATC GGGCATCCTT ATCGCAGCCG ACCCCGCGAC
TTAACCCTTA CACTGCCTAC CTGGGTTTAG CCCGTAGGAA TAGCGTCGGC TGGGGCGCTG

      2890       2900       2910       2920       2930       2940
TGTAGAACGG TCAGGGTTCG CCATCGGGAT TGGTGCCGGG CTGTCGGCCG GTTGCATGGG
ACATCTTGCC AGTCCCAAGC GGTAGCCCTA ACCACGGCCC GACAGCCGGC CAACGTACCC

      2950       2960       2970       2980       2990       3000
CAATCGGGGC AGGTCGGGGA TCAAGCCGGA AAAGCCACTG GCGTGGCATC GTGATCAGCC
GTTAGCCCCG TCCAGCCCCT AGTTCGGCCT TTTCGGTGAC CGCACCGTAG CACTAGTCGG
```

*FIG. 43E*

```
      3010       3020       3030       3040       3050       3060
GGGTTTGGAC GCCTCTTCTT CTACGAATCG TCCGCCTTTC ACGATGTCCC TCACAGCGCC
CCCAAACCTG CGGAGAAGAA GATGCTTAGC AGGCGGAAAG TGCTACAGGG AGTGTCGCGG

      3070       3080       3090       3100       3110       3120
CATGCGTCGG AGACGACGCG CAAAGGTTCG CTGTGGCACC GGAAAGACGC CGGGAAGGTG
GTACGCAGCC TCTGCTGCGC GTTTCCAAGC GACACCGTGG CCTTTCTGCG GCCCTTCCAC

      3130       3140       3150       3160       3170       3180
AGGCGGGCCG CTCGGGCCCT GACATCGGAA CCTTGCCGTT TAAGGGCGAG GCGATGTTCG
TCCGCCCGGC GAGCCCGGGA CTGTAGCCTT GGAACGGCAA ATTCCCGCTC CGCTACAAGC

      3190       3200       3210       3220       3230       3240
GCCCGTGACG CCGTGAGCCA GGAGACCTGC CATCCGGCAT GGGCATTCCG CCCGAGGGGA
CGGGCACTGC GGCACTCGGT CCTCTGGACG GTAGGCCGTA CCCGTAAGGC GGGCTCCCCT

      3250       3260       3270       3280       3290       3300
CTTTTGTCTC CAACGCCATC ACGGAGGTTG TTTTGGCTCG CAGATGTTTT CAAGAACGCG
GAAAACAGAG GTTGCGGTAG TGCCTCCAAC AAAACCGAGC GTGTACAAAA GTTCTTGCGC

      3310       3320       3330       3340       3350       3360
CCCGTGGCGC GTCCGATGGC TTTTGCCACC GACGGCTGAT TTGGGAATGT TGAGGCAGCC
GGGCACCGCG CAGGCTACCG AAAACGGTGG CTGCCGACTA AACCCTTACA ACTCCGTCGG

      3370       3380       3390       3400       3410       3420
ACGATGAGCA GTCTCAGCGC CGGGCCCGTG CTGGTCCTTG GCGGCGCCCG TTCCGGCAAG
TGCTACTCGT CAGAGTCGCG GCCCGGGCAC GACCAGGAAC CGCCGCGGGC AAGGCCGTTC

      3430       3440       3450       3460       3470       3480
TCCAGCTTTT CCGAGAGGCT CGTCGAAGCG TCCGGCTTCA CCATGCATTA TGTCGCCACG
AGGTCGAAAA GGCTCTCCGA GCAGCTTCGC AGGCCGAAGT GGTACGTAAT ACAGCGGTGC

      3490       3500       3510       3520       3530       3540
GGCCGCGCCT GGGACGACGA AATGCGCGAG CGCATCGACC ATCACCGGAC GCGCCGCGGC
CCGGCGCGGA CCCTGCTGCT TTACGCGCTC GCGTAGCTGG TAGTGGCCTG CGCGGCGCCG

      3550       3560       3570       3580       3590       3600
GAGGGCTGGA CGACGCATGA GGAGCCGCTC GATCTCGTCG GCATCCTCAG ACGCATCGAT
CTCCCGACCT GCTGCGTACT CCTCGGCGAG CTAGAGCAGC CGTAGGAGTC TGCGTAGCTA
```

FIG. 43F

```
      3610       3620       3630       3640       3650       3660
GATCCCAGCC ATGTGGTCCT GATCGACTGC CTGACGCTAT GGGTCACCAA TCTCATGCTG
CTAGGGTCGG TACACCAGGA CTAGCTGACG GACTGCGATA CCCAGTGGTT AGAGTACGAC

      3670       3680       3690       3700       3710       3720
GAAGAGCGCG ACATGACGGC GGAGTTCGCC GCCCTTGTTG CGTATCTGCC CGAGGCGCGG
CTTCTCGCGC TGTACTGCCG CCTCAAGCGG CGGGAACAAC GCATAGACGG GCTCCGCGCC

      3730       3740       3750       3760       3770       3780
GCGCGCCTCG TCTTTGTTTC CAATGAGGTC GGCCTCGGCA TCGTGCCCGA GAACCGCATG
CGCGCGGAGC AGAAACAAAG GTTACTCCAG CCGGAGCCGT AGCACGGGCT CTTGGCGTAC

      3790       3800       3810       3820       3830       3840
GCCCGCGAGT TTCGCGACCA TGCCGGCCGG CTTCACCAGA TCGTTGCGGA GAAATCCGCT
CGGGCGCTCA AAGCGCTGGT ACGGCCGGCC GAAGTGGTCT AGCAACGCCT CTTTAGGCGA

      3850       3860       3870       3880       3890       3900
GAAGTTTACT TTGTCGCGGC CGGTTTGCCG CTGAAAATGA AGGGTTGATC CATGACCACT
CTTCAAATGA AACAGCGCCG GCCAAACGGC GACTTTTACT TCCCAACTAG GTACTGGTGA

      3910       3920       3930       3940       3950       3960
GCGAGAGCCA ACCAGGGCAA GATCCCGGCG ACCGTCATCA CCGGCTTCCT CGGCGCCGGC
CGCTCTCGGT TGGTCCCGTT CTAGGGCCGC TGGCAGTAGT GGCCGAAGGA GCCGCGGCCG

      3970       3980       3990       4000       4010       4020
AAGACGACGA TGATCCGCAA CCTGCTGCAG AACGCCGACG GCAAGCGCAT CGGCCTGATC
TTCTGCTGCT ACTAGGCGTT GGACGACGTC TTGCGGCTGC CGTTCGCGTA GCCGGACTAG

      4030       4040       4050       4060       4070       4080
ATCAACGAGT TCGGCGATCT TGGCGTCGAC GGCGATGTCT TGAAGGGCTG CGGTGCCGAC
TAGTTGCTCA AGCCGCTAGA ACCGCAGCTG CCGCTACAGA ACTTCCCGAC GCCACGGCTC

      4090       4100       4110       4120       4130       4140
GCCTGCACCG AGGACGACAT CATCGAGCTC ACCAATGGCT GCATCTGCTG CACCGTGGCT
CGGACGTGGC TCCTGCTGTA GTAGCTCGAG TGGTTACCGA CGTAGACGAC GTGGCACCGA

      4150       4160       4170       4180       4190       4200
GACGATTTCA TCCCGACCAT GACGAAGCTG CTCGAGCGTG AAAACCGTCC TGACCACATC
CTGCTAAAGT AGGGCTGGTA CTGCTTCGAC GAGCTCGCAC TTTTGGCAGG ACTGGTGTAG
```

FIG. 43G

```
      4210       4220       4230       4240       4250       4260
ATCATCGAAA CCTCGGGCCT TGCCCTGCCG CAGCCGCTGA TCGCCGCTTT CAACTGGCCG
TAGTAGCTTT GGAGCCCGGA ACGGGACGGC GTCGGCGACT AGCGGCGAAA GTTGACCGGC

      4270       4280       4290       4300       4310       4320
GATATCCGCA GCGAAGTGAC CGTCGATGGC GTCGTCACCG TGGTCGACAG CGCCGCCGTT
CTATAGGCGT CGCTTCACTG GCAGCTACCG CAGCAGTGGC ACCAGCTGTC GCGGCGGCAA

      4330       4340       4350       4360       4370       4380
GCCGCTGGCC GCTTTGCCGA CGACCACGAC AAGGTCGATG CGCTGCGCGT CGAGGACGAC
CGGCGACCGG CGAAACGGCT GCTGGTGCTG TTCCAGCTAC GCGACGCGCA GCTCCTGCTG

      4390       4400       4410       4420       4430       4440
AATCTCGATC ACGAAAGCCC GATCGAGGAG CTGTTCGAGG ATCAACTGAC GGCTGCCGAT
TTAGAGCTAG TGCTTTCGGG CTAGCTCCTC GACAAGCTCC TAGTTGACTG CCGACGGCTA

      4450       4460       4470       4480       4490       4500
CTCATCGTTC TCAACAAGAC CGATCTGATC GATGCCTCCG GCCTCAAGGC CGTGCGCGAC
GAGTAGCAAG AGTTGTTCTG GCTAGACTAG CTACGGAGGC CGGAGTTCCG GCACGCGCTG

      4510       4520       4530       4540       4550       4560
GAGGTGTCTT CGCGCACCAG CCGCAAGCCC ACGATGATCG AGGCGAAAAA CGGCGAAGTC
CTCCACAGAA GCGCGTGGTC GGCGTTCGGG TGCTACTAGC TCCGCTTTTT GCCGCTTCAG

      4570       4580       4590       4600       4610       4620
GCCGCTGCCA TCCTGCTTGG CCTCGGTGTC GGCACGGAAA GCGATATCGC CAACCGCAAG
CGGCGACGGT AGGACGAACC GGAGCCACAG CCGTGCCTTT CGCTATAGCG GTTGGCGTTC

      4630       4640       4650       4660       4670       4680
TCGCATCACG AGATGGAGCA CGAGGCAGGT GAGGAGCACG ATCACGACGA GTTCGACAGC
AGCGTAGTGC TCTACCTCGT GCTCCGTCCA CTCCTCGTGC TAGTGCTGCT CAAGCTGTCG

      4690       4700       4710       4720       4730       4740
TTCGTCGTCG AGCTCGGTTC GATCGCCGAT CCGGCCGCCT TCATCGATCG CCTGAAGGGC
AAGCAGCAGC TCGAGCCAAG CTAGCGGCTA GGCCGGCGGA AGTAGCTAGC GGACTTCCCG

      4750       4760       4770       4780       4790       4800
GTAATCGCGG AGCACGACGT TCTGCGCCTC AAGGGTTTTG CAGACGTGCC CGGCAAGCCG
CATTAGCGCC TCGTGCTGCA AGACGCGGAG TTCCCAAAAC GTCTGCACGG GCCGTTCGGC
```

*FIG. 43H*

```
      4810       4820       4830       4840       4850       4860
ATGCGCCTCC TGATCCAGGC GGTCGGCGCC CGCATCGACC AATATTACGA CCGCGCCTGG
TACGCGGAGG ACTAGGTCCG CCAGCCGCGG GCGTAGCTGG TTATAATGCT GGCGCGGACC

      4870       4880       4890       4900       4910       4920
GGCGCTGGCG AAAAGCGCGG TACGCGCCTC GTCGTCATCG GCCTGCACGA CATGGACGAG
CCGCGACCGC TTTTCGCGCC ATGCGCGGAG CAGCAGTAGC CGGACGTGCT GTACCTGCTC

      4930       4940       4950       4960       4970       4980
GCGGCGGTGC GCGCCGCGAT CACCGCGCTC GTGTAGATCG TTCTTTGAAT GAAATGATCT
CGCCGCCACG CGCGGCGCTA GTGGCGCGAG CACATCTAGC AAGAAACTTA CTTTACTAGA

      4990       5000       5010       5020       5030       5040
AACGCATTGA AATGATGCAG TTCCGGATGG AGAACGCTTT TAGCGTTTTC GTTCGGAATT
TTGCGTAACT TTACTACGTC AAGGCCTACC TCTTGCGAAA ATCGCAAAAG CAAGCCTTAA

      5050       5060       5070       5080       5090       5100
GCCCCAACGG ACAAGACGAA TGCATCTGCT TCTCGCCCAG AAAGGAACGA TCGCCGACGG
CGGGGTTGCC TGTTCTGCTT ACGTAGACGA AGAGCGGGTC TTTCCTTGCT AGCGGCTGCC

      5110       5120       5130       5140       5150       5160
CAACGAGGCG ATCGACCTTG GGCAAACGCC GGCCGATATC CTTTTCCTAT CGGCCGCCGA
GTTGCTCCGC TAGCTGGAAC CCGTTTGCGG CCGGCTATAG GAAAAGGATA GCCGGCGGCT

      5170       5180       5190       5200       5210       5220
CACCGAGCTC TCCTCGATCG CCGCGGCTCA CGGCCGACGC GACGGAGGCT TGAGCCTGCG
GTGGCTCGAG AGGAGCTAGC GGCGCCGAGT GCCGGCTGCG CTGCCTCCGA ACTCGGACGC

      5230       5240       5250       5260       5270       5280
CATCGCCAGC CTGATGAGCC TGATGCACCC GATGTCGGTC GACACTTACG TCGAGCGCAC
GTAGCGGTCG GACTACTCGG ACTACGTGGG CTACAGCCAG CTGTGAATGC AGCTCGCGTG

      5290       5300       5310       5320       5330       5340
GGCGCGTCAC GCCAAGCTGA TCGTCGTCCG GCCGCTCGGT GGCGCCAGCT ATTTCCGTTA
CCGCGCAGTG CGGTTCGACT AGCAGCAGGC CGGCGAGCCA CCGCGGTCGA TAAAGGCAAT

      5350       5360       5370       5380       5390       5400
TCTGCTGGAA GCCCTGCATG CGGCTGCCGT CACCCATCGT TTCGAGATCG CGGTTCTGCC
AGACGACCTT CGGGACGTAC GCCGACGGCA GTGGGTAGCA AAGCTCTAGC GCCAAGACGG
```

FIG. 43I

```
      5410       5420       5430       5440       5450       5460
GGGTGACGAC AAGCCGGATC CGGGGCTGGA GCCTTTCTCC ACCGTCGCAG CCGACGACCG
CCCACTGCTG TTCGGCCTAG GCCCCGACCT CGGAAAGAGG TGGCAGCGTC GGCTGCTGGC

      5470       5480       5490       5500       5510       5520
CCAGCGCCTT TGGGCTTACT TCACCGAAGG CGGCTCGGAC AATGCCGGGC TGTTTCTCGA
GGTCGCGGAA ACCCGAATGA AGTGGCTTCC GCCGAGCCTG TTACGGCCCG ACAAAGAGCT

      5530       5540       5550       5560       5570       5580
CTATGCGGCC GCACTGGTCA CAGGTGCGGA GAAGCCGCAG CCGGCAAAGC CCCTGTTGAA
GATACGCCGG CGTGACCAGT GTCCACGCCT CTTCGGCGTC GGCCGTTTCG GGGACAACTT

      5590       5600       5610       5620       5630       5640
GGCCGGCATC TGGTGGCCGG GTGCTGGTGT GATCGGCGTC AGCGAATGGC AGTCCCTTGT
CCGGCCGTAG ACCACCGGCC CACGACCACA CTAGCCGCAG TCGCTTACCG TCAGGGAACA

      5650       5660       5670       5680       5690       5700
TCAGGGACGG ATGGTAGCGA GGGAGGGATT CGAACCCCCG ACGGTCGGGA TCTGCTTTTA
AGTCCCTGCC TACCATCGCT CCCTCCCTAA GCTTGGGGGC TGCCAGCCCT AGACGAAAAT

      5710       5720       5730       5740       5750       5760
CCGCGCGCTC GTGCAGAGTG GCGAGACACG GCCTGTGGAG GCGCTGATCG ATGCGCTGGA
GGCGCGCGAG CACGTCTCAC CGCTCTGTGC CGGACACCTC CGCGACTAGC TACGCGACCT

      5770       5780       5790       5800       5810       5820
GGCTGAAGGT GTGCGGGCAC TGCCGGTGTT TGTCTCAAGC CTCAAGGATG CCGTTTCCGT
CCGACTTCCA CACGCCCGTG ACGGCCACAA ACAGAGTTCG GAGTTCCTAC GGCAAAGGCA

      5830       5840       5850       5860       5870       5880
CGGCACGCTG CAGGCGATTT TTTCCGAGGC CGCACCCGAC GTGGTGATGA ACGCCACTGG
GCCGTGCGAC GTCCGCTAAA AAAGGCTCCG GCGTGGGCTG CACCACTACT TGCGGTGACC

      5890       5900       5910       5920       5930       5940
CTTTGCGGTC TCGTCGCCCG GTGCCGACCG TCAGCCGACG GTGCTGGAAT CGACCGGTGC
GAAACGCCAG AGCAGCGGGC CACGGCTGGC AGTCGGCTGC CACGACCTTA GCTGGCCACG

      5950       5960       5970       5980       5990       6000
GCCGGTGCTG CAGGTGATTT TCTCCGGCTC GTCGCGGGCG CAATGGGAAA CGTCGCCGCA
CGGCCACGAC GTCCACTAAA AGAGGCCGAG CAGCGCCCGC GTTACCCTTT GCAGCGGCGT
```

FIG. 43J

```
      6010       6020       6030       6040       6050       6060
GGGGCTGATG GCGCGCGACC TCGCCATGAA CGTGGCACTC CCCGAAGTCG ATGGCCGCAT
CCCCGACTAC CGCGCGCTGG AGCGGTACTT GCACCGTGAG GGGCTTCAGC TACCGGCGTA

      6070       6080       6090       6100       6110       6120
CCTTGCGCGC GCCGTCTCCT TCAAGGCGGC GTCGATCTAT GACGCCAAGG TGGAGGCCAA
GGAACGCGCG CGGCAGAGGA AGTTCCGCCG CAGCTAGATA CTGCGGTTCC ACCTCCGGTT

      6130       6140       6150       6160       6170       6180
TATCGTCGGC CATGAGCCGC TCGAAGGCCG GGTGCGCTTT GCCGCTGATC TTGCCGTCAA
ATAGCAGCCG GTACTCGGCG AGCTTCCGGC CCACGCGAAA CGGCGACTAG AACGGCAGTT

      6190       6200       6210       6220       6230       6240
CTGGGCGAAC GTGCGCCGGG CAGAGCCCGC CGAGCGCCGT ATTGCCATCG TCATGGCCAA
GACCCGCTTG CACGCGGCCC GTCTCGGGCG GCTCGCGGCA TAACGGTAGC AGTACCGGTT

      6250       6260       6270       6280       6290       6300
CTATCCGAAC CGCGACGGTC GCCTCGGCAA CGGTGTCGGG CTCGACACGC CGGCCGGTAC
GATAGGCTTG GCGCTGCCAG CGGAGCCGTT GCCACAGCCC GAGCTGTGCG GCCGGCCATG

      6310       6320       6330       6340       6350       6360
CGTCGAGGTG CTTAGCGCCA TGGCGCGGGA AGGCTATGCG GTCGGTGAGG TTCCCGCCGA
GCAGCTCCAC GAATCGCGGT ACCGCGCCCT TCCGATACGC CAGCCACTCC AAGGGCGGCT

      6370       6380       6390       6400       6410       6420
TGGCGACGCG CTGATCCGCT TTCTGATGGC CGGGCCGACC AATGCGGCGA GCCATGACCG
ACCGCTGCGC GACTAGGCGA AAGACTACCG GCCCGGCTGG TTACGCCGCT CGGTACTGGC

      6430       6440       6450       6460       6470       6480
TGAAATCCGC GAGCGTATTT CGCTGAACGA TTACAAAACG TTCTTCGATT CGCTTCCGAA
ACTTTAGGCG CTCGCATAAA GCGACTTGCT AATGTTTTGC AAGAAGCTAA GCGAAGGCTT

      6490       6500       6510       6520       6530       6540
ACAGATAAAG GATGAAGTTG CCGGTCGCTG GGGCGTGCCG GAGGCCGATC CCTTTTTCCT
TGTCTATTTC CTACTTCAAC GGCCAGCGAC CCCGCACGGC CTCCGGCTAG GGAAAAAGGA

      6550       6560       6570       6580       6590       6600
CGATGGCGCC TTCGCGCTGC CGCTCGCCCG CTTCGGCGAG GTGATCGTCG GCATCCAACC
GCTACCGCGG AAGCGCGACG GCGAGCGGGC GAAGCCGCTC CACTAGCAGC CGTAGGTTGG
```

FIG. 43K

```
      6610       6620       6630       6640       6650       6660
GGCGCGCGGC TACAACATCG ATCCGAAGGA AAGCTACCAT TCCCCGGACC TCGTGCCGCC
CCGCGCGCCG ATGTTGTAGC TAGGCTTCCT TTCGATGGTA AGGGGCCTGG AGCACGGCGG

      6670       6680       6690       6700     . 6710       6720
GCATGGCTAT CTCGCCTTCT ACGCCTTCCT GCGCCAGCAG TTCGGAGCGC AGGCGATCGT
CGTACCGATA GAGCGGAAGA TGCGGAAGGA CGCGGTCGTC AAGCCTCGCG TCCGCTAGCA

      6730       6740       6750       6760       6770       6780
CCACATGGGC AAGCACGGCA ATCTCGAATG GCTGCCGGGC AAGGCGCTGG CGCTGTCGGA
GGTGTACCCG TTCGTGCCGT TAGAGCTTAC CGACGGCCCG TTCCGCGACC GCGACAGCCT

      6790       6800       6810       6820       6830       6840
AACCTGCTAT CCCGAAGCGA TCTTCGGGCC GCTGCCGCAC ATCTATCCCT TCATCGTCAA
TTGGACGATA GGGCTTCGCT AGAAGCCCGG CGACGGCGTG TAGATAGGGA AGTAGCAGTT

      6850       6860       6870       6880       6890       6900
CGATCCGGGC GAAGGTACGC AGGCCAAGCG CCGCACCAGC GCCGTCATCA TCGACCACCT
GCTAGGCCCG CTTCCATGCG TCCGGTTCGC GGCGTGGTCG CGGCAGTAGT AGCTGGTGGA

      6910       6920       6930       6940       6950       6960
GACCCCGCCC TTGACGCGCG CCGAATCCTA CGGCCCGCTC AAGGATCTGG AAGCGCTCGT
CTGGGGCGGG AACTGCGCGC GGCTTAGGAT GCCGGGCGAG TTCCTAGACC TTCGCGAGCA

      6970       6980       6990       7000       7010       7020
CGACGAATAT TACGACGCCG CCGGCGGTGA TCCGCGCCGC CTCAGGCTGC TCAGCCGCCA
GCTGCTTATA ATGCTGCGGC GGCCGCCACT AGGCGCGGCG GAGTCCGACG AGTCGGCGGT

      7030       7040       7050       7060       7070       7080
GATCCTCGAT CTCGTGCGCG ACATCGGCCT CGACAGCGAC GCAGGCATCG ACAGGGGCGA
CTAGGAGCTA GAGCACGCGC TGTAGCCGGA GCTGTCGCTG CGTCCGTAGC TGTCCCCGCT

      7090       7100       7110       7120       7130       7140
CAGCGACGAC AAGGCGCTGG AAAAGCTCGA CGCCTATCTC TGCGACCTCA AGGAAATGCA
GTCGCTGCTG TTCCGCGACC TTTTCGAGCT GCGGATAGAG ACGCTGGAGT TCCTTTACGT

      7150       7160       7170       7180       7190       7200
GATCCGCGAC GGCCTGCACA TCTTCGGCGT TGCGCCGGAA GGGCGGTTGT TGACGGACCT
CTAGGCGCTG CCGGACGTGT AGCCGCCGCA ACGCGGCCTT CCCGCCAACA ACTGCCTGGA
```

*FIG. 43L*

```
      7210       7220       7230       7240       7250       7260
CACCGTAGCG CTGGCGCGCG TGCCCCGAGG TCTCGGCGAG GGCGGCGACC AGAGCCTGCA
GTGGCATCGC GACCGCGCGC ACGGGGCTCC AGAGCCGCTC CCGCCGCTGG TCTCGGACGT

      7270       7280       7290       7300       7310       7320
GCGGGCGATC GCAGCGGATG CGGGGCTGCG TGGGTTTGCT ATTCCCACCT CGGCGGGGGG
CGCCCGCTAG CGTCGCCTAC GCCCCGACGC ACCCAAACGA TAAGGGTGGA GCCGCCCCCC

      7330       7340       7350       7360       7370       7380
CAACCCCGCA CGCGACGCCC AACCCTTCGA CCCGCTCGAC TGCGTCATGT CCGACACCTG
GTTGGGGCGT GCGCTGCGGG TTGGGAAGCT GGGCGAGCTG ACGCAGTACA GGCTGTGGAC

      7390       7400       7410       7420       7430       7440
GACAGGCCCG AAACCGTCCA TCCTCGCTGA CCTCTCGGAC GCCCCCTGGC GCACCGCCGG
CTGTCCGGGC TTTGGCAGGT AGGAGCGACT GGAGAGCCTG CGGGGGACCG CGTGGCGGCC

      7450       7460       7470       7480       7490       7500
CGATACGGTC GAGCGCATCG AGTTGCTTGC CGCAAATCTC GTGTCGGGTG AACTGGCTTG
GCTATGCCAG CTCGCGTAGC TCAACGAACG GCGTTTAGAG CACAGCCCAC TTGACCGAAC

      7510       7520       7530       7540       7550       7560
CCCGGACCAC TGGGCCAACA CCCGCGCCGT GCTCGGCGAA ATCGAAACGC GCCTGAAGCC
GGGCCTGGTG ACCCGGTTGT GGGCGCGGCA CGAGCCGCTT TAGCTTTGCG CGGACTTCGG

      7570       7580       7590       7600       7610       7620
GTCGATTTCA AACTCGGGTG CCGCCGAGAT GACCGGCTTC CTCACCGGTC TCAGCGGCCG
CAGCTAAAGT TTGAGCCCAC GGCGGCTCTA CTGGCCGAAG GAGTGGCCAG AGTCGCCGGC

      7630       7640       7650       7660       7670       7680
CTTCGTCGCC CCCGGTCCAT CGGGCGCGCC GACGCGCGGC CGGCCGGATG TGTTGCCGAC
GAAGCAGCGG GGGCCAGGTA GCCCGCGCGG CTGCGCGCCG GCCGGCCTAC ACAACGGCTG

      7690       7700       7710       7720       7730       7740
GGGGCGCAAT TTCTACTCGG TCGACAGCCG CGCCGTGCCG ACGCCGGCGG CTTACGAGCT
CCCCGCGTTA AAGATGAGCC AGCTGTCGGC GCGGCACGGC TGCGGCCGCC GAATGCTCGA

      7750       7760       7770       7780       7790       7800
TGGCAAGAAA TCGGCCGAGC TTCTGATCCG CCGCTACCTG CAGGACCATG GCGAATGGCC
ACCGTTCTTT AGCCGGCTCG AAGACTAGGC GGCGATGGAC GTCCTGGTAC CGCTTACCGG
```

*FIG. 43M*

```
      7810       7820       7830       7840       7850       7860
GTCCTCCTTT GGCCTGACCG CCTGGGGCAC GGCGAACATG CGCACCGGCG GCGACGACAT
CAGGAGGAAA CCGGACTGGC GGACCCCGTG CCGCTTGTAC GCGTGGCCGC CGCTGCTGTA

      7870       7880       7890       7900       7910       7920
CGCCCAGGCC CTGGCGCTGA TCGGCGCCAA GCCCACCTGG GACATGGTCT CTCGCCGGGT
GCGGGTCCGG GACCGCGACT AGCCGCGGTT CGGGTGGACC CTGTACCAGA GAGCGGCCCA

      7930       7940       7950       7960       7970       7980
GATGGGCTAC GAGATCGTGC CGCTCGCAGT CCTCGGCCGC CCACGCGTCG ACGTGACCTT
CTACCCGATG CTCTAGCACG GCGAGCGTCA GGAGCCGGCG GGTGCGCAGC TGCACTGGAA

      7990       8000       8010       8020       8030       8040
GCGCATTTCC GGCTTCTTCC GCGATGCCTT CCCGGACCAG ATCGCGCTCT TCGACAAGGC
CGCGTAAAGG CCGAAGAAGG CGCTACGGAA GGGCCTGGTC TAGCGCGAGA AGCTGTTCCG

      8050       8060       8070       8080       8090       8100
GATCCGCGCC GTCGCGCTGG AGGAAGACGA TGCCGACAAC ATGATCGCCG CACGCATGCG
CTAGGCGCGG CAGCGCGACC TCCTTCTGCT ACGGCTGTTG TACTAGCGGC GTGCGTACGC

      8110       8120       8130       8140       8150       8160
GGCGGAAAGC CGGCGGCTGG AGGCCGAAGG CGTGGAAGCC GCCGAGGCCG CGCGTCGCGC
CCGCCTTTCG GCCGCCGACC TCCGGCTTCC GCACCTTCGG CGGCTCCGGC GCGCAGCGCG

      8170       8180       8190       8200       8210       8220
CTCCTACCGC GTCTTTGGCG CAAAGCCCGG TGCCTATGGC GCCGCCCTGC AGGCGCTGAT
GAGGATGGCG CAGAAACCGC GTTTCGGGCC ACGGATACCG CGGCGGGACG TCCGCGACTA

      8230       8240       8250       8260       8270       8280
CGACGAGAAG GGCTGGGAAA CCAAAGCAGA TCTCGCCGAG GCCTATCTTA CCTGGGGCGC
GCTGCTCTTC CCGACCCTTT GGTTTCGTCT AGAGCGGCTC CGGATAGAAT GGACCCCGCG

      8290       8300       8310       8320       8330       8340
CTATGCCTAT GGCGCCGGCG AGGAGGGCAA GGCCGAGCGC GATCTTTTCG AGGAGCGCCT
GATACGGATA CCGCGGCCGC TCCTCCCGTT CCGGCTCGCG CTAGAAAAGC TCCTCGCGGA

      8350       8360       8370       8380       8390       8400
GCGCACGATA GAGGCGGTGG TGCAGAACCA GGACAACCGC GAGCACGATC TGCTCGACAG
CGCGTGCTAT CTCCGCCACC ACGTCTTGGT CCTGTTGGCG CTCGTGCTAG ACGAGCTGTC
```

*FIG. 43N*

```
      8410       8420       8430       8440       8450       8460
CGACGACTAC TACCAGTTCG AAGGCGGCAT GAGCGCTGCC GCCGAACAGC TCGGCGGTCA
GCTGCTGATG ATGGTCAAGC TTCCGCCGTA CTCGCGACGG CGGCTTGTCG AGCCGCCAGT

      8470       8080       8490       8500       8510       8520
CCGTCCGGCG ATCTACCACA ACGACCATTC CCGTCCGGAA AAGCCTGTGA TCCGGTCGCT
GGCAGGCCGC TAGATGGTGT TGCTGGTAAG GGCAGGCCTT TTCGGACACT AGGCCAGCGA

      8530       8540       8550       8560       8570       8580
CGAAGAAGAG ATCGGCCGCG TGGTCCGGGC CCGCGTCGTC AATCCCAAGT GGATCGATGG
GCTTCTTCTC TAGCCGGCAC ACCAGGCCCG GGCGCAGCAG TTAGGGTTCA CCTAGCTACC

      8590       8600       8610       8620       8630       8640
CGTCATGCGC CACGGATACA AGGGCGCCTT CGAGATCGCT GCCACGGTCG ACTACATGTT
GCAGTACGCG GTGCCTATGT TCCCGCGGAA GCTCTAGCGA CGGTGCCAGC TGATGTACAA

      8650       8660       8670       8680       8690       8700
CGCCTTTGCC GCGACCACGG GTGCGGTGCG CGACCATCAT TTCGAGGCCG CTTATCAGGC
GCGGAAACGG CGCTGGTGCC CACGCCACGC GCTGGTAGTA AAGCTCCGGC GAATAGTCCG

      8710       8720       8730       8740       8750       8760
GTTCATTGTC GACGAGCGCG TGGCTGACTT CATGCGCGAC AAGAACCCGG CCGCCTTTGC
CAAGTAACAG CTGCTCGCGC ACCGACTGAA GTACGCGCTG TTCTTGGGCC GGCGGAAACG

      8770       8780       8790       8800       8810       8820
CGAGCTTGCC GAACGCCTGC TTGAAGCAAT CGACCGCAAT CTCTGGACGC CGCGCTCGAA
GCTCGAACGG CTTGCGGACG AACTTCGTTA GCTGGCGTTA GAGACCTGCG GCGCGAGCTT

      8830       8840       8850       8860       8870       8880
TTCGGCGCGG TTTGAACTTG CCGGCATCGG CACGGCAGCA ACCCGGCTTC GTGCCGGCAA
AAGCCGCGCC AAACTTGAAC GGCCGTAGCC GTGCCGTCGT TGGGCCGAAG CACGGCCGTT

      8890       8900       8910       8920       8930       8940
TGAATAGAGC GGTTCCGGGC TGGCGGTTAT CCGTCCGGAA TTGCTTGGAA ACAAAGACCT
ACTTATCTCG CCAAGGCCCG ACCGCCAATA GGCAGGCCTT AACGAACCTT TGTTTCTGGA

      8950       8960       8970       8980       8990       9000
GGTTCCGTTT CGCTGCTCAG TGAAGTGCGA AAAGGAACCG AAGCGGGACG AGGGCGTCTG
CCAAGGCAAA GCGACGAGTC ACTTCACGCT TTTCCTTGGC TTCACCCTGC TCCCGCAGAC
```

FIG. 43O

```
      9010       9020       9030       9040       9050       9060
CCCATCCCGA ACTTGAGAAC TGAGGGAGTG ATCATGAGCG ACGAGACGAC AGTAGGCGGC
GGGTAGGGCT TGAACTCTTG ACTCCCTCAC TAGTACTCGC TGCTCTGCTG TCATCCGCCG

      9070       9080       9090       9100       9110       9120
GAAGCCCCGG CCGAGAAGGA CGATGCCCGC CACGCCATGA AGATGGCGAA GAAGAAGGCA
CTTCGGGGCC GGCTCTTCCT GCTACGGGCG GTGCGGTACT TCTACCGCTT CTTCTTCCGT

      9130       9140       9150       9160       9170       9180
GCACGCGAAA AGATCATGGC GACGAAGACC GACGAGAAGG GTCTGATCAT CGTCAACACC
CGTGCGCTTT TCTAGTACCG CTGCTTCTGG CTGCTCTTCC CAGACTAGTA GCAGTTGTGG

      9190       9200       9210       9220       9230       9240
GGCAAAGGCA AGGGCAAGTC GACCGCCGGC TTCGGCATGA TCTTCCGCCA TATCGCCCAC
CCGTTTCCGT TCCCGTTCAG CTGGCGGCCG AAGCCGTACT AGAAGGCGGT ATAGCGGGTG

      9250       9260       9270       9280       9290       9300
GGCATGCCCT GCGCCGTCGT GCAGTTCATC AAGGGTGCGA TGGCAACCGG CGAGCGCGAG
CCGTACGGGA CGCGGCAGCA CGTCAAGTAG TTCCCACGCT ACCGTTGGCC GCTCGCGCTC

      9310       9320       9330       9340       9350       9360
TTGATCGAGA AGCATTTCGG CGATGTCTGC CAGTTCTACA CGCTCGGCGA GGGCTTCACC
AACTAGCTCT TCGTAAAGCC GCTACAGACG GTCAAGATGT GCGAGCCGCT CCCGAAGTGG

      9370       9380       9390       9400       9410       9420
TGGGAAACGC AGGATCGCGC CCGCGATGTT GCGATGGCTG AAAAGGCCTG GGAGAAGGCG
ACCCTTTGCG TCCTAGCGCG GGCGCTACAA CGCTACCGAC TTTTCCGGAC CCTCTTCCGC

      9430       9440       9450       9460       9470       9480
AAGGAACTGA TCCGTGACGA GCGCAACTCG ATGGTGCTGC TCGACGAGAT CAACATTGCT
TTCCTTGACT AGGCACTGCT CGCGTTGAGC TACCACGACG AGCTGCTCTA GTTGTAACGA

      9490       9500       9510       9520       9530       9540
CTGCGCTACG ACTACATCGA CGTCGCCGAA GTGGTGCGCT TCCTGAAGGA AGAAAAGCCG
GACGCGATGC TGATGTAGCT GCAGCGGCTT CACCACGCGA AGGACTTCCT TCTTTTCGGC

      9550       9560       9570       9580       9590       9600
CACATGACGC ATGTGGTGCT CACCGGCCGC AACGCGAAAG AAGACCTGAT CGAAGTCGCC
GTGTACTGCG TACACCACGA GTGGCCGGCG TTGCGCTTTC TTCTGGACTA GCTTCAGCGG
```

FIG. 43P

```
      9610       9620       9630       9640       9650       9660
GATCTCGTCA CTGAGATGGA GCTGATCAAG CATCCGTTCC GTTCCGGCAT CAAGGCGCAG
CTAGAGCAGT GACTCTACCT CGACTAGTTC GTAGGCAAGG CAAGGCCGTA GTTCCGCGTC

      9670       9680       9690       9700       9710       9720
CAGGGCGTGG AGTTCTGATG AGCCAGAGCT GGCAGTTCTG GGCGCTGCTT TCGGCCGCCT
GTCCCGCACC TCAAGACTAC TCGGTCTCGA CCGTCAAGAC CCGCGACGAA AGCCGGCGGA

      9730       9740       9750       9760       9770       9780
TCGCTGCGCT CACGGCGGTG TTTGCCAAGG TCGGGGTTGC GCAGATCAAC TCCGACTTCG
AGCGACGCGA GTGCCGCCAC AAACGGTTCC AGCCCCAACG CGTCTAGTTG AGGCTGAAGC

      9790       9800       9810       9820       9830       9840
CAACGCTGAT CCGCACCGTC GTCATCCTCT GCGTGATCGC CGCCATCGTG GCGGCGACAG
GTTGCGACTA GGCGTGGCAG CAGTAGGAGA CGCACTAGCG GCGGTAGCAC CGCCGCTGTC

      9850       9860       9870       9880       9890       9900
GGCAGTGGCA GAAGCCATCG GAAATCCCGG GCCGCACCTG GCTGTTCCTG GCGCTGTCAG
CCGTCACCGT CTTCGGTAGC CTTTAGGGCC CGGCGTGGAC CGACAAGGAC CGCGACAGTC

      9910       9920       9930       9940       9950       9960
GGCTTGCGAC TGGCGCTTCC TGGCTTGCCT ATTTCCGCGC GCTGAAGCTC GGCGACGCCG
CCGAACGCTG ACCGCGAAGG ACCGAACGGA TAAAGGCGCG CGACTTCGAG CCGCTGCGGC

      9970       9980       9990      10000      10010      10020
CCCGCGTGGC GCCGCTCGAC AAGCTCTCGA TCGTCATGGT CGCGATCTTC GGCGTGCTCT
GGGCGCACCG CGGCGAGCTG TTCGAGAGCT AGCAGTACCA GCGCTAGAAG CCGCACGAGA

     10030      10040      10050      10060      10070      10080
TCCTCGGTGA AAAGCTCAAC CTGATGAACT GGCTCGGCGT CGCCTTCATT GCCGCCGGGG
AGGAGCCACT TTTCGAGTTG GACTACTTGA CCGAGCCGCA GCGGAAGTAA CGGCGGCCCC

     10090      10100      10110      10120      10130      10140
CGCTGTTGCT GGCGGTGTTT TGAGCGCGCC TGCTCTGGTG CCTGTTCACT GAATGCTCGC
GCGACAACGA CCGCCACAAA ACTCGCGCGG ACGAGACCAC GGACAAGTGA CTTACGAGCG

     10150      10160      10170      10180      10190      10200
CTCAATCAAT CCGTAATCCC GACACATGCA GTGGTTGTGA CGAGCGGGAG GACGGCATGC
GAGTTAGTTA GGCATTAGGG CTGTGTACGT CACCAACACT GCTCGCCCTC CTGCCGTACG
```

FIG. 43Q

```
     10210      10220      10230      10240      10250      10260
AGATTGAAGG CAATTGGAGC GAGCGCCTTC CTGATCCGTC GGGCCACGTC GCGCAGTTCG
TCTAACTTCC GTTAACCTCG CTCGCGGAAG GACTAGGCAG CCCGGTGCAG CGCGTCAAGC

     10270      10280      10290      10300      10310      10320
GCAGACGCTG GAAGCGTCGC AGCCTGAGGG TGAGCCCTGC TTCAGACCCA CCGGCGGACA
CGTCTGCGAC CTTCGCAGCG TCGGACTCCC ACTCGGGACG AAGTCTGGGT GGCCGCCTGT

     10330      10340      10350      10360      10370      10380
CGCCTGCAAT AGGCACCGTA GGCGTCGCCG AAGACCTTGG CGAGGTGGGT TTCCTCCATG
GCGGACGTTA TCCGTGGCAT CCGCAGCGGC TTCTGGAACC GCTCCACCCA AAGGAGGTAC

     10390      10400      10410      10420      10430      10440
CGGATCTGGT AGGAAATCGA GATCCAGGCG GAGAGCGCCA GCGCCACCGA GATGACGTTG
GCCTAGACCA TCCTTTAGCT CTAGGTCCGC CTCTCGCGGT CGCGGTGGCT CTACTGCAAC

     10450      10460      10470      10480      10490      10500
GGCACCGCCA TCACCGTGCC GATCAGCGCG GTCACCATGC CGACATAGAT CGGGTTGCGC
CCGTGGCGGT AGTGGCACGG CTAGTCGCGC CAGTGGTACG GCTGTATCTA GCCCAACGCG

     10510      10520      10530      10540      10550      10560
GAGAAGGCAT AGAGGCCTGA GGTCACAAGC GGCGCGTCCT GCTTTTCAGG GATGCCGATC
CTCTTCCGTA TCTCCGGACT CCAGTGTTCG CCGCGCAGGA CGAAAAGTCC CTACGGCTAG

     10570      10580      10590      10600      10610      10620
TTCCAGGAAT GACGCATCGC CCATTGCGAC AGCATCGTCA GCCCGCCGCC GAGCGTCATC
AAGGTCCTTA CTGCGTAGCG GGTAACGCTG TCGTAGCAGT CGGGCGGCGG CTCGCAGTAG

     10630      10640      10650      10660      10670      10680
AGCGCCAGGC CGACGGCGTG AAGGATGGGC GTGTCGAGCG CCGGGATCCG GCCGAGGGCA
TCGCGGTCCG GCTGCCGCAC TTCCTACCCG CACAGCTCGC GGCCCTAGGC CGGCTCCCGT

     10690      10700      10710      10720      10730      10740
GCATCGACGG AGGCCGGGAG CATGGCGACC GCCAGCAGGT GGATCACCAG CGCTGCGACG
CGTAGCTGCC TCCGGCCCTC GTACCGCTGG CGGTCGTCCA CCTAGTGGTC GCGACGCTGC

     10750      10760      10770      10780      10790      10800
ATCAGGCGGA AAAGCCTGCC CGCAAACCCT TCCGCATCGT CGCCATAGGT TAGCACGACC
TAGTCCGCCT TTTCGGACGG GCGTTTGGGA AGGCGTAGCA GCGGTATCCA ATCGTGCTGG
```

FIG. 43R

```
     10810      10820      10830      10840      10850      10860
GGCGAGCGGC CGGATTGCAC GCGGCGGAGG ATCGCCAGCG CGAGCGTGGA CAATCCCACG
CCGCTCGCCG GCCTAACGTG CGCCGCCTCC TAGCGGTCGC GCTCGCACCT GTTAGGGTGC

     10870      10880      10890      10900      10910      10920
ACGAGCATCA GGATGGTGGG AAGGGTGGTG GACATGGAAA CCTCTGGAGC GAGCTGACAA
TGCTCGTAGT CCTACCACCC TTCCCACCAC CTGTACCTTT GGAGACCTCG CTCGACTGTT

     10930      10940      10950      10960      10970      10980
GACAGGAGCG CACGACGGGT AGGCGGCCCA TATGAGCGTC TACCCGGCGA AGCATTCTGA
CTGTCCTCGC GTGCTGCCCA TCCGCCGGGT ATACTCGCAG ATGGGCCGCT TCGTAAGACT

     10990      11000      11010      11020      11030      11040
TCACCTTGCA ATCTCTAGTA ACTAGAGGTT CAAGCGTCGG ACCTGTCCGA CTTTCGTCGT
AGTGGAACGT TAGAGATCAT TGATCTCCAA GTTCGCAGCC TGGACAGGCT GAAAGCAGCA

     11050      11060      11070      11080      11090      11100
GGTTACCGGA TCTTATTGCC AAGCGTTGGA GGCTGTCATC GTCGCCCCCG CCGTGTCGGA
CCAATGGCCT AGAATAACGG TTCGCAACCT CCGACAGTAG CAGCGGGGGC GGCACAGCCT

     11110      11120      11130      11140      11150      11160
AGGTCGGCAA AATTCGTCTC TTGACGGCTG CTCCTTCCGT CGAGCGATTG CATAGGCAGG
TCCAGCCGTT TTAAGCAGAG AACTGCCGAC GAGGAAGGCA GCTCGCTAAC GTATCCGTCC

     11170      11180      11190      11200      11210      11220
AGGCCGCACC CATGTTAGAC CGTCGACAGG CTAAATACGG GTGAACCTTG AAGAATACTC
TCCGGCGTGG GTACAATCTG GCAGCTGTCC GATTTATGCC CACTTGGAAC TTCTTATGAG

     11230      11240      11250      11260      11270      11280
TCAGAGCTGC GGTTGGTGTC GCATCGGTCT TGCTGTTCTT GTCATCAGGT GTGGCGGGGC
AGTCTCGACG CCAACCACAG CGTAGCCAGA ACGACAAGAA CAGTAGTCCA CACCGCCCCG

     11290      11300      11310      11320      11330      11340
AGGCGCAAAC CGTGAAGAGC GGGGCGTCAC GAGCTCAAGA AACGACGACC ACCCAGAAGG
TCCGCGTTTG GCACTTCTCG CCCCGCAGTG CTCGAGTTCT TTGCTGCTGG TGGGTCTTCC

     11350      11360      11370      11380      11390      11400
CGAAACCGAA AACTAAAACG ACGCGCAAGC AAAGGGCTGC GGATGAAGCC AAGGCCAAGG
GCTTTGGCTT TTGATTTTGC TGCGCGTTCG TTTCCCGACG CCTACTTCGG TTCCGGTTCC
```

*FIG. 43S*

```
      11410      11420      11430      11440      11450      11460
CGCTCGCCGA AGCGCGCCGT CCACGGATTT GCAAGACGCG GGAGAGCGAA TGCAGCTATG
GCGAGCGGCT TCGCGCGGCA GGTGCCTAAA CGTTCTGCGC CCTCTCGCTT ACGTCGATAC

      11470      11480      11490      11500      11510      11520
GCGCAGGTCC GGTCGGAGAG CAGTGCTCGT GCTGGTCGAA ATCCGGTGCG CCTGATCTTG
CGCGTCCAGG CCAGCCTCTC GTCACGAGCA CGACCAGCTT TAGGCCACGC GGACTAGAAC

      11530      11540      11550      11560      11570      11580
GCATAACTGT CAGGCGTTGA CCGCCCGCGA CCTTCGCGCG GGCAGGCAAG CGTGCGTCGC
CGTATTGACA GTCCGCAACT GGCGGGCGCT GGAAGCGCGC CCGTCCGTTC GCACGCAGCG

      11590      11600      11610      11620      11630      11640
TCGAAGCGAC GCCTGACGCG ATAGAAATCA CGGGTCGCCT GGTTCGTTCT GAAAGCTTGG
AGCTTCGCTG CGGACTGCGC TATCTTTAGT GCCCAGCGGA CCAAGCAAGA CTTTCGAACC

      11650      11660      11670      11680      11690      11700
GATTGGGTTT AGGTGATGGA AGCCGGCGTT GAACGCAAAA TAATGATCGA TCTCGAGAAC
CTAACCCAAA TCCACTACCT TCGGCCGCAA CTTGCGTTTT ATTACTAGCT AGAGCTCTTG

      11710      11720      11730      11740      11750      11760
AGCGCGCTCC AGTTTGCAAC CCGAGCACAC GGCGAACAGA AGCGTAAGTA TGACGGTCGG
TCGCGCGAGG TCAAACGTTG GGCTCGTGTG CCGCTTGTCT TCGCATTCAT ACTGCCAGCC

      11770      11780      11790      11800      11810      11820
CCCTATATCG TTCATCCGAT TGCGGTGGCG GAGATTGTTC GAAGCGTGCC CCATACGCCC
GGGATATAGC AAGTAGGCTA ACGCCACCGC CTCTAACAAG CTTCGCACGG GGTATGCGGG

      11830      11840      11850      11860      11870      11880
GAAATGATCG CCGCAGCGCT GCTTCACGAT ACGGTCGAAG ATACCGACGC GACGCTGCTG
CTTTACTAGC GGCGTCGCGA CGAAGTGCTA TGCCAGCTTC TATGGCTGCG CTGCGACGAC

      11890      11900      11910      11920      11930      11940
GAGATCAAGG AAGCGTTCGG CCCCAAGGTC GCAACACTGG TTGCGTGGCT CACCGACATA
CTCTAGTTCC TTCGCAAGCC GGGGTTCCAG CGTTGTGACC AACGCACCGA GTGGCTGTAT

      11950      11960      11970      11980      11990      12000
TCCACTCCGT TCCACGGCAA CCGACAGGTG CGCAAGGAAC TGGATCGCCA GCACCTCGCA
AGGTGAGGCA AGGTGCCGTT GGCTGTCCAC GCGTTCCTTG ACCTAGCGGT CGTGGAGCGT
```

*FIG. 43T*

```
      12010      12020      12030      12040      12050      12060
TCGGCGCCCG CCGCGGCGAA AACCGTCAAG CTCGCCGACC TGATCGACAA TGCGATAGCG
AGCCGCGGGC GGCGCCGCTT TTGGCAGTTC GAGCGGCTGG ACTAGCTGTT ACGCTATCGC

      12070      12080      12090      12100      12110      12120
ATCAAAGCCG GCGATCCGAA TTTCTGGAAA GTGTTCGGCG CCGAGATGAA ACGCTTGCTG
TAGTTTCGGC CGCTAGGCTT AAAGACCTTT CACAAGCCGC GGCTCTACTT TGCGAACGAC

      12130      12140      12150      12160      12170      12180
GAGGTCTTGG GCGACGGCGA CGAGACCCTT CTCGCAAAGG CCCGTGCATT AGCGCCGGAA
CTCCAGAACC CGCTGCCGCT GCTCTGGGAA GAGCGTTTCC GGGCACGTAA TCGCGGCCTT

      12190      12200      12210      12220      12230      12240
TGAGAGTGCC GCCGTTTATC GGCAAGCATG TCTGTGCCAT GTCGACCCGG TCAACCGGTC
ACTCTCACGG CGGCAAATAG CCGTTCGTAC AGACACGGTA CAGCTGGGCC AGTTGGCCAG

      12250      12260      12270      12280      12290      12300
ATCCAAGATC GCAGAACGGA CATGCATTTG CGGTTTTGCC CGCCGGTGTG GCCCAGCCAC
TAGGTTCTAG CGTCTTGCCT GTACGTAAAC GCCAAAACGG GCGGCCACAC CGGGTCGGTG

      12310      12320      12330      12340      12350      12360
GCCTCACAGG CTGCGCGGTT GCGGCCGTTA GGACAGCGCA GAATTTGCCG ACCGCGCCGC
CGGAGTGTCC GACGCGCCAA CGCCGGCAAT CCTGTCGCGT CTTAAACGGC TGGCGCGGCG

      12370      12380      12390      12400      12410      12420
GCCTCAATGC CCCAGCCAGA TCCGCAAGGG ATGCGTCGGA TCTGCGAGCA GCCGGATCGC
CGGAGTTACG GGGTCGGTCT AGGCGTTCCC TACGCAGCCT AGACGCTCGT CGGCCTAGCG

      12430      12440      12450      12460      12470      12480
GAGCGCGATC GAGACGATGA CGAGCAGCGG CTTGATGATC TTGGCGCCCT TGGCCATGGC
CTCGCGCTAG CTCTGCTACT GCTCGTCGCC GAACTACTAG AACCGCGGGA ACCGGTACCG

      12490      12500      12510      12520      12530      12540
ATAGCGCGAG CCGACCTGGG CGCCGAGGAA CTGGCCGAGG CCCATCAACA GGCCGACCTT
TATCGCGCTC GGCTGGACCC GCGGCTCCTT GACCGGCTCC GGGTAGTTGT CCGGCTGGAA

      12550      12560      12570      12580      12590      12600
CCAGAGAACG GCGCCGAAGA AGAGGAAGAC GCCGAAGGCG CCGACGTTGG AGCCAAAGTT
GGTCTCTTGC CGCGGCTTCT TCTCCTTCTG CGGCTTCCGC GGCTGCAACC TCGGTTTCAA
```

FIG. 43U

```
     12610      12620      12630      12640      12650      12660
GAGGAACTTC GTGTGCGCCG TCGCCTTCAA CACGCCGAAG CCGGCGAGGG TAACGAAGCC
CTCCTTGAAG CACACGCGGC AGCGGAAGTT GTGCGGCTTC GGCCGCTCCC ATTGCTTCGG

     12670      12680      12690      12700      12710      12720
GAGCATGAAG AACGAGCCGG TGCCGGGGCC GAAGACGCCG TCATAAAAGC CGATTAGCGG
CTCGTACTTC TTGCTCGGCC ACGGCCCCGG CTTCTGCGGC AGTATTTTCG GCTAATCGCC

     12730      12740      12750      12760      12770      12780
CACCAGTGTC AGCGTGAAGA CGAAGGGGGT GACGCGGCTG TGCTGGTCGA CGTCGCCCAT
GTGGTCACAG TCGCACTTCT GCTTCCCCCA CTGCGCCGAC ACGACCAGCT GCAGCGGGTA

     12790      12800      12810      12820      12830      12840
GTTCGGCTTC AGGCCGAAAT AAAGCGCAAT GGCGATCAGC AGAAAGGGCA GGATCGCCTT
CAAGCCGAAG TCCGGCTTTA TTTCGCGTTA CCGCTAGTCG TCTTTCCCGT CCTAGCGGAA

     12850      12860      12870      12880      12890      12900
CAGCACGTCG CCGGGAACGA TGGTTGCGAG CAGGGCGCCG AGCACGGCGC CGGCGGCCGA
GTCGTGCAGC GGCCCTTGCT ACCAACGCTC GTCCCGCGGC TCGTGCCGCG GCCGCCGGCT

     12910      12920      12930      12940      12950      12960
CATCAGCGCC ATCGGCAGCT GCTCTTTCAG GTTCACGTGG CCGCGCCGGG CATAGGACAG
GTAGTCGCGG TAGCCGTCGA CGAGAAAGTC CAAGTGCACC GGCGCGGCCC GTATCCTGTC

     12970      12980      12990      13000      13010      13020
CGTGGCCGAG CCGGAGCCGA ACAATCCCTG CAGCTTGTTG GTGCCGAGCG TCTGCAAGGG
GCACCGGCTC GGCCTCGGCT TGTTAGGGAC GTCGAACAAC CACGGCTCGC AGACGTTCCC

     13030      13040      13050      13060      13070      13080
CGGGATGCCC GCAATGAGCA TGGCCGGAAT GGTGATCATG CCACCGCCGC CGGCGATCGA
GCCCTACGGG CGTTACTCGT ACCGGCCTTA CCACTAGTAC GGTGGCGGCG GCCGCTAGCT

     13090      13100      13110      13120      13130      13140
ATCGATGAAG CCTGCGATGA AGGCGGCGAC GAACAGGAAG GCGAGCAGGT GGAAGGCGAG
TAGCTACTTC GGACGCTACT TCCGCCGCTG CTTGTCCTTC CGCTCGTCCA CCTTCCGCTC

ATCT
TAGA
```

*FIG. 43V*

RESTRICTION MAP OF THE 13144-BP SEQUENCE

| | | | | | | |
|---|---|---|---|---|---|---|
| ApaLI | 642, | | | | | |
| EcoRI | 8818, | | | | | |
| HindIII | 11633, | | | | | |
| MluI | 7963, | | | | | |
| NdeI | 10950, | | | | | |
| PvuII | 12918, | | | | | |
| SfiI | 3133, | | | | | |
| SplI | 99, | | | | | |
| BglII | 8248, | 13139, | | | | |
| KpnI | 2315, | 6300, | | | | |
| NotI | 5526, | 7615, | | | | |
| SmaI | 1322, | 9868, | | | | |
| SspI | 4843, | 6968, | | | | |
| XmnI | 9313, | 12091, | | | | |
| AatII | 1033, | 9503, | 12773, | | | |
| AflIII | 550, | 7963, | 8634, | | | |
| BalI | 2107, | 6236, | 12473, | | | |
| BamHI | 2266, | 5416, | 10664, | | | |
| BspMII | 5002, | 8494, | 8914, | | | |
| EcoRV | 4263, | 4605, | 5137, | | | |
| NcoI | 6318, | 7786, | 12474, | | | |
| NsiI | 3467, | 5064, | 12266, | | | |
| PflMI | 7870, | 10718, | 11065, | | | |
| XhoI | 1512, | 4171, | 11692, | | | |
| ApaI | 1928, | 3138, | 3386, | 8551, | | |
| AsuII | 784, | 5670, | 8418, | 11799, | | |
| FspII | 784, | 5670, | 8418, | 11799, | | |
| MaeI | 1883, | 2647, | 10995, | 11002, | | |
| NruI | 1827, | 3794, | 10002, | 12419, | | |
| SauI | 852, | 7001, | 10284, | 10517, | | |
| BstEII | 995, | 3642, | 8456, | 10470, | 11041, | |
| Eco47III | 6954, | 7209, | 8434, | 10731, | 11837, | |
| SacI | 5, | 4109, | 4694, | 5169, | 11315, | |
| StuI | 204, | 4081, | 8261, | 9406, | 10515, | |
| BstXI | 761, | 2982, | 3612, | 6031, | 6232, | 9102, |
| SacII | 932, | 1025, | 2096, | 3537, | 5184, | 12014, |
| SphI | 966, | 2740, | 5360, | 8098, | 9246, | 10199, |

FIG. 44A

RESTRICTION MAP OF THE 13144-BP SEQUENCE

| | | | | | | | | |
|---|---|---|---|---|---|---|---|---|
| BclI | 2992, | 4016, | 9029, | 9164, | 9623, | 10978, | 13053, | |
| RsaI | 101, | 1201, | 1918, | 2313, | 4881, | 6298, | 6856, | |
| Tth111I | 1821, | 2424, | 4351, | 7361, | 7904, | 12227, | 12697, | |
| PstI | 613, | 3989, | 5832, | 5952, | 7260, | 7782, | 8211, | 12992, |
| ClaI | 1351, | 3596, | 4469, | 4724, | 5748, | 6618, | 8574, | 11687, |
| | 13082, | | | | | | | |
| FspI | 1363, | 1551, | 1653, | 5219, | 7841, | 7982, | 8342, | 9760, |
| | 11971, | | | | | | | |
| HinfI | 1137, | 2564, | 2592, | 3025, | 5667, | 5927, | 6467, | 6923, |
| | 13079, | | | | | | | |
| StyI | 2488, | 3396, | 5116, | 6105, | 6318, | 7786, | 9745, | 10355, |
| | 11389, | 11395, | 11903, | 12468, | 12474, | | | |
| DdeI | 852, | 1875, | 3373, | 3586, | 6311, | 7001, | 7010, | 7610, |
| | 8956, | 9020, | 9611, | 10284, | 10517, | 11220, | | |
| Nsp7524I | 554, | 966, | 2394, | 2740, | 5360, | 7840, | 8098, | 8638, |
| | 9246, | 9553, | 10168, | 10199, | 12210, | 12264, | | |
| PvuI | 26, | 1853, | 2453, | 4403, | 4703, | 4728, | 5091, | 5112, |
| | 5178, | 6717, | 7269, | 9991, | 12429, | 13077, | | |
| AvaI | 975, | 1320, | 1503, | 1512, | 3131, | 3231, | 3709, | 3766, |
| | 4171, | 4212, | 7224, | 7573, | 9866, | 11692, | 11720, | |
| BanII | 5, | 496, | 1723, | 1928, | 2254, | 3138, | 3386, | 4109, |
| | 4694, | 5196, | 6207, | 6282, | 8551, | 10296, | 11315, | |
| SalI | 83, | 1296, | 2418, | 4045, | 4303, | 5258, | 6959, | 7700, |
| | 7967, | 8627, | 8708, | 9198, | 11182, | 12221, | 12766, | |
| XhoII | 2266, | 3920, | 5416, | 5688, | 6943, | 7020, | 7140, | 8248, |
| | 10382, | 10400, | 10664, | 11048, | 12378, | 12398, | 13139, | |

*FIG. 44B*

OPEN READING FRAME 24

A = ATG

*: STOP CODON

CS: COMPLEMENTARY STRAND

13144-BP SEQUENCE FROM 429 TO 1328 cobQ GENE

```
  M  T  R  R  I  M  L  Q  G  T  G  S  D  V  G  K  S  V  L  V  A  G  L  C  R
   ATGACACGCAGGATCATGTTGCAGGGAACCGGCTCGGATGTCGGAAAATCGGTATTGGTGGCGGGGCTCTGCCGG
429       439       449       459       469       479       489       499
  L  A  A  N  Q  G  L  K  V  R  P  F  K  P  Q  N  M  S  N  N  A  A  V  S  D
   CTTGCCGCCAATCAGGGCCTGAAGGTCCGGCCGTTCAAGCCGCAGAACATGTCGAACAACGCCGCCGTTTCCGAC
504       514       524       534       544       554       564       574
  D  G  G  E  I  G  R  A  Q  W  L  Q  A  L  A  A  R  V  P  S  S  V  H  M  N
   GACGGCGGCGAGATCGGCCGCGCGCAATGGCTGCAGGCGCTGGCCGCGCGCGTGCCGTCGTCGGTGCACATGAAC
579       589       599       609       619       629       639       649
  P  V  L  L  K  P  Q  S  D  V  G  S  Q  I  V  V  Q  G  K  V  A  G  Q  A  R
   CCGGTGCTCCTGAAGCCGCAGTCGGACGTGGGCAGCCAGATCGTCGTTCAGGGCAAGGTCGCCGGGCAGGCCAGG
654       664       674       684       694       704       714       724
  G  R  E  Y  Q  A  L  K  P  K  L  L  G  A  V  M  E  S  F  E  Q  I  S  A  G
   GGGCGGGAATATCAGGCGCTCAAGCCCAAGCTGCTGGGCGCCGTCATGGAGAGTTTCGAACAAATATCGGCCGGT
729       739       749       759       769       779       789       799
  A  D  L  V  V  V  E  G  A  G  S  P  A  E  I  N  L  R  P  G  D  I  A  N  M
   GCCGATCTCGTGGTGGTCGAAGGCGCCGGCTCGCCGGCCGAAATCAACCTCAGGCCCGGCGACATCGCCAATATG
804       814       824       834       844       854       864       874
  G  F  A  T  R  A  N  V  P  V  V  L  V  G  D  I  D  R  G  G  V  I  R  S  L
   GGCTTTGCGACACGGGCCAATGTGCCGGTCGTGCTGGTCGGCGACATCGACCGCGGGGGGGTGATCGCCTCGCTG
879       889       899       909       919       929       939       949
  V  G  T  H  A  I  L  P  E  E  D  R  R  M  V  T  G  Y  L  I  N  K  F  R  G
   GTCGGCACGCATGCGATCCTGCCCGAGGAAGACCGGCGCATGGTGACCGGCTATCTCATCAACAAGTTCCGCGGC
954       964       974       984       994       1004      1014      1024
  D  V  T  L  F  D  D  G  I  A  A  V  N  R  Y  T  G  W  P  C  F  G  V  V  P
   GACGTCACGCTGTTCGACGACGGCATTGCTGCCGTCAACCGCTACACCGGCTGGCCCTGCTTCGGCGTCGTGCCG
1029      1039      1049      1059      1069      1079      1089      1099
  W  L  K  A  A  A  R  L  P  A  E  D  S  V  V  L  E  K  L  T  R  G  E  G  R
   TGGCTGAAGGCGGCGGCACGCCTGCCGGCGGAAGATTCCGTCGTGCTGGAGAAGCTGACGCGCGGCGAGGGGCGG
1104      1114      1124      1134      1144      1154      1164      1174
  A  L  K  V  A  V  P  V  L  S  R  I  A  N  F  D  D  L  D  P  L  A  A  E  P
   GCGCTGAAGGTTGCCGTCCCGGTACTGTCGCGCATCGCCAATTTCGACGACCTCGATCCGCTCGCCGCCGAACCG
1179      1189      1199      1209      1219      1229      1239      1249
  E  I  D  L  V  F  V  R  P  G  S  P  I  P  V  D  A  G  L  V  V  I  P  G  S
   GAGATTGATCTCGTCTTCGTGCGGCCTGGCAGTCCCATTCCGGTCGACGCTGGCCTCGTCGTCATTCCCGGGTCG
1254      1264      1274      1284      1294      1304      1314      1324
```

FIG. 47A

13144-BP SEQUENCE FROM 1329 TO 1886 cobQ GENE

```
   K  S  T  I  G  D  L  I  D  F  R  A  Q  G  W  D  R  D  L  E  R  H  V  R  R
    AAATCGACCATCGGCGACCTCATCGATTTCCGTGCGCAAGGGTGGGACCGTGACCTCGAACGTCATGTGCGCCGG
1329      1339      1349      1359      1369      1379      1389      1399
   G  G  R  V  I  G  I  C  G  G  Y  Q  M  L  G  R  R  V  T  D  P  L  G  I  E
    GGCGGCCGGGTCATCGGCATCTGCGGCGGCTACCAGATGCTCGGCCGGCGCGTCACCGATCCGCTCGGCATCGAG
1404      1414      1424      1434      1444      1454      1464      1474
   G  G  E  R  A  V  E  G  L  G  L  L  E  V  E  T  E  M  A  P  E  K  T  V  R
    GGCGGCGAACGTGCGGTCGAGGGCCTCGGGCTGCTCGAGGTCGAGACCGAGATGGCGCCGGAAAAGACGGTGCGC
1479      1489      1499      1509      1519      1529      1539      1549
   N  S  R  A  W  S  L  E  H  D  V  V  L  E  G  Y  E  I  H  L  G  K  T  Q  G
    AACAGCCGCGCCTGGTCGCTGGAGCATGATGTGGTGCTCGAAGGCTACGAAATCCATCTTGGCAAGACGCAAGGT
1554      1564      1574      1584      1594      1604      1614      1624
   A  D  C  G  R  P  S  V  R  I  D  N  R  A  D  G  A  L  S  A  D  G  R  V  M
    GCGGACTGTGGCCGGCCGTCGGTGCGCATCGACAATCGCGCCGACGGCGCCCTTTCGGCCGATGGCCGCGTGATG
1629      1639      1649      1659      1669      1679      1689      1699
   G  T  Y  L  H  G  L  F  T  S  D  A  Y  R  G  A  L  L  K  S  F  G  I  E  G
    GGCACCTACCTGCATGGGCTCTTCACCAGCGACGCCTATCGCGGCGCGCTGCTCAAGAGTTTCGGCATCGAAGGC
1704      1714      1724      1734      1744      1754      1764      1774
   G  A  N  N  Y  R  Q  S  V  D  A  A  L  D  D  V  A  N  E  L  E  A  V  L  D
    GGCGCCAACAACTACCGCCAATCGGTCGATGCGGCGCTCGACGATGTCGCGAACGAACTGGAGGCTGTGCTCGAT
1779      1789      1799      1809      1819      1829      1839      1849
   R  R  W  L  D  E  L  L  R  H  *  (SEQ ID NO:43)
    CGTCGCTGGCTGGACGAGTTGCTCAGGCACTAG (SEQ ID NO:42)
1854      1864      1874      1884
```

FIG. 47B

COBQ PROTEIN

FIRST RESIDUE = 1
LAST RESIDUE = 485

| | | | NUMBER | NO.% | WEIGHT | WEIGHT % |
|---|---|---|---|---|---|---|
| 1 | PHE | F | 11 | 2.27 | 1617.75 | 3.11 |
| 2 | LEU | L | 50 | 10.31 | 5654.20 | 10.88 |
| 3 | ILE | I | 23 | 4.74 | 2600.93 | 5.01 |
| 4 | MET | M | 10 | 2.06 | 1310.41 | 2.52 |
| 5 | VAL | V | 50 | 10.31 | 4953.42 | 9.53 |
| 6 | SER | S | 24 | 4.95 | 2088.77 | 4.02 |
| 7 | PRO | P | 23 | 4.74 | 2232.21 | 4.30 |
| 8 | THR | T | 15 | 3.09 | 1515.72 | 2.92 |
| 9 | ALA | A | 49 | 10.10 | 3480.82 | 6.70 |
| 10 | TYR | Y | 8 | 1.65 | 1304.51 | 2.51 |
| 11 | * | * | 0 | 0.00 | 0.00 | 0.00 |
| 12 | HIS | H | 7 | 1.44 | 959.41 | 1.85 |
| 13 | GLN | Q | 15 | 3.09 | 1920.88 | 3.70 |
| 14 | ASN | N | 16 | 3.30 | 1824.69 | 3.51 |
| 15 | LYS | K | 15 | 3.09 | 1921.42 | 3.70 |
| 16 | ASP | D | 34 | 7.01 | 3910.92 | 7.53 |
| 17 | GLU | E | 28 | 5.77 | 3613.19 | 6.96 |
| 18 | CYS | C | 4 | 0.82 | 412.04 | 0.79 |
| 19 | TRP | W | 6 | 1.24 | 1116.48 | 2.15 |
| 20 | ARG | R | 40 | 8.25 | 6244.04 | 12.02 |
| 21 | GLY | G | 57 | 11.75 | 3250.22 | 6.26 |
| 22 | - | - | 0 | 0.00 | 0.00 | 0.00 |

RESIDUES = 485
MOLECULAR WEIGHT (MONOISOTOPIC) = 51950.1016
MOLECULAR WEIGHT (AVERAGE) = 51982.3711
INDEX OF POLARITY (%) = 40.00
ISOELECTRIC POINT = 6.16
OD 260 (1mg/ml) = 0.558 OD 280 (1mg/ml) = 0.825

13144-BP SEQUENCE FROM 3364 TO 3888 cobP GENE

```
  M  S  S  L  S  A  G  P  V  L  V  L  G  G  A  R  S  G  K  S  S  F  S  E  R
   ATGAGCAGTCTCAGCGCCGGGCCCGTGCTGGTCCTTGGCGGCGCCCGTTCCGGCAAGTCCAGCTTTTCCGAGAGG
3364      3374      3384      3394      3404      3414      3424      3434
  L  V  E  A  S  G  F  T  M  H  Y  V  A  T  G  R  A  W  D  D  E  M  R  E  R
   CTCGTCGAAGCGTCCGGCTTCACCATGCATTATGTCGCCACGGGCCGCGCCTGGGACGACGAAATGCGCGAGCGC
3439      3449      3459      3469      3479      3489      3499      3509
  I  D  H  H  R  T  R  R  G  E  G  W  T  T  H  E  E  P  L  D  L  V  G  I  L
   ATCGACCATCACCGGACGCGCCGCGGCGAGGGCTGGACGACGCATGAGGAGCCGCTCGATCTCGTCGGCATCCTC
3514      3524      3534      3544      3554      3564      3574      3584
  R  R  I  D  D  P  S  H  V  V  L  I  D  C  L  T  L  W  V  T  N  L  M  L  E
   AGACGCATCGATGATCCCAGCCATGTGGTCCTGATCGACTGCCTGACGCTATGGGTCACCAATCTCATGCTGGAA
3589      3599      3609      3619      3629      3639      3649      3659
  E  R  D  M  T  A  E  F  A  A  L  V  A  Y  L  P  E  A  R  A  R  L  V  F  V
   GAGCGCGACATGACGGCGGAGTTCGCCGCCCTTGTTGCGTATCTGCCCGAGGCGCGGGCGCGCCTCGTCTTTGTT
3664      3674      3684      3694      3704      3714      3724      3734
  S  N  E  V  G  L  G  I  V  P  E  N  R  M  A  R  E  F  R  D  H  A  G  R  L
   TCCAATGAGGTCGGCCTCGGCATCGTGCCCGAGAACCGCATGGCCCGCGAGTTTCGCGACCATGCCGGCCGGCTT
3739      3749      3759      3769      3779      3789      3799      3809
  H  Q  I  V  A  E  K  S  A  E  V  Y  F  V  R  A  G  L  P  L  K  M  K  G  *
   CACCAGATCGTTGCGGAGAAATCCGCTGAAGTTTACTTTGTCGCGGCCGGTTTGCCGCTGAAAATGAAGGGTTGA
3814      3824      3834      3844      3854      3864      3874      3884
(SEQ ID NO: 45)
(SEQ ID NO: 44)
```

FIG. 47D

COBP PROTEIN FIRST RESIDUE = 1
LAST RESIDUE = 174

| | | | NUMBER | NO.% | WEIGHT | WEIGHT % |
|---|---|---|---|---|---|---|
| 1 | PHE | F | 6 | 3.45 | 882.41 | 4.54 |
| 2 | LEU | L | 19 | 10.92 | 2148.60 | 11.06 |
| 3 | ILE | I | 6 | 3.45 | 678.50 | 3.49 |
| 4 | MET | M | 7 | 4.02 | 917.28 | 4.72 |
| 5 | VAL | V | 16 | 9.20 | 1585.09 | 8.16 |
| 6 | SER | S | 11 | 6.32 | 957.35 | 4.93 |
| 7 | PRO | P | 6 | 3.45 | 582.32 | 3.00 |
| 8 | THR | T | 8 | 4.60 | 808.38 | 4.16 |
| 9 | ALA | A | 17 | 9.77 | 1207.63 | 6.22 |
| 10 | TYR | Y | 3 | 1.72 | 489.19 | 2.52 |
| 11 | * | * | 0 | 0.00 | 0.00 | 0.00 |
| 12 | HIS | H | 7 | 4.02 | 959.41 | 4.94 |
| 13 | GLN | Q | 1 | 0.57 | 128.06 | 0.66 |
| 14 | ASN | N | 3 | 1.72 | 342.13 | 1.76 |
| 15 | LYS | K | 4 | 2.30 | 512.38 | 2.64 |
| 16 | ASP | D | 9 | 5.17 | 1035.24 | 5.33 |
| 17 | GLU | E | 16 | 9.20 | 2064.68 | 10.63 |
| 18 | CYS | C | 1 | 0.57 | 103.01 | 0.53 |
| 19 | TRP | W | 3 | 1.72 | 558.24 | 2.87 |
| 20 | ARG | R | 17 | 9.77 | 2653.72 | 13.66 |
| 21 | GLY | G | 14 | 8.05 | 798.30 | 4.11 |
| 22 | - | - | 0 | 0.00 | 0.00 | 0.00 |

RESIDUES = 174
MOLECULAR WEIGHT (MONOISOTOPIC) = 19429.9473
MOLECULAR WEIGHT (AVERAGE) = 19442.2637
INDEX OF POLARITY (%) = 43.68
ISOELECTRIC POINT = 6.71
OD 260 (1mg/ml) = 0.720 OD 280 (1mg/ml) = 1.042

13144-BP SEQUENCE FROM 3892 TO 4956 <u>cobW</u> GENE

```
  M  T  T  A  R  A  N  Q  G  K  I  P  A  T  V  I  T  G  F  L  G  A  G  K  T
 ATGACCACTGCGAGAGCCAACCAGGGCAAGATCCCGGCGACCGTCATCACCGGCTTCCTCGGCGCCGGCAAGACG
3892      3902      3912      3922      3932      3942      3952      3962
  T  M  I  R  N  L  L  Q  N  A  D  G  K  R  I  G  L  I  I  N  E  F  G  D  L
 ACGATGATCCGCAACCTGCTGCAGAACGCCGACGGCAAGCGCATCGGCCTGATCATCAACGAGTTCGGCGATCTT
3967      3977      3987      3997      4007      4017      4027      4037
  G  V  D  G  D  V  L  K  G  C  G  A  E  A  C  T  E  D  D  I  I  E  L  T  N
 GGCGTCGACGGCGATGTCTTGAAGGGCTGCGGTGCCGAGGCCTGCACCGAGGACGACATCATCGAGCTCACCAAT
4042      4052      4062      4072      4082      4092      4102      4112
  G  C  I  C  C  T  V  A  D  D  F  I  P  T  M  T  K  L  L  E  R  E  N  R  P
 GGCTGCATCTGCTGCACCGTGGCTGACGATTTCATCCCGACCATGACGAAGCTGCTCGAGCGTGAAAACCGTCCT
4117      4127      4137      4147      4157      4167      4177      4187
  D  H  I  I  I  E  T  S  G  L  A  L  P  Q  P  L  I  A  A  F  N  W  P  D  I
 GACCACATCATCATCGAAACCTCGGGCCTTGCCCTGCCGCAGCCGCTGATCGCCGCTTTCAACTGGCCGGATATC
4192      4202      4212      4222      4232      4242      4252      4262
  R  S  E  V  T  V  D  G  V  V  T  V  V  D  S  A  A  V  A  A  G  R  F  A  D
 CGCAGCGAAGTGACCGTCGATGGCGTCGTCACCGTGGTCGACAGCGCCGCCGTTGCCGCTGGCCGCTTTGCCGAC
4267      4277      4287      4297      4307      4317      4327      4337
  D  H  D  K  V  D  A  L  R  V  E  D  D  N  L  D  H  E  S  P  I  E  E  L  F
 GACCACGACAAGGTCGATGCGCTGCGCGTCGAGGACGACAATCTCGATCACGAAAGCCCGATCGAGGAGCTGTTC
4342      4352      4362      4372      4382      4392      4402      4412
  E  D  Q  L  T  A  A  D  L  I  V  L  N  K  T  D  L  I  D  A  S  G  L  K  A
 GAGGATCAACTGACGGCTGCCGATCTCATCGTTCTCAACAAGACCGATCTGATCGATGCCTCCGGCCTCAAGGCC
4417      4427      4437      4447      4457      4467      4477      4487
  V  R  D  E  V  S  S  R  T  S  R  K  P  T  M  I  E  A  K  N  G  E  V  A  A
 GTGCGCGACGAGGTGTCTTCGCGCACCAGCCGCAAGCCCACGATGATCGAGGCGAAAAACGGCGAAGTCGCCGCT
4492      4502      4512      4522      4532      4542      4552      4562
  A I  L L  G  L  G  V  G  T  E  S  D  I  A  N  R  K  S  H  H  E  M  E H
 GCCATCCTGCTTGGCCTCGGTGTCGGCACGGAAAGCGATATCGCCAACCGCAAGTCGCATCACGAGATGGAGCAC
4567      4577      4587      4597      4607      4617      4627      4637
  E A  G  E  E  H  D  H  D  E  F  D  S  F  V  V  E  L  G  S  I  A  D  P A
 GAGGCAGGTGAGGAGCACGATCACGACGAGTTCGACAGCTTCGTCGTCGAGCTCGGTTCGATCGCCGATCCGGCC
4642      4652      4662      4672      4682      4692      4702      4712
  A F  I  D  R  L  K  G  V  I  A  E  H  D  V  L  R  L  K  G  F  A  D  V P
 GCCTTCATCGATCGCCTGAAGGGCGTAATCGCGGAGCACGACGTTCTGCGCCTCAAGGGTTTTGCAGACGTGCCC
4717      4727      4737      4747      4757      4767      4777      4787
```

FIG. 47F

```
   G  K  P  M  R  L  L  I  Q  R  V  G  A  R  I  D  Q  Y  Y  D  R  A  W  G  A
    GGCAAGCCGATGCGCCTCCTGATCCAGGCGGTCGGCGCCCGCATCGACCAATATTACGACCGCGCCTGGGGCGCT
4792      4802      4812      4822      4832      4842      4852      4862
   G  E  K  R  G  T  R  L  V  V  I  G  L  H  D  M  D  E  A  A  V  R  A  A  I
    GGCGAAAAGCGCGGTACGCGCCTCGTCGTCATCGGCCTGCACGACATGGACGAGGCGGCGGTGCGCGCCGCGATC
4867      4877      4887      4897      4907      4917      4927      4937
   T  A  L  V  *   (SEQ. ID. NO: 47)
    ACCGCGCTCGTGTAG (SEQ. ID. NO: 46)
4942      4952
```

FIG. 47G

COBW PROTEIN FIRST RESIDUE = 1
LAST RESIDUE = 354

| | | | NUMBER | NO.% | WEIGHT | WEIGHT % |
|---|---|---|---|---|---|---|
| 1 | PHE | F | 10 | 2.82 | 1470.68 | 3.86 |
| 2 | LEU | L | 32 | 9.04 | 3618.69 | 9.50 |
| 3 | ILE | I | 28 | 7.91 | 3166.35 | 8.31 |
| 4 | MET | M | 7 | 1.98 | 917.28 | 2.41 |
| 5 | VAL | V | 28 | 7.91 | 2773.92 | 7.28 |
| 6 | SER | S | 12 | 3.39 | 1044.38 | 2.74 |
| 7 | PRO | P | 11 | 3.11 | 1067.58 | 2.80 |
| 8 | THR | T | 21 | 5.93 | 2122.00 | 5.57 |
| 9 | ALA | A | 41 | 11.58 | 2912.52 | 7.64 |
| 10 | TYR | Y | 2 | 0.56 | 326.13 | 0.86 |
| 11 | * | * | 0 | 0.00 | 0.00 | 0.00 |
| 12 | HIS | H | 10 | 2.82 | 1370.59 | 3.60 |
| 13 | GLN | Q | 6 | 1.69 | 768.35 | 2.02 |
| 14 | ASN | N | 11 | 3.11 | 1254.47 | 3.29 |
| 15 | LYS | K | 15 | 4.24 | 1921.42 | 5.04 |
| 16 | ASP | D | 36 | 10.17 | 4140.97 | 10.87 |
| 17 | GLU | E | 27 | 7.63 | 3484.15 | 9.15 |
| 18 | CYS | C | 5 | 1.41 | 515.05 | 1.35 |
| 19 | TRP | W | 2 | 0.56 | 372.16 | 0.98 |
| 20 | ARG | R | 20 | 5.65 | 3122.02 | 8.19 |
| 21 | GLY | G | 30 | 8.47 | 1710.64 | 4.49 |
| 22 | - | - | 0 | 0.00 | 0.00 | 0.00 |

RESIDUES = 354
MOLECULAR WEIGHT (MONOISOTOPIC) = 38097.4258
MOLECULAR WEIGHT (AVERAGE) = 38121.1055
INDEX OF POLARITY (%) = 44.63
ISOELECTRIC POINT = 4.90
OD 260 (1mg/ml) = 0.268 OD 280 (1mg/ml) = 0.354

13144-BP SEQUENCE FROM 5060 TO 8887 cobN GENE

```
 M  H  L  L  L  A  Q  K  G  T  I  A  D  G  N  E  A  I  D  L  G  Q  T  P  A
  ATGCATCTGCTTCTCGCCCAGAAAGGAACGATCGCCGACGGCAACGAGGCGATCGACCTTGGGCAAACGCCGGCC
5060      5070      5080      5090      5100      5110      5120      5130
 D  I  L  F  L  S  A  A  D  T  E  L  S  S  I  A  A  A  H  G  R  R  D  G  G
  GATATCCTTTTCCTATCGGCCGCCGACACCGAGCTCTCCTCGATCGCCGCGGCTCACGGCCGACGCGACGGAGGC
5135      5145      5155      5165      5175      5185      5195      5205
 L  S  L  R  I  A  S  L  M  S  L  M  H  P  M  S  V  D  T  Y  V  E  R  T  A
  TTGAGCCTGCGCATCGCCAGCCTGATGAGCCTGATGCACCCGATGTCGGTCGACACTTACGTCGAGCGCACGGCG
5210      5220      5230      5240      5250      5260      5270      5280
 R  H  A  K  L  I  V  V  R  P  L  G  G  A  S  Y  F  R  Y  L  L  E  A  L  H
  CGTCACGCCAAGCTGATCGTCGTCCGGCCGCTCGGTGGCGCCAGCTATTTCCGTTATCTGCTGGAAGCCCTGCAT
5285      5295      5305      5315      5325      5335      5345      5355
 A  A  A  V  T  H  R  F  E  I  A  V  L  P  G  D  D  K  P  D  P  G  L  E  P
  GCGGCTGCCGTCACCCATCGTTTCGAGATCGCGGTTCTGCCGGGTGACGACAAGCCGGATCCGGGGCTGGAGCCT
5360      5370      5380      5390      5400      5410      5420      5430
 F  S  T  V  A  A  D  D  R  Q  R  L  W  A  Y  F  T  E  G  G  S  D  N  A  G
  TTCTCCACCGTCGCAGCCGACGACCGCCAGCGCCTTTGGGCTTACTTCACCGAAGGCGGCTCGGACAATGCCGGG
5435      5445      5455      5465      5475      5485      5495      5505
 L  F  L  D  Y  A  A  A  L  V  T  G  A  E  K  P  Q  P  A  K  P  L  L  K  A
  CTGTTTCTCGACTATGCGGCCGCACTGGTCACAGGTGCGGAGAAGCCGCAGCCGGCAAAGCCCCTGTTGAAGGCC
5510      5520      5530      5540      5550      5560      5570      5580
 G  I  W  W  P  G  A  G  V  I  G  V  S  E  W  Q  S  L  V  Q  G  R  M  V  A
  GGCATCTGGTGGCCGGGTGCTGGTGTGATCGGCGTCAGCGAATGGCAGTCCCTTGTTCAGGGACGGATGGTAGCG
5585      5595      5605      5615      5625      5635      5645      5655
 R  E  G  F  E  P  P  T  V  G  I  C  F  Y  R  A  L  V  Q  S  G  E  T  R  P
  AGGGAGGGATTCGAACCCCCGACGGTCGGGATCTGCTTTTACCGCGCGCTCGTGCAGAGTGGCGAGACACGGCCT
5660      5670      5680      5690      5700      5710      5720      5730
 V  E  A  L  I  D  A  L  E  A  E  G  V  R  A  L  P  V  F  V  S  S  L  K  D
  GTGGAGGCGCTGATCGATGCGCTGGAGGCTGAAGGTGTGCGGGCACTGCCGGTGTTTGTCTCAAGCCTCAAGGAT
5735      5745      5755      5765      5775      5785      5795      5805
 A  V  S  V  G  T  L  Q  A  I  F  S  E  A  A  P  D  V  V  M  N  A  T  G  F
  GCCGTTTCCGTCGGCACGCTGCAGGCGATTTTTTCCGAGGCCGCACCCGACGTGGTGATGAACGCCACTGGCTTT
5810      5820      5830      5840      5850      5860      5870      5880
 A  V  S  S  P  G  A  D  R  Q  P  T  V  L  E  S  T  G  A  P  V  L  Q  V  I
  GCGGTCTCGTCGCCCGGTGCCGACCGTCAGCCGACGGTGCTGGAATCGACCGGTGCGCCGGTGCTGCAGGTGATT
5885      5895      5905      5915      5925      5935      5945      5955
```

*FIG. 47I*

```
 F  S  G  S  S  R  A  Q  W  E  T  S  P  Q  G  L  M  A  R  D  L  A  M  N  V
 TTCTCCGGCTCGTCGCGGGCGCAATGGGAAACGTCGCCGCAGGGGCTGATGGCGCGCGACCTCGCCATGAACGTG
5960      5970      5980      5990      6000      6010      6020      6030
 A  L  P  E  V  D  G  R  I  L  A  R  R  V  S  F  K  A  A  S  I  Y  D  A  K
 GCACTCCCCGAAGTCGATGGCCGCATCCTTGCGCGCGCCGTCTCCTTCAAGGCGGCGTCGATCTATGACGCCAAG
6035      6045      6055      6065      6075      6085      6095      6105
 V  E  A  N  I  V  G  H  E  P  L  E  G  R  V  R  F  A  A  D  L  A  V  N  W
 GTGGAGGCCAATATCGTCGGCCATGAGCCGCTCGAAGGCCGGGTGCGCTTTGCCGCTGATCTTGCCGTCAACTGG
6110      6120      6130      6140      6150      6160      6170      6180
 A  N  V  R  R  A  E  P  A  E  R  R  I  A  I  V  M  A  N  Y  P  N  R  D  G
 GCGAACGTGCGCCGGGCAGAGCCCGCCGAGCGCCGTATTGCCATCGTCATGGCCAACTATCCGAACCGCGACGGT
6185      6195      6205      6215      6225      6235      6245      6255
 R  L  G  N  G  V  G  L  D  T  P  A  G  T  V  E  V  L  S  A  M  A  R  E  G
 CGCCTCGGCAACGGTGTCGGGCTCGACACGCCGGCCGGTACCGTCGAGGTGCTTAGCGCCATGGCGCGGGAAGGC
6260      6270      6280      6290      6300      6310      6320      6330
 Y  A  V  G  E  V  P  A  D  G  D  A  L  I  R  F  L  M  A  G  P  T  N  A  A
 TATGCGGTCGGTGAGGTTCCCGCCGATGGCGACGCGCTGATCCGCTTTCTGATGGCCGGGCCGACCAATGCGGCG
6335      6345      6355      6365      6375      6385      6395      6405
 S  H  D  R  E  I  R  E  R  I  S  L  N  D  Y  K  T  F  F  D  S  L  P  K  Q
 AGCCATGACCGTGAAATCCGCGAGCGTATTTCGCTGAACGATTACAAAACGTTCTTCGATTCGCTTCCGAAACAG
6410      6420      6430      6440      6450      6460      6470      6480
 I  K  D  E  V  A  G  R  W  G  V  P  E  A  D  P  F  F  L  D  G  A  F  A  L
 ATAAAGGATGAAGTTGCCGGTCGCTGGGGCGTGCCGGAGGCCGATCCCTTTTTCCTCGATGGCGCCTTCGCGCTG
6485      6495      6505      6515      6525      6535      6545      6555
 P  L  A  R  F  G  E  V  I  V  G  I  Q  P  A  R  G  Y  N  I  D  P  K  E  S
 CCGCTCGCCCGCTTCGGCGAGGTGATCGTCGGCATCCAACCGGCGCGCGGCTACAACATCGATCCGAAGGAAAGC
6560      6570      6580      6590      6600      6610      6620      6630
 Y  H  S  P  D  L  V  P  P  H  G  Y  L  A  F  Y  A  F  L  R  Q  Q  F  G  A
 TACCATTCCCCGGACCTCGTGCCGCCGCATGGCTATCTCGCCTTCTACGCCTTCCTGCGCCAGCAGTTCGGAGCG
6635      6645      6655      6665      6675      6685      6695      6705
 Q  A  I  V  H  M  G  K  H  G  N  L  E  W  L  P  G  K  A  L  A  L  S  E  T
 CAGGCGATCGTCCACATGGGCAAGCACGGCAATCTCGAATGGCTGCCGGGCAAGGCGCTGGCGCTGTCGGAAACC
6710      6720      6730      6740      6750      6760      6770      6780
 C  Y  P  E  A  I  F  G  P  L  P  H  I  Y  P  F  I  V  N  D  P  G  E  G  T
 TGCTATCCCGAAGCGATCTTCGGGCCGCTGCCGCACATCTATCCCTTCATCGTCAACGATCCGGGCGAAGGTACG
6785      6795      6805      6815      6825      6835      6845      6855
```

FIG. 47J

Q A K R R T S A V I I D H L T P P L T R A E S Y G
CAGGCCAAGCGCCGCACCAGCGCCGTCATCATCGACCACCTGACCCCGCCCTTGACGCGCGCCGAATCCTACGGC
6860 6870 6880 6890 6900 6910 6920 6930

P L K D L E A L V D E Y Y D A A G G D P R R L R L
CCGCTCAAGGATCTGGAAGCGCTCGTCGACGAATATTACGACGCCGCCGGCGGTGATCCGCGCCGCCTCAGGCTG
6935 6945 6955 6965 6975 6985 6995 7005

L S R Q I L D L V R D I G L D S D A G I D R G D S
CTCAGCCGCCAGATCCTCGATCTCGTGCGCGACATCGGCCTCGACAGCGACGCAGGCATCGACAGGGGCGACAGC
7010 7020 7030 7040 7050 7060 7070 7080

D D K A L E K L D A Y L C D L K E M Q I R D G L H
GACGACAAGGCGCTGGAAAAGCTCGACGCCTATCTCTGCGACCTCAAGGAAATGCAGATCCGCGACGGCCTGCAC
7085 7095 7105 7115 7125 7135 7145 7155

I F G V A P E G R L L T D L T V A L A R V P R G L
ATCTTCGGCGTTGCGCCGGAAGGGCGGTTGTTGACGGACCTCACCGTAGCGCTGGCGCGCGTGCCCCGAGGTCTC
7160 7170 7180 7190 7200 7210 7220 7230

G E G G D Q S L Q R A I A A D A G L R G F A I P T
GGCGAGGGCGGCGACCAGAGCCTGCAGCGGGCGATCGCAGCGGATGCGGGGCTGCGTGGGTTTGCTATTCCCACC
7235 7245 7255 7265 7275 7285 7295 7305

S A G G N P A R D A Q P F D P L D C V M S D T W T
TCGGCGGGGGGCAACCCCGCACGCGACGCCCAACCCTTCGACCCGCTCGACTGCGTCATGTCCGACACCTGGACA
7310 7320 7330 7340 7350 7360 7370 7380

G P K P S I L A D L S D A P W R T A G D T V E R I
GGCCCGAAACCGTCCATCCTCGCTGACCTCTCGGACGCCCCCTGGCGCACCGCCGGCGATACGGTCGAGCGCATC
7385 7395 7405 7415 7425 7435 7445 7455

E L L A A N L V S G E L A C P D H W A N T R A V L
GAGTTGCTTGCCGCAAATCTCGTGTCGGGTGAACTGGCTTGCCCGGACCACTGGGCCAACACCCGCGCCGTGCTC
7460 7470 7480 7490 7500 7510 7520 7530

G E I E T R L K P S I S N S G A A E M T G F L T G
GGCGAAATCGAAACGCGCCTGAAGCCGTCGATTTCAAACTCGGGTGCCGCCGAGATGACCGGCTTCCTCACCGGT
7535 7545 7555 7565 7575 7585 7595 7605

L S G R F V A P G P S G A P T R G R P D V L P T G
CTCAGCGGCCGCTTCGTCGCCCCCGGTCCATCGGGCGCGCCGACGCGCGGCCGGCCGGATGTGTTGCCGACGGGG
7610 7620 7630 7640 7650 7660 7670 7680

R N F Y S V D S R A V P T P A A Y E L G K K S A E
CGCAATTTCTACTCGGTCGACAGCCGCGCCGTGCCGACGCCGGCGGCTTACGAGCTTGGCAAGAAATCGGCCGAG
7685 7695 7705 7715 7725 7735 7745 7755

FIG. 47K

```
 L  L  I  R  R  Y  L  Q  D  H  G  E  W  P  S  S  F  G  L  T  A  W  G  T  A
 CTTCTGATCCGCCGCTACCTGCAGGACCATGGCGAATGGCCGTCCTCCTTTGGCCTGACCGCCTGGGGCACGGCG
7760      7770      7780      7790      7800      7810      7820      7830
 N  M  R  T  G  G  D  D  I  A  Q  A  L  A  L  I  G  A  K  P  T  W  D  M  V
 AACATGCGCACCGGCGGCGACGACATCGCCCAGGCCCTGGCGCTGATCGGCGCCAAGCCCACCTGGGACATGGTC
7835      7845      7855      7865      7875      7885      7895      7905
 S  R  R  V  M  G  Y  E  I  V  P  L  A  V  L  G  R  P  R  V  D  V  T  L  R
 TCTCGCCGGGTGATGGGCTACGAGATCGTGCCGCTCGCAGTCCTCGGCCGCCCACGCGTCGACGTGACCTTGCGC
7910      7920      7930      7940      7950      7960      7970      7980
 I  S  G  F  F  R  D  A  F  P  D  Q  I  A  L  F  D  K  A  I  R  A  V  A  L
 ATTTCCGGCTTCTTCCGCGATGCCTTCCCGGACCAGATCGCGCTCTTCGACAAGGCGATCCGCGCCGTCGCGCTG
7985      7995      8005      8015      8025      8035      8045      8055
 E  E  D  D  A  D  N  M  I  A  A  R  M  R  A  E  S  R  R  L  E  A  E  G  V
 GAGGAAGACGATGCCGACAACATGATCGCCGCACGCATGCGGGCGGAAAGCCGGCGGCTGGAGGCCGAAGGCGTG
8060      8070      8080      8090      8100      8110      8120      8130
 E  A  A  E  A  A  R  R  A  S  Y  R  V  F  G  R  K  P  G  A  Y  G  A  A  L
 GAAGCCGCCGAGGCCGCGCGTCGCGCCTCCTACCGCGTCTTTGGCGCAAAGCCCGGTGCCTATGGCGCCGCCCTG
8135      8145      8155      8165      8175      8185      8195      8205
 Q  A  L  I  D  E  K  G  W  E  T  K  A  D  L  A  E  A  Y  L  T  W  G  A  Y
 CAGGCGCTGATCGACGAGAAGGGCTGGGAAACCAAAGCAGATCTCGCCGAGGCCTATCTTACCTGGGGCGCCTAT
8210      8220      8230      8240      8250      8260      8270      8280
 A  Y  G  A  G  E  E  G  K  A  E  R  D  L  F  E  E  R  L  R  T  I  E  A  V
 GCCTATGGCGCCGGCGAGGAGGGCAAGGCCGAGCGCGATCTTTTCGAGGAGCGCCTGCGCACGATAGAGGCGGTG
8285      8295      8305      8315      8325      8335      8345      8355
 V  Q  N  Q  D  N  R  E  H  D  L  L  D  S  D  D  Y  Y  Q  F  E  G  G  M  S
 GTGCAGAACCAGGACAACCGCGAGCACGATCTGCTCGACAGCGACGACTACTACCAGTTCGAAGGCGGCATGAGC
8360      8370      8380      8390      8400      8410      8420      8430
 A  A  A  E  Q  L  G  G  H  R  P  A  I  Y  H  N  D  H  S  R  P  E  K  P  V
 GCTGCCGCCGAACAGCTCGGCGGTCACCGTCCGGCGATCTACCACAACGACCATTCCCGTCCGGAAAAGCCTGTG
8435      8445      8455      8465      8475      8485      8495      8505
 I  R  S  L  E  E  E  I  G  R  V  V  R  A  R  V  V  N  P  K  W  I  D  G  V
 ATCCGGTCGCTCGAAGAAGAGATCGGCCGCGTGGTCCGGGCCCGCGTCGTCAATCCCAAGTGGATCGATGGCGTC
8510      8520      8530      8540      8550      8560      8570      8580
 M  R  H  G  Y  K  G  A  F  E  I  A  A  T  V  D  Y  M  F  A  F  A  A  T  T
 ATGCGCCACGGATACAAGGGCGCCTTCGAGATCGCTGCCACGGTCGACTACATGTTCGCCTTTGCCGCGACCACG
8585      8595      8605      8615      8625      8635      8645      8655
```

*FIG. 47L*

```
 G  A  V  R  D  H  H  F  E  A  A  Y  Q  A  F  I  V  D  E  R  V  A  D  F  M
  GGTGCGGTGCGCGACCATCATTTCGAGGCCGCTTATCAGGCGTTCATTGTCGACGAGCGCGTGGCTGACTTCATG
8660      8670      8680      8690      8700      8710      8720      8730
 R  D  K  N  P  A  A  F  A  E  L  A  E  R  L  L  E  A  I  D  R  N  L  W  T
  CGCGACAAGAACCCGGCCGCCTTTGCCGAGCTTGCCGAACGCCTGCTTGAAGCAATCGACCGCAATCTCTGGACG
8735      8745      8755      8765      8775      8785      8795      8805
 P  R  S  N  S  A  R  F  E  L  A  G  I  G  T  A  A  T  R  L  R  A  G  N  E
  CCGCGCTCGAATTCGGCGCGGTTTGAACTTGCCGGCATCGGCACGGCAGCAACCCGGCTTCGTGCCGGCAATGAA
8810      8820      8830      8840      8850      8860      8870      8880
 *    (SEQ ID NO: 49)
TAG   (SEQ ID NO: 48)
8885
```

FIG. 47M

COBN PROTEIN

FIRST RESIDUE = 1
LAST RESIDUE = 1275

| | | | NUMBER | NO.% | WEIGHT | WEIGHT % |
|---|---|---|---|---|---|---|
| 1 | PHE | F | 48 | 3.76 | 7059.28 | 5.12 |
| 2 | LEU | L | 121 | 9.49 | 13683.17 | 9.92 |
| 3 | ILE | I | 60 | 4.71 | 6785.04 | 4.92 |
| 4 | MET | M | 24 | 1.88 | 3144.97 | 2.28 |
| 5 | VAL | V | 82 | 6.43 | 8123.61 | 5.89 |
| 6 | SER | S | 64 | 5.02 | 5570.05 | 4.04 |
| 7 | PRO | P | 76 | 5.96 | 7376.01 | 5.35 |
| 8 | THR | T | 53 | 4.16 | 5355.53 | 3.88 |
| 9 | ALA | A | 180 | 14.12 | 12786.68 | 9.27 |
| 10 | TYR | Y | 35 | 2.75 | 5707.22 | 4.14 |
| 11 | * | * | 0 | 0.00 | 0.00 | 0.00 |
| 12 | HIS | H | 24 | 1.88 | 3289.41 | 2.38 |
| 13 | GLN | Q | 32 | 2.51 | 4097.87 | 2.97 |
| 14 | ASN | N | 30 | 2.35 | 3421.29 | 2.48 |
| 15 | LYS | K | 34 | 2.67 | 4355.23 | 3.16 |
| 16 | ASP | D | 90 | 7.06 | 10352.42 | 7.50 |
| 17 | GLU | E | 85 | 6.67 | 10968.62 | 7.95 |
| 18 | CYS | C | 5 | 0.39 | 515.05 | 0.37 |
| 19 | TRP | W | 18 | 1.41 | 3349.43 | 2.43 |
| 20 | ARG | R | 99 | 7.76 | 15454.01 | 11.20 |
| 21 | GLY | G | 115 | 9.02 | 6557.47 | 4.75 |
| 22 | - | - | 0 | 0.00 | 0.00 | 0.00 |

RESIDUES = 1275
MOLECULAR WEIGHT (MONOISOTOPIC) = 137970.5000
MOLECULAR WEIGHT (AVERAGE) = 138055.8594
INDEX OF POLARITY (%) = 40.08
ISOELECTRIC POINT = 5.42
OD 260 (1mg/ml) = 0.693 OD 280 (1mg/ml) = 1.027

13144-BP SEQUENCE 9034 TO 9678 cobO GENE

```
   M  S  D  E  T  T  V  G  G  E  A  P  A  E  K  D  D  A  R  H  A  M  K  M  A
   ATGAGCGACGAGACGACAGTAGGCGGCGAAGCCCCGGCCGAGAAGGACGATGCCCGCCACGCCATGAAGATGGCG
9034      9044      9054      9064      9074      9084      9094      9104
   K  K  K  A  A  R  E  K  I  M  A  T  K  T  D  E  K  G  L  I  I  V  N  T  G
   AAGAAGAAGGCAGCACGCGAAAAGATCATGGCGACGAAGACCGACGAGAAGGGTCTGATCATCGTCAACACCGGC
9109      9119      9129      9139      9149      9159      9169      9179
   K  G  K  G  K  S  T  A  G  F  G  M  I  F  R  H  I  A  H  G  M  P  C  A  V
   AAAGGCAAGGGCAAGTCGACCGCCGGCTTCGGCATGATCTTCCGCCATATCGCCCACGGCATGCCCTGCGCCGTC
9184      9194      9204      9214      9224      9234      9244      9254
   V  Q  F  I  K  G  A  M  A  T  G  E  R  E  L  I  E  K  H  F  G  D  V  C  Q
   GTGCAGTTCATCAAGGGTGCGATGGCAACCGGCGAGCGCGAGTTGATCGAGAAGCATTTCGGCGATGTCTGCCAG
9259      9269      9279      9289      9299      9309      9319      9329
   F  Y  T  L  G  E  G  F  T  W  E  T  Q  D  R  A  R  D  V  A  M  A  E  K  A
   TTCTACACGCTCGGCGAGGGCTTCACCTGGGAAACGCAGGATCGCGCCCGCGATGTTGCGATGGCTGAAAAGGCC
9334      9344      9354      9364      9374      9384      9394      9404
   W  E  K  A  K  E  L  I  R  D  E  R  N  S  M  V  L  L  D  E  I  N  I  R  L
   TGGGAGAAGGCGAAGGAACTGATCCGTGACGAGCGCAACTCGATGGTGCTGCTCGACGAGATCAACATTGCTCTG
9409      9419      9429      9439      9449      9459      9469      9479
   R  Y  D  Y  I  D  V  A  E  V  V  R  F  L  K  E  E  K  P  H  M  T  H  V  V
   CGCTACGACTACATCGACGTCGCCGAAGTGGTGCGCTTCCTGAAGGAAGAAAAGCCGCACATGACGCATGTGGTG
9484      9494      9504      9514      9524      9534      9544      9554
   L  T  G  R  N  A  K  E  D  L  I  E  V  A  D  L  V  T  E  M  E  L  I  K  H
   CTCACCGGCCGCAACGCGAAAGAAGACCTGATCGAAGTCGCCGATCTCGTCACTGAGATGGAGCTGATCAAGCAT
9559      9569      9579      9589      9599      9609      9619      9629
   P  F  R  S  G  I  K  A  Q  Q  G  V  E  F  *        (SEQ ID NO: 51)
   CCGTTCCGTTCCGGCATCAAGGCGCAGCAGGGCGTGGAGTTCTGA      (SEQ ID NO: 50)
9634      9644      9654      9664      9674
```

FIG. 47O

COBO PROTEIN

FIRST RESIDUE = 1
LAST RESIDUE = 214

| | | | NUMBER | NO.% | WEIGHT | WEIGHT % |
|---|---|---|---|---|---|---|
| 1 | PHE | F | 9 | 4.21 | 1323.62 | 5.51 |
| 2 | LEU | L | 12 | 5.61 | 1357.01 | 5.65 |
| 3 | ILE | I | 14 | 6.54 | 1583.18 | 6.59 |
| 4 | MET | M | 11 | 5.14 | 1441.45 | 6.00 |
| 5 | VAL | V | 15 | 7.01 | 1486.03 | 6.19 |
| 6 | SER | S | 4 | 1.87 | 348.13 | 1.45 |
| 7 | PRO | P | 4 | 1.87 | 388.21 | 1.62 |
| 8 | THR | T | 13 | 6.07 | 1313.62 | 5.47 |
| 9 | ALA | A | 23 | 10.75 | 1633.85 | 6.80 |
| 10 | TYR | Y | 3 | 1.40 | 489.19 | 2.04 |
| 11 | * | * | 0 | 0.00 | 0.00 | 0.00 |
| 12 | HIS | H | 7 | 3.27 | 959.41 | 4.00 |
| 13 | GLN | Q | 5 | 2.34 | 640.29 | 2.67 |
| 14 | ASN | N | 4 | 1.87 | 456.17 | 1.90 |
| 15 | LYS | K | 21 | 9.81 | 2689.99 | 11.20 |
| 16 | ASP | D | 13 | 6.07 | 1495.35 | 6.23 |
| 17 | GLU | E | 23 | 10.75 | 2967.98 | 12.36 |
| 18 | CYS | C | 2 | 0.93 | 206.02 | 0.86 |
| 19 | TRP | W | 2 | 0.93 | 372.16 | 1.55 |
| 20 | ARG | R | 12 | 5.61 | 1873.21 | 7.80 |
| 21 | GLY | G | 17 | 7.94 | 969.36 | 4.04 |
| 22 | - | - | 0 | 0.00 | 0.00 | 0.00 |

RESIDUES = 214
MOLECULAR WEIGHT (MONOISOTOPIC) = 24012.2500
MOLECULAR WEIGHT (AVERAGE) = 24027.6973
INDEX OF POLARITY (%) = 47.66
ISOELECTRIC POINT = 6.94
OD 260 (1mg/ml) = 0.443 OD 280 (1mg/ml) = 0.612

COBO FROM 1 TO 214

$NH_2$-TERMINAL SEQUENCE OF SUMT OF M. ivanovii

VVYLVGAGPGDPELITLKAVNVLK-ADVVL (AMINO ACID FRAGMENT 2-31 OF SEQ ID NO: 54)

923 946

SENSE OLIGONUCLEOTIDE 946 (27-mer)

```
                P   G   D   P   E   L    (AMINO ACIDS 10-15 OFSEQ ID NO: 54)
5' CGCGGAATTC CCA GGA GAT CCA GAA CT 3'  (SEQ ID NO: 56)
        EcoRI   T   T   C   T   G
                C   C       C
                G   G       G
```

SENSE OLIGONUCLEOTIDE 923 (27-mer)

```
                V   Y   L   V   G   A    (AMINO ACIDS 3-8 OF SEQ ID NO: 54)
5' CGCGGAATTC GTA TAT CTA GTA GGA GC 3'  (SEQ ID NO: 57)
        EcoRI   G   C   T   T   T
                            G
```

$NH_2$-TERMINAL SEQUENCE OF A FRAGMENT DERIVED FROM A TRYPTIC DIGESTION OF M. ivanovii SUMT

IITGTLENIAGK (AMINO ACIDS 201-212 OF SEQ ID NO: 54)

947

ANTISENSE OLIGONUCLEOTIDE 947 (25-mer)

```
               N   E   L   T   G      (CO2→NH2 ORIENTATION OF AMINO
5' CGCGAAGCTT GTT TTC TAG AGT ACC 3'  ACIDS 207-203 OF SEQ ID NO: 54)
      HindIII A   C   A   T   T       (SEQ ID NO: 58)
                          G   C
                              G
```

FIG. 48A

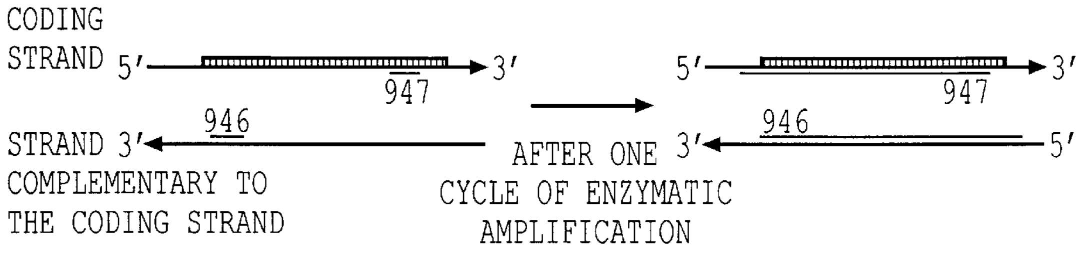

M. ivanovii SUMT STRUCTURAL GENE (SEQ ID NO: 54)

FIG. 48B

```
        10         20         30         40         50         60
CCATAATTCT TTTATAATTT AAACGGTGAA CACATGGTAG TTTATTTAGT AGGTGCGGGT
GGTATTAAGA AAATATTAAA TTTGCCACTT GTGTACCATC AAATAAATCA TCCACGCCCA

        70         80         90        100        110        120
CCAGGAGATC CCGAACTTAT CACTCTCAAA GCTGTAAACG TGTTAAAAAA AGCGGATGTT
GGTCCTCTAG GGCTTGAATA GTGAGAGTTT CGACATTTGC ACAATTTTTT TCGCCTACAA

       130        140        150        160        170        180
GTACTGTACG ACAAACCTGC AAATGAAGAA ATTTTAAAGT ATGCTGAAGG TGCAAAACTA
CATGACATGC TGTTTGGACG TTTACTTCTT TAAAATTTCA TACGACTTCC ACGTTTTGAT

       190        200        210        220        230        240
ATATATGTCG GAAAACAAGC AGGACATCAT TACAAATCTC AAAATGAAAT CAATACTCTT
TATATACAGC CTTTTGTTCG TCCTGTAGTA ATGTTTAGAG TTTTACTTTA GTTATGAGAA

       250        260        270        280        290        300
CTTGTTGAAG AAGCAAAAGA AAATGATTTA GTAGTACGCC TTAAAGGTGG AGACCCCTTT
GAACAACTTC TTCGTTTTCT TTTACTAAAT CATCATGCGG AATTTCCACC TCTGGGGAAA

       310        320        330        340        350        360
GTATTTGGAA GAGGAGGCGA GGAAATTCTG GCCCTTGTAG AAGAAGGAAT TGATTTTGAG
CATAAACCTT CTCCTCCGCT CCTTTAAGAC CGGGAACATC TTCTTCCTTA ACTAAAACTC

       370        380        390        400        410        420
TTAGTTCCAG GGGTAACTTC TGCAATTGGA GTTCCAACAA CAATTGGGCT TCCAGTTACT
AATCAAGGTC CCCATTGAAG ACGTTAACCT CAAGGTTGTT GTTAACCCGA AGGTCAATGA

       430        440        450        460        470        480
CATAGAGGTG TTGCAACATC GTTTACAGTT GTTACAGGTC ATGAAGACCC AACAAAATGC
GTATCTCCAC AACGTTGTAG CAAATGTCAA CAATGTCCAG TACTTCTGGG TTGTTTTACG

       490        500        510        520        530        540
AAGAAACAGG TAGGATGGGA CTTTAAAGCA GATACTATTG TAATACTTAT GGGTATTGGA
TTCTTTGTCC ATCCTACCCT GAAATTTCGT CTATGATAAC ATTATGAATA CCCATAACCT

       550        560        570        580        590        600
AATTTAGCTG AAAATACAGC AGAAATTATG AAACATAAAG ATCCTGAAAC TCCAGTTTGT
TTAAATCGAC TTTTATGTCG TCTTTAATAC TTTGTATTTC TAGGACTTTG AGGTCAAACA
```

*FIG. 51A*

```
       610        620        630        640        650        660
GTAATTGAAA ATGGTACGAT GGAAGGTCAA AGGATAATAA CGGGCACACT GGAAAATATA
CATTAACTTT TACCATGCTA CCTTCCAGTT TCCTATTATT GCCCGTGTGA CCTTTTATAT

       670        680        690        700        710        720
GCTGGAAAGG ATATTAAACC TCCTGCTTTA GTGGTATTGG AAATGTTGTC AATGTTTTTA
CGACCTTTCC TATAATTTGG AGGACGAAAT CACCATAACC TTTACAACAG TTACAAAAAT

       730        740        750        760        770        780
AAGAAATGAA TCAAATCAGT GGCTGATCTA TTAAGAAGGC AATATCATGA ATGGATTAGA
TTCTTTACTT AGTTTAGTCA CCGACTAGAT AATTCTTCCG TTATAGTACT TACCTAATCT

       790        800        810        820        830        840
AGGTAAAAAA ATTGTTATAA CAAGACCTGC TGAAAGGGCT AAAGACTCAG TTGAAATGGT
TCCATTTTTT TAACAATATT GTTCTGGACG ACTTTCCCGA TTTCTGAGTC AACTTTACCA

       850        860        870        880        890        900
AAAATCTTAT GGAGCAGTTC CAATTGTAAC TCCTACAATT GAACTCAAAG ATTCCAAGCC
TTTTAGAATA CCTCGTCAAG GTTAACATTG AGGATGTTAA CTTGAGTTTC TAAGGTTCGG

       910        920        930        940        950        960
AGAAGAAGTG ATAAAATTAT GTAATATGAT AAATGAACCT TGATTGGCCT TATAT
TCTTCTTCAC TATTTTAATA CATTATACTA TTTACTTGGA ACTAACCGGA ATATA
```

*FIG. 51B* corA GENE AND CORA PROTEIN (SUMT) OF METHANOBACTERIUM IVANOVII SEQUENCE OF 955-BP FRAGMENT FROM 34 TO 729

```
 M  V  V  Y  L  V  G  A  G  P  G  D  P  E  L  I  T  L  K  A  V  N  V  L  K
 ATGGTAGTTTATTTAGTAGGTGCGGGTCCAGGAGATCCCGAACTTATCACTCTCAAAGCTGTAAACGTGTTAAAA
34        44        54        64        74        84        94        104
 K  A  D  V  V  L  Y  D  K  P  A  N  E  E  I  L  K  Y  A  E  G  A  K  L  I
 AAAGCGGATGTTGTACTGTACGACAAACCTGCAAATGAAGAAATTTTAAAGTATGCTGAAGGTGCAAAACTAATA
109       119       129       139       149       159       169       179
 Y  V  G  K  Q  A  G  H  H  Y  K  S  Q  N  E  I  N  T  L  L  V  E  E  A  K
 TATGTCGGAAAACAAGCAGGACATCATTACAAATCTCAAAATGAAATCAATACTCTTCTTGTTGAAGAAGCAAAA
184       194       204       214       224       234       244       254
 E  N  D  L  V  V  R  L  K  G  G  D  P  F  V  F  G  R  G  G  E  E  I  L  A
 GAAAATGATTTAGTAGTACGCCTTAAAGGTGGAGACCCCTTTGTATTTGGAAGAGGAGGCGAGGAAATTCTGGCC
259       269       279       289       299       309       319       329
 L  V  E  E  G  I  D  F  E  L  V  P  G  V  T  S  A  I  G  V  P  T  T  I  G
 CTTGTAGAAGAAGGAATTGATTTTGAGTTAGTTCCAGGGGTAACTTCTGCAATTGGAGTTCCAACAACAATTGGG
334       344       354       364       374       384       394       404
 L  P  V  T  H  R  G  V  A  T  S  F  T  V  V  T  G  H  E  D  P  T  K  C  K
 CTTCCAGTTACTCATAGAGGTGTTGCAACATCGTTTACAGTTGTTACAGGTCATGAAGACCCAACAAAATGCAAG
409       419       429       439       449       459       469       479
 K  Q  V  G  W  D  F  K  A  D  T  I  V  I  L  M  G  I  G  N  L  A  E  N  T
 AAACAGGTAGGATGGGACTTTAAAGCAGATACTATTGTAATACTTATGGGTATTGGAAATTTAGCTGAAAATACA
484       494       504       514       524       534       544       554
 A  E  I  M  K  H  K  D  P  E  T  P  V  C  V  I  E  N  G  T  M  E  G  Q  R
 GCAGAAATTATGAAACATAAAGATCCTGAAACTCCAGTTTGTGTAATTGAAAATGGTACGATGGAAGGTCAAAGG
559       569       579       589       599       609       619       629
 I  I  T  G  T  L  E  N  I  A  G  K  D  I  K  P  P  A  L  V  V  L  E  M  L
 ATAATAACGGGCACACTGGAAAATATAGCTGGAAAGGATATTAAACCTCCTGCTTTAGTGGTATTGGAAATGTTG
634       644       654       664       674       684       694       704
 S  M  F  L  K  K  *
 TCAATGTTTTTAAAGAAATGA
709       719       729
```

FIG. 52A

CORA PROTEIN

| | | | NUMBER | NO. % | WEIGHT | WEIGHT % |
|---|---|---|---|---|---|---|
| 1 | PHE | F | 6 | 2.60 | 882.41 | 3.54 |
| 2 | LEU | L | 22 | 9.52 | 2487.85 | 9.99 |
| 3 | ILE | I | 17 | 7.36 | 1922.43 | 7.72 |
| 4 | MET | M | 6 | 2.60 | 786.24 | 3.16 |
| 5 | VAL | V | 26 | 11.26 | 2575.78 | 10.34 |
| 6 | SER | S | 4 | 1.73 | 348.13 | 1.40 |
| 7 | PRO | P | 12 | 5.19 | 1164.63 | 4.68 |
| 8 | THR | T | 16 | 6.93 | 1616.76 | 6.49 |
| 9 | ALA | A | 16 | 6.93 | 1136.59 | 4.56 |
| 10 | TYR | Y | 5 | 2.16 | 815.32 | 3.27 |
| 11 | * | * | 0 | 0.00 | 0.00 | 0.00 |
| 12 | HIS | H | 5 | 2.16 | 685.29 | 2.75 |
| 13 | GLN | Q | 4 | 1.73 | 512.23 | 2.06 |
| 14 | ASN | N | 9 | 3.90 | 1026.39 | 4.12 |
| 15 | LYS | K | 20 | 8.66 | 2561.90 | 10.29 |
| 16 | ASP | D | 11 | 4.76 | 1265.30 | 5.08 |
| 17 | GLU | E | 21 | 9.09 | 2709.89 | 10.88 |
| 18 | CYS | C | 2 | 0.87 | 206.02 | 0.83 |
| 19 | TRP | W | 1 | 0.43 | 186.08 | 0.75 |
| 20 | ARG | R | 4 | 1.73 | 624.40 | 2.51 |
| 21 | GLY | G | 24 | 10.39 | 1368.52 | 5.50 |
| 22 | - | - | 0 | 0.00 | 0.00 | 0.00 |

RESIDUES = 231
MOLECULAR WEIGHT (MONOISOTOPIC) = 24900.1855
MOLECULAR WEIGHT (AVERAGE) = 24915.9766
INDEX OF POLARITY (%) = 40.69
ISOELECTRIC POINT = 5.45
OD 260 (1mg/ml) = 0.304 OD 280 (1mg/ml) = 0.462

*FIG. 52B*

```
M. IVANOVII CORA             3 TO 227
P. DENITRIFICANS COBA        17 TO 251

       10        20        30        40         50        60        70
VYLVGAGPGDPELITLKAVNVLKKADVVLYDKPANEEILKYAE-GAKLIYVGKQAGHHYKSQNEINTLLV
=-========= =-==  = = =- ====- =   ==- == =  == = - == -=      = -=  ==
VWLVGAGPGDPGLLTLHAANALRQADVIVHDALVNEDCLKLARPGAVLEFAGKRGGKPSPKQRDISLRLV
  20        30        40        50        60        70        80
        80        90       100       110       120       130       140
EEAKENDLVVRLKGGDPFVFGRGGEEILALVEEGIDFELVPGVTSAIGVPTTIGLPVTHRGVATSFTVVT
= =-   - =================  =-===   - = -===-=-==   -   =-===== =  - = -=
ELARAGNRVLRLKGGDPFVFGRGGEEALTLVEHQVPFRIVPGITAGIGGLAYAGIPVTHREVNHAVTFLT
  90       100       110       120       130       140       150
       150        160         170       180        190       200
GHEDPTKCKKQVGWD-FKADT-IVIL-MGIGNLAENTAEIMKH-KDPETPVCVIENGTMEGQRIITGTL-
==-   -      - =-   - - ---- =--  --  ==---    - -- ==  - =--   = -- -==
GHDSSGLVPDRINWQGIASGSPVIVMYMAMKHIGAITANLIAGGRSPDEPVAFVCNAATPQQAVLETTLA
 160       170       180       190       200       210       220
    210       220
--E-NIAGKDIKPPALVVL-EMLSM
  = --=-  - ===-==- =-- -
RAEADVAAAGLEPPAIVVVGEVVRL
 230       240       250

PERCENTAGE OF STRICT HOMOLOGY : 40.4
```

FIG. 53

PURIFICATION OF PSEUDOMONAS DENITRIFICANS COBINAMIDE KINASE - COBINAMIDEPHOSPHATE GUANYLYL TRANSFERASE

| PURIFICATION STEP | VOL (ml) | PROTEIN (mg) | COBINAMIDE KINASE | | | COBINAMIDEPHOSPHATE GUANYLYL TRANSFERASE | RATIO OF sp. act. 2/1 |
|---|---|---|---|---|---|---|---|
| | | | sp. act. 1 (U/mg of protein) | YIELD (%) | PURIFICATION FACTOR | sp. act. 2 (U/mg OF PROTEIN) | |
| CRUDE EXTRACT* | 4.5 | 120 | 16 | - | - | 214 | 13 |
| MONO Q HR 10/10 ELUATE | 9.0 | 8.98 | 188 | 88 | 12 | - | - |
| HYDROXYAPATITE ELUATE | 2.0 | 4.55 | 325 | 77 | 20 | 3640 | 11 |
| PHENYL-SUPEROSE ELUATE | 2.0 | 1.51 | 560 | 44 | 35 | - | - |
| MONO Q HR 5/5 ELUATE | 3.0 | 0.90 | 786 | 37 | 49 | 11282 | 14 |

*FROM 1 G OF WET SC510 PXL622 CELLS CULTURED ON PS4 MEDIUM (CAMERON ET AL., 1989) WITHOUT COBALT.

*FIG. 55*

SEQUENCE LISTING

```
(1) GENERAL INFORMATION:

   (iii) NUMBER OF SEQUENCES:  60


(2) INFORMATION FOR SEQ ID NO: 1:

     (i) SEQUENCE CHARACTERISTICS:
          (A) LENGTH:  5398 base pairs
          (B) TYPE:  Nucleic acid
          (C) STRANDEDNESS:  Double
          (D) TOPOLOGY:  Unknown

    (ii) MOLECULE TYPE:  cDNA

   (iii) HYPOTHETICAL: No

    (iv) ORIGINAL SOURCE:
          (A) ORGANISM: Pseudomonas denitrificans
          (B) STRAIN:
          (C) INDIVIDUAL ISOLATE:
          (D) DEVELOPMENTAL STAGE:
          (E) HAPLOTYPE:
          (F) TISSUE TYPE:
          (G) CELL TYPE:
          (H) CELL LINE:
          (I) ORGANELLE:

    (ix) FEATURE:
          (A) NAME/KEY:
          (B) LOCATION:
          (C) IDENTIFICATION METHOD:
          (D) OTHER INFORMATION:Nucleotide Sequence of the 5' to 3'
               strand from the 5398 bp ClaI-HindIII-HindIII-HindIII
               fragment of Pseudomonas denitrificans

    (xi) SEQUENCE DESCRIPTION: SEQ ID NO: 1:

GGGCTGCAGG TCGACTCTAG AATCGATGAA GCCTGCGATG AAGGCGGCGA CGAACAGGAA      60

GGCGAGCAGG TGGAAGGCGA GATCTTGCAC GGCGGGGACT CGAGAGGAGA GCTGTCAGGC     120
```

-continued

```
GGGATTTTCC GCCTTGTGTC AGAGCCCGGC GCGATTTGCA AAGCCTTCTG TCGCGGTGTT    180
GCTGTCCATG CAGGTGTCGA AATTGAAAAA CCGACAAAGA TTCACAGCCT TGTTCCAGCT    240
CGCTGTCTTT CTGGATGGAG GCGCTCTCGC CCGCATGGTG CCGAAGAAGG GCTGTCCTTG    300
CGATACGGTA GGCGGATGAC GATCTTCCTC AAACGCGACA TGGCGATGGC GCAATCCGGT    360
TTGACCGGCC TTCCGCGCTC CGGTAAAAAT GAAGGATATG CGACGGCGTC CGCTTTGGCG    420
GACTGAAAGA GCGTCCGGTG CGGCCGACCC AGTCAGGGGG GCATCAGCCG GTGCTGTCCA    480
GATCGGCCGG GACGGATCGT CCCAGCCGGC GCTTCGTTAA GGAGAACAAC GAAGGGAGCC    540
GGCCGCCGAT GCCATCGGGC CAACACTCTG CACAGACGAC GAAAGCAGGA GCCGGGCTGG    600
TGCTCGGGCT CGGCTGCGAG CGTCGCACGC CGGCCGAAGA GGTGATCGCC CTTGCCGAGC    660
GTGCGCTTGC CGATGCCGGT GTTGCGCCCG GCGATCTGCG GCTGGTCGCC TCGCTCGATG    720
CTCGCGCCGA GGAGCCGGCG ATCCTGGCGG CCGCTCAGCA TTTCGCGGTT CCGGCCGCGT    780
TCTACGATGC CGCCACGCTC GAAGCCGAAG CTTCCCGGCT CGCCAACCCG TCCGAGATCG    840
TCTTTGCCTA CACGGGTTGT CATGGCGTTG CCGAGGGTGC AGCGCTCGTC GGCGCCGGTC    900
GCGAAGCCGT GCTGATTGTG CAGAAGATCG TCTCCGCCCA TGCGACGGCC GCACTTGCCG    960
GGCCGGCGAC CTTGCGCGCC GAAAAGCGCA TCCAGGCGGC GGAGGCTGTC TGATGCATTC   1020
TTATGTTGTT GAATTGAATC AATCTTTTGC CCGGGGTTTC TCTCAAGTGG AATCCGGTTC   1080
TTTAGAGAGC GCGTCAGGCG TGCCGTTGGG TGGCGCCGAA ATACAGGTGG GACAGCACGC   1140
ATGATCGACG ACCTCTTTGC CGGATTGCCG GCGCTCGAAA AAGGTTCGGT CTGGCTGGTC   1200
GGCGCCGGCC CCGGCGATCC CGGCCTGTTG ACGCTGCATG CGGCCAATGC GCTGCGCCAG   1260
GCGGATGTGA TCGTGCATGA TGCGCTGGTC AACGAGGATT GCCTGAAGCT CGCGCGGCCG   1320
GGCGCCGTGC TGGAGTTTGC GGGCAAGCGT GGCGGCAAGC CGTCGCCGAA GCAGCGCGAC   1380
ATCTCGCTTC GCCTCGTCGA ACTCGCGCGC GCCGGCAACC GGGTGCTGCG CCTCAAAGGC   1440
GGCGATCCCT TCGTCTTCGG TCGCGGTGGC GAGGAGGCGC TGACGCTGGT CGAACACCAG   1500
GTGCCGTTCC GAATCGTGCC CGGCATCACC GCCGGTATCG GCGGGCTTGC CTATGCCGGC   1560
ATTCCCGTGA CCCATCGCGA GGTCAACCAC GCGGTCACTT TCCTGACTGG CCATGATTCC   1620
TCCGGCCTGG TGCCGGATCG CATCAACTGG CAGGGCATCG CCAGCGGCTC GCCTGTCATC   1680
GTCATGTACA TGGCGATGAA ACATATCGGC GCGATCACCG CCAACCTCAT TGCCGGCGGC   1740
CGCTCGCCGG ACGAACCGGT CGCCTTCGTC TGCAACGCCG CGACGCCGCA GCAGGCGGTG   1800
CTGGAAACGA CGCTTGCGCG TGCAGAGGCC GATGTTGCGG CGGCAGGGCT GGAGCCGCCG   1860
GCGATCGTCG TCGTCGGCGA GGTGGTGCGG CTGCGCGCAG CGCTCGACTG GATCGGCGCG   1920
CTGGACGGGC GCAAGCTTGC CGCCGACCCG TTCGCCAATC GCATTCTCAG GAACCCGGCA   1980
TGAGCGGATT GCTGATTGCC GCACCCGCGT CCGGCTCCGG CAAGACGACG GTGACGCTCG   2040
GGCTGATGCG CGCCCTGAAG AGGCGCGGCG TGGCGATCGC GCCCGGCAAG GCGGGGCCGG   2100
ACTATATCGA TCCCGCTTTC CACGCGGCAG CGACCGGCGA GCCCTGCTTC AACTACGACC   2160
CCTGGGCGAT GCGCCCGGAA CTGCTGCTTG CCAATGCGTC GCATGTGGCC TCCGGCGGGC   2220
GCACATTGAT CGTCGAGGCG ATGATGGGAC TGCATGACGG TGCTGCCGAC GGCTCGGGAA   2280
CGCCAGCGGA CCTCGCCGCG ACGCTGAACC TTGCGGTCAT TCTGGTGGTC GATTGCGCCC   2340
GCATGTCCCA GTCGGTTGCC GCCCTCGTGC GCGGCTATGC GGATCATCGC GACGATATCC   2400
GGGTGGTTGG CGTCATCCTC AACAAGGTCG GCAGCGATCG GCATGAAATG ATGCTGCGCG   2460
```

-continued

```
ATGCGCTCGG CAAGGTGCGC ATGCCTGTCT TCGGCGTGCT CCGGCAGGAC AGCGCATTGC   2520
AACTGCCGGA GCGCCATCTC GGGCTCGTGC AGGCGGGCGA ACACTCAGCG CTTGAGGGCT   2580
TCATCGAGGC GGCGGCCGCG CGGGTCGAGG CTGCCTGCGA TCTCGACGCC ATCCGCCTGA   2640
TCGCGACGAT TTTCCCGCAG GTGCCCGCGG CGGCCGATGC CGAGCGTTTG CGGCCGCTCG   2700
GTCAGCGCAT CGCGGTCGCG CGCGATATCG CCTTTGCCTT CTGCTACGAG CACCTGCTTT   2760
ACGGCTGGCG GCAAGGCGGC GCGGAGATTT CCTTCTTCTC GCCGCTCGCC GACGAGGGGC   2820
CGGATGCGGC AGCCGATGCC GTCTATCTTC CGGGGGGTTA TCCGGAGCTG CATGCGGGGC   2880
AGCTGAGCGC CGCCGCCCGA TTCCGTTCCG GCATGCATTC CGCGGCGGAA CGCGGCGCCC   2940
GCATCTTCGG CGAGTGCGGC GGCTATATGG TGCTCGGCGA AGGGCTTGTC GCTGCCGATG   3000
GCACACGCTA CGACATGCTC GGCCTGCTGC CGCTCGTAAC CAGTTTTGCC GAGCGCAGGC   3060
GGCACCTCGG CTATCGCCGC GTCGTGCCTG TCGACAACGC CTTCTTCGAT GGACCCATGA   3120
CGGCGCACGA ATTCCACTAT GCGACCATCG TCGCCGAAGG GGCGGCCGAT CGGCTGTTTG   3180
CGGTCAGCGA CGCCGCCGGC GAGGATCTCG GCCAGGCGGG CCTCCGGCGC GGCCCTGTCG   3240
CCGGTTCCTT CATGCATCTG ATCGACGTCG CAGGTGCTGC ATGAGCGCAC CGATCGTTCA   3300
TGGTGGCGGC ATCACCGAGG CCGCAGCGCG CTATGGCGGC CGGCCTGAAG ACTGGCTCGA   3360
TCTGTCGACC GGCATCAATC CATGCCCCGT CGCCTTGCCC GCGGTCCCTG AGCGCGCCTG   3420
GCACCGGCTG CCGGATCGGC AGACGGTAGA TGATGCGCGG AGCGCCGCCG CCGACTACTA   3480
CCGCACCAAC GGCGTGCTGC CTTTGCCGGT GCCGGGCACC CAGTCGGTGA TCCAGCTCCT   3540
GCCACGTCTT GCTCCGGCCA ACAGGCACGT CGCGATTTTC GGGCCGACCT ATGGCGAGTA   3600
TGCCCGCGTG CTTGAAGCGG CCGGCTTTGC TGTCGATCGC GTCGCGGATG CCGACGCGCT   3660
CACGGCCGAA CATGGGCTTG TCATCGTCGT CAACCCCAAC AACCCGACCG GCCGCGCCTT   3720
GGCGCCGGCG GAGCTTCTGG CGATCGCCGC AAGGCAGAAG GCGAGCGGCG GACTGCTGCT   3780
GGTCGATGAG GCCTTCGGCG ATCTTGAGCC GCAACTGAGT GTCGCTGGTC ACGCGTCAGG   3840
GCAAGGCAAC CTCATCGTCT TCCGCTCCTT CGGCAAGTTC TTCGGCCTTG CGGGCCTGCG   3900
CCTCGGCTTC GTCGTTGCGA CCGAGCCAGT GCTTGCATCC TTTGCCGATT GGCTCGGTCC   3960
CTGGGCTGTC TCCGGCCCGG CGTTGACGAT CTCGAAAGCG CTGATGCAGG GCGATACGAA   4020
GGCGATCGCG GCGGGCATCC TCGAGCGTCG CGCCGGCCTC GATGCGGCTC TCGATGGGGC   4080
AGGGCTCAAC CGTATCGGCG GCACGGGGCT ATTCGTGCTG GTCGAGCATC CCAGGGCAGC   4140
TCTGCTGCAG GAGCGGCTCT GCGAGGCCCA TATTCTCACG CGCAAGTTCG ACTATGCCCC   4200
GACCTGGCTC AGGGTCGGTC TTGCGCCTGA CGCGGCTGGT GACCGACGGC TGGCGGACGC   4260
GCTTGCCCGC ATGGAGCTCT GAGGTGTCGG AGACGATCCT GCTCATTCTC GCGCTGGCGC   4320
TGGTGATCGA CCGCGTTGTC GGCGATCCGG ACTGGCTCTG GGCGCGCGTG CCGCATCCGG   4380
TCGTGTTTTT CGGCAAGGCC ATCGGCTTTT TCGACGCGCG GCTGAACCGG GAGGACCTCG   4440
AGGATAGCGC GCGCAAATTT CGTGGCGTCG TCGCGATCCT TTTGTTGCTT GGCATCAGCG   4500
CCTGGTTCGG CCATCTGCTG CATCGCCTGT TCGCCGTCCT CGGACCGCTC GGCTTTCTGC   4560
TCGAGGCGGT TCTGGTCGCG GTCTTCCTGG CACAGAAGAG CCTCGCCGAT CACGTGCGTC   4620
GCGTGGCCGG GGGCTTGCGA CAGGGCGGGC TGGAAGGCGG GCGTGCCGCC GTGTCGATGA   4680
TCGTTGGTCG CGATCCAAAG ACGCTCGACG AGCCGGCGGT CTGCCGTGCC GCGATCGAAA   4740
GCCTTGCCGA GAATTTCTCC GACGGCGTCG TGGCGCCGGC CTTCTGGTAC GCGGTTGCCG   4800
GCCTGCCGGG GCTTCTTGCC TACAAGATGC TGAACACCGC CGATTCGATG ATCGGCCACA   4860
```

-continued

AGTCGCCGAA ATATCTGCAC TTCGGCTGGG CCTCGGCCCG ACTCGACGAT CTCGCCAACC 4920

TGCCGGCAGC GAGGCTCTCG ATCCTTTTGA TCTCAGCCGG TGCGCTGATC CATCGTGGCG 4980

CCAGCGCCGC CAAGGATGCG CTGACCGTGG CCCTTCGCGA CCATGGCCTG CACCGCTCGC 5040

CGAACTCCGG CTGGCCGGAA GCGGCCATGG CCGGCGCGCT CGATCTGCAG CTTGCCGGTC 5100

CGCGGATCTA TGGCGGCGTC AAGGTCAGCG AACCTATGAT CAACGGTCCG GGCCGAGCGG 5160

TTGCAACAAG CGAAGACATC GACGCCGGTA TTGCTGTATT TTATGGCGCC TGTACGGTCA 5220

TGGCCGGGTT TGTTCTTGCA ATCGCAATGA TTTGATCGCG GAAGTTGACC TTCGCATTAA 5280

GACTCTGCTT TCCATATGTA TTAAGATCGT ATCATATTCG ATCAGTTATT CTCCTGGAAC 5340

GTTTGGTTCC ACCGGTACGT GTTCGTCTTC CCGGAGAGAG AAGCATGCGC AAAAGCTT 5398

(2) INFORMATION FOR SEQ ID NO: 2:

(i) SEQUENCE CHARACTERISTICS:
(A) LENGTH: 8753 base pairs
(B) TYPE: Nucleic Acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY:
(B) LOCATION:
(C) IDENTIFICATION METHOD:
(D) OTHER INFORMATION: Nucleotide Sequence of the 5' to 3' strand from the 8753 bp EcoRII fragment of Pseudomonas denitrificans (xi) SEQUENCE DESCRIPTION: SEQ ID NO: 2:

GAATTCGCCA GCGCCTACAT GGCTGACCTC AAGCAGTTCC TCGTGGCCCA GAAGAACGAG 60

GGCCGGCAGA TTTTCCCTCG CGGGCCTGAG TATTTTCGCG CGCTCGACCT GACGCCGCTC 120

GACAAGGTGC GCGTGGTCAT TCTCGGCCAG GATCCCTATC ACGGTGACGG CCAGCGGCAT 180

GGGCTCTGCT TCAGCGTTCG CCCCGGTGTC CGGACGCCGC CGTCGCTGGT CAACATCTAC 240

AAGGAACTGA ATACCGATCT CGGTATTCCG CCGGCGCGTC ACGGTTTTCT CGAAAGCTGG 300

GCAAGGCAGG GCGTGCTGCT TTTGAACAGC GTGCTGACGG TAGAGCGCGG GAACGTGCGT 360

CACACCAGGG TCACGGTTGG GAAAAGTTCA CGGATGCGAT CATCCGTGCG GTCAACGAGG 420

CCGAGCATCC CGTCGTCTTC ATGCTTTGGG GCTCCTATGC GCAGAAGAAG GCGGCCTTCG 480

TCGACCGCTC GCGCCATCTT GTCCTGAGGG CACCACATCC GTCGCCGCTC TCAGCCCATT 540

CCGGCTTTCT CGGCTGCCGG CATTTTTCCC AGGCCAATGC CTTCCTCGAA AGCAAAGGCT 600

TCGATCCGAT CGACTGGCGG CTGCCGGAAA ATCCGGCTGC GGACATCAAC TGAAGGCTTG 660

GCGCGAATGA CGGCTTTGTC GTCGCCCTGA GGTCTTGCCT TGGCGGCGGC GATCCGCCTA 720

AGACGCCCGA ACGAAATGGC GGAGGCGGGC ATGCGCAAAA TTCTGATCAT CGGCATCGGT 780

-continued

```
TCGGGCAATC CCGAACACAT GACCGTGCAG GCGATCAACG CGCTGAACTG CGCCGACGTG    840
CTCTTTATCC CGACCAAGGG AGCGAAGAAG ACCGAGCTTG CCGAAGTGCG CCGCGACATC    900
TGCGCCCGCT ACGTCACGCG CAAGGACAGC CGCACCGTCG AGTTCGCGGT GCCCGTGCGG    960
CGCACCGAAG GCGTCAGCTA TGACGGCAGC GTCGATGACT GGCACGCCCA GATCGCTGGG   1020
ATTTACGAAG CGCTTCTATC GAAGGAGTTG GGCGAAGAGG GAACTGGCGC GTTTCTCGTC   1080
TGGGGCGACC CGATGCTCTA TGACAGCACC ATTCGCATCG TCGAGCGGGT CAAGGCACGC   1140
GGTGAGGTCG CCTTCGCCTA CGACGTCATT CCCGGGATCA CCAGTCTGCA GGCGCTTTGC   1200
GCCAGCCACC GCATTCCGCT GAACCTCGTC GGCAAGCCGG TGGAGATCAC CACGGGGCGT   1260
CGGCTGCACG AAAGCTTTCC CGAGAAGAGC CAGACCTCGG TCGTCATGCT CGATGGCGAA   1320
CAGGCGTTTC AGCGGGTCGA GGACCCGGAG GCGGAGATCT ATTGGGGCGC CTATCTCGGC   1380
ACGCGGGATG AGATCGTCAT TTCCGGCCGC GTGGCTGAGG TGAAGGACCG GATCCTTGAA   1440
ACGCGGGCGG CGGCGCGCGC GAAGATGGGA TGGATCATGG ACATCTATCT CCTGCGCAAG   1500
GGCGCCGACT TCGACGAGTG ACGGGGAGGG CCGATCTGCG TCGTGTTTGA TCTCACTCAA   1560
GGTTTGCGGC TGTGTTATAG CGTCTTAAGA GGCTTCTTCA GGGAGGAGAA CCTCAAGTGA   1620
TGACGGATTT GATGACCAGC TGCGCCCTTC CATTGACCGG AGATGCCGGC ACCGTCGCTT   1680
CGATGCGCCG CGGCGCCTGC CCGTCCTTGG CAGAGCCGAT GCAGACCGGC GACGGCCTGC   1740
TCGTGAGGGT GAGGCCAACG GATGACAGCC TGACGCTGCC GAAGGTCATT GCCCTTGCCA   1800
CGGCTGCCGA GCGCTTCGGC AATGGCATCA TCGAGATTAC CGCGCGCGGA AACCTGCAGC   1860
TTCGCGGCCT GAGCGCGGCT TCGGTGCCAA GGCTGGCGCA GGCGATCGGC GATGCGGAGA   1920
TCGCCATTGC CGAGGGGCTC GCGATCGAGG TGCCGCCCCT GGCCGGCATC GACCCGGACG   1980
AGATCGCCGA TCCGCGGCCG ATTGCCACTG AGCTTCGTGA AGCGTTGGAT GTGCGCCAGG   2040
TGCCGTTGAA GCTTGCACCC AAATTATCCG TCGTCATCGA TAGCGGTGGC CGGTTTGGTC   2100
TCGGCGCTGT CGTCGCCGAC ATTCGCCTTC AGGCGGTTTC GACTGTCGCG GGGGTGGCCT   2160
GGGTGCTGTC GCTTGGCGGC ACGTCAACGA AGGCATCGAG CGTCGGGACG TTGGCCGGCA   2220
ACGCGGTCGT GCCGGCCCTG ATCACCATTC TCGAGAAACT GGCGAGCCTG GGCACGACGA   2280
TGCGCGGGCG CGATCTGGAC CCGTCGGAAA TCCGCGCGCT CTGTCGCTGT GAGACATCGT   2340
CCGAACGCCC GGCCGCTCCG CGTTCGGCCG CAATACCCGG CATTCATGCG CTGGGTAACG   2400
CCGACACCGT TCTCGGCCTC GGTCTGGCCT TTGCTCAGGT GGAGGCCGCC GCGCTGGCAT   2460
CCTACCTGCA TCAGGTCCAG GCGCTTGGCG CCAATGCGAT CCGGCTTGCG CCCGGGCACG   2520
CCTTCTTCGT CCTCGGCCTT TGCCCCGAGA CCGCGGCTGT GGCGCAGAGC CTGGCAGCGT   2580
CACACGGTTT TCGCATTGCC GAGCAGGATC CGCGCAATGC GATCGCCACC TGCGCCGGCA   2640
GCAAGGGTTG CGCCTCGGCG TGGATGGAAA CCAAGGGCAT GGCCGAGCGC CTCGTCGAGA   2700
CGGCGCCGGA ATTGCTCGAC GGGTCGCTCA CCGTGCATCT CTCCGGCTGC GCCAAGGGCT   2760
GCGCCCGGCC GAAGCCGTCC GAACTGACGC TTGTCGGTGC GCCATCAGGA TACGGGCTTG   2820
TCGTAAATGG GGCTGCCAAT GGCTTGCCAA GCGCCTACAC CGATGAGAAT GGAATGGGAT   2880
CCGCCCTTGC CCGGCTCGGC CGGCTGGTGC GGCAAAACAA AGACGCTGGC GAATCGGCGC   2940
AGTCCTGTCT TACACGGCTC GGAGCTGCGC GCGTCTCGGC AGCGTTCGAA CAGGGATAGA   3000
CATGCCTGAG TATGATTACA TTCGCGATGG CAACGCCATC TACGAGCGTT CCTTCGCCAT   3060
CATCCGCGCC GAGGCCGATC TGTCGCGCTT CTCCGAAGAG GAAGCGGATC TGGCTGTGCG   3120
CATGGTGCAC GCCTGCGGTT CCGTCGAGGC GACCAGGCAG TTCGTGTTTT CTCCCGATTT   3180
```

-continued

CGTAAGCTCG GCCCGTGCGG CGCTGAAAGC CGGTGCGCCG ATCCTCTGCG ATGCCGAGAT 3240

GGTTGCGCAC GGTGTCACCC GCGCCCGTCT GCCGGCCGGC AACGAGGTGA TCTGCACGCT 3300

GCGCGATCCT CGCACGCCCG CACTTGCGGC CGAGATCGGC AACACCCGCT CCGCCGCAGC 3360

CCTGAAGCTC TGGAGCGAGC GGCTGGCCGG TTCGGTGGTC GCGATCGGCA ACGCGCCGAC 3420

GGCGTTGTTC TTCCTCTTGG AAATGCTGCG CGACGGCGCG CCGAAGCCGG CGGCAATCCT 3480

CGGCATGCCC GTCGGTTTCG TCGGTGCGGC GGAATCGAAG GATGCGCTGG CCGAGAACTC 3540

CTATGGCGTT CCCTTCGCCA TCGTGCGCGG CCGCCTCGGC GGGAGTGCCA TGACGGCGGC 3600

AGCGCTTAAC TCGCTCGCGA GGCCGGGCCT GTGAGCGGCG TCGGCGTGGG GCGCCTGATC 3660

GGTGTTGGGA CCGGCCCCGG TGATCCGGAA CTTTTGACGG TCAAGGCGGT GAAGGCGCTC 3720

GGGCAAGCCG ATGTGCTTGC CTATTTCGCC AAGGCCGGGC GAAGCGGTAA CGGCCGCGCG 3780

GTGGTCGAGG GTCTGCTGAA GCCCGATCTT GTCGAGCTGC CGCTATACTA TCCGGTGACG 3840

ACCGAAATCG ACAAGGACGA TGGCGCCTAC AAGACCCAGA TCACCGACTT CTACAATGCG 3900

TCGGCCGAAG CGGTAGCGGC GCATCTTGCC GCCGGGCGCA CGGTCGCCGT GCTCAGTGAA 3960

GGCGACCCGC TGTTCTATGG TTCCTACATG CATCTGCATG TGCGGCTCGC CAATCGTTTC 4020

CCGGTCGAGG TGATCCCCGG CATTACCGCC ATGTCCGGCT GTTGGTCGCT TGCCGGCCTG 4080

CCGCTGGTGC AGGGCGACGA CGTGCTCTCG GTGCTTCCGG GCACCATGGC CGAGGCCGAG 4140

CTCGGCCGCA GGCTTGCGGA TACCGAAGCC GCCGTGATCA TGAAGGTCGG GCGCAATTTG 4200

CCGAAGATCC GTCGGGCGCT CGCTGCCTCC GGCCGTCTCG ACCAGGCCGT CTATGTCGAA 4260

CGCGGCACGA TGAAGAACGC GGCGATGACG GCTCTTGCGG AAAAGGCCGA CGACGAGGCG 4320

CCCTATTTCT CGCTGGTGCT CGTTCCCGGC TGGAAGGACC GACCATGACC GGTACGCTCT 4380

ATGTCGTCGG TACCGGACCG GGCAGCGCCA AGCAGATGAC GCCGGAAACG GCGGAAGCCG 4440

TTGCGGCCGC TCAGGAGTTT TACGGCTACT TTCCCTATCT CGACCGGCTG AACCTCAGAC 4500

CGGATCAGAT CCGTGTCGCC TCGGACAACC GCGAGGAGCT CGATCGGGCA CAGGTCGCGC 4560

TGACGCGGGC TGCGGCAGGC GTGAAGGTCT GCATGGTCTC CGGTGGCGAT CCCGGTGTCT 4620

TTGCCATGGC GGCCGCCGTC TGCGAGGCGA TCGACAAGGG ACCGGCGGAA TGGAAGTCGG 4680

TTGAACTGGT GATCACGCCC GGCGTGACCG CGATGCTCGC CGTTGCCGCC CGCATCGGCG 4740

CGCCGCTCGG TCATGATTTC TGTGCGATCT CGCTTTCCGA CAATCTGAAG CCCTGGGAAG 4800

TCATCACCCG GCGTCTCAGG CTGGCGGCGG AAGCGGGCTT CGTCATTGCC CTCTACAATC 4860

CGATCAGCAA GGCGCGGCCC TGGCAGCTCG GTGAGGCCTT CGAGCTTCTG CGCAGCGTTC 4920

TGCCGGCAAG CGTTCCGGTC ATCTTCGGCC GTGCGGCCGG GCGGCCGGAC GAACGGATCG 4980

CGGTGATGCC GCTCGGCGAG GCCGATGCCA ACCGCGCCGA CATGGCGACC TGCGTCATCA 5040

TCGGCTCGCC GGAGACGCGC ATCGTCGAGC GCGACGGCCA ACCCGATCTC GTCTACACAC 5100

CGCGCTTCTA TGCAGGGGCG AGCCAGTGAG CGATGCGGTT GAGTGCCTCG TCGCAACTGC 5160

CGACCGTCGG CACGTCCGCG GGCTTGCGCC GCTCGACCAT GATCACCTCG ATGCCGAGCC 5220

GGCGCGCTGC GGCAATCTTG CCGTAGGTGG CGCTGCCACC GCTGTTCTTG GCGACGATCA 5280

CATCGATCTG CCGACTCCTG AGCAACGCGG CTTCGTCGGC TTCCGCAAAG GGACCGGTCG 5340

CCAGGATCGC CTCCTGGTCG GGCAGATTAA GCGGCGGCGT CACCGGATCG ACGCTGCGGA 5400

TGACGTAGCT GTGCTGCGGC GCGACCTCGA AGTGGAAAGC TTCCTGTCGA CCTATCGCCA 5460

GGAAGACGCG GCGTCGCCGA TCACCGAGCG CGCTGACGGC CTCGACAACG CTATCGACAG 5520

-continued

```
CAGTCCAGCG GTCGCCAGGC AGGGGCACCC ATTCCGGTCG GCGGAGGGCG ATAAGCGCAA   5580
CGCCGGTTCT TTGCGCTGCG TCCGCGGCGT TGTGCGAAAT GCGTGCGGCA AAGGGGTGCG   5640
TCGCATCGAC CAGCAGCGCG ATGTTTTCGT CATGCACGAA ATGCGCCAGC CCATCCGCGC   5700
CGCCAAAGCC GCCGATGCGC GTCTTGACCG GCTGCGGCCG CGGGTCCGCG GTGCGGCCGG   5760
CCAGCGAGAT GGCGGTGTCG TAGCGGACAT CTTCGGCCAA GCGGCGCGCG AGTTCGCGTG   5820
CCTCGGTGGT GCCACCCAGA ATCAGAATAC GAGGTTTTTC CATGGCTGAC GTGTCGAACA   5880
GCGAACCCGC CATAGTCTCC CCCTGGCTGA CCGTCATCGG TATCGGTGAG GATGGTGTAG   5940
CGGGTCTCGG CGACGAGGCC AAGCGGCTGA TCGCCGAAGC GCCGGTCGTC TACGGCGGCC   6000
ATCGTCATCT GGAGCTCGCC GCCTCCCTCA TCACCGGCGA AGCGCACAAT TGGCTAAGCC   6060
CCCTCGAACG CTCGGTCGTC GAGATCGTCG CGCGTCGCGG CAGCCCGGTG GTGGTGCTTG   6120
CCTCGGGCGA CCCGTTCTTC TTCGGCGTCG GCGTGACGCT GGCGCGCCGC ATCGCCTCGG   6180
CCGAAATACG CACGCTTCCG GCGCCGTCGT CGATCAGTCT TGCCGCCTCG CGCCTCGGCT   6240
GGGCGCTGCA GGATGCGACG CTCGTCTCCG TACATGGGCG GCCGCTGGAT CTGGTGCGAC   6300
CGCATTTGCA TCCGGGGGCG CGTGTGCTTA CGCTCACGTC GGACGGTGCG GGTCCGCGAG   6360
ACCTTGCCGA GCTTCTGGTT TCAAGCGGCT TCGGTCAGTC GCGACTGACC GTGCTCGAAG   6420
CGCTGGGCGG CGCCGGCGAA CGGGTGACGA CGCAGATCGC CGCGCGCTTC ATGCTCGGCC   6480
TCGTGCATCC TTTGAACGTC TGCGCCATTG AGGTGGCGGC CGACGAGGGC GCGCGCATCC   6540
TGCCGCTTGC CGCCGGCCGC GACGATGCGC TGTTCGAACA TGACGGGCAG ATCACCAAGC   6600
GCGAGGTGCG GGCGCTGACG CTGTCGGCAC TCGCACCGCG CAAGGGCGAA CTGCTATGGG   6660
ACATCGGCGG CGGCTCCGGC TCGATCGGCA TCGAATGGAT GCTCGCCGAT CCGACCATGC   6720
AGGCGATCAC CATCGAGGTT GAGCCGGAGC GGGCAGCGCG CATCGGCCGC AACGCGACGA   6780
TGTTCGGCGT GCCCGGGCTG ACGGTTGTCG AAGGCGAGGC GCCGGCGGCG CTTGCCGGCC   6840
TGCCACAACC GGACGCGATC TTCATCGGCG GCGGCGGCAG CGAAGACGGC GTCATGGAAG   6900
CAGCGATCGA GGCGCTCAAG TCAGGCGGAC GGCTGGTTGC CAACGCGGTG ACGACGGACA   6960
TGGAAGCGGT GCTGCTCGAT CATCACGCGC GGCTCGGCGG TTCGCTGATC CGCATCGATA   7020
TCGCGCGTGC AGGACCCATC GGCGGCATGA CCGGCTGGAA GCCGGCCATG CCGGTCACCC   7080
AATGGTCGTG GACGAAGGGC TAAAGCAGTT CCAGCGAAAG TGTGACGCGG TTTTGCGTCC   7140
GGAACTGCGC AAGAAAAAGA AAGAGTAACC TATGACGGTA CATTTCATCG GCGCCGGCCC   7200
GGGAGCCGCA GACCTGATCA CGGTGCGTGG TCGCGACCTG ATCGGGCGCT GCCCGGTCTG   7260
CCTTTACGCC GGCTCGATCG TCTCGCCGGA GCTGCTGCGA TATTGCCCGC CGGGCGCCCG   7320
CATTGTCGAT ACGGCGCCGA TGTCCCTCGA CGAGATCGAG GCGGAGTATG TGAAGGCCGA   7380
AGCCGAAGGG CTCGACGTGG CGCGGCTTCA TTCGGGCGAC CTTTCGGTCT GGAGTGCTGT   7440
GGCCGAACAG ATCCGCCGGC TCGAGAAGCA TGGCATCGCC TATACGATGA CGCCGGGCGT   7500
TCCTTCCTTT GCGGCGGCGG CTTCAGCGCT CGGTCGCGAA TTGACCATTC CGGCCGTGGC   7560
CCAGAGCCTG GTGCTGACCC GCGTTTCGGG CCGCGCCTCG CCGATGCCGA ACTCAGAAAC   7620
GCTTTCCGCT TTCGGCGCTA CGGGATCGAC GCTGGCAATC CACCTTGCGA TCCATGCGCT   7680
TCAGCAGGTG GTCGAGGAAC TGACGCCGCT CTACGGTGCC GACTGCCCGG TCGCCATCGT   7740
CGTCAAGGCC TCCTGGCCGG ACGAACGCGT GGTGCGCGGC ACGCTCGGTG ACATCGCCGC   7800
CAAGGTGGCG GAAGAGCCGA TCGAGCGCAC GGCGCTGATC TTCGTCGGTC CGGGGCTCGA   7860
AGCCTCCGAT TTCCGTGAAA GCTCGCTCTA CGATCCCGCC TATCAGCGGC GCTTCAGAGG   7920
```

-continued

GCGCGGCGAA TAGGCCGCAC TCCCTCGGGG GTCGGCCTAA GTTTCCCGCT GAGAGGGTTT 7980

TGAAACCTAT TCTGCCGGTT CTTCGCGCGG CGGCCGCTGC TTGAGCGGGA CGCCGCGCTT 8040

TTCCTCGACG CGGTCGCGGT AGAGCGCTGC CTGTCCAAGC AGCATCAGCG TCACCGGCGT 8100

GGTGGCGACG ACGAAGACGA TGATCAGGAT TTCGTGGAAT ACCCAGCGGC TCTGCAGCAC 8160

GGCAAAGCAG ATGATAGAGG CGGCGCAGAT CATCAGTACG CCGCCGCTGG TCGCCAGCGT 8220

CGGTGCGTGC AGGCGCTCGT AGAAGCTGGT GAACCGGAGC AAGCCGACGG AGCCGATCAG 8280

CGCCACTGCG GCGCCGAGGA CGGTGAGCCC GCAGACGAGA ACGGCTGCCC AGACGGGAAG 8340

GTCGGTGAGG TGGCTCATTC GATGATCTCC CCGCGCATCA GGAACTTGCC GAAGGCGATC 8400

GACGAGACGA AGCCGATCAA AGCCACGATC AGGGCGGACT CGAAATAGAG CGAGTTGGCC 8460

GTGCGGATGC CGAAGGTCAA GAGCATCAGC ATGGCGTTGA TATAGAGCGT GTCGAGGCCG 8520

AGGATACGGT CCTGGGCGCG CGGTCCCCTC ACCATGCGAT AGAAGGCAAA AGCCATCGCC 8580

AGGCCGAGCA TGATCTGGGC AATCAGGATC GACCAGATGA TTGAAAGTTC CATCATCCGA 8640

ATATCTCCTT CAGGGCGGTC TCATAGCGCT TGACCGTATC GAGCCAGATG TCCTCGTTCT 8700

CCATGTCGAG CACGTGGAAG AGCAGGGACT TGCGGCCGCG ATCCGGGGAA TTC 8753

(2) INFORMATION FOR SEQ ID NO: 3:

(i) SEQUENCE CHARACTERISTICS:
(A) LENGTH: 843 base pairs
(B) TYPE: Nucleic Acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobA
(B) LOCATION: 1141-1980 bp of SEQ ID NO: 1
(C) IDENTIFICATION METHOD:
(D) OTHER INFORMATION:

(xi) SEQUENCE DESCRIPTION: SEQ ID NO: 3:

ATGATCGACG ACCTCTTTGC CGGATTGCCG GCGCTCGAAA AAGGTTCGGT CTGGCTGGTC 60

GGCGCCGGCC CCGGCGATCC CGGCCTGTTG ACGCTGCATG CGGCCAATGC GCTGCGCCAG 120

GCGGATGTGA TCGTGCATGA TGCGCTGGTC AACGAGGATT GCCTGAAGCT CGCGCGGCCG 180

GGCGCCGTGC TGGAGTTTGC GGGCAAGCGT GGCGGCAAGC CGTCGCCGAA GCAGCGCGAC 240

ATCTCGCTTC GCCTCGTCGA ACTCGCGCGC GCCGGCAACC GGGTGCTGCG CCTCAAAGGC 300

GGCGATCCCT TCGTCTTCGG TCGCGGTGGC GAGGAGGCGC TGACGCTGGT CGAACACCAG 360

GTGCCGTTCC GAATCGTGCC CGGCATCACC GCCGGTATCG GCGGGCTTGC CTATGCCGGC 420

ATTCCCGTGA CCCATCGCGA GGTCAACCAC GCGGTCACTT TCCTGACTGG CCATGATTCC 480

TCCGGCCTGG TGCCGGATCG CATCAACTGG CAGGGCATCG CCAGCGGCTC GCCTGTCATC 540

-continued

```
GTCATGTACA TGGCGATGAA ACATATCGGC GCGATCACCG CCAACCTCAT TGCCGGCGGC    600

CGCTCGCCGG ACGAACCGGT CGCCTTCGTC TGCAACGCCG CGACGCCGCA GCAGGCGGTG    660

CTGGAAACGA CGCTTGCGCG TGCAGAGGCC GATGTTGCGG CGGCAGGGCT GGAGCCGCCG    720

GCGATCGTCG TCGTCGGCGA GGTGGTGCGG CTGCGCGCAG CGCTCGACTG GATCGGCGCG    780

CTGGACGGGC GCAAGCTTGC CGCCGACCCG TTCGCCAATC GCATTCTCAG GAACCCGGCA    840

TGA                                                                  843
```

(2) INFORMATION FOR SEQ ID NO: 4:

(i) SEQUENCE CHARACTERISTICS:
(A) LENGTH: 280 amino acids
(B) TYPE: Amino Acid
(C) STRANDEDNESS:
(D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBA
(B) LOCATION:
(C) IDENTIFICATION METHOD:
(D) OTHER INFORMATION: Translation product of SEQ ID NO:3

(xi) SEQUENCE DESCRIPTION: SEQ ID NO: 4:

```
Met Ile Asp Asp Leu Phe Ala Gly Leu Pro Ala Leu Glu Lys Gly Ser
1               5                   10                  15

Val Trp Leu Val Gly Ala Gly Pro Gly Asp Pro Gly Leu Leu Thr Leu
            20                  25                  30

His Ala Ala Asn Ala Leu Arg Gln Ala Asp Val Ile Val His Asp Ala
        35                  40                  45

Leu Val Asn Glu Asp Cys Leu Lys Leu Ala Arg Pro Gly Ala Val Leu
    50                  55                  60

Glu Phe Ala Gly Lys Arg Gly Gly Lys Pro Ser Pro Lys Gln Arg Asp
65                  70                  75                  80

Ile Ser Leu Arg Leu Val Glu Leu Ala Arg Ala Gly Asn Arg Val Leu
                85                  90                  95

Arg Leu Lys Gly Gly Asp Pro Phe Val Phe Gly Arg Gly Gly Glu Glu
            100                 105                 110

Ala Leu Thr Leu Val Glu His Gln Val Pro Phe Arg Ile Val Pro Gly
        115                 120                 125

Ile Thr Ala Gly Ile Gly Gly Leu Ala Tyr Ala Gly Ile Pro Val Thr
    130                 135                 140

His Arg Glu Val Asn His Ala Val Thr Phe Leu Thr Gly His Asp Ser
145                 150                 155                 160

Ser Gly Leu Val Pro Asp Arg Ile Asn Trp Gln Gly Ile Ala Ser Gly
                165                 170                 175

Ser Pro Val Ile Val Met Tyr Met Ala Met Lys His Ile Gly Ala Ile
            180                 185                 190
```

-continued

Thr Ala Asn Leu Ile Ala Gly Gly Arg Ser Pro Asp Glu Pro Val Ala
195 200 205

Phe Val Cys Asn Ala Ala Thr Pro Gln Gln Ala Val Leu Glu Thr Thr
210 215 220

Leu Ala Arg Ala Glu Ala Asp Val Ala Ala Ala Gly Leu Glu Pro Pro
225 230 235 240

Ala Ile Val Val Val Gly Glu Val Val Arg Leu Arg Ala Ala Leu Asp
245 250 255

Trp Ile Gly Ala Leu Asp Gly Arg Lys Leu Ala Ala Asp Pro Phe Ala
260 265 270

Asn Arg Ile Leu Arg Asn Pro Ala
275 280

(2) INFORMATION FOR SEQ ID NO: 5:

(i) SEQUENCE CHARACTERISTICS:
(A) LENGTH: 1305 base pairs
(B) TYPE: Nucleic Acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobB
(B) LOCATION: 1980-3283 bp of SEQ ID NO: 1
(C) IDENTIFICATION METHOD:
(D) OTHER INFORMATION:

(xi) SEQUENCE DESCRIPTION: SEQ ID NO: 5:

ATGAGCGGAT TGCTGATTGC CGCACCCGCG TCCGGCTCCG GCAAGACGAC GGTGACGCTC 60

GGGCTGATGC GCGCCCTGAA GAGGCGCGGC GTGGCGATCG CGCCCGGCAA GGCGGGGCCG 120

GACTATATCG ATCCCGCTTT CCACGCGGCA GCGACCGGCG AGCCCTGCTT CAACTACGAC 180

CCCTGGGCGA TGCGCCCGGA ACTGCTGCTT GCCAATGCGT CGCATGTGGC CTCCGGCGGG 240

CGCACATTGA TCGTCGAGGC GATGATGGGA CTGCATGACG GTGCTGCCGA CGGCTCGGGA 300

ACGCCAGCGG ACCTCGCCGC GACGCTGAAC CTTGCGGTCA TTCTGGTGGT CGATTGCGCC 360

CGCATGTCCC AGTCGGTTGC CGCCCTCGTG CGCGGCTATG CGGATCATCG CGACGATATC 420

CGGGTGGTTG GCGTCATCCT CAACAAGGTC GGCAGCGATC GGCATGAAAT GATGCTGCGC 480

GATGCGCTCG GCAAGGTGCG CATGCCTGTC TTCGGCGTGC TCCGGCAGGA CAGCGCATTG 540

CAACTGCCGG AGCGCCATCT CGGGCTCGTG CAGGCGGGCG AACACTCAGC GCTTGAGGGC 600

TTCATCGAGG CGGCGGCCGC GCGGGTCGAG GCTGCCTGCG ATCTCGACGC CATCCGCCTG 660

ATCGCGACGA TTTTCCCGCA GGTGCCCGCG GCGGCCGATG CCGAGCGTTT GCGGCCGCTC 720

GGTCAGCGCA TCGCGGTCGC GCGCGATATC GCCTTTGCCT TCTGCTACGA GCACCTGCTT 780

TACGGCTGGC GGCAAGGCGG CGCGGAGATT TCCTTCTTCT CGCCGCTCGC CGACGAGGGG 840

-continued

```
CCGGATGCGG CAGCCGATGC CGTCTATCTT CCGGGGGGTT ATCCGGAGCT GCATGCGGGG    900

CAGCTGAGCG CCGCCGCCCG ATTCCGTTCC GGCATGCATT CCGCGGCGGA ACGCGGCGCC    960

CGCATCTTCG GCGAGTGCGG CGGCTATATG GTGCTCGGCG AAGGGCTTGT CGCTGCCGAT   1020

GGCACACGCT ACGACATGCT CGGCCTGCTG CCGCTCGTAA CCAGTTTTGC CGAGCGCAGG   1080

CGGCACCTCG GCTATCGCCG CGTCGTGCCT GTCGACAACG CCTTCTTCGA TGGACCCATG   1140

ACGGCGCACG AATTCCACTA TGCGACCATC GTCGCCGAAG GGGCGGCCGA TCGGCTGTTT   1200

GCGGTCAGCG ACGCCGCCGG CGAGGATCTC GGCCAGGCGG GCCTCCGGCG CGGCCCTGTC   1260

GCCGGTTCCT TCATGCATCT GATCGACGTC GCAGGTGCTG CATGA                   1305
```

(2) INFORMATION FOR SEQ ID NO: 6:

(i) SEQUENCE CHARACTERISTICS:
(A) LENGTH: 434 amino acids
(B) TYPE: Amino Acid
(C) STRANDEDNESS:
(D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBB
(B) LOCATION:
(C) IDENTIFICATION METHOD:
(D) OTHER INFORMATION:Translation product of SEQ ID NO:5

(xi) SEQUENCE DESCRIPTION: SEQ ID NO: 6:

```
Met Ser Gly Leu Leu Ile Ala Ala Pro Ala Ser Gly Ser Gly Lys Thr
1               5                   10                  15

Thr Val Thr Leu Gly Leu Met Arg Ala Leu Lys Arg Arg Gly Val Ala
            20                  25                  30

Ile Ala Pro Gly Lys Ala Gly Pro Asp Tyr Ile Asp Pro Ala Phe His
        35                  40                  45

Ala Ala Ala Thr Gly Glu Pro Cys Phe Asn Tyr Asp Pro Trp Ala Met
    50                  55                  60

Arg Pro Glu Leu Leu Leu Ala Asn Ala Ser His Val Ala Ser Gly Gly
65                  70                  75                  80

Arg Thr Leu Ile Val Glu Ala Met Met Gly Leu His Asp Gly Ala Ala
                85                  90                  95

Asp Gly Ser Gly Thr Pro Ala Asp Leu Ala Ala Thr Leu Asn Leu Ala
            100                 105                 110

Val Ile Leu Val Val Asp Cys Ala Arg Met Ser Gln Ser Val Ala Ala
        115                 120                 125

Leu Val Arg Gly Tyr Ala Asp His Arg Asp Asp Ile Arg Val Val Gly
    130                 135                 140

Val Ile Leu Asn Lys Val Gly Ser Asp Arg His Glu Met Met Leu Arg
145                 150                 155                 160

Asp Ala Leu Gly Lys Val Arg Met Pro Val Phe Gly Val Leu Arg Gln
```

-continued

```
                165                 170                 175

Asp Ser Ala Leu Gln Leu Pro Glu Arg His Leu Gly Leu Val Gln Ala
            180                 185                 190

Gly Glu His Ser Ala Leu Glu Gly Phe Ile Glu Ala Ala Ala Ala Arg
        195                 200                 205

Val Glu Ala Ala Cys Asp Leu Asp Ala Ile Arg Leu Ile Ala Thr Ile
    210                 215                 220

Phe Pro Gln Val Pro Ala Ala Ala Asp Ala Glu Arg Leu Arg Pro Leu
225                 230                 235                 240

Gly Gln Arg Ile Ala Val Ala Arg Asp Ile Ala Phe Ala Phe Cys Tyr
                245                 250                 255

Glu His Leu Leu Tyr Gly Trp Arg Gln Gly Gly Ala Glu Ile Ser Phe
            260                 265                 270

Phe Ser Pro Leu Ala Asp Glu Gly Pro Asp Ala Ala Ala Asp Ala Val
        275                 280                 285

Tyr Leu Pro Gly Gly Tyr Pro Glu Leu His Ala Gly Gln Leu Ser Ala
    290                 295                 300

Ala Ala Arg Phe Arg Ser Gly Met His Ser Ala Ala Glu Arg Gly Ala
305                 310                 315                 320

Arg Ile Phe Gly Glu Cys Gly Gly Tyr Met Val Leu Gly Glu Gly Leu
                325                 330                 335

Val Ala Ala Asp Gly Thr Arg Tyr Asp Met Leu Gly Leu Leu Pro Leu
            340                 345                 350

Val Thr Ser Phe Ala Glu Arg Arg Arg His Leu Gly Tyr Arg Arg Val
        355                 360                 365

Val Pro Val Asp Asn Ala Phe Phe Asp Gly Pro Met Thr Ala His Glu
    370                 375                 380

Phe His Tyr Ala Thr Ile Val Ala Glu Gly Ala Ala Asp Arg Leu Phe
385                 390                 395                 400

Ala Val Ser Asp Ala Ala Gly Glu Asp Leu Gly Gln Ala Gly Leu Arg
                405                 410                 415

Arg Gly Pro Val Ala Gly Ser Phe Met His Leu Ile Asp Val Ala Gly
            420                 425                 430

Ala Ala
```

(2) INFORMATION FOR SEQ ID NO: 7:

(i) SEQUENCE CHARACTERISTICS:
- (A) LENGTH: 1002 base pairs
- (B) TYPE: Nucleic Acid
- (C) STRANDEDNESS: Double
- (D) TOPOLOGY: Unknown (ii) MOLECULE TYPE: cDNA (iii) HYPOTHETICAL: No (iv) ORIGINAL SOURCE:
- (A) ORGANISM: Pseudomonas denitrificans
- (B) STRAIN:
- (C) INDIVIDUAL ISOLATE:
- (D) DEVELOPMENTAL STAGE:
- (E) HAPLOTYPE:
- (F) TISSUE TYPE:
- (G) CELL TYPE:
- (H) CELL LINE:
- (I) ORGANELLE:

(ix) FEATURE:
- (A) NAME/KEY: cobC
- (B) LOCATION: 3281-4279 bp of SEQ ID NO: 1

-continued (C) IDENTIFICATION METHOD:
(D) OTHER INFORMATION:

(xi) SEQUENCE DESCRIPTION: SEQ ID NO: 7:

```
ATGAGCGCAC CGATCGTTCA TGGTGGCGGC ATCACCGAGG CCGCAGCGCG CTATGGCGGC     60

CGGCCTGAAG ACTGGCTCGA TCTGTCGACC GGCATCAATC CATGCCCCGT CGCCTTGCCC    120

GCGGTCCCTG AGCGCGCCTG GCACCGGCTG CCGGATCGGC AGACGGTAGA TGATGCGCGG    180

AGCGCCGCCG CCGACTACTA CCGCACCAAC GGCGTGCTGC CTTTGCCGGT GCCGGGCACC    240

CAGTCGGTGA TCCAGCTCCT GCCACGTCTT GCTCCGGCCA ACAGGCACGT CGCGATTTTC    300

GGGCCGACCT ATGGCGAGTA TGCCCGCGTG CTTGAAGCGG CCGGCTTTGC TGTCGATCGC    360

GTCGCGGATG CCGACGCGCT CACGGCCGAA CATGGGCTTG TCATCGTCGT CAACCCCAAC    420

AACCCGACCG GCCGCGCCTT GGCGCCGGCG GAGCTTCTGG CGATCGCCGC AAGGCAGAAG    480

GCGAGCGGCG GACTGCTGCT GGTCGATGAG GCCTTCGGCG ATCTTGAGCC GCAACTGAGT    540

GTCGCTGGTC ACGCGTCAGG GCAAGGCAAC CTCATCGTCT TCCGCTCCTT CGGCAAGTTC    600

TTCGGCCTTG CGGGCCTGCG CCTCGGCTTC GTCGTTGCGA CCGAGCCAGT GCTTGCATCC    660

TTTGCCGATT GGCTCGGTCC CTGGGCTGTC TCCGGCCCGG CGTTGACGAT CTCGAAAGCG    720

CTGATGCAGG GCGATACGAA GGCGATCGCG GCGGGCATCC TCGAGCGTCG CGCCGGCCTC    780

GATGCGGCTC TCGATGGGGC AGGGCTCAAC CGTATCGGCG GCACGGGGCT ATTCGTGCTG    840

GTCGAGCATC CCAGGGCAGC TCTGCTGCAG GAGCGGCTCT GCGAGGCCCA TATTCTCACG    900

CGCAAGTTCG ACTATGCCCC GACCTGGCTC AGGGTCGGTC TTGCGCCTGA CGCGGCTGGT    960

GACCGACGGC TGGCGGACGC GCTTGCCCGC ATGGAGCTCT GA                      1002
```

(2) INFORMATION FOR SEQ ID NO: 8:

(i) SEQUENCE CHARACTERISTICS:
(A) LENGTH: 333 amino acids
(B) TYPE: Amino Acid
(C) STRANDEDNESS:
(D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBC
(B) LOCATION:
(C) IDENTIFICATION METHOD:
(D) OTHER INFORMATION: Translation product of SEQ ID NO:7

(xi) SEQUENCE DESCRIPTION: SEQ ID NO: 8:

```
Met Ser Ala Pro Ile Val His Gly Gly Gly Ile Thr Glu Ala Ala Ala
1               5                   10                  15

Arg Tyr Gly Gly Arg Pro Glu Asp Trp Leu Asp Leu Ser Thr Gly Ile
            20                  25                  30

Asn Pro Cys Pro Val Ala Leu Pro Ala Val Pro Glu Arg Ala Trp His
        35                  40                  45
```

-continued

```
Arg Leu Pro Asp Arg Gln Thr Val Asp Asp Ala Arg Ser Ala Ala Ala
    50                  55                  60

Asp Tyr Tyr Arg Thr Asn Gly Val Leu Pro Leu Pro Val Pro Gly Thr
65                  70                  75                  80

Gln Ser Val Ile Gln Leu Leu Pro Arg Leu Ala Pro Ala Asn Arg His
                85                  90                  95

Val Ala Ile Phe Gly Pro Thr Tyr Gly Glu Tyr Ala Arg Val Leu Glu
            100                 105                 110

Ala Ala Gly Phe Ala Val Asp Arg Val Ala Asp Ala Asp Ala Leu Thr
        115                 120                 125

Ala Glu His Gly Leu Val Ile Val Val Asn Pro Asn Asn Pro Thr Gly
    130                 135                 140

Arg Ala Leu Ala Pro Ala Glu Leu Leu Ala Ile Ala Ala Arg Gln Lys
145                 150                 155                 160

Ala Ser Gly Gly Leu Leu Leu Val Asp Glu Ala Phe Gly Asp Leu Glu
                165                 170                 175

Pro Gln Leu Ser Val Ala Gly His Ala Ser Gly Gln Gly Asn Leu Ile
            180                 185                 190

Val Phe Arg Ser Phe Gly Lys Phe Phe Gly Leu Ala Gly Leu Arg Leu
        195                 200                 205

Gly Phe Val Val Ala Thr Glu Pro Val Leu Ala Ser Phe Ala Asp Trp
    210                 215                 220

Leu Gly Pro Trp Ala Val Ser Gly Pro Ala Leu Thr Ile Ser Lys Ala
225                 230                 235                 240

Leu Met Gln Gly Asp Thr Lys Ala Ile Ala Ala Gly Ile Leu Glu Arg
                245                 250                 255

Arg Ala Gly Leu Asp Ala Ala Leu Asp Gly Ala Gly Leu Asn Arg Ile
            260                 265                 270

Gly Gly Thr Gly Leu Phe Val Leu Val Glu His Pro Arg Ala Ala Leu
        275                 280                 285

Leu Gln Glu Arg Leu Cys Glu Ala His Ile Leu Thr Arg Lys Phe Asp
    290                 295                 300

Tyr Ala Pro Thr Trp Leu Arg Val Gly Leu Ala Pro Asp Ala Ala Gly
305                 310                 315                 320

Asp Arg Arg Leu Ala Asp Ala Leu Ala Arg Met Glu Leu
                325                 330
```

(2) INFORMATION FOR SEQ ID NO: 9:

(i) SEQUENCE CHARACTERISTICS:
(A) LENGTH: 972 base pairs
(B) TYPE: Nucleic Acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

-continued (ix) FEATURE:
(A) NAME/KEY: cobD
(B) LOCATION: 4284-5252 bp of SEQ ID NO: 1
(C) IDENTIFICATION METHOD:
(D) OTHER INFORMATION:

(xi) SEQUENCE DESCRIPTION: SEQ ID NO: 9:

```
GTGTCGGAGA CGATCCTGCT CATTCTCGCG CTGGCGCTGG TGATCGACCG CGTTGTCGGC     60

GATCCGGACT GGCTCTGGGC GCGCGTGCCG CATCCGGTCG TGTTTTTCGG CAAGGCCATC    120

GGCTTTTTCG ACGCGCGGCT GAACCGGGAG GACCTCGAGG ATAGCGCGCG CAAATTTCGT    180

GGCGTCGTCG CGATCCTTTT GTTGCTTGGC ATCAGCGCCT GGTTCGGCCA TCTGCTGCAT    240

CGCCTGTTCG CCGTCCTCGG ACCGCTCGGC TTTCTGCTCG AGGCGGTTCT GGTCGCGGTC    300

TTCCTGGCAC AGAAGAGCCT CGCCGATCAC GTGCGTCGCG TGGCCGGGGG CTTGCGACAG    360

GGCGGGCTGG AAGGCGGGCG TGCCGCCGTG TCGATGATCG TTGGTCGCGA TCCAAAGACG    420

CTCGACGAGC CGGCGGTCTG CCGTGCCGCG ATCGAAAGCC TTGCCGAGAA TTTCTCCGAC    480

GGCGTCGTGG CGCCGGCCTT CTGGTACGCG GTTGCCGGCC TGCCGGGGCT TCTTGCCTAC    540

AAGATGCTGA ACACCGCCGA TTCGATGATC GGCCACAAGT CGCCGAAATA TCTGCACTTC    600

GGCTGGGCCT CGGCCCGACT CGACGATCTC GCCAACCTGC CGGCAGCGAG GCTCTCGATC    660

CTTTTGATCT CAGCCGGTGC GCTGATCCAT CGTGGCGCCA GCGCCGCCAA GGATGCGCTG    720

ACCGTGGCCC TTCGCGACCA TGGCCTGCAC CGCTCGCCGA ACTCCGGCTG GCCGGAAGCG    780

GCCATGGCCG GCGCGCTCGA TCTGCAGCTT GCCGGTCCGC GGATCTATGG CGGCGTCAAG    840

GTCAGCGAAC CTATGATCAA CGGTCCGGGC CGAGCGGTTG CAACAAGCGA AGACATCGAC    900

GCCGGTATTG CTGTATTTTA TGGCGCCTGT ACGGTCATGG CCGGGTTTGT TCTTGCAATC    960

GCAATGATTT GA                                                        972
```

(2) INFORMATION FOR SEQ ID NO: 10:

(i) SEQUENCE CHARACTERISTICS:
(A) LENGTH: 323 amino acids
(B) TYPE: Amino Acid
(C) STRANDEDNESS:
(D) TOPOLOGY: Linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBD
(B) LOCATION:
(C) IDENTIFICATION METHOD:
(D) OTHER INFORMATION: Translation product of SEQ ID NO:9

(xi) SEQUENCE DESCRIPTION: SEQ ID NO: 10:

```
Met Ser Glu Thr Ile Leu Leu Ile Leu Ala Leu Ala Leu Val Ile Asp
1               5                   10                  15

Arg Val Val Gly Asp Pro Asp Trp Leu Trp Ala Arg Val Pro His Pro
            20                  25                  30
```

-continued

```
Val Val Phe Phe Gly Lys Ala Ile Gly Phe Phe Asp Ala Arg Leu Asn
        35                  40                  45

Arg Glu Asp Leu Glu Asp Ser Ala Arg Lys Phe Arg Gly Val Val Ala
    50                  55                  60

Ile Leu Leu Leu Leu Gly Ile Ser Ala Trp Phe Gly His Leu Leu His
65                  70                  75                  80

Arg Leu Phe Ala Val Leu Gly Pro Leu Gly Phe Leu Leu Glu Ala Val
                85                  90                  95

Leu Val Ala Val Phe Leu Ala Gln Lys Ser Leu Ala Asp His Val Arg
            100                 105                 110

Arg Val Ala Gly Gly Leu Arg Gln Gly Gly Leu Glu Gly Gly Arg Ala
        115                 120                 125

Ala Val Ser Met Ile Val Gly Arg Asp Pro Lys Thr Leu Asp Glu Pro
    130                 135                 140

Ala Val Cys Arg Ala Ala Ile Glu Ser Leu Ala Glu Asn Phe Ser Asp
145                 150                 155                 160

Gly Val Val Ala Pro Ala Phe Trp Tyr Ala Val Ala Gly Leu Pro Gly
                165                 170                 175

Leu Leu Ala Tyr Lys Met Leu Asn Thr Ala Asp Ser Met Ile Gly His
            180                 185                 190

Lys Ser Pro Lys Tyr Leu His Phe Gly Trp Ala Ser Ala Arg Leu Asp
        195                 200                 205

Asp Leu Ala Asn Leu Pro Ala Ala Arg Leu Ser Ile Leu Leu Ile Ser
    210                 215                 220

Ala Gly Ala Leu Ile His Arg Gly Ala Ser Ala Ala Lys Asp Ala Leu
225                 230                 235                 240

Thr Val Ala Leu Arg Asp His Gly Leu His Arg Ser Pro Asn Ser Gly
                245                 250                 255

Trp Pro Glu Ala Ala Met Ala Gly Ala Leu Asp Leu Gln Leu Ala Gly
            260                 265                 270

Pro Arg Ile Tyr Gly Gly Val Lys Val Ser Glu Pro Met Ile Asn Gly
        275                 280                 285

Pro Gly Arg Ala Val Ala Thr Ser Glu Asp Ile Asp Ala Gly Ile Ala
    290                 295                 300

Val Phe Tyr Gly Ala Cys Thr Val Met Ala Gly Phe Val Leu Ala Ile
305                 310                 315                 320

Ala Met Ile
```

(2) INFORMATION FOR SEQ ID NO: 11:

(i) SEQUENCE CHARACTERISTICS:
(A) LENGTH: 465 base pairs
(B) TYPE: Nucleic Acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:

-continued (I) ORGANELLE:

(ix) FEATURE:
(A) NAME/KEY: cobE
(B) LOCATION: 549-1011 bp of SEQ ID NO: 1
(C) IDENTIFICATION METHOD:
(D) OTHER INFORMATION:

(xi) SEQUENCE DESCRIPTION: SEQ ID NO: 11:

```
ATGCCATCGG GCCAACACTC TGCACAGACG ACGAAAGCAG GAGCCGGGCT GGTGCTCGGG     60

CTCGGCTGCG AGCGTCGCAC GCCGGCCGAA GAGGTGATCG CCCTTGCCGA GCGTGCGCTT    120

GCCGATGCCG GTGTTGCGCC CGGCGATCTG CGGCTGGTCG CCTCGCTCGA TGCTCGCGCC    180

GAGGAGCCGG CGATCCTGGC GGCCGCTCAG CATTTCGCGG TTCCGGCCGC GTTCTACGAT    240

GCCGCCACGC TCGAAGCCGA AGCTTCCCGG CTCGCCAACC CGTCCGAGAT CGTCTTTGCC    300

TACACGGGTT GTCATGGCGT TGCCGAGGGT GCAGCGCTCG TCGGCGCCGG TCGCGAAGCC    360

GTGCTGATTG TGCAGAAGAT CGTCTCCGCC CATGCGACGG CCGCACTTGC CGGGCCGGCG    420

ACCTTGCGCG CCGAAAAGCG CATCCAGGCG GCGGAGGCTG TCTGA                    465
```

(2) INFORMATION FOR SEQ ID NO: 12:

(i) SEQUENCE CHARACTERISTICS:
(A) LENGTH: 154 amino acids
(B) TYPE: Amino Acid
(C) STRANDEDNESS:
(D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBE
(B) LOCATION:
(C) IDENTIFICATION METHOD:
(D) OTHER INFORMATION: Translation product of SEQ ID NO:11

(xi) SEQUENCE DESCRIPTION: SEQ ID NO: 12:

```
Met Pro Ser Gly Gln His Ser Ala Gln Thr Thr Lys Ala Gly Ala Gly
1               5                   10                  15

Leu Val Leu Gly Leu Gly Cys Glu Arg Arg Thr Pro Ala Glu Glu Val
            20                  25                  30

Ile Ala Leu Ala Glu Arg Ala Leu Ala Asp Ala Gly Val Ala Pro Gly
        35                  40                  45

Asp Leu Arg Leu Val Ala Ser Leu Asp Ala Arg Ala Glu Glu Pro Ala
    50                  55                  60

Ile Leu Ala Ala Ala Gln His Phe Ala Val Pro Ala Ala Phe Tyr Asp
65                  70                  75                  80

Ala Ala Thr Leu Glu Ala Glu Ala Ser Arg Leu Ala Asn Pro Ser Glu
                85                  90                  95

Ile Val Phe Ala Tyr Thr Gly Cys His Gly Val Ala Glu Gly Ala Ala
            100                 105                 110
```

-continued

```
Leu Val Gly Ala Gly Arg Glu Ala Val Leu Ile Val Gln Lys Ile Val
        115                 120                 125

Ser Ala His Ala Thr Ala Ala Leu Ala Gly Pro Ala Thr Leu Arg Ala
    130                 135                 140

Glu Lys Arg Ile Gln Ala Ala Glu Ala Val
145                 150
```

(2) INFORMATION FOR SEQ ID NO: 13:

(i) SEQUENCE CHARACTERISTICS:
(A) LENGTH: 786 base pairs
(B) TYPE: Nucleic Acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobF
(B) LOCATION: 736-1521 bp of SEQ ID NO: 2
(C) IDENTIFICATION METHOD:
(D) OTHER INFORMATION:

(xi) SEQUENCE DESCRIPTION: SEQ ID NO: 13:

```
ATGGCGGAGG CGGGCATGCG CAAAATTCTG ATCATCGGCA TCGGTTCGGG CAATCCCGAA     60

CACATGACCG TGCAGGCGAT CAACGCGCTG AACTGCGCCG ACGTGCTCTT TATCCCGACC    120

AAGGGAGCGA AGAAGACCGA GCTTGCCGAA GTGCGCCGCG ACATCTGCGC CCGCTACGTC    180

ACGCGCAAGG ACAGCCGCAC CGTCGAGTTC GCGGTGCCCG TGCGGCGCAC CGAAGGCGTC    240

AGCTATGACG GCAGCGTCGA TGACTGGCAC GCCCAGATCG CTGGGATTTA CGAAGCGCTT    300

CTATCGAAGG AGTTGGGCGA AGAGGGAACT GGCGCGTTTC TCGTCTGGGG CGACCCGATG    360

CTCTATGACA GCACCATTCG CATCGTCGAG CGGGTCAAGG CACGCGGTGA GGTCGCCTTC    420

GCCTACGACG TCATTCCCGG GATCACCAGT CTGCAGGCGC TTTGCGCCAG CCACCGCATT    480

CCGCTGAACC TCGTCGGCAA GCCGGTGGAG ATCACCACGG GGCGTCGGCT GCACGAAAGC    540

TTTCCCGAGA AGAGCCAGAC CTCGGTCGTC ATGCTCGATG GCGAACAGGC GTTTCAGCGG    600

GTCGAGGACC CGGAGGCGGA GATCTATTGG GGCGCCTATC TCGGCACGCG GGATGAGATC    660

GTCATTTCCG GCCGCGTGGC TGAGGTGAAG GACCGGATCC TTGAAACGCG GGCGGCGGCG    720

CGCGCGAAGA TGGGATGGAT CATGGACATC TATCTCCTGC GCAAGGGCGC CGACTTCGAC    780

GAGTGA                                                               786
```

(2) INFORMATION FOR SEQ ID NO: 14:

(i) SEQUENCE CHARACTERISTICS:
(A) LENGTH: 261 amino acids
(B) TYPE: Amino Acid
(C) STRANDEDNESS:
(D) TOPOLOGY: linear (ii) MOLECULE TYPE: protein -continued (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBF
(B) LOCATION:
(C) IDENTIFICATION METHOD:
(D) OTHER INFORMATION: Translation product of SEQ ID NO:13

(xi) SEQUENCE DESCRIPTION: SEQ ID NO: 14:

```
Met Ala Glu Ala Gly Met Arg Lys Ile Leu Ile Ile Gly Ile Gly Ser
1               5                   10                  15

Gly Asn Pro Glu His Met Thr Val Gln Ala Ile Asn Ala Leu Asn Cys
            20                  25                  30

Ala Asp Val Leu Phe Ile Pro Thr Lys Gly Ala Lys Lys Thr Glu Leu
        35                  40                  45

Ala Glu Val Arg Arg Asp Ile Cys Ala Arg Tyr Val Thr Arg Lys Asp
    50                  55                  60

Ser Arg Thr Val Glu Phe Ala Val Pro Val Arg Arg Thr Glu Gly Val
65                  70                  75                  80

Ser Tyr Asp Gly Ser Val Asp Asp Trp His Ala Gln Ile Ala Gly Ile
                85                  90                  95

Tyr Glu Ala Leu Leu Ser Lys Glu Leu Gly Glu Glu Gly Thr Gly Ala
            100                 105                 110

Phe Leu Val Trp Gly Asp Pro Met Leu Tyr Asp Ser Thr Ile Arg Ile
        115                 120                 125

Val Glu Arg Val Lys Ala Arg Gly Glu Val Ala Phe Ala Tyr Asp Val
    130                 135                 140

Ile Pro Gly Ile Thr Ser Leu Gln Ala Leu Cys Ala Ser His Arg Ile
145                 150                 155                 160

Pro Leu Asn Leu Val Gly Lys Pro Val Glu Ile Thr Thr Gly Arg Arg
                165                 170                 175

Leu His Glu Ser Phe Pro Glu Lys Ser Gln Thr Ser Val Val Met Leu
            180                 185                 190

Asp Gly Glu Gln Ala Phe Gln Arg Val Glu Asp Pro Glu Ala Glu Ile
        195                 200                 205

Tyr Trp Gly Ala Tyr Leu Gly Thr Arg Asp Glu Ile Val Ile Ser Gly
    210                 215                 220

Arg Val Ala Glu Val Lys Asp Arg Ile Leu Glu Thr Arg Ala Ala Ala
225                 230                 235                 240

Arg Ala Lys Met Gly Trp Ile Met Asp Ile Tyr Leu Leu Arg Lys Gly
                245                 250                 255

Ala Asp Phe Asp Glu
            260
```

(2) INFORMATION FOR SEQ ID NO: 15:

(i) SEQUENCE CHARACTERISTICS:
(A) LENGTH: 1380 base pairs
(B) TYPE: Nucleic Acid -continued (C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobG
(B) LOCATION: 1620-2999 bp of SEQ ID NO: 2
(C) IDENTIFICATION METHOD:
(D) OTHER INFORMATION:

(xi) SEQUENCE DESCRIPTION: SEQ ID NO: 15:

ATGACGGATT TGATGACCAG CTGCGCCCTT CCATTGACCG GAGATGCCGG CACCGTCGCT 60

TCGATGCGCC GCGGCGCCTG CCCGTCCTTG GCAGAGCCGA TGCAGACCGG CGACGGCCTG 120

CTCGTGAGGG TGAGGCCAAC GGATGACAGC CTGACGCTGC CGAAGGTCAT TGCCCTTGCC 180

ACGGCTGCCG AGCGCTTCGG CAATGGCATC ATCGAGATTA CCGCGCGCGG AAACCTGCAG 240

CTTCGCGGCC TGAGCGCGGC TTCGGTGCCA AGGCTGGCGC AGGCGATCGG CGATGCGGAG 300

ATCGCCATTG CCGAGGGGCT CGCGATCGAG GTGCCGCCCC TGGCCGGCAT CGACCCGGAC 360

GAGATCGCCG ATCCGCGGCC GATTGCCACT GAGCTTCGTG AAGCGTTGGA TGTGCGCCAG 420

GTGCCGTTGA AGCTTGCACC CAAATTATCC GTCGTCATCG ATAGCGGTGG CCGGTTTGGT 480

CTCGGCGCTG TCGTCGCCGA CATTCGCCTT CAGGCGGTTT CGACTGTCGC GGGGGTGGCC 540

TGGGTGCTGT CGCTTGGCGG CACGTCAACG AAGGCATCGA GCGTCGGGAC GTTGGCCGGC 600

AACGCGGTCG TGCCGGCCCT GATCACCATT CTCGAGAAAC TGGCGAGCCT GGGCACGACG 660

ATGCGCGGGC GCGATCTGGA CCCGTCGGAA ATCCGCGCGC TCTGTCGCTG TGAGACATCG 720

TCCGAACGCC CGGCCGCTCC GCGTTCGGCC GCAATACCCG GCATTCATGC GCTGGGTAAC 780

GCCGACACCG TTCTCGGCCT CGGTCTGGCC TTTGCTCAGG TGGAGGCCGC CGCGCTGGCA 840

TCCTACCTGC ATCAGGTCCA GGCGCTTGGC GCCAATGCGA TCCGGCTTGC GCCCGGGCAC 900

GCCTTCTTCG TCCTCGGCCT TTGCCCCGAG ACCGCGGCTG TGGCGCAGAG CCTGGCAGCG 960

TCACACGGTT TTCGCATTGC CGAGCAGGAT CCGCGCAATG CGATCGCCAC CTGCGCCGGC 1020

AGCAAGGGTT GCGCCTCGGC GTGGATGGAA ACCAAGGGCA TGGCCGAGCG CCTCGTCGAG 1080

ACGGCGCCGG AATTGCTCGA CGGGTCGCTC ACCGTGCATC TCTCCGGCTG CGCCAAGGGC 1140

TGCGCCCGGC CGAAGCCGTC CGAACTGACG CTTGTCGGTG CGCCATCAGG ATACGGGCTT 1200

GTCGTAAATG GGGCTGCCAA TGGCTTGCCA AGCGCCTACA CCGATGAGAA TGGAATGGGA 1260

TCCGCCCTTG CCCGGCTCGG CCGGCTGGTG CGGCAAAACA AAGACGCTGG CGAATCGGCG 1320

CAGTCCTGTC TTACACGGCT CGGAGCTGCG CGCGTCTCGG CAGCGTTCGA ACAGGGATAG 1380

(2) INFORMATION FOR SEQ ID NO: 16:

(i) SEQUENCE CHARACTERISTICS:
(A) LENGTH: 459 amino acids
(B) TYPE: Amino Acid
(C) STRANDEDNESS:

-continued (D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBG
(B) LOCATION:
(C) IDENTIFICATION METHOD:
(D) OTHER INFORMATION: Translation product of SEQ ID NO:15

(xi) SEQUENCE DESCRIPTION: SEQ ID NO: 16:

```
Met Thr Asp Leu Met Thr Ser Cys Ala Leu Pro Leu Thr Gly Asp Ala
1               5                   10                  15

Gly Thr Val Ala Ser Met Arg Arg Gly Ala Cys Pro Ser Leu Ala Glu
            20                  25                  30

Pro Met Gln Thr Gly Asp Gly Leu Leu Val Arg Val Arg Pro Thr Asp
        35                  40                  45

Asp Ser Leu Thr Leu Pro Lys Val Ile Ala Leu Ala Thr Ala Ala Glu
    50                  55                  60

Arg Phe Gly Asn Gly Ile Ile Glu Ile Thr Ala Arg Gly Asn Leu Gln
65                  70                  75                  80

Leu Arg Gly Leu Ser Ala Ala Ser Val Pro Arg Leu Ala Gln Ala Ile
                85                  90                  95

Gly Asp Ala Glu Ile Ala Ile Ala Glu Gly Leu Ala Ile Glu Val Pro
            100                 105                 110

Pro Leu Ala Gly Ile Asp Pro Asp Glu Ile Ala Asp Pro Arg Pro Ile
        115                 120                 125

Ala Thr Glu Leu Arg Glu Ala Leu Asp Val Arg Gln Val Pro Leu Lys
    130                 135                 140

Leu Ala Pro Lys Leu Ser Val Val Ile Asp Ser Gly Gly Arg Phe Gly
145                 150                 155                 160

Leu Gly Ala Val Val Ala Asp Ile Arg Leu Gln Ala Val Ser Thr Val
                165                 170                 175

Ala Gly Val Ala Trp Val Leu Ser Leu Gly Gly Thr Ser Thr Lys Ala
            180                 185                 190

Ser Ser Val Gly Thr Leu Ala Gly Asn Ala Val Val Pro Ala Leu Ile
        195                 200                 205

Thr Ile Leu Glu Lys Leu Ala Ser Leu Gly Thr Thr Met Arg Gly Arg
    210                 215                 220

Asp Leu Asp Pro Ser Glu Ile Arg Ala Leu Cys Arg Cys Glu Thr Ser
225                 230                 235                 240

Ser Glu Arg Pro Ala Ala Pro Arg Ser Ala Ala Ile Pro Gly Ile His
                245                 250                 255

Ala Leu Gly Asn Ala Asp Thr Val Leu Gly Leu Gly Leu Ala Phe Ala
            260                 265                 270

Gln Val Glu Ala Ala Ala Leu Ala Ser Tyr Leu His Gln Val Gln Ala
        275                 280                 285
```

-continued

```
Leu Gly Ala Asn Ala Ile Arg Leu Ala Pro Gly His Ala Phe Phe Val
    290                 295                 300

Leu Gly Leu Cys Pro Glu Thr Ala Ala Val Ala Gln Ser Leu Ala Ala
305                 310                 315                 320

Ser His Gly Phe Arg Ile Ala Glu Gln Asp Pro Arg Asn Ala Ile Ala
                325                 330                 335

Thr Cys Ala Gly Ser Lys Gly Cys Ala Ser Ala Trp Met Glu Thr Lys
            340                 345                 350

Gly Met Ala Glu Arg Leu Val Glu Thr Ala Pro Glu Leu Leu Asp Gly
        355                 360                 365

Ser Leu Thr Val His Leu Ser Gly Cys Ala Lys Gly Cys Ala Arg Pro
    370                 375                 380

Lys Pro Ser Glu Leu Thr Leu Val Gly Ala Pro Ser Gly Tyr Gly Leu
385                 390                 395                 400

Val Val Asn Gly Ala Ala Asn Gly Leu Pro Ser Ala Tyr Thr Asp Glu
                405                 410                 415

Asn Gly Met Gly Ser Ala Leu Ala Arg Leu Gly Arg Leu Val Arg Gln
            420                 425                 430

Asn Lys Asp Ala Gly Glu Ser Ala Gln Ser Cys Leu Thr Arg Leu Gly
        435                 440                 445

Ala Ala Arg Val Ser Ala Ala Phe Glu Gln Gly
    450                 455
```

(2) INFORMATION FOR SEQ ID NO: 17:

(i) SEQUENCE CHARACTERISTICS:
(A) LENGTH: 633 base pairs
(B) TYPE: Nucleic Acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobH
(B) LOCATION: 3002-3634 bp of SEQ ID NO: 2
(C) IDENTIFICATION METHOD:
(D) OTHER INFORMATION:

(xi) SEQUENCE DESCRIPTION: SEQ ID NO: 17:

```
ATGCCTGAGT ATGATTACAT TCGCGATGGC AACGCCATCT ACGAGCGTTC CTTCGCCATC     60

ATCCGCGCCG AGGCCGATCT GTCGCGCTTC TCCGAAGAGG AAGCGGATCT GGCTGTGCGC    120

ATGGTGCACG CCTGCGGTTC CGTCGAGGCG ACCAGGCAGT TCGTGTTTTC TCCCGATTTC    180

GTAAGCTCGG CCCGTGCGGC GCTGAAAGCC GGTGCGCCGA TCCTCTGCGA TGCCGAGATG    240

GTTGCGCACG GTGTCACCCG CGCCCGTCTG CCGGCCGGCA ACGAGGTGAT CTGCACGCTG    300

CGCGATCCTC GCACGCCCGC ACTTGCGGCC GAGATCGGCA ACACCCGCTC CGCCGCAGCC    360

CTGAAGCTCT GGAGCGAGCG GCTGGCCGGT TCGGTGGTCG CGATCGGCAA CGCGCCGACG    420
```

-continued

```
GCGTTGTTCT TCCTCTTGGA AATGCTGCGC GACGGCGCGC CGAAGCCGGC GGCAATCCTC    480

GGCATGCCCG TCGGTTTCGT CGGTGCGGCG GAATCGAAGG ATGCGCTGGC CGAGAACTCC    540

TATGGCGTTC CCTTCGCCAT CGTGCGCGGC CGCCTCGGCG GGAGTGCCAT GACGGCGGCA    600

GCGCTTAACT CGCTCGCGAG GCCGGGCCTG TGA                                 633
```

(2) INFORMATION FOR SEQ ID NO: 18:

(i) SEQUENCE CHARACTERISTICS:
(A) LENGTH: 210 amino acids
(B) TYPE: Amino Acid
(C) STRANDEDNESS:
(D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBH
(B) LOCATION:
(C) IDENTIFICATION METHOD:
(D) OTHER INFORMATION: Translation product of SEQ ID NO:17

(xi) SEQUENCE DESCRIPTION: SEQ ID NO: 18:

```
Met Pro Glu Tyr Asp Tyr Ile Arg Asp Gly Asn Ala Ile Tyr Glu Arg
1               5                   10                  15

Ser Phe Ala Ile Ile Arg Ala Glu Ala Asp Leu Ser Arg Phe Ser Glu
            20                  25                  30

Glu Glu Ala Asp Leu Ala Val Arg Met Val His Ala Cys Gly Ser Val
        35                  40                  45

Glu Ala Thr Arg Gln Phe Val Phe Ser Pro Asp Phe Val Ser Ser Ala
    50                  55                  60

Arg Ala Ala Leu Lys Ala Gly Ala Pro Ile Leu Cys Asp Ala Glu Met
65                  70                  75                  80

Val Ala His Gly Val Thr Arg Ala Arg Leu Pro Ala Gly Asn Glu Val
                85                  90                  95

Ile Cys Thr Leu Arg Asp Pro Arg Thr Pro Ala Leu Ala Ala Glu Ile
            100                 105                 110

Gly Asn Thr Arg Ser Ala Ala Ala Leu Lys Leu Trp Ser Glu Arg Leu
        115                 120                 125

Ala Gly Ser Val Val Ala Ile Gly Asn Ala Pro Thr Ala Leu Phe Phe
    130                 135                 140

Leu Leu Glu Met Leu Arg Asp Gly Ala Pro Lys Pro Ala Ala Ile Leu
145                 150                 155                 160

Gly Met Pro Val Gly Phe Val Gly Ala Ala Glu Ser Lys Asp Ala Leu
                165                 170                 175

Ala Glu Asn Ser Tyr Gly Val Pro Phe Ala Ile Val Arg Gly Arg Leu
            180                 185                 190

Gly Gly Ser Ala Met Thr Ala Ala Ala Leu Asn Ser Leu Ala Arg Pro
        195                 200                 205
```

-continued

Gly Leu
210

(2) INFORMATION FOR SEQ ID NO: 19:

(i) SEQUENCE CHARACTERISTICS:
(A) LENGTH: 738 base pairs
(B) TYPE: Nucleic Acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobI
(B) LOCATION: 3631-4368 bp of SEQ ID NO: 2
(C) IDENTIFICATION METHOD:
(D) OTHER INFORMATION:

(xi) SEQUENCE DESCRIPTION: SEQ ID NO: 19:

GTGAGCGGCG TCGGCGTGGG GCGCCTGATC GGTGTTGGGA CCGGCCCCGG TGATCCGGAA 60

CTTTTGACGG TCAAGGCGGT GAAGGCGCTC GGGCAAGCCG ATGTGCTTGC CTATTTCGCC 120

AAGGCCGGGC GAAGCGGTAA CGGCCGCGCG GTGGTCGAGG GTCTGCTGAA GCCCGATCTT 180

GTCGAGCTGC CGCTATACTA TCCGGTGACG ACCGAAATCG ACAAGGACGA TGGCGCCTAC 240

AAGACCCAGA TCACCGACTT CTACAATGCG TCGGCCGAAG CGGTAGCGGC GCATCTTGCC 300

GCCGGGCGCA CGGTCGCCGT GCTCAGTGAA GGCGACCCGC TGTTCTATGG TTCCTACATG 360

CATCTGCATG TGCGGCTCGC CAATCGTTTC CCGGTCGAGG TGATCCCCGG CATTACCGCC 420

ATGTCCGGCT GTTGGTCGCT TGCCGGCCTG CCGCTGGTGC AGGGCGACGA CGTGCTCTCG 480

GTGCTTCCGG GCACCATGGC CGAGGCCGAG CTCGGCCGCA GGCTTGCGGA TACCGAAGCC 540

GCCGTGATCA TGAAGGTCGG GCGCAATTTG CCGAAGATCC GTCGGGCGCT CGCTGCCTCC 600

GGCCGTCTCG ACCAGGCCGT CTATGTCGAA CGCGGCACGA TGAAGAACGC GGCGATGACG 660

GCTCTTGCGG AAAAGGCCGA CGACGAGGCG CCCTATTTCT CGCTGGTGCT CGTTCCCGGC 720

TGGAAGGACC GACCATGA 738

(2) INFORMATION FOR SEQ ID NO: 20:

(i) SEQUENCE CHARACTERISTICS:
(A) LENGTH: 245 amino acids
(B) TYPE: Amino Acid
(C) STRANDEDNESS:
(D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:

-continued

```
          (E) HAPLOTYPE:
          (F) TISSUE TYPE:
          (G) CELL TYPE:
          (H) CELL LINE:
          (I) ORGANELLE:

    (ix) FEATURE:
          (A) NAME/KEY: COBI
          (B) LOCATION:
          (C) IDENTIFICATION METHOD:
          (D) OTHER INFORMATION: Translation product of SEQ ID NO:19

    (xi) SEQUENCE DESCRIPTION: SEQ ID NO: 20:

Met Ser Gly Val Gly Val Gly Arg Leu Ile Gly Val Gly Thr Gly Pro
1               5                   10                  15

Gly Asp Pro Glu Leu Leu Thr Val Lys Ala Val Lys Ala Leu Gly Gln
            20                  25                  30

Ala Asp Val Leu Ala Tyr Phe Ala Lys Ala Gly Arg Ser Gly Asn Gly
        35                  40                  45

Arg Ala Val Val Glu Gly Leu Leu Lys Pro Asp Leu Val Glu Leu Pro
    50                  55                  60

Leu Tyr Tyr Pro Val Thr Thr Glu Ile Asp Lys Asp Asp Gly Ala Tyr
65                  70                  75                  80

Lys Thr Gln Ile Thr Asp Phe Tyr Asn Ala Ser Ala Glu Ala Val Ala
                85                  90                  95

Ala His Leu Ala Ala Gly Arg Thr Val Ala Val Leu Ser Glu Gly Asp
            100                 105                 110

Pro Leu Phe Tyr Gly Ser Tyr Met His Leu His Val Arg Leu Ala Asn
        115                 120                 125

Arg Phe Pro Val Glu Val Ile Pro Gly Ile Thr Ala Met Ser Gly Cys
    130                 135                 140

Trp Ser Leu Ala Gly Leu Pro Leu Val Gln Gly Asp Asp Val Leu Ser
145                 150                 155                 160

Val Leu Pro Gly Thr Met Ala Glu Ala Glu Leu Gly Arg Arg Leu Ala
                165                 170                 175

Asp Thr Glu Ala Ala Val Ile Met Lys Val Gly Arg Asn Leu Pro Lys
            180                 185                 190

Ile Arg Arg Ala Leu Ala Ala Ser Gly Arg Leu Asp Gln Ala Val Tyr
        195                 200                 205

Val Glu Arg Gly Thr Met Lys Asn Ala Ala Met Thr Ala Leu Ala Glu
    210                 215                 220

Lys Ala Asp Asp Glu Ala Pro Tyr Phe Ser Leu Val Leu Val Pro Gly
225                 230                 235                 240

Trp Lys Asp Arg Pro
                245


(2) INFORMATION FOR SEQ ID NO: 21:

     (i) SEQUENCE CHARACTERISTICS:
          (A) LENGTH: 764 base pairs
          (B) TYPE: Nucleic Acid
          (C) STRANDEDNESS:  Double
          (D) TOPOLOGY:  Unknown

    (ii) MOLECULE TYPE:  cDNA

   (iii) HYPOTHETICAL: No

    (iv) ORIGINAL SOURCE:
          (A) ORGANISM: Pseudomonas denitrificans
          (B) STRAIN:
          (C) INDIVIDUAL ISOLATE:
```

-continued (D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobJ
(B) LOCATION: 4365-5129 bp of SEQ ID NO: 2
(C) IDENTIFICATION METHOD:
(D) OTHER INFORMATION:

(xi) SEQUENCE DESCRIPTION: SEQ ID NO: 21:

```
ATGACCGGTA CGCTCTATGT CGTCGGTACC GGACCGGGCA GCGCCAAGCA GATGACGCCG     60

GAAACGGCGG AAGCCGTTGC GGCCGCTCAG GAGTTTTACG GCTACTTTCC CTATCTCGAC    120

CGGCTGAACC TCAGACCGGA TCAGATCCGT GTCGCCTCGG ACAACCGCGA GGAGCTCGAT    180

CGGGCACAGG TCGCGCTGAC GCGGGCTGCG GCAGGCGTGA AGGTCTGCAT GGTCTCCGGT    240

GGCGATCCCG GTGTCTTTGC CATGGCGGCC GCCGTCTGCG AGGCGATCGA CAAGGGACCG    300

GCGGAATGGA AGTCGGTTGA ACTGGTGATC ACGCCCGGCG TGACCGCGAT GCTCGCCGTT    360

GCCGCCCGCA TCGGCGCGCC GCTCGGTCAT GATTTCTGTG CGATCTCGCT TTCCGACAAT    420

CTGAAGCCCT GGGAAGTCAT CACCCGGCGT CTCAGGCTGG CGGCGGAAGC GGGCTTCGTC    480

ATTGCCCTCT ACAATCCGAT CAGCAAGGCG CGGCCCTGGC AGCTCGGTGA GGCCTTCGAG    540

CTTCTGCGCA GCGTTCTGCC GGCAAGCGTT CCGGTCATCT TCGGCCGTGC GGCCGGGCGG    600

CCGGACGAAC GGATCGCGGT GATGCCGCTC GGCGAGGCCG ATGCCAACCG CGCCGACATG    660

GCGACCTGCG TCATCATCGG CTCGCCGGAG ACGCGCATCG TCGAGCGCGA CGGCCAACCC    720

GATCTCGTCT ACACACCGCG CTTCTATGCA GGGGCGAGCC AGTG                     764
```

(2) INFORMATION FOR SEQ ID NO: 22:

(i) SEQUENCE CHARACTERISTICS:
(A) LENGTH: 254 base pairs
(B) TYPE: Amino Acid
(C) STRANDEDNESS:
(D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBJ
(B) LOCATION:
(C) IDENTIFICATION METHOD:
(D) OTHER INFORMATION: Translation product of SEQ ID NO:21

(xi) SEQUENCE DESCRIPTION: SEQ ID NO: 22:

```
Met Thr Gly Thr Leu Tyr Val Val Gly Thr Gly Pro Gly Ser Ala Lys
1               5                   10                  15

Gln Met Thr Pro Glu Thr Ala Glu Ala Val Ala Ala Ala Gln Glu Phe
            20                  25                  30
```

-continued

```
Tyr Gly Tyr Phe Pro Tyr Leu Asp Arg Leu Asn Leu Arg Pro Asp Gln
        35                  40                  45

Ile Arg Val Ala Ser Asp Asn Arg Glu Glu Leu Asp Arg Ala Gln Val
    50                  55                  60

Ala Leu Thr Arg Ala Ala Ala Gly Val Lys Val Cys Met Val Ser Gly
65                  70                  75                  80

Gly Asp Pro Gly Val Phe Ala Met Ala Ala Ala Val Cys Glu Ala Ile
                85                  90                  95

Asp Lys Gly Pro Ala Glu Trp Lys Ser Val Glu Leu Val Ile Thr Pro
            100                 105                 110

Gly Val Thr Ala Met Leu Ala Val Ala Ala Arg Ile Gly Ala Pro Leu
        115                 120                 125

Gly His Asp Phe Cys Ala Ile Ser Leu Ser Asp Asn Leu Lys Pro Trp
    130                 135                 140

Glu Val Ile Thr Arg Arg Leu Arg Leu Ala Ala Glu Ala Gly Phe Val
145                 150                 155                 160

Ile Ala Leu Tyr Asn Pro Ile Ser Lys Ala Arg Pro Trp Gln Leu Gly
                165                 170                 175

Glu Ala Phe Glu Leu Leu Arg Ser Val Leu Pro Ala Ser Val Pro Val
            180                 185                 190

Ile Phe Gly Arg Ala Ala Gly Arg Pro Asp Glu Arg Ile Ala Val Met
        195                 200                 205

Pro Leu Gly Glu Ala Asp Ala Asn Arg Ala Asp Met Ala Thr Cys Val
    210                 215                 220

Ile Ile Gly Ser Pro Glu Thr Arg Ile Val Glu Arg Asp Gly Gln Pro
225                 230                 235                 240

Asp Leu Val Tyr Thr Pro Arg Phe Tyr Ala Gly Ala Ser Gln
                245                 250
```

(2) INFORMATION FOR SEQ ID NO: 23:

(i) SEQUENCE CHARACTERISTICS:
(A) LENGTH: 786 base pairs
(B) TYPE: Nucleic Acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobK
(B) LOCATION: compl. strand of 2861-3634 bp of SEQ ID NO:2
(C) IDENTIFICATION METHOD:
(D) OTHER INFORMATION:

(xi) SEQUENCE DESCRIPTION: SEQ ID NO: 23:

```
ATGGCGGGTT CGCTGTTCGA CACGTCAGCC ATGGAAAAAC CTCGTATTCT GATTCTGGGT     60

GGCACCACCG AGGCACGCGA ACTCGCGCGC CGCTTGGCCG AAGATGTCCG CTACGACACC    120

GCCATCTCGC TGGCCGGCCG CACCGCGGAC CCGCGGCCGC AGCCGGTCAA GACGCGCATC    180
```

-continued

```
GGCGGCTTTG GCGGCGCCGA TGGGCTGGCG CATTTCGTGC ATGACGAAAA CATCGCGCTG    240

CTGGTCGATG CGACGCACCC CTTTGCCGCA CGCATTTCGC ACAACGCCGC GGACGCAGCG    300

CAAAGAACCG GCGTTGCGCT TATCGCCCTC CGCCGACCGG AATGGGTGCC CCTGCCTGGC    360

GACCGCTGGA CTGCTGTCGA TAGCGTTGTC GAGGCCGTCA GCGCGCTCGG TGATCGGCGA    420

CGCCGCGTCT TCCTGGCGAT AGGTCGACAG GAAGCTTTCC ACTTCGAGGT CGCGCCGCAG    480

CACAGCTACG TCATCCGCAG CGTCGATCCG GTGACGCCGC CGCTTAATCT GCCCGACCAG    540

GAGGCGATCC TGGCGACCGG TCCCTTTGCG GAAGCCGACG AAGCCGCGTT GCTCAGGAGT    600

CGGCAGATCG ATGTGATCGT CGCCAAGAAC AGCGGTGGCA GCGCCACCTA CGGCAAGATT    660

GCCGCAGCGC GCCGGCTCGG CATCGAGGTG ATCATGGTCG AGCGGCGCAA GCCCGCGGAC    720

GTGCCGACGG TCGGCAGTTG CGACGAGGCA CTCAACCGCA TCGCTCACTG GCTCGCCCCT    780

GCATGA                                                               786
```

(2) INFORMATION FOR SEQ ID NO: 24:

(i) SEQUENCE CHARACTERISTICS:
(A) LENGTH: 261 amino acids
(B) TYPE: Amino Acid
(C) STRANDEDNESS:
(D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBK
(B) LOCATION:
(C) IDENTIFICATION METHOD:
(D) OTHER INFORMATION:Translation product of SEQ ID NO:23

(xi) SEQUENCE DESCRIPTION: SEQ ID NO: 24:

```
Met Ala Gly Ser Leu Phe Asp Thr Ser Ala Met Glu Lys Pro Arg Ile
1               5                   10                  15

Leu Ile Leu Gly Gly Thr Thr Glu Ala Arg Glu Leu Ala Arg Arg Leu
            20                  25                  30

Ala Glu Asp Val Arg Tyr Asp Thr Ala Ile Ser Leu Ala Gly Arg Thr
        35                  40                  45

Ala Asp Pro Arg Pro Gln Pro Val Lys Thr Arg Ile Gly Gly Phe Gly
    50                  55                  60

Gly Ala Asp Gly Leu Ala His Phe Val His Asp Glu Asn Ile Ala Leu
65                  70                  75                  80

Leu Val Asp Ala Thr His Pro Phe Ala Ala Arg Ile Ser His Asn Ala
                85                  90                  95

Ala Asp Ala Ala Gln Arg Thr Gly Val Ala Leu Ile Ala Leu Arg Arg
            100                 105                 110

Pro Glu Trp Val Pro Leu Pro Gly Asp Arg Trp Thr Ala Val Asp Ser
        115                 120                 125
```

-continued

```
Val Val Glu Ala Val Ser Ala Leu Gly Asp Arg Arg Arg Arg Val Phe
    130                 135                 140

Leu Ala Ile Gly Arg Gln Glu Ala Phe His Phe Glu Val Ala Pro Gln
145                 150                 155                 160

His Ser Tyr Val Ile Arg Ser Val Asp Pro Val Thr Pro Pro Leu Asn
                165                 170                 175

Leu Pro Asp Gln Glu Ala Ile Leu Ala Thr Gly Pro Phe Ala Glu Ala
            180                 185                 190

Asp Glu Ala Ala Leu Leu Arg Ser Arg Gln Ile Asp Val Ile Val Ala
        195                 200                 205

Lys Asn Ser Gly Gly Ser Ala Thr Tyr Gly Lys Ile Ala Ala Ala Arg
    210                 215                 220

Arg Leu Gly Ile Glu Val Ile Met Val Glu Arg Arg Lys Pro Ala Asp
225                 230                 235                 240

Val Pro Thr Val Gly Ser Cys Asp Glu Ala Leu Asn Arg Ile Ala His
                245                 250                 255

Trp Leu Ala Pro Ala
            260
```

(2) INFORMATION FOR SEQ ID NO: 25:

(i) SEQUENCE CHARACTERISTICS:
(A) LENGTH: 1242 base pairs
(B) TYPE: Nucleic Acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobL
(B) LOCATION: 5862-7103 bp of SEQ ID NO: 2
(C) IDENTIFICATION METHOD:
(D) OTHER INFORMATION:

(xi) SEQUENCE DESCRIPTION: SEQ ID NO: 25:

```
ATGGCTGACG TGTCGAACAG CGAACCCGCC ATAGTCTCCC CCTGGCTGAC CGTCATCGGT     60

ATCGGTGAGG ATGGTGTAGC GGGTCTCGGC GACGAGGCCA AGCGGCTGAT CGCCGAAGCG    120

CCGGTCGTCT ACGGCGGCCA TCGTCATCTG GAGCTCGCCG CCTCCCTCAT CACCGGCGAA    180

GCGCACAATT GGCTAAGCCC CCTCGAACGC TCGGTCGTCG AGATCGTCGC GCGTCGCGGC    240

AGCCCGGTGG TGGTGCTTGC CTCGGGCGAC CCGTTCTTCT TCGGCGTCGG CGTGACGCTG    300

GCGCGCCGCA TCGCCTCGGC CGAAATACGC ACGCTTCCGG CGCCGTCGTC GATCAGTCTT    360

GCCGCCTCGC GCCTCGGCTG GGCGCTGCAG GATGCGACGC TCGTCTCCGT ACATGGGCGG    420

CCGCTGGATC TGGTGCGACC GCATTTGCAT CCGGGGGCGC GTGTGCTTAC GCTCACGTCG    480

GACGGTGCGG GTCCGCGAGA CCTTGCCGAG CTTCTGGTTT CAAGCGGCTT CGGTCAGTCG    540

CGACTGACCG TGCTCGAAGC GCTGGGCGGC GCCGGCGAAC GGGTGACGAC GCAGATCGCC    600
```

-continued

```
GCGCGCTTCA TGCTCGGCCT CGTGCATCCT TTGAACGTCT GCGCCATTGA GGTGGCGGCC    660

GACGAGGGCG CGCGCATCCT GCCGCTTGCC GCCGGCCGCG ACGATGCGCT GTTCGAACAT    720

GACGGGCAGA TCACCAAGCG CGAGGTGCGG GCGCTGACGC TGTCGGCACT CGCACCGCGC    780

AAGGGCGAAC TGCTATGGGA CATCGGCGGC GGCTCCGGCT CGATCGGCAT CGAATGGATG    840

CTCGCCGATC CGACCATGCA GGCGATCACC ATCGAGGTTG AGCCGGAGCG GGCAGCGCGC    900

ATCGGCCGCA ACGCGACGAT GTTCGGCGTG CCCGGGCTGA CGGTTGTCGA AGGCGAGGCG    960

CCGGCGGCGC TTGCCGGCCT GCCACAACCG GACGCGATCT TCATCGGCGG CGGCGGCAGC   1020

GAAGACGGCG TCATGGAAGC AGCGATCGAG GCGCTCAAGT CAGGCGGACG GCTGGTTGCC   1080

AACGCGGTGA CGACGGACAT GGAAGCGGTG CTGCTCGATC ATCACGCGCG GCTCGGCGGT   1140

TCGCTGATCC GCATCGATAT CGCGCGTGCA GGACCCATCG GCGGCATGAC CGGCTGGAAG   1200

CCGGCCATGC CGGTCACCCA ATGGTCGTGG ACGAAGGGCT AA                       1242
```

(2) INFORMATION FOR SEQ ID NO: 26:

(i) SEQUENCE CHARACTERISTICS:
(A) LENGTH: 413 amino acids
(B) TYPE: Amino Acid
(C) STRANDEDNESS:
(D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBL
(B) LOCATION:
(C) IDENTIFICATION METHOD:
(D) OTHER INFORMATION: Translation product of SEQ ID NO:25

(xi) SEQUENCE DESCRIPTION: SEQ ID NO: 26:

```
Met Ala Asp Val Ser Asn Ser Glu Pro Ala Ile Val Ser Pro Trp Leu
1               5                   10                  15

Thr Val Ile Gly Ile Gly Glu Asp Gly Val Ala Gly Leu Gly Asp Glu
            20                  25                  30

Ala Lys Arg Leu Ile Ala Glu Ala Pro Val Val Tyr Gly Gly His Arg
        35                  40                  45

His Leu Glu Leu Ala Ala Ser Leu Ile Thr Gly Glu Ala His Asn Trp
    50                  55                  60

Leu Ser Pro Leu Glu Arg Ser Val Val Glu Ile Val Ala Arg Arg Gly
65                  70                  75                  80

Ser Pro Val Val Val Leu Ala Ser Gly Asp Pro Phe Phe Phe Gly Val
                85                  90                  95

Gly Val Thr Leu Ala Arg Arg Ile Ala Ser Ala Glu Ile Arg Thr Leu
            100                 105                 110

Pro Ala Pro Ser Ser Ile Ser Leu Ala Ala Ser Arg Leu Gly Trp Ala
        115                 120                 125

Leu Gln Asp Ala Thr Leu Val Ser Val His Gly Arg Pro Leu Asp Leu
```

-continued

```
    130                 135                 140

Val Arg Pro His Leu His Pro Gly Ala Arg Val Leu Thr Leu Thr Ser
145                 150                 155                 160

Asp Gly Ala Gly Pro Arg Asp Leu Ala Glu Leu Leu Val Ser Ser Gly
                165                 170                 175

Phe Gly Gln Ser Arg Leu Thr Val Leu Glu Ala Leu Gly Gly Ala Gly
            180                 185                 190

Glu Arg Val Thr Thr Gln Ile Ala Ala Arg Phe Met Leu Gly Leu Val
        195                 200                 205

His Pro Leu Asn Val Cys Ala Ile Glu Val Ala Ala Asp Glu Gly Ala
    210                 215                 220

Arg Ile Leu Pro Leu Ala Ala Gly Arg Asp Asp Ala Leu Phe Glu His
225                 230                 235                 240

Asp Gly Gln Ile Thr Lys Arg Glu Val Arg Ala Leu Thr Leu Ser Ala
                245                 250                 255

Leu Ala Pro Arg Lys Gly Glu Leu Leu Trp Asp Ile Gly Gly Gly Ser
            260                 265                 270

Gly Ser Ile Gly Ile Glu Trp Met Leu Ala Asp Pro Thr Met Gln Ala
        275                 280                 285

Ile Thr Ile Glu Val Glu Pro Glu Arg Ala Ala Arg Ile Gly Arg Asn
    290                 295                 300

Ala Thr Met Phe Gly Val Pro Gly Leu Thr Val Val Glu Gly Glu Ala
305                 310                 315                 320

Pro Ala Ala Leu Ala Gly Leu Pro Gln Pro Asp Ala Ile Phe Ile Gly
                325                 330                 335

Gly Gly Gly Ser Glu Asp Gly Val Met Glu Ala Ala Ile Glu Ala Leu
            340                 345                 350

Lys Ser Gly Gly Arg Leu Val Ala Asn Ala Val Thr Thr Asp Met Glu
        355                 360                 365

Ala Val Leu Leu Asp His His Ala Arg Leu Gly Gly Ser Leu Ile Arg
    370                 375                 380

Ile Asp Ile Ala Arg Ala Gly Pro Ile Gly Gly Met Thr Gly Trp Lys
385                 390                 395                 400

Pro Ala Met Pro Val Thr Gln Trp Ser Trp Thr Lys Gly
                405                 410
```

(2) INFORMATION FOR SEQ ID NO: 27:

(i) SEQUENCE CHARACTERISTICS:
(A) LENGTH: 762 base pairs
(B) TYPE: Nucleic Acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobM

-continued (B) LOCATION: 7172-7930 bp of SEQ ID NO: 2
(C) IDENTIFICATION METHOD:
(D) OTHER INFORMATION:

(xi) SEQUENCE DESCRIPTION: SEQ ID NO: 27:

```
ATGACGGTAC ATTTCATCGG CGCCGGCCCG GGAGCCGCAG ACCTGATCAC GGTGCGTGGT     60

CGCGACCTGA TCGGGCGCTG CCCGGTCTGC CTTTACGCCG GCTCGATCGT CTCGCCGGAG    120

CTGCTGCGAT ATTGCCCGCC GGGCGCCCGC ATTGTCGATA CGGCGCCGAT GTCCCTCGAC    180

GAGATCGAGG CGGAGTATGT GAAGGCCGAA GCCGAAGGGC TCGACGTGGC GCGGCTTCAT    240

TCGGGCGACC TTTCGGTCTG GAGTGCTGTG GCCGAACAGA TCCGCCGGCT CGAGAAGCAT    300

GGCATCGCCT ATACGATGAC GCCGGGCGTT CCTTCCTTTG CGGCGGCGGC TTCAGCGCTC    360

GGTCGCGAAT TGACCATTCC GGCCGTGGCC CAGAGCCTGG TGCTGACCCG CGTTTCGGGC    420

CGCGCCTCGC CGATGCCGAA CTCAGAAACG CTTTCCGCTT TCGGCGCTAC GGGATCGACG    480

CTGGCAATCC ACCTTGCGAT CCATGCGCTT CAGCAGGTGG TCGAGGAACT GACGCCGCTC    540

TACGGTGCCG ACTGCCCGGT CGCCATCGTC GTCAAGGCCT CCTGGCCGGA CGAACGCGTG    600

GTGCGCGGCA CGCTCGGTGA CATCGCCGCC AAGGTGGCGG AAGAGCCGAT CGAGCGCACG    660

GCGCTGATCT TCGTCGGTCC GGGGCTCGAA GCCTCCGATT TCCGTGAAAG CTCGCTCTAC    720

GATCCCGCCT ATCAGCGGCG CTTCAGAGGG CGCGGCGAAT AG                       762
```

(2) INFORMATION FOR SEQ ID NO: 28:

(i) SEQUENCE CHARACTERISTICS:
(A) LENGTH: 253 amino acids
(B) TYPE: Amino Acid
(C) STRANDEDNESS:
(D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBM
(B) LOCATION:
(C) IDENTIFICATION METHOD:
(D) OTHER INFORMATION: Translation product of SEQ ID NO:27

(xi) SEQUENCE DESCRIPTION: SEQ ID NO: 28:

```
Met Thr Val His Phe Ile Gly Ala Gly Pro Gly Ala Ala Asp Leu Ile
1               5                   10                  15

Thr Val Arg Gly Arg Asp Leu Ile Gly Arg Cys Pro Val Cys Leu Tyr
            20                  25                  30

Ala Gly Ser Ile Val Ser Pro Glu Leu Leu Arg Tyr Cys Pro Pro Gly
        35                  40                  45

Ala Arg Ile Val Asp Thr Ala Pro Met Ser Leu Asp Glu Ile Glu Ala
    50                  55                  60

Glu Tyr Val Lys Ala Glu Ala Glu Gly Leu Asp Val Ala Arg Leu His
65                  70                  75                  80
```

-continued

```
Ser Gly Asp Leu Ser Val Trp Ser Ala Val Ala Glu Gln Ile Arg Arg
                85                  90                  95

Leu Glu Lys His Gly Ile Ala Tyr Thr Met Thr Pro Gly Val Pro Ser
            100                 105                 110

Phe Ala Ala Ala Ala Ser Ala Leu Gly Arg Glu Leu Thr Ile Pro Ala
        115                 120                 125

Val Ala Gln Ser Leu Val Leu Thr Arg Val Ser Gly Arg Ala Ser Pro
    130                 135                 140

Met Pro Asn Ser Glu Thr Leu Ser Ala Phe Gly Ala Thr Gly Ser Thr
145                 150                 155                 160

Leu Ala Ile His Leu Ala Ile His Ala Leu Gln Gln Val Val Glu Glu
                165                 170                 175

Leu Thr Pro Leu Tyr Gly Ala Asp Cys Pro Val Ala Ile Val Val Lys
            180                 185                 190

Ala Ser Trp Pro Asp Glu Arg Val Val Arg Gly Thr Leu Gly Asp Ile
        195                 200                 205

Ala Ala Lys Val Ala Glu Glu Pro Ile Glu Arg Thr Ala Leu Ile Phe
    210                 215                 220

Val Gly Pro Gly Leu Glu Ala Ser Asp Phe Arg Glu Ser Ser Leu Tyr
225                 230                 235                 240

Asp Pro Ala Tyr Gln Arg Arg Phe Arg Gly Arg Gly Glu
                245                 250
```

(2) INFORMATION FOR SEQ ID NO: 29:

(i) SEQUENCE CHARACTERISTICS:
(A) LENGTH: 4748 base pairs
(B) TYPE: Nucleic Acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY:
(B) LOCATION:
(C) IDENTIFICATION METHOD:
(D) OTHER INFORMATION:Nucleotide Sequence of the 5' to 3' strand from the 4748 bp SalI-SalI-SalI-SalI-SalI-BglI fragment of Pseudomonas denitrificans (xi) SEQUENCE DESCRIPTION: SEQ ID NO: 29:

```
GTCGACGAGT ATGGTCAGGT TCAGGGTCTG GTGACGCTGG AGGACATTCT GGAGGAGATC     60

GTCGGCGATA TCGCCGATGA GCACGACCTC GACATTCAGG GCGTGCGCCA GGAAGCCGAT    120

GGCTCGATCG TCGTCGATGG CTCGGTGCCG ATCCGCGATC TCAACCGCGC GCTCGACTGG    180

TCGCTGCCGG ACGAGGAGGC GACGACGGTG GCCGGTCTGG TCATCCACGA GTCCAAGAGC    240

ATTCCGGAGG AGCGCCAGGC CTTCACCTTC CACGGCAAAC GCTTCATCGT GATGAAGCGG    300

GTGAAGAACC GCATTACCAA GCTGCGCATC CGTCCGGCGG AAGAGGGTGC TCCGCCGGCG    360
```

-continued

```
TGATGGCCGC GATTGCCTCT ACCAGCGGGT CGGCTCGCCG GGGGCTGCCG GCTCGACGGC    420

GAGCGCATGC AGGCCGGCGT CGAGTTCTGG CTTCAGGAGA TCATTGATGG CGCGGTGGCG    480

GGCGACACGG CTCATGCCGG CAAAGGCGCT AGAAACGATA CGCACCCGCA TGTGGGACTC    540

GCCGGTACCA TCGAAGCCCG GCTGATGGCC GGTATGCTGA TGGCTCTCGT TGATGACCTC    600

GAGCCGTTCA GGGTGGAAGG CCTCGATCAG CTTCTTTTCG ATGGTCTCGG TGAGCGACAT    660

TCTTCCGTCC CATTTTGCTG TTTGCTTGGC GCCCCCTCGC AGTTAAGAAC CCGGTAATCG    720

CTGGCACGGC GGCGCAAAAT GCCCGCACAA AGCCAGCAAC ATTCCGCTTT GTCAATTCTT    780

GTTGTGACTC CCGCCAAACC CCATAATGAG CGCCATGAGA CTCGATTCAA AATACTTCGA    840

TCGCATTCGA ACCCGGCGCA AGGTCGAGCC GCAGCAGAGC CGGCGGCTCC CGTCTGTCAG    900

TGGGACGGCT GCGATCAGAA GGGTGTGCAC CGGGCGCCCG TCGGTCGCAA CGCCGAGGGG    960

CAGTACTTCA TGTTCTGCTT CGAGCACGTG AAGGAATACA ACAAGGGCTA CAACTTCTTC   1020

TCCGGCCTCT CCGACAGCGA GGTCGCCCGC TACCAGAAGG AAGCGATCAC CGGTCATCGG   1080

CCCACCTGGA CCGTCGGCGT CAACAAGAAC GCCAAGAACG GCCCGACCCA GTCGCAGACG   1140

CGGTCTGGCT CTGCCGGCGC CCAGGCCCGC ATGCGCGATC CCTTCGGCTT TGTCAGCGAG   1200

GCGCGGGCGC GATCCGGTCG TCCCGAGCCA CGCCAGCGCA AGCTGAAGAC GCTCGAGGCG   1260

AAGGCCTTCG AAACGCTTGG TCTCGGAGCC TCGGCGACCA CTGCCGACAT CAAGGCGGCC   1320

TACAAGGACC TCGTCAAGAA GCATCACCCC GATGCCAATG GCGGAGATAG AGGATCGGAA   1380

GAGCGTTTTC GCGCGGTTAT TCAGGCCTAC CAATTGTTAA AACAGGCTGG TTTCTGCTAA   1440

CAACCCGGAT TAATACAGAA GCACTTTTGC AGGCGAATGC GCGGGTGCCG TCCGGTGGCC   1500

GCTCTGGAGA CATGATGAGC AAGATTGACC TCGACATTTC CAACCTCCCC GACACCACGA   1560

TTTCCGTCCG GGAGGTTTTC GGTATTGATA CGGATTTGCG CGTTCCTGCC TATTCGAAGG   1620

GCGACGCCTA TGTCCCGGAT CTGGATCCGG ACTACCTCTT CGACCGCGAA ACGACGCTCG   1680

CCATTCTCGC AGGCTTCGCC CACAACCGAC GCGTGATGGT GTCGGGCTAT CACGGCACCG   1740

GCAAGTCCAC CCATATCGAG CAGGTCGCCG CGCGCCTCAA CTGGCCGTGC GTGCGCGTCA   1800

ACCTCGATAG CCATGTCAGC CGTATCGACC TCGTCGGCAA GGACGCGATC GTCGTCAAGG   1860

ACGGCCTGCA GGTCACCGAA TTCAAGGACG GCATCCTGCC CTGGGCCTAC CAGCACAATG   1920

TCGCGCTCGT CTTCGACGAA TACGATGCCG GCCGCCCGGA CGTCATGTTC GTCATCCAGC   1980

GCGTGCTGGA ATCCTCCGGC CGCCTGACGC TGCTCGACCA GAGCCGTGTC ATCCGTCCGC   2040

ACCCGGCCTT CCGCCTGTTT GCGACCGCCA ACACCGTCGG CCTCGGCGAC ACGACCGGCC   2100

TCTATCACGG CACGCAGCAG ATCAACCAGG CGCAGATGGA CCGCTGGTCG ATCGTCACCA   2160

CGCTGAACTA CCTGCCGCAC GACAAGGAAG TCGACATCGT CGCCGCCAAG GTCAAGGGCT   2220

TCACCGCCGA CAAGGGCCGC GAGACCGTCT CCAAGATGGT ACGTGTCGCC GACCTCACGC   2280

GCGCAGCCTT CATCAATGGC GATCTCTCGA CTGTCATGAG CCCGCGTACG GTCATCACCT   2340

GGGCCGAGAA CGCCCACATC TTCGGCGACA TCGCTTTCGC CTTCCGCGTG ACCTTCCTCA   2400

ACAAGTGCGA CGAGCTGGAG CGGGCGCTGG TCGCCGAGCA CTACCAGCGC GCCTTCGGCA   2460

TCGAGCTGAA GGAATGCGCT GCCAACATCG TGCTCGAAGC CACCGCCTGA TCCCACGGCC   2520

TGCCGTCCCC TTTGGGAGGG CGGGTCATGA CGCTGTGGCA AACCGGATGA CGCCCCACTG   2580

GGGCGCCGTC GCCTCTGGCT GAAGAAGGAA CTGTCGTGAG CTCGAATTCG AAGGCAAAGC   2640

CAACCACGCG CGAGAATGCT GCGGAACCGT TCAAGCGGGC GCTTTCCGGC TGCATCCGAT   2700

CGATCGCGGG CGATGCCGAG GTGGAAGTCG CCTTCGCCAA CGAGCGGCCG GGCATGACCG   2760
```

-continued

```
GCGAACGCAT CCGTCTGCCG GAACTTTCCA AGCGCCCGAC CCTGCAGGAA CTTGCCGTGA   2820
CCCGCGGGCT CGGTGACAGC ATGGCGCTGC GCAAGGCCTG TACGCATGCG CGGATCCAGC   2880
GCACCATGTC GCCGCAAGGG GCGGACGCCC GCGCGATCTT CGATGCGGTG GAGCAGGCTC   2940
GTGTCGAGGC GATCGGGTCG TTGCGCATGG CGGGTGTCGC CAAGAACCTC AACGTCATGC   3000
TCGAAGAGAA ATACGCCAAG GCGAATTTCG CAACGATCGA GCGCCAGGCG GACGCGCCGC   3060
TCGGCGAGGC CGTAGCGCTG CTGGTGCGCG AGAAGCTGAC GGGCCAGAAG CCGCCGGCGT   3120
CTGCCGGCAA GGTGCTCGAC CTCTGGCGCG AGTTCATCGA GGGCAAGGCT GCCGGCGACA   3180
TTGAGCACCT GTCGTCGACG ATCAACAACC AGCAGGCCTT TGCCCGGGTC GTTCGCGACA   3240
TGCTGACCTC GATGGAAGTC GCCGAGAAAT ACGGTGACGA CGACAACGAG CCGGACGAGC   3300
AGGAAAGCGA GACCGACGAA GACCAGCCGC GCAGCCAGGA GCAGGACGAG AACGCCAGCG   3360
ACGAGGAAGC CGGCGACGAT GCCGCACCCG CCGACGAGAA CCAGGCTGCC GAAGAGCAGA   3420
TGGAAGAAGG CGAGATGGAC GGCGCGGAGA TCTCCGACGA CGATCTCCAG GACGAAGGCG   3480
ACGAGGACAG CGAAACGCCC GGCGAGGTCA AGCGTCCGAA CCAGCCCTTC GCCGACTTCA   3540
ACGAGAAGGT CGACTACGCC GTCTTCACCC GCGAGTTCGA CGAGACGATT GCCTCGGAAG   3600
AGCTTTGCGA CGAGGCCGAG CTCGACCGGC TGCGCGCCTT CCTCGACAAG CAGCTTGCCC   3660
ATCTTCAAGG CGCGGTCGGC CGCCTTGCCA ACCGGCTGCA GCGCCGCCTG ATGGCGCAGC   3720
AGAACCGCTC CTGGGAGTTC GATCTCGAAG AGGGGTATCT CGATTCGGCG CGGCTTCAGC   3780
GCATCATCAT CGATCCGATG CAGCCGCTTT CCTTCAAGCG CGAAAAGGAC ACCAACTTCC   3840
GCGATACCGT CGTGACGCTG CTGATCGACA ATTCCGGCTC GATGCGCGGC CGTCCGATCA   3900
CGGTTGCCGC CACCTGCGCC GATATCCTGG CGCGCACGCT CGAGCGCTGC GGCGTCAAGG   3960
TCGAGATCCT CGGTTTTACC ACCAAGGCGT GGAAGGGTGG GCAGTCACGC GAGAAGTGGC   4020
TGGCCGGCGG CAAGCCACAG GCCCCGGGTC GCCTCAACGA CCTGCGACAC ATCGTCTACA   4080
AGTCTGCCGA CGCTCCGTGG CGCCGGGCAC GACGCAATCT CGGCCTGATG ATGCGGGAAG   4140
GCCTGCTCAA GGAAAACATC GACGGCGAGG CGTTGATTTG GGCGCATGAG CGGCTGATGG   4200
CGCGGCGCGA ACAGCGGCGC ATCCTGATGA TGATTTCGGA CGGCGCGCCG GTCGACGACT   4260
CGACGCTGTC GGTCAATCCA GGAAACTATC TGGAGCGTCA CCTGCGCGCG GTCATCGAGC   4320
AGATCGAAAC GCGCTCGCCG GTGGAACTGC TGGCGATCGG TATCGGCCAC GACGTGACGC   4380
GCTACTATCG CCGTGCCGTC ACCATCGTCG ATGCCGATGA GCTTGCCGGC GCGATGACCG   4440
AACAGCTGGC CGCACTCTTC GAGGACGAAA GCCAGCGCCG CGGTTCTTCG CGTCTTCGCC   4500
GCGCCGGGTG ATGCTTCCCC CTTGGGGGCG GTGGAACATC GCCTCCGAGC TGCCAATCGG   4560
CACCTGCACG CATCGCTGGC GGCCGAAGTC AATTTACGGA CATAGTTTTA CAGTCTACCA   4620
AGCTACCATG CGTGGCGGGC TCACTTTGAG CGCACGCCGC GTCATTCCCG ATGCCCCCTG   4680
AAGGTACTTC TCTTGATGCT TGGCCGCGGT CTCCTAGCCC TTTTCCTCCT GGCTTCGGCC   4740
TGCCCGGC                                                            4748
```

(2) INFORMATION FOR SEQ ID NO: 30:

(i) SEQUENCE CHARACTERISTICS:
- (A) LENGTH: 3855 base pairs
- (B) TYPE: Nucleic acid
- (C) STRANDEDNESS: Double
- (D) TOPOLOGY: Unknown (ii) MOLECULE TYPE: cDNA -continued (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY:
(B) LOCATION:
(C) IDENTIFICATION METHOD:
(D) OTHER INFORMATION: Nucleotide Sequence of the 5' to 3' strand from the 3855 bp SstI-SstI-BamHI fragment of Pseudomonas denitrificans (xi) SEQUENCE DESCRIPTION: SEQ ID NO: 30:

```
GAGCTCATAG AGCAGTTCCT CGATCGACTT CAGCAGTCGC ATGAAATCCA TGCCGTGCTC     60
CCCTTGCTTC TATGCGTGGC ACGACCGCGC GCCGGGGCCG ATGCCGGTCA GTCGCGCAGA    120
CGCAGCTCGT CGGTACGCAT CTGCAGCATC TCCAGCGTCG ACAGGAAGCT CATGCCGAGC    180
AGGCTCTGAT CGAGCTTGCC CTTGGCTGCG ACCGTTGCGC CGATGTTGCG GCGGGTGATC    240
GGGCCGATCG AGATCTCCTG AAGCATCACG GGGGCTGCCT GGGCCCGGCC ATTGGCTGTC    300
ATGACCGTGA CGATAAAGTT GAGGTTGGCC GGGTCGAGGC CGATCTTTTC CGCATCTTCA    360
TAGGTGAGCG CGATGTTGCT GGCGCCGGTA TCGACCAGCA TGCTGATGTC CTTGCCGTCG    420
ACCGTCGCAG TGGTCTCGAA ATGACCGTTC AGCATCTTCT GCAGCACCAC TTCCTGCTGT    480
CCCTCGCTGT CAGTGATGAT GGTGGCGCGG CCGGGGATGA GGCCGGCGAG CAGGCGGTTA    540
CCGAAGCCCT CCAACTCGAA GCGGTAGACA TAGGCCGAGA CCAGCGCCAG AACGACGAAG    600
AGCCAGATGG CGATCTGACG CAGGCCTTCG CCGAAGCGGT GGCGGCTCTG CAGGATGCCG    660
GCGCCGATCA GCGTGGCGAT GGCGCCGAGC GAGACCAGTT GCCCGAACTG GTCATTGGCA    720
AGCCCCATGG TGCGGCCGGT GTCGTGGTTG ATGATCAGCA GGATGAGGCC GATGGCCAGG    780
ATCGAGAGCA GGATGGCAAG ACGGGTCATG CTTCGCCGCG TTCCCTCGCC ATGCGCGTGC    840
GTCGGGTTTC GCGCCGCGGC TTGCGTTCGA CGGTCTCAAG CCGTGCAGGC AACGCGCTCA    900
TGATCGCGCG GCGTTCGGCA TCGGTATAGA GCGTCCAGCG TCCGACTTCG TCGCGGGTAC    960
GGCCGCAGCC GAAACAGTAG CCGGTCTTGT CATCGATCGA ACAGACGAGA ATGCAGGGAG   1020
ATTCCATGGG CGTGCTCAGT TTTCCCTTGA TATATCGATG TTTCAAACCG TCAGCGCAAG   1080
GGCACCGAGC ACGGCGATTT CGGTCAGTTG CTGCGTCGCC CCGATCGTGT CGCCCGTTTG   1140
TCCGCCGATC TTGCGCATCG CCAGCCGAGC GAAGCCCTTG ACCGTGGCAA GGAATGCGAC   1200
GAGCGCCGCG ATGACGCCGA GCGCCGGGAC CTGCGCGAGA TAGAAGAGCA GCATTGCGAC   1260
AAGAAGTCCG AAGGCAAGCG CGAAGCGCGT GGCCGCCGGT TCCGGCTCGC CAGCCGAGGC   1320
CGCGACGCCG CTGCTGCGCG CCGGCGGAAG CGACGACCAG TGCCAGACCA TGGCGGCGCG   1380
GCTGAGGCAC GCTGCGCCAA GGATCGCCAT GGCGGCGCCC AGCGGCGAAA AGAGCGGCAG   1440
GATCGAGGCG AACGCCGAGA CGCGCAGGCC GAAGGAGAGG ATGAGGGCGA CGGCCGCATA   1500
GGTGCCGATG CGGCTGTCCT TCATGATCGC AAGCGCCGCT TCGCGGTCGC GACCGCCGCC   1560
AAAGCCATCG GCCGTGTCGC CAAGCCCGTC TTCGTGCAGT GCGCCGGTGA CAAGCGCCTG   1620
GATGGCGACG ACGACAAAGG CGGCAAAGAG CGAGCTCACC TGCAGCGCCA TGAGGGCCAT   1680
```

-continued

```
GGCGACGGCC GCCGATGGCA GTGCGATCGC CAGGCCGGCG AACGGGAAGG CGCGCACGGC   1740
ACGGCTCAAG CGCCCGTCAT AACCTTCGAA ATGACGCGCA GGCATCGGGA TGCGGCTGAG   1800
AAAGCCGATC GACCGCGCCA CATCGTCACA GAAATCGCCA ACGAAGCCCA TGGCTCCTCC   1860
AAGGTTGCGG CCATTGACCC GGCCGCTGCC AAACTCGCCG ACTGCGGCGA GTCTCGCAAG   1920
CCGGGCGGGC GCACCCGCGA GGGCCGCGCA CACTTTTCCC AGACCTTTCA TAGGCCGTCT   1980
GCGACCGCTC GCGGATCGAG ACGGCGACGC CGATTGGCGC AAATGTCGTT GCCCGAATTT   2040
TCGGCGCCCT CTATGAGGGG CGTAGATAGA GCTTCACGAT GATGCAAGGA TTCCTCCCAT   2100
GAGTGCCAGC GGCCTGCCGT TTGATGATTT TCGCGAATTG TTGCGCAACC TGCCGGGCCC   2160
GGATGCGGCA GCCCTCGTTG CCGCGCGGGA GCGGGACGCC CAGCTGACGA AGCCGCCGGG   2220
CGCGCTCGGC CGCCTCGAGG AAATCGCCTT CTGGCTCGCC GCCTGGACGG GCAAGGCGCC   2280
GGTGGTCAAC CGGCCGCTGG TGGCGATCTT TGCCGGCAAC CACGGCGTCA CCCGCCAGGG   2340
GGTGACCCCG TTCCCGTCAT CCGTCACCGC ACAGATGGTC GAGAATTTTG CCGCCGGTGG   2400
CGCTGCGATC AACCAGATCT GCGTCAGCCA CGACCTCGGG CTGAAGGTCT TCGACCTCGC   2460
ACTCGAATAC CCGACCGGTG ATATCACCGA GGAAGCCGCG CTGTCCGAGC GCGATTGCGC   2520
CGCGACCATG GCCTTTGGCA TGGAGGCGAT TGCCGGCGGC ACGGATCTTC TGTGCATCGG   2580
CGAAATGGGC ATCGGCAACA CCACGATCGC GGCCGCGATC AATCTCGGCC TTTATGGTGG   2640
CACGGCCGAA GAATGGGTCG GTCCGGGTAC CGGCTCCGAG GGCGAGGTGC TGAAGCGCAA   2700
GATCGCCGCG GTCGAAAAGG CCGTGGCGCT GCATCGCGAT CACCTGTCCG ATCCGCTCGA   2760
ACTGATGCGT CGCCTCGGCG GTCGTGAGAT CGCGGCCATG GCTGGCGCCA TCCTGGCCGC   2820
CCGCGTCCAG AAGGTACCTG TCATCATCGA CGGCTACGTG GCGACCGCTG CGGCTTCGAT   2880
CCTGAAGGCG GCCAACCCGT CGGCCCTCGA CCATTGCCTG ATCGGCCATG TTTCGGGCGA   2940
ACCGGGGCAT CTGCGCGCGA TCGAGAAGCT CGGCAAGACG CCGCTGCTGG CACTCGGCAT   3000
GCGGCTTGGC GAAGGCACGG GCGCGGCCCT TGCCGCCGGT ATCGTCAAGG CGGCGGCCGC   3060
TTGCCACAGC GGCATGGCGA CCTTTGCCCA GGCCGGCGTC AGCAACAAGG AATAGTGAAG   3120
TTCCGGCCGG GCTTTGCAGG AAGGCCGGCC GGTTTCTGTC CAAGGCCTGT CACGGGCGCG   3180
AAGCTGTCGC GTGCCGGGCC TTGATGGATG CGTCCTTCTC GCCTATCCAA AGCGCAAATG   3240
CGCGCCCTAG CTATAGTCTT GGGTGCCTGC AACCGAGACC GCCTTGCATT CGCCTCAATC   3300
ACGATGTCGA AGCAAGCACA GTTTCAAGCC CTGTCGAGAC GAAATGGACG CCAAGAACAC   3360
CACGCACCGC ATTGGACAGA CGGGTCCTGT CGAGAAGCAG ACCGGCATTC GGCATCTCTT   3420
TGCCGCTGCG AGCTATTCGC TCGGCGGCGC CAAGCGGCTG ATCGGCGAGG CTGCCTTTCG   3480
CCACGAGCTG ATCGCCTTTG CCGCCGCGAT GATCGCTTTC ATCATCGTCG GCGCAACCTT   3540
CTTCCAATAT GTGGCGATGG CGATCCTGTT CCTGCTGATG ATGGCCTTCG AGGCGATCAA   3600
CACGGCAATC GAGGAAATTG TCGATCGCGT TTCTCCCGAA ATCTCGGAAA TGGGTAAGAA   3660
CGCCAAGGAT CTCGGCTCCT TCGCCTGCCT CTGCCTGATT GTCGCCAACG GTGTCTATGC   3720
CGCCTATGTC GTGATCTTCG ACGGCTTCAT GAACTGACCG GCTAGCGGGC CGGCGCCTTC   3780
ACCCGATAAA GCACATGCGG ACGCAGCGGG TTGCCCCCGG GTACCGTGAC GTCGTCGAAA   3840
TCATCAGCCG GATCC                                                    3855
```

(2) INFORMATION FOR SEQ ID NO: 31:

(i) SEQUENCE CHARACTERISTICS:

-continued (A) LENGTH: 999 base pairs
(B) TYPE: Nucleic Acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobS
(B) LOCATION: 1512-2510 bp of SEQ ID NO: 29
(C) IDENTIFICATION METHOD:
(D) OTHER INFORMATION:

(xi) SEQUENCE DESCRIPTION: SEQ ID NO: 31:

ATGATGAGCA AGATTGACCT CGACATTTCC AACCTCCCCG ACACCACGAT TTCCGTCCGG 60

GAGGTTTTCG GTATTGATAC GGATTTGCGC GTTCCTGCCT ATTCGAAGGG CGACGCCTAT 120

GTCCCGGATC TGGATCCGGA CTACCTCTTC GACCGCGAAA CGACGCTCGC CATTCTCGCA 180

GGCTTCGCCC ACAACCGACG CGTGATGGTG TCGGGCTATC ACGGCACCGG CAAGTCCACC 240

CATATCGAGC AGGTCGCCGC GCGCCTCAAC TGGCCGTGCG TGCGCGTCAA CCTCGATAGC 300

CATGTCAGCC GTATCGACCT CGTCGGCAAG GACGCGATCG TCGTCAAGGA CGGCCTGCAG 360

GTCACCGAAT TCAAGGACGG CATCCTGCCC TGGGCCTACC AGCACAATGT CGCGCTCGTC 420

TTCGACGAAT ACGATGCCGG CCGCCCGGAC GTCATGTTCG TCATCCAGCG CGTGCTGGAA 480

TCCTCCGGCC GCCTGACGCT GCTCGACCAG AGCCGTGTCA TCCGTCCGCA CCCGGCCTTC 540

CGCCTGTTTG CGACCGCCAA CACCGTCGGC CTCGGCGACA CGACCGGCCT CTATCACGGC 600

ACGCAGCAGA TCAACCAGGC GCAGATGGAC CGCTGGTCGA TCGTCACCAC GCTGAACTAC 660

CTGCCGCACG ACAAGGAAGT CGACATCGTC GCCGCCAAGG TCAAGGGCTT CACCGCCGAC 720

AAGGGCCGCG AGACCGTCTC CAAGATGGTA CGTGTCGCCG ACCTCACGCG CGCAGCCTTC 780

ATCAATGGCG ATCTCTCGAC TGTCATGAGC CCGCGTACGG TCATCACCTG GGCCGAGAAC 840

GCCCACATCT TCGGCGACAT CGCTTTCGCC TTCCGCGTGA CCTTCCTCAA CAAGTGCGAC 900

GAGCTGGAGC GGGCGCTGGT CGCCGAGCAC TACCAGCGCG CCTTCGGCAT CGAGCTGAAG 960

GAATGCGCTG CCAACATCGT GCTCGAAGCC ACCGCCTGA 999

(2) INFORMATION FOR SEQ ID NO: 32:

(i) SEQUENCE CHARACTERISTICS:
(A) LENGTH: 332 amino acids
(B) TYPE: Amino acid
(C) STRANDEDNESS:
(D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:

-continued (D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBS
(B) LOCATION:
(C) IDENTIFICATION METHOD:
(D) OTHER INFORMATION: Translation product of SEQ ID NO:31

(xi) SEQUENCE DESCRIPTION: SEQ ID NO: 32:

```
Met Met Ser Lys Ile Asp Leu Asp Ile Ser Asn Leu Pro Asp Thr Thr
1               5                   10                  15

Ile Ser Val Arg Glu Val Phe Gly Ile Asp Thr Asp Leu Arg Val Pro
            20                  25                  30

Ala Tyr Ser Lys Gly Asp Ala Tyr Val Pro Asp Leu Asp Pro Asp Tyr
        35                  40                  45

Leu Phe Asp Arg Glu Thr Thr Leu Ala Ile Leu Ala Gly Phe Ala His
    50                  55                  60

Asn Arg Arg Val Met Val Ser Gly Tyr His Gly Thr Gly Lys Ser Thr
65                  70                  75                  80

His Ile Glu Gln Val Ala Ala Arg Leu Asn Trp Pro Cys Val Arg Val
                85                  90                  95

Asn Leu Asp Ser His Val Ser Arg Ile Asp Leu Val Gly Lys Asp Ala
            100                 105                 110

Ile Val Val Lys Asp Gly Leu Gln Val Thr Glu Phe Lys Asp Gly Ile
        115                 120                 125

Leu Pro Trp Ala Tyr Gln His Asn Val Ala Leu Val Phe Asp Glu Tyr
    130                 135                 140

Asp Ala Gly Arg Pro Asp Val Met Phe Val Ile Gln Arg Val Leu Glu
145                 150                 155                 160

Ser Ser Gly Arg Leu Thr Leu Leu Asp Gln Ser Arg Val Ile Arg Pro
                165                 170                 175

His Pro Ala Phe Arg Leu Phe Ala Thr Ala Asn Thr Val Gly Leu Gly
            180                 185                 190

Asp Thr Thr Gly Leu Tyr His Gly Thr Gln Gln Ile Asn Gln Ala Gln
        195                 200                 205

Met Asp Arg Trp Ser Ile Val Thr Thr Leu Asn Tyr Leu Pro His Asp
    210                 215                 220

Lys Glu Val Asp Ile Val Ala Ala Lys Val Lys Gly Phe Thr Ala Asp
225                 230                 235                 240

Lys Gly Arg Glu Thr Val Ser Lys Met Val Arg Val Ala Asp Leu Thr
                245                 250                 255

Arg Ala Ala Phe Ile Asn Gly Asp Leu Ser Thr Val Met Ser Pro Arg
            260                 265                 270

Thr Val Ile Thr Trp Ala Glu Asn Ala His Ile Phe Gly Asp Ile Ala
        275                 280                 285

Phe Ala Phe Arg Val Thr Phe Leu Asn Lys Cys Asp Glu Leu Glu Arg
    290                 295                 300

Ala Leu Val Ala Glu His Tyr Gln Arg Ala Phe Gly Ile Glu Leu Lys
305                 310                 315                 320

Glu Cys Ala Ala Asn Ile Val Leu Glu Ala Thr Ala
                325                 330
```

-continued (2) INFORMATION FOR SEQ ID NO: 33:

(i) SEQUENCE CHARACTERISTICS:
(A) LENGTH: 1896 base pairs
(B) TYPE: Nucleic acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobT
(B) LOCATION: 2616-4511 bp of SEQ ID NO: 29
(C) IDENTIFICATION METHOD:
(D) OTHER INFORMATION:

(xi) SEQUENCE DESCRIPTION: SEQ ID NO: 33:

GTGAGCTCGA ATTCGAAGGC AAAGCCAACC ACGCGCGAGA ATGCTGCGGA ACCGTTCAAG 60

CGGGCGCTTT CCGGCTGCAT CCGATCGATC GCGGGCGATG CCGAGGTGGA AGTCGCCTTC 120

GCCAACGAGC GGCCGGGCAT GACCGGCGAA CGCATCCGTC TGCCGGAACT TTCCAAGCGC 180

CCGACCCTGC AGGAACTTGC CGTGACCCGC GGGCTCGGTG ACAGCATGGC GCTGCGCAAG 240

GCCTGTACGC ATGCGCGGAT CCAGCGCACC ATGTCGCCGC AAGGGGCGGA CGCCCGCGCG 300

ATCTTCGATG CGGTGGAGCA GGCTCGTGTC GAGGCGATCG GGTCGTTGCG CATGGCGGGT 360

GTCGCCAAGA ACCTCAACGT CATGCTCGAA GAGAAATACG CCAAGGCGAA TTTCGCAACG 420

ATCGAGCGCC AGGCGGACGC GCCGCTCGGC GAGGCCGTAG CGCTGCTGGT GCGCGAGAAG 480

CTGACGGGCC AGAAGCCGCC GGCGTCTGCC GGCAAGGTGC TCGACCTCTG GCGCGAGTTC 540

ATCGAGGGCA AGGCTGCCGG CGACATTGAG CACCTGTCGT CGACGATCAA CAACCAGCAG 600

GCCTTTGCCC GGGTCGTTCG CGACATGCTG ACCTCGATGG AAGTCGCCGA GAAATACGGT 660

GACGACGACA ACGAGCCGGA CGAGCAGGAA AGCGAGACCG ACGAAGACCA GCCGCGCAGC 720

CAGGAGCAGG ACGAGAACGC CAGCGACGAG GAAGCCGGCG ACGATGCCGC ACCCGCCGAC 780

GAGAACCAGG CTGCCGAAGA GCAGATGGAA GAAGGCGAGA TGGACGGCGC GGAGATCTCC 840

GACGACGATC TCCAGGACGA AGGCGACGAG GACAGCGAAA CGCCCGGCGA GGTCAAGCGT 900

CCGAACCAGC CCTTCGCCGA CTTCAACGAG AAGGTCGACT ACGCCGTCTT CACCCGCGAG 960

TTCGACGAGA CGATTGCCTC GGAAGAGCTT TGCGACGAGG CCGAGCTCGA CCGGCTGCGC 1020

GCCTTCCTCG ACAAGCAGCT TGCCCATCTT CAAGGCGCGG TCGGCCGCCT TGCCAACCGG 1080

CTGCAGCGCC GCCTGATGGC GCAGCAGAAC CGCTCCTGGG AGTTCGATCT CGAAGAGGGG 1140

TATCTCGATT CGGCGCGGCT TCAGCGCATC ATCATCGATC CGATGCAGCC GCTTTCCTTC 1200

AAGCGCGAAA AGGACACCAA CTTCCGCGAT ACCGTCGTGA CGCTGCTGAT CGACAATTCC 1260

GGCTCGATGC GCGGCCGTCC GATCACGGTT GCCGCCACCT GCGCCGATAT CCTGGCGCGC 1320

ACGCTCGAGC GCTGCGGCGT CAAGGTCGAG ATCCTCGGTT TTACCACCAA GGCGTGGAAG 1380

GGTGGGCAGT CACGCGAGAA GTGGCTGGCC GGCGGCAAGC CACAGGCCCC GGGTCGCCTC 1440

-continued

```
AACGACCTGC GACACATCGT CTACAAGTCT GCCGACGCTC CGTGGCGCCG GGCACGACGC   1500

AATCTCGGCC TGATGATGCG GGAAGGCCTG CTCAAGGAAA ACATCGACGG CGAGGCGTTG   1560

ATTTGGGCGC ATGAGCGGCT GATGGCGCGG CGCGAACAGC GGCGCATCCT GATGATGATT   1620

TCGGACGGCG CGCCGGTCGA CGACTCGACG CTGTCGGTCA ATCCAGGAAA CTATCTGGAG   1680

CGTCACCTGC GCGCGGTCAT CGAGCAGATC GAAACGCGCT CGCCGGTGGA ACTGCTGGCG   1740

ATCGGTATCG GCCACGACGT GACGCGCTAC TATCGCCGTG CCGTCACCAT CGTCGATGCC   1800

GATGAGCTTG CCGGCGCGAT GACCGAACAG CTGGCCGCAC TCTTCGAGGA CGAAAGCCAG   1860

CGCCGCGGTT CTTCGCGTCT TCGCCGCGCC GGGTGA                             1896
```

(2) INFORMATION FOR SEQ ID NO: 34:

(i) SEQUENCE CHARACTERISTICS:
(A) LENGTH: 631 amino acids
(B) TYPE: Amino acid
(C) STRANDEDNESS:
(D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBT
(B) LOCATION:
(C) IDENTIFICATION METHOD:
(D) OTHER INFORMATION: Translation product ofSEQ ID NO:33

(xi) SEQUENCE DESCRIPTION: SEQ ID NO: 34:

```
Val Ser Ser Asn Ser Lys Ala Lys Pro Thr Thr Arg Glu Asn Ala Ala
1               5                   10                  15

Glu Pro Phe Lys Arg Ala Leu Ser Gly Cys Ile Arg Ser Ile Ala Gly
            20                  25                  30

Asp Ala Glu Val Glu Val Ala Phe Ala Asn Glu Arg Pro Gly Met Thr
        35                  40                  45

Gly Glu Arg Ile Arg Leu Pro Glu Leu Ser Lys Arg Pro Thr Leu Gln
    50                  55                  60

Glu Leu Ala Val Thr Arg Gly Leu Gly Asp Ser Met Ala Leu Arg Lys
65                  70                  75                  80

Ala Cys Thr His Ala Arg Ile Gln Arg Thr Met Ser Pro Gln Gly Ala
                85                  90                  95

Asp Ala Arg Ala Ile Phe Asp Ala Val Glu Gln Ala Arg Val Glu Ala
            100                 105                 110

Ile Gly Ser Leu Arg Met Ala Gly Val Ala Lys Asn Leu Asn Val Met
        115                 120                 125

Leu Glu Glu Lys Tyr Ala Lys Ala Asn Phe Ala Thr Ile Glu Arg Gln
    130                 135                 140

Ala Asp Ala Pro Leu Gly Glu Ala Val Ala Leu Leu Val Arg Glu Lys
145                 150                 155                 160

Leu Thr Gly Gln Lys Pro Pro Ala Ser Ala Gly Lys Val Leu Asp Leu
```

-continued

```
                165                 170                 175

Trp Arg Glu Phe Ile Glu Gly Lys Ala Ala Gly Asp Ile Glu His Leu
            180                 185                 190

Ser Ser Thr Ile Asn Asn Gln Gln Ala Phe Ala Arg Val Val Arg Asp
        195                 200                 205

Met Leu Thr Ser Met Glu Val Ala Glu Lys Tyr Gly Asp Asp Asp Asn
    210                 215                 220

Glu Pro Asp Glu Gln Glu Ser Glu Thr Asp Glu Asp Gln Pro Arg Ser
225                 230                 235                 240

Gln Glu Gln Asp Glu Asn Ala Ser Asp Glu Glu Ala Gly Asp Asp Ala
                245                 250                 255

Ala Pro Ala Asp Glu Asn Gln Ala Ala Glu Glu Gln Met Glu Glu Gly
            260                 265                 270

Glu Met Asp Gly Ala Glu Ile Ser Asp Asp Asp Leu Gln Asp Glu Gly
        275                 280                 285

Asp Glu Asp Ser Glu Thr Pro Gly Glu Val Lys Arg Pro Asn Gln Pro
    290                 295                 300

Phe Ala Asp Phe Asn Glu Lys Val Asp Tyr Ala Val Phe Thr Arg Glu
305                 310                 315                 320

Phe Asp Glu Thr Ile Ala Ser Glu Glu Leu Cys Asp Glu Ala Glu Leu
                325                 330                 335

Asp Arg Leu Arg Ala Phe Leu Asp Lys Gln Leu Ala His Leu Gln Gly
            340                 345                 350

Ala Val Gly Arg Leu Ala Asn Arg Leu Gln Arg Arg Leu Met Ala Gln
        355                 360                 365

Gln Asn Arg Ser Trp Glu Phe Asp Leu Glu Glu Gly Tyr Leu Asp Ser
    370                 375                 380

Ala Arg Leu Gln Arg Ile Ile Ile Asp Pro Met Gln Pro Leu Ser Phe
385                 390                 395                 400

Lys Arg Glu Lys Asp Thr Asn Phe Arg Asp Thr Val Val Thr Leu Leu
                405                 410                 415

Ile Asp Asn Ser Gly Ser Met Arg Gly Arg Pro Ile Thr Val Ala Ala
            420                 425                 430

Thr Cys Ala Asp Ile Leu Ala Arg Thr Leu Glu Arg Cys Gly Val Lys
        435                 440                 445

Val Glu Ile Leu Gly Phe Thr Thr Lys Ala Trp Lys Gly Gly Gln Ser
    450                 455                 460

Arg Glu Lys Trp Leu Ala Gly Gly Lys Pro Gln Ala Pro Gly Arg Leu
465                 470                 475                 480

Asn Asp Leu Arg His Ile Val Tyr Lys Ser Ala Asp Ala Pro Trp Arg
                485                 490                 495

Arg Ala Arg Arg Asn Leu Gly Leu Met Met Arg Glu Gly Leu Leu Lys
            500                 505                 510

Glu Asn Ile Asp Gly Glu Ala Leu Ile Trp Ala His Glu Arg Leu Met
        515                 520                 525

Ala Arg Arg Glu Gln Arg Arg Ile Leu Met Met Ile Ser Asp Gly Ala
    530                 535                 540

Pro Val Asp Asp Ser Thr Leu Ser Val Asn Pro Gly Asn Tyr Leu Glu
545                 550                 555                 560

Arg His Leu Arg Ala Val Ile Glu Gln Ile Glu Thr Arg Ser Pro Val
                565                 570                 575

Glu Leu Leu Ala Ile Gly Ile Gly His Asp Val Thr Arg Tyr Tyr Arg
            580                 585                 590
```

-continued

```
Arg Ala Val Thr Ile Val Asp Ala Asp Glu Leu Ala Gly Ala Met Thr
        595                 600                 605

Glu Gln Leu Ala Ala Leu Phe Glu Asp Glu Ser Gln Arg Arg Gly Ser
    610                 615                 620

Ser Arg Leu Arg Arg Ala Gly
625                 630
```

(2) INFORMATION FOR SEQ ID NO: 35:

(i) SEQUENCE CHARACTERISTICS:
(A) LENGTH: 282 base pairs
(B) TYPE: Nucleic acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobX
(B) LOCATION: 4089-4370 bp of SEQ ID NO:29
(C) IDENTIFICATION METHOD:
(D) OTHER INFORMATION:

(xi) SEQUENCE DESCRIPTION: SEQ ID NO: 35:

```
ATGTCGCTCA CCGAGACCAT CGAAAAGAAG CTGATCGAGG CCTTCCACCC TGAACGGCTC     60

GAGGTCATCA ACGAGAGCCA TCAGCATACC GGCCATCAGC CGGGCTTCGA TGGTACCGGC    120

GAGTCCCACA TGCGGGTGCG TATCGTTTCT AGCGCCTTTG CCGGCATGAG CCGTGTCGCC    180

CGCCACCGCG CCATCAATGA TCTCCTGAAG CCAGAACTCG ACGCCGGCCT GCATGCGCTC    240

GCCGTCGAGC CGGCAGCCCC CGGCGAGCCG ACCCGCTGGT AG                       282
```

(2) INFORMATION FOR SEQ ID NO: 36:

(i) SEQUENCE CHARACTERISTICS:
(A) LENGTH: 93 amino acids
(B) TYPE: Amino acid
(C) STRANDEDNESS:
(D) TOPOLOGY: Linear (ii) MOLECULE TYPE: Protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBX
(B) LOCATION:

-continued (C) IDENTIFICATION METHOD:
(D) OTHER INFORMATION: Translation product of SEQ ID NO:35

(xi) SEQUENCE DESCRIPTION: SEQ ID NO: 36:

```
Met Ser Leu Thr Glu Thr Ile Glu Lys Lys Leu Ile Glu Ala Phe His
1               5                   10                  15

Pro Glu Arg Leu Glu Val Ile Asn Glu Ser His Gln His Thr Gly His
            20                  25                  30

Gln Pro Gly Phe Asp Gly Thr Gly Glu Ser His Met Arg Val Arg Ile
        35                  40                  45

Val Ser Ser Ala Phe Ala Gly Met Ser Arg Val Ala Arg His Arg Ala
    50                  55                  60

Ile Asn Asp Leu Leu Lys Pro Glu Leu Asp Ala Gly Leu His Ala Leu
65                  70                  75                  80

Ala Val Glu Pro Ala Ala Pro Gly Glu Pro Thr Arg Trp
                85                  90
```

(2) INFORMATION FOR SEQ ID NO: 37:

(i) SEQUENCE CHARACTERISTICS:
(A) LENGTH: 1017 base pairs
(B) TYPE: Nucleic acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobU
(B) LOCATION: 2099-3115 bp of SEQ ID NO: 30
(C) IDENTIFICATION METHOD:
(D) OTHER INFORMATION:

(xi) SEQUENCE DESCRIPTION: SEQ ID NO: 37:

```
ATGAGTGCCA GCGGCCTGCC GTTTGATGAT TTTCGCGAAT TGTTGCGCAA CCTGCCGGGC     60

CCGGATGCGG CAGCCCTCGT TGCCGCGCGG GAGCGGGACG CCCAGCTGAC GAAGCCGCCG    120

GGCGCGCTCG GCCGCCTCGA GGAAATCGCC TTCTGGCTCG CCGCCTGGAC GGGCAAGGCG    180

CCGGTGGTCA ACCGGCCGCT GGTGGCGATC TTTGCCGGCA ACCACGGCGT CACCCGCCAG    240

GGGGTGACCC CGTTCCCGTC ATCCGTCACC GCACAGATGG TCGAGAATTT TGCCGCCGGT    300

GGCGCTGCGA TCAACCAGAT CTGCGTCAGC CACGACCTCG GGCTGAAGGT CTTCGACCTC    360

GCACTCGAAT ACCCGACCGG TGATATCACC GAGGAAGCCG CGCTGTCCGA GCGCGATTGC    420

GCCGCGACCA TGGCCTTTGG CATGGAGGCG ATTGCCGGCG GCACGGATCT TCTGTGCATC    480

GGCGAAATGG GCATCGGCAA CACCACGATC GCGGCCGCGA TCAATCTCGG CCTTTATGGT    540

GGCACGGCCG AAGAATGGGT CGGTCCGGGT ACCGGCTCCG AGGGCGAGGT GCTGAAGCGC    600

AAGATCGCCG CGGTCGAAAA GGCCGTGGCG CTGCATCGCG ATCACCTGTC CGATCCGCTC    660

GAACTGATGC GTCGCCTCGG CGGTCGTGAG ATCGCGGCCA TGGCTGGCGC CATCCTGGCC    720
```

-continued

```
GCCCGCGTCC AGAAGGTACC TGTCATCATC GACGGCTACG TGGCGACCGC TGCGGCTTCG    780

ATCCTGAAGG CGGCCAACCC GTCGGCCCTC GACCATTGCC TGATCGGCCA TGTTTCGGGC    840

GAACCGGGGC ATCTGCGCGC GATCGAGAAG CTCGGCAAGA CGCCGCTGCT GGCACTCGGC    900

ATGCGGCTTG GCGAAGGCAC GGGCGCGGCC CTTGCCGCCG GTATCGTCAA GGCGGCGGCC    960

GCTTGCCACA GCGGCATGGC GACCTTTGCC CAGGCCGGCG TCAGCAACAA GGAATAG      1017
```

(2) INFORMATION FOR SEQ ID NO: 38:

(i) SEQUENCE CHARACTERISTICS:
(A) LENGTH: 338 amino acids
(B) TYPE: Amino acid
(C) STRANDEDNESS:
(D) TOPOLOGY: Linear (ii) MOLECULE TYPE: Protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBU
(B) LOCATION:
(C) IDENTIFICATION METHOD:
(D) OTHER INFORMATION: Translation product of SEQ ID NO:37

(xi) SEQUENCE DESCRIPTION: SEQ ID NO: 38:

```
Met Ser Ala Ser Gly Leu Pro Phe Asp Asp Phe Arg Glu Leu Leu Arg
1               5                   10                  15

Asn Leu Pro Gly Pro Asp Ala Ala Ala Leu Val Ala Ala Arg Glu Arg
            20                  25                  30

Asp Ala Gln Leu Thr Lys Pro Pro Gly Ala Leu Gly Arg Leu Glu Glu
        35                  40                  45

Ile Ala Phe Trp Leu Ala Ala Trp Thr Gly Lys Ala Pro Val Val Asn
    50                  55                  60

Arg Pro Leu Val Ala Ile Phe Ala Gly Asn His Gly Val Thr Arg Gln
65                  70                  75                  80

Gly Val Thr Pro Phe Pro Ser Ser Val Thr Ala Gln Met Val Glu Asn
                85                  90                  95

Phe Ala Ala Gly Gly Ala Ala Ile Asn Gln Ile Cys Val Ser His Asp
            100                 105                 110

Leu Gly Leu Lys Val Phe Asp Leu Ala Leu Glu Tyr Pro Thr Gly Asp
        115                 120                 125

Ile Thr Glu Glu Ala Ala Leu Ser Glu Arg Asp Cys Ala Ala Thr Met
    130                 135                 140

Ala Phe Gly Met Glu Ala Ile Ala Gly Gly Thr Asp Leu Leu Cys Ile
145                 150                 155                 160

Gly Glu Met Gly Ile Gly Asn Thr Thr Ile Ala Ala Ala Ile Asn Leu
                165                 170                 175

Gly Leu Tyr Gly Gly Thr Ala Glu Glu Trp Val Gly Pro Gly Thr Gly
            180                 185                 190

Ser Glu Gly Glu Val Leu Lys Arg Lys Ile Ala Ala Val Glu Lys Ala
```

-continued

```
        195                 200                 205

Val Ala Leu His Arg Asp His Leu Ser Asp Pro Leu Glu Leu Met Arg
    210                 215                 220

Arg Leu Gly Gly Arg Glu Ile Ala Ala Met Ala Gly Ala Ile Leu Ala
225                 230                 235                 240

Ala Arg Val Gln Lys Val Pro Val Ile Ile Asp Gly Tyr Val Ala Thr
                245                 250                 255

Ala Ala Ala Ser Ile Leu Lys Ala Ala Asn Pro Ser Ala Leu Asp His
            260                 265                 270

Cys Leu Ile Gly His Val Ser Gly Glu Pro Gly His Leu Arg Ala Ile
        275                 280                 285

Glu Lys Leu Gly Lys Thr Pro Leu Leu Ala Leu Gly Met Arg Leu Gly
    290                 295                 300

Glu Gly Thr Gly Ala Ala Leu Ala Ala Gly Ile Val Lys Ala Ala Ala
305                 310                 315                 320

Ala Cys His Ser Gly Met Ala Thr Phe Ala Gln Ala Gly Val Ser Asn
                325                 330                 335

Lys Glu
```

(2) INFORMATION FOR SEQ ID NO: 39:

(i) SEQUENCE CHARACTERISTICS:
(A) LENGTH: 909 base pairs
(B) TYPE: Nucleic acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobV
(B) LOCATION: 1885-2793 bp of SEQ ID NO:30
(C) IDENTIFICATION METHOD:
(D) OTHER INFORMATION:

(xi) SEQUENCE DESCRIPTION: SEQ ID NO: 39:

```
ATGAAAGGTC TGGGAAAAGT GTGCGCGGCC CTCGCGGGTG CGCCCGCCCG GCTTGCGAGA     60

CTCGCCGCAG TCGGCGAGTT TGGCAGCGGC CGGGTCAATG GCCGCAACCT TGGAGGAGCC    120

ATGGGCTTCG TTGGCGATTT CTGTGACGAT GTGGCGCGGT CGATCGGCTT TCTCAGCCGC    180

ATCCCGATGC CTGCGCGTCA TTTCGAAGGT TATGACGGGC GCTTGAGCCG TGCCGTGCGC    240

GCCTTCCCGT TCGCCGGCCT GGCGATCGCA CTGCCATCGG CGGCCGTCGC CATGGCCCTC    300

ATGGCGCTGC AGGTGAGCTC GCTCTTTGCC GCCTTTGTCG TCGTCGCCAT CCAGGCGCTT    360

GTCACCGGCG CACTGCACGA AGACGGGCTT GGCGACACGG CCGATGGCTT TGGCGGCGGT    420

CGCGACCGCG AAGCGGCGCT TGCGATCATG AAGGACAGCC GCATCGGCAC CTATGCGGCC    480

GTCGCCCTCA TCCTCTCCTT CGGCCTGCGC GTCTCGGCGT TCGCCTCGAT CCTGCCGCTC    540

TTTTCGCCGC TGGGCGCCGC CATGGCGATC CTTGGCGCAG CGTGCCTCAG CCGCGCCGCC    600
```

-continued

```
ATGGTCTGGC ACTGGTCGTC GCTTCCGCCG GCGCGCAGCA GCGGCGTCGC GGCCTCGGCT    660

GGCGAGCCGG AACCGGCGGC CACGCGCTTC GCGCTTGCCT TCGGACTTCT TGTCGCAATG    720

CTGCTCTTCT ATCTCGCGCA GGTCCCGGCG CTCGGCGTCA TCGCGGCGCT CGTCGCATTC    780

CTTGCCACGG TCAAGGGCTT CGCTCGGCTG GCGATGCGCA AGATCGGCGG ACAAACGGGC    840

GACACGATCG GGGCGACGCA GCAACTGACC GAAATCGCCG TGCTCGGTGC CCTTGCGCTG    900

ACGGTTTGA                                                            909
```

(2) INFORMATION FOR SEQ ID NO: 40:

(i) SEQUENCE CHARACTERISTICS:
(A) LENGTH: 302 amino acids
(B) TYPE: Amino acid
(C) STRANDEDNESS:
(D) TOPOLOGY: Linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBV
(B) LOCATION:
(C) IDENTIFICATION METHOD:
(D) OTHER INFORMATION: Translation product of SEQ ID NO:39

(xi) SEQUENCE DESCRIPTION: SEQ ID NO: 40:

```
Met Lys Gly Leu Gly Lys Val Cys Ala Ala Leu Ala Gly Ala Pro Ala
1               5                   10                  15

Arg Leu Ala Arg Leu Ala Ala Val Gly Glu Phe Gly Ser Gly Arg Val
            20                  25                  30

Asn Gly Arg Asn Leu Gly Gly Ala Met Gly Phe Val Gly Asp Phe Cys
        35                  40                  45

Asp Asp Val Ala Arg Ser Ile Gly Phe Leu Ser Arg Ile Pro Met Pro
    50                  55                  60

Ala Arg His Phe Glu Gly Tyr Asp Gly Arg Leu Ser Arg Ala Val Arg
65                  70                  75                  80

Ala Phe Pro Phe Ala Gly Leu Ala Ile Ala Leu Pro Ser Ala Ala Val
                85                  90                  95

Ala Met Ala Leu Met Ala Leu Gln Val Ser Ser Leu Phe Ala Ala Phe
            100                 105                 110

Val Val Val Ala Ile Gln Ala Leu Val Thr Gly Ala Leu His Glu Asp
        115                 120                 125

Gly Leu Gly Asp Thr Ala Asp Gly Phe Gly Gly Gly Arg Asp Arg Glu
    130                 135                 140

Ala Ala Leu Ala Ile Met Lys Asp Ser Arg Ile Gly Thr Tyr Ala Ala
145                 150                 155                 160

Val Ala Leu Ile Leu Ser Phe Gly Leu Arg Val Ser Ala Phe Ala Ser
                165                 170                 175

Ile Leu Pro Leu Phe Ser Pro Leu Gly Ala Ala Met Ala Ile Leu Gly
```

-continued

```
            180                 185                 190

Ala Ala Cys Leu Ser Arg Ala Ala Met Val Trp His Trp Ser Ser Leu
        195                 200                 205

Pro Pro Ala Arg Ser Ser Gly Val Ala Ala Ser Ala Gly Glu Pro Glu
    210                 215                 220

Pro Ala Ala Thr Arg Phe Ala Leu Ala Phe Gly Leu Leu Val Ala Met
225                 230                 235                 240

Leu Leu Phe Tyr Leu Ala Gln Val Pro Ala Leu Gly Val Ile Ala Ala
                245                 250                 255

Leu Val Ala Phe Leu Ala Thr Val Lys Gly Phe Ala Arg Leu Ala Met
            260                 265                 270

Arg Lys Ile Gly Gly Gln Thr Gly Asp Thr Ile Gly Ala Thr Gln Gln
        275                 280                 285

Leu Thr Glu Ile Ala Val Leu Gly Ala Leu Ala Leu Thr Val
    290                 295                 300
```

(2) INFORMATION FOR SEQ ID NO: 41:

(i) SEQUENCE CHARACTERISTICS:
(A) LENGTH: 13144 base pairs
(B) TYPE: Nucleic acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY:
(B) LOCATION:
(C) IDENTIFICATION METHOD:
(D) OTHER INFORMATION: Nucleotide Sequence of the 5' to 3' strand from the 13144 bp SstI-SstI-SstI-SstI-BglII-BglII fragment of Pseudomonas denitrificans (xi) SEQUENCE DESCRIPTION: SEQ ID NO: 41:

```
GAGCTCGAAG GGGCTTCCGC CCCGATCGCT GGCGTTAGCC GACGTTCGAC GTGCGGATGA     60

CGCCGAGCGG GCCGAAGGGC GCGTCGACGA CGAGGTTGCG TACGCGCGAC TGGCTGGACG    120

GAACCTTCGA GTTCCAGGCG ATCTGAACGA AATTGGGCTT GCTGAAAATA TACAGCATGG    180

ACATGAACCT TGAGAGGCCG GAGGCCTATC CTCCGGGGCG TGTTGCTATG CCGCTGATAT    240

AGGTGTGCGC TGCAAAAAAT TGAATGCCAA ACTCGCCACG CCATGTCGCA TTCTGGCTAT    300

CGGCCGCGAC ATTTTCGACA AGCCTTGCGA AAGCGCGAAA CAATGCGTGA AAGGGCTTTG    360

TCAATTGCGG CGAAATCGTG TCGAAACAGA CCTTTGCCGC TGCCCGTTTC AGTGTTACCG    420

ATGGCCGCAT GACACGCAGG ATCATGTTGC AGGGAACCGG CTCGGATGTC GGAAAATCGG    480

TATTGGTGGC GGGGCTCTGC CGGCTTGCCG CCAATCAGGG CCTGAAGGTC CGGCCGTTCA    540

AGCCGCAGAA CATGTCGAAC AACGCCGCCG TTTCCGACGA CGGCGGCGAG ATCGGCCGCG    600

CGCAATGGCT GCAGGCGCTG GCCGCGCGCG TGCCGTCGTC GGTGCACATG AACCCGGTGC    660
```

-continued

```
TCCTGAAGCC GCAGTCGGAC GTGGGCAGCC AGATCGTCGT TCAGGGCAAG GTCGCCGGGC    720
AGGCCAGGGG GCGGGAATAT CAGGCGCTCA AGCCCAAGCT GCTGGGCGCC GTCATGGAGA    780
GTTTCGAACA AATATCGGCC GGTGCCGATC TCGTGGTGGT CGAAGGCGCC GGCTCGCCGG    840
CCGAAATCAA CCTCAGGCCC GGCGACATCG CCAATATGGG CTTTGCGACA CGGGCCAATG    900
TGCCGGTCGT GCTGGTCGGC GACATCGACC GCGGGGGGGT GATCGCCTCG CTGGTCGGCA    960
CGCATGCGAT CCTGCCCGAG GAAGACCGGC GCATGGTGAC CGGCTATCTC ATCAACAAGT   1020
TCCGCGGCGA CGTCACGCTG TTCGACGACG GCATTGCTGC CGTCAACCGC TACACCGGCT   1080
GGCCCTGCTT CGGCGTCGTG CCGTGGCTGA AGGCGGCGGC ACGCCTGCCG GCGGAAGATT   1140
CCGTCGTGCT GGAGAAGCTG ACGCGCGGCG AGGGGCGGGC GCTGAAGGTT GCCGTCCCGG   1200
TACTGTCGCG CATCGCCAAT TTCGACGACC TCGATCCGCT CGCCGCCGAA CCGGAGATTG   1260
ATCTCGTCTT CGTGCGGCCT GGCAGTCCCA TTCCGGTCGA CGCTGGCCTC GTCGTCATTC   1320
CCGGGTCGAA ATCGACCATC GGCGACCTCA TCGATTTCCG TGCGCAAGGG TGGGACCGTG   1380
ACCTCGAACG TCATGTGCGC CGGGGCGGCC GGGTCATCGG CATCTGCGGC GGCTACCAGA   1440
TGCTCGGCCG GCGCGTCACC GATCCGCTCG GCATCGAGGG CGGCGAACGT GCGGTCGAGG   1500
GCCTCGGGCT GCTCGAGGTC GAGACCGAGA TGGCGCCGGA AAAGACGGTG CGCAACAGCC   1560
GCGCCTGGTC GCTGGAGCAT GATGTGGTGC TCGAAGGCTA CGAAATCCAT CTTGGCAAGA   1620
CGCAAGGTGC GGACTGTGGC CGGCCGTCGG TGCGCATCGA CAATCGCGCC GACGGCGCCC   1680
TTTCGGCCGA TGGCCGCGTG ATGGGCACCT ACCTGCATGG GCTCTTCACC AGCGACGCCT   1740
ATCGCGGCGC GCTGCTCAAG AGTTTCGGCA TCGAAGGCGG CGCCAACAAC TACCGCCAAT   1800
CGGTCGATGC GGCGCTCGAC GATGTCGCGA ACGAACTGGA GGCTGTGCTC GATCGTCGCT   1860
GGCTGGACGA GTTGCTCAGG CACTAGGGAC GCGGCAACGG TCAGCCAGCA GGTCCGGTAC   1920
GTCGGGCCCA ACAGGAGCAA CGAGCTTATC CGACGGAACT ACGCTGCGAC ATCGTGCTCC   1980
TCGCTTGCGG CTTCCCAGAC TTCCCGCGCG GCATCCAGGT TCATCAGGGC AATCCCCAGG   2040
CCGACGATCA GGTCCGGCCA GGCCGACTGC CACAGATAGG CTGTCGCCAG ACCCGCGGCG   2100
ATGATGGCCA CATTGGCGAA GGCATCGTTG CGGGCCGAGA GAAATGCTGC CCGCGTGAGC   2160
GTGCCGCTCG TGTGACGGTA GGCGACGAGC AGATAGGCGC AGAAGAGGTT GACCACCAGC   2220
GCCCCAAGTC CGGTCAGGGA CAGGGCAAAG GGCTCTGGCG GGACCGGATC CATGAACTTC   2280
GCCCAGGCCG TCCAAAGGAA GGCCAGCGCC GGTACCAGTA GAATGAACGC CATCGCCATG   2340
CCGACCCGCG CGCGGGTTCG CGCCGTCCAG GCCAGAGCAA AGAAAATCAG CATGTTGACG   2400
GAGGCGTCTT CGAGGAAGTC GACGCTGTCG GCCATGAGGG ACACCGAGCC GATCGAAAGC   2460
GCGACAAGGA GTTCGACCCC GAAATAGCCA AGGTTCAACA GGGAGACGAT GAGGACGACG   2520
CGGCGCAGGT CGGTATCCAC TCGAAAGGTT CCCTTTCTGG CGAGATTCGC CCTCGGCACT   2580
TTTTTTGGCG AGATTCGCCC TCGGCACTTT GGCACAGGTG TTAGCAGCAG TTTGCTATCC   2640
ATAGCACTAG GTTTCGACAT CGGTTCCGTT CACACTGCCG TCGTGCCTGA CGCCCGACAA   2700
ATCGTCGCGT GGCGCAACTC GGCCGGGGAG GCGTCGCATG CGTCGATTGA CTTTGGGCTG   2760
CCCGCTTCCT AATCATCAGG TGTTGGATGG TTCCCCCTTG TCGTGGCGAT CTGGGGGAAT   2820
AATTGGGAAT GTGACGGATG GACCCAAATC GGGCATCCTT ATCGCAGCCG ACCCCGCGAC   2880
TGTAGAACGG TCAGGGTTCG CCATCGGGAT TGGTGCCGGG CTGTCGGCCG GTTGCATGGG   2940
CAATCGGGGC AGGTCGGGGA TCAAGCCGGA AAAGCCACTG GCGTGGCATC GTGATCAGCC   3000
GGGTTTGGAC GCCTCTTCTT CTACGAATCG TCCGCCTTTC ACGATGTCCC TCACAGCGCC   3060
```

-continued

```
CATGCGTCGG AGACGACGCG CAAAGGTTCG CTGTGGCACC GGAAAGACGC CGGGAAGGTG   3120
AGGCGGGCCG CTCGGGCCCT GACATCGGAA CCTTGCCGTT TAAGGGCGAG GCGATGTTCG   3180
GCCCGTGACG CCGTGAGCCA GGAGACCTGC CATCCGGCAT GGGCATTCCG CCCGAGGGGA   3240
CTTTTGTCTC CAACGCCATC ACGGAGGTTG TTTTGGCTCG CAGATGTTTT CAAGAACGCG   3300
CCCGTGGCGC GTCCGATGGC TTTTGCCACC GACGGCTGAT TTGGGAATGT TGAGGCAGCC   3360
ACGATGAGCA GTCTCAGCGC CGGGCCCGTG CTGGTCCTTG GCGGCGCCCG TTCCGGCAAG   3420
TCCAGCTTTT CCGAGAGGCT CGTCGAAGCG TCCGGCTTCA CCATGCATTA TGTCGCCACG   3480
GGCCGCGCCT GGGACGACGA AATGCGCGAG CGCATCGACC ATCACCGGAC GCGCCGCGGC   3540
GAGGGCTGGA CGACGCATGA GGAGCCGCTC GATCTCGTCG GCATCCTCAG ACGCATCGAT   3600
GATCCCAGCC ATGTGGTCCT GATCGACTGC CTGACGCTAT GGGTCACCAA TCTCATGCTG   3660
GAAGAGCGCG ACATGACGGC GGAGTTCGCC GCCCTTGTTG CGTATCTGCC CGAGGCGCGG   3720
GCGCGCCTCG TCTTTGTTTC CAATGAGGTC GGCCTCGGCA TCGTGCCCGA GAACCGCATG   3780
GCCCGCGAGT TTCGCGACCA TGCCGGCCGG CTTCACCAGA TCGTTGCGGA GAAATCCGCT   3840
GAAGTTTACT TTGTCGCGGC CGGTTTGCCG CTGAAAATGA AGGGTTGATC CATGACCACT   3900
GCGAGAGCCA ACCAGGGCAA GATCCCGGCG ACCGTCATCA CCGGCTTCCT CGGCGCCGGC   3960
AAGACGACGA TGATCCGCAA CCTGCTGCAG AACGCCGACG GCAAGCGCAT CGGCCTGATC   4020
ATCAACGAGT TCGGCGATCT TGGCGTCGAC GGCGATGTCT TGAAGGGCTG CGGTGCCGAG   4080
GCCTGCACCG AGGACGACAT CATCGAGCTC ACCAATGGCT GCATCTGCTG CACCGTGGCT   4140
GACGATTTCA TCCCGACCAT GACGAAGCTG CTCGAGCGTG AAAACCGTCC TGACCACATC   4200
ATCATCGAAA CCTCGGGCCT TGCCCTGCCG CAGCCGCTGA TCGCCGCTTT CAACTGGCCG   4260
GATATCCGCA GCGAAGTGAC CGTCGATGGC GTCGTCACCG TGGTCGACAG CGCCGCCGTT   4320
GCCGCTGGCC GCTTTGCCGA CGACCACGAC AAGGTCGATG CGCTGCGCGT CGAGGACGAC   4380
AATCTCGATC ACGAAAGCCC GATCGAGGAG CTGTTCGAGG ATCAACTGAC GGCTGCCGAT   4440
CTCATCGTTC TCAACAAGAC CGATCTGATC GATGCCTCCG GCCTCAAGGC CGTGCGCGAC   4500
GAGGTGTCTT CGCGCACCAG CCGCAAGCCC ACGATGATCG AGGCGAAAAA CGGCGAAGTC   4560
GCCGCTGCCA TCCTGCTTGG CCTCGGTGTC GGCACGGAAA GCGATATCGC CAACCGCAAG   4620
TCGCATCACG AGATGGAGCA CGAGGCAGGT GAGGAGCACG ATCACGACGA GTTCGACAGC   4680
TTCGTCGTCG AGCTCGGTTC GATCGCCGAT CCGGCCGCCT TCATCGATCG CCTGAAGGGC   4740
GTAATCGCGG AGCACGACGT TCTGCGCCTC AAGGGTTTTG CAGACGTGCC CGGCAAGCCG   4800
ATGCGCCTCC TGATCCAGGC GGTCGGCGCC CGCATCGACC AATATTACGA CCGCGCCTGG   4860
GGCGCTGGCG AAAAGCGCGG TACGCGCCTC GTCGTCATCG GCCTGCACGA CATGGACGAG   4920
GCGGCGGTGC GCGCCGCGAT CACCGCGCTC GTGTAGATCG TTCTTTGAAT GAAATGATCT   4980
AACGCATTGA AATGATGCAG TTCCGGATGG AGAACGCTTT TAGCGTTTTC GTTCGGAATT   5040
GCCCCAACGG ACAAGACGAA TGCATCTGCT TCTCGCCCAG AAAGGAACGA TCGCCGACGG   5100
CAACGAGGCG ATCGACCTTG GGCAAACGCC GGCCGATATC CTTTTCCTAT CGGCCGCCGA   5160
CACCGAGCTC TCCTCGATCG CCGCGGCTCA CGGCCGACGC GACGGAGGCT TGAGCCTGCG   5220
CATCGCCAGC CTGATGAGCC TGATGCACCC GATGTCGGTC GACACTTACG TCGAGCGCAC   5280
GGCGCGTCAC GCCAAGCTGA TCGTCGTCCG GCCGCTCGGT GGCGCCAGCT ATTTCCGTTA   5340
TCTGCTGGAA GCCCTGCATG CGGCTGCCGT CACCCATCGT TTCGAGATCG CGGTTCTGCC   5400
```

-continued

```
GGGTGACGAC AAGCCGGATC CGGGGCTGGA GCCTTTCTCC ACCGTCGCAG CCGACGACCG   5460
CCAGCGCCTT TGGGCTTACT TCACCGAAGG CGGCTCGGAC AATGCCGGGC TGTTTCTCGA   5520
CTATGCGGCC GCACTGGTCA CAGGTGCGGA GAAGCCGCAG CCGGCAAAGC CCCTGTTGAA   5580
GGCCGGCATC TGGTGGCCGG GTGCTGGTGT GATCGGCGTC AGCGAATGGC AGTCCCTTGT   5640
TCAGGGACGG ATGGTAGCGA GGGAGGGATT CGAACCCCCG ACGGTCGGGA TCTGCTTTTA   5700
CCGCGCGCTC GTGCAGAGTG GCGAGACACG GCCTGTGGAG GCGCTGATCG ATGCGCTGGA   5760
GGCTGAAGGT GTGCGGGCAC TGCCGGTGTT TGTCTCAAGC CTCAAGGATG CCGTTTCCGT   5820
CGGCACGCTG CAGGCGATTT TTTCCGAGGC CGCACCCGAC GTGGTGATGA ACGCCACTGG   5880
CTTTGCGGTC TCGTCGCCCG GTGCCGACCG TCAGCCGACG GTGCTGGAAT CGACCGGTGC   5940
GCCGGTGCTG CAGGTGATTT TCTCCGGCTC GTCGCGGGCG CAATGGGAAA CGTCGCCGCA   6000
GGGGCTGATG GCGCGCGACC TCGCCATGAA CGTGGCACTC CCCGAAGTCG ATGGCCGCAT   6060
CCTTGCGCGC GCCGTCTCCT TCAAGGCGGC GTCGATCTAT GACGCCAAGG TGGAGGCCAA   6120
TATCGTCGGC CATGAGCCGC TCGAAGGCCG GGTGCGCTTT GCCGCTGATC TTGCCGTCAA   6180
CTGGGCGAAC GTGCGCCGGG CAGAGCCCGC CGAGCGCCGT ATTGCCATCG TCATGGCCAA   6240
CTATCCGAAC CGCGACGGTC GCCTCGGCAA CGGTGTCGGG CTCGACACGC CGGCCGGTAC   6300
CGTCGAGGTG CTTAGCGCCA TGGCGCGGGA AGGCTATGCG GTCGGTGAGG TTCCCGCCGA   6360
TGGCGACGCG CTGATCCGCT TTCTGATGGC CGGGCCGACC AATGCGGCGA GCCATGACCG   6420
TGAAATCCGC GAGCGTATTT CGCTGAACGA TTACAAAACG TTCTTCGATT CGCTTCCGAA   6480
ACAGATAAAG GATGAAGTTG CCGGTCGCTG GGGCGTGCCG GAGGCCGATC CCTTTTTCCT   6540
CGATGGCGCC TTCGCGCTGC CGCTCGCCCG CTTCGGCGAG GTGATCGTCG GCATCCAACC   6600
GGCGCGCGGC TACAACATCG ATCCGAAGGA AAGCTACCAT TCCCCGGACC TCGTGCCGCC   6660
GCATGGCTAT CTCGCCTTCT ACGCCTTCCT GCGCCAGCAG TTCGGAGCGC AGGCGATCGT   6720
CCACATGGGC AAGCACGGCA ATCTCGAATG GCTGCCGGGC AAGGCGCTGG CGCTGTCGGA   6780
AACCTGCTAT CCCGAAGCGA TCTTCGGGCC GCTGCCGCAC ATCTATCCCT TCATCGTCAA   6840
CGATCCGGGC GAAGGTACGC AGGCCAAGCG CCGCACCAGC GCCGTCATCA TCGACCACCT   6900
GACCCCGCCC TTGACGCGCG CCGAATCCTA CGGCCCGCTC AAGGATCTGG AAGCGCTCGT   6960
CGACGAATAT TACGACGCCG CCGGCGGTGA TCCGCGCCGC CTCAGGCTGC TCAGCCGCCA   7020
GATCCTCGAT CTCGTGCGCG ACATCGGCCT CGACAGCGAC GCAGGCATCG ACAGGGGCGA   7080
CAGCGACGAC AAGGCGCTGG AAAAGCTCGA CGCCTATCTC TGCGACCTCA AGGAAATGCA   7140
GATCCGCGAC GGCCTGCACA TCTTCGGCGT TGCGCCGGAA GGGCGGTTGT TGACGGACCT   7200
CACCGTAGCG CTGGCGCGCG TGCCCCGAGG TCTCGGCGAG GGCGGCGACC AGAGCCTGCA   7260
GCGGGCGATC GCAGCGGATG CGGGGCTGCG TGGGTTTGCT ATTCCCACCT CGGCGGGGGG   7320
CAACCCCGCA CGCGACGCCC AACCCTTCGA CCCGCTCGAC TGCGTCATGT CCGACACCTG   7380
GACAGGCCCG AAACCGTCCA TCCTCGCTGA CCTCTCGGAC GCCCCCTGGC GCACCGCCGG   7440
CGATACGGTC GAGCGCATCG AGTTGCTTGC CGCAAATCTC GTGTCGGGTG AACTGGCTTG   7500
CCCGGACCAC TGGGCCAACA CCCGCGCCGT GCTCGGCGAA ATCGAAACGC GCCTGAAGCC   7560
GTCGATTTCA AACTCGGGTG CCGCCGAGAT GACCGGCTTC CTCACCGGTC TCAGCGGCCG   7620
CTTCGTCGCC CCCGGTCCAT CGGGCGCGCC GACGCGCGGC CGGCCGGATG TGTTGCCGAC   7680
GGGGCGCAAT TTCTACTCGG TCGACAGCCG CGCCGTGCCG ACGCCGGCGG CTTACGAGCT   7740
TGGCAAGAAA TCGGCCGAGC TTCTGATCCG CCGCTACCTG CAGGACCATG GCGAATGGCC   7800
```

-continued

```
GTCCTCCTTT GGCCTGACCG CCTGGGGCAC GGCGAACATG CGCACCGGCG GCGACGACAT   7860
CGCCCAGGCC CTGGCGCTGA TCGGCGCCAA GCCCACCTGG GACATGGTCT CTCGCCGGGT   7920
GATGGGCTAC GAGATCGTGC CGCTCGCAGT CCTCGGCCGC CCACGCGTCG ACGTGACCTT   7980
GCGCATTTCC GGCTTCTTCC GCGATGCCTT CCCGGACCAG ATCGCGCTCT TCGACAAGGC   8040
GATCCGCGCC GTCGCGCTGG AGGAAGACGA TGCCGACAAC ATGATCGCCG CACGCATGCG   8100
GGCGGAAAGC CGGCGGCTGG AGGCCGAAGG CGTGGAAGCC GCCGAGGCCG CGCGTCGCGC   8160
CTCCTACCGC GTCTTTGGCG CAAAGCCCGG TGCCTATGGC GCCGCCCTGC AGGCGCTGAT   8220
CGACGAGAAG GGCTGGGAAA CCAAAGCAGA TCTCGCCGAG GCCTATCTTA CCTGGGGCGC   8280
CTATGCCTAT GGCGCCGGCG AGGAGGGCAA GGCCGAGCGC GATCTTTTCG AGGAGCGCCT   8340
GCGCACGATA GAGGCGGTGG TGCAGAACCA GGACAACCGC GAGCACGATC TGCTCGACAG   8400
CGACGACTAC TACCAGTTCG AAGGCGGCAT GAGCGCTGCC GCCGAACAGC TCGGCGGTCA   8460
CCGTCCGGCG ATCTACCACA ACGACCATTC CCGTCCGGAA AAGCCTGTGA TCCGGTCGCT   8520
CGAAGAAGAG ATCGGCCGCG TGGTCCGGGC CCGCGTCGTC AATCCCAAGT GGATCGATGG   8580
CGTCATGCGC CACGGATACA AGGGCGCCTT CGAGATCGCT GCCACGGTCG ACTACATGTT   8640
CGCCTTTGCC GCGACCACGG GTGCGGTGCG CGACCATCAT TTCGAGGCCG CTTATCAGGC   8700
GTTCATTGTC GACGAGCGCG TGGCTGACTT CATGCGCGAC AAGAACCCGG CCGCCTTTGC   8760
CGAGCTTGCC GAACGCCTGC TTGAAGCAAT CGACCGCAAT CTCTGGACGC CGCGCTCGAA   8820
TTCGGCGCGG TTTGAACTTG CCGGCATCGG CACGGCAGCA ACCCGGCTTC GTGCCGGCAA   8880
TGAATAGAGC GGTTCCGGGC TGGCGGTTAT CCGTCCGGAA TTGCTTGGAA ACAAAGACCT   8940
GGTTCCGTTT CGCTGCTCAG TGAAGTGCGA AAAGGAACCG AAGCGGGACG AGGGCGTCTG   9000
CCCATCCCGA ACTTGAGAAC TGAGGGAGTG ATCATGAGCG ACGAGACGAC AGTAGGCGGC   9060
GAAGCCCCGG CCGAGAAGGA CGATGCCCGC CACGCCATGA AGATGGCGAA GAAGAAGGCA   9120
GCACGCGAAA AGATCATGGC GACGAAGACC GACGAGAAGG GTCTGATCAT CGTCAACACC   9180
GGCAAAGGCA AGGGCAAGTC GACCGCCGGC TTCGGCATGA TCTTCCGCCA TATCGCCCAC   9240
GGCATGCCCT GCGCCGTCGT GCAGTTCATC AAGGGTGCGA TGGCAACCGG CGAGCGCGAG   9300
TTGATCGAGA AGCATTTCGG CGATGTCTGC CAGTTCTACA CGCTCGGCGA GGGCTTCACC   9360
TGGGAAACGC AGGATCGCGC CCGCGATGTT GCGATGGCTG AAAAGGCCTG GGAGAAGGCG   9420
AAGGAACTGA TCCGTGACGA GCGCAACTCG ATGGTGCTGC TCGACGAGAT CAACATTGCT   9480
CTGCGCTACG ACTACATCGA CGTCGCCGAA GTGGTGCGCT TCCTGAAGGA AGAAAAGCCG   9540
CACATGACGC ATGTGGTGCT CACCGGCCGC AACGCGAAAG AAGACCTGAT CGAAGTCGCC   9600
GATCTCGTCA CTGAGATGGA GCTGATCAAG CATCCGTTCC GTTCCGGCAT CAAGGCGCAG   9660
CAGGGCGTGG AGTTCTGATG AGCCAGAGCT GGCAGTTCTG GGCGCTGCTT TCGGCCGCCT   9720
TCGCTGCGCT CACGGCGGTG TTTGCCAAGG TCGGGGTTGC GCAGATCAAC TCCGACTTCG   9780
CAACGCTGAT CCGCACCGTC GTCATCCTCT GCGTGATCGC CGCCATCGTG GCGGCGACAG   9840
GGCAGTGGCA GAAGCCATCG GAAATCCCGG GCCGCACCTG GCTGTTCCTG GCGCTGTCAG   9900
GGCTTGCGAC TGGCGCTTCC TGGCTTGCCT ATTTCCGCGC GCTGAAGCTC GGCGACGCCG   9960
CCCGCGTGGC GCCGCTCGAC AAGCTCTCGA TCGTCATGGT CGCGATCTTC GGCGTGCTCT  10020
TCCTCGGTGA AAAGCTCAAC CTGATGAACT GGCTCGGCGT CGCCTTCATT GCCGCCGGGG  10080
CGCTGTTGCT GGCGGTGTTT TGAGCGCGCC TGCTCTGGTG CCTGTTCACT GAATGCTCGC  10140
```

-continued

```
CTCAATCAAT CCGTAATCCC GACACATGCA GTGGTTGTGA CGAGCGGGAG GACGGCATGC  10200
AGATTGAAGG CAATTGGAGC GAGCGCCTTC CTGATCCGTC GGGCCACGTC GCGCAGTTCG  10260
GCAGACGCTG GAAGCGTCGC AGCCTGAGGG TGAGCCCTGC TTCAGACCCA CCGGCGGACA  10320
CGCCTGCAAT AGGCACCGTA GGCGTCGCCG AAGACCTTGG CGAGGTGGGT TTCCTCCATG  10380
CGGATCTGGT AGGAAATCGA GATCCAGGCG GAGAGCGCCA GCGCCACCGA GATGACGTTG  10440
GGCACCGCCA TCACCGTGCC GATCAGCGCG GTCACCATGC CGACATAGAT CGGGTTGCGC  10500
GAGAAGGCAT AGAGGCCTGA GGTCACAAGC GGCGCGTCCT GCTTTTCAGG GATGCCGATC  10560
TTCCAGGAAT GACGCATCGC CCATTGCGAC AGCATCGTCA GCCCGCCGCC GAGCGTCATC  10620
AGCGCCAGGC CGACGGCGTG AAGGATGGGC GTGTCGAGCG CCGGGATCCG GCCGAGGGCA  10680
GCATCGACGG AGGCCGGGAG CATGGCGACC GCCAGCAGGT GGATCACCAG CGCTGCGACG  10740
ATCAGGCGGA AAAGCCTGCC CGCAAACCCT TCCGCATCGT CGCCATAGGT TAGCACGACC  10800
GGCGAGCGGC CGGATTGCAC GCGGCGGAGG ATCGCCAGCG CGAGCGTGGA CAATCCCACG  10860
ACGAGCATCA GGATGGTGGG AAGGGTGGTG GACATGGAAA CCTCTGGAGC GAGCTGACAA  10920
GACAGGAGCG CACGACGGGT AGGCGGCCCA TATGAGCGTC TACCCGGCGA AGCATTCTGA  10980
TCACCTTGCA ATCTCTAGTA ACTAGAGGTT CAAGCGTCGG ACCTGTCCGA CTTTCGTCGT  11040
GGTTACCGGA TCTTATTGCC AAGCGTTGGA GGCTGTCATC GTCGCCCCCG CCGTGTCGGA  11100
AGGTCGGCAA AATTCGTCTC TTGACGGCTG CTCCTTCCGT CGAGCGATTG CATAGGCAGG  11160
AGGCCGCACC CATGTTAGAC CGTCGACAGG CTAAATACGG GTGAACCTTG AAGAATACTC  11220
TCAGAGCTGC GGTTGGTGTC GCATCGGTCT TGCTGTTCTT GTCATCAGGT GTGGCGGGGC  11280
AGGCGCAAAC CGTGAAGAGC GGGGCGTCAC GAGCTCAAGA AACGACGACC ACCCAGAAGG  11340
CGAAACCGAA AACTAAAACG ACGCGCAAGC AAAGGGCTGC GGATGAAGCC AAGGCCAAGG  11400
CGCTCGCCGA AGCGCGCCGT CCACGGATTT GCAAGACGCG GGAGAGCGAA TGCAGCTATG  11460
GCGCAGGTCC GGTCGGAGAG CAGTGCTCGT GCTGGTCGAA ATCCGGTGCG CCTGATCTTG  11520
GCATAACTGT CAGGCGTTGA CCGCCCGCGA CCTTCGCGCG GGCAGGCAAG CGTGCGTCGC  11580
TCGAAGCGAC GCCTGACGCG ATAGAAATCA CGGGTCGCCT GGTTCGTTCT GAAAGCTTGG  11640
GATTGGGTTT AGGTGATGGA AGCCGGCGTT GAACGCAAAA TAATGATCGA TCTCGAGAAC  11700
AGCGCGCTCC AGTTTGCAAC CCGAGCACAC GGCGAACAGA AGCGTAAGTA TGACGGTCGG  11760
CCCTATATCG TTCATCCGAT TGCGGTGGCG GAGATTGTTC GAAGCGTGCC CCATACGCCC  11820
GAAATGATCG CCGCAGCGCT GCTTCACGAT ACGGTCGAAG ATACCGACGC GACGCTGCTG  11880
GAGATCAAGG AAGCGTTCGG CCCCAAGGTC GCAACACTGG TTGCGTGGCT CACCGACATA  11940
TCCACTCCGT TCCACGGCAA CCGACAGGTG CGCAAGGAAC TGGATCGCCA GCACCTCGCA  12000
TCGGCGCCCG CCGCGGCGAA AACCGTCAAG CTCGCCGACC TGATCGACAA TGCGATAGCG  12060
ATCAAAGCCG GCGATCCGAA TTTCTGGAAA GTGTTCGGCG CCGAGATGAA ACGCTTGCTG  12120
GAGGTCTTGG GCGACGGCGA CGAGACCCTT CTCGCAAAGG CCCGTGCATT AGCGCCGGAA  12180
TGAGAGTGCC GCCGTTTATC GGCAAGCATG TCTGTGCCAT GTCGACCCGG TCAACCGGTC  12240
ATCCAAGATC GCAGAACGGA CATGCATTTG CGGTTTTGCC CGCCGGTGTG GCCCAGCCAC  12300
GCCTCACAGG CTGCGCGGTT GCGGCCGTTA GGACAGCGCA GAATTTGCCG ACCGCGCCGC  12360
GCCTCAATGC CCCAGCCAGA TCCGCAAGGG ATGCGTCGGA TCTGCGAGCA GCCGGATCGC  12420
GAGCGCGATC GAGACGATGA CGAGCAGCGG CTTGATGATC TTGGCGCCCT TGGCCATGGC  12480
ATAGCGCGAG CCGACCTGGG CGCCGAGGAA CTGGCCGAGG CCCATCAACA GGCCGACCTT  12540
```

-continued

```
CCAGAGAACG GCGCCGAAGA AGAGGAAGAC GCCGAAGGCG CCGACGTTGG AGCCAAAGTT  12600

GAGGAACTTC GTGTGCGCCG TCGCCTTCAA CACGCCGAAG CCGGCGAGGG TAACGAAGCC  12660

GAGCATGAAG AACGAGCCGG TGCCGGGGCC GAAGACGCCG TCATAAAAGC CGATTAGCGG  12720

CACCAGTGTC AGCGTGAAGA CGAAGGGGGT GACGCGGCTG TGCTGGTCGA CGTCGCCCAT  12780

GTTCGGCTTC AGGCCGAAAT AAAGCGCAAT GGCGATCAGC AGAAAGGGCA GGATCGCCTT  12840

CAGCACGTCG CCGGGAACGA TGGTTGCGAG CAGGGCGCCG AGCACGGCGC CGGCGGCCGA  12900

CATCAGCGCC ATCGGCAGCT GCTCTTTCAG GTTCACGTGG CCGCGCCGGG CATAGGACAG  12960

CGTGGCCGAG CCGGAGCCGA ACAATCCCTG CAGCTTGTTG GTGCCGAGCG TCTGCAAGGG  13020

CGGGATGCCC GCAATGAGCA TGGCCGGAAT GGTGATCATG CCACCGCCGC CGGCGATCGA  13080

ATCGATGAAG CCTGCGATGA AGGCGGCGAC GAACAGGAAG GCGAGCAGGT GGAAGGCGAG  13140

ATCT                                                               13144
```

(2) INFORMATION FOR SEQ ID NO: 42:

(i) SEQUENCE CHARACTERISTICS:
(A) LENGTH: 1458 base pairs
(B) TYPE: Nucleic acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobQ
(B) LOCATION: 429-1886 bp of SEQ ID NO:41
(C) IDENTIFICATION METHOD:
(D) OTHER INFORMATION:

(xi) SEQUENCE DESCRIPTION: SEQ ID NO: 42:

```
ATGACACGCA GGATCATGTT GCAGGGAACC GGCTCGGATG TCGGAAAATC GGTATTGGTG     60

GCGGGGCTCT GCCGGCTTGC CGCCAATCAG GGCCTGAAGG TCCGGCCGTT CAAGCCGCAG    120

AACATGTCGA ACAACGCCGC CGTTTCCGAC GACGGCGGCG AGATCGGCCG CGCGCAATGG    180

CTGCAGGCGC TGGCCGCGCG CGTGCCGTCG TCGGTGCACA TGAACCCGGT GCTCCTGAAG    240

CCGCAGTCGG ACGTGGGCAG CCAGATCGTC GTTCAGGGCA AGGTCGCCGG GCAGGCCAGG    300

GGGCGGGAAT ATCAGGCGCT CAAGCCCAAG CTGCTGGGCG CCGTCATGGA GAGTTTCGAA    360

CAAATATCGG CCGGTGCCGA TCTCGTGGTG GTCGAAGGCG CCGGCTCGCC GGCCGAAATC    420

AACCTCAGGC CCGGCGACAT CGCCAATATG GGCTTTGCGA CACGGGCCAA TGTGCCGGTC    480

GTGCTGGTCG GCGACATCGA CCGCGGGGGG GTGATCGCCT CGCTGGTCGG CACGCATGCG    540

ATCCTGCCCG AGGAAGACCG GCGCATGGTG ACCGGCTATC TCATCAACAA GTTCCGCGGC    600

GACGTCACGC TGTTCGACGA CGGCATTGCT GCCGTCAACC GCTACACCGG CTGGCCCTGC    660

TTCGGCGTCG TGCCGTGGCT GAAGGCGGCG GCACGCCTGC CGGCGGAAGA TTCCGTCGTG    720
```

-continued

```
CTGGAGAAGC TGACGCGCGG CGAGGGGCGG GCGCTGAAGG TTGCCGTCCC GGTACTGTCG    780

CGCATCGCCA ATTTCGACGA CCTCGATCCG CTCGCCGCCG AACCGGAGAT TGATCTCGTC    840

TTCGTGCGGC CTGGCAGTCC CATTCCGGTC GACGCTGGCC TCGTCGTCAT TCCCGGGTCG    900

AAATCGACCA TCGGCGACCT CATCGATTTC CGTGCGCAAG GGTGGGACCG TGACCTCGAA    960

CGTCATGTGC GCCGGGGCGG CCGGGTCATC GGCATCTGCG GCGGCTACCA GATGCTCGGC   1020

CGGCGCGTCA CCGATCCGCT CGGCATCGAG GGCGGCGAAC GTGCGGTCGA GGGCCTCGGG   1080

CTGCTCGAGG TCGAGACCGA GATGGCGCCG GAAAAGACGG TGCGCAACAG CCGCGCCTGG   1140

TCGCTGGAGC ATGATGTGGT GCTCGAAGGC TACGAAATCC ATCTTGGCAA GACGCAAGGT   1200

GCGGACTGTG GCCGGCCGTC GGTGCGCATC GACAATCGCG CCGACGGCGC CCTTTCGGCC   1260

GATGGCCGCG TGATGGGCAC CTACCTGCAT GGGCTCTTCA CCAGCGACGC CTATCGCGGC   1320

GCGCTGCTCA AGAGTTTCGG CATCGAAGGC GGCGCCAACA ACTACCGCCA ATCGGTCGAT   1380

GCGGCGCTCG ACGATGTCGC GAACGAACTG GAGGCTGTGC TCGATCGTCG CTGGCTGGAC   1440

GAGTTGCTCA GGCACTAG                                                 1458
```

(2) INFORMATION FOR SEQ ID NO: 43:

(i) SEQUENCE CHARACTERISTICS:
(A) LENGTH: 485 amino acids
(B) TYPE: Amino acid
(C) STRANDEDNESS:
(D) TOPOLOGY: linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBQ
(B) LOCATION:
(C) IDENTIFICATION METHOD:
(D) OTHER INFORMATION: Translation product of SEQ ID NO:42

(xi) SEQUENCE DESCRIPTION: SEQ ID NO: 43:

```
Met Thr Arg Arg Ile Met Leu Gln Gly Thr Gly Ser Asp Val Gly Lys
1               5                   10                  15

Ser Val Leu Val Ala Gly Leu Cys Arg Leu Ala Ala Asn Gln Gly Leu
            20                  25                  30

Lys Val Arg Pro Phe Lys Pro Gln Asn Met Ser Asn Asn Ala Ala Val
        35                  40                  45

Ser Asp Asp Gly Gly Glu Ile Gly Arg Ala Gln Trp Leu Gln Ala Leu
    50                  55                  60

Ala Ala Arg Val Pro Ser Ser Val His Met Asn Pro Val Leu Leu Lys
65                  70                  75                  80

Pro Gln Ser Asp Val Gly Ser Gln Ile Val Val Gln Gly Lys Val Ala
                85                  90                  95

Gly Gln Ala Arg Gly Arg Glu Tyr Gln Ala Leu Lys Pro Lys Leu Leu
            100                 105                 110
```

-continued

```
Gly Ala Val Met Glu Ser Phe Glu Gln Ile Ser Ala Gly Ala Asp Leu
        115                 120                 125

Val Val Val Glu Gly Ala Gly Ser Pro Ala Glu Ile Asn Leu Arg Pro
    130                 135                 140

Gly Asp Ile Ala Asn Met Gly Phe Ala Thr Arg Ala Asn Val Pro Val
145                 150                 155                 160

Val Leu Val Gly Asp Ile Asp Arg Gly Gly Val Ile Ala Ser Leu Val
                165                 170                 175

Gly Thr His Ala Ile Leu Pro Glu Glu Asp Arg Arg Met Val Thr Gly
            180                 185                 190

Tyr Leu Ile Asn Lys Phe Arg Gly Asp Val Thr Leu Phe Asp Asp Gly
        195                 200                 205

Ile Ala Ala Val Asn Arg Tyr Thr Gly Trp Pro Cys Phe Gly Val Val
    210                 215                 220

Pro Trp Leu Lys Ala Ala Ala Arg Leu Pro Ala Glu Asp Ser Val Val
225                 230                 235                 240

Leu Glu Lys Leu Thr Arg Gly Glu Gly Arg Ala Leu Lys Val Ala Val
                245                 250                 255

Pro Val Leu Ser Arg Ile Ala Asn Phe Asp Asp Leu Asp Pro Leu Ala
            260                 265                 270

Ala Glu Pro Glu Ile Asp Leu Val Phe Val Arg Pro Gly Ser Pro Ile
        275                 280                 285

Pro Val Asp Ala Gly Leu Val Val Ile Pro Gly Ser Lys Ser Thr Ile
    290                 295                 300

Gly Asp Leu Ile Asp Phe Arg Ala Gln Gly Trp Asp Arg Asp Leu Glu
305                 310                 315                 320

Arg His Val Arg Arg Gly Gly Arg Val Ile Gly Ile Cys Gly Gly Tyr
                325                 330                 335

Gln Met Leu Gly Arg Arg Val Thr Asp Pro Leu Gly Ile Glu Gly Gly
            340                 345                 350

Glu Arg Ala Val Glu Gly Leu Gly Leu Leu Glu Val Glu Thr Glu Met
        355                 360                 365

Ala Pro Glu Lys Thr Val Arg Asn Ser Arg Ala Trp Ser Leu Glu His
    370                 375                 380

Asp Val Val Leu Glu Gly Tyr Glu Ile His Leu Gly Lys Thr Gln Gly
385                 390                 395                 400

Ala Asp Cys Gly Arg Pro Ser Val Arg Ile Asp Asn Arg Ala Asp Gly
                405                 410                 415

Ala Leu Ser Ala Asp Gly Arg Val Met Gly Thr Tyr Leu His Gly Leu
            420                 425                 430

Phe Thr Ser Asp Ala Tyr Arg Gly Ala Leu Leu Lys Ser Phe Gly Ile
        435                 440                 445

Glu Gly Gly Ala Asn Asn Tyr Arg Gln Ser Val Asp Ala Ala Leu Asp
    450                 455                 460

Asp Val Ala Asn Glu Leu Glu Ala Val Leu Asp Arg Arg Trp Leu Asp
465                 470                 475                 480

Glu Leu Leu Arg His
                485
```

(2) INFORMATION FOR SEQ ID NO: 44:

(i) SEQUENCE CHARACTERISTICS:
(A) LENGTH: 525 base pairs
(B) TYPE: Nucleic acid
(C) STRANDEDNESS: Double -continued (D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobP
(B) LOCATION: 3364-3888 bp of SEQ ID NO:41
(C) IDENTIFICATION METHOD:
(D) OTHER INFORMATION:

(xi) SEQUENCE DESCRIPTION: SEQ ID NO: 44:

```
ATGAGCAGTC TCAGCGCCGG GCCCGTGCTG GTCCTTGGCG GCGCCCGTTC CGGCAAGTCC     60

AGCTTTTCCG AGAGGCTCGT CGAAGCGTCC GGCTTCACCA TGCATTATGT CGCCACGGGC    120

CGCGCCTGGG ACGACGAAAT GCGCGAGCGC ATCGACCATC ACCGGACGCG CCGCGGCGAG    180

GGCTGGACGA CGCATGAGGA GCCGCTCGAT CTCGTCGGCA TCCTCAGACG CATCGATGAT    240

CCCAGCCATG TGGTCCTGAT CGACTGCCTG ACGCTATGGG TCACCAATCT CATGCTGGAA    300

GAGCGCGACA TGACGGCGGA GTTCGCCGCC CTTGTTGCGT ATCTGCCCGA GGCGCGGGCG    360

CGCCTCGTCT TTGTTTCCAA TGAGGTCGGC CTCGGCATCG TGCCCGAGAA CCGCATGGCC    420

CGCGAGTTTC GCGACCATGC CGGCCGGCTT CACCAGATCG TTGCGGAGAA ATCCGCTGAA    480

GTTTACTTTG TCGCGGCCGG TTTGCCGCTG AAAATGAAGG GTTGA                    525
```

(2) INFORMATION FOR SEQ ID NO: 45:

(i) SEQUENCE CHARACTERISTICS:
(A) LENGTH: 174 amino acids
(B) TYPE: Amino acid
(C) STRANDEDNESS:
(D) TOPOLOGY: Linear (ii) MOLECULE TYPE: Protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBP
(B) LOCATION:
(C) IDENTIFICATION METHOD:
(D) OTHER INFORMATION: Translation product of SEQ ID NO:44

(xi) SEQUENCE DESCRIPTION: SEQ ID NO: 45:

```
Met Ser Ser Leu Ser Ala Gly Pro Val Leu Val Leu Gly Gly Ala Arg
1               5                   10                  15

Ser Gly Lys Ser Ser Phe Ser Glu Arg Leu Val Glu Ala Ser Gly Phe
```

-continued

```
            20                  25                  30

Thr Met His Tyr Val Ala Thr Gly Arg Ala Trp Asp Asp Glu Met Arg
        35                  40                  45

Glu Arg Ile Asp His His Arg Thr Arg Arg Gly Glu Gly Trp Thr Thr
    50                  55                  60

His Glu Glu Pro Leu Asp Leu Val Gly Ile Leu Arg Arg Ile Asp Asp
65                  70                  75                  80

Pro Ser His Val Val Leu Ile Asp Cys Leu Thr Leu Trp Val Thr Asn
                85                  90                  95

Leu Met Leu Glu Glu Arg Asp Met Thr Ala Glu Phe Ala Ala Leu Val
            100                 105                 110

Ala Tyr Leu Pro Glu Ala Arg  Ala Arg Leu Val Phe Val Ser Asn Glu
        115                  120                 125

Val Gly Leu Gly Ile Val Pro Glu Asn Arg Met Ala Arg Glu Phe Arg
    130                 135                 140

Asp His Ala Gly Arg Leu His Gln Ile Val Ala Glu Lys Ser Ala Glu
145                 150                 155                 160

Val Tyr Phe Val Ala Ala Gly Leu Pro Leu Lys Met Lys Gly
                165                 170
```

(2) INFORMATION FOR SEQ ID NO: 46:

(i) SEQUENCE CHARACTERISTICS:
(A) LENGTH: 1065 base pairs
(B) TYPE: Nucleic acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobW
(B) LOCATION: 3892-4956 bp of SEQ ID NO:41
(C) IDENTIFICATION METHOD:
(D) OTHER INFORMATION:

(xi) SEQUENCE DESCRIPTION: SEQ ID NO: 46:

```
ATGACCACTG CGAGAGCCAA CCAGGGCAAG ATCCCGGCGA CCGTCATCAC CGGCTTCCTC     60

GGCGCCGGCA AGACGACGAT GATCCGCAAC CTGCTGCAGA ACGCCGACGG CAAGCGCATC    120

GGCCTGATCA TCAACGAGTT CGGCGATCTT GGCGTCGACG GCGATGTCTT GAAGGGCTGC    180

GGTGCCGAGG CCTGCACCGA GGACGACATC ATCGAGCTCA CCAATGGCTG CATCTGCTGC    240

ACCGTGGCTG ACGATTTCAT CCCGACCATG ACGAAGCTGC TCGAGCGTGA AAACCGTCCT    300

GACCACATCA TCATCGAAAC CTCGGGCCTT GCCCTGCCGC AGCCGCTGAT CGCCGCTTTC    360

AACTGGCCGG ATATCCGCAG CGAAGTGACC GTCGATGGCG TCGTCACCGT GGTCGACAGC    420

GCCGCCGTTG CCGCTGGCCG CTTTGCCGAC GACCACGACA AGGTCGATGC GCTGCGCGTC    480

GAGGACGACA ATCTCGATCA CGAAAGCCCG ATCGAGGAGC TGTTCGAGGA TCAACTGACG    540
```

-continued

```
GCTGCCGATC TCATCGTTCT CAACAAGACC GATCTGATCG ATGCCTCCGG CCTCAAGGCC    600

GTGCGCGACG AGGTGTCTTC GCGCACCAGC CGCAAGCCCA CGATGATCGA GGCGAAAAAC    660

GGCGAAGTCG CCGCTGCCAT CCTGCTTGGC CTCGGTGTCG GCACGGAAAG CGATATCGCC    720

AACCGCAAGT CGCATCACGA GATGGAGCAC GAGGCAGGTG AGGAGCACGA TCACGACGAG    780

TTCGACAGCT TCGTCGTCGA GCTCGGTTCG ATCGCCGATC CGGCCGCCTT CATCGATCGC    840

CTGAAGGGCG TAATCGCGGA GCACGACGTT CTGCGCCTCA AGGGTTTTGC AGACGTGCCC    900

GGCAAGCCGA TGCGCCTCCT GATCCAGGCG GTCGGCGCCC GCATCGACCA ATATTACGAC    960

CGCGCCTGGG GCGCTGGCGA AAAGCGCGGT ACGCGCCTCG TCGTCATCGG CCTGCACGAC   1020

ATGGACGAGG CGGCGGTGCG CGCCGCGATC ACCGCGCTCG TGTAG                   1065
```

(2) INFORMATION FOR SEQ ID NO: 47:

(i) SEQUENCE CHARACTERISTICS:
(A) LENGTH: 354 amino acids
(B) TYPE: Amino acid
(C) STRANDEDNESS:
(D) TOPOLOGY: Linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBW
(B) LOCATION:
(C) IDENTIFICATION METHOD:
(D) OTHER INFORMATION: Translation product of SEQ ID NO:46

(xi) SEQUENCE DESCRIPTION: SEQ ID NO: 47:

```
Met Thr Thr Ala Arg Ala Asn Gln Gly Lys Ile Pro Ala Thr Val Ile
1               5                   10                  15

Thr Gly Phe Leu Gly Ala Gly Lys Thr Thr Met Ile Arg Asn Leu Leu
            20                  25                  30

Gln Asn Ala Asp Gly Lys Arg Ile Gly Leu Ile Ile Asn Glu Phe Gly
        35                  40                  45

Asp Leu Gly Val Asp Gly Asp Val Leu Lys Gly Cys Gly Ala Glu Ala
    50                  55                  60

Cys Thr Glu Asp Asp Ile Ile Glu Leu Thr Asn Gly Cys Ile Cys Cys
65                  70                  75                  80

Thr Val Ala Asp Asp Phe Ile Pro Thr Met Thr Lys Leu Leu Glu Arg
                85                  90                  95

Glu Asn Arg Pro Asp His Ile Ile Ile Glu Thr Ser Gly Leu Ala Leu
            100                 105                 110

Pro Gln Pro Leu Ile Ala Ala Phe Asn Trp Pro Asp Ile Arg Ser Glu
        115                 120                 125

Val Thr Val Asp Gly Val Val Thr Val Val Asp Ser Ala Ala Val Ala
    130                 135                 140

Ala Gly Arg Phe Ala Asp Asp His Asp Lys Val Asp Ala Leu Arg Val
145                 150                 155                 160
```

-continued

```
Glu Asp Asp Asn Leu Asp His Glu Ser Pro Ile Glu Glu Leu Phe Glu
                165                 170                 175

Asp Gln Leu Thr Ala Ala Asp Leu Ile Val Leu Asn Lys Thr Asp Leu
            180                 185                 190

Ile Asp Ala Ser Gly Leu Lys Ala Val Arg Asp Glu Val Ser Ser Arg
        195                 200                 205

Thr Ser Arg Lys Pro Thr Met Ile Glu Ala Lys Asn Gly Glu Val Ala
    210                 215                 220

Ala Ala Ile Leu Leu Gly Leu Gly Val Gly Thr Glu Ser Asp Ile Ala
225                 230                 235                 240

Asn Arg Lys Ser His His Glu Met Glu His Glu Ala Gly Glu Glu His
                245                 250                 255

Asp His Asp Glu Phe Asp Ser Phe Val Val Glu Leu Gly Ser Ile Ala
            260                 265                 270

Asp Pro Ala Ala Phe Ile Asp Arg Leu Lys Gly Val Ile Ala Glu His
        275                 280                 285

Asp Val Leu Arg Leu Lys Gly Phe Ala Asp Val Pro Gly Lys Pro Met
    290                 295                 300

Arg Leu Leu Ile Gln Ala Val Gly Ala Arg Ile Asp Gln Tyr Tyr Asp
305                 310                 315                 320

Arg Ala Trp Gly Ala Gly Glu Lys Arg Gly Thr Arg Leu Val Val Ile
                325                 330                 335

Gly Leu His Asp Met Asp Glu Ala Ala Val Arg Ala Ala Ile Thr Ala
            340                 345                 350

Leu Val
```

(2) INFORMATION FOR SEQ ID NO: 48:

(i) SEQUENCE CHARACTERISTICS:
- (A) LENGTH: 3828 base pairs
- (B) TYPE: Nucleic acid
- (C) STRANDEDNESS: Double
- (D) TOPOLOGY: Unknown (ii) MOLECULE TYPE: cDNA (iii) HYPOTHETICAL: No (iv) ORIGINAL SOURCE:
- (A) ORGANISM: Pseudomonas denitrificans
- (B) STRAIN:
- (C) INDIVIDUAL ISOLATE:
- (D) DEVELOPMENTAL STAGE:
- (E) HAPLOTYPE:
- (F) TISSUE TYPE:
- (G) CELL TYPE:
- (H) CELL LINE:
- (I) ORGANELLE:

(ix) FEATURE:
- (A) NAME/KEY: cobN
- (B) LOCATION: 5060-8887 bp of SEQ ID NO:41
- (C) IDENTIFICATION METHOD:
- (D) OTHER INFORMATION:

(xi) SEQUENCE DESCRIPTION: SEQ ID NO: 48:

```
ATGCATCTGC TTCTCGCCCA GAAAGGAACG ATCGCCGACG GCAACGAGGC GATCGACCTT     60

GGGCAAACGC CGGCCGATAT CCTTTTCCTA TCGGCCGCCG ACACCGAGCT CTCCTCGATC    120

GCCGCGGCTC ACGGCCGACG CGACGGAGGC TTGAGCCTGC GCATCGCCAG CCTGATGAGC    180

CTGATGCACC CGATGTCGGT CGACACTTAC GTCGAGCGCA CGGCGCGTCA CGCCAAGCTG    240
```

-continued

```
ATCGTCGTCC GGCCGCTCGG TGGCGCCAGC TATTTCCGTT ATCTGCTGGA AGCCCTGCAT    300

GCGGCTGCCG TCACCCATCG TTTCGAGATC GCGGTTCTGC CGGGTGACGA CAAGCCGGAT    360

CCGGGGCTGG AGCCTTTCTC CACCGTCGCA GCCGACGACC GCCAGCGCCT TTGGGCTTAC    420

TTCACCGAAG GCGGCTCGGA CAATGCCGGG CTGTTTCTCG ACTATGCGGC CGCACTGGTC    480

ACAGGTGCGG AGAAGCCGCA GCCGGCAAAG CCCCTGTTGA AGGCCGGCAT CTGGTGGCCG    540

GGTGCTGGTG TGATCGGCGT CAGCGAATGG CAGTCCCTTG TTCAGGGACG GATGGTAGCG    600

AGGGAGGGAT TCGAACCCCC GACGGTCGGG ATCTGCTTTT ACCGCGCGCT CGTGCAGAGT    660

GGCGAGACAC GGCCTGTGGA GGCGCTGATC GATGCGCTGG AGGCTGAAGG TGTGCGGGCA    720

CTGCCGGTGT TTGTCTCAAG CCTCAAGGAT GCCGTTTCCG TCGGCACGCT GCAGGCGATT    780

TTTTCCGAGG CCGCACCCGA CGTGGTGATG AACGCCACTG GCTTTGCGGT CTCGTCGCCC    840

GGTGCCGACC GTCAGCCGAC GGTGCTGGAA TCGACCGGTG CGCCGGTGCT GCAGGTGATT    900

TTCTCCGGCT CGTCGCGGGC GCAATGGGAA ACGTCGCCGC AGGGGCTGAT GGCGCGCGAC    960

CTCGCCATGA ACGTGGCACT CCCCGAAGTC GATGGCCGCA TCCTTGCGCG CGCCGTCTCC   1020

TTCAAGGCGG CGTCGATCTA TGACGCCAAG GTGGAGGCCA ATATCGTCGG CCATGAGCCG   1080

CTCGAAGGCC GGGTGCGCTT TGCCGCTGAT CTTGCCGTCA ACTGGGCGAA CGTGCGCCGG   1140

GCAGAGCCCG CCGAGCGCCG TATTGCCATC GTCATGGCCA ACTATCCGAA CCGCGACGGT   1200

CGCCTCGGCA ACGGTGTCGG GCTCGACACG CCGGCCGGTA CCGTCGAGGT GCTTAGCGCC   1260

ATGGCGCGGG AAGGCTATGC GGTCGGTGAG GTTCCCGCCG ATGGCGACGC GCTGATCCGC   1320

TTTCTGATGG CCGGGCCGAC CAATGCGGCG AGCCATGACC GTGAAATCCG CGAGCGTATT   1380

TCGCTGAACG ATTACAAAAC GTTCTTCGAT TCGCTTCCGA AACAGATAAA GGATGAAGTT   1440

GCCGGTCGCT GGGGCGTGCC GGAGGCCGAT CCCTTTTTCC TCGATGGCGC CTTCGCGCTG   1500

CCGCTCGCCC GCTTCGGCGA GGTGATCGTC GGCATCCAAC CGGCGCGCGG CTACAACATC   1560

GATCCGAAGG AAAGCTACCA TTCCCCGGAC CTCGTGCCGC CGCATGGCTA TCTCGCCTTC   1620

TACGCCTTCC TGCGCCAGCA GTTCGGAGCG CAGGCGATCG TCCACATGGG CAAGCACGGC   1680

AATCTCGAAT GGCTGCCGGG CAAGGCGCTG GCGCTGTCGG AAACCTGCTA TCCCGAAGCG   1740

ATCTTCGGGC CGCTGCCGCA CATCTATCCC TTCATCGTCA ACGATCCGGG CGAAGGTACG   1800

CAGGCCAAGC GCCGCACCAG CGCCGTCATC ATCGACCACC TGACCCCGCC CTTGACGCGC   1860

GCCGAATCCT ACGGCCCGCT CAAGGATCTG GAAGCGCTCG TCGACGAATA TTACGACGCC   1920

GCCGGCGGTG ATCCGCGCCG CCTCAGGCTG CTCAGCCGCC AGATCCTCGA TCTCGTGCGC   1980

GACATCGGCC TCGACAGCGA CGCAGGCATC GACAGGGGCG ACAGCGACGA CAAGGCGCTG   2040

GAAAAGCTCG ACGCCTATCT CTGCGACCTC AAGGAAATGC AGATCCGCGA CGGCCTGCAC   2100

ATCTTCGGCG TTGCGCCGGA AGGGCGGTTG TTGACGGACC TCACCGTAGC GCTGGCGCGC   2160

GTGCCCCGAG GTCTCGGCGA GGGCGGCGAC CAGAGCCTGC AGCGGGCGAT CGCAGCGGAT   2220

GCGGGGCTGC GTGGGTTTGC TATTCCCACC TCGGCGGGGG GCAACCCCGC ACGCGACGCC   2280

CAACCCTTCG ACCCGCTCGA CTGCGTCATG TCCGACACCT GGACAGGCCC GAAACCGTCC   2340

ATCCTCGCTG ACCTCTCGGA CGCCCCCTGG CGCACCGCCG GCGATACGGT CGAGCGCATC   2400

GAGTTGCTTG CCGCAAATCT CGTGTCGGGT GAACTGGCTT GCCCGGACCA CTGGGCCAAC   2460

ACCCGCGCCG TGCTCGGCGA AATCGAAACG CGCCTGAAGC CGTCGATTTC AAACTCGGGT   2520

GCCGCCGAGA TGACCGGCTT CCTCACCGGT CTCAGCGGCC GCTTCGTCGC CCCCGGTCCA   2580

TCGGGCGCGC CGACGCGCGG CCGGCCGGAT GTGTTGCCGA CGGGGCGCAA TTTCTACTCG   2640
```

-continued

GTCGACAGCC GCGCCGTGCC GACGCCGGCG GCTTACGAGC TTGGCAAGAA ATCGGCCGAG 2700

CTTCTGATCC GCCGCTACCT GCAGGACCAT GGCGAATGGC CGTCCTCCTT TGGCCTGACC 2760

GCCTGGGGCA CGGCGAACAT GCGCACCGGC GGCGACGACA TCGCCCAGGC CCTGGCGCTG 2820

ATCGGCGCCA AGCCCACCTG GGACATGGTC TCTCGCCGGG TGATGGGCTA CGAGATCGTG 2880

CCGCTCGCAG TCCTCGGCCG CCCACGCGTC GACGTGACCT TGCGCATTTC CGGCTTCTTC 2940

CGCGATGCCT TCCCGGACCA GATCGCGCTC TTCGACAAGG CGATCCGCGC CGTCGCGCTG 3000

GAGGAAGACG ATGCCGACAA CATGATCGCC GCACGCATGC GGGCGGAAAG CCGGCGGCTG 3060

GAGGCCGAAG GCGTGGAAGC CGCCGAGGCC GCGCGTCGCG CCTCCTACCG CGTCTTTGGC 3120

GCAAAGCCCG GTGCCTATGG CGCCGCCCTG CAGGCGCTGA TCGACGAGAA GGGCTGGGAA 3180

ACCAAAGCAG ATCTCGCCGA GGCCTATCTT ACCTGGGGCG CCTATGCCTA TGGCGCCGGC 3240

GAGGAGGGCA AGGCCGAGCG CGATCTTTTC GAGGAGCGCC TGCGCACGAT AGAGGCGGTG 3300

GTGCAGAACC AGGACAACCG CGAGCACGAT CTGCTCGACA GCGACGACTA CTACCAGTTC 3360

GAAGGCGGCA TGAGCGCTGC CGCCGAACAG CTCGGCGGTC ACCGTCCGGC GATCTACCAC 3420

AACGACCATT CCCGTCCGGA AAAGCCTGTG ATCCGGTCGC TCGAAGAAGA GATCGGCCGC 3480

GTGGTCCGGG CCCGCGTCGT CAATCCCAAG TGGATCGATG GCGTCATGCG CCACGGATAC 3540

AAGGGCGCCT TCGAGATCGC TGCCACGGTC GACTACATGT TCGCCTTTGC CGCGACCACG 3600

GGTGCGGTGC GCGACCATCA TTTCGAGGCC GCTTATCAGG CGTTCATTGT CGACGAGCGC 3660

GTGGCTGACT TCATGCGCGA CAAGAACCCG GCCGCCTTTG CCGAGCTTGC CGAACGCCTG 3720

CTTGAAGCAA TCGACCGCAA TCTCTGGACG CCGCGCTCGA ATTCGGCGCG GTTTGAACTT 3780

GCCGGCATCG GCACGGCAGC AACCCGGCTT CGTGCCGGCA ATGAATAG 3828

(2) INFORMATION FOR SEQ ID NO: 49:

(i) SEQUENCE CHARACTERISTICS:
(A) LENGTH: 1275 amino acids
(B) TYPE: Amino acid
(C) STRANDEDNESS:
(D) TOPOLOGY: Linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBN
(B) LOCATION:
(C) IDENTIFICATION METHOD:
(D) OTHER INFORMATION: Translation product of SEQ ID NO:48

(xi) SEQUENCE DESCRIPTION: SEQ ID NO: 49:

Met His Leu Leu Leu Ala Gln Lys Gly Thr Ile Ala Asp Gly Asn Glu
1 5 10 15

Ala Ile Asp Leu Gly Gln Thr Pro Ala Asp Ile Leu Phe Leu Ser Ala
20 25 30

-continued

```
Ala Asp Thr Glu Leu Ser Ser Ile Ala Ala Ala His Gly Arg Arg Asp
        35                  40                  45

Gly Gly Leu Ser Leu Arg Ile Ala Ser Leu Met Ser Leu Met His Pro
    50                  55                  60

Met Ser Val Asp Thr Tyr Val Glu Arg Thr Ala Arg His Ala Lys Leu
65                  70                  75                  80

Ile Val Val Arg Pro Leu Gly Gly Ala Ser Tyr Phe Arg Tyr Leu Leu
                85                  90                  95

Glu Ala Leu His Ala Ala Ala Val Thr His Arg Phe Glu Ile Ala Val
            100                 105                 110

Leu Pro Gly Asp Asp Lys Pro Asp Pro Gly Leu Glu Pro Phe Ser Thr
        115                 120                 125

Val Ala Ala Asp Asp Arg Gln Arg Leu Trp Ala Tyr Phe Thr Glu Gly
    130                 135                 140

Gly Ser Asp Asn Ala Gly Leu Phe Leu Asp Tyr Ala Ala Ala Leu Val
145                 150                 155                 160

Thr Gly Ala Glu Lys Pro Gln Pro Ala Lys Pro Leu Leu Lys Ala Gly
                165                 170                 175

Ile Trp Trp Pro Gly Ala Gly Val Ile Gly Val Ser Glu Trp Gln Ser
            180                 185                 190

Leu Val Gln Gly Arg Met Val Ala Arg Glu Gly Phe Glu Pro Pro Thr
        195                 200                 205

Val Gly Ile Cys Phe Tyr Arg Ala Leu Val Gln Ser Gly Glu Thr Arg
    210                 215                 220

Pro Val Glu Ala Leu Ile Asp Ala Leu Glu Ala Glu Gly Val Arg Ala
225                 230                 235                 240

Leu Pro Val Phe Val Ser Ser Leu Lys Asp Ala Val Ser Val Gly Thr
                245                 250                 255

Leu Gln Ala Ile Phe Ser Glu Ala Ala Pro Asp Val Val Met Asn Ala
            260                 265                 270

Thr Gly Phe Ala Val Ser Ser Pro Gly Ala Asp Arg Gln Pro Thr Val
        275                 280                 285

Leu Glu Ser Thr Gly Ala Pro Val Leu Gln Val Ile Phe Ser Gly Ser
    290                 295                 300

Ser Arg Ala Gln Trp Glu Thr Ser Pro Gln Gly Leu Met Ala Arg Asp
305                 310                 315                 320

Leu Ala Met Asn Val Ala Leu Pro Glu Val Asp Gly Arg Ile Leu Ala
                325                 330                 335

Arg Ala Val Ser Phe Lys Ala Ala Ser Ile Tyr Asp Ala Lys Val Glu
            340                 345                 350

Ala Asn Ile Val Gly His Glu Pro Leu Glu Gly Arg Val Arg Phe Ala
        355                 360                 365

Ala Asp Leu Ala Val Asn Trp Ala Asn Val Arg Arg Ala Glu Pro Ala
    370                 375                 380

Glu Arg Arg Ile Ala Ile Val Met Ala Asn Tyr Pro Asn Arg Asp Gly
385                 390                 395                 400

Arg Leu Gly Asn Gly Val Gly Leu Asp Thr Pro Ala Gly Thr Val Glu
                405                 410                 415

Val Leu Ser Ala Met Ala Arg Glu Gly Tyr Ala Val Gly Glu Val Pro
            420                 425                 430

Ala Asp Gly Asp Ala Leu Ile Arg Phe Leu Met Ala Gly Pro Thr Asn
        435                 440                 445

Ala Ala Ser His Asp Arg Glu Ile Arg Glu Arg Ile Ser Leu Asn Asp
```

-continued

```
    450                 455                 460

Tyr Lys Thr Phe Phe Asp Ser Leu Pro Lys Gln Ile Lys Asp Glu Val
465                 470                 475                 480

Ala Gly Arg Trp Gly Val Pro Glu Ala Asp Pro Phe Phe Leu Asp Gly
                485                 490                 495

Ala Phe Ala Leu Pro Leu Ala Arg Phe Gly Glu Val Ile Val Gly Ile
            500                 505                 510

Gln Pro Ala Arg Gly Tyr Asn Ile Asp Pro Lys Glu Ser Tyr His Ser
        515                 520                 525

Pro Asp Leu Val Pro Pro His Gly Tyr Leu Ala Phe Tyr Ala Phe Leu
    530                 535                 540

Arg Gln Gln Phe Gly Ala Gln Ala Ile Val His Met Gly Lys His Gly
545                 550                 555                 560

Asn Leu Glu Trp Leu Pro Gly Lys Ala Leu Ala Leu Ser Glu Thr Cys
                565                 570                 575

Tyr Pro Glu Ala Ile Phe Gly Pro Leu Pro His Ile Tyr Pro Phe Ile
            580                 585                 590

Val Asn Asp Pro Gly Glu Gly Thr Gln Ala Lys Arg Arg Thr Ser Ala
        595                 600                 605

Val Ile Ile Asp His Leu Thr Pro Pro Leu Thr Arg Ala Glu Ser Tyr
    610                 615                 620

Gly Pro Leu Lys Asp Leu Glu Ala Leu Val Asp Glu Tyr Tyr Asp Ala
625                 630                 635                 640

Ala Gly Gly Asp Pro Arg Arg Leu Arg Leu Leu Ser Arg Gln Ile Leu
                645                 650                 655

Asp Leu Val Arg Asp Ile Gly Leu Asp Ser Asp Ala Gly Ile Asp Arg
            660                 665                 670

Gly Asp Ser Asp Asp Lys Ala Leu Glu Lys Leu Asp Ala Tyr Leu Cys
        675                 680                 685

Asp Leu Lys Glu Met Gln Ile Arg Asp Gly Leu His Ile Phe Gly Val
    690                 695                 700

Ala Pro Glu Gly Arg Leu Leu Thr Asp Leu Thr Val Ala Leu Ala Arg
705                 710                 715                 720

Val Pro Arg Gly Leu Gly Glu Gly Gly Asp Gln Ser Leu Gln Arg Ala
                725                 730                 735

Ile Ala Ala Asp Ala Gly Leu Arg Gly Phe Ala Ile Pro Thr Ser Ala
            740                 745                 750

Gly Gly Asn Pro Ala Arg Asp Ala Gln Pro Phe Asp Pro Leu Asp Cys
        755                 760                 765

Val Met Ser Asp Thr Trp Thr Gly Pro Lys Pro Ser Ile Leu Ala Asp
    770                 775                 780

Leu Ser Asp Ala Pro Trp Arg Thr Ala Gly Asp Thr Val Glu Arg Ile
785                 790                 795                 800

Glu Leu Leu Ala Ala Asn Leu Val Ser Gly Glu Leu Ala Cys Pro Asp
                805                 810                 815

His Trp Ala Asn Thr Arg Ala Val Leu Gly Glu Ile Glu Thr Arg Leu
            820                 825                 830

Lys Pro Ser Ile Ser Asn Ser Gly Ala Ala Glu Met Thr Gly Phe Leu
        835                 840                 845

Thr Gly Leu Ser Gly Arg Phe Val Ala Pro Gly Pro Ser Gly Ala Pro
    850                 855                 860

Thr Arg Gly Arg Pro Asp Val Leu Pro Thr Gly Arg Asn Phe Tyr Ser
865                 870                 875                 880
```

-continued

```
Val Asp Ser Arg Ala Val Pro Thr Pro Ala Ala Tyr Glu Leu Gly Lys
            885                 890                 895

Lys Ser Ala Glu Leu Leu Ile Arg Arg Tyr Leu Gln Asp His Gly Glu
            900                 905                 910

Trp Pro Ser Ser Phe Gly Leu Thr Ala Trp Gly Thr Ala Asn Met Arg
        915                 920                 925

Thr Gly Gly Asp Asp Ile Ala Gln Ala Leu Ala Leu Ile Gly Ala Lys
    930                 935                 940

Pro Thr Trp Asp Met Val Ser Arg Arg Val Met Gly Tyr Glu Ile Val
945                 950                 955                 960

Pro Leu Ala Val Leu Gly Arg Pro Arg Val Asp Val Thr Leu Arg Ile
                965                 970                 975

Ser Gly Phe Phe Arg Asp Ala Phe Pro Asp Gln Ile Ala Leu Phe Asp
            980                 985                 990

Lys Ala Ile Arg Ala Val Ala Leu Glu Glu Asp Asp Ala Asp Asn Met
        995                 1000                1005

Ile Ala Ala Arg Met Arg Ala Glu Ser Arg Arg Leu Glu Ala Glu Gly
    1010                1015                1020

Val Glu Ala Ala Glu Ala Ala Arg Arg Ala Ser Tyr Arg Val Phe Gly
1025                1030                1035                1040

Ala Lys Pro Gly Ala Tyr Gly Ala Ala Leu Gln Ala Leu Ile Asp Glu
                1045                1050                1055

Lys Gly Trp Glu Thr Lys Ala Asp Leu Ala Glu Ala Tyr Leu Thr Trp
            1060                1065                1070

Gly Ala Tyr Ala Tyr Gly Ala Gly Glu Glu Gly Lys Ala Glu Arg Asp
        1075                1080                1085

Leu Phe Glu Glu Arg Leu Arg Thr Ile Glu Ala Val Val Gln Asn Gln
    1090                1095                1100

Asp Asn Arg Glu His Asp Leu Leu Asp Ser Asp Asp Tyr Tyr Gln Phe
1105                1110                1115                1120

Glu Gly Gly Met Ser Ala Ala Ala Glu Gln Leu Gly Gly His Arg Pro
                1125                1130                1135

Ala Ile Tyr His Asn Asp His Ser Arg Pro Glu Lys Pro Val Ile Arg
            1140                1145                1150

Ser Leu Glu Glu Glu Ile Gly Arg Val Val Arg Ala Arg Val Val Asn
        1155                1160                1165

Pro Lys Trp Ile Asp Gly Val Met Arg His Gly Tyr Lys Gly Ala Phe
    1170                1175                1180

Glu Ile Ala Ala Thr Val Asp Tyr Met Phe Ala Phe Ala Ala Thr Thr
1185                1190                1195                1200

Gly Ala Val Arg Asp His His Phe Glu Ala Ala Tyr Gln Ala Phe Ile
                1205                1210                1215

Val Asp Glu Arg Val Ala Asp Phe Met Arg Asp Lys Asn Pro Ala Ala
            1220                1225                1230

Phe Ala Glu Leu Ala Glu Arg Leu Leu Glu Ala Ile Asp Arg Asn Leu
        1235                1240                1245

Trp Thr Pro Arg Ser Asn Ser Ala Arg Phe Glu Leu Ala Gly Ile Gly
    1250                1255                1260

Thr Ala Ala Thr Arg Leu Arg Ala Gly Asn Glu
1265                1270                1275
```

(2) INFORMATION FOR SEQ ID NO: 50:

-continued (i) SEQUENCE CHARACTERISTICS:
(A) LENGTH: 645 base pairs
(B) TYPE: Nucleic acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: cobO
(B) LOCATION: 9034-9678 bp of SEQ ID NO:41
(C) IDENTIFICATION METHOD:
(D) OTHER INFORMATION:

(xi) SEQUENCE DESCRIPTION: SEQ ID NO: 50:

```
ATGAGCGACG AGACGACAGT AGGCGGCGAA GCCCCGGCCG AGAAGGACGA TGCCCGCCAC     60

GCCATGAAGA TGGCGAAGAA GAAGGCAGCA CGCGAAAAGA TCATGGCGAC GAAGACCGAC    120

GAGAAGGGTC TGATCATCGT CAACACCGGC AAAGGCAAGG GCAAGTCGAC CGCCGGCTTC    180

GGCATGATCT TCCGCCATAT CGCCCACGGC ATGCCCTGCG CCGTCGTGCA GTTCATCAAG    240

GGTGCGATGG CAACCGGCGA GCGCGAGTTG ATCGAGAAGC ATTTCGGCGA TGTCTGCCAG    300

TTCTACACGC TCGGCGAGGG CTTCACCTGG GAAACGCAGG ATCGCGCCCG CGATGTTGCG    360

ATGGCTGAAA AGGCCTGGGA GAAGGCGAAG GAACTGATCC GTGACGAGCG CAACTCGATG    420

GTGCTGCTCG ACGAGATCAA CATTGCTCTG CGCTACGACT ACATCGACGT CGCCGAAGTG    480

GTGCGCTTCC TGAAGGAAGA AAAGCCGCAC ATGACGCATG TGGTGCTCAC CGGCCGCAAC    540

GCGAAAGAAG ACCTGATCGA AGTCGCCGAT CTCGTCACTG AGATGGAGCT GATCAAGCAT    600

CCGTTCCGTT CCGGCATCAA GGCGCAGCAG GGCGTGGAGT TCTGA                    645
```

(2) INFORMATION FOR SEQ ID NO: 51:

(i) SEQUENCE CHARACTERISTICS:
(A) LENGTH: 214 amino acid
(B) TYPE: Amino acid
(C) STRANDEDNESS:
(D) TOPOLOGY: Linear (ii) MOLECULE TYPE: protein (iii) HYPOTHETICAL: No (iv) ORIGINAL SOURCE:
(A) ORGANISM: Pseudomonas denitrificans
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: COBO
(B) LOCATION:
(C) IDENTIFICATION METHOD:

-continued (D) OTHER INFORMATION: Translation product of SEQ ID NO: 50

(xi) SEQUENCE DESCRIPTION: SEQ ID NO: 51:

```
Met Ser Asp Glu Thr Thr Val Gly Gly Glu Ala Pro Ala Glu Lys Asp
1               5                   10                  15

Asp Ala Arg His Ala Met Lys Met Ala Lys Lys Lys Ala Ala Arg Glu
            20                  25                  30

Lys Ile Met Ala Thr Lys Thr Asp Glu Lys Gly Leu Ile Ile Val Asn
        35                  40                  45

Thr Gly Lys Gly Lys Gly Lys Ser Thr Ala Gly Phe Gly Met Ile Phe
    50                  55                  60

Arg His Ile Ala His Gly Met Pro Cys Ala Val Val Gln Phe Ile Lys
65                  70                  75                  80

Gly Ala Met Ala Thr Gly Glu Arg Glu Leu Ile Glu Lys His Phe Gly
                85                  90                  95

Asp Val Cys Gln Phe Tyr Thr Leu Gly Glu Gly Phe Thr Trp Glu Thr
            100                 105                 110

Gln Asp Arg Ala Arg Asp Val Ala Met Ala Glu Lys Ala Trp Glu Lys
        115                 120                 125

Ala Lys Glu Leu Ile Arg Asp Glu Arg Asn Ser Met Val Leu Leu Asp
    130                 135                 140

Glu Ile Asn Ile Ala Leu Arg Tyr Asp Tyr Ile Asp Val Ala Glu Val
145                 150                 155                 160

Val Arg Phe Leu Lys Glu Glu Lys Pro His Met Thr His Val Val Leu
                165                 170                 175

Thr Gly Arg Asn Ala Lys Glu Asp Leu Ile Glu Val Ala Asp Leu Val
            180                 185                 190

Thr Glu Met Glu Leu Ile Lys His Pro Phe Arg Ser Gly Ile Lys Ala
        195                 200                 205

Gln Gln Gly Val Glu Phe
    210
```

(2) INFORMATION FOR SEQ ID NO: 52:

(i) SEQUENCE CHARACTERISTICS:
(A) LENGTH: 955 base pairs
(B) TYPE: Nucleic acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Methanobacterium ivanovii
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: containing corA or sumT gene
(B) LOCATION:
(C) IDENTIFICATION METHOD:
(D) OTHER INFORMATION: Nucleotide Sequence of the 5' to 3' strand from the 955 bp fragment of Methanobacterium ivanovii (xi) SEQUENCE DESCRIPTION: SEQ ID NO: 52:

-continued

```
CCATAATTCT TTTATAATTT AAACGGTGAA CACATGGTAG TTTATTTAGT AGGTGCGGGT     60

CCAGGAGATC CCGAACTTAT CACTCTCAAA GCTGTAAACG TGTTAAAAAA AGCGGATGTT    120

GTACTGTACG ACAAACCTGC AAATGAAGAA ATTTTAAAGT ATGCTGAAGG TGCAAAACTA    180

ATATATGTCG GAAAACAAGC AGGACATCAT TACAAATCTC AAAATGAAAT CAATACTCTT    240

CTTGTTGAAG AAGCAAAAGA AAATGATTTA GTAGTACGCC TTAAAGGTGG AGACCCCTTT    300

GTATTTGGAA GAGGAGGCGA GGAAATTCTG GCCCTTGTAG AAGAAGGAAT TGATTTTGAG    360

TTAGTTCCAG GGGTAACTTC TGCAATTGGA GTTCCAACAA CAATTGGGCT TCCAGTTACT    420

CATAGAGGTG TTGCAACATC GTTTACAGTT GTTACAGGTC ATGAAGACCC AACAAAATGC    480

AAGAAACAGG TAGGATGGGA CTTTAAAGCA GATACTATTG TAATACTTAT GGGTATTGGA    540

AATTTAGCTG AAAATACAGC AGAAATTATG AAACATAAAG ATCCTGAAAC TCCAGTTTGT    600

GTAATTGAAA ATGGTACGAT GGAAGGTCAA AGGATAATAA CGGGCACACT GGAAAATATA    660

GCTGGAAAGG ATATTAAACC TCCTGCTTTA GTGGTATTGG AAATGTTGTC AATGTTTTTA    720

AAGAAATGAA TCAAATCAGT GGCTGATCTA TTAAGAAGGC AATATCATGA ATGGATTAGA    780

AGGTAAAAAA ATTGTTATAA CAAGACCTGC TGAAAGGGCT AAAGACTCAG TTGAAATGGT    840

AAAATCTTAT GGAGCAGTTC CAATTGTAAC TCCTACAATT GAACTCAAAG ATTCCAAGCC    900

AGAAGAAGTG ATAAAATTAT GTAATATGAT AAATGAACCT TGATTGGCCT TATAT         955
```

(2) INFORMATION FOR SEQ ID NO: 53:

(i) SEQUENCE CHARACTERISTICS:
(A) LENGTH: 696 base pairs
(B) TYPE: Nucleic acid
(C) STRANDEDNESS: Double
(D) TOPOLOGY: Unknown (ii) MOLECULE TYPE: cDNA (iii) HYPOTHETICAL: No (iv) ORIGINAL SOURCE:
(A) ORGANISM: Methanobacterium ivanovii
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: corA or sumT
(B) LOCATION: 34-729 bp of SEQ ID NO:52
(C) IDENTIFICATION METHOD:
(D) OTHER INFORMATION:

(xi) SEQUENCE DESCRIPTION: SEQ ID NO: 53:

```
ATGGTAGTTT ATTTAGTAGG TGCGGGTCCA GGAGATCCCG AACTTATCAC TCTCAAAGCT     60

GTAAACGTGT TAAAAAAAGC GGATGTTGTA CTGTACGACA AACCTGCAAA TGAAGAAATT    120

TTAAAGTATG CTGAAGGTGC AAAACTAATA TATGTCGGAA AACAAGCAGG ACATCATTAC    180

AAATCTCAAA ATGAAATCAA TACTCTTCTT GTTGAAGAAG CAAAAGAAAA TGATTTAGTA    240

GTACGCCTTA AAGGTGGAGA CCCCTTTGTA TTTGGAAGAG GAGGCGAGGA AATTCTGGCC    300

CTTGTAGAAG AAGGAATTGA TTTTGAGTTA GTTCCAGGGG TAACTTCTGC AATTGGAGTT    360

CCAACAACAA TTGGGCTTCC AGTTACTCAT AGAGGTGTTG CAACATCGTT TACAGTTGTT    420
```

-continued

```
ACAGGTCATG AAGACCCAAC AAAATGCAAG AAACAGGTAG GATGGGACTT TAAAGCAGAT    480

ACTATTGTAA TACTTATGGG TATTGGAAAT TTAGCTGAAA ATACAGCAGA AATTATGAAA    540

CATAAAGATC CTGAAACTCC AGTTTGTGTA ATTGAAAATG GTACGATGGA AGGTCAAAGG    600

ATAATAACGG GCACACTGGA AAATATAGCT GGAAAGGATA TTAAACCTCC TGCTTTAGTG    660

GTATTGGAAA TGTTGTCAAT GTTTTTAAAG AAATGA                              696
```

(2) INFORMATION FOR SEQ ID NO: 54:

(i) SEQUENCE CHARACTERISTICS:
(A) LENGTH: 231 amino acids
(B) TYPE: Amino acid
(C) STRANDEDNESS:
(D) TOPOLOGY: Linear (ii) MOLECULE TYPE: protein (iii) HYPOTHETICAL: No (iv) ORIGINAL SOURCE:
(A) ORGANISM: Methanobacterium ivanovii
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: CORA
(B) LOCATION:
(C) IDENTIFICATION METHOD:
(D) OTHER INFORMATION: Translation product of SEQ ID NO:53

(xi) SEQUENCE DESCRIPTION: SEQ ID NO: 54:

```
Met Val Val Tyr Leu Val Gly Ala Gly Pro Gly Asp Pro Glu Leu Ile
1               5                   10                  15

Thr Leu Lys Ala Val Asn Val Leu Lys Lys Ala Asp Val Val Leu Tyr
            20                  25                  30

Asp Lys Pro Ala Asn Glu Glu Ile Leu Lys Tyr Ala Glu Gly Ala Lys
        35                  40                  45

Leu Ile Tyr Val Gly Lys Gln Ala Gly His His Tyr Lys Ser Gln Asn
    50                  55                  60

Glu Ile Asn Thr Leu Leu Val Glu Glu Ala Lys Glu Asn Asp Leu Val
65                  70                  75                  80

Val Arg Leu Lys Gly Gly Asp Pro Phe Val Phe Gly Arg Gly Gly Glu
                85                  90                  95

Glu Ile Leu Ala Leu Val Glu Glu Gly Ile Asp Phe Glu Leu Val Pro
            100                 105                 110

Gly Val Thr Ser Ala Ile Gly Val Pro Thr Thr Ile Gly Leu Pro Val
        115                 120                 125

Thr His Arg Gly Val Ala Thr Ser Phe Thr Val Val Thr Gly His Glu
    130                 135                 140

Asp Pro Thr Lys Cys Lys Lys Gln Val Gly Trp Asp Phe Lys Ala Asp
145                 150                 155                 160

Thr Ile Val Ile Leu Met Gly Ile Gly Asn Leu Ala Glu Asn Thr Ala
                165                 170                 175

Glu Ile Met Lys His Lys Asp Pro Glu Thr Pro Val Cys Val Ile Glu
            180                 185                 190

Asn Gly Thr Met Glu Gly Gln Arg Ile Ile Thr Gly Thr Leu Glu Asn
```

-continued

```
        195                 200                     205

Ile Ala Gly Lys Asp Ile Lys Pro Pro Ala Leu Val Val Leu Glu Met
    210                 215                     220

Leu Ser Met Phe Leu Lys Lys
225                 230
```

(2) INFORMATION FOR SEQ ID NO: 55:

(i) SEQUENCE CHARACTERISTICS:
(A) LENGTH: 251
(B) TYPE: Amino Acid
(C) STRANDEDNESS:single
(D) TOPOLOGY: Unknown (ii) MOLECULE TYPE: polypeptide (iii) HYPOTHETICAL: No (iv) ORIGINAL SOURCE:
(A) ORGANISM: E. coli
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(ix) FEATURE:
(A) NAME/KEY: fragment of cysG protein
(B) LOCATION: amino acids 204-460
(C) IDENTIFICATION METHOD:
(D) OTHER INFORMATION:

(xi) SEQUENCE DESCRIPTION: SEQ ID NO: 55:

```
Glu Gln Leu Ile Asn Glu Pro Leu Asp His Arg Gly Glu Val Val Leu
                  5                  10                  15

Val Gly Ala Gly Pro Gly Asp Ala Gly Leu Leu Thr Leu Lys Gly Leu
             20                  25                  30

Gln Gln Ile Gln Gln Ala Asp Val Val Val Tyr Asp Arg Leu Val Ser
        35                  40                  45

Asp Asp Ile Met Asn Leu Val Arg Arg Asp Ala Asp Arg Val Phe Val
     50                  55                  60

Gly Lys Arg Ala Gly Tyr His Cys Val Pro Gln Glu Glu Ile Asn Gln
65                  70                  75                  80

Ile Leu Leu Arg Glu Ala Gln Lys Gly Lys Arg Val Val Arg Leu Lys
                 85                  90                  95

Gly Gly Asp Pro Phe Ile Phe Gly Arg Gly Gly Glu Glu Leu Glu Thr
            100                 105                 110

Leu Cys Asn Ala Gly Ile Pro Phe Ser Val Val Pro Gly Ile Thr Ala
        115                 120                 125

Ala Ser Gly Cys Ser Ala Tyr Ser Gly Ile Pro Leu Thr His Arg Asp
    130                 135                 140

Tyr Ala Gln Ser Val Arg Leu Ile Thr Gly His Leu Lys Thr Gly Gly
145                 150                 155                 160

Glu Leu Asp Trp Glu Asn Leu Ala Ala Glu Lys Gln Thr Leu Val Phe
                165                 170                 175

Tyr Met Gly Leu Asn Gln Ala Ala Thr Ile Gln Gln Lys Leu Ile Glu
            180                 185                 190

His Gly Met Pro Gly Glu Met Pro Val Ala Ile Val Glu Asn Gly Thr
        195                 200                 205
```

-continued

Ala Val Thr Gln Arg Val Ile Asp Gly Thr Leu Thr Gln Leu Gly Glu
    210                 215                 220

Leu Ala Gln Gln Met Asn Ser Pro Ser Leu Ile Ile Ile Gly Arg Val
225                 230                 235                 240

Val Gly Leu Arg Asp Lys Leu Asn Trp Phe Ser
                245                 250

(2) INFORMATION FOR SEQ ID NO: 56:

(i) SEQUENCE CHARACTERISTICS:
(A) LENGTH: 27
(B) TYPE: Nucleic Acid
(C) STRANDEDNESS: Single
(D) TOPOLOGY: Unknown (ii) MOLECULE TYPE: Oligonucleotide (iii) HYPOTHETICAL: No (ix) FEATURE:
(A) NAME/KEY: fragment of sumT gene
(B) LOCATION:
(C) IDENTIFICATION METHOD:
(D) OTHER INFORMATION:

(xi) SEQUENCE DESCRIPTION: SEQ ID NO: 56:

CGCGGAATTC CCNGGNGAYC CNGARCT 27

(2) INFORMATION FOR SEQ ID NO: 57:

(i) SEQUENCE CHARACTERISTICS:
(A) LENGTH: 27
(B) TYPE: Nucleic Acid
(C) STRANDEDNESS: single
(D) TOPOLOGY: Unknown (ii) MOLECULE TYPE: Oligonucleotide (iii) HYPOTHETICAL: No (ix) FEATURE:
(A) NAME/KEY: fragment of sumT gene
(B) LOCATION:
(C) IDENTIFICATION METHOD:
(D) OTHER INFORMATION:

(xi) SEQUENCE DESCRIPTION: SEQ ID NO: 57:

CGCGGAATTC GTRTAYCTWG TDGGWGC 27

(2) INFORMATION FOR SEQ ID NO: 58:

(i) SEQUENCE CHARACTERISTICS:
(A) LENGTH: 25
(B) TYPE: Nucleic Acid
(C) STRANDEDNESS: single
(D) TOPOLOGY: Unknown (ii) MOLECULE TYPE: Oligonucleotide (iii) HYPOTHETICAL: No (ix) FEATURE:
(A) NAME/KEY: fragment of sumT gene
(B) LOCATION:
(C) IDENTIFICATION METHOD:
(D) OTHER INFORMATION:

(xi) SEQUENCE DESCRIPTION: SEQ ID NO: 58:

CGCGAAGCTT RTTYTCWAGD GTNCC 25

-continued

```
(2) INFORMATION FOR SEQ ID NO: 59:

     (i) SEQUENCE CHARACTERISTICS:
          (A) LENGTH: 27
          (B) TYPE:  Nucleic Acid
          (C) STRANDEDNESS: single
          (D) TOPOLOGY:  Unknown

    (ii) MOLECULE TYPE: Oligonucleotide

    (ix) FEATURE:
          (A) NAME/KEY: fragment of sumT gene
          (B) LOCATION: -12 - 15
          (C) IDENTIFICATION METHOD:
          (D) OTHER INFORMATION: as seen in specification, p. 182,
               line 5.

    (xi) SEQUENCE DESCRIPTION: SEQ ID NO: 59:

GGCCGAATTC ATATGGTAGT TTATTTA                                          27


(2) INFORMATION FOR SEQ ID NO: 60:

     (i) SEQUENCE CHARACTERISTICS:
          (A) LENGTH: 22
          (B) TYPE:  Nucleic Acid
          (C) STRANDEDNESS: single
          (D) TOPOLOGY:  Unknown

    (ii) MOLECULE TYPE: Oligonucleotide

    (ix) FEATURE:
          (A) NAME/KEY:
          (B) LOCATION:
          (C) IDENTIFICATION METHOD:
          (D) OTHER INFORMATION: As seen in specification on p. 182,
               line 10. Hybrid fragment complementary strand derived
               from sumT gene sequence.

    (xi) SEQUENCE DESCRIPTION: SEQ ID NO: 60:

GGCCGAGCTC TATTACATAA TT                                               22
```

METHODS OF INCREASING THE PRODUCTION OF COBALAMINS USING COB GENE EXPRESSION

This is a continuation of application Ser. No. 07/916,151, filed on Sep. 14, 1992 now abandoned which is a 371 of PCT/FR91/00054 filed Jan. 30, 1991.

The present invention relates to new polypeptides involved in the biosynthesis of cobalamins and/or cobamides, and especially of coenzyme $B_{12}$. It also relates to the genetic material responsible for the expression of these polypeptides, as well as to a method by means of which they may be prepared. It relates, lastly, to a method for amplification of the production of cobalamins, and more especially of coenzyme $B_{12}$, by recombinant DNA techniques.

Vitamin $B_{12}$ belongs to the B group of vitamins. It is a water-soluble vitamin which has been identified as the factor enabling patients suffering from pernicious anaemia to be treated. It is generally prescribed to stimulate haematopoiesis in fatigue subjects, but it is also used in many other cases comprising liver disorders and nervous deficiencies or as an appetite stimulant or an active principle with tonic activity, as well as in dermatology (Berck, 1982, Fraser et al., 1983). In the industrial rearing of non-ruminant animals, the feed being essentially based on proteins of vegetable origin, it is necessary to incorporate vitamin $B_{12}$ in the feed rations in amounts of 10 to 15 mg per tonne of feed (Barrère et al., 1981).

Vitamin $B_{12}$ belongs to a class of molecules known as cobalamins, the structure of which is presented in FIG. 1. Cobamides differ from cobalamins in the base of the lower nucleotide, which is no longer 5,6-dimethylbenzimidazole but another base, e.g. 5-hydroxybenzimidazole for vitamin $B_{12}$-factor III synthesised, inter alia, by *Clostridium thermoaceticum* and *Methanosarcina barkeri* (Iron et al., 1984). These structural similarities explain the fact that the metabolic pathways of biosynthesis of cobalamins and cobamides are, for the most part, shared.

Cobalamins are synthesised almost exclusively by bacteria, according to a complex and still poorly understood process which may be divided into four steps (FIG. 2):

i) synthesis of uroporphyrinogen III (or uro'gen III), then
ii) conversion of uro'gen III to cobyrinic acid, followed by
iii) conversion of the latter to cobinamide, and
iv) construction of the lower nucleotide loop with incorporation of the particular base (5,6-dimethylbenzimidazole in the case of cobalamins).

For coenzyme $B_{12}$, it is probable that the addition of the 5'-deoxyadenosyl group occurs shortly after the corrin ring-system is synthesised (Huennekens et al., 1982).

In the case of cobamides, only the step of synthesis and incorporation of the lower base is different.

The first part of the biosynthesis of cobalamins is very well known, since it is common to that of haemes as well as to that of chlorophylls (Battersby et al., 1980). It involves, successively, δ-aminolevulinate synthase (EC 2.3.137), δ-aminolevulinate dehydrase (EC 4.2.1.24), porphobilinogen deaminase (EC 4.3.1.8) and uro'gen III cosynthase (EC 4.2.1.75), which convert succinyl-CoA and glycine to uro'gen III. However, the first step takes place in some organisms [e.g. *E. coli* (Avissar et al., 1989) and in methanogenic bacteria (Kannangara et al., 1989), for example] by the conversion by means of a multi-enzyme complex of glutamic acid to δ-aminolevulinic acid.

Between uro'gen III and cobyrinic acid, only three intermediate derivatives have been purified to date; they are the factors FI, FII and FIII, which are oxidation products, respectively, of the three intermediates precorrin-1, precorrin-2 and precorrin-3, which correspond to the mono-, di- and trimethylated derivatives of uro'gen III (FIG. 3); these intermediates are obtained by successive transfers of methyl groups from SAM (S-adenosyl-L-methionine) to uro'gen III at positions C-2, C-7 and C-20, respectively. The other reactions which take place to give cobyrinic acid are, apart from five further transfers of methyl groups from SAM at C-17, C-12, C-1, C-15 and C-5, elimination of the carbon at C-20, decarboxylation at C-12 and insertion of a cobalt atom (FIG. 4). These biosynthetic steps have been deduced from experiments performed in vitro on acellular extracts of *Propionibacterium shermanii* or of *Clostridium tetanomorphum*. In these extracts, cobyrinic acid is obtained by conversion of uro'gen III after incubation under suitable anaerobic conditions (Batterby et al., 1982). No intermediate between precorrin-3 and cobyrinic acid capable of being converted to corrinoids by subsequent incubation with extracts of cobalamin-producing bacteria has been isolated to date. The difficulty of isolating and identifying these intermediates is linked to i) their great instability,
ii) their sensitivity to oxygen, and
iii) their low level of accumulation in vivo.

In this part of the pathway, only one enzyme of *Pseudomonas denitrificans* has been purified and studied; it is SAM:uro'gen III methyltransferase (Blanche et al., 1989), referred to as SUMT.

Between cobyrinic acid and cobinamide, the following reactions are performed:

i) addition of the 5'-deoxyadenosyl group (if coenzyme $B_{12}$ is the compound to be synthesised),
ii) amidation of six of the seven carboxyl functions by addition of amine groups, and
iii) amidation of the last carboxyl function (propionic acid chain of pyrrole ring D) by addition of (R)-1-amino-2-propanol (FIG. 2).

Whether there was really an order in the amidations was not elucidated (Herbert et al., 1970). Lastly, no assay of activity in this part of the pathway has been described, except as regards the addition of the 5'-deoxyadenosyl group (Huennekens et al., 1982).

The final step of the biosynthesis of a cobalamin, e.g. coenzyme $B_{12}$, comprises four successive phases described in FIG. 5 (Huennekens et al., 1982), namely:

i) phosphorylation of the hydroxyl group of the amino-propanol residue of cobinamide to cobinamide phosphate, then
ii) addition of a guanosine diphosphate by reaction with guanosine 5'-triphosphate; the compound obtained is GDP-cobinamide (Friedmann, 1975), which
iii) reacts with 5,6-dimethylbenzimidazole, itself synthesised from riboflavin, to give adenosylcobalamin 5'-phosphate (Friedmann et al., 1968), which
iv) on dephosphorylation leads to coenzyme $B_{12}$ (Schneider and Friedmann, 1972).

Among bacteria capable of producing cobalamins, the following may be mentioned in particular:

*Agrobacterium tumefaciens*
*Agrobacterium radiobacter*
*Bacillus megaterium*
*Clostridium sticklandii*
*Clostridium tetanomorphum*

*Clostridium thermoaceticum*
*Corynebacterium XG*
*Eubacterium limosum*
*Methanobacterium arbophilicum*
*Methanobacterium ivanovii*
*Methanobacterium ruminantium*
*Methanobacterium thermoautotrophicum*
*Methanosarcina barkeri*
*Propionobacterium shermanii*
*Protaminobacter ruber*
*Pseudomonas denitrificans*
*Pseudomonas putida*
*Rhizobium meliloti*
*Rhodopseudomonas sphaeroides*
*Salmonella typhimurium*
*Spirulina platensis*
*Streptomyces antibioticus*
*Streptomyces aureofaciens*
*Streptomyces griseus*
*Streptomyces olivaceus*

At the industrial level, as a result of the great complexity of the biosynthetic mechanisms, the production of cobalamins, and especially of vitamin $B_{12}$, is exclusively microbiological. It is carried out by large-volume cultures of the bacteria *Pseudomonas denitrificans, Propionibacterium shermanii* and *Propionibacterium freudenreichii* (Florent, 1986). The strains used for the industrial production are derived from wild-type strains; they may have undergone a large number of cycles of random mutation and then of selection of improved clones for the production of cobalamins (Florent, 1986). The mutations are obtained by mutagenesis with mutagenic agents or by physical treatments such as treatments with ultraviolet rays (Barrère et al., 1981). By this empirical method, random mutations are obtained and improve the production of cobalamins. For example, it is described that, from the original strain of *Pseudomonas denitrificans* initially isolated by Miller and Rosenblum (1960, U.S. Pat. No. 2,938,822), the production of this microorganism was gradually increased in the space of ten years, by the techniques mentioned above, from 0.6 mg/l to 60 mg/l (Florent, 1986). For bacteria of the genus Propionibacterium [*Propionibacterium shermanii* (ATCC 13673) and *freudenreichii* (ATCC 6207)], the same production values appear to be described in the literature; e.g. a production of 65 mg/l has been described (European Patent 87,920). However, no screen has yet been described enabling either mutants overproductive of cobalamins or mutants markedly improved in their production of cobalamins to be readily selected or identified.

At the genetic level, little work has been performed to date. The cloning of cob genes (coding for enzymes involved in the biosynthetic process) has been described in *Bacillus megaterium* (Brey et al., 1986). Eleven complementation groups have been identified by complementation of cob mutants of *Bacillus megaterium* with plasmids carrying different fragments of *Bacillus megaterium* DNA. These genes are grouped on the same locus, carried by a 12-kb fragment.

Studies have also been carried out on the cob genes of *Salmonella typhimurium*. Although the cloning of these has not been described, it has been shown that almost all the genes for cobalamin biosynthesis are grouped together between minutes 40 and 42 of the chromosome (Jeter and Roth, 1987). Only the cysG locus, which must permit the conversion of uro'gen III to precorrin-2, does not form part of this group of genes. However, the activity encoded by this locus and also its biochemical properties have not been described.

In addition, some phenotypes have been associated with cob mutations. In *Salmonella typhimurium* and in *Bacillus megaterium*, cob mutants no longer show growth on minimum medium with ethanolamine as a carbon source or as a nitrogen source (Roof and Roth, 1988). This is due to the fact that an enzyme of ethanolamine catabolism, ethanolamine ammonia-lyase (EC 4.3.1.7), has coenzyme $B_{12}$ as a cofactor; the cob mutants no longer synthesise coenzyme $B_{12}$, and they can no longer grow with ethanolamine as a carbon source and/or as a nitrogen source. metE mutants of *Salmonella typhimurium* retain only a methylcobalamin-dependent homocysteine methyltransferase (EC 2.1.1.13). cob mutants of *Salmonella typhimurium* metE are auxotrophic for methionine (Jeter et al., 1984).

In *Pseudomonas denitrificans* and *Agrobacterium tumefaciens*, phenotypes associated with a total deficiency of cobalamin synthesis have not been described to date.

Finally, work on *Pseudomosas denitrificans* (Cameron et al., 1989) has led to the cloning of DNA fragments carrying cob genes of this bacterium. These are distributed in four complementation groups carried by at least 30 kb of DNA. At least fourteen complementation groups have been identified by heterologous complementation of cob mutants of *Agrobacterium tumefaciens* and of *Pseudomonas putida* with DNA fragments of *Pseudomonas denitrificans* carrying cob genes.

However, hitherto, none of these genes has been purified, and no nucleotide sequence has been described. Similarly, no protein identification nor any catalytic function attributed to the product of these genes has been described. Furthermore, no improvement in production of cobalamins by recombinant DNA techniques could be obtained. The amplification of cob genes of *Bacillus megaterium* does not bring about, in the strain from which they have been cloned, an improvement in production of cobalamins (Brey et al., 1986). In *Salmonella typhimurium*, physiological studies have been carried out in order to determine conditions under which a strong transcription of the cob genes studied was observed (Escalante and Roth, 1987). Under these conditions, there is no improvement in the production of cobalamins, although genes of the biosynthetic pathway are more expressed than under standard culture conditions.

The present invention results from the precise identification of DNA sequences coding for polypeptides involved in the biosynthesis of cobalamins and/or cobamides. A subject of the invention hence relates to the DNA sequences coding for the polypeptides involved in the biosynthesis of cobalamines and/or cobamides. More especially, the subject of the invention is the cobA, cobB, cobC, cobD, cobE, cobF, cobG, cobH, cobI, cobJ, cobK, cobL, cobM, cobN, cobO, cobP, cobQ, cobS, cobT, cobU, cobV, cobW, cobX and corA genes, any DNA sequence homologous with these genes resulting from the degeneracy of the genetic code, and also DNA sequences, of any origin (natural, synthetic, recombinant), which hybridise and/or which display significant homologies with these sequences or with fragments of the latter, and which code for polypeptides involved in the biosynthesis of cobalamins and/or cobamides. The subject of the invention is also the genes containing these DNA sequences.

The DNA sequences according to the present invention were isolated from an industrial strain, *Pseudomonas denitrificans* SC510, derived from strain MB580 (U.S. Pat. No.

3,018,225), by complementation of cob mutants of *A. tumefaciens* and *P. putida*; and of *Methanobacterium ivanovii*. The clones obtained could be analysed precisely, in particular by mapping using insertions of a derivative of transposon Tn5. These genetic studies have enabled the cob or cor genes to be localised on the restriction map and their sequencing to be carried out. An analysis of the open reading frames then enabled the coding regions of these DNA fragments to be demonstrated.

The subject of the present invention is also the use of these nucleotide sequences for cloning the cob genes of other bacteria. In effect, it is known that, for proteins catalysing the same activities, sequences are conserved, the divergence being the evolutionary divergence (Wein-Hsiung et al., 1985). It is shown in the present invention that there is a significant homology between the nucleotide sequences of different microorganisms coding for polypeptides involved in the biosynthesis of cobalamins and/or cobamides. The differences which are seen result from the evolutionary degeneracy, and from the degeneracy of the genetic code which is linked to the percentage of GC in the genome of the microorganism studied (Wein-Hsiung et al., 1985).

According to the present invention, a probe may be made with one or more DNA sequences of *Pseudomonas denitrificans* in particular, or with fragments of these, or with similar sequences displaying a specific degree of degeneracy in respect of the use of the codons and the percentage of GC in the DNA of the bacterium which it is desired to study. Under these conditions, it is possible to detect a specific hybridisation signal between the probe and fragments of genomic DNA of the bacterium studied; this specific hybridisation signal corresponds to the hybridisation of the probe with the isofunctional cob genes of the bacterium. The cob genes as well as their products may then be isolated, purified and characterised. The invention thus provides a means enabling access to be gained, by hybridisation, to the nucleotide sequences and the polypeptides involved in the biosynthesis of cobalamins and/or cobamides of any microorganism.

The subject of the present invention is also a recombinant DNA containing at least one DNA sequence coding for a polypeptide involved in the biosynthesis of cobalamins and/or cobamides, and in particular a recombinant DNA in which the said sequence or sequences are placed under the control of expression signals.

In this connection, promoter regions may, in particular be positioned at the 5' end of the DNA sequence. Such regions may be homologous or heterologous to the DNA sequence. In particular, strong bacterial promoters such as the promoter of the tryptophan operon Ptrp or of the lactose operon Plac of *E. coli*, the leftward or rightward promoter of bacteriophage lambda, the strong promoters of phages of bacteria such as Corynebacteria, the functional promoters in Gram-negative bacteria such as the Ptac promoter of *E. coli*, the PxylS promoter of the xylene catabolism genes of the TOL plasmid and the amylase promoter of *Bacillus subtilis* Pamy may be used. Promoters derived from glycolytic genes of yeasts may also be mentioned, such as the promoters of the genes coding for phosphoglycerate kinase, glyceraldehyde-3-phosphate dehydrogenase, lactase or enolase, which may be used when the recombinant DNA is to be introduced into a eukaryotic host. A ribosome binding site will also be positioned at the 5' end of the DNA sequence, and it may be homologous or heterologous, such as the ribosome binding site of the cII gene of bacteriophage lambda.

Signals necessary to transcription termination may be placed at the 3' end of the DNA sequence.

The recombinant DNA according to the present invention may then be introduced directly into a host cell compatible with the chosen expression signals, or be cloned into a plasmid vector to enable the DNA sequence in question to be introduced in a stable manner into the host cell.

Another subject of the invention relates to the plasmids thereby obtained, containing a DNA sequence coding for a polypeptide involved in the biosynthesis of cobalamins and/or cobamides. More specifically, these plasmids also contain a functional replication system and a selectable marker.

The subject of the invention is also the host cells into which one or more DNA sequences as defined above, or a plasmid as defined hereinbefore, has/have been introduced.

Another subject of the invention relates to a method for production of polypeptides involved in the biosynthesis of cobalamins and/or cobamides. According to this method, a host cell is transformed with a DNA sequence as described above, this transformed cell is cultured under conditions for expression of the said sequence and the polypeptides produced are then recovered.

The host cells which may be used for this purpose are either prokaryotes or eukaryotes, animal cells or plant cells. Preferably, they will be chosen from bacteria, and especially bacteria of the genus *E. coli, P. denitrificans, A. tumefaciens* or *R. meliloti*.

Another use of the DNA sequences according to the present invention lies in a method for amplification of the production of cobalamins and/or cobamides, by recombinant DNA techniques. In effect, if the limitation of the metabolic flux of the biosynthesis of cobalamins and/or cobamides is due to a limitation in the activity of an enzyme in the biosynthetic pathway, an increase in this activity by increasing the expression of this same enzyme using recombinant DNA techniques (gene amplification, substitution of the transcription/translation signals with more effective signals, etc.) will lead to an increase in the biosynthesis of cobalamins and/or cobamides. It is also possible that the limitation of the production of cobalamins and/or cobamides results from a biochemical regulation. In this case, the cob gene or genes corresponding to the regulated enzyme may be specifically mutagenised in vitro in order to obtain mutated genes whose products will have lost the regulation mechanisms impeding an improvement in the production.

The method according to the present invention consists in transforming a microorganism productive of cobalamins and/or cobamides, or only potentially productive of these compounds (i.e. deficient in one or more steps of the biosynthesis), with a DNA sequence as defined above, then in culturing this microorganism under conditions for expression of the said sequence and for synthesis of cobalamins and/or cobamides, and lastly in recovering the cobalamins and/or cobamides produced. Such a method is applicable, in particular, to all the productive microorganisms mentioned on pages 5 and 6, and more specifically to microorganisms of the genus *P. denitrificans, Rhizobium meliloti*, or *Agrobacterium tumefaciens*. In a preferred embodiment, the microorganism is *P. denitrificans*, and especially strain SC510. As regards potentially productive microorganisms, the DNA sequences used will be those corresponding to the steps of the biosynthesis which the microorganism cannot carry out.

Using the present invention, and by the various stragegies described above, an improvement in the production of cobalamins and/or cobamides may be obtained for any microorganism productive or potentially productive of cobalamins and/or cobamides. It will suffice to culture this recombinant microorganism under suitable conditions for the production of cobalamins and for the expression of the DNA sequences introduced. This culturing may be carried out batchwise or alternatively in continuous fashion, and the purification of the cobalamins may be carried out by the methods already used industrially (Florent, 1986). These methods comprise, inter alia:

i) solubilisation of the cobalamins and their conversion to their cyano form (e.g. by heat treatment of the fermentation must, with potassium cyanide in the presence of sodium nitrite), then ii) purification of the cyanocobalamins in various steps which can be, e.g.

a) adsorption on different substrates such as Amberlite IRC-50, Dowex 1×2 or Amberlite XAD-2, followed by an elution with a water/alcohol or water/phenol mixture, then b) extraction in an organic solvent, and lastly c) precipitation or crystallisation from the organic phase, either by the addition of reagents or dilution in a suitable solvent, or by evaporation.

The present invention shows, furthermore, that it is possible by recombinant DNA techniques to improve the cobalamin production of a bacterium productive of cobalamins by cumulating improvements. This amounts to obtaining a first improvement as described above, and then in improving this improvement, still using recombinant DNA techniques, i.e., e.g. by amplifying genes for cobalamin biosynthesis.

Another subject of the present invention relates to the polypeptides involved in the biosynthesis of cobalamins and/or cobamides. In particular, the subject of the present invention is all polypeptides, or derivatives or fragments of these polypeptides, which are encoded by the DNA sequences described above, and which are involved in the pathway of biosynthesis of cobalamins and/or cobamides. The amino acid sequence of these polypeptides is described, as well as some of their physicochemical properties. An enzymatic activity or specific properties have also been associated with each of them.

In this connection, the subject of the invention is the polypeptides participating in the conversion of precorrin-3 to cobyrinic acid a,c-diamide, and more especially in the transfer of a methyl group from SAM to positions C-1, C-5, C-11, C-15 and C-17.

The subject of the invention is also the polypeptides:

participating in the conversion of cobyric acid to cobinamide, or possessing an S-adenosyl-L-methionine:precorrin-2 methyltransferase (SP2MT) activity, or possessing a cobyrinic and/or hydrogenobyrinic acid a,c-diamide synthase activity, or possessing a precorrin-8x mutase activity, or possessing a nicotinate-nucleotide: dimethylbenzimidazole phosphoribosyltransferase activity, or possessing a cobalamin-5'-phosphate synthase activity, or possessing a cobyric acid synthase activity, or possessing a cob(I)alamin adenosyl-transferase activity, or possessing a precorrin-6x reductase activity, or participating in the conversion of hydrogenobyrinic acid a,c-diamide to cobyrinic acid a,c-diamide.

Advantageously, the subject of the invention is a polypeptide chosen from the COBA, COBB, COBC, COBD, COBE, COBF, COBG, COBH, COBI, COBJ, COBK, COBL, COBM, COBN, COBO, COBP, COBQ, COBS, COBT, COBU, COBV, COBW, COBX and CORA proteins presented in FIGS. 15, 16, 40, 41 and 47.

Furthermore, the use of the hybridisation probes described above makes it possible, from genes isolated in other microorganisms, to characterise and isolate the isofunctional polypeptides of other microorganisms. In this manner, the present invention shows that the sequence of a COB protein of *Pseudomonas denitrificans* is significantly homologous with the protein sequences of other microorganisms displaying the same type of activity. Between these COB proteins catalysing the same reaction in different microorganisms, only the evolutionary distances have introduced variations (Wein-Hsiung et al., 1985). The subject of the present invention is also these isofunctional polypeptides.

The assignment of a particular enzymatic activity is the result of an analysis which may be performed according to various strategies. In particular, in vitro affinity studies with respect to SAM (S-adenosyl-L-methionine) make it possible to assign a methyl transferase activity to a protein capable of binding SAM, and hence to assign its involvement in one of the steps of transfer of methyl groups which occur between uro'gen III and cobyrinic acid. Another means of assessing the activity of these polypeptides consists in assaying the intermediates in the pathway of biosynthesis of cobalamins which are accumulated in mutants incapable of expressing these polypeptides (identified by complementation experiments). These analyses enable it to be deduced that the polypeptide in question has the accumulated intermediate as its substrate, thereby enabling its activity in the biosynthetic pathway to be situated and defined. The present invention also describes a method for assaying the enzymatic activities of the biosynthetic pathway, applicable to any strain productive of cobalamins and/or cobamides. These assays enable the enzymatic activity assayed to be purified from any strain productive of these compounds. From this purified activity, the $NH_2$-terminal sequence of the COB protein in question, or alternatively that of the subunits of this protein, may be determined, thereby enabling the structural gene or genes which code for the activity in question to be identified. For *Pseudomonas denitrificans*, the structural genes which code for activities of the biosynthetic pathway are identified by finding, for each $NH_2$-terminal sequence, the COB protein having the same $NH_2$-terminal sequence.

The present invention also describes a method enabling intermediates in the pathway of biosynthesis of cobalamins or of other corrinoids to be identified and assayed in strains productive of cobalamins. These intermediates may be assayed both in culture musts and in the cells themselves. The intermediates which may be assayed are all the corrinoids which occur in the biosynthetic pathway after cobyrinic acid, namely, apart from cobyrinic acid, cobyrinic acid monoamide, cobyrinic acid diamide, cobyrinic acid triamide, cobyrinic acid tetraamide, cobyrinic acid pentaamide, cobyric acid, cobinamide, cobinamide phosphate, GDP-cobinamide, coenzyme $B_{12}$ phosphate and coenzyme $B_{12}$. The non-adenosylated forms of these products may also be assayed by this technique.

Other subjects and advantages of the present invention will become apparent on reading the examples and the drawings which follow, which are to be considered as illustrative and not limiting.

Definition of the Terms Employed and Abbreviations.

| | |
|---|---|
| ATP: | adenosine 5'-triphosphate |
| bp: | base pairs |

-continued

| | |
|---|---|
| BSA: | bovine serum albumin |
| CADAS: | cobyrinic acid a,c-diamide synthase |
| cluster: | group of genes |
| Cob: | corresponds to the phenotype with a reduced level (at least 10-fold lower than the control) of production of cobalamins |
| cob gene: | gene involved in the biosynthesis of cobalamins and/or cobamides from uro'gen III |
| COB protein: | protein participating either as a catalyst in the pathway of biosynthesis of cobalamins, or as a regulatory protein in the network of regulation of the cob genes, or both. |
| cor gene: | gene involved in the biosynthesis of corrinoids from uro'gen III |
| COR protein: | protein participating either as a catalyst in the pathway of biosynthesis of corrinoids, or as a regulatory protein in the network of regulation of the cor genes, or both |
| Corrinoids: | cobyrinic acid derivatives possessing the corrin ring-system |
| dGTP: | 2'-deoxyguanosine 5'-triphosphate |
| DMBI: | dimethylbenzimidazole |
| dNTP: | 2'-deoxyribonucleoside 5'-triphosphates |
| DTT: | dithiothreitol |
| HPLC: | high performance liquid chromatography |
| kb: | kilobases |
| NN:DMBI PRT: | nicotinate-nucleotide:dimethylbenzimidazole phosphoribosyltransferase |
| ORF: | open reading frame |
| recombinant DNA: | set of techniques making it possible either to combine within the same microorganism DNA sequences which are not naturally so combined, or to mutagenise specifically a DNA fragment |
| SAM: | S-adenosyl-L-methionine |
| SDS: | sodium dodecyl sulphate |
| $SP_2MT$: | SAM-L-methionine:precorrin-2 methyltransferase |
| Stop codon: | translation termination codon |
| SUMT: | SAM:uro'gen III methyltransferase |
| Uro'gen III: | uroporphyrinogen III |

BRIEF DESCRIPTION OF THE DRAWINGS

FIG. 3: Structures of uro'gen III, precorrin-1, precorrin-2 and precorrin-3.

FIG. 4: Structural formulae of uro'gen III and cobyrinic acid. Between uro'gen III and cobyrinic acid, there occur 8 SAM-dependent methyl transfers successively at C-2, C-7, C-20, C-17, C-12, C-1, C-15 and C-5, a decarboxylation at C-12, elimination of the carbon at C-20 and insertion of the cobalt atom. X: axial ligands of the cobalt; the ligand at a may be different from the ligand at b.

Figure 1:
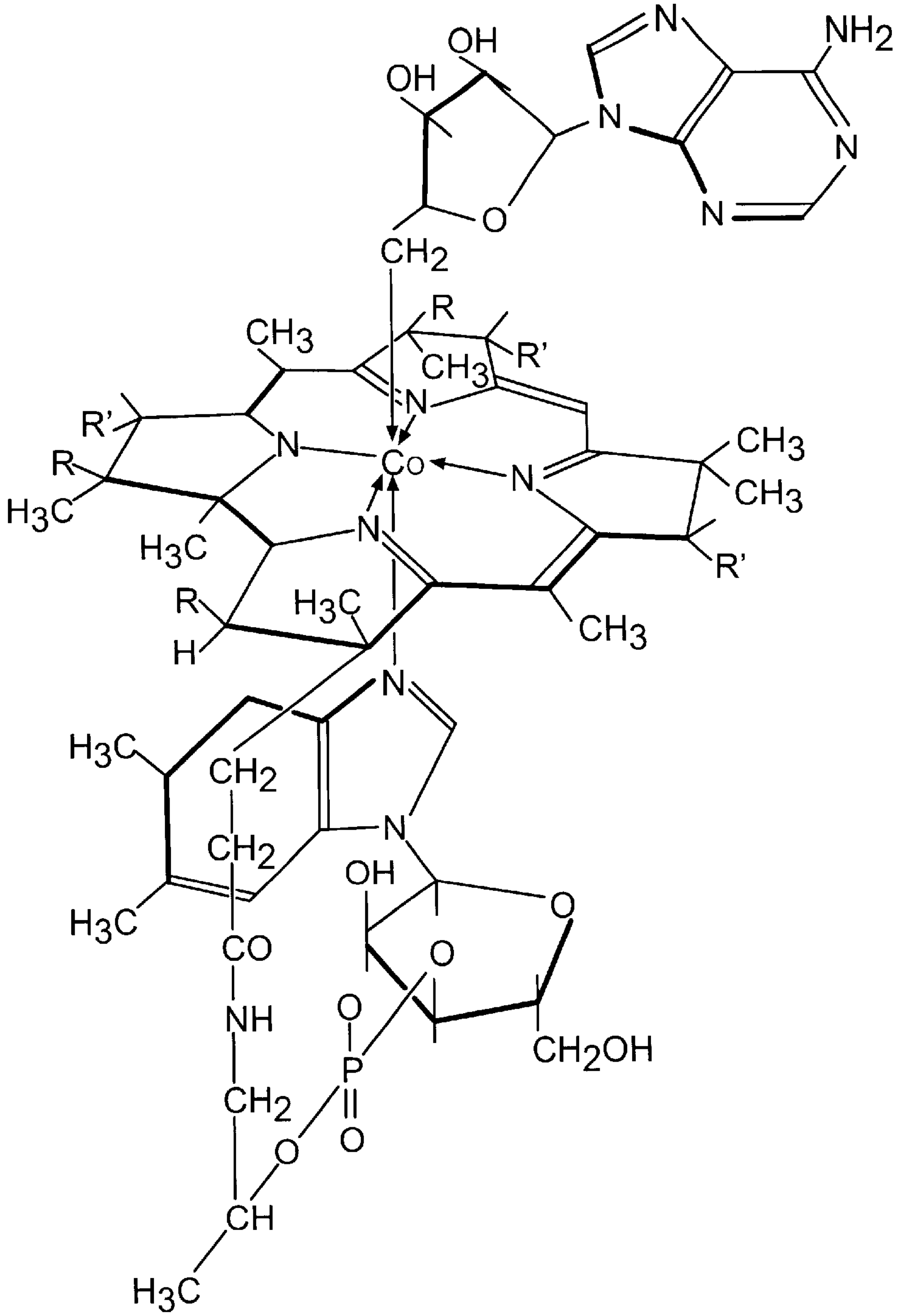
FIG. 1: Structure of coenzyme $B_{12}$; the 5'-deoxyadenosyl group is replaced by a $CH_3$ group for methylcobalamin, by a cyano group for cyanocobalamin, by a hydroxyl group for hydroxocobalamin.
Figure 2:
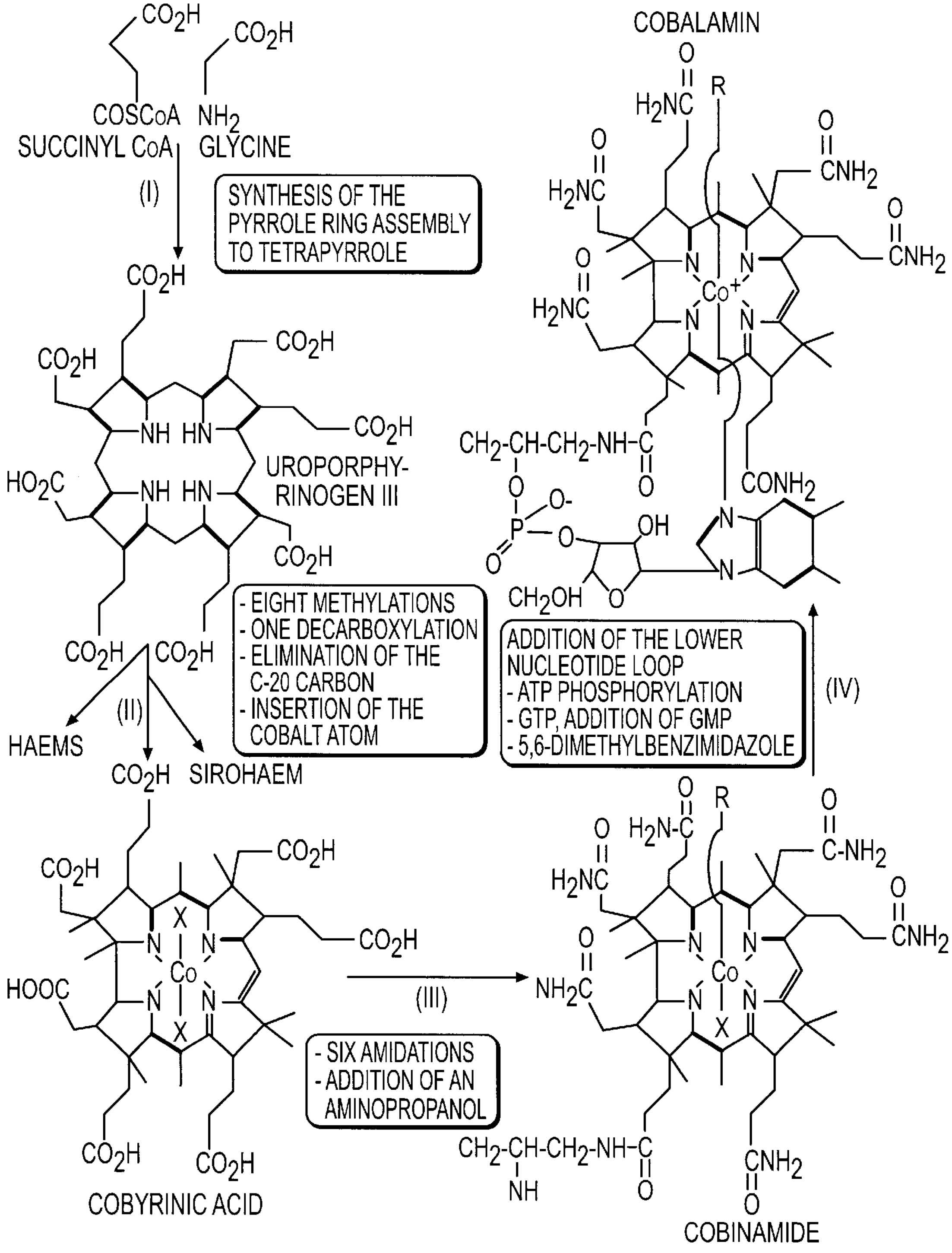
FIG. 2: Biosynthesis of cobalamins and various steps of this biosynthesis. X: axial ligands of the cobalt; the ligand at a may be different from the ligand at b. R: ligand at a of the cobalt which defines the cobalamin type (see FIG. 1).

In order to clarify the diagram, details of the corrin ring-system have been omitted. The five enzymatic steps are represented: 1, cobinamide kinase; 2, cobinamidephosphate guanylyltransferase; 3, cobalamin-5'-phosphate synthase; 4, cobalamin-5'-phosphate phosphohydrolase; 5, nicotinate-nucleotide:DMBI phosphoribosyltransferase.

FIGS. 6A–6D: Restriction maps of the 5.4-kb ClaI-HindIII-HindIII-HindIII, 8.7-kb EcoRI, 4748-bp SalI-SalI-SalI-SalI-SalI-BglI and 3855-bp SstI-SstI-BamHI fragments. Only the 20 restriction enzymes which cut the DNA least frequently are shown. The cleavage sites of each enzyme are indicated by a vertical line.

FIGS. 7A–7I: Nucleotide sequence of both strands of the 5378-bp ClaI-HindIII-HindIII-HindIII fragment of *Pseudomonas denitrificans* (SEQ ID NO: 1). The strand situated at the top is to be read from 5' to 3' in the left-to-right direction which corresponds to the left-to-right orientation of the sequenced fragment presented in FIG. 6. The ClaI site occurs at position 23 (beginning of the cleavage site) since, in this sequence, there occur PstI, SalI and XbaI restriction sites which have appeared during clonings in multisites with a view to sequencing. The sequence of the ClaI-HindIII-HindIII-HindIII fragment hence begins at position 23.

FIG. 8: Nucleotide sequence of both strands of the 8753-bp EcoRI fragment of *Pseudomonas denitrificans* SEQ ID NO: 2. The strand situated at the top is to be read from 5' to 3' in the left-to-right direction which corresponds to the left-to-right orientation of the fragment of the restriction map presented in FIG. 6.

FIGS. 9A–9E: Analysis of the probabilities of the coding frames on the basis of codon preference using the programme of Staden and MacLachlan (1982) on the 6 reading frames of the 5378-bp ClaI-HindIII-HindIII-HindIII fragment. For the frames belonging to the same coding strand, the most probable frame corresponds to that in which a dotted line, not interrupted by stop codons, is placed under the probability line for this frame.

A. Sequence extending from nucleotide 1 to nucleotide 1200. By means of this analysis, open reading frame 1 is identified. It begins at the ATG at position 549 and ends at the TGA at position 1011.

B. Sequence extending from nucleotide 1000 to nucleotide 2200. By means of this analysis, open reading frame 2 is identified. It begins at the ATG at position 1141 and ends at the TGA at position 1981.

C. Sequence extending from nucleotide 1800 to nucleotide 3400. By means of this analysis, open reading frame 3 is identified. It begins at the ATG at position 1980 and ends at the TGA at position 3282.

D. Sequence extending from nucleotide 3000 to nucleotide 4500. By means of this analysis, open reading frame 4 is identified. It begins at the ATG at position 3281 and ends at the TGA at position 4280.

E. Sequence extending from nucleotide 3800 to nucleotide 5378. By means of this analysis, open reading frame 5 is identified. It begins at the GTG at position 4284 and ends at the TGA at position 5253.

FIGS. 10A–10H: Analysis of the probabilities of the coding frames on the basis of codon preference using the programme of Staden and MacLachlan (1982) on the 6 reading frames of the 8753-bp EcoRI fragment. For the frames belonging to the same coding strand, the most probable frame corresponds to that in which a dotted line, not interrupted by stop codons, is placed under the probability line for this frame.

A. Sequence extending from nucleotide 650 to nucleotide 1650. By means of this analysis, open reading frame 6 is identified. It begins at the ATG at position 736 and ends at the TGA at position 1519.

B. Sequence extending from nucleotide 1400 to nucleotide 3100. By means of this analysis, open reading frame 7 is identified. It begins at the ATG at position 1620 and ends at the TAG at position 2997.

C. Sequence extending from nucleotide 2700 to nucleotide 3700. By means of this analysis, open reading frame 8 is identified. It begins at the ATG at position 3002 and ends at the TGA at position 3632.

D. Sequence extending from nucleotide 3500 to nucleotide 4100. By means of this analysis, open reading frame 9 is identified. It begins at the GTG at position 3631 and ends at the TGA at position 4366.

E. Sequence extending from nucleotide 4150 to nucleotide 5150. By means of this analysis, open reading frame 10 is identified. It begins at the ATG at position 4365 and ends at the TGA at position 5127.

F. Sequence extending from nucleotide 5000 to nucleotide 6000. By means of this analysis, open reading frame 11 is identified. It begins at the ATG at position 5893 and ends at the TAG at position 5110.

G. Sequence extending from nucleotide 5700 to nucleotide 7200. By means of this analysis, frame 12 is identified. It begins at the ATG at position 5862 and ends at the TAA at position 7101.

H. Sequence extending from nucleotide 7000 to nucleotide 8000. By means of this analysis, open reading frame 13 is identified. It begins at the ATG at position 7172 and ends at the TTG at position 7931.

Figure 11:
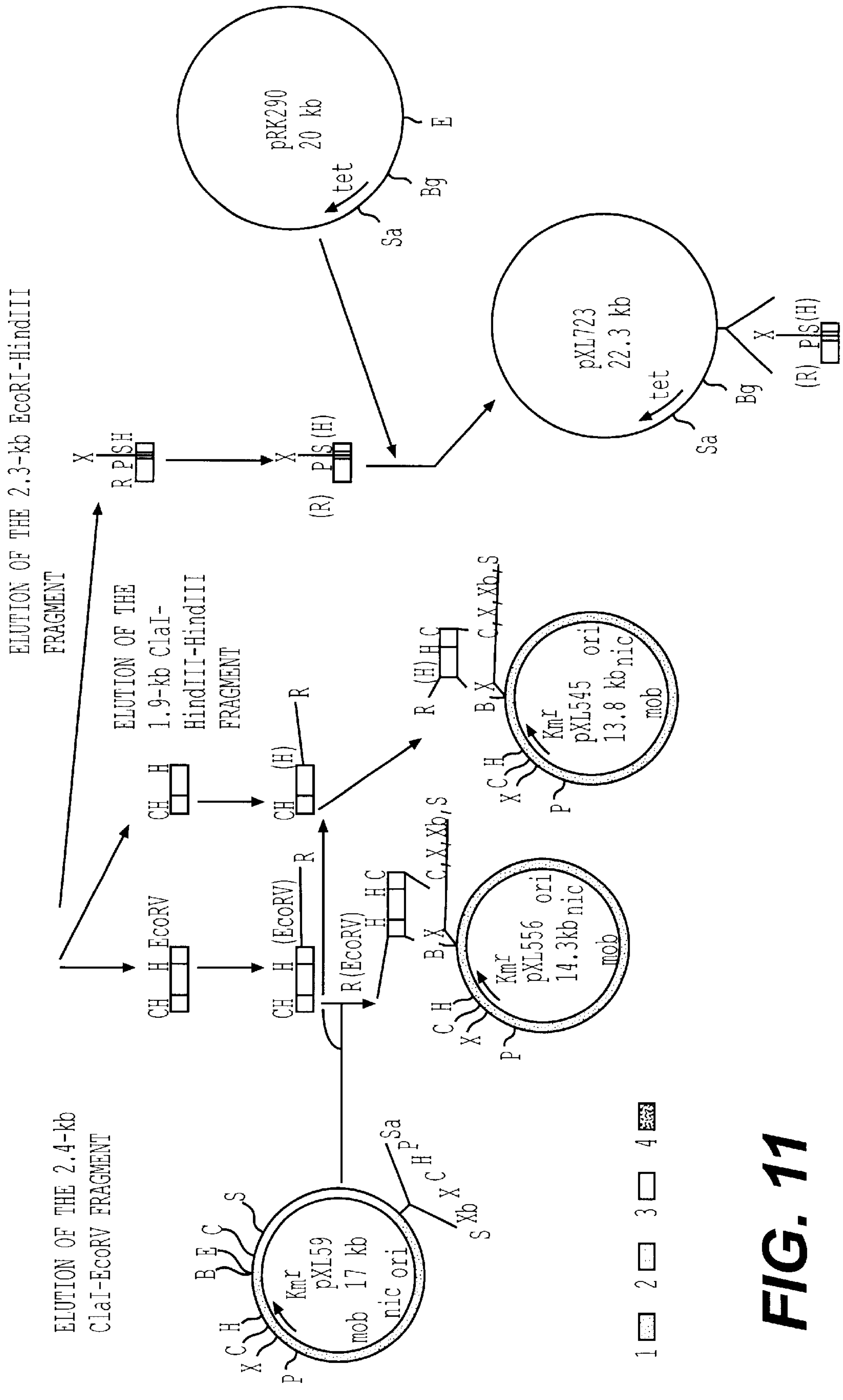

FIG. 11: Construction of plasmids pXL556, pXL545 and pXL723.

A 2.4-kb ClaI-EcoRV fragment containing the cobA and cobE genes is excised from the 5.4-kb fragment and then purified. An EcoRI linker is added at the EcoRV site and the fragment is then inserted into pXL59 between the ClaI-EcoRI sites. The plasmid thereby constructed is designated pXL556.

The construction is comparable for pXL545: a 1.9-kb ClaI-HindIII-HindIII fragment is excised from the 5.4-kb fragment and then purified. This fragment contains only the CobE gene. An EcoRI linker is added at the HindIII site and the fragment is then inserted into pXL59 between the ClaI-EcoRI sites. pXL723 is constructed as follows: a 2.3-kb EcoRI-HindIII fragment is excised from the 5.4-kb fragment and purified, and the ends are then filled in with the large fragment of *E. coli* DNA polymerase I. This fragment is cloned into pRK290 (Ditta et al., 1981) digested with EcoRI and then treated with the large fragment of *E. coli* DNA polymerase I in order to fill in the ends.

The restriction sites which are shown in brackets correspond to sites which have disappeared after treatment with the large fragment of *E. coli* DNA polymerase I. 1, PstI-SstI fragment of RSF1010 (De Graff et al., 1978); 2, PstI-BamHI fragment of pACYC177 (Bagdasarian et al., 1981); 3, BamHI-SstI fragment containing the lactose operon of *E. coli* without its promoter, the operator, the translation initiation site and the first 8 non-essential codons of lacZ (Casadaban et al., 1983); 4, Sau3AI fragment of *Pseudomonas putida* KT2440 (Bagdasarian et al., 1981); ori, origin of replication; nic, relaxation site; mob, locus essential for mobilisation; $Km^r$, kanamycin resistance gene (Bagdasarian et al., 1981); B, BamHI; C, ClaI; E, EcoRI; H, HindIII; P, PstI; S, SstI; Sa, SalI; X, XhoI; Xb, XbaI.

Figure 12:
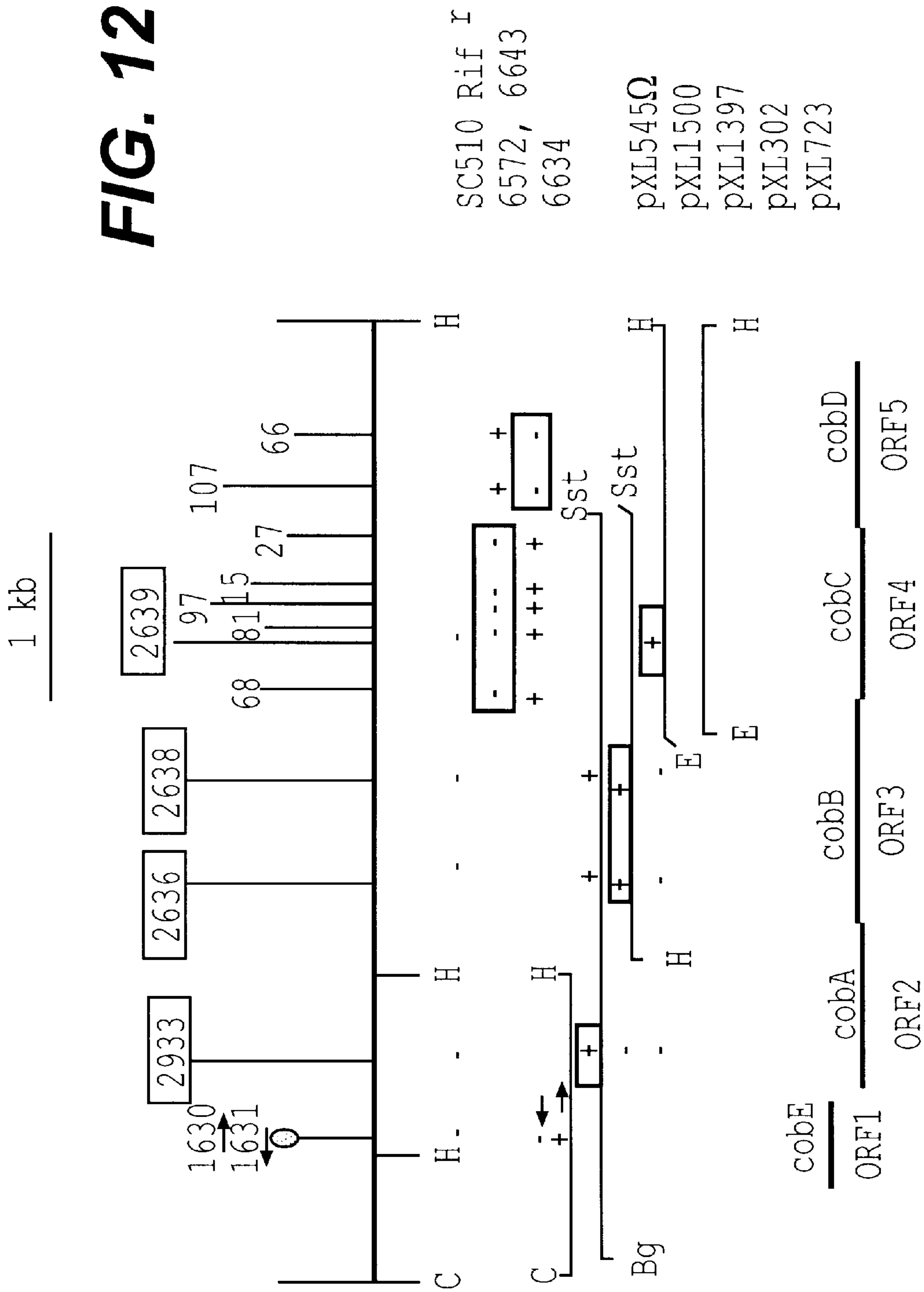
Figure 30:
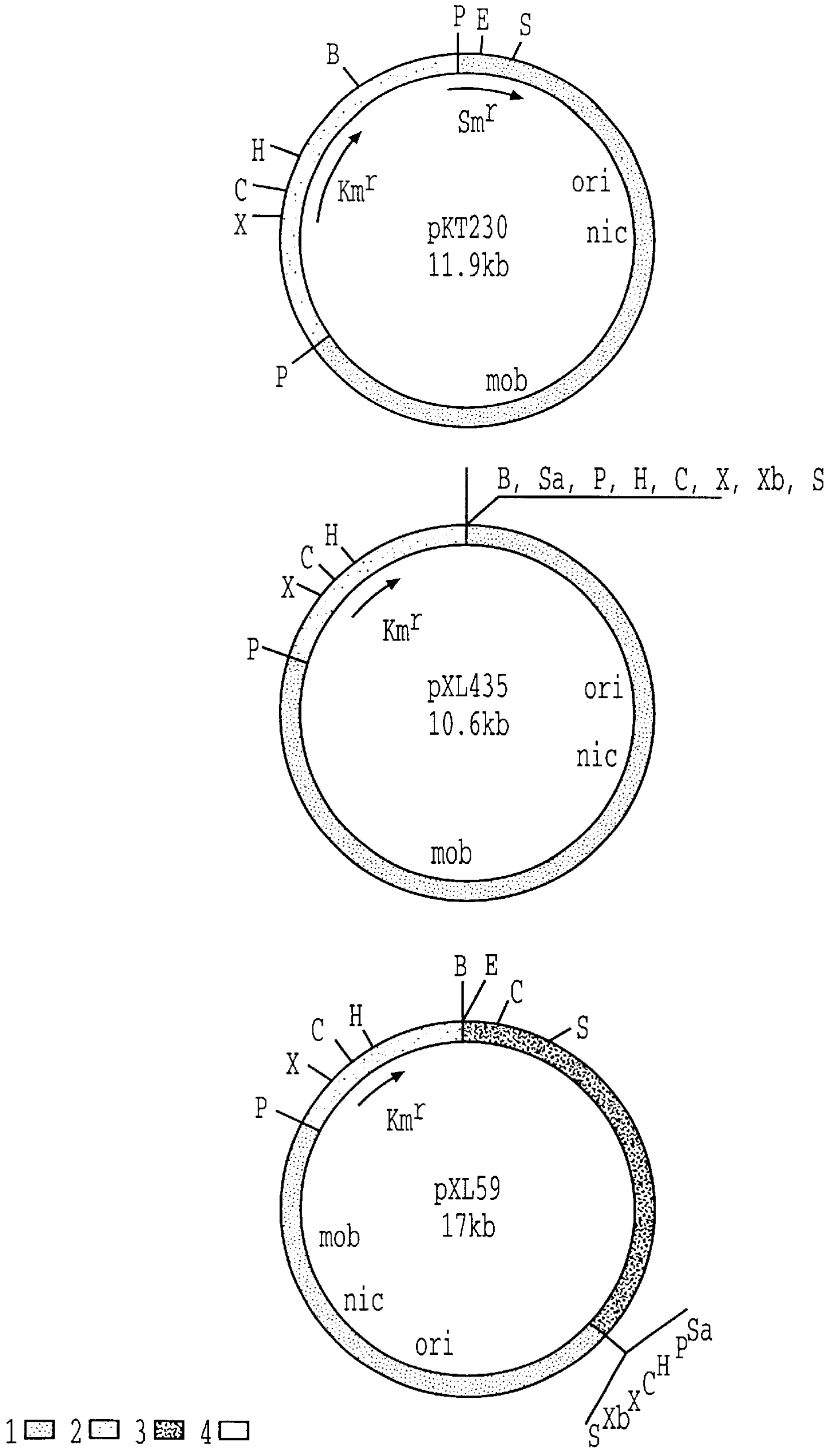

FIG. 12: Studies of the insertions of transposons $Tn5Sp^r$ and Tn5 into the 5378-bp fragment. The insertions of transposon Tn5 into plasmid pXL723 are shown as in FIG. 14; those of transposon $Tn5Sp^r$, into the chromosome of strain G2 $Rif^r$, are boxed; the insertions into the chromosome of SC510 $Rif^r$ of cassettes carrying the kanamycin resistance gene (1630 and 1631) are shown with an arrow, according to the orientation of transcription of the kanamycin resistance gene, under the insertion number. The open reading frames deduced from the sequence are given in this figure (from cobA to cobE); + or − signs are shown under each insertion of transposon or of resistance cassette to indicate that the insertion is inactivating (−) or otherwise (+), i.e. for the complementation of different mutants (the case with the insertions of transposons Tn5), or that the insertion abolishes the cobalamin production of the strain in which it takes place. There is an absence of complementation when the recombinant mutant synthesises less than threefold less cobalamins than the level of synthesis of the strain from which the mutant is derived. The inserts of plasmids pXL545, pXL1500, pXL1397 and pXL302 are shown with the restriction sites occurring at their ends. These inserts are cloned into broad host range plasmids, pXL435 and pXL59 (Cameron et al., 1989):

plasmid pXL545 corresponds to plasmid pXL545 described in FIG. 11 with, in addition, the 2-kb BamHI fragment of pHP45 (Prentki and Krisch) containing a spectinomycin resistance gene cloned at the BamHI site of pXL545;

plasmid pXL1500 corresponds to the 4.2-kb BglII-SstI fragment presented in this figure, cloned at the BamHI and SstI sites of pKT230 (Bagdasarian et al., 1981); presented in FIG. 30;

plasmid pXL1397 corresponds to the 2.4-kb HindIII-SstI fragment indicated in the figure, inserted between the HindIII and SstI sites of the multisite of pXL435 (Cameron et al., 1989) described in FIG. 30; plasmid pXL302 corresponds to the 2.3-kb EcoRI-HindIII fragment as described in the figure, inserted between the EcoRI and HindIII sites of pXL59 (Cameron et al., 1989) described in FIG. 30, the HindIII site used being the site occurring in the cloning multisite of pXL59;

pXL723 is described in FIG. 11, like pXL545.

+ or − signs are shown above each of these inserts to indicate whether there is complementation by the plasmid in question of the chromosomal insertions shown underneath. C, ClaI; E, EcoRI; H, HindIII; RV, EcoRV; Sau, Sau3AI; S, SstI.

Figure 13:
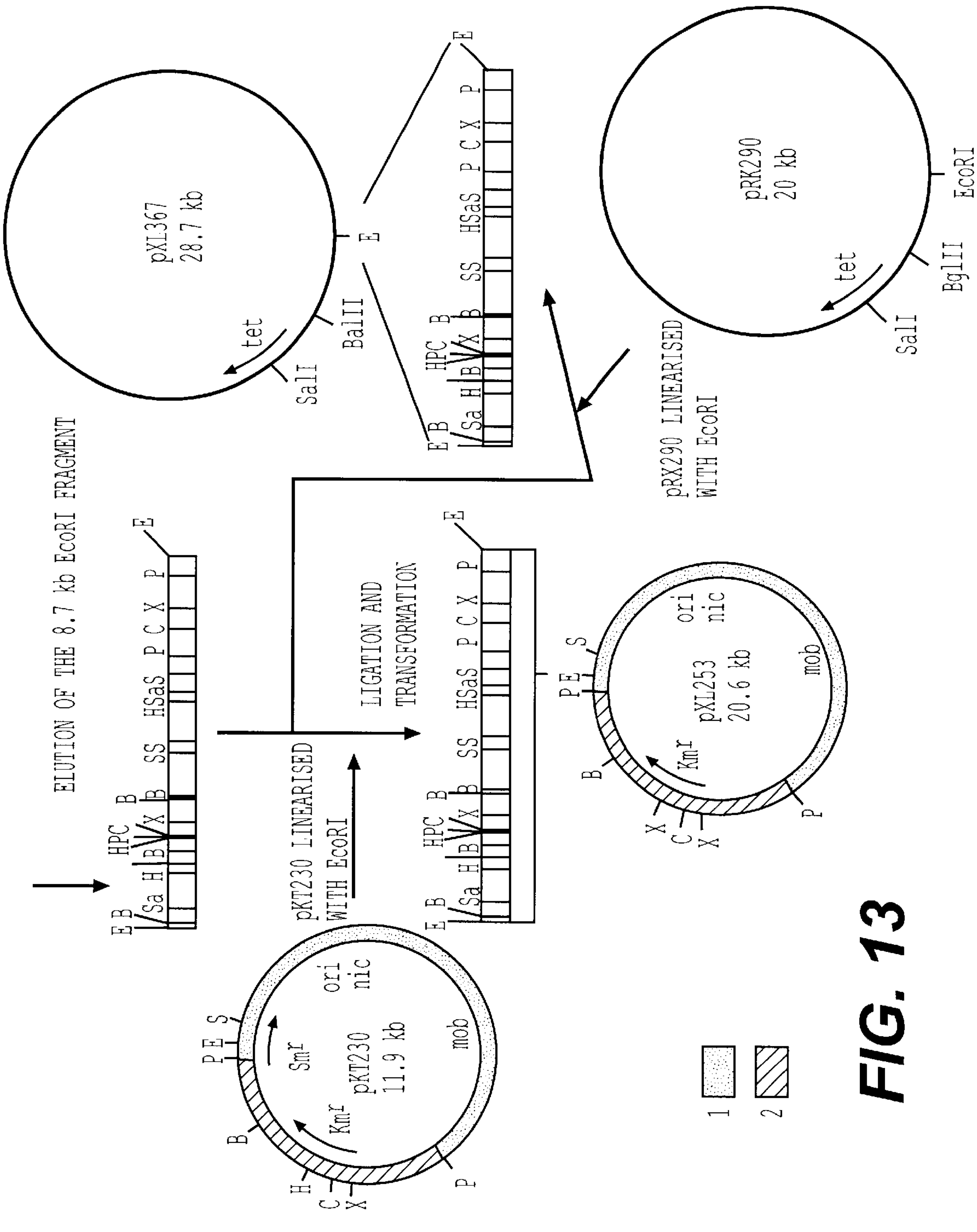

FIG. 13: Construction of plasmids pXL253 and pXL367.

The 8.7-kb EcoRI fragment is excised and then purified from plasmid pXL151. It is cloned at the EcoRI site of pKT230 to give pXL253. This same fragment is inserted at the EcoRI site of pRK290 (Ditta et al., 1981) to give pXL367. 1, PstI-SstI fragment of RSF1010 (De Graff et al., 1978); 2, PstI-BamHI fragment of pACYC177 (Bagdasarian et al., 1981); ori, origin of replication; nic, relaxation site; mob, locus essential for mobilisation (Bagdasarian et al., 1981); B, BamHI; C, ClaI; E, EcoRI; H, HindIII; P, PstI; S, SstI; Sa, SalI; X, XhoI; Xb, XbaI; $tet^r$, tetracycline resistance gene; $Km^r$, kanamycin resistance gene.

Figure 14:
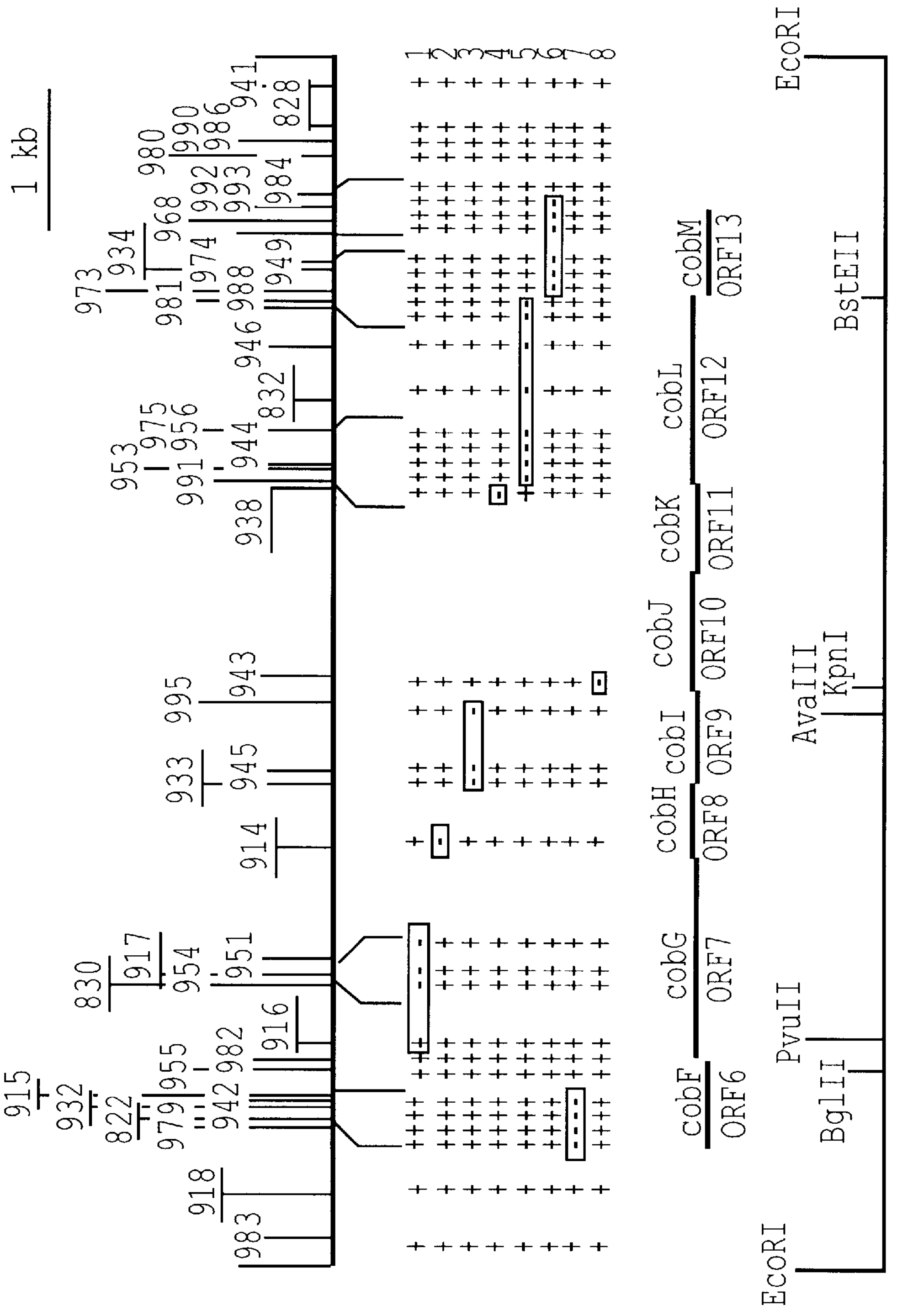
Figure 15B:
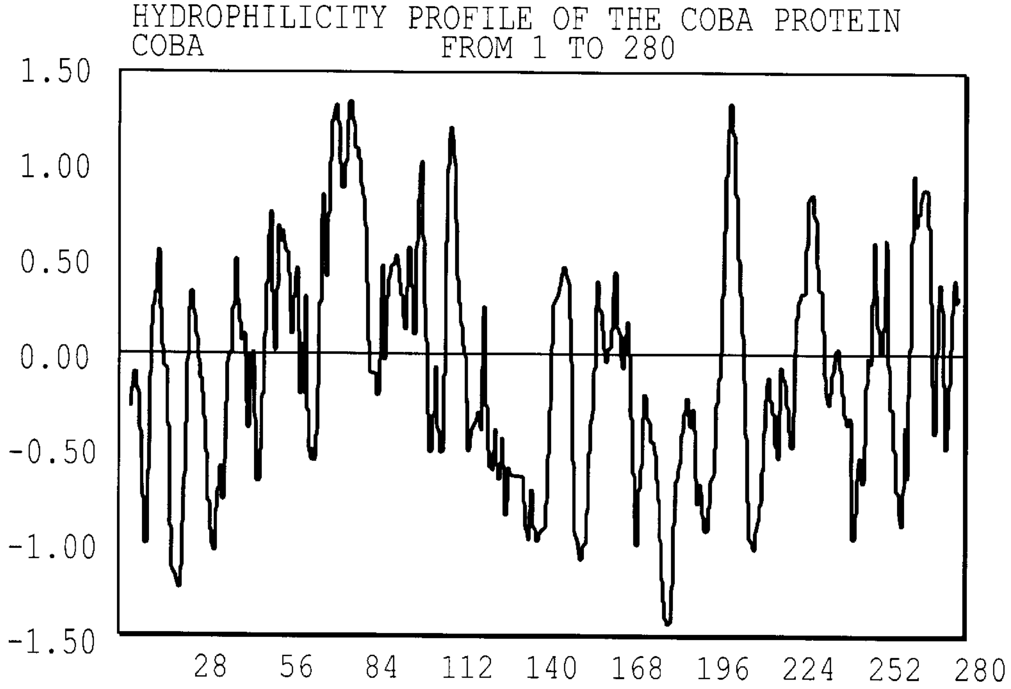
Figure 15E:
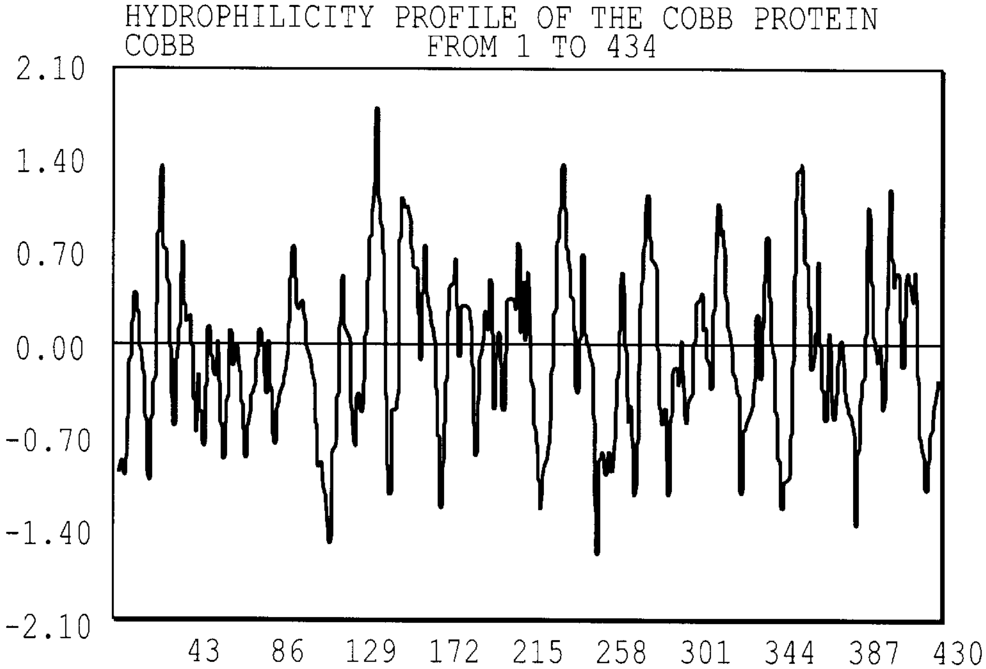
Figure 15G:
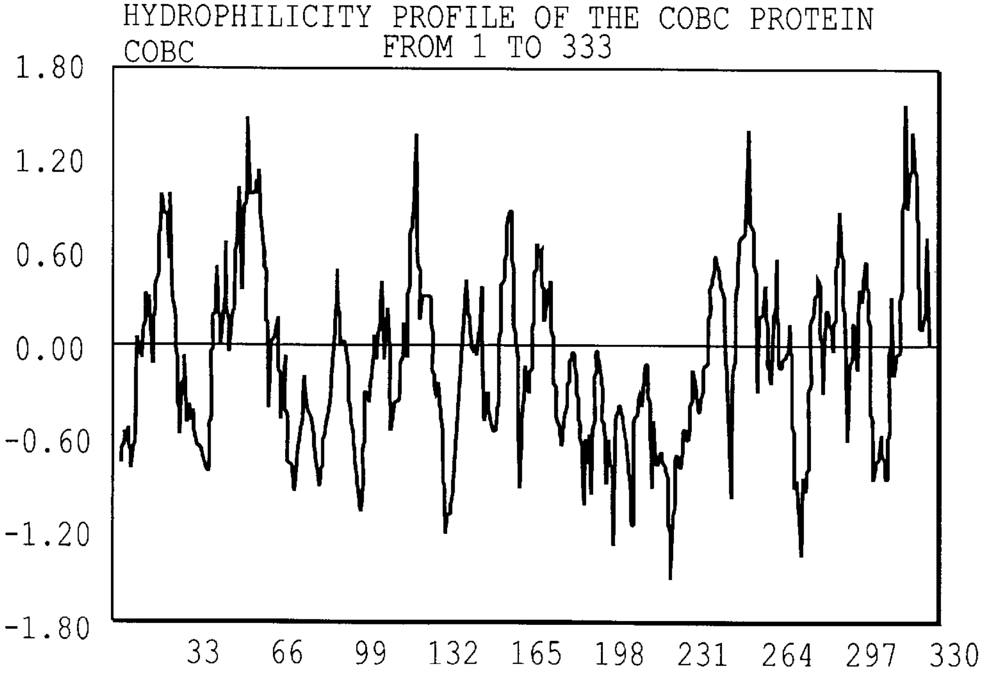
Figure 15I:
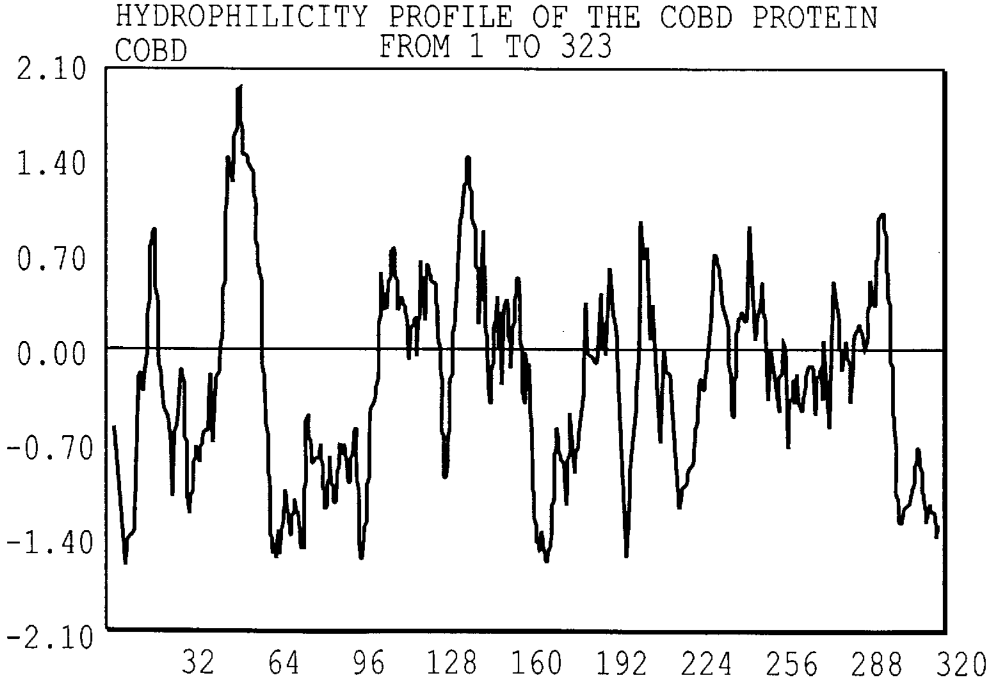
Figure 15K:
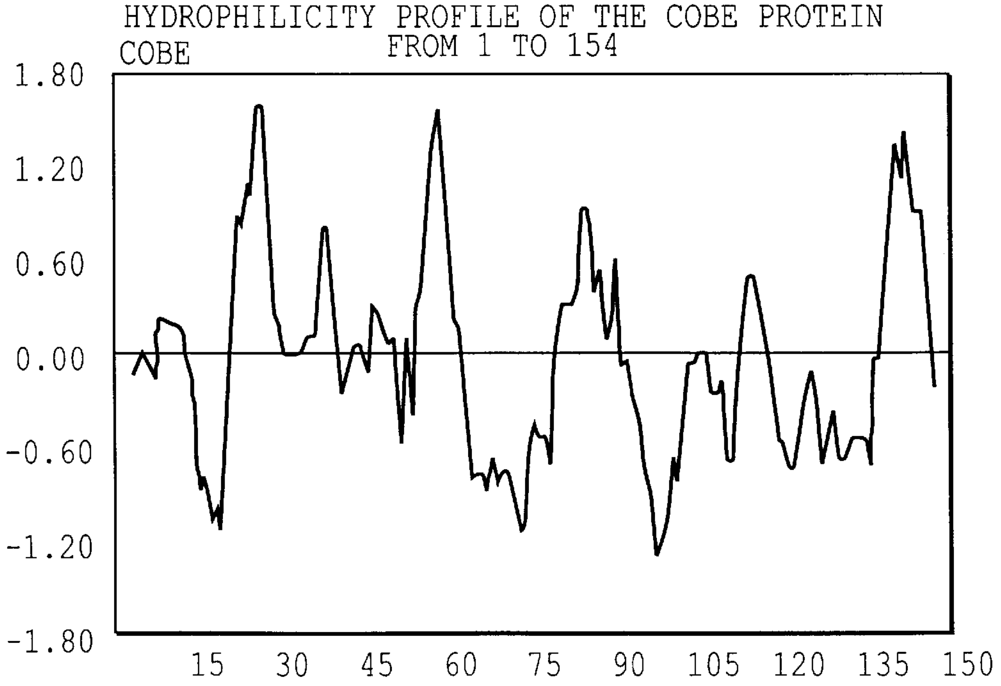

FIG. 14: Studies of the insertions of transposons Tn3lacZ and Tn5 into the 8.7-kb EcoRI fragment cloned into pRK290 (Ditta et al., 1980). The insertions of transposons Tn3lacZ are underlined, in contrast to those of transposons Tn5. The open reading frames deduced from the sequence (cobF to cobM) are given in this figure, and the eight groups of inactivating insertions (numbered from 1 to 8) are presented; + or − signs are shown under each transposon insertion to indicate that the insertion is inactivating (−) or otherwise (+) for the complementation of different mutants. There is an absence of complementation when the recombinant mutant synthesises less than threefold less cobalamins than the level of synthesis of the strain from which the mutant is derived. These groups of inactivating insertions correspond to the following mutants: 1, G615; 2, G614 and G616; 3, G613 and G614; 4, G620; 5, G638; 6, G610 and G609; 7, G612; 8, G611. These mutants are Cob mutants of *Agrobacterium tumefaciens* already described (Cameron et al., 1989). A restriction map of the 8.7-kb fragment is given at the bottom of the figure.

FIGS. 15A–15K: The coding sequences of each of the genes of the 5.4-kb fragment, cobA to cobE, respectively, are indicated. The sequences of the proteins COBA to COBE encoded by these sequences appear under their respective coding sequence, cobA to cobE. The amino acid composition of each protein, in number and in percentage, respectively, of COBA to COBE, is presented, as well as the molecular weight, the index of polarity, the isoelectric point and the optical density at 260 nm and 280 nm of a solution containing 1 mg/ml of purified protein. The hydrophilicity profile of each COBA to COBE protein, respectively, is shown; it was calculated on the basis of the programme of Hopp and Woods (1981). Positive values correspond to regions of the protein which are hydrophilic. The position of the amino acids is indicated as abscissa, while the value of the index of hydrophilicity is shown as ordinate; when this value is positive, this indicates that the region of the protein is hydrophilic.

Figure 16B:
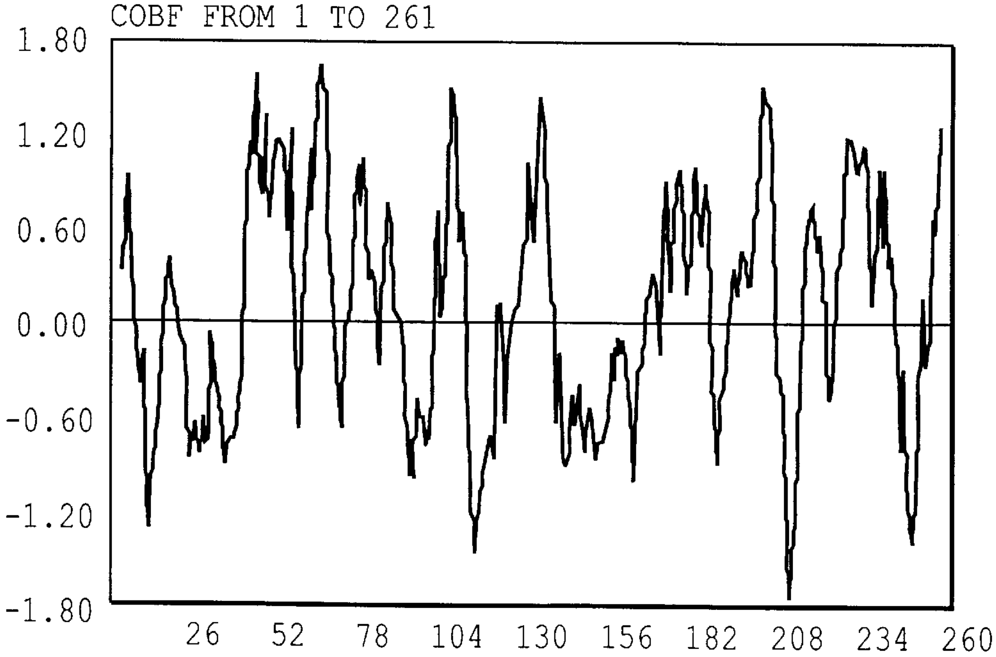
Figure 16E:
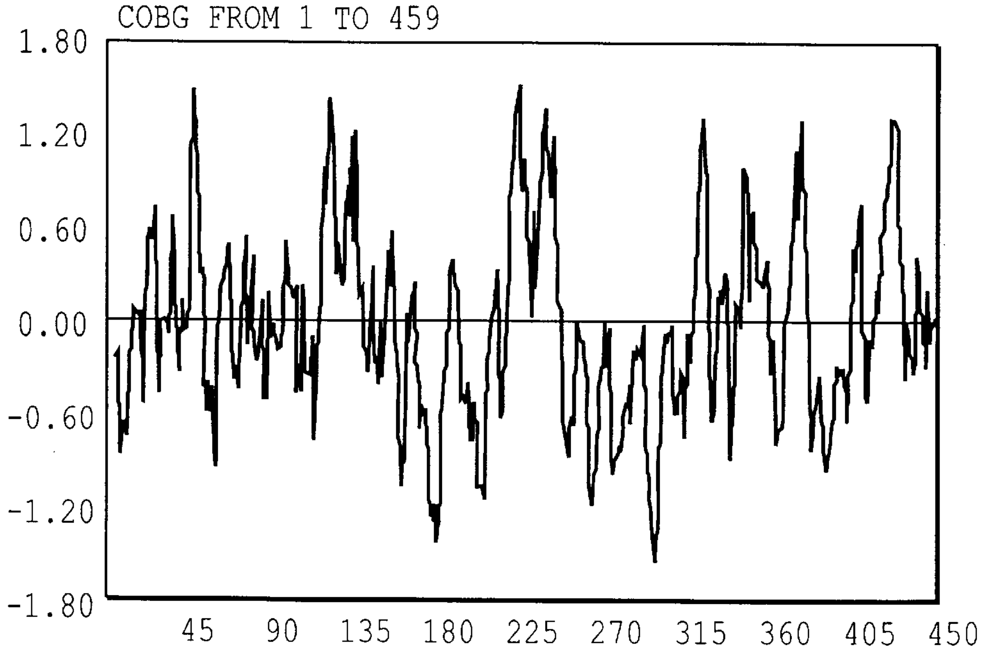
Figure 16G:
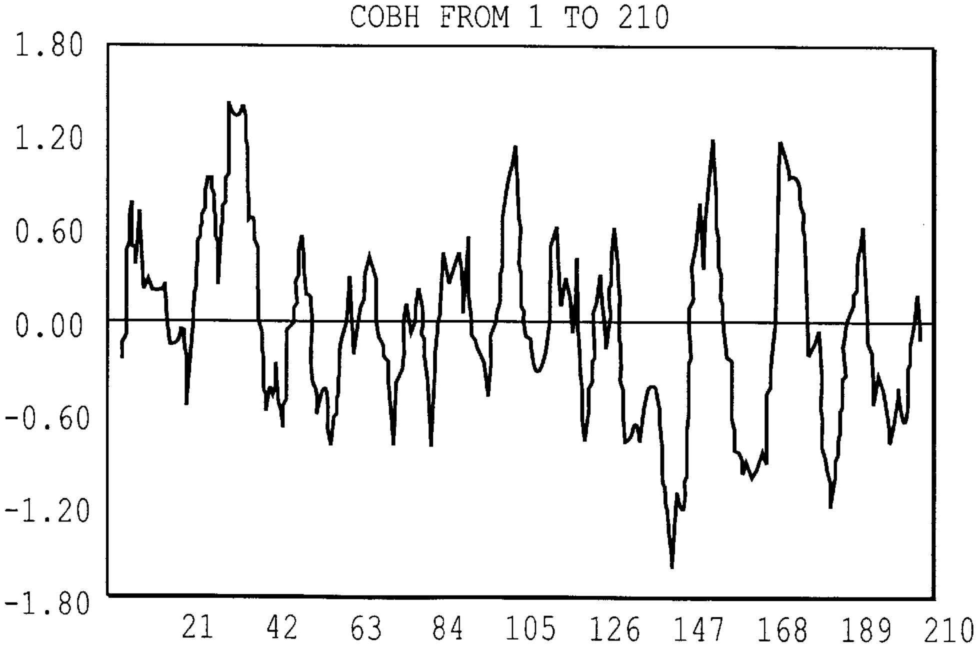
Figure 16I:
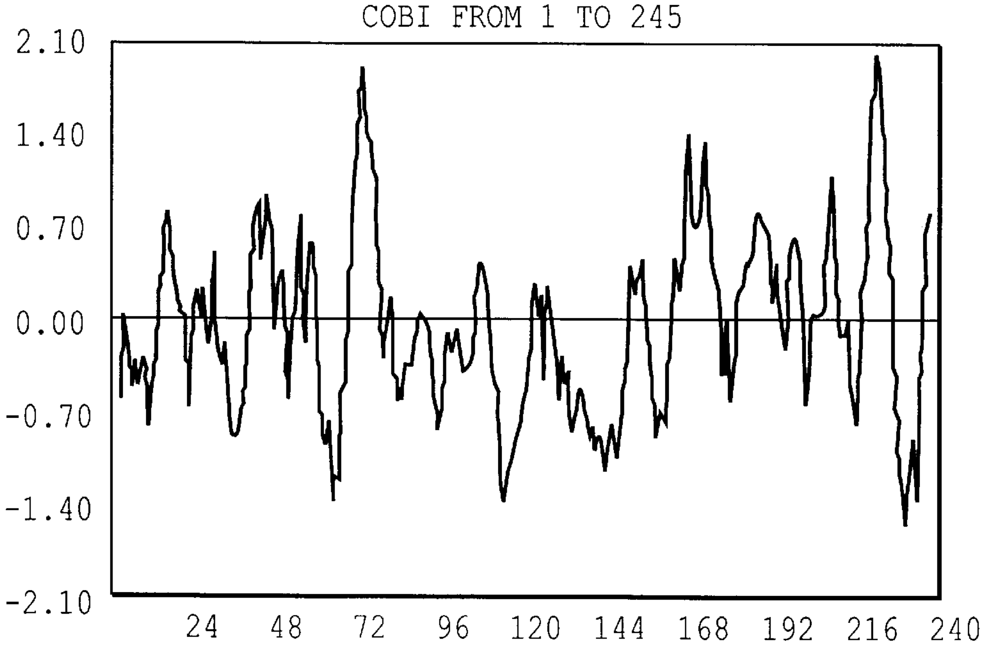
Figure 16K:
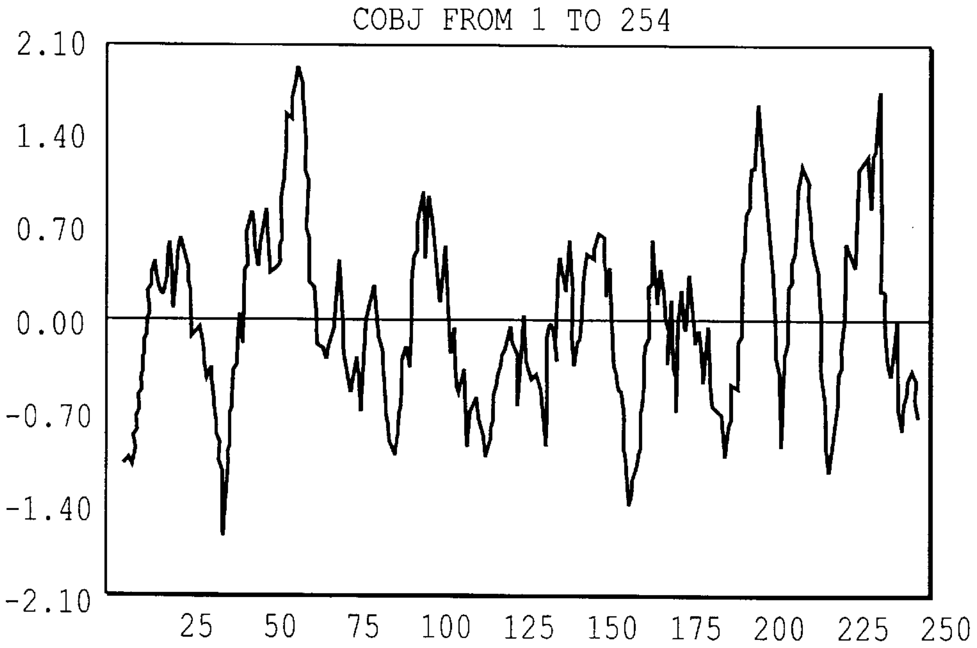
Figure 16M:
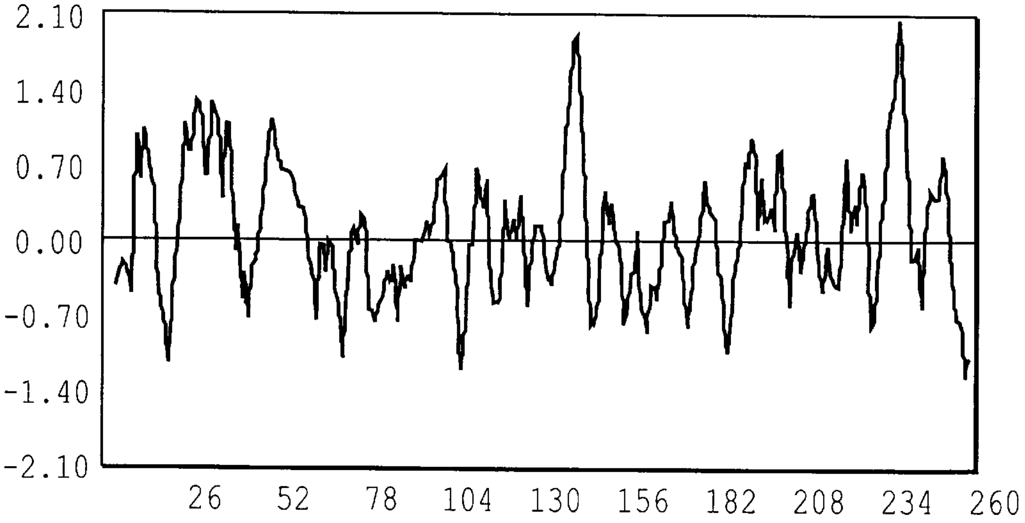
Figure 16P:
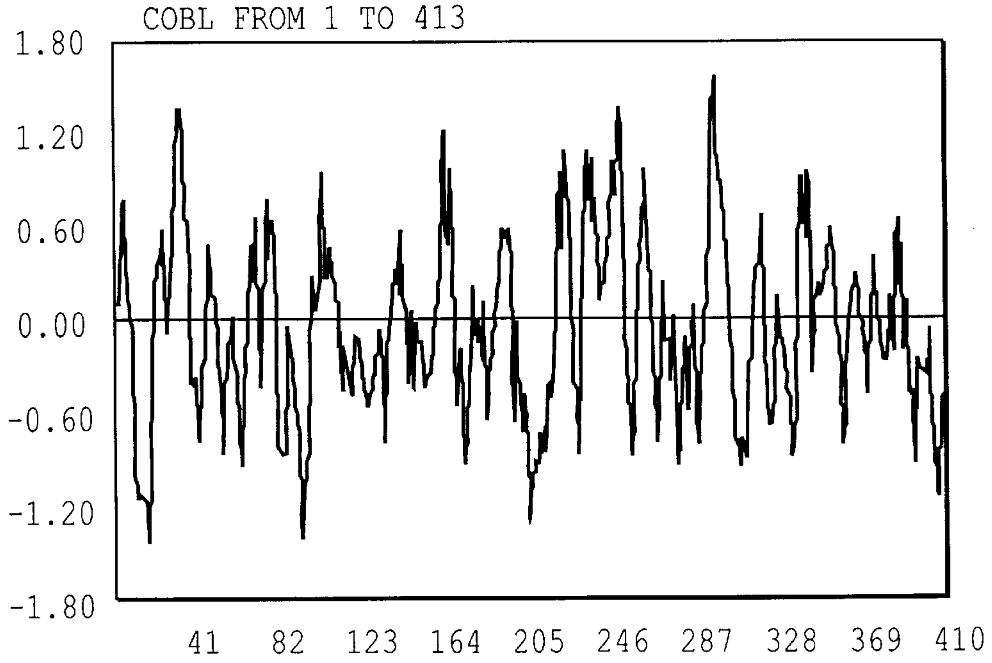
Figure 16R:
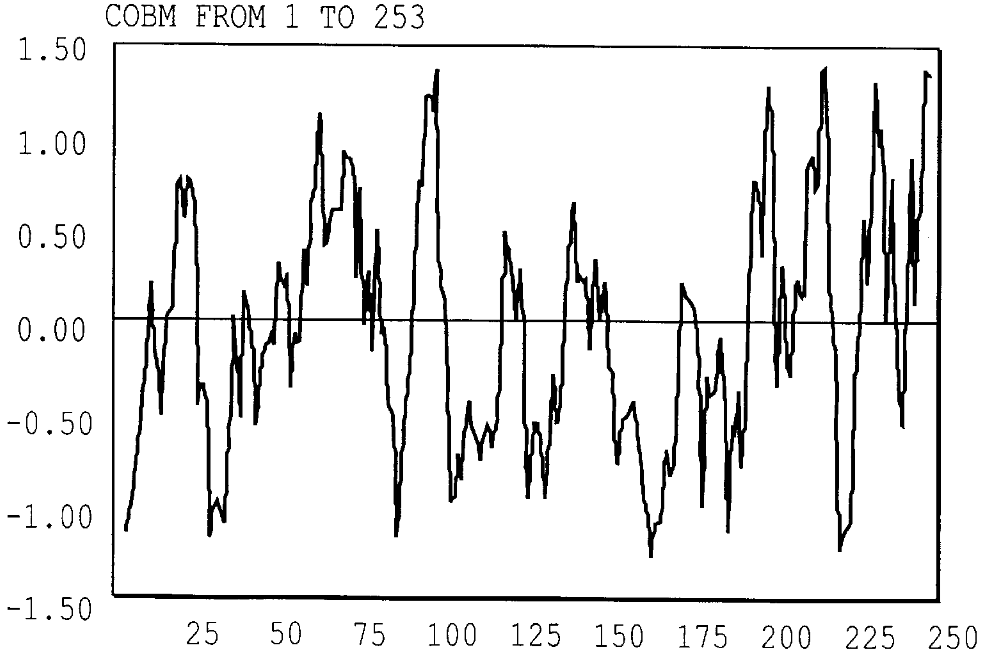

FIGS. 16A–16R: The coding sequences of each of the genes of the 8.7-kb fragment, cobF to cobM respectively, are indicated. The sequences of the COBF to COBM proteins encoded by these sequences appear under their sequence. The legend is identical to that for FIG. 15. NB. We have shown the COBF protein as beginning at the ATG located at position 736; it is possible that the ATG located at position 751 is the true initiation codon of this protein.

Figure 17:
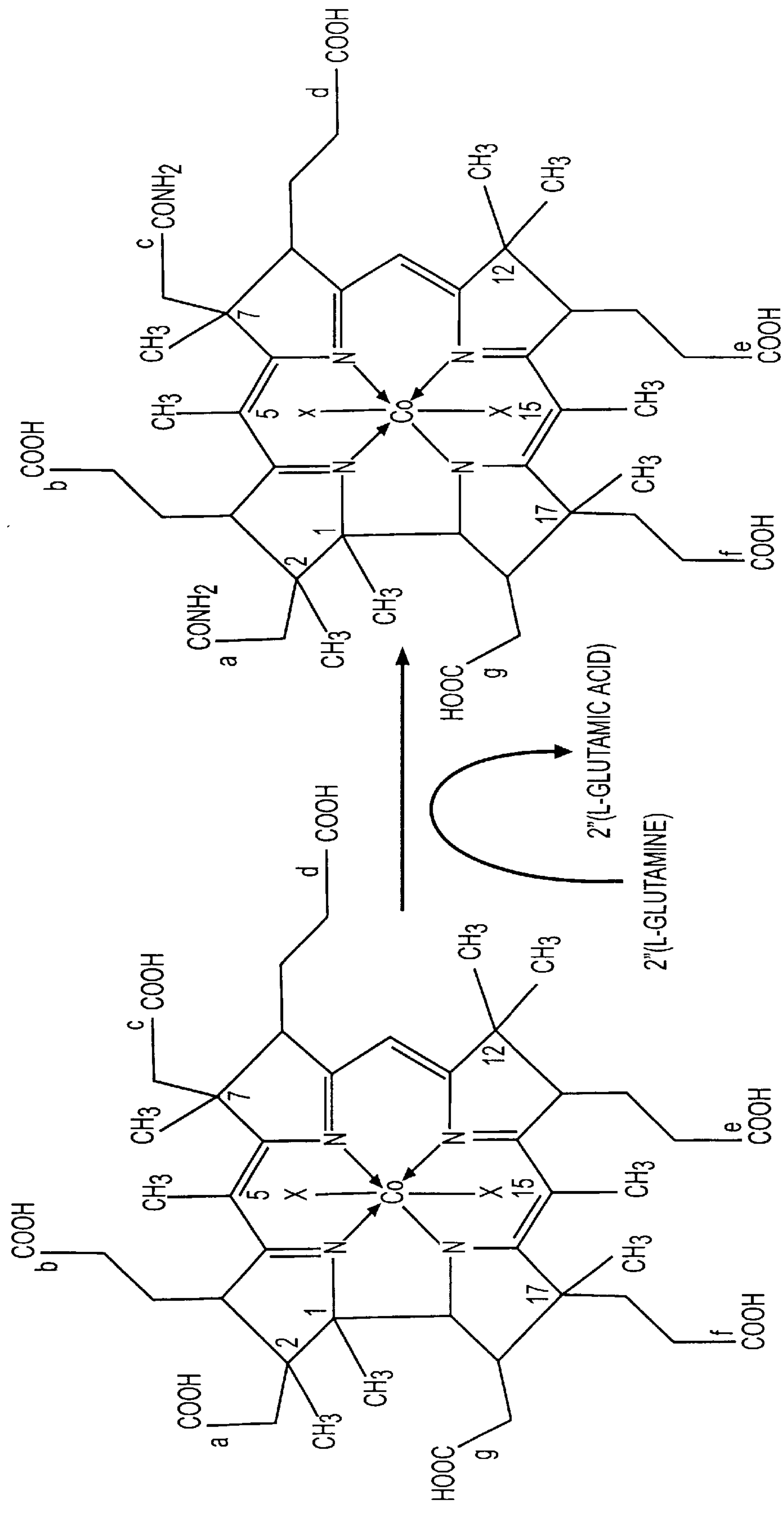

FIG. 17: Reaction catalysed by cobyrinic acid a,c-diamide synthase. CADAS catalyses the amidation of the carboxylic acid functions of the peripheral acetate chains a and c of cobyrihic acid to give cobyrinic acid diamide; the donor of the amine group used in the enzymatic test is L-glutamine; it gives L-glutamic acid on deamination. X corresponds to the axial ligands of the cobalt, which may be different from one another.

Figure 18:
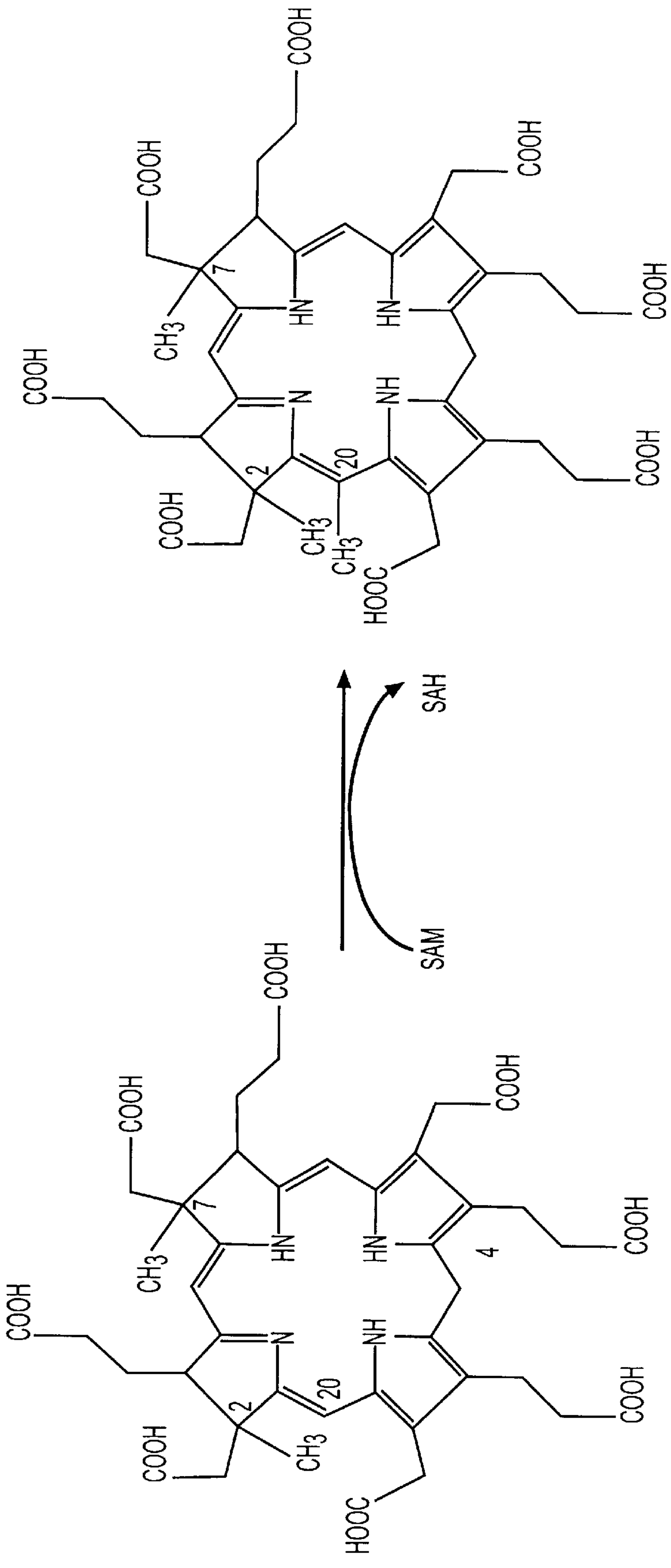

FIG. 18: Reaction catalysed by $SP_2MT$. $SP_2MT$ catalyses the transfer of a methyl from SAM to dihydrosirohydrochlorin or precorrin-2 to give precorrin-3. The methyl group is transferred to position C-20 of the porphyrin ring-system.

FIG. 19: Structure of hydrogenobyrinic acid and of hydrogenobyrinic acid a,c-diamide.

Figure 20:
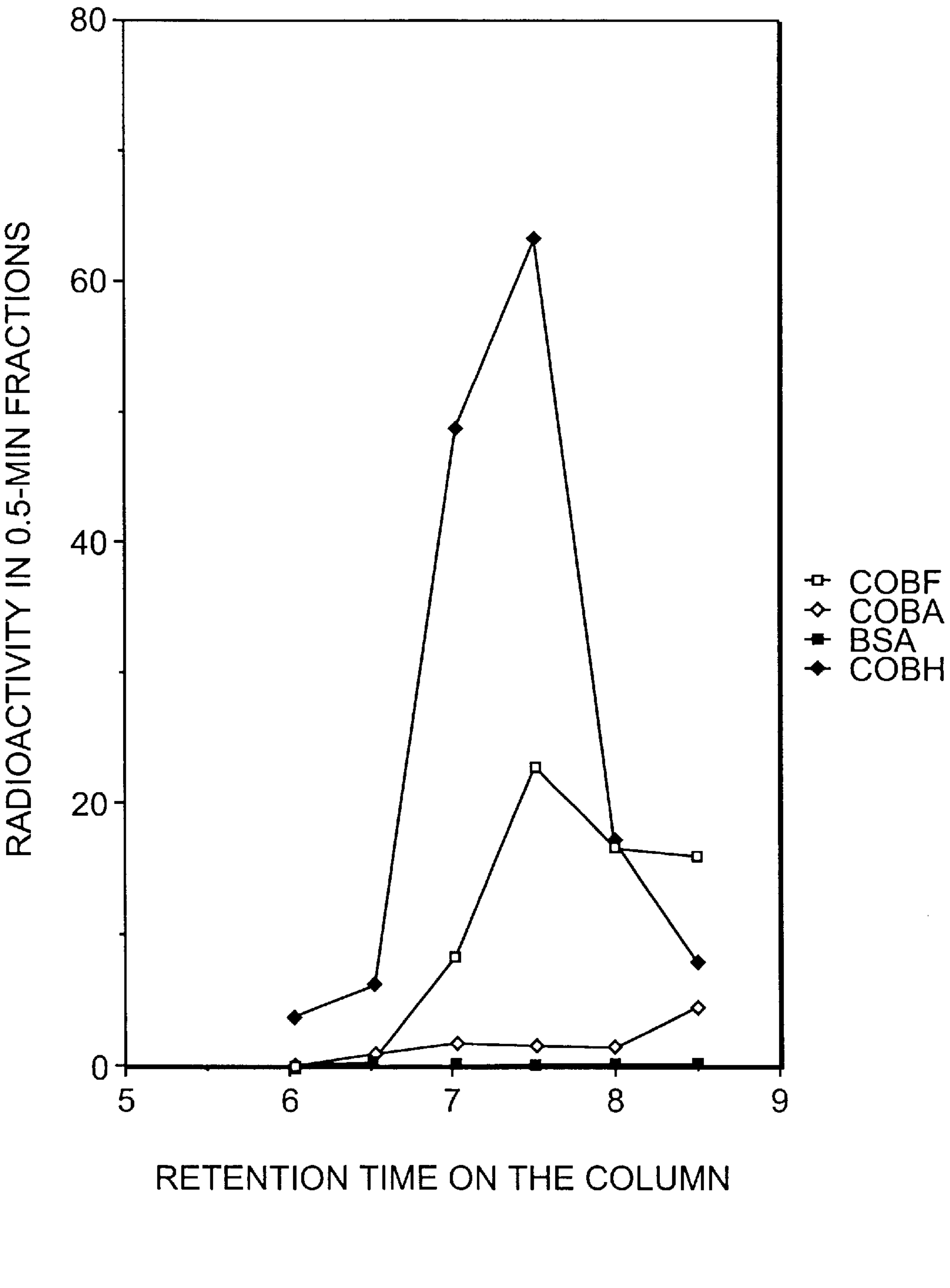

FIG. 20: Affinities of the COBA and COBF proteins for SAM. The curves give in arbitrary units the radioactivity at emergence from the TSK-125 column for each protein applied to this column. The retention times are indicated in minutes and the radioactivity peak corresponding to free SAM is observed at the time of 10 min 30 sec.

FIG. 21: Comparison of the sequences of COBA and COBI.

Only the regions 1, 2 and 3, of strong homology, are presented. = signs are placed between identical residues and – signs between homologous residues (H K R, LIVM, A G S T, Y F W, D E Q N B Z, P, C).

FIG. 22: Comparison of the primary sequences of the proteins COBA of *Pseudomonas denitrificans* and CYSG of *E. coli*. The alignment has been done according to the programme of Kanehisa, 1984. = signs are placed between identical residues and – signs between homologous residues (HKR, LIVM, A G S T, Y F W, D E Q N B Z, P, C). The regions 1, 2 and 3 correspond to zones of strong homology between the proteins.

FIG. 23: Comparison of the sequences of CYSG of *E. coli* with COB proteins of *Pseudomonas denitrificans* (COBA, COBF, COBI, COBJ, COBL and COBM). The comparisons concern the regions 1, 2 and 3, of strong homologies, which exist between CYSG, COBA and COBI. The positions in the protein sequences of the regions displaying homologies are presented in the figure. We have considered the following groups of homologous residues: H K R, L I V M, A G S T, Y F W, D E Q N B Z, P, C. If there are at least 3 homologous residues at the same position, we have boxed these amino acids.

Figure 24:
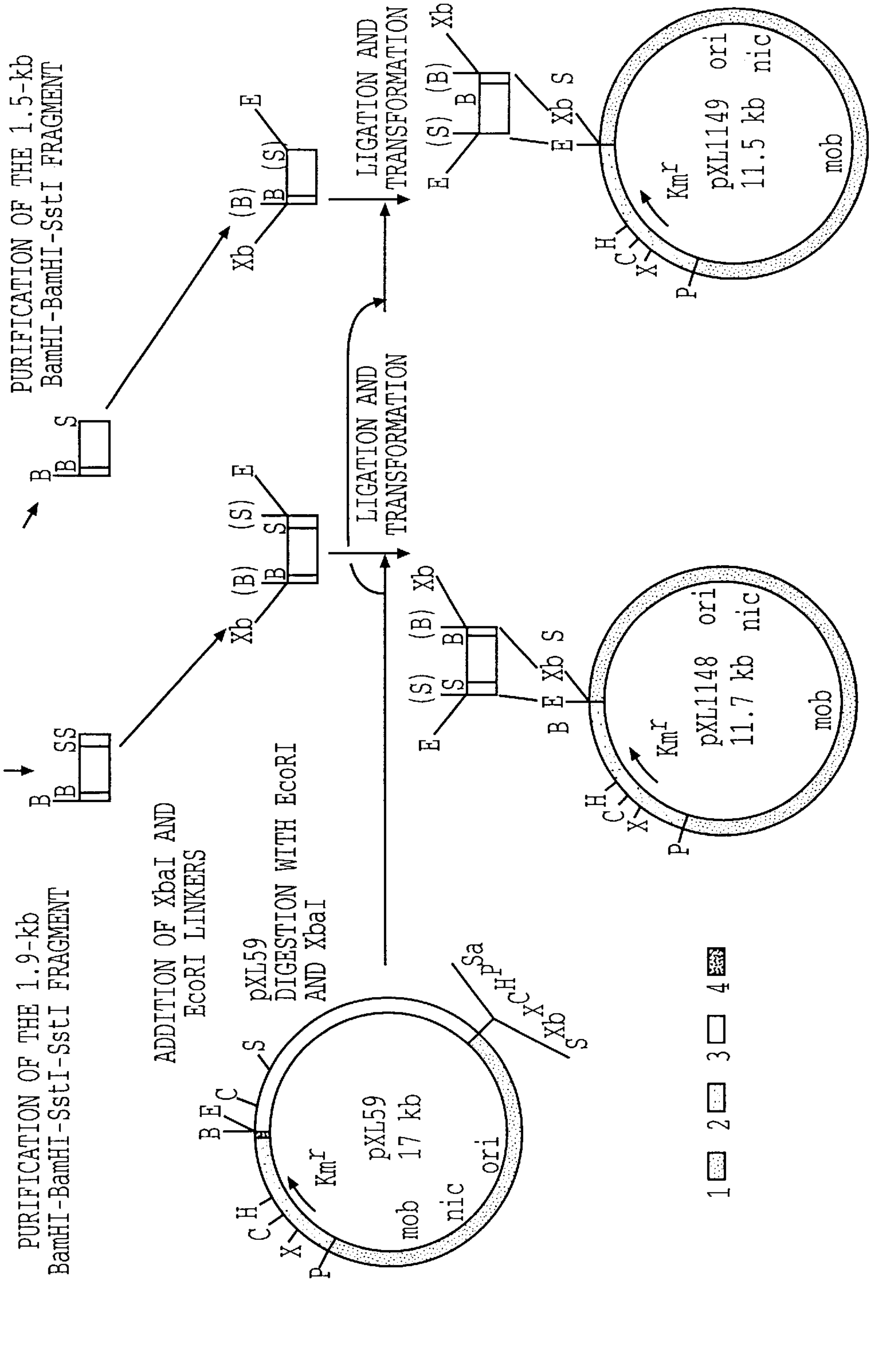

FIG. 24: Construction of plasmids pXL1148 and pXL1149.

pXL1148 is constructed as follows: the 1.9-kb BamHI-BamHI-SstI-SstI fragment of the 8.7-kb fragment containing the cobH and cobI genes is purified, and XbaI and EcoRI linkers are placed at the BamHI and SstI ends respectively. This fragment is then inserted. between the XbaI and EcoRI sites of the broad host range plasmid pXL59 (Cameron et al., 1989) to give plasmid pXL1148.

pXL1149 is constructed like pXL1148, apart from the fact that the fragment initially purified is the 1.5-kb BamHI-BamHI-SstI fragment instead of the fragment additionally containing the small 400-bp SstI fragment used for pXL1148. The fragment then undergoes the same enzymatic treatments and the same cloning into pXL59.

1, PstI-SstI fragment of RSF1010 (De Graff et al., 1978); 2, PstI-BamHI fragment of pACYC177 (Bagdasarian et al., 1981); 3, BamHI-SstI fragment containing the lactose operon of *E. coli* without promoter, operator, translation initiation site and the first 8 non-essential codons of lacZ (Casadaban et al., 1983); 4, Sau3AI fragment of *Pseudomonas putida* KT2440 (Bagdasarian et al., 1981); ori, origin of replication; nic, relaxation site; $Km^r$, kanamycin resistance gene; mob, locus essential for mobilisation (Bagdasarian et al., 1981); B, BamHI; C, ClaI; E, EcoRI; H, HindIII; P, PstI; S, SstI; Sa, SalI; X, XhoI; Xb, XbaI.

Figure 25:
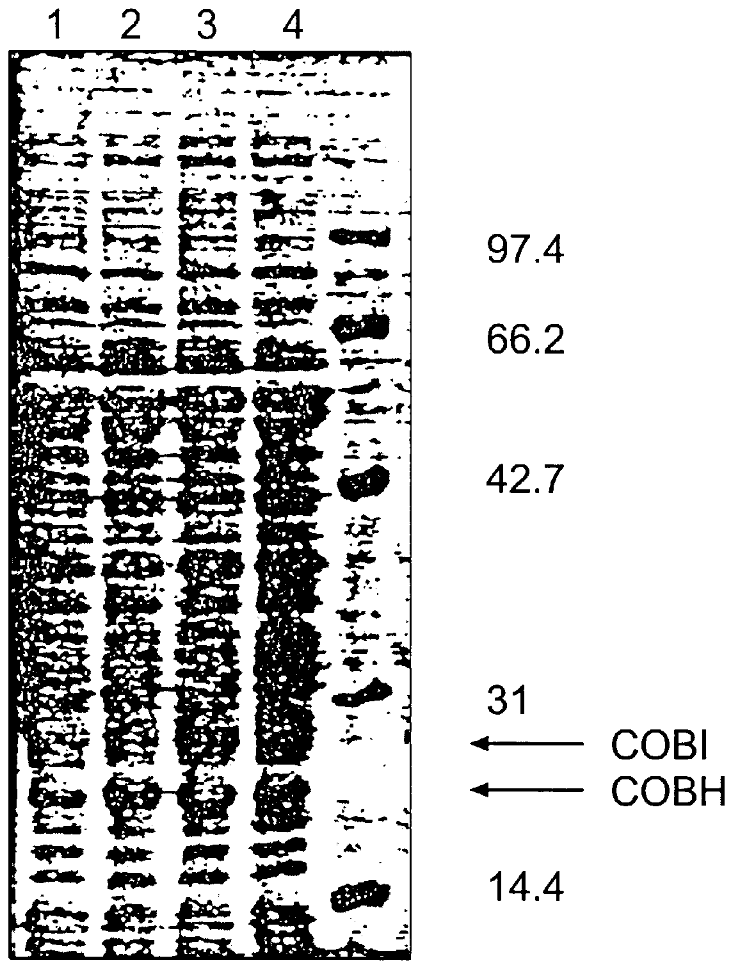

FIG. 25: Total proteins of strains SC510 $Rif^r$, SC510 $Rif^r$ pKT230, SC510 $Rif^r$ pXL1148, SC510 $Rif^r$ pXL1149 analysed in 10% SDS-PAGE as described. The bacteria were cultured for 4 days in PS4 medium, and lysates of the total proteins were then made. Lane 1, SC510 $Rif^r$; lane 2, SC510 $Rif^r$ pXL1149; lane 3, SC510 $Rif^r$ pXL1148; lane 4, SC510 $Rif^r$ pKT230. The molecular masses of the molecular mass markers are indicated. The positions to which the COBI and COBH proteins migrate are indicated.

Figure 26:
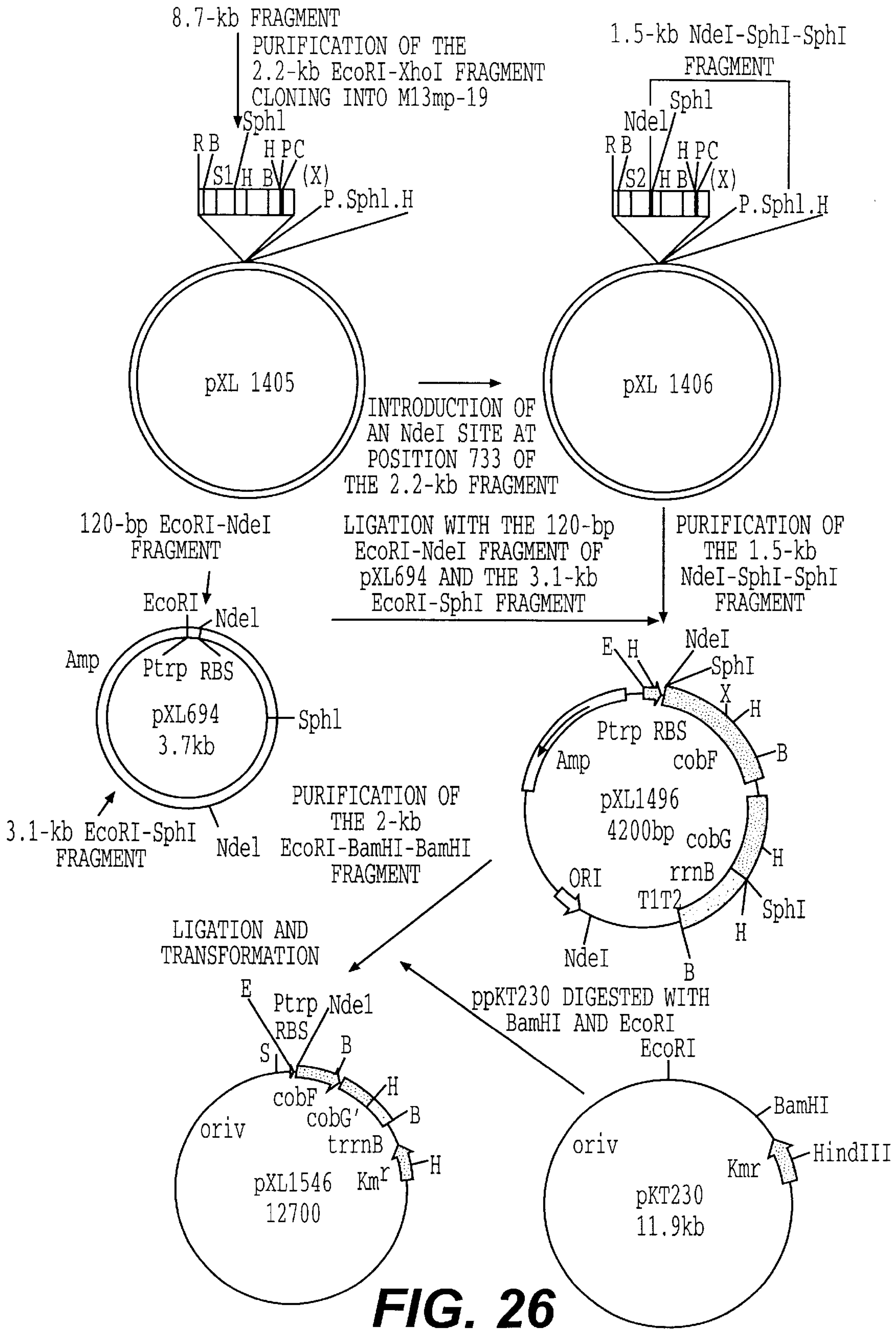

FIG. 26: Construction of plasmids pXL1496 and pXL1546.

Plasmid pXL1496 enables the COBF protein to be overexpressed in *E. coli*, and plasmid pXL1546 enables COBF to be overexpressed in *Pseudomonas denitrificans.*

The 2.2-kb EcoRI-XhoI fragment is excised and purified from the 8.7-kb fragment. It is cloned at the EcoRI site of phage M13mp19 to give plasmid pXL1405. An NdeI site is then introduced by directed mutagenesis, as described above, at position 733 of this fragment; in this manner, an NdeI site occurs exactly on the presumed initiation codon of the cobF gene. The new plasmid thereby obtained is designated pXL1406. A 1.5-kb NdeI-SphI-SphI fragment, containing the cobF gene starting from its presumed initiation codon, is purified after partial digestion with the appropriate enzymes and ligated with the appropriate fragments of plasmid pXL694 (120-bp EcoRI-NdeI fragment containing expression signals of *E. coli*—see text—and 3.1-kb EcoRI-SphI fragment containing the ampicillin resistance gene, the replication functions of the plasmid and also the terminators of the rrnB operon of *E. coli*, as described in the text). The plasmid thereby constructed is designated pXL1496.

pXL1546 is constructed as follows: the 2-kb EcoRI-BamHI-BamHI fragment of pXL1496 is purified by partial digestion with the appropriate enzymes; this fragment contains the expression signals of *E. coli*, followed by the cobF gene and then the 5' portion of the cobG gene, this portion itself being followed by terminators of the rrnB operon of *E. coli*, as described in the text. This fragment is cloned into the multihost plasmid pKT230 (Bagdasarian et al., 1981) described in FIG. 30. B, BamHI; C, ClaI; E, EcoRI; H, HindIII; P, PstI; S, SstI, Sa, SalI; X, XhoI; Xb, XbaI; Kmr, kanamycin resistance gene; Amp, ampicillin resistance gene.

Figure 27:
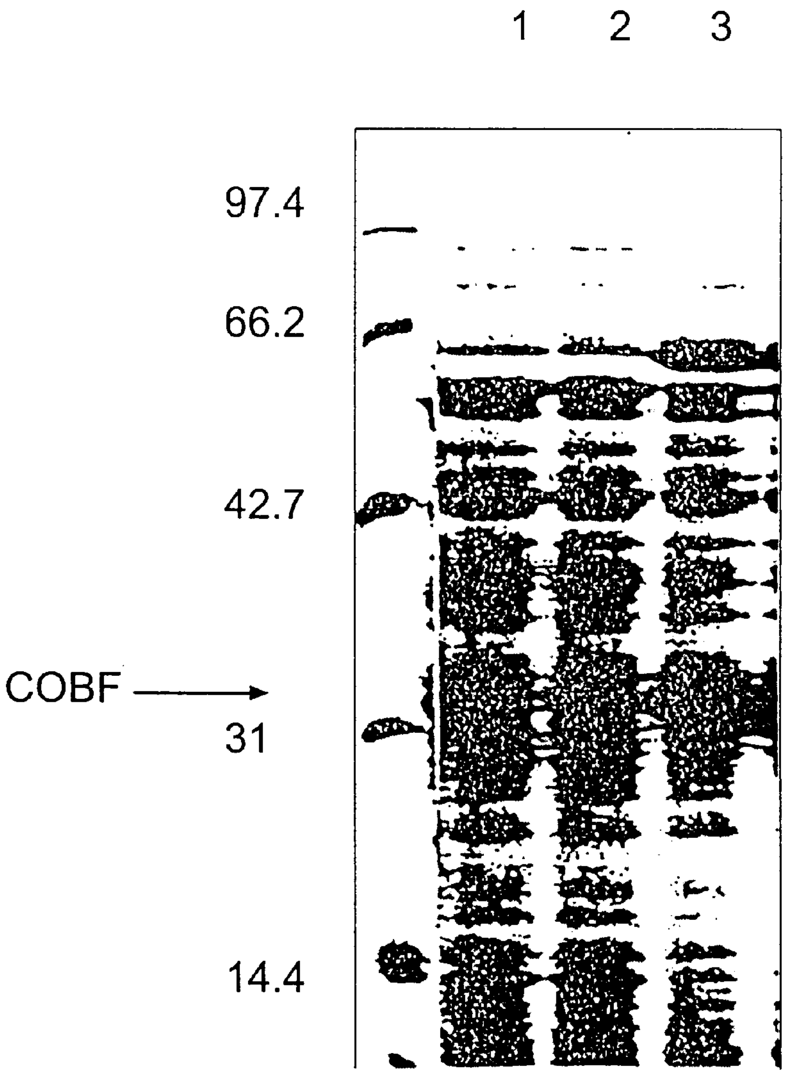

FIG. 27: Total proteins of strains SC510 Rif$^r$, SC510 Rif$^r$ pKT230, SC510 Rif$^r$ pXL1546 analysed in 10% SDS-PAGE as described. The bacteria were cultured for 4 days in PS4 medium, and lysates of the total proteins were then made. Lane 1, SC510 Rif$^r$; lane 2, SC510 Rif$^r$ pKT230; lane 3, SC510 Rif$^r$ pXL1546. The molecular masses of the molecular mass markers are indicated. The position to which the COBF protein migrates is indicated.

Figure 28:
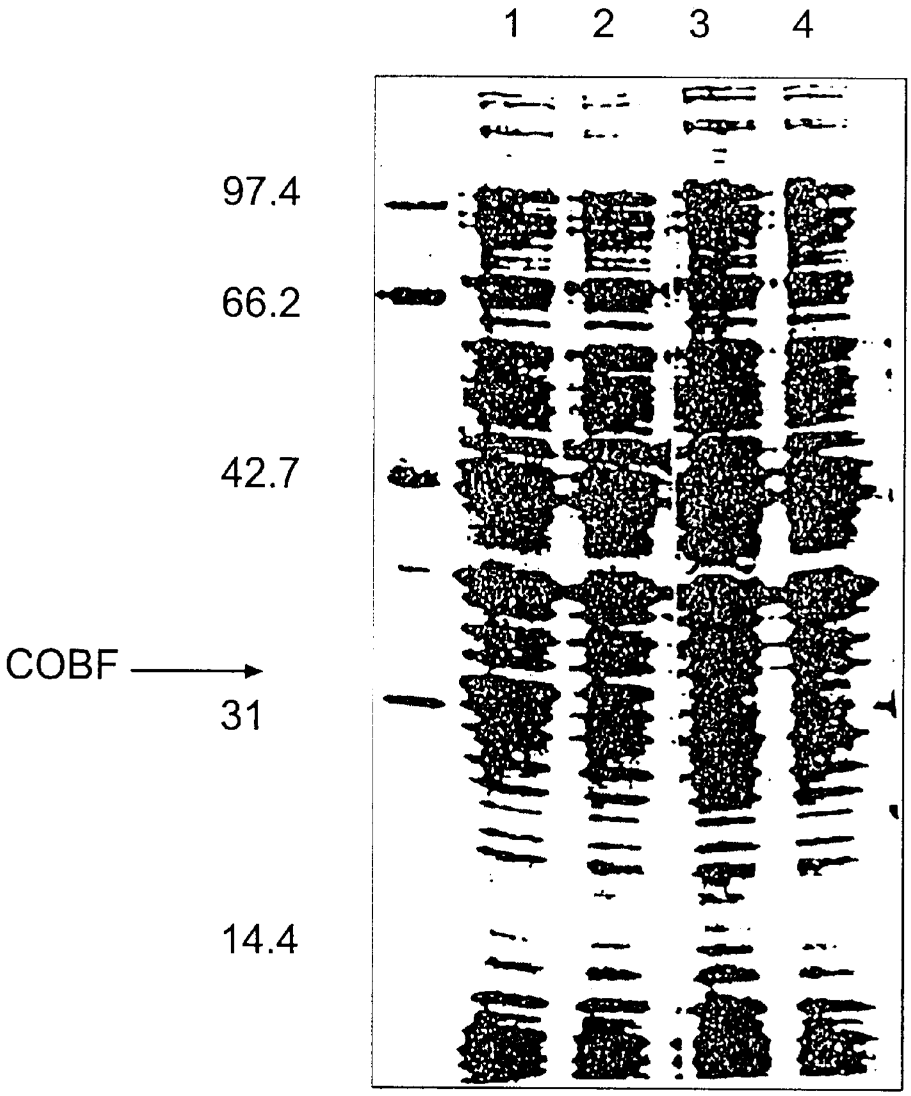

FIG. 28: Total proteins of the strains *E. coli* B and *E. coli* B pXL1496 analysed in 10% SDS-PAGE as described. Lane 1*, E. coli* pXL1496 cultured in the absence of tryptophan; lane 2*, E. coli* pXL1496 cultured under the same conditions in the presence of tryptophan; lane 3*, E. coli* cultured in the absence of tryptophan; lane 4*, E. coli* cultured under the same conditions in the presence of tryptophan. The molecular masses of the markers are indicated. The position of migration of the COBF protein is indicated.

Figure 29:
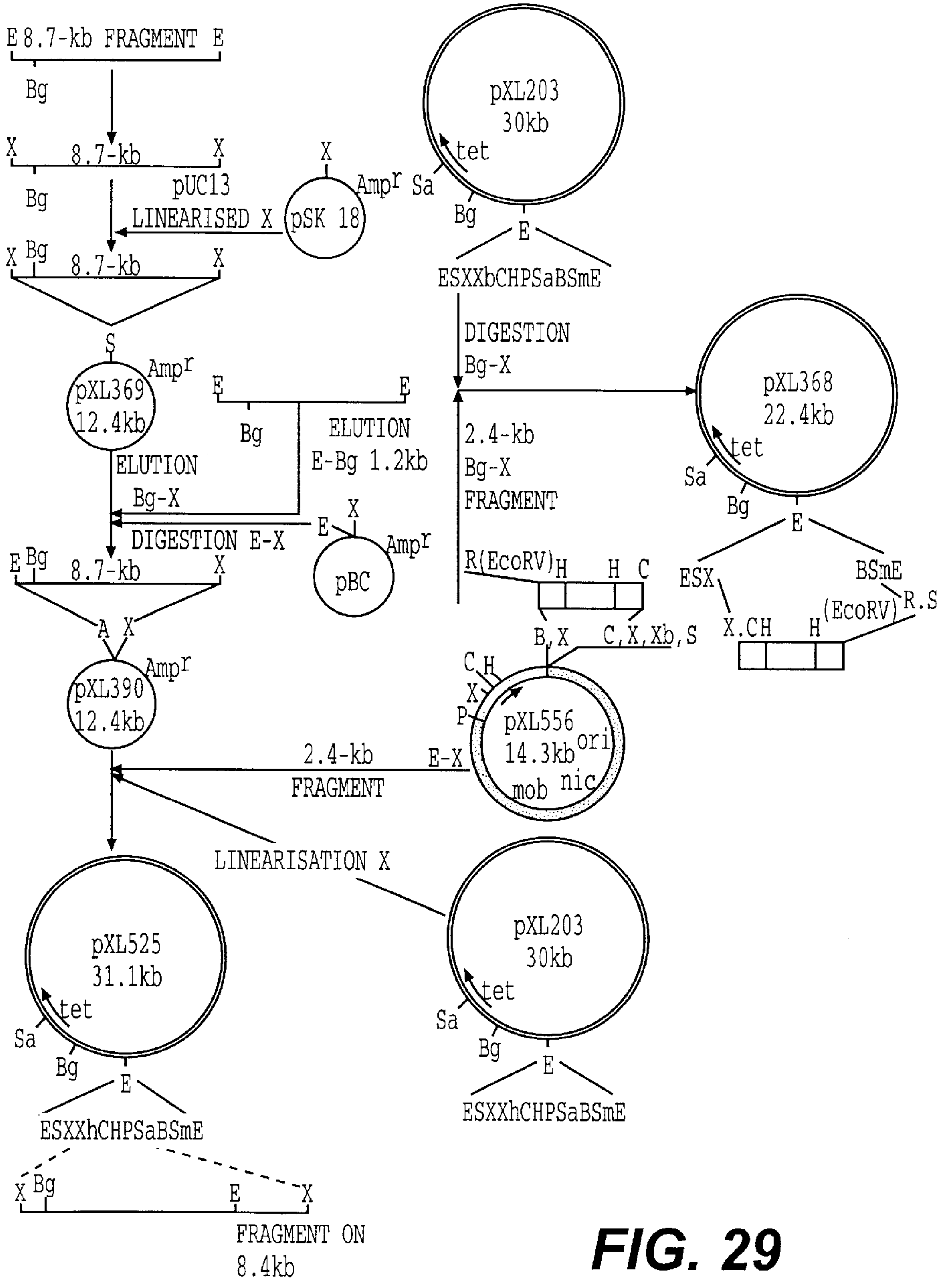

FIG. 29: Construction of plasmids pXL525 and pXL368.

Plasmid pXL368 is constructed as follows: the 2.4-kb EcoRV-ClaI fragment (containing the cobA and cobE genes) is purified from plasmid pXL556, thereby enabling this fragment to be obtained with a BamHI site and an XbaI site at the ends; this fragment is cloned into pXL203 at the BamHI and XbaI sites.

For the construction of pXL525, an XbaI linker is added at the EcoRI site situated at the right-hand end of the 8.7-kb EcoRI fragment; this 8.7-kb EcoRI-XbaI fragment is then cocloned with the 2.4-kb EcoRI-XbaI fragment originating from pXL556 and containing cobA and cobE.

The restriction sites which are shown in brackets correspond to sites which have disappeared after treatment with the large fragment of *E. coli* DNA polymerase I. 1, PstI-SstI fragment of RSF1010 (De Graff et al., 1978); 2, PstI-BamHI fragment of pACYC177 (Bagdasarian et al., 1981); ori, origin of replication; nic, relaxation site; mob, locus essential for mobilisation; Km$^r$, kanamycin resistance gene (Bagdasarian et al., 1981); B, BamHI; C, ClaI; E, EcoRI; H, HindIII; P, PstI; S, SstI; Sa, SalI; X, XhoI; Xb, XbaI; tet, tetracycline resistance gene; Amp$^r$ and Amp, ampicillin resistance gene.

FIG. 30: Plasmids of the incompatibility group Q having a broad host range in Gram-negative bacteria. These plasmids are described in a previous publication (Cameron et al., 1989) and are used in the present invention.

1, PstI-SstI fragment of RSF1010 (De Graff et al., 1978); 2, PstI-BamHI fragment of pACYC177 (Bagdasarian et al., 1981); 3, BamHI-SstI fragment containing the lactose operon of *E. coli* without promoter, operator, translation initiation site and the first 8 non-essential codons of lacZ (Casadaban et al., 1983); 4, Sau3AI fragment of *Pseudomonas putida* KT2440 (Bagdasarian et al., 1981); ori, origin of replication; nic, relaxation site; Km$^r$, kanamycin resistance gene; Sm$^r$, streptomycin resistance gene; mob, locus essential for mobilisation (Bagdasarian et al., 1981); B, BamHI; C, ClaI; E, EcoRI; H, HindIII; P, PstI; S, SstI; Sa, SAI; X, XhoI; Xb, XbaI.

Figure 31:
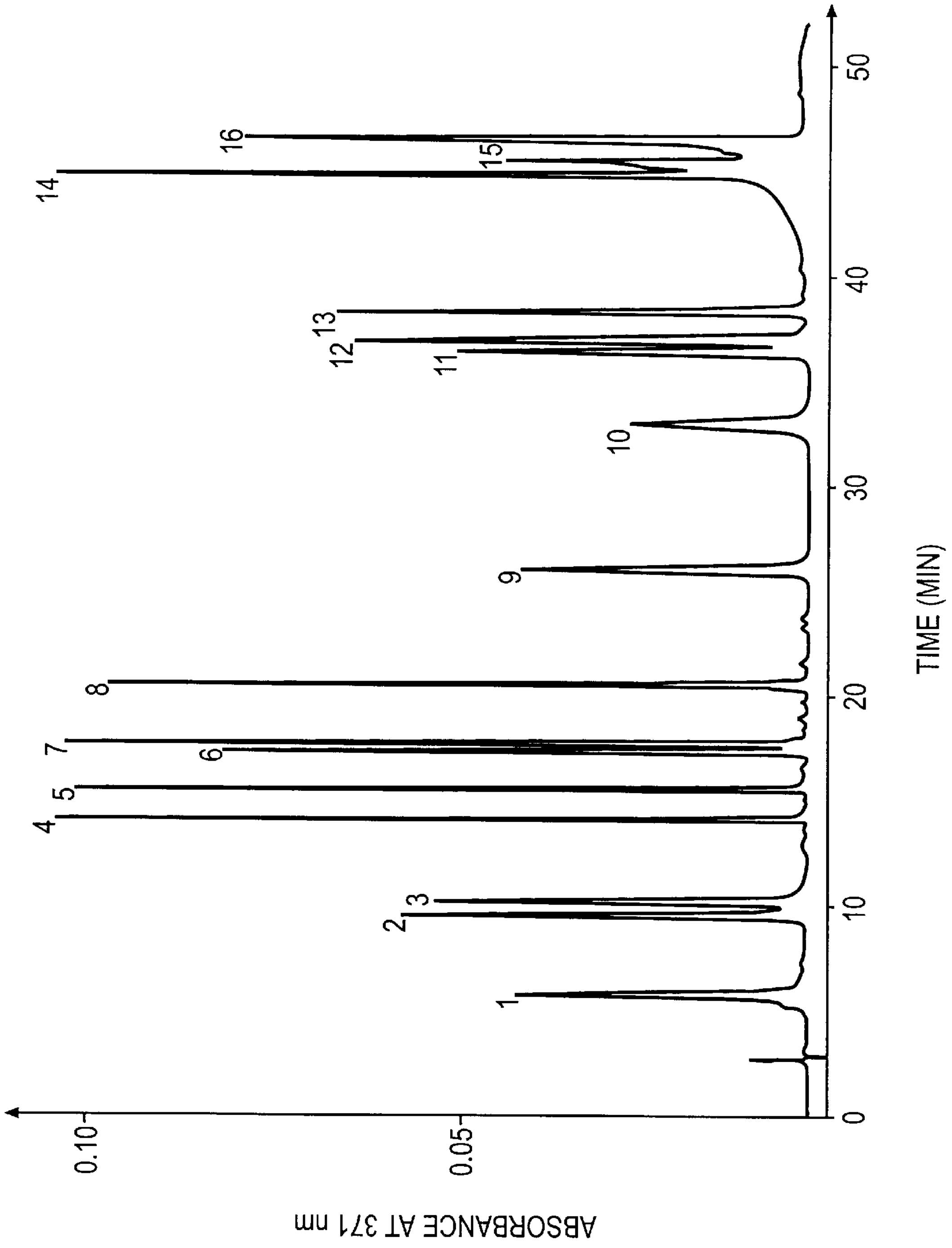
Figure 34A:
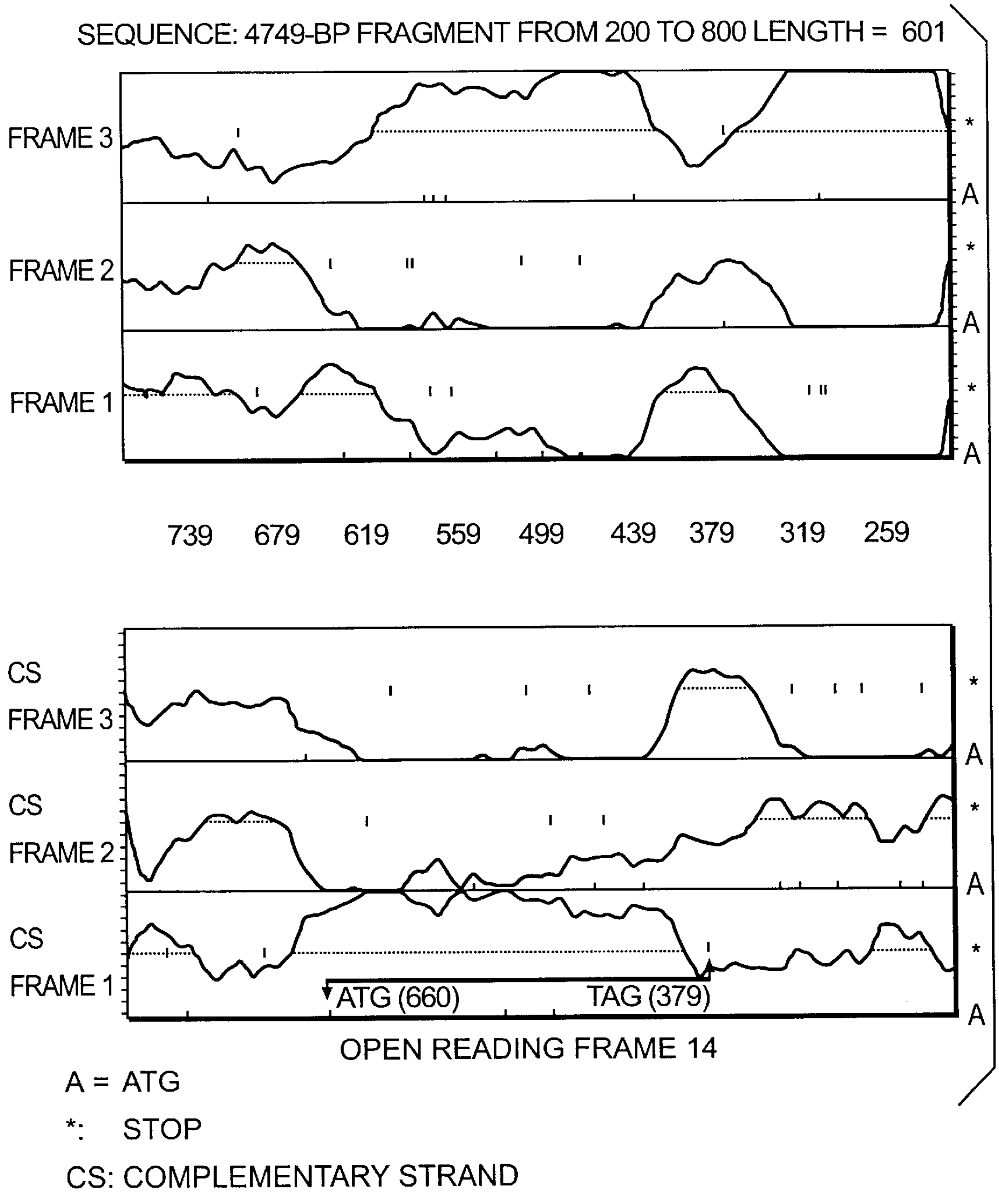
Figure 34B:
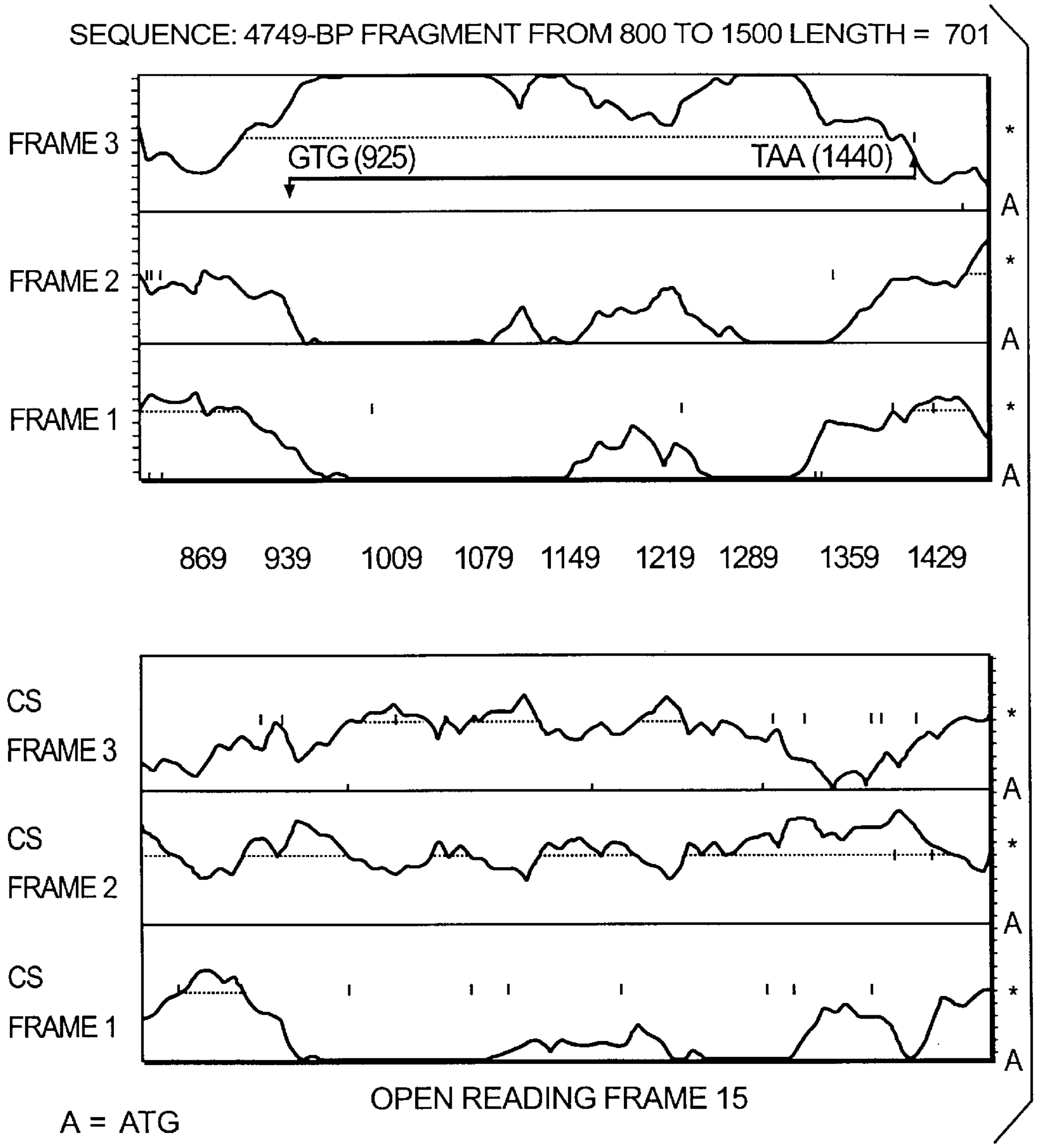
Figure 34C:
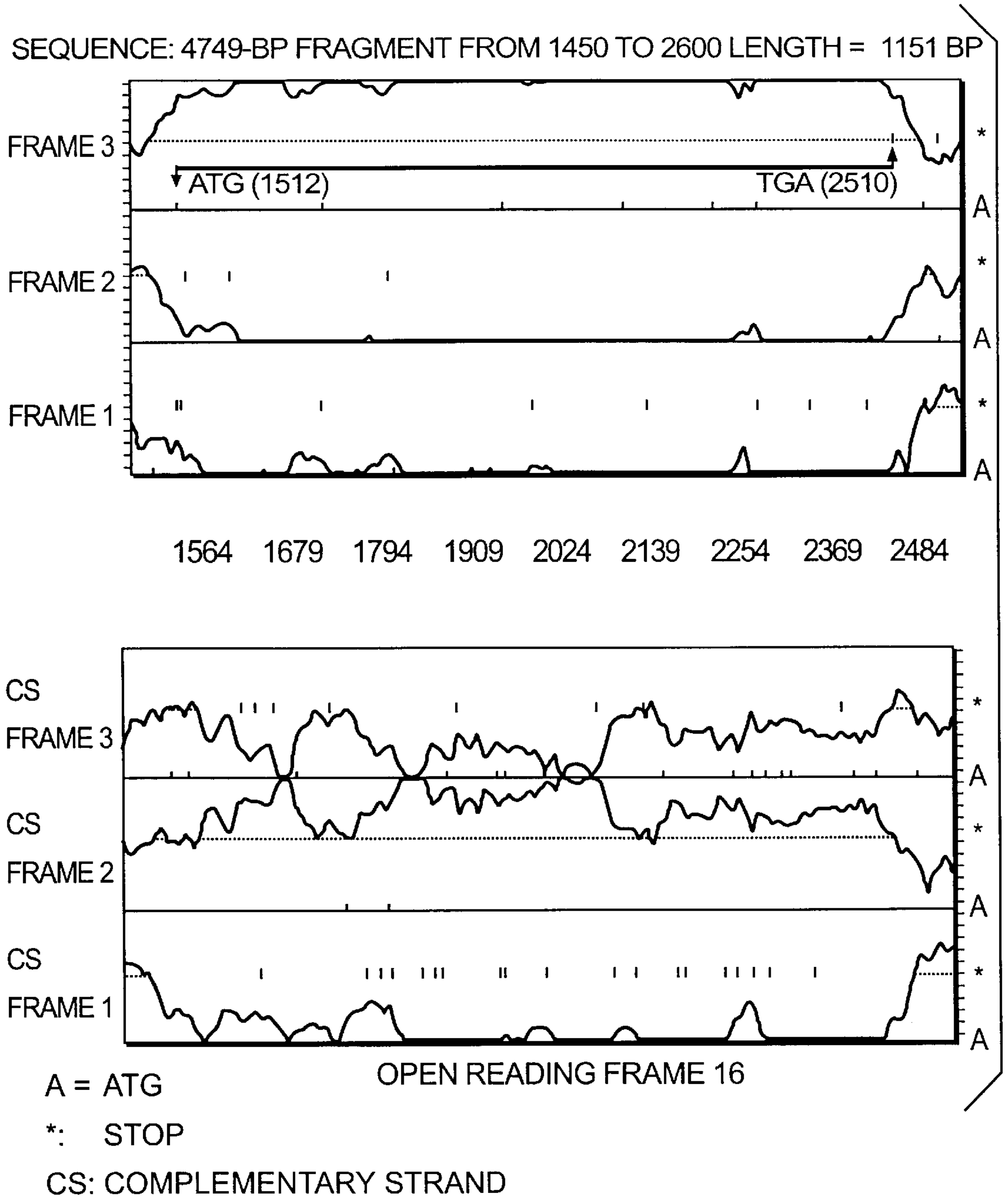
Figure 34D:
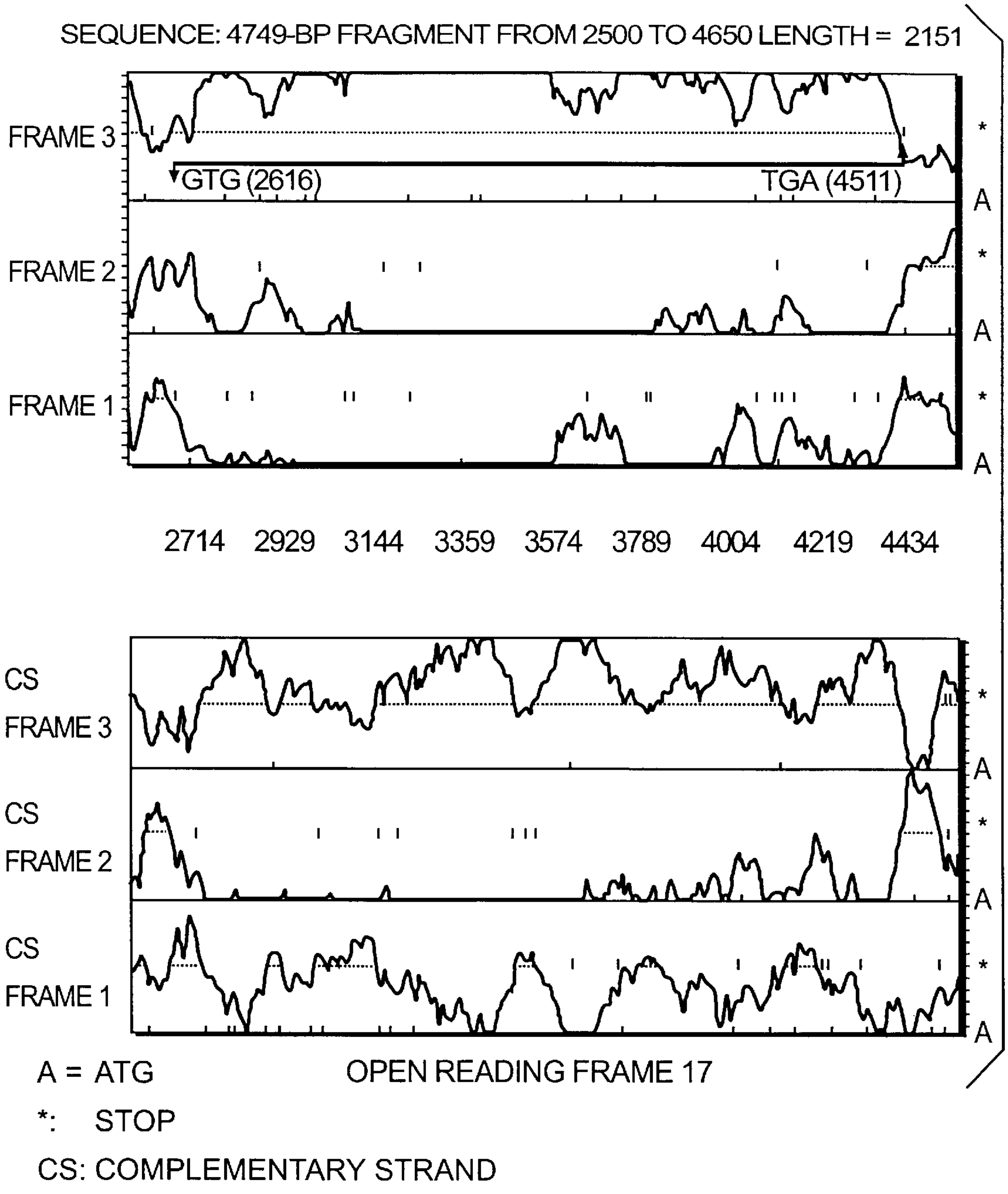
Figure 35A:
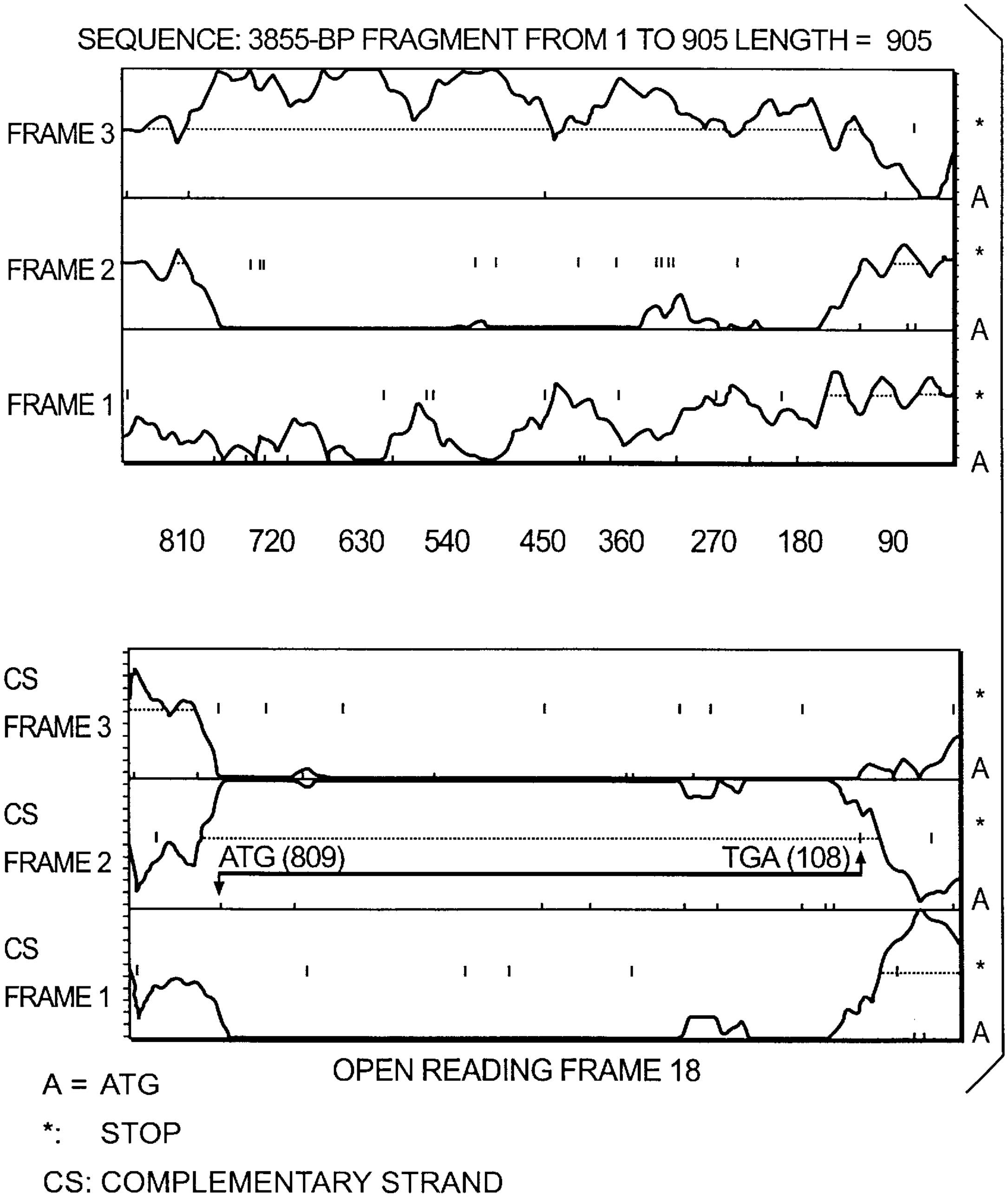
Figure 35B:
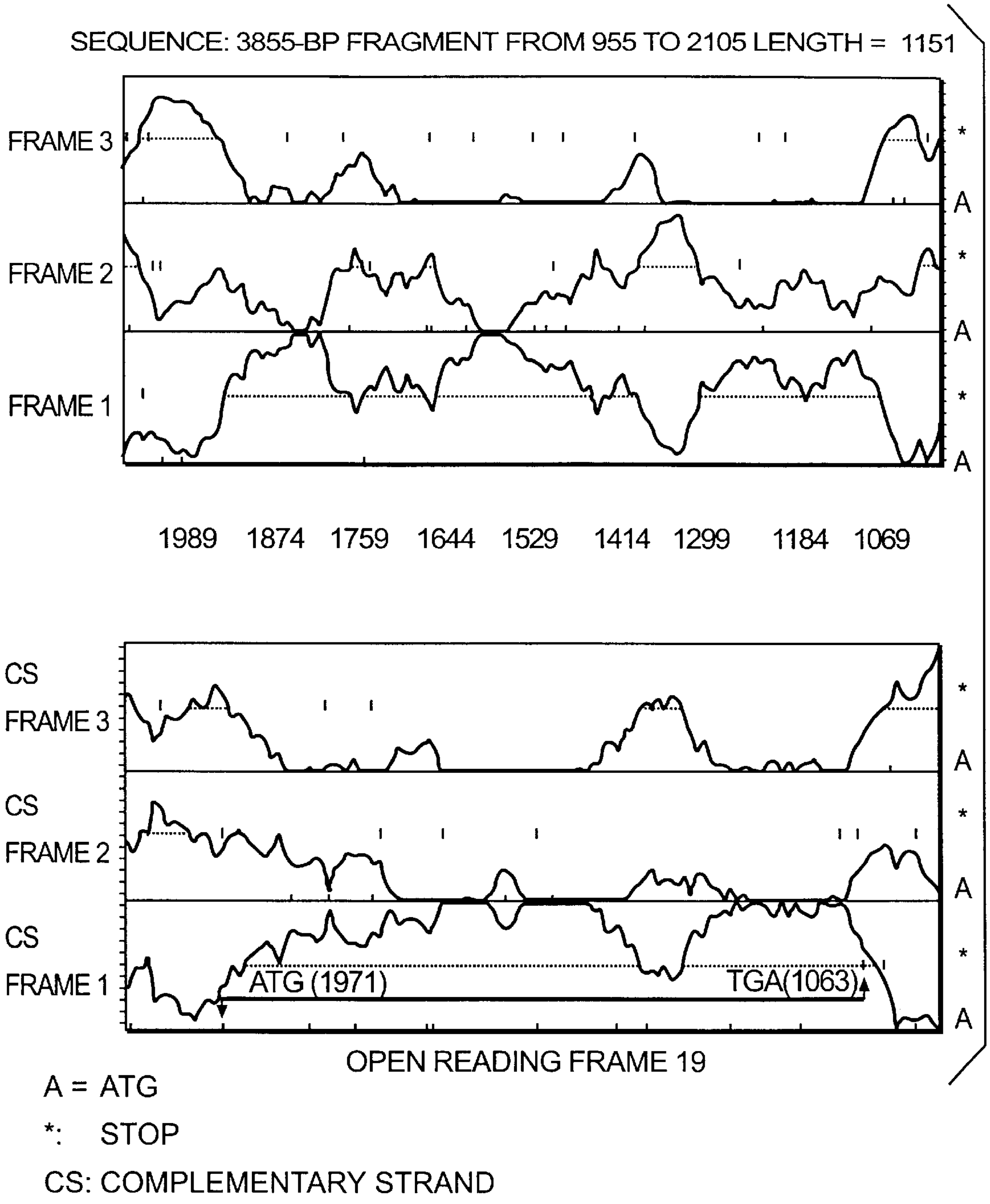
Figure 35C:
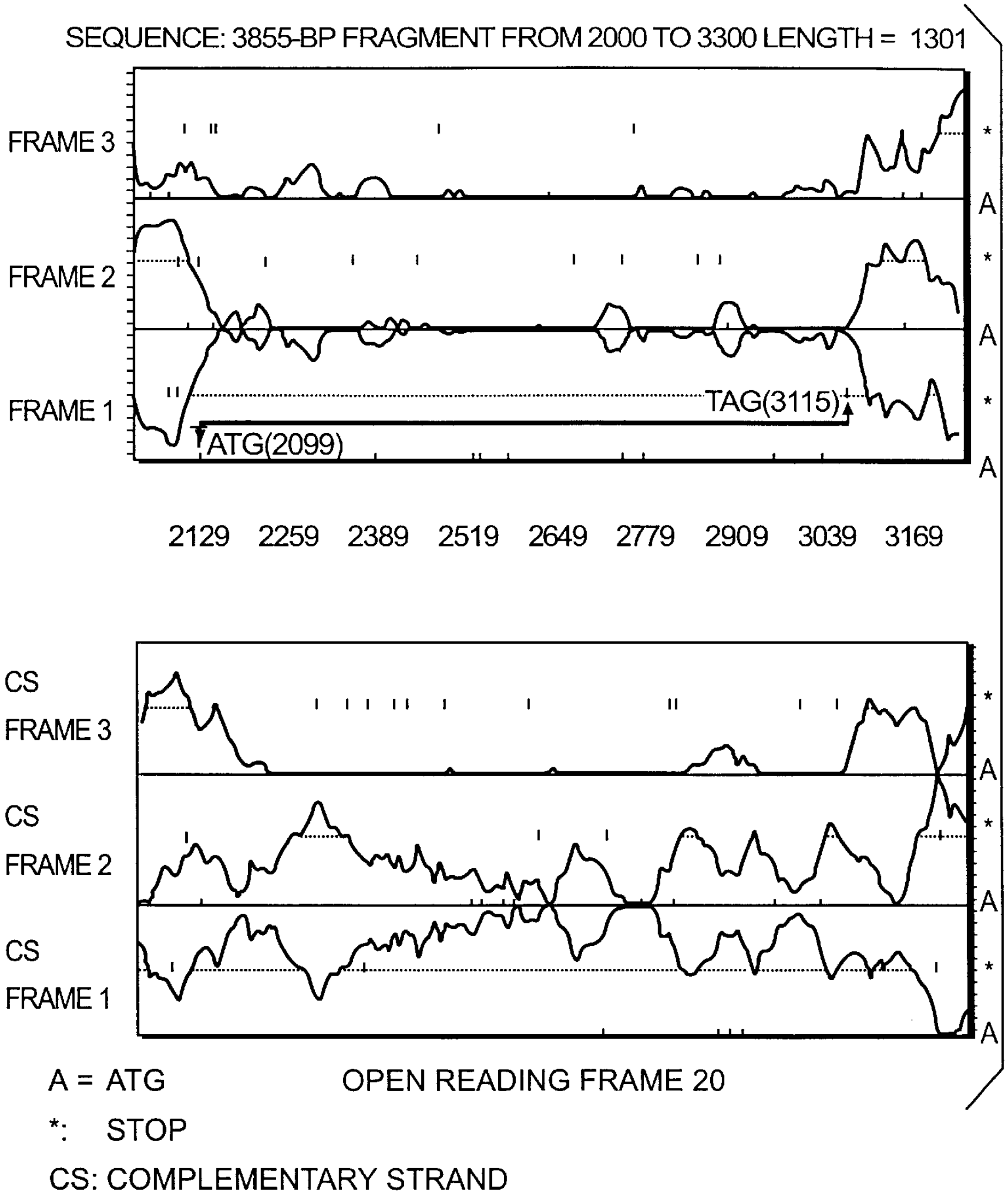
Figure 35D:
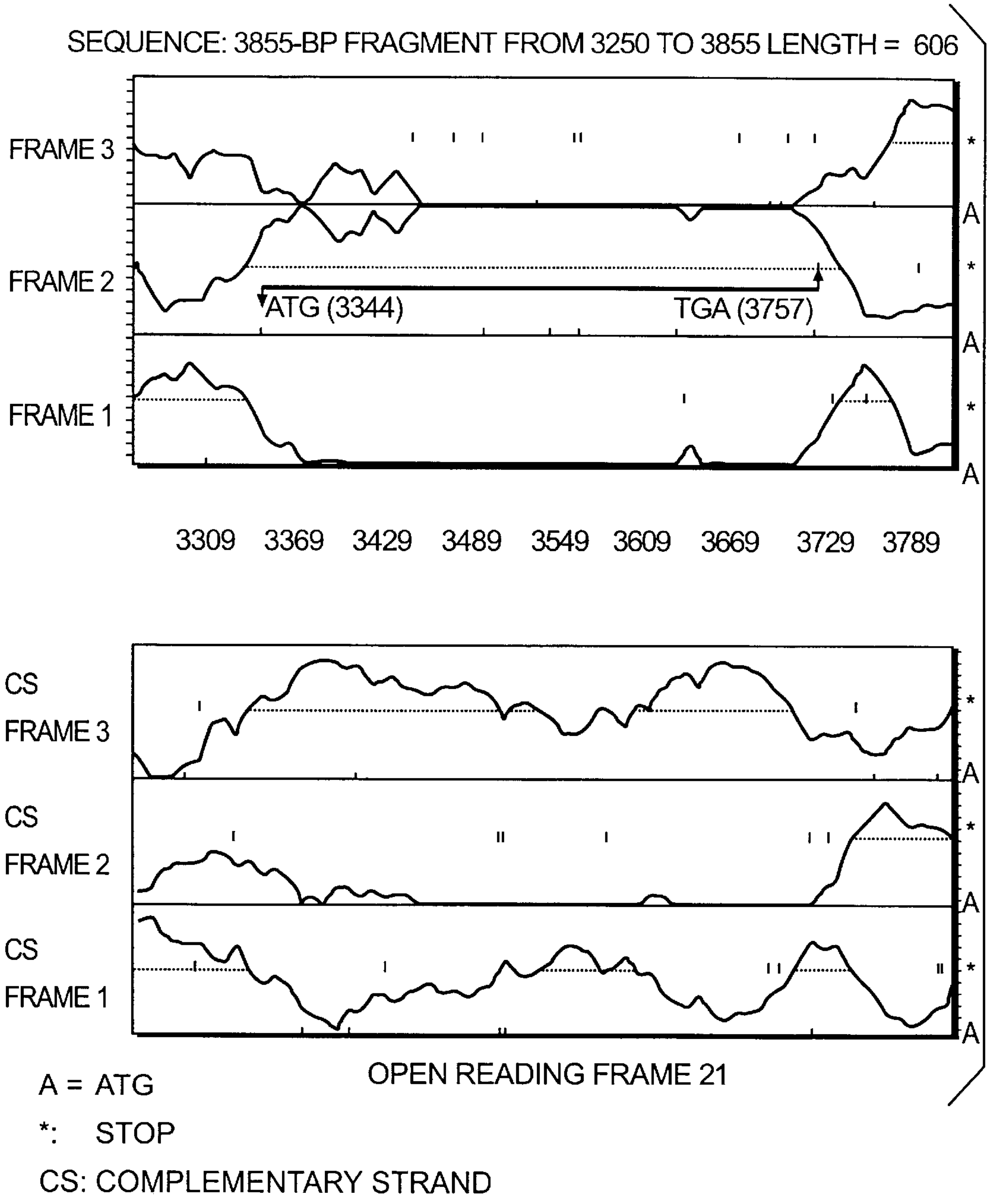

FIG. 31: Retention time of different corrinoid standards (1 mg/standard) on the separation system described in Example 7. The column used is a Nucleosil C-18 column (Macherey-Nagel). Against each absorbance peak, a number is shown corresponding to the corrinoid described below. The retention time is shown as abscissa and the absorbance at 371 nm appears as ordinate.

1, cobyrinic acid; 2, cobyrinic acid a-amide; 3, cobyrinic acid g-amide; 4, cobyrinic acid a,g-diamide; 5, cobyrinic acid c-amide; 6, cobyrinic acid c,g-diamide; 7, cobyrinic acid a,c-diamide; 8, cobyrinic acid triamide; 9, cobyrinic acid tetraamide; 10, cobyrinic acid pentaamide; 11, cobyric acid; 12, GDP-cobinamide; 13, cobinamide phosphate; 14, cobinamide; 15, cyanocobalamin 5'-phosphate; 16, cyanocobalamin.

FIGS. 32A–32H: Nucleotide sequence of both strands of the 4748-bp SalI-SalI-SalI-SalI-SalI-BglI fragment of *Pseudomonas denitrificans* (SEQ ID NO: 29). The strand situated at the top is to be read from 5' to 3' in the left-to-right direction which corresponds to the left-to-right orientation of the fragment of the restriction map presented in FIG. 6.

FIGS. 33A–33G: Nucleotide sequence of both strands of the 3855-bp SstI-SstI-BamHI fragment of *Pseudomonas denitrificans* (SEQ ID NO: 30). The strand situated at the top is to be read from 5' to 3' in the left-to-right direction which corresponds to the left-to-right orientation of the fragment of the restriction map presented in FIG. 6.

FIGS. 34A–34D: Analysis of the probabilities of the coding frames on the basis of codon preference using the programme of Staden and MacLachlan (1982) on the six reading frames of the 4748-bp SalI-SalI-SalI-SalI-SalI-BglI fragment. For the frames belonging to the same coding strand, the most probable frame corresponds to that in which a dotted line, not interrupted by stop codons, is placed under the probability line for this frame. 4a. Analysis of the sequence corresponding to nucleotides 200 to 800. This analysis enables open reading frame 14 to be identified. It begins at the ATG at position 660 and ends at the TGA at position 379. 4b. Analysis of the sequence corresponding to nucleotides 800 to 1500. This analysis enables open reading frame 15 to be identified. It begins at the GTG at position 925 and ends at the TAA at position 1440. 4c. Analysis of the sequence corresponding to nucleotides 1450 to 2600. This analysis enables open reading frame 16 to be identified. It begins at the ATG at position 1512 and ends at the TGA at position 2510. 4d. Analysis of the sequence corresponding to nucleotides 2500 to 4650. This analysis enables open reading frame 17 to be identified. It begins at the GTG at position 2616 and ends at the TGA at position 4511.

FIGS. 35A–35D: Analysis of the probabilities of the coding frames on the basis of codon preference using the programme of Staden and MacLachlan (1982) on the six reading frames of the 3855-bp SstI-SstI-BamHI fragment. For the frames belonging to the same coding strand, the most probable frame corresponds to that in which a dotted line, not interrupted by stop codons, is placed under the probability line for this frame. 5a. Analysis of the sequence corresponding to nucleotides 1 to 905. This analysis enables open reading frame 18 to be identified. It begins at the ATG at position 809 and ends at the TGA at position 108. 5b. Analysis of the sequence corresponding to nucleotides 955 to 2105. This analysis enables open reading frame 19 to be identified. It begins at the ATG at position 1971 and ends at the TGA at position 1063. 5c. Analysis of the sequence corresponding to nucleotides 2000 to 3300. This analysis enables open reading frame 20 to be identified. It begins at the ATG at position 2099 and ends at the TAG at position 3115. 5d. Analysis of the sequence corresponding to nucleotides 3250 to 3855. This analysis enables open reading frame 21 to be identified. It begins at the ATG at position 3344 and ends at the TGA at position 3757.

Figure 36:
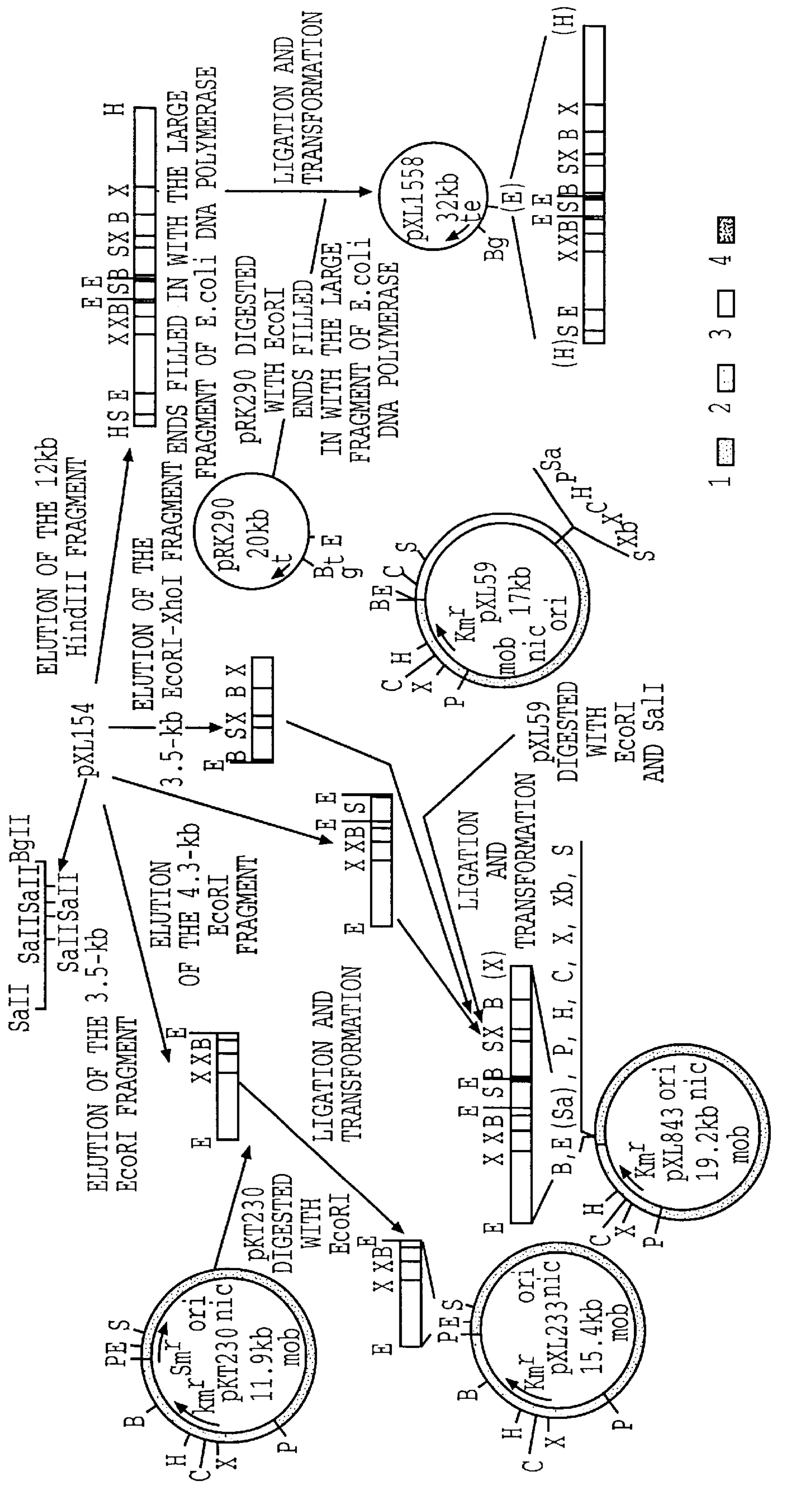

FIG. 36: Construction of plasmids pXL233, pXL843 and pXL1558 from pXL154.

The plasmids are constructed in the following manner. The 3.5-kb EcoRI fragment containing the truncated cobS gene and the sequence upstream is excised from pXL154, then purified and cloned to the EcoRI site of pKT230. The plasmid thereby constructed is designated pXL233. The 3.5-kb EcoRI-XhoI-XhoI fragment containing the cobT gene and the sequence downstream is excised and purified from pXL154 by partial digestions. The 4.3-kb EcoRI-EcoRI-EcoRI fragment containing the cobS gene and the sequence upstream is excised and purified from pXL154 and then ligated to the above 3.5-kb fragment. The approximately 8-kb EcoRI-XhoI fragment thereby attained is cloned into the EcoRI and SalI sites of pXL59 to generate plasmid pXL843. Plasmid pXL1558 is constructed in the following manner: the 12-kb HindIII-HindIII fragment is excised from pXL154 and purified, and the ends are then filled in with the large fragment of *E. coli* DNA polymerase I. This insert is cloned in PRK290 (Ditta et al., 1981) digested with EcoRI and then treated with the large fragment of *E. coli* DNA polymerase I in order to make the ends blunt. Restriction sites which are shown in brackets correspond to sites which have disappeared during cloning. 1, PstI-SstI fragment of RSF1010 (Degraff et al., 1978); 2, PstI-BamHI fragment of pACYC177 (Bagdasarian et al., 1981); B, BamHI; C, ClaI; E, EcoRI; H, HindIII; P, PstI; S, SstI; Sa, SalI; X, XhoI; Xb, XbaI;

Tet tetracycline resistance gene; $Km^r$, kanamycin resistance gene; $Sm^r$, streptomycin resistance gene.

Figure 37:
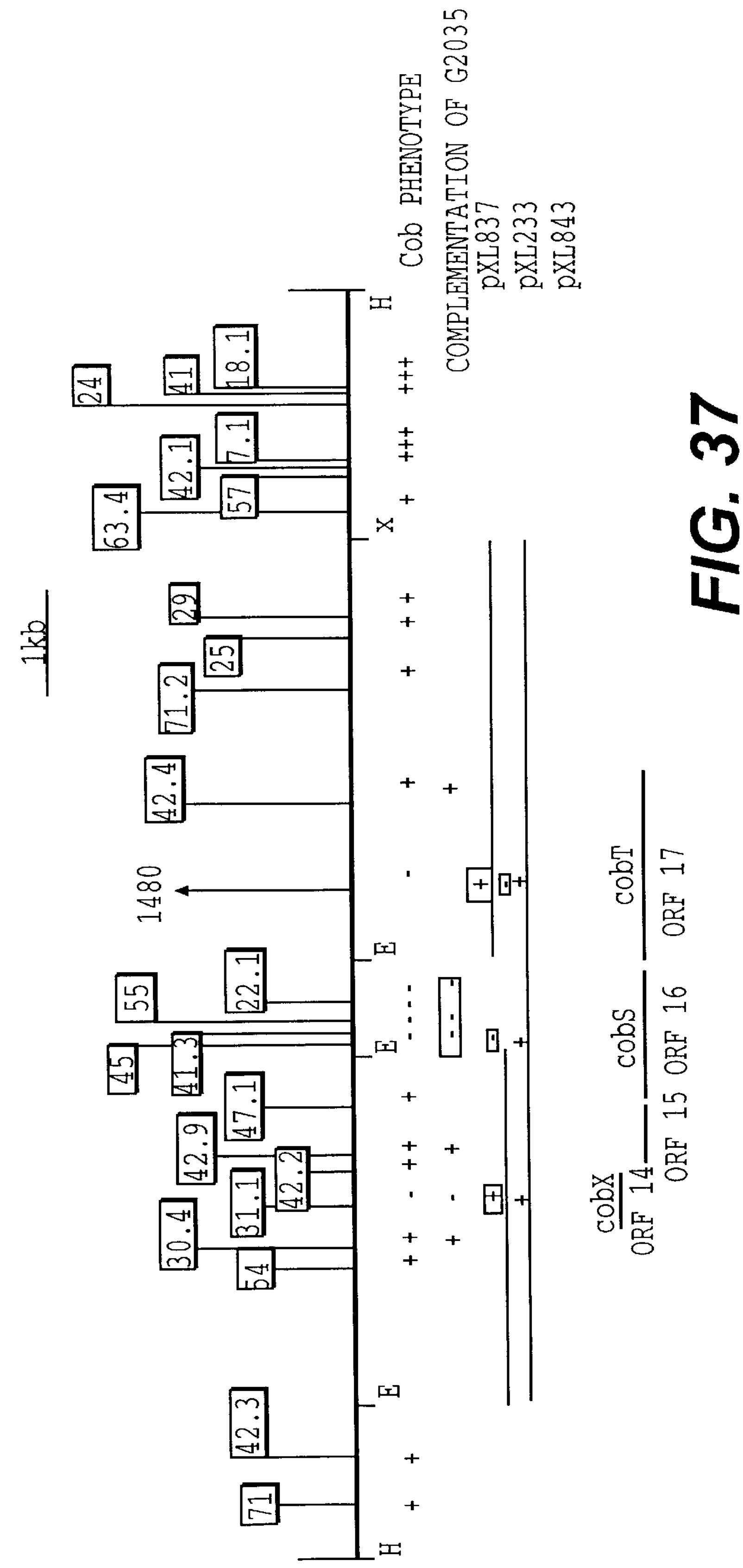

FIG. 37: Study of the insertions of the transposon Tn5Sp into the 12-kb HindIII-HindIII insert of pXL154.

The insertions of the transposon are mapped on the 12-kb HindIII-HindIII insert cloned into pXL1558. The chromosomal insertions into strain SC510 $Rif^r$ are boxed, that which is not is introduced into strain SBL27 $Rif^r$. A plus or minus sign is shown under each insertion to indicate the Cob phenotype of the strain having this insertion. Absence of complementation (or complementation) of strain G2035 by plasmids pXL1558::Tn5Sp is indicated by minus (or plus) signs below each insertion. The inserts of the plasmids described in FIG. 36 are shown. The plus (or minus) signs over these plasmids, and aligned with the transposon insertions, show diagrammatically the complementation (or absence) of the transposon-mutated strain by the plasmid. The open reading frames deduced from the sequence are also given in this figure (ORF14 to 17, as well as the corresponding cob genes (cobS and cobT)). E: EcoRI; H: HindIII; X: XhoI.

Figure 38:
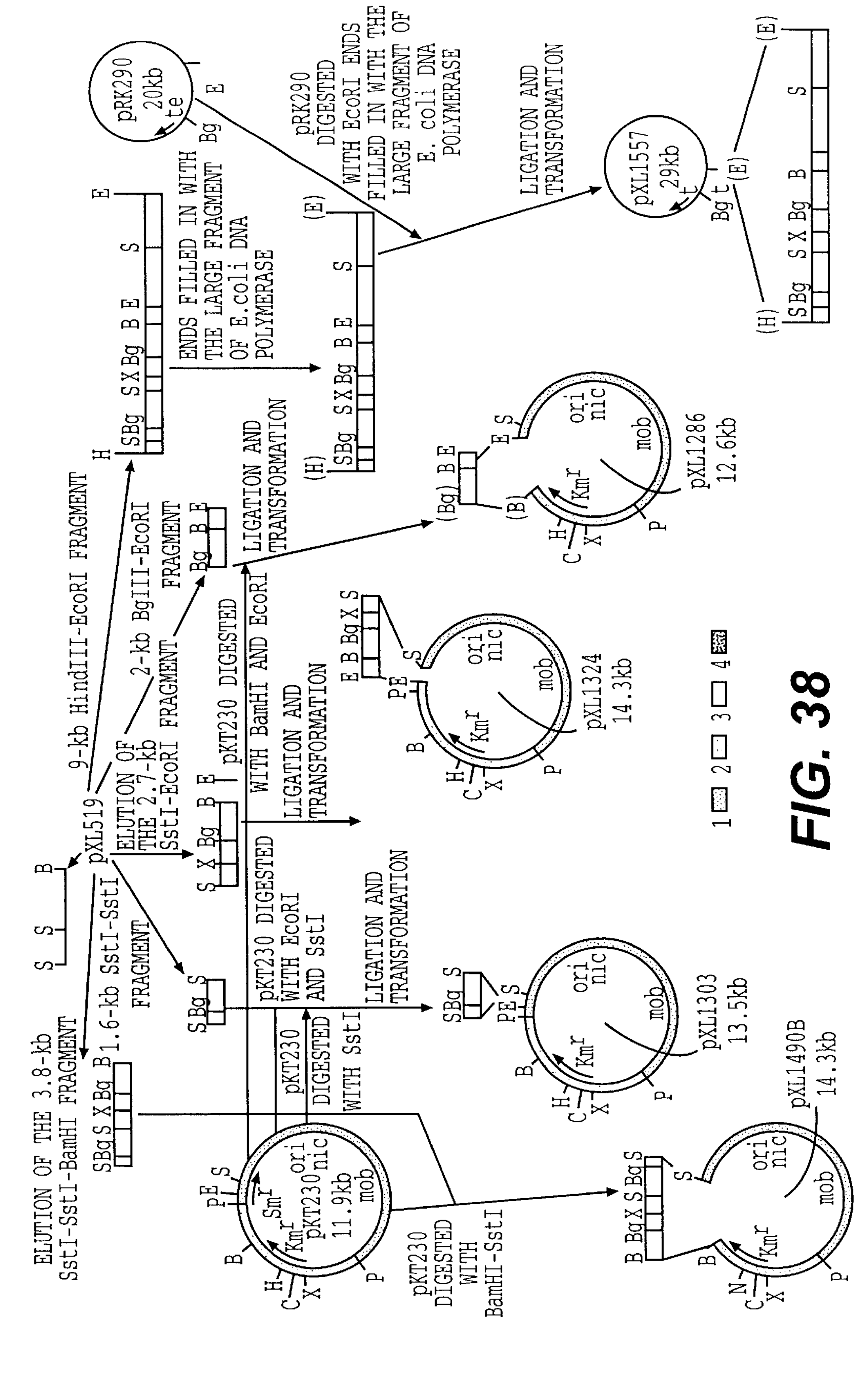

FIG. 38: Construction of plasmids pXL1286, pXL1303, pXL1324, pXL1490B and pXL1557 from pXL519. The position of the sequenced fragment appears in the upper part of the figure above the restriction map of the cluster; it is a 3.9-kb SstI-SstI-SstI-BamHI fragment. The plasmids are constructed in the following manner. The 2-kb BglII-EcoRI fragment containing the cobU gene and the sequence downstream is excised from pXL519, then purified and cloned at the BamHI and EcoRI sites of pKT230 to generate plasmid pXL1286. The 2.7-kb SstI-EcoRI fragment containing the truncated cobV gene, cobU gene and the sequence downstream is excised on pXL519, then purified and cloned at the SstI and EcoRI sites of pKT230 to generate plasmid pxL1324. The 1.6-kb SstI-SstI fragment containing the truncated cobV gene and the sequence upstream is excised from pXL519, then purified and cloned at the SstI site of pKT230 to generate plasmid pXL1303. The 3.85-kb SstI-SstI-BamHI fragment is purified after total digestion of pXL519 with BamHI and partial digestion with SstI. This fragment is then cloned at the BamHI and SstI sites of pKT230 to generate pXL1490B. Plasmid pXL1557 is constructed in the following manner: the 9-kb HindIII-BamHI fragment is excised from pXL519 and purified, and the ends are then filled in with the large fragment of *E. coli* DNA polymerase I. This insert is cloned into pRK290 (Ditta et al., 1981) digested with EcoRI and then treated with the large fragment of *E. coli* DNA polymerase I to make the ends blunt. The restriction sites which are shown in brackets correspond to sites which have disappeared during cloning. 1, PstI-SstI fragment of RSF1010 (Degraff et al., 1978); 2, PstI-BamHI fragment of pACYC177 (Bagdasarian et al., 1981); B, BamHI;Bg, BglII; C, ClaI; E, EcoRI; H, HindIII; P, PstI; S, SstI; Sa, SalI; X, XhoI; Xb, XbaI; $Tet^r$, tetracycline resistance gene; Kmr kanamycin resistance gene; $Sm^r$, streptomycin resistance gene.

Figure 39:
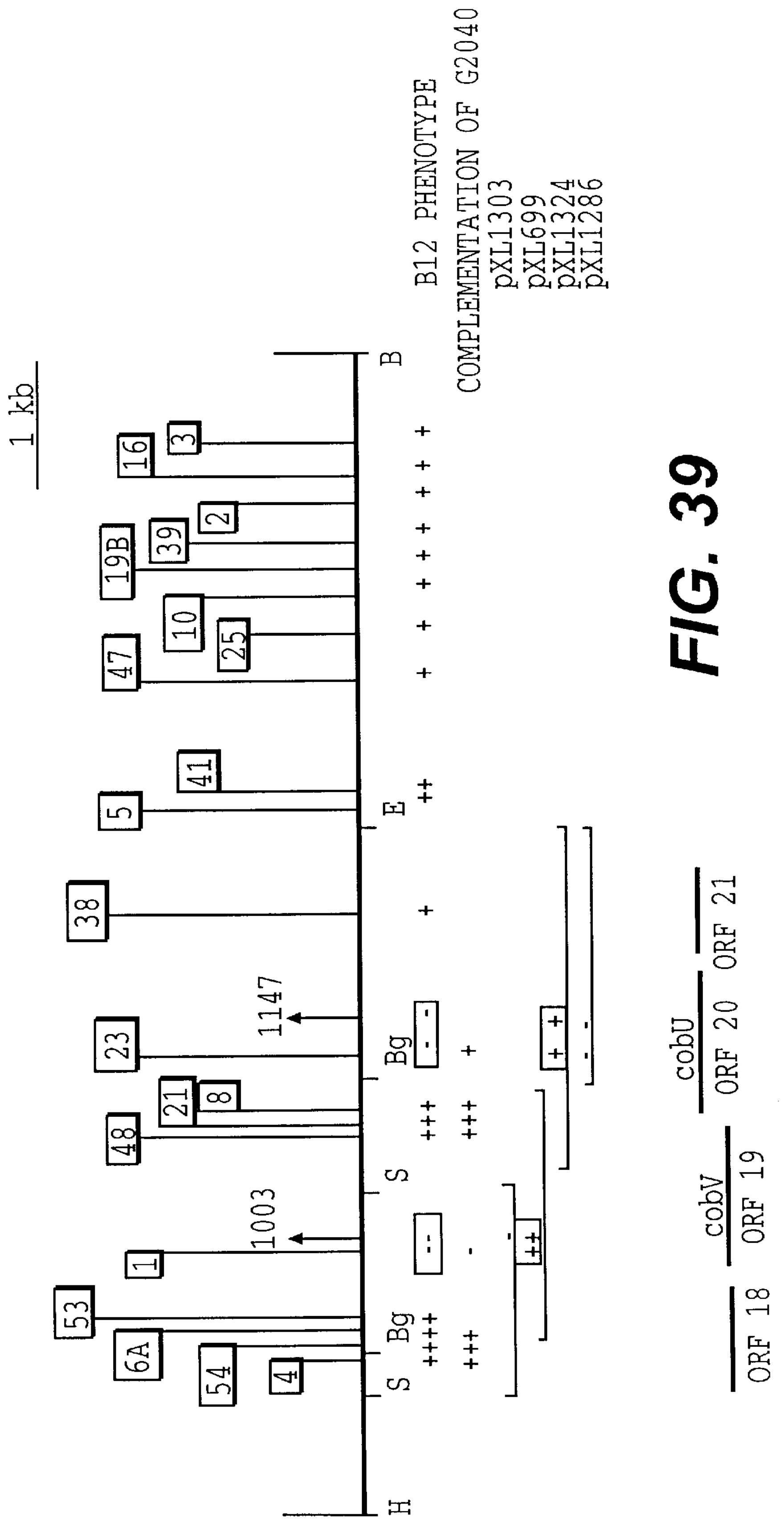
Figure 40A:
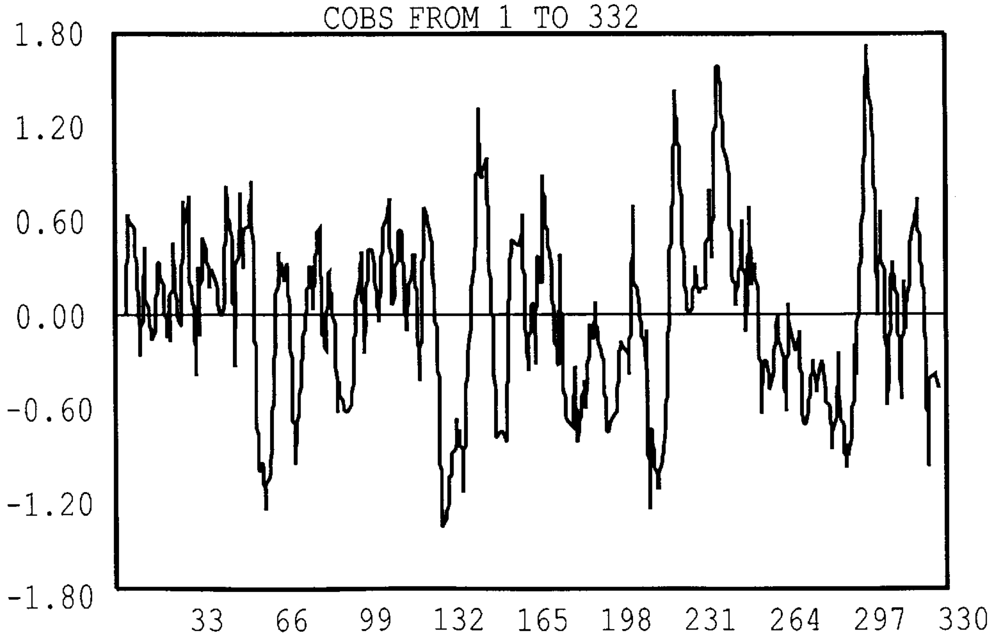
Figure 40C:
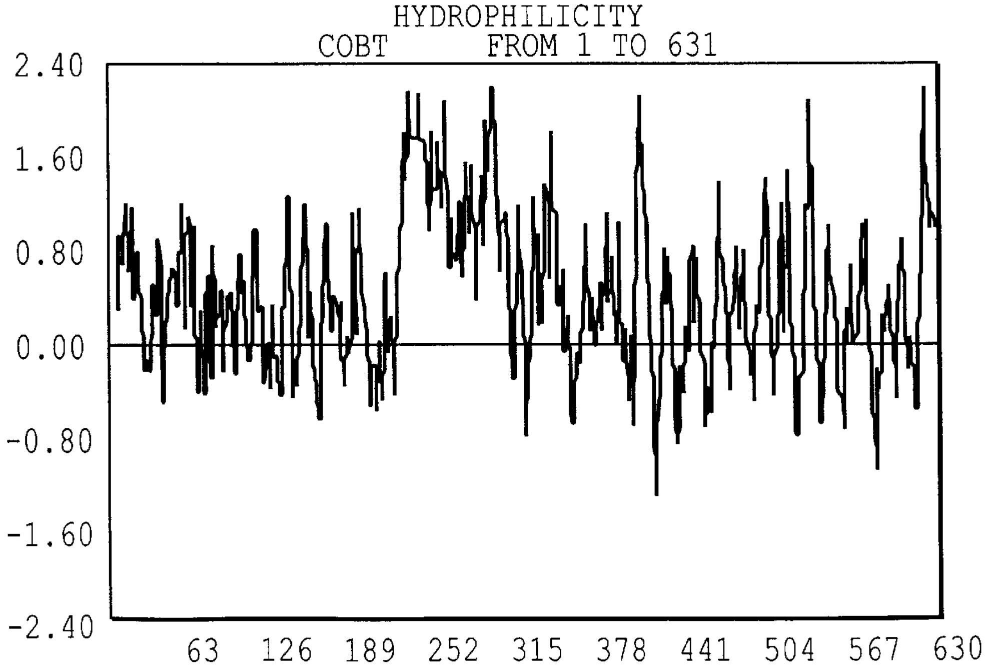
Figure 40F:
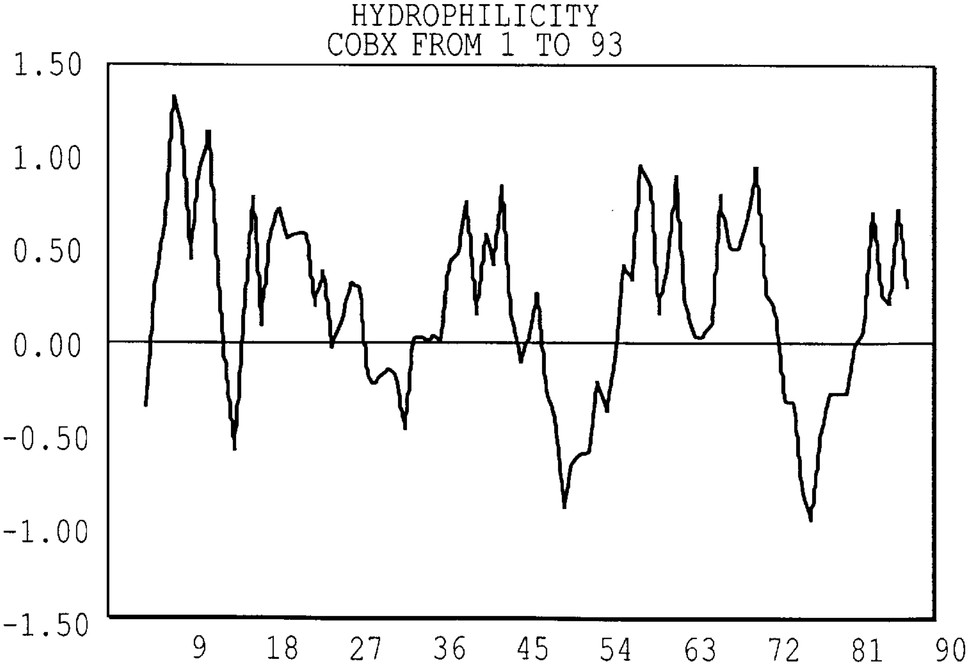
Figure 41A:
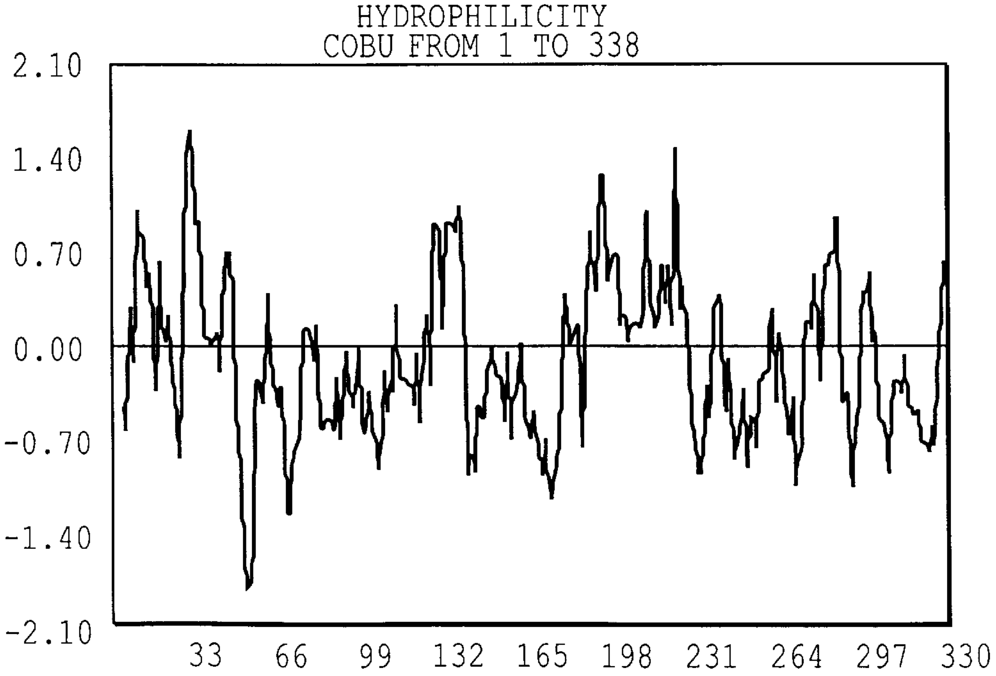
Figure 41C:
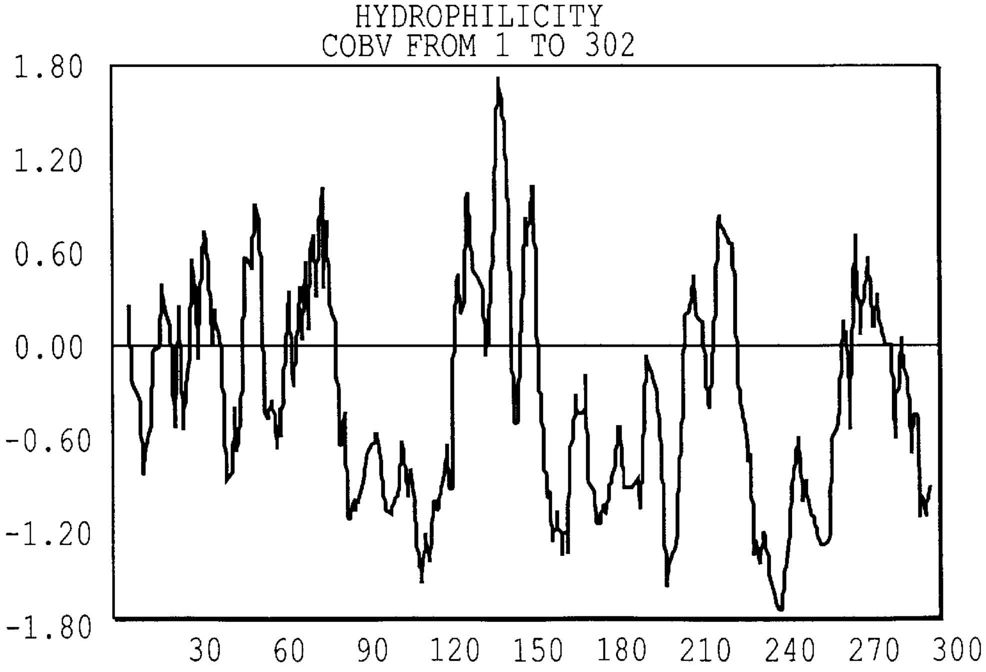

FIG. 39: Study of the insertions of the transposon Tn5Sp into the 9-kb HindIII-BamHI insert of pXL519. The insertions of the transposon are mapped on the 9-kb HindIII-BamHI insert cloned into pXL1557. The chromosomal insertions into strain SC510 $Rif^r$ are boxed, those which are not are introduced into strain SBL27 $Rif^r$. A plus or minus sign is shown under each insertion to indicate the Cob phenotype of the strain having this insertion. Absence of complementation (or complementation) of strain G2040 by plasmids pXL1557::Tn5Sp is indicated by minus (or plus) signs below each insertion. The inserts of the plasmids described in FIG. 6 are shown. The plus (or minus) signs over these plasmids and aligned with the transposon insertions, show diagrammatically the complementation (or absence) of the transposon-mutated strain by the plasmid. The open reading frames deduced from the sequence are also given in this figure (ORF18 to 21), as well as the corresponding cob genes (cobU and cobV).

FIGS. 40A–40G: Coding sequences of each of the genes of the 4.8-kb fragment, cobX, cobS and cobT, respectively, are indicated. The sequence of the COBX, COBS and COBT proteins encoded by these sequences appears under the respective coding sequences cobX, cobS and cobT. The legend is identical to that for FIG. 15.

FIGS. 41A–41D: Coding sequences of each of the genes of the 3.9-kb fragment, cobU and cobV, respectively, are indicated. The sequence of the COBU and COBV proteins encoded by these sequences appears under the respective coding sequences cobU and cobV. The legend is identical to that of FIG. 15.

FIG. 42: A. Total proteins of the strains *E. coli* BL21 pLysS pET3b and *E. coli* BL21 pLysS pXL1937 analysed in 10% SDS-PAGE. Lane 1, BL21 pLyspET3b; lane 2, *E. coli* BL21 pLysS pXL1937. B. Total proteins of the strains *E. coli* BL21, *E. coli* BL21 pXL1874 and *E. coli* BL21 pXL1875 analysed in 10% SDS-PAGE. Lane 1, *E. coli* BL21; lane 2, *E. coli* BL21 pXL1874; lane 3, *E. coli* BL21 pXL1875.

The molecular masses of the markers are indicated. The band corresponding to the overexpressed protein is indicated by an arrow.

FIGS. 43A–43V: Nucleotide sequence of both strands of the 13144-bp SstI-SstI-SstI-SstI-BglII-BglII fragment of *Pseudomonas denitrificans* (SEQ ID NO: 41). The strand situated at the top is to be read from 5' to 3' in left-to-right direction which corresponds to the left-to-right orientation of the fragment of the restriction map presented in FIG. 46.

FIGS. 44A–44G: Restriction map of the 13144-bp SstI-SstI-SstI-SstI-BglII-SstI-BglII fragment of *Pseudomonas denitrificans*. The position or positions of restriction sites occurring are indicated in increasing order of the cut number on the fragment sequenced; the positions correspond to the sequence presented in FIG. 43.

FIGS. 45A–45E: Analysis of the probabilities of the coding frames on the basis of codon preference using the programme of Staden and MacLachlan (1982) on the six reading frames of the 13144-bp SstI-SstI-SstI-SstI-BglII-SstI-BglII fragment of *Pseudomonas denitrificans*. For the frames belonging to the same coding strand, the most probable frame corresponds to that in which a dotted line, not interrupted by stop codons, is placed under the probability line for this frame.

A. Sequence corresponding to nucleotides 1 to 2266. This analysis enables open reading frame 22 to be identified. It begins at the ATG at position 429 and ends at the TAG at position 1884.

Sequence corresponding to nucleotides 2266 to 4000. This analysis enables open reading frame 23 to be identified. It begins at the ATG at position 3364 and ends at the TGA at position 3886.

B. Sequence corresponding to nucleotides 3800 to 5000. This analysis enables open reading frame 24 to be identified. It begins at the ATG at position 3892 and ends at the TAG at position 4954.

C. Sequence corresponding to nucleotides 5000 to 9000. This analysis enables open reading frame 25 to be identified. It begins at the ATG at position 5060 and ends at the TAG at position 8885.

D. Sequence corresponding to nucleotides 9000 to 9700. This analysis enables open reading frame 26 to be identified. It begins at the ATG at position 9034 and ends at the TGA position 9676.

E. Sequence corresponding to nucleotides 9600 to 13144. This analysis enables open reading frames 27, 28, 29 and 30 to be identified. They begin, respectively, at the ATGs at positions 9678, 10895, 11656 and 13059, and end at the stop codons at positions 10101, 10304, 12181 and 12366. Open reading frames 28 and 30 occur on the strand complementary to the coding strand corresponding to all the other open reading frames.

Figure 46:
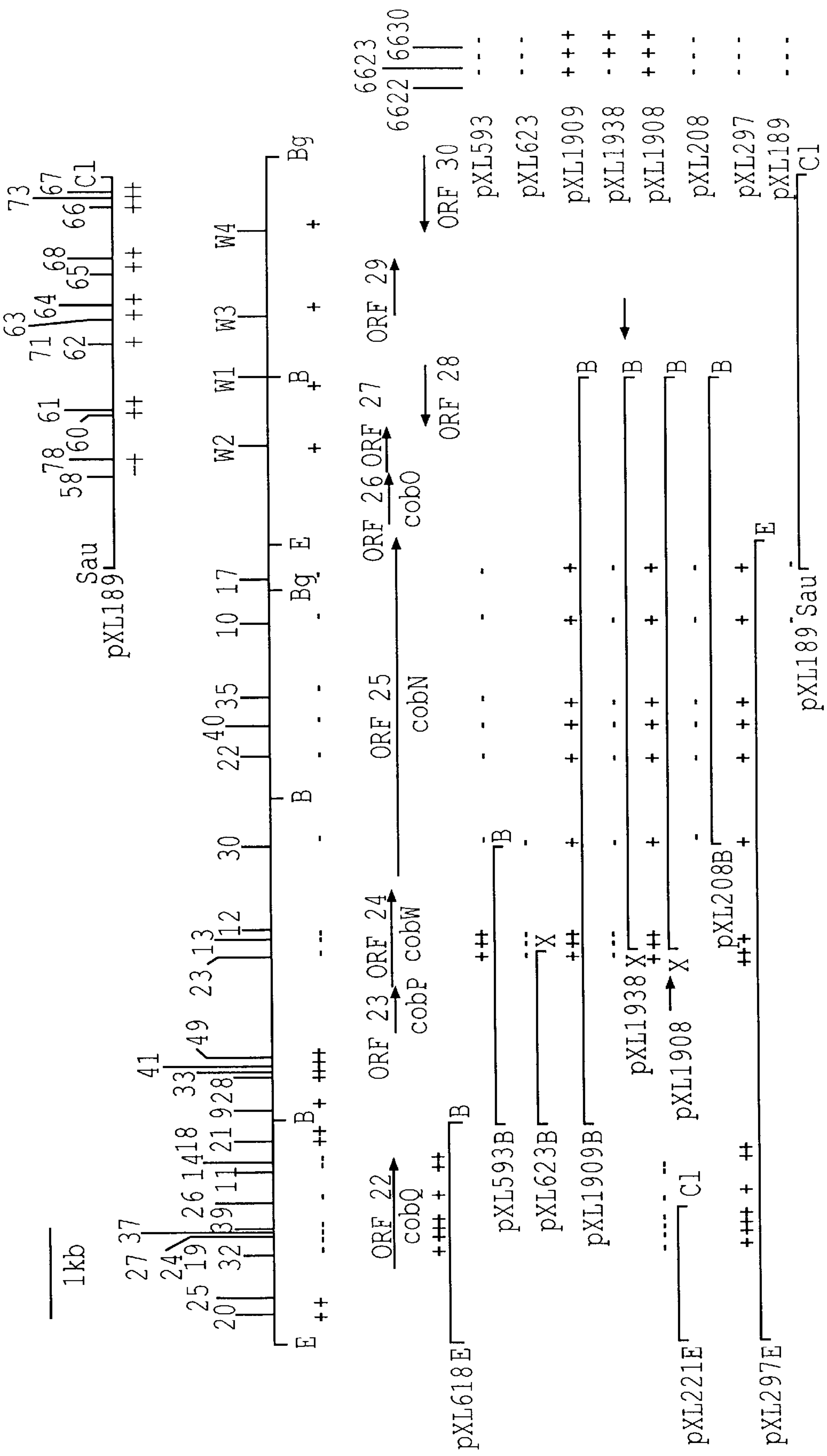

FIG. 46: 13.4-kb EcoRI-BglII-EcoRI-BglII fragment, positions of the insertions of transposons Tn5Sp into the 9.1-kb EcoRI fragment, positions of the insertions of transposons Tn5 into the insert of plasmid pXL189 as well as the inserts of the various plasmids used during the experiments on complementation of strains SC510 Rif$^r$::Tn5Sp. The complementations of the mutants SC510 Rif$^r$::Tn5Sp by the plasmids are indicated (+)—between 5% and 100% of the level of the parent strain SC510 Rif$^r$-(.)—partial complementation, between 0.5 and 5% of the level of SC510 Rif$^r$-, or (–)—absence of complementation, i.e. less than one thousand times less than SC510 Rif$^r$-, positioned immediately above the lines showing diagrammatically the insert of the plasmids and aligned with the insertion sites of the corresponding mutants. Below the mapping of the insertions of transposons Tn5 into the insert of plasmid pXL189, the complementation (+) or absence of complementation (–) of these mutant plasmids for the *Agrobacterium tumefaciens* mutants G632 and G633 is shown. On the right-hand part of the figure, there is a table showing the complementation of the mutants G622, G623 and G630 (Cameron et al., 1989) by different plasmids; (+)—total complementation, 100% of the level of the parent strain C58C9 Rif$^r$-, (.)—partial complementation, between 10 and 50% of the level of C58C9 Rif$^r$-, or (–)—absence of complementation.

The different plasmids whose insert is shown are constructed as follows (the fragments are excised either from pXL156 or from pXL157): pXL618 corresponds to the 2.5-kb EcoRI-BamHI fragment cloned at the same sites of pKT230 (Bagdasarian et al., 1981); pXL593 corresponds to the 3.1-kb BamHI fragment cloned at the BamHI site of pKT230 (Bagdasarian et al., 1981); pXL623 corresponds to the 1.9-kb BamHI-XhoI fragment cloned at the BamHI-SalI sites of pXL59 (Cameron et al., 1989); pXL1909 corresponds to the 8.4-kb BamHI-BamHI-BamHI fragment cloned at the BamHI of pKT230 (Bagdasarian et al., 1981); pXL221 corresponds to the 1.6-kb EcoRI-ClaI fragment cloned at the same sites of pXL59 (the ClaI site into which this fragment is cloned is the ClaI site of the multisite of pXL59) (Cameron et al., 1989); pXL1908 and 1938 correspond to the same insert, 6.5-kb XhoI-BamHI-BamHI fragment, to which XbaI linkers have been added; this insert is cloned in both orientations at the XbaI site of pXL435 (Cameron et al., 1989); an arrow positioned on the figure indicates the position of the kanamycin resistance gene with respect to the ends of the insert of the two plasmids; pXL208 corresponds to the 5.2-kb BamHI fragment cloned at the BamHI site of pKT230 (Bagdasarian et al., 1981); pXL297 corresponds to the 9.1-kb EcoRI fragment cloned at the EcoRI site of pKT230 (Bagdasarian et al., 1981).

The open reading frames (ORF) defined by the sequencing of the fragment (ORF 22 to 30) are shown, as well as the corresponding cob genes; an arrow indicates the polarity of the transcription.

Figure 47C:
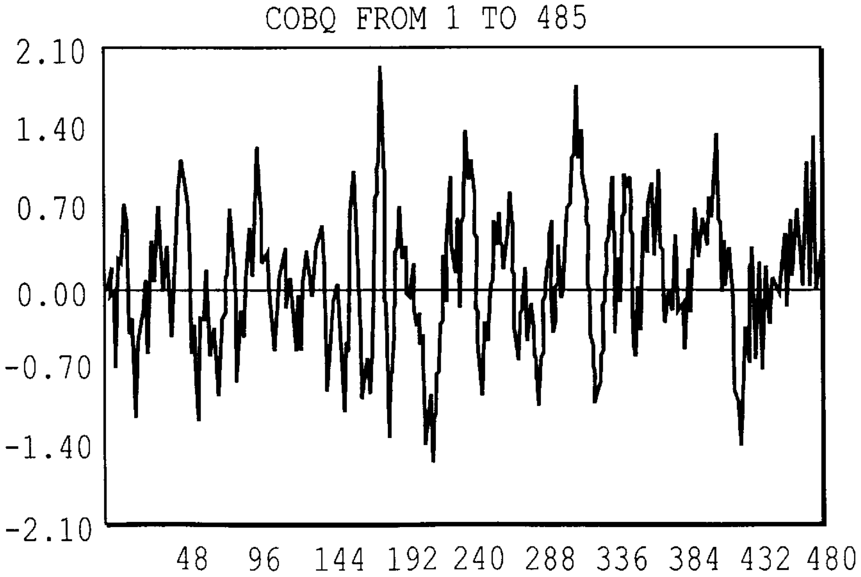
Figure 47E:
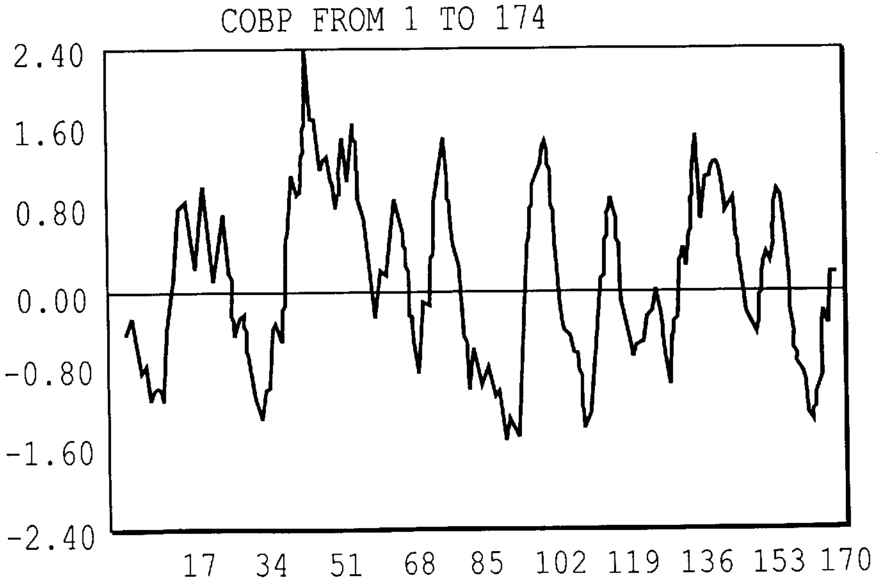
Figure 47H:
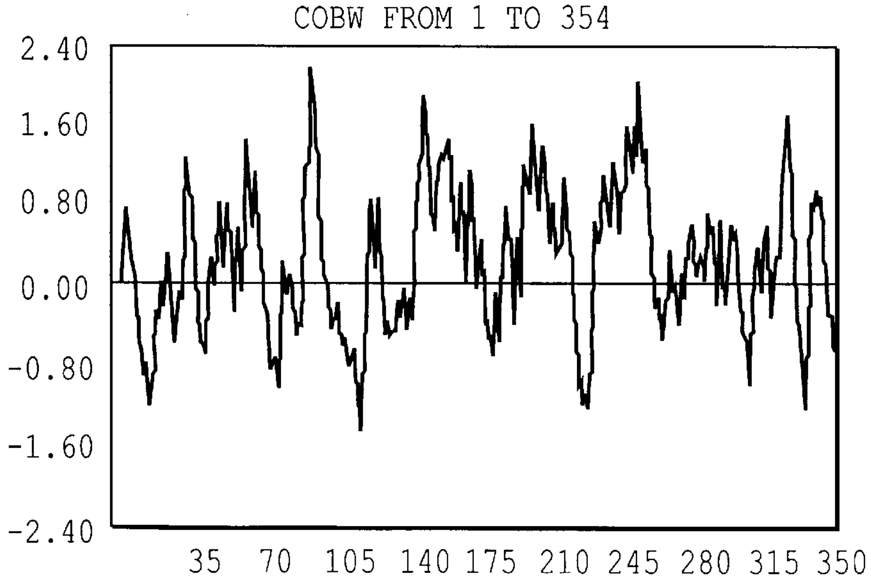
Figure 47N:
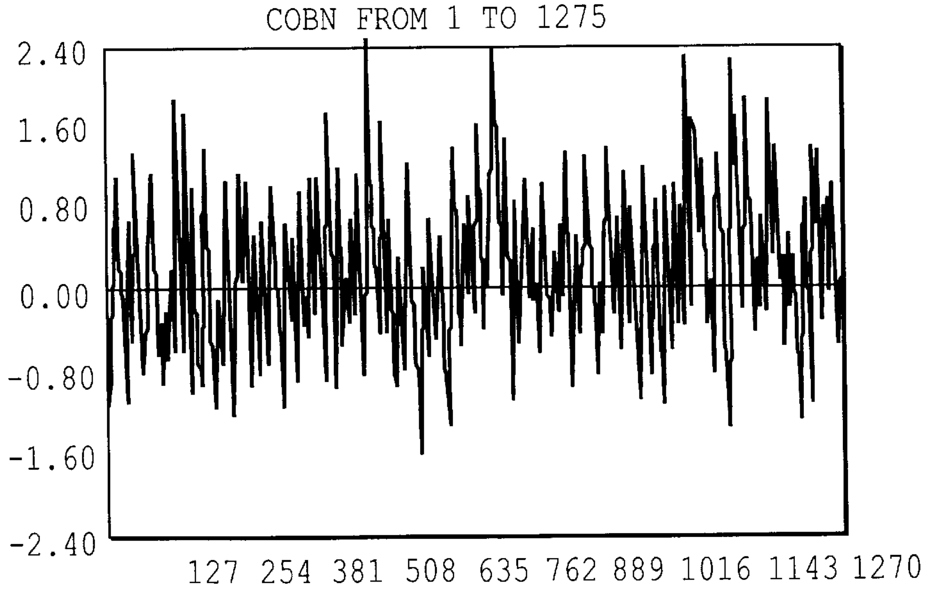
Figure 47P:
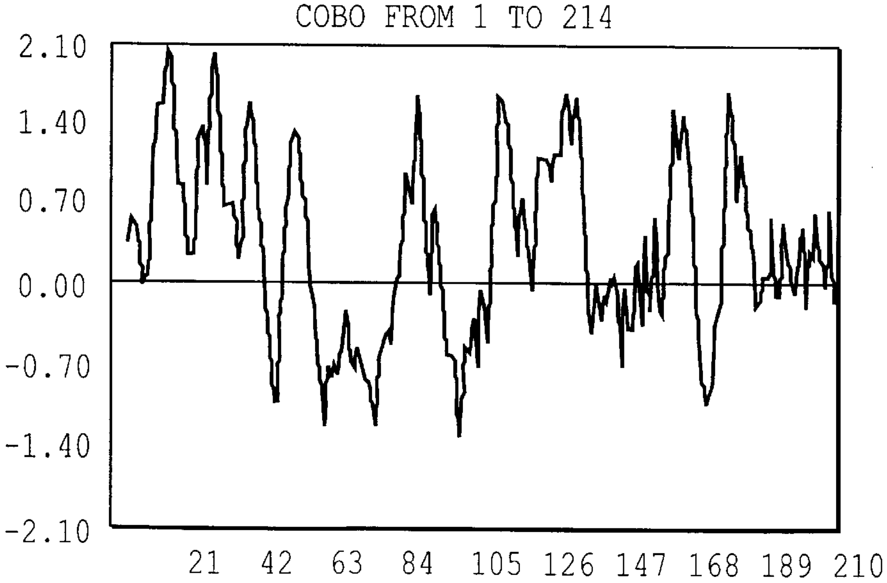

E, EcoRI; B, BamHI; Bg, BglII; Cl, ClaI; Sau, Sau3AI; X, XhoI;

FIGS. 47A–47P: Coding sequences of each of the genes of the 13.4-kb fragment, cobQ, cobP and cobW, cobN and cobO, respectively, are indicated. The sequences of the COBQ, COBP, COBW, COBN and COBO proteins encoded by these sequences appear under their respective coding sequence cobQ, cobP, cobW, cobN and cobO. The legend is identical to that for FIG. 15.

FIGS. 48A–48B: A—$NH_2$-terminal sequence of SUMT of *M. ivanovii* and sequence of the oligonucleotides 923, 946, 947; -, means that, at this position, the residue could not be determined; for the antisense oligonucleotide, the amino acids indicated below the sequence correspond to the anticodons shown. B—Presentation of the enzymatic amplification of a fragment internal to the structural gene of SUMT of *M. ivanovii* with the oligonnucleotides 946 and 947.

Figure 49:
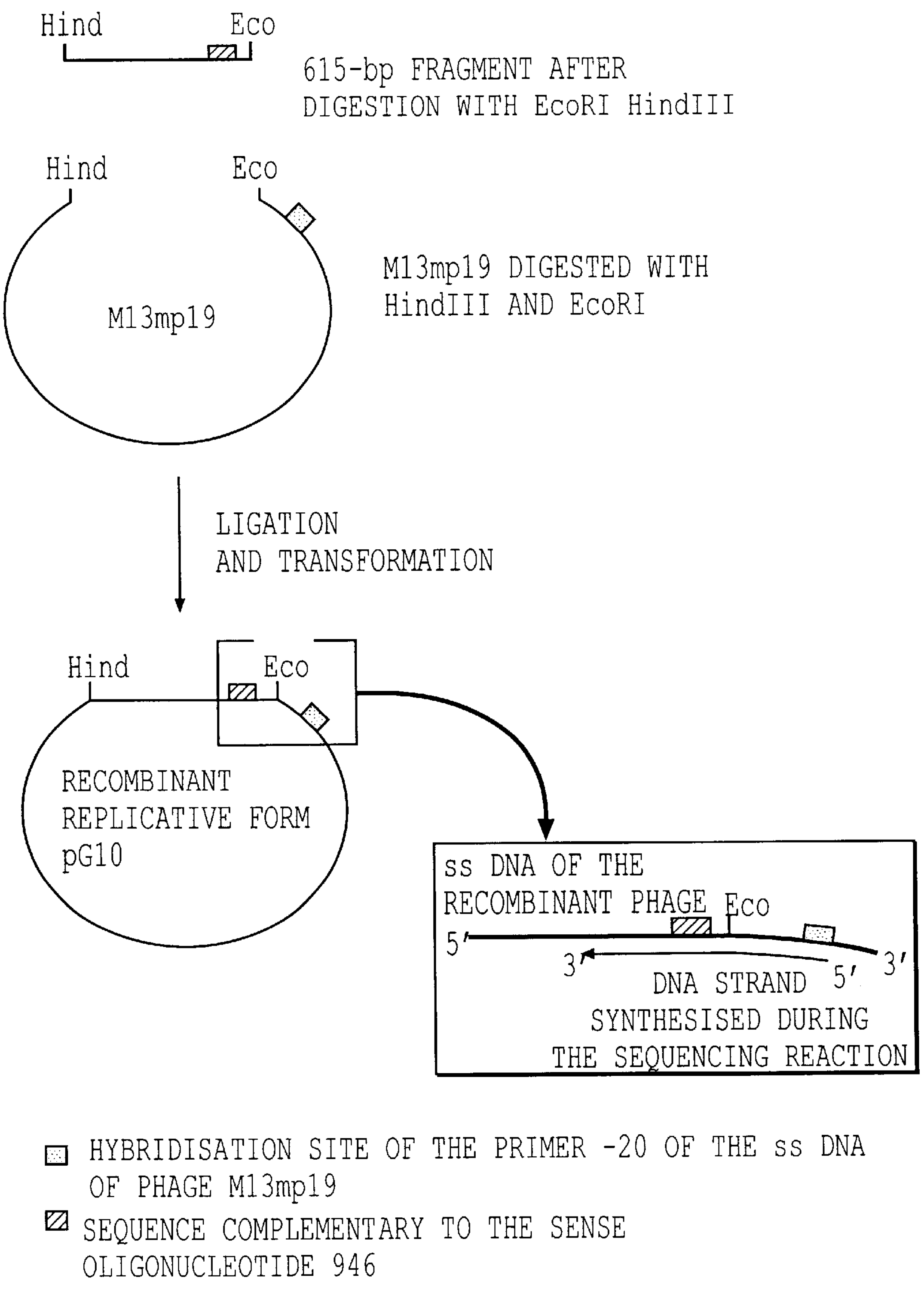

FIG. 49: Construction of the recombinant replicative form pG10. The 615-bp fragment obtained by amplification is digested with HindIII and EcoRI and then purified as described. This fragment is then ligated with the replicative form of phage M13mp19 digested with the same enzymes. The recombinant clone is found as described in the text.

Figure 50:
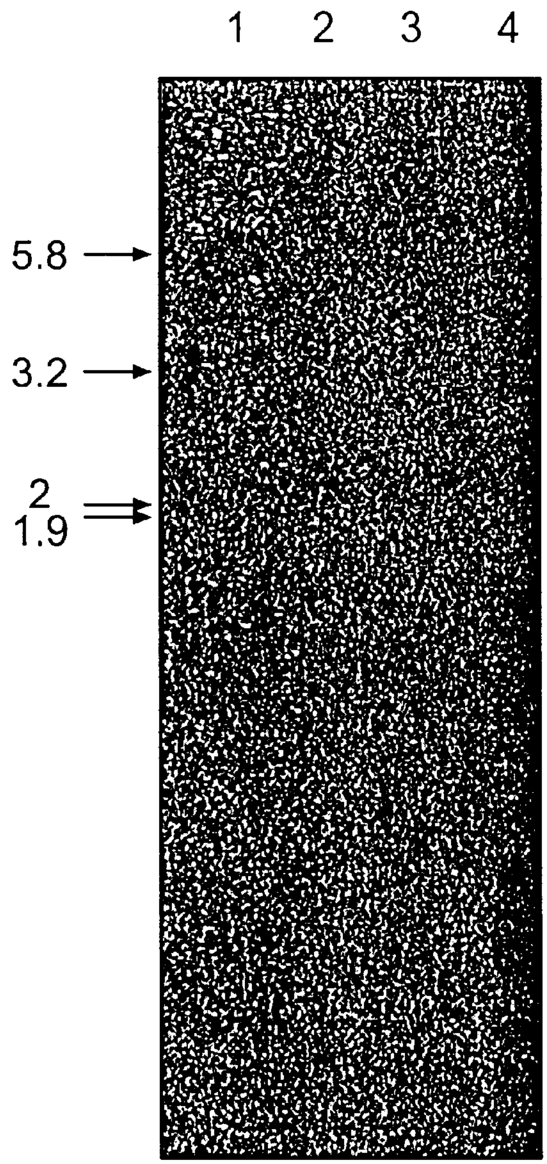

FIG. 50: Autoradiograph of a genomic DNA blot of *M. ivanovii* digested with various enzymes, separated by agarose gel electrophoresis and then transferred onto a nylon membrane as described previously. The membrane is hybridised with the pG10probe as described previously. 1, HindIII-BglII; 2, KpnI-BglII; 3, EcoRI-BglII; 4, BglII-PstI. The sizes of the different fragments which hybridise with the probe are shown in kb.

FIGS. 51A–51B: Nucleotide sequence of both strands of the 955-bp fragment of *M. ivanovii* (SEQ ID NO: 52). The strand situated at the top is to be read from 5' to 3' in the left-to-right direction.

Figure 52C:
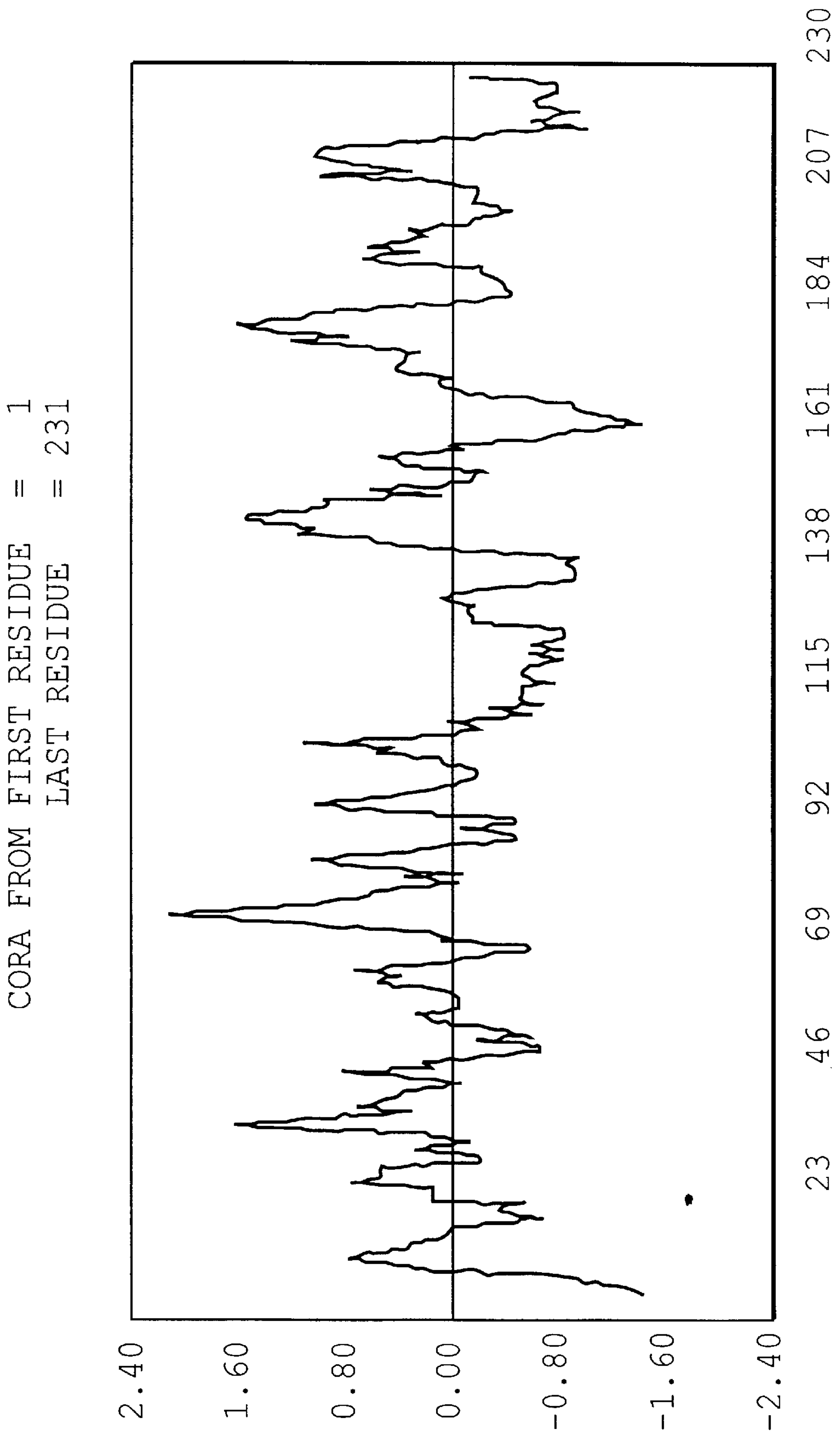

FIGS. 52A–52C: Coding sequence of the corA gene of *M. ivanovii* obtained from the 955-bp sequence (nucleotides of 34–729 SEQ ID NO: 52). The primary sequence of the CORA protein is also shown (SEQ ID NO: 53). The amino acids are shown above their codon and the stop codon is designated by a star. The main physical properties of the CORA protein of *M. ivanovii*, namely the amino acid composition, in number and in percentage, the molecular weight, the index of polarity, the isoelectric point and the optical density at 280 nm of a solution containing 1 mg/l of purified protein. The hydrophobicity profile of the CORA protein of *M. ivanovii*; this profile was obtained on the basis of the programme of Hopp and Woods (1981). Positive values correspond to regions of the protein which are hydrophilic. The position of the amino acids is indicated as abscissa, and the value of the index of hydrophilicity as ordinate; when this value is positive, this indicates that the protein is hydrophilic in this region.

FIG. 53: Comparison of the primary sequences of the proteins COBA of *P. denitrificans* (amino acids 17–251 of SEQ ID NO: 54) and CORA of *M. ivanovii* (amino acids 3–227 of (SEQ ID NO: 54). The proteins have been aligned by means of the programme of Kanehisa (1984). identical amino acids; -, homologous amino acids on the basis of the criteria defined above (see FIGS. 22 and 23).

Figure 54A:
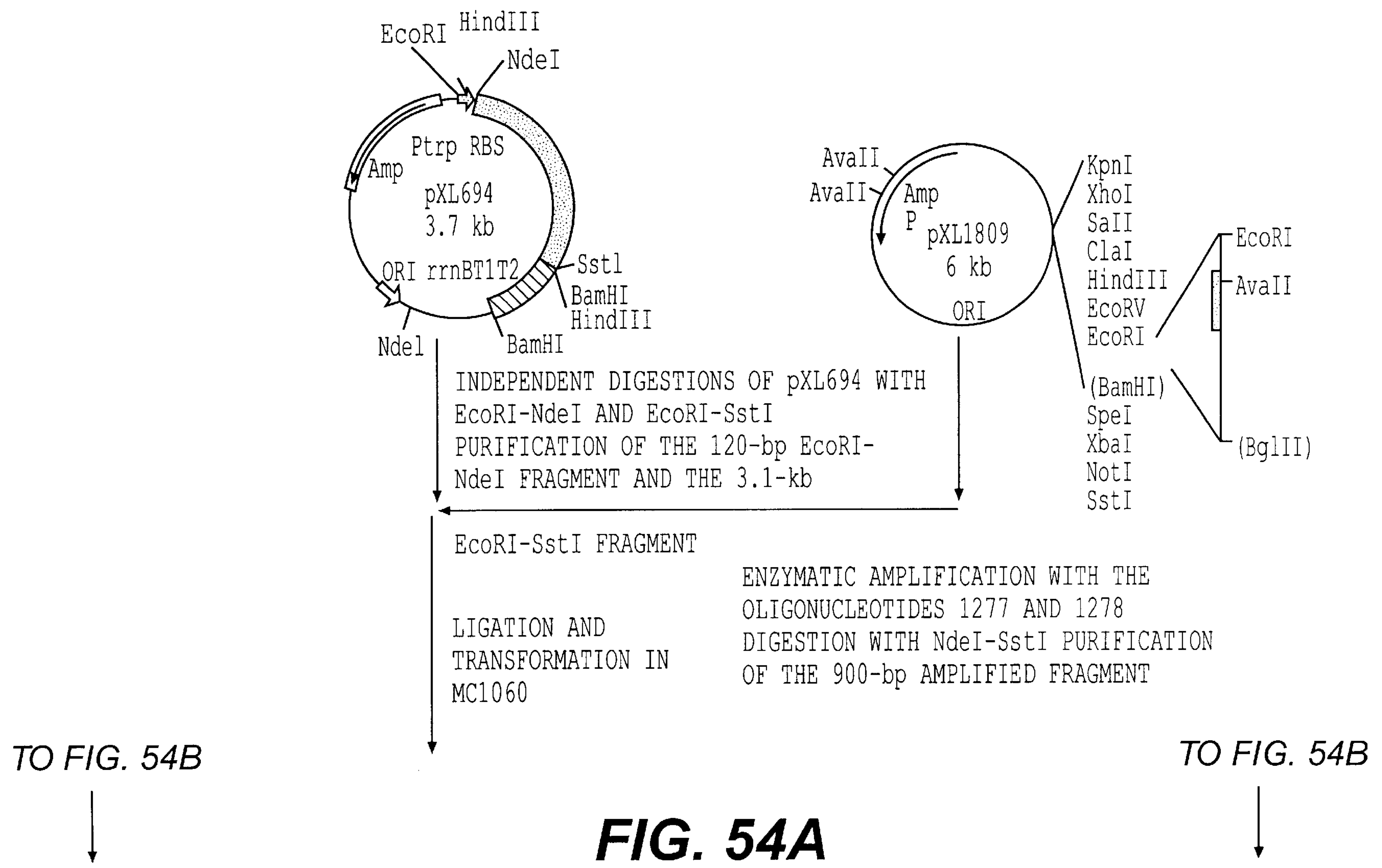
Figure 54B:
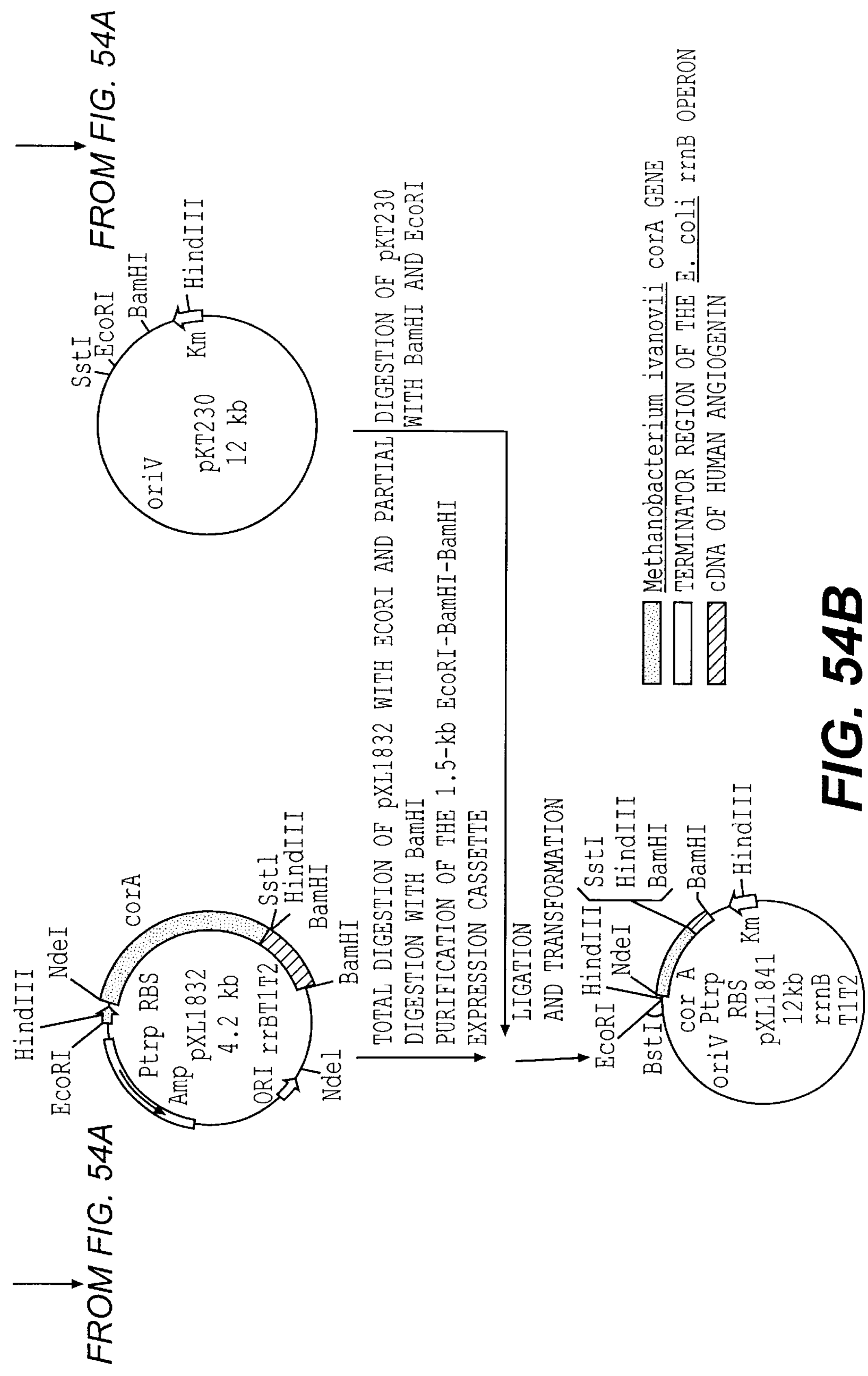

FIGS. 54A–54B: Construction of plasmids pXL1832 and pXL1841.

The legends described, placed on the figure, enable the constructions to be followed.

FIG. 55: Purification of *Pseudomonas denitrificans* cobinamide kinase-cobinamidephosphate guanylyl transferase.

GENERAL TECHNIQUES OF CLONING, MOLECULAR BIOLOGY AND BIOCHEMISTRY

The classical methods of molecular biology, such as centrifugation of plasmid DNA in a caesium chloride/ethidium bromide gradient, digestions with restriction enzymes, gel electrophoresis, electroelution of DNA fragments from agarose gels, transformation in *E. coli*, and the like, are described in the literature (Maniatis et al., 1982, Ausubel et al., 1987).

Restriction enzymes were supplied by New-England Biolabs (Biolabs), Bethesda Research Laboratories (BRL) or Amersham Ltd (Amersham). Linker oligonucleotides were supplied by Biolabs.

For the ligations, the DNA fragments are separated according to their size on 0.7% agarose or 8% acrylamide gels, purified by electroelution, extracted with phenol, precipitated with ethanol and then incubated in 50 mM Tris-HCl buffer pH 7.4, 10 mM $MgCl_2$, 10 mM DTT, 2 mM ATP, in the presence of phage T4 DNA ligase (Biolabs).

If necessary, DNA fragments having protuberant 5' ends are dephosphorylated by a treatment with calf intestinal alkaline phosphatase (CIP, Pharmacia) at 37° C. for 30 min in the following buffer: 100 mM glycine, 1 mM $MgCl_2$, 1 mM $ZnCl_{21}$ pH 10.5. The same technique is used for dephosphorylation of protuberant or blunt 3' ends, but the treatment is for 15 min at 37° C. and then 15 min at 56° C. The enzyme is inactivated by heating the reaction mixture to 68° C. for 15 min in the presence of 1% SDS and 100 mM NaCl, followed by a phenol/chloroform extraction and an ethanol precipitation.

Filling-in of protuberant 5' ends is performed with the Klenow fragment of *E. coli* DNA polymerase I (Biolabs). The reaction is performed at room temperature for 30 min in 50 mM Tris-HCl buffer pH 7.2, 0.4 mM dNTPs, 10 mM $MgSO_4$, 0.1 mM DTT, 50 mg/ml BSA. Filling-in of protuberant 3' ends is performed in the presence of phage T4 DNA polymerase (Biolabs) according to the manufacturer's recommendations. Digestion of the protuberant ends is performed by limited treatment with S1 nuclease (BRL) according to the manufacturer's recommendations. Linker oligonucleotides are added onto ends of DNA fragments as already described (Maniatis, 1982).

In vitro mutagenesis with oligodeoxynucleotides is performed according to the method developed by Taylor et al., 1985, using the kit distributed by Amersham.

The ligated DNAs are used for transforming the strain rendered competent: *E. coli* MC 1060 [D(lacIOPZYA)X74, galU, galK, $strA^r$, hsdR] for plasmids or *E. coli* TG1[D(lac proA,B), supE, thi, hsdD5/F' traD36, $proA^+$, $B^+$, $lacI^q$, lacZDM15] for replicative forms of phages derived from bacteriophage M13.

Plasmid DNAs are purified according to the technique of Birnboim and Doly, 1979. Minipreparations of plasmid DNA are made according to the protocol of Klein et al., 1980. Preparations of chromosomal DNA of Gram-negative bacteria are produced as already described (Cameron et al., 1989).

Radioactive probes are prepared by nick translation according to the method already detailed (Rigby et al., 1977). Hybridisations between DNA sequences as well as the immobilisation of nucleic acids on nitrocellulose membranes are performed as already described (Cameron et al., 1989). In clonings for which there is a small probability of finding the desired recombinant clone, the latter are found after hybridisation on filters as already described (Maniatis et al., 1982).

The nucleotide sequence of DNA fragments is determined by the chain-termination method (Sanger et al., 1977). In the reaction mixture, dGTP is replaced by 7-deaza-dGTP, in order to avoid compression of bands during acrylamide gel electrophoresis caused by the high percentage of GC in the DNA.

The culture media used for the bacteriological part have already appeared (Maniatis et al., 1982). Culturing in PS4 medium is carried out as already described (Cameron et al., 1989); *Pseudomonas denitrificans* strains SC510 $Rif^r$ and G2 $Rif^r$ are cultured in PS4 medium as follows: 250-ml Erlenmeyers containing PS4 medium (25 ml), with, if necessary, the selective antibiotic for the plasmid carried by each strain, are inoculated with a 1/100 dilution of saturated preculture in L medium (Miller 1972), with, if necessary, the selective antibiotic for the plasmid carried by each strain;

these cultures are incubated for 6 days at 30° C. and the musts are then analysed for their cobalamin content or alternatively the enzymatic activity of some enzymes of the pathway. Strains of *Agrobacterium tumefaciens, Pseudomonas putida* and *Rhizobium meliloti* are cultured at 30° C.; except where otherwise stated, they are cultured in L medium.

Bacterial conjugations are carried out as already described (Cameron et al., 1989).

Extracts of total proteins are produced as already described (Ausubel et al., 1987).

Analytical electrophoresis (SDS-PAGE) of proteins in acrylamide gel under denaturing conditions is performed as already described (Ausubel et al., 1987). The PhastSystem apparatus (Pharmacia) using Laemli's discontinuous-buffer system (Laemli, 1970) is also used; different gels are used in accordance with the molecular weights of the proteins to be analysed as well as their purity:

PhastGel gradient 8–25

PhastGel Homogeneous 12.5

Staining is performed either with Coomassie blue with the aid of PhastGel Blue R (Pharmacia), or with silver nitrate using the PhastGel silver Kit (Pharmacia) in accordance with the manufacturer's instructions.

$NH_2$-terminal sequences of the proteins are determined by the Edman degradation technique, using an automated sequencer (Applied Biosystems model 407A) coupled to an HPLC apparatus for identification of the phenylthiohydantoin derivatives.

EXAMPLE 1

Isolation of DNA Fragments of *P. denitrificans* Containing Cob Genes

This example describes the isolation of DNA fragments of *Pseudomonas denitrificans* carrying Cob genes. These fragments were demonstrated by complementation experiments on Cob mutants of A. tumefaciens and *P. putida* (Cameron et al., 1989).

These Cob mutants were obtained by mutagenesis with N-methyl-N'-nitro-N-nitrosoguanidine according to the technique of Miller (Miller et al., 1972), or by insertions of transposon Tn5. In this manner, strains incapable of synthesising cobalamins were demonstrated, and especially the Cob mutant G572 of *P. putida* and the Cob mutants G159, G161, G164, G169, G171, G258, G609, G610, G611, G612, G613, G614, G615, G616, G620, G622, G623, G630, G632, G633, G634, G638, G642, G643, G2034, G2035, G2037, G2038, G2039, G2040, G2041, G2042 and G2043 of *A. tumefaciens.*

At the same time, a library of genomic DNA of *P. denitrificans* is produced in a mobilisable broad host range vector pXL59, by digestion of 5 $\mu$g of DNA in the presence of restriction enzymes (Cameron et al., 1989).

By complementation, several plasmids could be isolated, enabling the Cob mutants of *P. putida* and of *A. tumefaciens* to be complemented. Among these, plasmids pXL151, pXL154, pXL156, pXL157 and pXL519 will be noted more especially.

These plasmids were isolated and DNA fragments could be excised, purified and analysed by restriction. These fragments are presented in FIGS. 6 and 44: a 5.4-kb ClaI-HindIII-HindIII-HindIII fragment, an 8.7-kb EcoRI-EcoRI fragment, a 4.8-kb SalI-SalI-SalI-SalI-SalI-BglI fragment, a 3.9-kb SstI-SstI-BamHI fragment and a 13.4-kb EcoRI-BglII-EcoRI-BglII fragment.

EXAMPLE 2

Sequencing of the DNA Fragments Isolated

This example illustrates the sequencing of DNA fragments carrying cob genes of *Pseudomonas denitrificans* SC510.

2.1. Sequencing of a 5.4-kb ClaI-HindIII-HindIII-HindIII Fragment

This fragment is contained in plasmid pXL157 described in Example 1. After excision, the subfragments of the 5.4-kb fragment were cloned into phages M13mp18 or M13mp19 (Norrander et al., 1983) or M13tg130 or M13tg131 (Kieny et al., 1983) in both orientations. Deletions were then produced in vitro by the method of Henikoff (1987). These deletions were then sequenced with the "universal primer" as a synthetic primer of chain-termination reactions. The overlap between these different deletions enabled the total sequence, over both strands, of the 5.4-kb fragment to be established (FIG. 7). This fragment comprises 5378 bp. In the sequence described in FIG. 7, there are seen, before the ClaI site, three restriction sites (PstI, SalI and XbaI) which have appeared during the cloning of the fragment in question with a view to sequencing in cloning multisites. When subsequent reference is made, in the present invention, to the sequence of this ClaI-HindIII-HindIII-HindIII fragment, this will be to the sequence presented in FIG. 7 in which the first 22 bases do not correspond to the DNA of *Pseudomonas denitrificans* (thus, all the positions of restriction site or of beginning of open reading frame refer to the sequence presented in FIG. 7).

2.2. Nucleotide Sequence of an 8.7-kb EcoRI-EcoRI Fragment

This fragment is carried by pXL151 described in Example 1. The EcoRI site as well as the adjacent 70 bp located to the right of this fragment originate from pXL59, which is the vector used for constructing pXL151 by cloning an Sau3AI fragment of *Pseudomonas denitrificans* SC510. After excision, subfragments of the 8.7-kb fragment were cloned into phages M13mp18 or M13mp19 (Norrander et al., 1983) or M13tg130 or M13tg131 in both orientations (Kieny et al., 1983). Deletions were then produced in vitro by the method of Henikoff (1987). These deletions were then sequenced with the "universal primer" as a synthetic primer of chain-termination reactions. The overlap between these different deletions enabled the total sequence, over both strands, of the 8.7-kb fragment to be established (FIG. 8). This fragment comprises 8753 bp.

2.3. Sequencing of a 4.8-kb SalI-SalI-SalI-SalI-SalI-BglI Fragment

This fragment is contained in plasmid pXL154 described in Example 1. The protocol is identical to that used in Example 2.2. The total sequence on both strands of the 4.8-kb fragment is presented in FIG. 32. This fragment contains 4749 bp.

2.4. Nucleotide Sequence of a 3.9-kb SstI-SstI-BamHI Fragment

This fragment is included in plasmid pXL519 described in Example 1. The protocol is identical to that used in Example 2.2. The total sequence on both strands of the 3.9-kb fragment is presented in FIG. 33. This fragment contains 3855 bp.

2.5. Nucleotide Sequence of a 13.4-kb EcoRI-BglII-EcoRI-BglII Fragment

This fragment is contained in plasmids pXL156 and pXL157 described in Example 1. The protocol used is identical to that of Example 2.2. The sequence on both strands of the 13.15-kb fragment is presented in FIG. 43. It corresponds to the total sequence of the 13.4-kb fragment except for 250 bp, corresponding to an EcoRI-SstI fragment, occurring at the left-hand end of the fragment.

From these nucleotide sequences, restriction maps were obtained for the enzymes which cut least frequently (FIGS. 6 and 44). The percentage of GC bases in *Pseudomonas denitrificans* SC150 DNA is relatively high (65.5%) and manifests itself in compression on the sequencing gels. To avoid these problems, two approaches are adopted:

i) the use of 7-deaza-dGTP instead of dGTP in the sequencing reactions to decrease the secondary structures which form during electrophoresis in the sequencing gel, and ii) the sequencing of both strands.

EXAMPLE 3

Analysis of These Nucleotide Sequences: Determination of the Open Reading Frames The nucleotide sequences of the 5.4-kb ClaI-HindIII-HindIII-HindIII (FIG. 7), 8.7-kb EcoRI-EcoRI (FIG. 8), 4.8-kb SalI-SalI-SalI-SalI-SalI-BglI (FIG. 32), 3.9-kb SstI-SstI-BamHI (FIG. 33) and 13.4-kb EcoRI-BglII-EcoRI-BglII (FIG. 43) fragments enable open reading frames to be defined. Since the DNA in question contains a high percentage of GC, the open reading frames are numerous in view of the low frequency of translation stop codons. A study of the probability of the coding frames on the basis of codon preference using the method of Staden and MacLachlan (1982) is carried out. It characterises the open reading frames which have the greatest probability of being coding relative to the other frames of the same DNA strand, this probability being dependent on the codon preference of genes already sequenced originating from bacteria of the genus Pseudomonas. In this manner:

3.1. Five open reading frames are characterised for the 5.4-kb ClaI-HindIII-HindIII-HindIII fragment. They are designated frames 1 to 5, and their positions in the sequence of the 5.4-kb fragment are as follows (in the 5'→3' sequence from the ClaI site to the HindIII sites):

TABLE

Probable open reading frames of the 5.4-kb ClaI-HindIII-HindIII-HindIII fragment. The positions in the sequence correspond to the positions in the sequence described in FIG. 7; the coding strand is the 5'→3' strand corresponding to the upper strand in this FIGURE.

| Frame number | Translation initiation codon | Stop codon | Molecular weight in kD of the encoded protein |
|---|---|---|---|
| 1 | 549 | 1011 | 15.5 |
| 2 | 1141 | 1980 | 29.2 |
| 3 | 1980 | 3282 | 5.7 |
| 4 | 3281 | 4280 | 35.0 |
| 5 | 4284 | 5253 | 34.1 |

The representations of the probabilities that these open reading frames are coding frames, with those observed on the other frames (5 in total) in parallel, are given in FIG. 9. These five frames are encoded by the same strand. Four of them (open reading frames 1 to 4) display the characteristics of coding frames in translational coupling (Normak et al., 1983), namely, the translation initiation codon of frame x+1 overlaps the translation termination codon of frame x, or else these codons are very close.

3.2. Eight frames are characterised for the 8.7-kb EcoRI-EcoRI fragment. They are designated frames 6 to 13 and their positions in the sequence of the 8.7-kb fragment are given in the table below.

TABLE

Probable open reading frames of the 8.7-kb EcoRI fragment. The positions in the sequence correspond to the positions in the sequence described in FIG. 8; in this FIGURE, the coding strand is the upper strand.

| Translation frame number | Initiation codon | Stop codon | Molecular weight in kD of the encoded protein |
|---|---|---|---|
| 6 | 736 | 1519 | 28.9 |
| 7 | 1620 | 2997 | 46.7 |
| 8 | 3002 | 3632 | 22.0 |
| 9 | 3631 | 4366 | 25.8 |
| 10 | 4365 | 5127 | 27.1 |
| 11 | 5126 | 5867 | 26.8 |
| 12 | 5862 | 7101 | 42.9 |
| 13 | 7172 | 7931 | 26.8 |

The representations of the probabilities of these open reading frames, with those observed on the other frames (6 frames in total) in parallel, are given in FIG. 10. With the exception of frame 11, these eight frames are encoded by the same strand. Four of them (from 7 to 10) display the characteristics of coding frames in translational coupling (Normark et al., 1983), namely, the translation initiation codon of frame x+1 overlaps the translation termination codon of frame x, or else these codons are very close.

3.3. Four open reading frames are characterised for the 4.8-kb SalI-SalI-SalI-SalI-SalI-BglI fragment. They are designated phases 14 to 17 and their positions in the sequence of the 4.8-kb fragment are as follows (in the 5'-3' sequence from the SalI sites to the BglI site):

TABLE

Probable open reading frames of the 4.8-kb SalI-SalI-SalI-SalI-SalI-BglI fragment. The positions in the sequence corresponds to the positions described in FIG. 32, where the upper strand is given in its 5'–3' orientation. Frames 15, 16 and 17 are encoded by the upper strand, in contrast to frame 14.

| Frame number | Translation initiation codon | Stop codon | Molecular weight in D of the encoded protein |
|---|---|---|---|
| 14 | 660 | 379 | 10286 |
| 15 | 925 | 1440 | 18941 |
| 16 | 1512 | 2510 | 36983 |
| 17 | 2616 | 4511 | 70335 |

The representations of the probabilities that these open reading frames are coding, with those observed on the other frames (4 in total) in parallel, are given in FIG. 34. Frames 15, 16 and 17 are encoded by the same strand, frame 14 by the complementary strand.

3.4. Four frames are characterised for the 3.9-kb SstI-SstI-BamHI fragment. They are designated 18 to 21 and their positions in the sequence of the 3.9-kb fragment are given in the table below.

TABLE

Probable open reading frames of the 3.9-kb SstI-SstI-BamHI fragment. The positions in the sequence correspond to the positions described in FIG. 33, where the polarity of the upper strand is 5'–3'. Frames 18 and 19 are encoded by the lower strand, in contrast to frames 20 and 21.

| Frame number | Translation initiation codon | Stop codon | Molecular weight in D of the encoded protein |
|---|---|---|---|
| 18 | 809 | 108 | 25148 |
| 19 | 1971 | 1063 | 30662 |
| 20 | 2099 | 3115 | 34682 |
| 21 | 3344 | 3757 | 14802 |

The representations of the probabilities that these open reading frames are coding, with those observed on the other frames (4 in total) in parallel, are given in FIG. 35. Frames 19 and 20 are transcribed in a differing manner.

3.5. Nine open reading frames are characterised for the 13.1-kb EcoRI-BglII-EcoRI-BglII fragment. They are designated frames 22 to 30 and their positions in the sequence of the 13.1-kb fragment are as follows (in the 5'-3' sequence from the EcoRI site to the BglII site):

TABLE

Probable open reding frames of the 13.1-kb EcoRI-BglII-EcoRI-BglII fragment. The positions in the sequence correspond to the positions described in FIG. 43, where the upper strand is given in its 5'–3' orientation. The frames 22, 23, 24, 25, 26, 27 and 29 are encoded by the upper strand, in contrast to the frames 28 and 30.

| Translation frame number | Initiation codon | Stop codon | Molecular weight in D of the encoded protein |
|---|---|---|---|
| 22 | 429 | 1884 | 51982 |
| 23 | 3364 | 3886 | 19442 |
| 24 | 3892 | 4954 | 38121 |
| 25 | 5060 | 8885 | 138055 |
| 26 | 9034 | 9676 | 24027 |
| 27 | 9678 | 10101 | 14990 |
| 28 | 10835 | 10306 | 21057 |
| 29 | 11656 | 12181 | 19183 |
| 30 | 13059 | 12368 | 24321 |

The representations of the probabilities that open reading frames 22, 23, 24, 25 and 26 are coding, with those observed on the other frames (5 in total) in parallel, are given in FIG. 45. These 5 frames are encoded by the same strand.

EXAMPLE 4

Genetic Studies on the DNA Fragments Carrying cob Genes

This example shows the relationship which exists between the different open reading frames identified above and the genes involved in the biosynthesis of cobalamins and/or cobamides carried by these same fragments. These genes are identified by a genetic study as described below.

4.1—Genetic study of the 5.4-kb fragment

Plasmid pXL723 is plasmid pRK290 (Ditta et al., 1980) containing the 2264-bp EcoRI-HindIII fragment corresponding to the right-hand portion of the fragment studied, cloned at the EcoRI site of pRK290 (FIG. 11). The construction of the other plasmids used in this study (pXL302, pXL1397, pXL545, pXL545Ω, pXL556 and pXL1500) is described in the legend to FIGS. 11 and 12.

Insertions were obtained in plasmid pXL723 using the technique of de Bruijn and Lupski, 1984. Insertions of transposon Tn5 into plasmid pXL723 were selected and then mapped in the 5.4-kb fragment (FIG. 12). pXL723 complements the Cob mutant G572 of *Pseudomonas putida* and the Cob mutant G634 of *Agrobacterium tumefaciens*. These insertions are classified in two groups of inactivating insertions: either those which no longer permit complementation of the Cob mutant G572, or those which abolish the complementation of the Cob mutant G634 (FIG. 12). Insertions which inactivate the complementation of mutant G572 are mapped in open reading frame 4 (these are insertions 15, 27, 68, 81 and 97); open reading frame 4 hence corresponds to a cob gene. The latter is designated cobC. Insertions which inactivate the complementation of mutant G634 are mapped in frame 5 (these are insertions 66 and 107, FIG. 12); open reading frame 5 hence corresponds to a cob gene. The latter is designated cobD. Moreover, insertions with a transposon Tn5Sp$^r$ were produced. Transposon Tn5Sp$^r$ was constructed in the laboratory by cloning a BamHI cassette, containing the spectinomycin resistance gene originating from plasmid pHP45Ω (Prentki and Krisch, 1984), at the BamHI site of transposon Tn5 (Jorgensen et al., 1979). These insertions were made in the chromosome of *Pseudonomas denitrificans* strain SBL27 Rif$^r$. Strain SBL27 is a strain of *Pseudomonas denitrificans* from which SC510 is derived by several mutageneses. SBL27 produces 10-fold less cobalamins than SC510 on PS4 medium. Of 10,000 clones of strain SBL27 Rif$^r$ each carrying an insertion of transposon, more than 30 had lost the capacity to synthesise cobalamins. Some of these clones possessed an insertion in the fragment studied in this example. These insertions were mapped by restriction analysis according to Southern's method (Southern, 1975). The sites of insertions of the transposon in these different mutants are given in FIG. 12. One of these insertions, number 2639, occurs in the cobC gene; this insertion is complemented by plasmid pXL302, which carries a fragment containing the cobC gene (FIG. 12). Two insertions, designated 2636 and 2638, are in open reading frame 3. These mutants are blocked in the biosynthesis of cobalamins, and they are complemented by plasmid pXL1397 which contains only open reading frame 3, but non-complemented by plasmid pXL302 which contains the cobC and cobD genes (FIG. 12). Both of these insertions are hence in another gene. With open reading frame 3, we associate the cobB gene. An insertion 2933 is placed in open reading frame 2; it is complemented by plasmid pXL1500 which contains open reading frame 2; this insertion is non-complemented by plasmid pXL1397, which contains the cobB gene and which complements the two insertions in cobB. In this instance, the insertion is hence in another gene; with open reading frame 2, we associate a gene designated cobA.

A kanamycin resistance cassette originating from plasmid pUC4K (Barany et al., 1985) was introduced at the NotI site of the ClaI (position 0 in the sequence)-RsaI (position 1686 in the sequence) fragment cloned into a plasmid pUC8 (Viera and Messing, 1982); the NotI site in question is located at position 771 in frame 1 (see the sequence in FIG. 7); two insertions were adopted, each corresponding to a different orientation of the resistance cassette. These fragments, each carrying an insertion of the resistance cassette, were cloned into plasmid pRK404 (Ditta and al.) to give plasmids pXL1630 and 1631. These plasmids were introduced by conjugative transfer into *Pseudomonas denitrificans* strain SC510 Rif$^r$, and then, by a series of cultures/dilutions in the absence of the selective antibiotic for the plasmid (tetracycline), double recombinants which had exchanged the plasmid fragment with the chromosomal fragment and had lost the plasmid were found. Two strains were thereby characterised:

i) one is designated SC510:1631 Rir$^r$; in this strain, the kanamycin resistance cassette is inserted in the chromosome at the NotI site (occurring in frame 1); the polarities of the transcriptions of the kanamycin resistance gene and that of open frame 1 are opposite, ii) the other insertion is designated SC510:1630 Rif$^r$; the resistance cassette is inserted at the same site, but the transcription of the resistance gene has the same polarity as that of the complete open reading frame 1.

These two strains both have a rate of synthesis of cobalamins at least 100-fold lower than that of SC510.

Plasmid pXL545n corresponds to plasmid pXL5A5 into which the spectinomycin resistance cassette of plasmid pHP45Ω has been inserted at the BamHI site. This plasmid (FIG. 12), which contains the 814-bp ClaI-HindIII fragment (in which only open reading frame 1 is complete) complements only mutant SC510:1630 Rif$^r$. This suffices to define a new gene, since this mutant is complemented by a plasmid which only contains the complete open reading frame 1. Open reading frame 1 corresponds to a gene of the pathway of biosynthesis of cobalamins and/or cobamides. This gene is designated cobE. The absence of complementation of mutant SC510: 1631 Rif$^r$ by plasmid pXL545Ω is possibly due to the fact that the cobA, cobB, cobC, cobD and cobE genes, or a part of them, belong to the same operon, and that the insertion in cobE which preserves a transcription in the direction of transcription of the operon may be complemented only by trans expression of the cobE gene. In contrast, mutant SC510:1631 Rif$^r$, for its part, can be complemented only by a plasmid which permits trans expression of the cobA to cobE genes.

The 5.4-kb ClaI-HindIII-HindIII-HindIII fragment hence contains five cob genes designated cobA, cobB, cobC, cobD and cobE.

4.2—Genetic Studies of the 8.7-kb Fragment

Plasmid pXL367 is pRK290 (Ditta et al., 1980) containing the 8.7-kb EcoRI fragment cloned at the EcoRI site (FIG. 13).

Insertions of transposon Tn5 into plasmid pXL367 were selected using the technique already described (de Bruijn and Lupski, 1984). The insertions in the 8.7-kb fragment were mapped. In the same manner, insertions of transposon Tn3lacZ were obtained according to the method already described (Stachel et al., 1985) and mapped. 29 insertions of transposon Tn5 and 13 insertions of transposon Tn3lacZ were thus mapped. The precise position of these insertions in the 8.7-kb fragment is given in FIG. 14. Plasmids each carrying a single insertion in the 8.7-kb fragment were introduced by conjugative transfers into the Cob mutants of *Agrobacterium tumefaciens* G164, G609, G610, G611, G612, G613, G614, G615, G616, G620 and G638. These mutants are all complemented by pXL367. Insertions which no longer permit the complementation of the different mutants were sought. They correspond to an insertion in the gene responsible for complementation of the corresponding mutant. The results of the complementations of the different mutants for their character of production of cobalamins (Cob phenotype) are given in FIG. 14. If the recombinant mutant produces less than threefold less cobalamins than are produced by the same mutant with plasmid pXL367, it is considered to be non-complemented. Of the mutants studied, G164, G609, G610, G611, G612, G613, G614, G615, G616, G620 and G638, eight different classes of inactivating insertions of transposons leading to a mutated phenotype are observed. These classes characterise insertions by the absence of complementation of one or more mutants by plasmids pXL367 carrying these same insertions. Each class hence corresponds to a mutated gene. It is observed that the insertions belonging to the same class are positioned beside one another. Eight classes of insertions are thus observed, which enable eight genes to be defined. Each class of insertions defines a minimum fragment which must be contained in the corresponding gene. FIG. 14 demonstrates a perfect correlation between the regions bounded by each class, in respect of the restriction map, and the open reading frames described above (Example 3). It is found, in effect, that, for each class of insertions, the transposons are always inserted in a portion of the 8.7-kb fragment which is contained in a single open reading frame. Each class of insertions is hence associated with one, and only one, open reading frame. The open reading frames indicated above hence each code for a protein involved in the pathway of biosynthesis of cobalamins and/or cobamides. The open reading frames each correspond to genes involved in the biosynthesis of cobalamins and/or cobamides. These open reading frames are referred to as cobF, cobG, cobH, cobI, cobJ, cobK, cobL and cobM for frames 6 to 13, respectively. The position of these genes relative to the restriction map is shown in FIG. 14.

4.3—Genetic Study of the 4.8-kb Sragment

Plasmid pXL1558 is plasmid pRK290 (Ditta et al., 1980) containing the 12-kb HindIII-HindIII fragment of pXL154 (Cameron et al., 1989) cloned at the EcoRI site of pRK290 (FIG. 36). The construction of the other plasmids used in this study (pXL233 and pXL843) is described in the legend to FIG. 36.

Tn5Sp insertions were obtained in plasmid pXL1558. First, a strain containing a transposon Tn5Sp was constructed; this was done by transforming strain C2110 (Stachel et al., 1985) using plasmid pRK2013Tn5Sp (Blanche et al., 1989); since it has a ColE1 origin of replication, plasmid pRK2013Tn5Sp does not replicate in strain C2110, which is polA-. The colonies obtained after transformation, which are resistant to spectinomycin, hence have transposon Tn5Sp in their chromosome; a colony is then reisolated, after which the insertion of the transposon is then transduced using phage P1 in strain MC1060 as described previously (Miller, 1972). Strain MC1060 Tn5Sp is transformed with plasmid pXL1558; plasmid pXL1558 is then mobilised by conjugation using pRK2013 in C600. Rif$^r$. Conjugants resistant to tetracycline (for plasmid pXL1558) and to spectinomycin (for the transposon) are then selected. Such conjugants must contain plasmid pXL1558 in which transposon Tn5Sp has been inserted. Insertions carried in plasmid pXL1558, and more precisely in the 12-kb fragment, are then mapped by restriction digestion; 23 insertions are thereby obtained and mapped on the 12-kb fragment; the position of these different insertions in the fragment is presented in FIG. 37. These 23 insertions were introduced into the chromosome of strain SC510 Rif$^r$ after conjugative transfer of p-XL1558::Tn5Sp, followed by introduction of plasmid pR751. Plasmid pR751 is a trimethoprim-resistant plasmid of the same incompatibility group as pXL1558 (incP, Thomas and Smith, 1987). By culturing non-selectively for pXL1558 (absence of tetracycline) but selectively for pR751 and the transposon (presence of trimethoprim and of spectinomycin), the exchange of the mutation carried by pXL1558::Tn5Sp with the chromosome and also the segregation of pXL1558 are obtained by the technique of marker exchange by double homologous recombination, as already described (Schell et al., 1988). The strains thereby selected carry the transposon in their chromosome. The double homologous recombination is verified by Southern's method (Southern, 1975). In this way, 23 SC510 Rif$^r$::Tn5Sp strains in the 12-kb fragment were identified.

Furthermore, another Tn5Sp insertion obtained by random mutagenesis of transposon Tn5Sp in strain SBL27 Rif$^r$ (Blanche et al., 1989) was mapped on the 12-kb fragment by restriction analysis according to Southern's method (Southern, 1975), see FIG. 37; this strain is designated SBL27 Rif$^r$::Tn5Sp 1480.

The level of cobalamin synthesis is determined for these 24 strains cultured in PS4 medium according to the protocol already described (Cameron et al., 1989), and the Cob- phenotype is assigned to strains producing at least 1000 (or 100) times less vitamin $B_{12}$ than the parent strain SC510 Rif$^r$ (or SBL27 Rif$^r$), FIG. 37. It is thus observed that 6 of these chromosomal insertions lead to a Cob- phenotype in *P. denitrificans*; they are the insertions 31.1, 41.3, 45, 55, 22.1 and 1480.

Three plasmids pxL233, pXL837 (Cameron et al.) and pXL843 are introduced by conjugative transfers into three strains possessing the Cob- phenotype, namely SC510 Rif$^r$::Tn5Sp 31.1, SC510 Rif$^r$::Tn5Sp 45 and SBL27 Rif$^r$::Tn5Sp 1480. These three mutants each have a different complementation profile for cobalamine synthesis. In effect, SBL27 Rif$^r$::Tn5Sp 1480 is complemented by pXL837 and pXL843 but not by pXL233; the mutant SC510 Rif$^r$::Tn5Sp 45 is complemented only by pXL843; the mutant SC510 Rif$^r$::Tn5Sp 31.1 is complemented by plasmid pXL843 and also by plasmid pXL233 (see FIG. 37). The data presented hence enable it to be concluded, on the basis of the results of the complementations of the three mutants, that the three mutants are different and that, for each of them, transposon Tn5Sp has been inserted into a different cob gene.

Furthermore, plasmids pXL1558::Tn5Sp 41.3, pXL1558::Tn5Sp 45 and pXL1558::Tn5Sp 22.1 are introduced by conjugative transfers into strain G2035 (Cameron et al., 1989), and do not complement it. Plasmid pXL1558 complements this mutant, in contrast to plasmid pXL1558::Tn5Sp 31.1.

The phenotype and complementation data enable us to define 3 classes of insertions; each of these classes is represented by the following insertions: 31.1, class 1; 45, 41.3, 55 and 22.1, class 2; 1480, class 3.

For each class of insertions, the transposons are always inserted in a portion of the 4.8-kb fragment which is contained in a single open reading frame (ORF14, ORF16 and ORF17, as defined in Example 3). Each class of insertions is associated with a single open reading frame. The open reading frames indicated above hence code for a protein involved in the pathway of biosynthesis of cobalamins and/or cobinamides. These open reading frames are referred to as cobX, cobS and cobT for frames 14, 16 and 17. The position of these genes relative to the restriction map is shown in FIG. 37. Open reading frame 15 is not a gene involved in the biosynthesis of coenzyme $B_{12}$.

4.4—Genetic Studies of the 3.9-kb Fragment

Plasmid pXL1557 is plasmid pRK290 (Ditta et al., 1980) containing the 9-kb HindIII-BamHI fragment of pXL519 cloned at the EcoRI site of pRK290 (FIG. 38). The construction of the other plasmids used in this study (pXL1286, pXL1303, pXL1324) is described in the legend to FIG. 38. Moreover, the 2-kb BglII-XhoI fragment (positions in the sequence presented in FIG. 33: 251 and 2234) of plasmid pXL519 is cloned at the BamHI-SalI sites of plasmid pXL435 (Cameron et al) to generate plasmid pXL699.

Tn5Sp insertions were obtained in plasmid pXL1557 according to the technique described in Example 4.3. Insertions of transposon Tn5Sp into plasmid pXL1557, then designated pXL1557::Tn5Sp, were selected. Those which are mapped in the 9-kb fragment (FIG. 39) were introduced into the chromosome of strain SC510 Rif$^r$ after conjugative transfer of pXL1557::Tn5Sp and marker exchange by double homologous recombination as described in 4.3.

The double homologous recombination is verified by Southern's method (Southern, 1975). In this way, 20 SC510 Rif$^r$::Tn5Sp strains were identified.

Furthermore, two other Tn5Sp insertions obtained by random mutagenesis of transposon Tn5Sp in strain SBL27 Rif$^r$ (Blanche et al., 1989) were mapped on the 9-kb fragment by restriction analysis according to Southern's method (Southern, 1975), see the insertions 1003 and 1147 in FIG. 39.

The level of cobalamin synthesis is determined for these 22 strains cultured in PS4 medium according to the protocol already described (Cameron et al., 1989), and the Cob- phenotype is assigned to strains producing 1000 (or 100) times less vitamin $B_{12}$ than the parent strain SC510 Rif$^r$ (or SBL27 Rif$^r$), FIG. 39. Only the 4 insertions 1, 1003, 23 and 1147 result in a Cob- phenotype in *P. denitrificans*.

Four plasmids pXL699, pXL1286, pXL1303 and pXL1324 are introduced by conjugative transfers into the four strains possessing the cob- phenotype, namely SC510 Rif$^r$::Tn5Sp 1, SBL27 Rif$^r$::Tn5Sp 1003, SC510 Rif$^r$::Tn5Sp 23 and SBL27 Rif$^r$::Tn5Sp 1147. Plasmid pXL699 complements the first two mutants (SC510 Rif$^r$::Tn5Sp 1, SBL27 Rif$^r$::Tn5Sp 1003), but plasmid pXL1303 does not complement them, plasmid pXL1324 complements the other two mutants (SC510 Rif$^r$::Tn5Sp 23 and SBL27 Rif$^r$::Tn5Sp 1147) but plasmid pXL1286 does not complement them.

Furthermore, plasmid pXL1557::Tn5Sp 1, is introduced by conjugative transfer into strain G2040, and does not complement it, whereas plasmids pXL1557, pXL1557::Tn5Sp 6A, pXL1557::Tn5Sp 54, pXL1557::Tn5Sp 48, pXL1557::Tn5Sp 21, pXL1557::Tn5Sp 8, pXL1557::Tn5Sp 23, also introduced by conjugative transfers, complement it (see FIG. 39).

The phenotype and complementation data enable 2 classes of insertions to be defined. For each class of insertions, the transposons are always inserted in a portion of the 3.9-kb fragment which is contained in a single open reading frame (ORF19 and ORF20 as defined in Example 3).

Each class of insertions is associated with a single open reading frame. The open reading frames indicated above code for a protein involved in the pathway of biosynthesis of cobalamins and/or cobinamides. These open reading frames are referred to as cobV and cobU for frames 19 and 20. Frames 18 and 21 are not genes involved in the pathway of biosynthesis of coenzyme $B_{12}$. The position of these genes relative to the restriction map is shown in FIG. 39. The insertions 48, 21 and 8 are mapped between the cobU and cobV genes.

4.5—Genetic Studies of the 13.4-kb Fragment 4.5.1. Studies on the 4327-bp EcoRI-BglII Fragment.

Plasmid pXL189 (Cameron et al., 1989), which contains at least one cob gene, carries a 3.1-kb insert which, except for 300 bp, corresponds to a 4.26-kb EcoRI-ClaI fragment (see FIG. 45). pXL189 was subjected to a mutagenesis with transposon Tn5, as described previously (De Bruijn and Lupski (1984)). 13 insertions were thereby mapped in the insert of pXL189, as presented in FIG. 46. These 13 mutant plasmids, as well as pXL189, were conjugated in two *A. tumefaciens* mutants, G632 and G633, which are mutants complemented by pXL189 (Cameron et al., 1989). Only the insertion 58 proved to be an inactivating insertion. This result shows that the two mutants G632 and G633 correspond to a mutation in the same gene, and that, moreover, the only gene of *P. denitrificans* which could be responsible for their complementation corresponds to open reading frame 26 (see FIG. 46), since insertion 58 is mapped in this open reading frame; in addition, it is the only insertion of the 13 which is mapped in this open reading frame. A cob gene, designated cobO, is hence associated with open reading frame 26.

To know whether the four open reading frames (open reading frames 27 to 30) identified in this fragment correspond to cob genes, a spectinomycin resistance cassette from plasmid pHP45Ω (Prentki and Krisch, 1984) was specifically inserted into each of these genes, and then introduced into the chromosome of *P. denitrificans* SC510 $Rif^r$ by homologous recombination so as to obtain mutants of insertions in each of these open reading frames. For this purpose, the EcoRI-ClaI fragment (respective positions 8818 and 13082 in the sequence presented in FIG. 43) was used. This fragment, which carries the open reading frames 27 to 30, was purified from pXL157 (Cameron et al., 1989); an EcoRI linker was added to the ClaI end after the latter had been filled in with the Klenow fragment of *E. coli* DNA polymerase. This fragment was then cloned into plasmid pUC13 (Viera et al., 1982) at the EcoRI site. The plasmid thus constructed was referred to as pXL332. Insertions of the spectinomycin resistance cassette from plasmid pHP45n (Prentki and Krisch, 1984) were carried out on pXL332. These insertions were done separately at the SmaI (position 9868, open reading frame 27), BamHI (position 10664, open reading frame 28), ClaI (position 11687, open reading frame 29) and NcoI (position 12474, open reading frame 30) sites by total or partial digestions of pXL332 with the corresponding enzymes, and then, if necessary, filling-in of these ends with the Klenow fragment of *E. coli* DNA polymerase, followed by ligation with the 2-kb SmaI fragment of pHP45Ω (Prentki and Krisch, 1984) containing a spectinomycin resistance gene; these insertions are designated Ω2, Ω1, Ω3 and Ω4, respectively, as presented in FIG. 46. The EcoRI fragments carrying these different insertions were then cloned into pRK404 (Ditta et al., 1985) at one of the two EcoRI sites. The 4 plasmids carrying these different insertions were then introduced by conjugation in SC510 $Rif^r$, as described above. Plasmid pR751 (Thomas and Smith, 1987) was then introduced into the transconjugants. The exchange of mutations carried by the 4 different derivatives of pRK404 and the chromosome of SC510 $Rif^r$ could be selected as described (see Example 4.3). 4 strains were thereby obtained. These strains each carry an insertion of the resistance cassette in one of the four open reading frames 27 to 30. These insertions were verified by analysis of the genomic DNA by Southern blotting (Southern, 1975). The cobalamin production of these different strains was studied. They all showed a Cob+ phenotype on culturing in PS4 medium. This result indicates that these four open reading frames do not participate in the biosynthesis of coenzyme $B_{12}$. However, it is possible that one or more of these frames code for proteins which participate, e.g., in the conversion of coenzyme $B_{12}$ to methylcobalamin for example, i.e. the synthesis of another cobalamin or even of another corrinoid.

4.5.2. Study of the 9.1-kb EcoRI-EcoRI Fragment.

Various plasmids are used in this study; plasmid pXL1560 is plasmid pRK290 (Ditta et al., 1980) containing the 9.1-kb EcoRI-EcoRI fragment of pXL156 (Example 1) cloned at the EcoRI site of pRK290 (see FIG. 46). The construction of the other plasmids used in this study (pXL618, pXL593, pXL623, pXL1909, pXL1938, pXL1908, pXL221, pXL208, pXL297) is described in the legend to FIG. 45.

Tn5Sp insertions were obtained in plasmid pXL1560. Strain MC1060 Tn5Sp transformed with plasmid pXL1560 was used to obtain insertions of transposon Tn5Sp into the pXL1560 fragment; 27 insertions were thereby obtained and mapped on the 9.1-kb fragment; the position of these different insertions in the fragment is presented in FIG. 4. These 27 insertions were introduced into the chromosome of strain SC510 $Rif^r$ after conjugated transfer of pXL1560::Tn5Sp, followed by introduction of plasmid pR751. Plasmid pR751 is a trimethoprim-resistant plasmid of the same incompatibility group as pXL1560 (incP, Thomas and Smith, 1987). By culturing non-selectively for pXL1560 (absence of tetracycline) but selectively for pR751 and the transposon (presence of trimethoprim and of spectinomycin), the exchange of the mutation carried by pXL1560::Tn5Sp with the chromosome and also the segregation of pXL1560 are obtained; this technique of marker exchange by double homologous recombination is equivalent to that already described by Schell et al., 1988. The strains thus selected carry the transposon in their chromosome.

The double homologous recombination is verified by Southern's method (Southern, 1975). In this way, 27 SC510 $Rif^r$::Tn5Sp strains each possessing a different insertion of transposon Tn5Sp in the 9.1-kb fragment were identified.

The level of cobalamin synthesis is determined for these 27 strains cultured in PS4 medium, and the Cob-phenotype is assigned to strains producing at least 1000 times less vitamin $B_{12}$ than the parent strain SC510 $Rif^r$, FIG. 46. It is thus observed that 18 out of the 27 of these chromosomal insertions lead to a Cob- phenotype in *P. denitrificans*, as shown in FIG. 46.

The insertions 19, 32, 24, 27, 37, 39, 26, 11 and 14 are mapped in open reading frame 22 (see FIG. 46). All these insertions are complemented by plasmid pXL618, which contains only open reading frame 22. We deduce from this that open reading frame 22 corresponds to a cob gene, which we referred to as cobO. No insertion was obtained in open reading frame 23; however, plasmid pXL623, which contains only this open reading frame (see FIG. 46), complements two cob mutants of *Agrobacterium tumefaciens*, G642 and G2043 (Cameron et al., 1989). Open reading frame 23 hence corresponds to a cob gene designated cobP. The insertions 23, 13, 12, 30, 22, 40, 35, 10 and 17 which are mapped in open reading frames 24 and 25 lead to a Cob- phenotype in SC510 $Rif^r$. There hence appear to be two open reading frames whose product is involved in the biosynthesis of cobalamins. However, it cannot be ruled out that these insertions have polar effects on the genes positioned on the 3' side, such as cobO. It is hence appropriate to study the complementation of these mutants in order to determine whether the Cob- phenotype does not result from a polar effect.

The Cob mutants of *Agrobacterium tumefaciens*, G622, G623 and G630, complemented by pXL156, were studied. These mutants are not complemented by plasmid pXL189 (Cameron et al., 1989), which contains cobO as the only cob gene. In contrast, they are complemented by plasmid pXL1908, which contains cobO and open reading frame 25 in addition to the open reading frames 27 to 30 (see FIG. 45). The latter frames cannot be responsible for the complementation of these mutants, since the proteins for which they code do not participate in the coenzyme $B_{12}$ pathway. Hence, the observed complementations can only result from open reading frame 25. In addition, the SC510 Rif$^r$ Tn5Sp mutants mapped in this same open reading frame (these are the mutants 22, 40, 35, 10 and 17) are complemented by plasmid pXL1908, see FIG. 46, (carrying cobO and frame 25), whereas at least two of them are not complemented by pXL189, which contains only cobO as a cob gene. These results show clearly that open reading frame 25 is a cob gene; this cob gene is designated cobN.

The SC510 Rif$^r$ Tn5Sp mutants 23, 13 and 12, which have the Cob- phenotype, are mapped in open reading frame 24. These mutants are not complemented by plasmid pXL623, which contains only the cobP gene. In contrast, these mutants are complemented by plasmid pXL593 which contains cobP and open reading frame 24, thereby indicating that open reading frame 24 is responsible for their complementation. Open reading frame 24 is hence a cob gene, which is designated cobW.

EXAMPLE 5

Genes and Proteins

5.1—5.4-kb Fragment

Five genes (cobA, cobB, cobC, cobD and cobE) are hence defined on the 5.4-kb ClaI-HindIII-HindIII-HindIII fragment. They code, respectively, for the following COB proteins: COBA, COBB, COBC, COBD and COBE. The coding portions of the genes (cobA to cobE) are described in FIG. 15, as well as the sequences of the COBA to COBE proteins. Properties of each of these proteins are also presented (amino acid composition, isoelectric point, index of polarity and hydrophilicity profile).

5.2—8.7-kb Fragment

Eight genes are hence defined on the 8.7-kb fragment. These cobF to cobM genes code, respectively, for the following COB proteins: COBF, COBG, COBH, COBI, COBJ, COBK, COBL, and COBM. The coding portions of the genes (cobF to cobM) are described in FIG. 16, as well as the sequences of the COBF to COBM proteins. Properties of each of these proteins are also presented (amino acid composition, molecular weight, isoelectric point, index of polarity and hydrophilicity profile).

5.3—4.8-kb Fragment

Three genes (cobX, cobS, cobT) are defined on the 4.8-kb SalI-SalI-SalI-SalI-SalI-BglI fragment. They code, respectively, for the following proteins: COBX, COBS and COBT. The coding portions of these genes are described in FIG. 40, as well as the sequences of the COBX, COBS and COBT proteins. Arbitrarily, the ATG at position 1512 of cobS has been chosen as the initiation codon, rather than that located at position 1485 (see FIG. 32). Properties of each of these proteins are also shown (amino acid composition, isoelectric point, index of polarity and hydrophobicity profile). COBT possesses a hydrophilic pocket corresponding to amino acids 214 to 305.

5.4—3.9-kb Fragment

Two genes (cobU and cobV) are defined on the 3.9-kb SstI-SstI-BamHI fragment. They code, respectively, for the following proteins: COBU and COBV. The coding portions of these genes are described in FIG. 41, as well as the sequences of the COBU to COBV proteins. Properties of each of these proteins is also shown (amino acid composition, isoelectric point, index of polarity and hydrophobicity profile).

5.5—13.4-kb Fragment

Five cob genes are defined on the 13.4-kb fragment (cobO, cobP, cobW, cobN and cobO and cobV). They code, respectively, for the following proteins: COBQ, COBP, COBW, COBN and COBO. The coding portions of these genes (cobQ, cobP, cobW, cobN and cobO) are described in FIG. 46, as well as the sequences of COBQ, COBP, COBW, COBN and COBO proteins. Properties of each of these proteins are also shown (amino acid composition, isoelectric point, index of polarity and hydrophobicity profile).

From the hydrophilicity profiles, which were produced according to the programmes of Hopp and Woods (1981), all the COB proteins with the exception of COBV are probably soluble proteins, as opposed to membrane proteins, since the absence of large hydrophobic domains is noted. COBV is either a membrane protein, since 4 long hydrophobic domains are noted (see FIG. 41), or a cytoplasmic protein having large hydrophobic domains.

For all the amino acid sequences of the COB proteins, a methionine is indicated as the first amino acid at the $NH_2$-terminal position. It is understood that this methionine may be excised in vivo (Ben Bassat and Bauer, 1984). Rules relating to the in vivo excision of $NH_2$-terminal methionine by methionine aminopeptidase are known to have been proposed. (Hirel et al., 1989).

Moreover, these protein sequences were compared with the Genpro proteins, Genpro being a Genbank protein extraction (version 59) augmented by putative coding portions larger than 200 amino acids, according to the programme of Kanehisa (1984). No significant homology could be demonstrated with the parameters used on Genbank version 59, except for COBT. In effect, the COBT protein possesses a "core of acidic amino acids" between (amino acid) positions 224 and 293 (see FIG. 40); in this portion of the protein, more than one amino acid out of 2 is a glutamic or aspartic acid residue; this core of acidic amino acids renders the protein homologous over this region, according to the programme of Kanehisa (1984), with other proteins also having such an acidic core. The most homologous proteins are: GARP protein of Plasmodium falciparum (Triglia et al., 1988), rat cardiac troponin T (Jin and Lin, 1989), human and rat prothymosin (Eschenfeld and Berger, 1986), an androgen-dependent rat protein that binds to spermine (Chang et al., 1987), and the human, rat and chicken "mid-size neurofilament subunit", proteins (Myers et al., 1987, Levy et al., 1987, Zopf et al., 1987). The function of these cores rich in acidic residues is unknown; however, this acidic core should either permit the binding of metal cations such as $Co^{++}$, which would give the COBT protein the role of a cobalt metallothionein, or else permit interactions with other proteins.

EXAMPLE 6

Enzymatic Studies

6.1—Identification of COB Proteins and Their Genes From Purified Enzymatic Activities This example describes how, from a purified protein, after its $NH_2$-terminal sequence has been established, it is possible to find the corresponding structural gene among sequenced cob genes.

6.1.1. Identification of the COBA Protein Encoded by the cobA Gene

The purification of *Pseudomonas denitrificans* SUMT has been described (F. Blanche et al., 1989). The $NH_2$-terminal sequence of the protein thus purified could be determined according to the technique described above. The first ten amino acids were identified:

1 2 3 4 5 6 7 8 9 10

Met Ile Asp Asp Leu Phe Ala Gly Leu Pro (amino acids 1–10 of SEQ ID NO: 4)

The $NH_2$ terminal sequence of the COBA protein (FIG. 15) corresponds exactly to this sequence. The molecular weight of the purified SUMT, estimated by 12.5% SDS-PAGE electrophoresis, is 30,000. The COBA protein has a molecular weight deduced from its sequence of 29,234 (FIG. 15). The correspondences between the $NH_2$-terminal sequences and the molecular weights indicate clearly that the COBA protein corresponds to SUMT. The cobA gene is the SUMT structural gene.

6.1.2. Identification of the COBB Protein Encoded by the cobB Gene a) Assay of Cobyrinic Acid a,c-Diamide Synthase Activity This example illustrates the assay of an activity of the pathway of biosynthesis of corrinoids which has never yet been described. The enzyme in question is cobyrinic acid a,c-diamide synthase (CADAS), which catalyses the amidation of two carboxylic acid functions of the corrin or decobalt-ocorrin ring-system at positions a and c (FIG. 17). The donor of the $NH_2$ group is L-glutamine, and the reaction consumes 1 molecule of ATP per amidation of each carboxylic acid function. The assay which is described below applies to the diamidation reaction of cobyrinic acid; with a few modifications (detection in HPLC at 330 nm in particular), it applies to the diamidation reaction of hydrogenobyrinic acid.

The incubation mixture (0.1 M Tris-HCl pH 8 (250 $\mu$l)) containing ATP (1 mM), $MgCl_2$ (2.5 mM), glut-amine (100 $\mu$m), cobyrinic acid (50 $\mu$M) or hydrogeno-byrinic acid (50 $\mu$M) and cobyrinic a,c-diamide synthase (approximately 1 unit of activity) is incubated for 1 hour at 30° C. At the end of the incubation, an aqueous solution (125 $\mu$l) of KCN (2.6 g/l) and 0.2 M HCl (125 $\mu$l) are added to the mixture, which is then heated to 80° C. for 10 minutes and thereafter centri-fuged for 5 minutes at 5,000 g. An aliquot (50 $\mu$l) of the centrifugation supernatant is analysed in HPLC. It is injected onto a 25-cm Nucleosil 5-$C_{18}$ column and eluted with a gradient from 0 to 100% of buffer B in A in the course of 30 minutes; buffer A: 0.1 M potassium phosphate pH 6.5, 10 mM KCN; buffer B: 0.1 M potassium phosphate pH 8, 10 mM KCN/acetonitrile (1:1). The corr-inoids are detected by means of their UV absorption at 371 nm. The unit of enzymatic activity is defined as the quantity of enzyme necessary for synthesising 1 nmol of amide groups per hour under the conditions described.

b) Purification of *Pseudomonas denitrificans* Cobyrinic Acid a,c-Diamide Synthase Activity This experiment illustrates how a *Pseudomonas denitrificans* protein participating in the pathway of biosynthesis of cobalamins may be purified.

Using the assay described in Example 6.1.2a), the purification of *Pseudomonas denitrificans* cobyrinic acid a,c-diamide synthase is carried out as described below.

In a typical purification experiment, wet cells (7 g) of strain SC 510 $Rif^r$, into which plasmid pXL1500 has been introduced (see Example 4.1. for the description of pXL1500, as well as FIG. 12), are suspended in 0.1 M Tris-HCl pH 7.7 (30 ml) and sonicated for 15 minutes at 4° C. The crude extract is then recovered by centrifugation for 1 hour at 50,000 g, and a portion (10 ml) of this extract is injected onto a Mono Q HR 10/10 column equilibrated with the same buffer. The proteins are eluted with a linear KCl gradient (0 to 0.5 M). The fractions containing the enzymatic activity (demonstrated by means of the test described in Example 6.2b)) are combined and . concentrated to 2.5 ml. After dilution with 25 mM Tris-HCl pH 7.7 (1 ml), the proteins are fractionated on a Mono Q HR 5/5 using the above KCl gradient (0 to 0.5 M). The active fractions are combined, and 0.1 M Tris-HCl pH 7.7 (1 ml) containing 1.7 M ammonium sulphate is added to the sample, which is then chromatographed on a Phenyl-Superose (Pharmacia) column with a decreasing ammonium sulphate gradient (1.0 M to 0 M). The fractions containing the desired activity are combined and chromatographed on a Bio-Gel HPHT (Bio-Rad) column with a potassium phosphate gradient (0 to 0.35 M).

After this step, the enzyme is more than 95% pure. It shows no contaminant protein in SDS-PAGE. The purity of the protein is confirmed by the uniqueness of the $NH_2$-terminal sequence. Its molecular weight in this technique is 45,000. The different steps of purification of CADAS, with their purification factor and their yield, are given in the table below.

TABLE

Purification of CADAS

| Purification step | Vol (ml) | Proteins (mg) | Sp.activity (u/mg of proteins) | Yield | Purification factor[1] |
|---|---|---|---|---|---|
| Crude extract | 10 | 200 | 8.5 | — | — |
| MonoQ 10/10 | 12 | 15.1 | 108 | 96 | 12.7 |
| MonoQ 5/5 | 3 | 3.75 | 272 | 60 | 32 |
| Phenyl-Superose | 1 | 0.865 | 850 | 43 | 100 |
| Bio-Gel HPHT | 2 | 0.451 | 1320 | 35 | 155 |

[1]This factor is calculated from the increase in the specific activity of the fractions during the purification.

c) $NH_2$-Terminal Sequence of *Pseudomonas denitrificans* Cobyrinic Acid a,c-Diamide Synthase and Identification of the *Pseudomonas denitrificans* Structural Gene Coding for This Activity This example illustrates how the $NH_2$-terminal sequence of a protein which participates in the pathway of biosynthesis of cobalamins enables the structural gene which codes for this protein to be identified.

The $NH_2$-terminal sequence of *Pseudomonas denitrificans* cobyrinic acid a,c-diamide synthase, purified as described in Example 6.1.2b), was determined as described above. 15 residues were identified:

1 2 3 4 5 6 7 8 9 10 11 12 13 14 15

Ser Gly Leu Leu Ile Ala Ala Pro Ala Ser Gly Ser Gly Lys Thr (amino acids 2–15 of SEQ ID NO: 6)

The $NH_2$-terminal sequence of the COBB protein (FIG. 15) corresponds exactly to this sequence except that, in the sequence presented in FIG. 15, a methionine precedes the peptide sequence determined by direct sequencing. It follows from this that the amino-terminal methionine is definitely excised in vivo by methionine aminopeptidase (Ben Bassat and Bauer, 1987). The molecular weight of the purified CADAS, estimated by 12.5% SDS-PAGE electrophoresis, is 45,000. The COBB protein has a molecular weight deduced from its sequence of 45,676 (FIG. 15).

The correspondences between the $NH_2$-terminal sequences and the molecular weights indicate clearly that the COBB protein corresponds to CADAS. The cobB gene is the CADAS structural gene.

6.1.3. Identification of the COBI Protein Encoded by the cobI Gene a) Assay of an S-Adenosyl-L-methionine:precorrin-2 Methyltransferase Activity This example illustrates the assay of an enzymatic activity of the pathway of biosynthesis of corrinoids which has never yet been described. The enzyme in question is S-adenosyl-L-methionine: precorrin-2 methyltransferase ($SP_2MT$), which catalyses the transfer of a methyl group from S-adenosyl-L-methionine (SAM) to precorrin-2 to give precorrin-3 (FIG. 18). Factors II and III, oxidation products of precorrin-2 and precorrin-3, respectively, have already been purified from cell extracts of *Propionibacterium shermanii* (Battersby and MacDonald, 1982, Scott et al., 1984); precorrin-2 and precorrin-3 are recognised as presumed intermediates of coenzyme $B_{12}$ biosynthesis, but they have never been purified as such. For this reason, the corresponding activity has never been either assayed or purified beforehand. The substrate of the enzymatic reaction, precorrin-2, is a very labile molecule which it is not possible to store, since it oxidises spontaneously in the presence of even infinitesimal traces of oxygen (Battersby and MacDonald, 1982). The principle of this enzymatic test hence lies in the possibility of generating precorrin-2 from SAM and δ-aminolevulinic acid at the required moment using an enzymatic extract of strain SC510 $Rif^r$ into which plasmid pXL1500 has been introduced. The incubation must be performed under strictly anaerobic conditions.

The fractions containing $SP_2MT$ are incubated in 0.1 M Tris-HCl pH 7.7 (1 ml) in the presence of 5 mM DTT, 1 mM EDTA, 100 μM [methyl-$^3$H]SAM (1 μCi), 0.8 mM δ-aminolevulinic acid and crude enzyme extract (6 mg) of *Pseudomonas denitrificans* strain SC510 $Rif^r$ pXL1500 for 3 hours at 30° C. Strain SC510 $Rif^r$ pXL1500 contains a strong SUMT activity (F. Blanche et al., 1989). The tetrapyrrole compounds produced during the incubation are bound to a DEAE-Sephadex anion exchange column and esterified in methanol containing 5% of sulphuric acid in the absence of oxygen. The dimethylated and trimethylated derivatives of uro'gen III are then separated by thin-layer chromatography on silica using dichloromethane/methanol (98.3:1.7) as an eluent system (F. Blanche et al., 1989). The $SP_2MT$ activity is expressed as the ratio of the quantity of trimethylated derivatives obtained to the total of (di- and tri-) methylated derivatives produced, referred to the quantity of protein. The SC510 $Rif^r$ pXL1500 extract introduced in the test does not display detectable $SP_2MT$ activity under the assay conditions (the ratio of precorrin-3 produced to precorrin-2 produced during the test is less than 0.05).

b) Purification of *Pseudomonas denitrificans* S-Adenosyl-L-methionine:precorrin-2 Methyltransferase This experiment illustrates how a *Pseudomonas denitrificans* protein participating in the pathway of biosynthesis of cobalamins may be purified when an assay for the activity in question exists.

The protein is purified from SC510 $Rif^r$ cells containing plasmid pXL253. This is plasmid pKT230 into which the 8.7-kb EcoRI fragment has been inserted (FIG. 13). In a typical purification experiment, wet cells (50 g) of strain SC150 $Rif^r$ into which plasmid pXL253 has been introduced are suspended in 0.1 M potassium phosphate pH 7.7, 5 mM DTT (250 ml) and sonicated for 15 minutes at 4° C. After centrifugation at 50,000 g for 1 hour, the supernatant is passed through a DEAE-Sephadex column (10 ml of gel) to remove the tetrapyrrole compounds. The pH of the crude extract thereby obtained is adjusted to pH 7.7 with 0.1 M KOH. The proteins precipitating at between 33% and 45% ammonium sulphate saturation are collected and dissolved in 0.1 M Tris-HCl pH 7.7, 5 mM DTT (40 ml). This solution is passed through a Sephadex G-25 column eluted with 10 mM Tris-HCl pH 7.7, 5 mM DTT, and the proteins collected are injected onto a DEAE-Trisacryl-M column. The proteins are eluted with a linear gradient of 0 to 0.25 M KC1, and the fractions containing the $SP_2MT$ activity are combined and passed a second time through a Sephadex G-25 column as above. The protein fraction is injected onto an Ultrogel HA (IBF) column equilibrated in 10 mM Tris-HCl pH 7.7, 5 mM DTT. The proteins are eluted with a linear gradient of 0 to 50 mM potassium phosphate pH 7.8 containing 5 mM DTT. The fractions containing the desired activity are combined and injected onto a MonoQ HR 5/5 (Pharmacia) column equilibrated with 50 mM Tris-HCl pH 7.7, 5 mM DTT. The $SP_2MT$ is eluted with a linear gradient (0 to 0.25 M) of KCl. At emergence from the MonoQ step, 12.5% SDS-PAGE electrophoresis with staining with silver salts reveals the enzyme is more than 99% pure. This is confirmed by the uniqueness of the $NH_2$-terminal sequence of the protein. The molecular weight calculated from the electrophoresis under denaturing conditions (12.5% SDS-PAGE) is 26,500. The steps of purification of $SP_2MT$ with their yields are described in the table below.

TABLE

Purification of $SP_2MT$

| Purification step | Vol (ml) | Proteins (mg) | Purification factor[1] |
|---|---|---|---|
| Crude extract | 300 | 6000 | — |
| Precipitation (33–45%) | 40 | 1530 | 3.9 |
| DEAE-Tris-acryl-M | 57 | 355 | 16.9 |
| Ultrogel HA | 30 | 71 | 85 |
| MonoQ HR 5/5 | 12 | 33.5 | 179 |

[1]This factor is calculated from the yield of protein.

c) $NH_2$-Terminal Sequence of $SP_2MT$ and Identification of the Structural Gene Coding for This Activity This example illustrates how the $NH_2$-terminal sequence of a protein participating in the biosynthetic pathway enables the structural gene which codes for this protein to be identified. In the present example, the structural gene in question is that for $SP_2MT$.

The $NH_2$-terminal sequence of the purified protein was determined as described above. The first 15 amino acids were identified:

1 2 3 4 5 6 7 8 9 10 11 12 13 14 15

Ser Gly Val Gly Val Gly Arg Leu Ile Gly Val Gly Thr Gly Pro (amino acids 2–16 of SEQ ID NO: 20)

The $NH_2$-terminal sequence of the COBI protein (FIG. 16) corresponds exactly to this sequence except that, in the sequence presented in FIG. 16, a methionine precedes the peptide sequence deduced from the nucleotide sequence. It follows from this that the amino-terminal methionine is definitely excised in vivo by methionine aminopeptidase (Ben Bassat and Bauer, 1987). The molecular weight of the purified $SP_2MT$, estimated by 12.5% SDS-PAGE electrophoresis, is 26,500. The COBI protein has a molecular weight deduced from its amino acid sequence of 25,878 (FIG. 16). The correspondences between the $NH_2$-terminal sequences and the molecular weights indicate clearly that the COBI protein corresponds to SP,MT. The cobI gene is the $SP_2MT$ structural gene.

6.1.4. Identification of the COBH Protein Encoded by the cobH Gene a) Assay of Precorrin-8x Mutase Activity This example illustrates the assay of an enzymatic activity of the pathway of biosynthesis of cobalamines which has never been described hitherto. The enzyme in question is precorrin-8x mutase. This enzyme catalyses the transfer of the methyl group from position C-11 to position C-12 during the conversion of precorrin-8x to hydrogenobyrinic acid (see the nomenclature of the carbon atoms in FIG. 19, More generally, it is the enzyme which catalyses the transfer of the methyl group C-11 to C-12, thereby leading to the corrin ring-system. The enzyme is referred to here as a mutase, although it has not been formally demonstrated that the transfer of the methyl group is intramolecular, even though this is very probable.

The enzymatic activity is demonstrated by the conversion of precorrin-8x (5 μM) to hydrogenobyrinic acid during incubations in the presence of enzyme fractions in 0.1 M Tris-HCl pH 7.7, 1 mM EDTA, at 30° C. for 1 h. At the end of the incubation, the reaction is stopped by heating to 80° C. for 10 min and, after centrifugation at 3000×g for 10 min, the hydrogenobyrinic acid formed, present in the supernatant, is analysed by HPLC (see Example 6.1.2.a).

b) Purification of Precorrin-8x Mutase.

The purification of *Pseudomonas denitrificans* precorrin-8x mutase is carried out as described below.

During this purification, all the buffer solutions are adjusted to pH 7.7.

In a typical purification experiment, cells (50 g) of strain SC510 $Rif^r$, carrying plasmid pXL253 (plasmid pKT230 into which the 8.7-kb fragment has been cloned at the EcoRI site, FIG. 13) and obtained after culture in PS4 medium, are resuspended in 0.1 M potassium phosphate buffer (200 ml) and sonicated for 12 minutes. After centrifugation at 50,000 g for 1 hour, the supernatant is passed through a DEAE-Sephadex column (10 ml of gel) to remove the tetrapyrrole compounds. The pH of the solution is immediately adjusted to 7.7 with 1 M KOH solution. The protein fraction precipitating at between 40 and 60% ammonium sulphate saturation is collected by centrifugation and dissolved in 0.1 M Tris-HCl (50 ml). This sample is then injected onto an Ultrogel AcA 54 (IBF, France) column (gel volume 1,000 ml) and the proteins are eluted at a flow rate of 60 ml/h with 50 mM Tris-HCl. The fractions containing the activity are pooled and injected onto a DEAE-Trisacryl M (IBF, France) column equilibrated with 50 mM Tris-HCl, and the proteins are eluted with a gradient of 0 to 0.2 M KCl. The fractions containing the protein to be purified are pooled and passed through a Sephadex G-25 column equilibrated in 10 mM Tris-HCl. The protein fraction is injected onto an Ultrogel HA (IBF, France) column equilibrated with 10 mM Tris-HCl, the proteins are eluted with a gradient of 0 to 0.1 M potassium phosphate, and the active fraction is then chromatographed on a Phenyl-Sepharose CL (Pharmacia) 4B column in 10 mM potassium phosphate, the column being eluted with a gradient of 0.65 to 0 M ammonium sulphate. The active fractions are pooled. The protein thereby obtained is more than 95% pure (according to the results of 12.5% SDS-PAGE electrophoresis and staining with silver salts). The purity of the protein is confirmed by the uniqueness of the N-terminal sequence. Its molecular weight calculated using this technique is 22,000. The steps of purification of precorrin-8x mutase with their purification yields are described in the table below.

TABLE

Purification of precorrin-8x mutase

| Purification step | Vol (ml) | Proteins (mg) | Purification factor[1] |
|---|---|---|---|
| Crude extract | 250 | 6000 | — |
| Precipitation (40–60%) | 50 | 2350 | 2.6 |
| Ultrogel ACA 54 | 70 | 655 | 9.2 |
| DEAE-Tris-acryl-M | 30 | 271 | 22 |
| Ultrogel HA | 22 | 93 | 65 |
| Phenyl-Sepharose | 12 | 31 | 194 |

[1]This factor is calculated from the yield of protein.

c) $NH_2$-Terminal Sequence of Precorrin-8x Mutase and Identification of its Structural Gene This example illustrates how the $NH_2$-terminal sequence of a protein participating in the biosynthetic pathway enables the structural gene which codes for this protein to be identified.

The $NH_2$-terminal sequence of this protein was determined as described above. 15 residues were identified:

1 2 3 4 5 6 7 8 9 10 11 12 13 14 15 (amino acids 2–16 of SEQ ID NO: 18)

Pro Glu Tyr Asp Tyr Ile Arg Asp Gly Asn Ala Ile Tyr Glu Arg

The $NH_2$-terminal sequence of the COBH protein (FIG. 16) corresponds exactly to this sequence except that, in the sequence presented in FIG. 16, a methionine precedes the peptide sequence determined by the sequencing described above. It follows from this that the amino-terminal methionine is definitely excised in vivo by methionine aminopeptidase (Ben Bassat and Bauer, 1987). Since the second residue is a proline, this excision is in keeping with the rules already stated (Hirel et al., 1989). The molecular weight of the purified precorrin-8x mutase, estimated by 12.5% SDS-PAGE electrophoresis, is 22,000. The COBH protein has a molecular weight deduced from its sequence of 22,050 (FIG. 16). The correspondences between the $NH_2$-terminal sequences and the molecular weights of these proteins indicate clearly that the COBH protein corresponds to precorrin-8x mutase. cobH is the precorrin-8x mutase structural gene.

d) Preparation, Isolation and Identification of Precorrin-8x.

In a typical experiment for preparation of precorrin-8x, a crude enzyme extract of strain SC510 $Rif^r$ pXL253 (1000 mg of proteins) is incubated anaerobically for 20 h at 30° C. in 0.1 M Tris-HCl buffer pH 7.7 (100 ml) with trimethylisobacteriochlorin (1000 nmol) prepared as described previously (Battersby et al., 1982), EDTA (1 mM), ATP (100 μmol), $MgCl_2$ (250 μmol), NADH (50 μmol), NADPH (50 μmol), SAM (50 μmol) and hydrogenobyrinic acid (20 μmol). At the end of the incubation, precorrin-8x is the preponderant tetrapyrrole product formed. It is isolated and purified by HPLC on a μBondapak C18 (Waters) column using a linear elution gradient of 0 to 50% of acetonitrile in a potassium phosphate buffer pH 5.8. The mass of precorrin-8x (m/z=880) and the mass of its methyl ester derivative (m/z=978) indicate that it is a compound having the same empirical formula as hydrogenobyrinic acid. The UV/visible and fluorescence characteristics are very different from those of hydrogenobyrinic acid, and indicate that the molecule possesses two separate chromophors. Since the only enzymatic isomerisation reaction between precorrin-6x (Thibaut et al., 1990) and hydrogenobyrinic acid is the migration of the methyl from C-11 to C-12, precorrin-8x is the last intermediate before hydrogenobyrinic acid, and the corresponding reaction is the migration of the methyl from C-11 to C-12, catalysed by precorrin-8x mutase.

Figure 5:
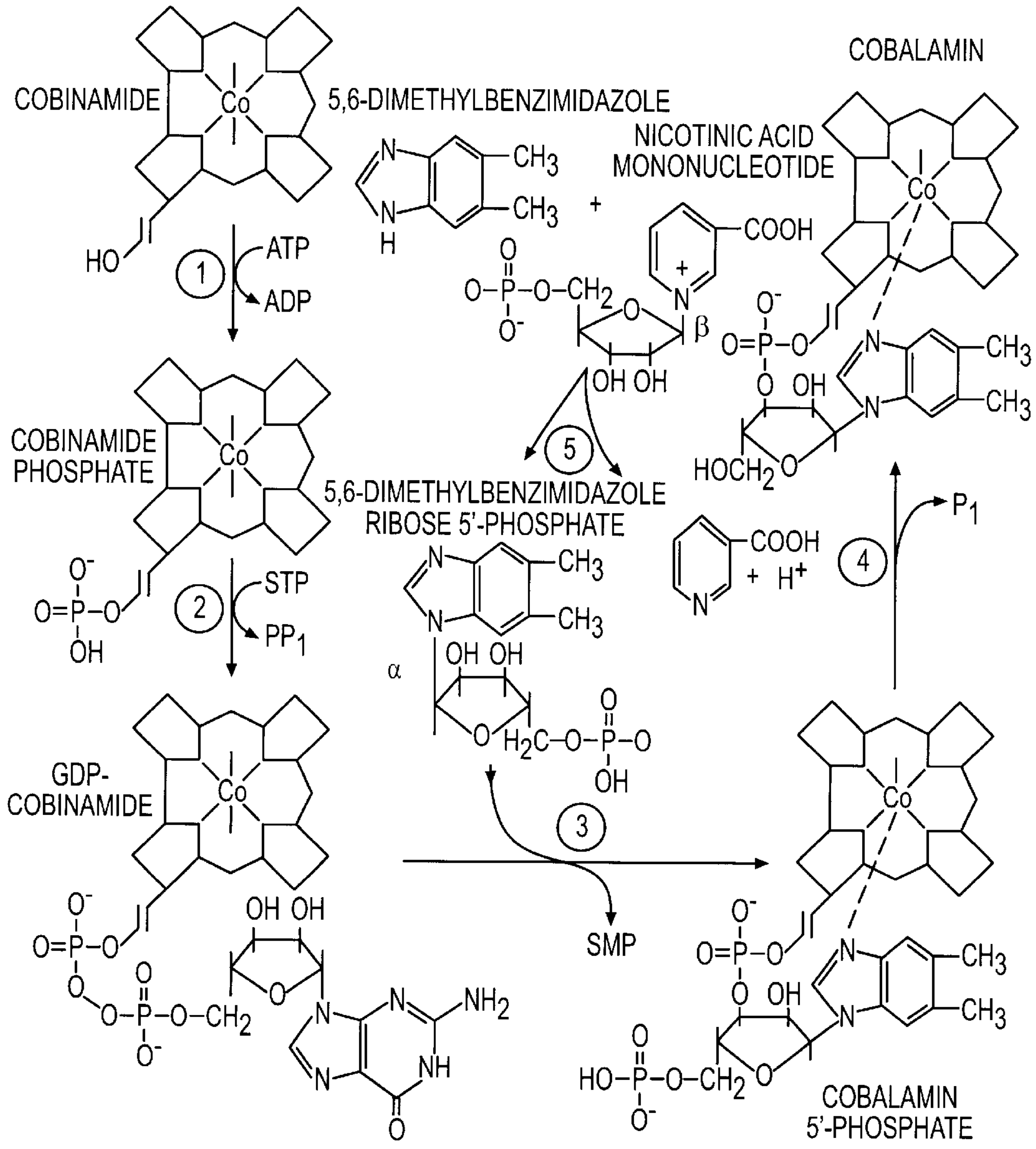
FIG. 5: Final steps of the biosynthesis of cobalamins.
Figure 6A:
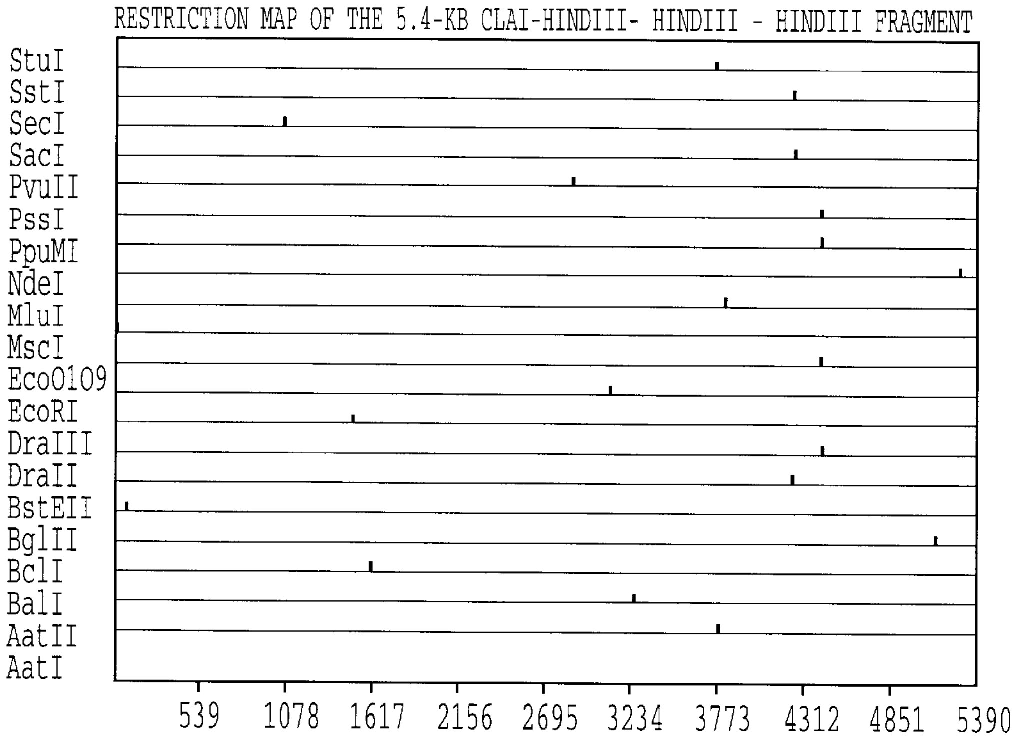
Figure 6B:
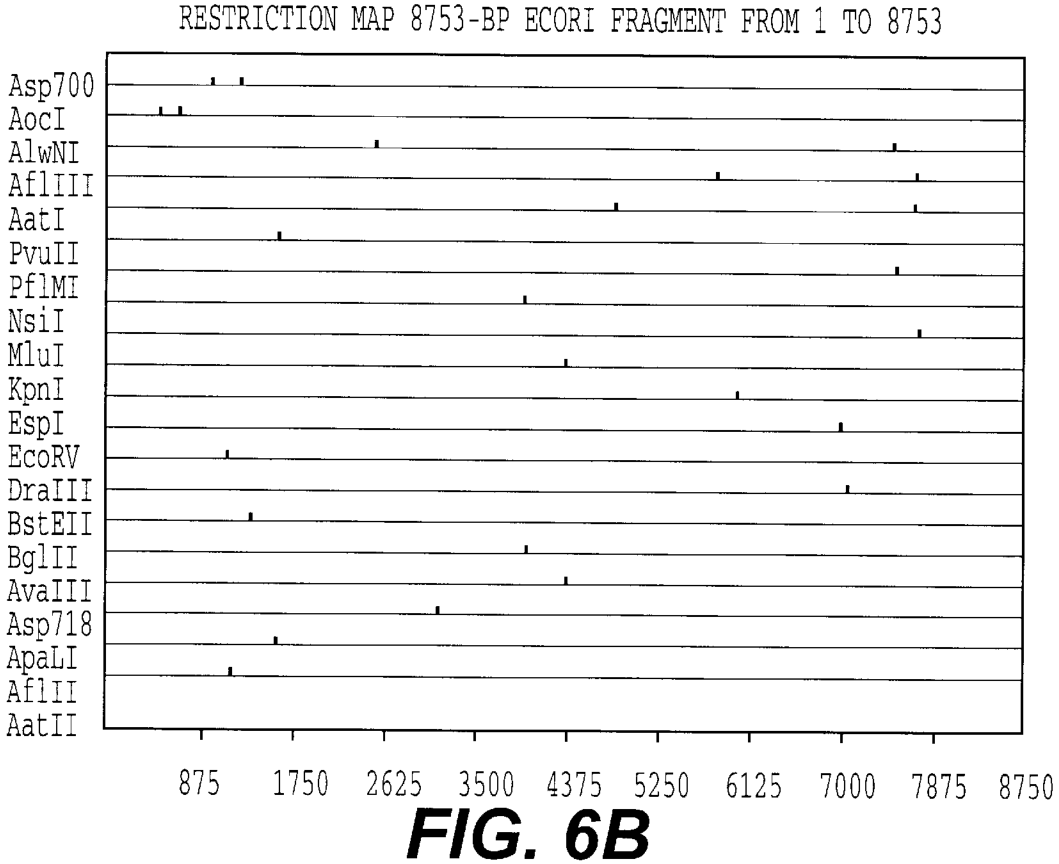
Figure 6C:
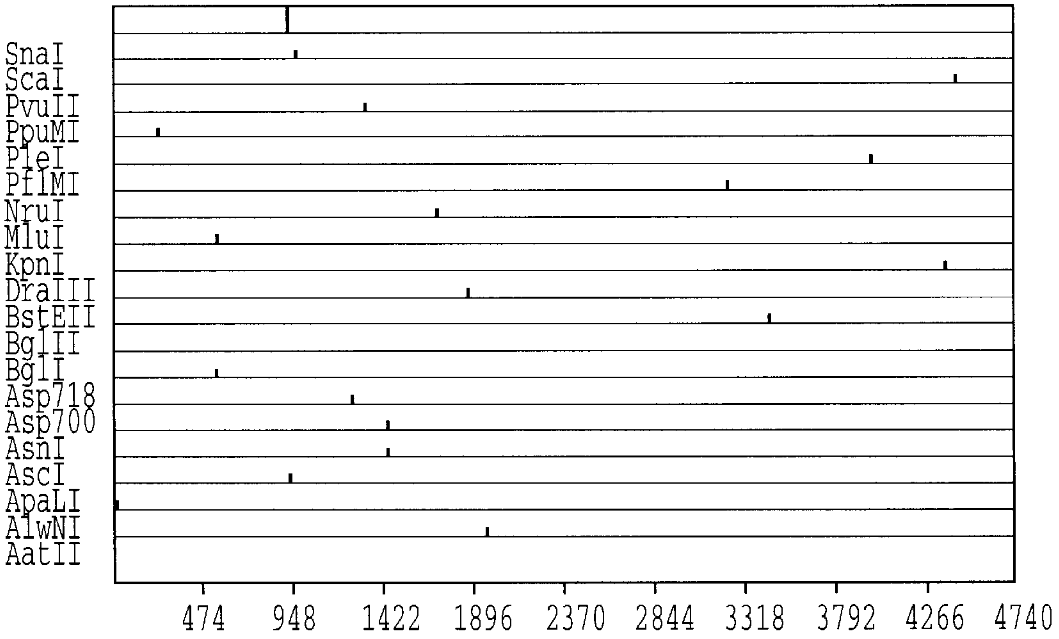
Figure 6D:
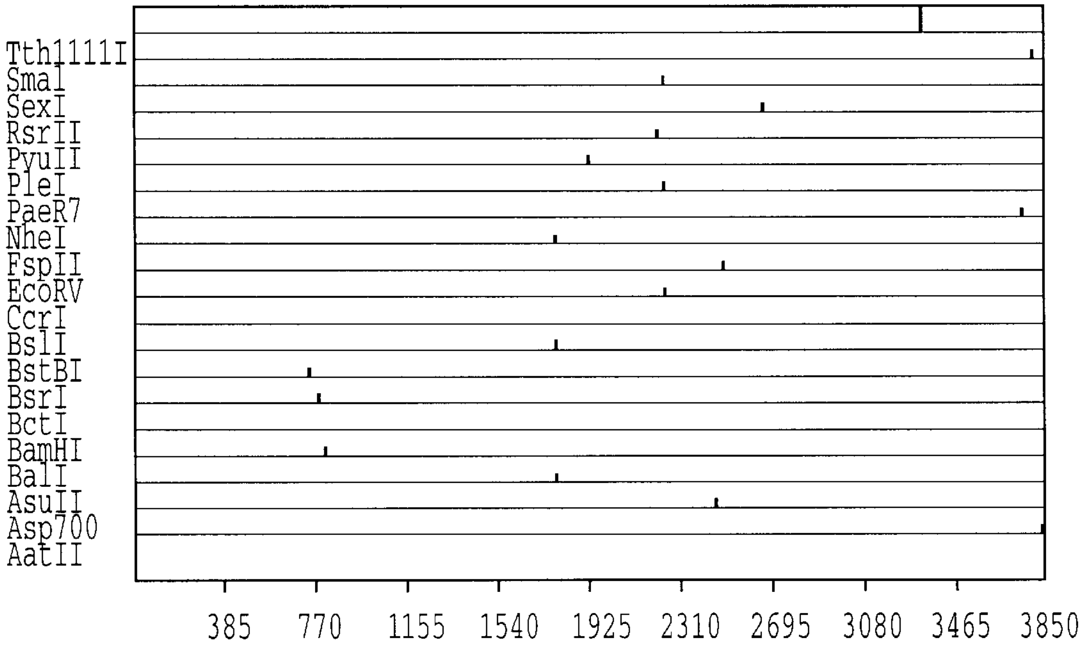
Figure 9A:
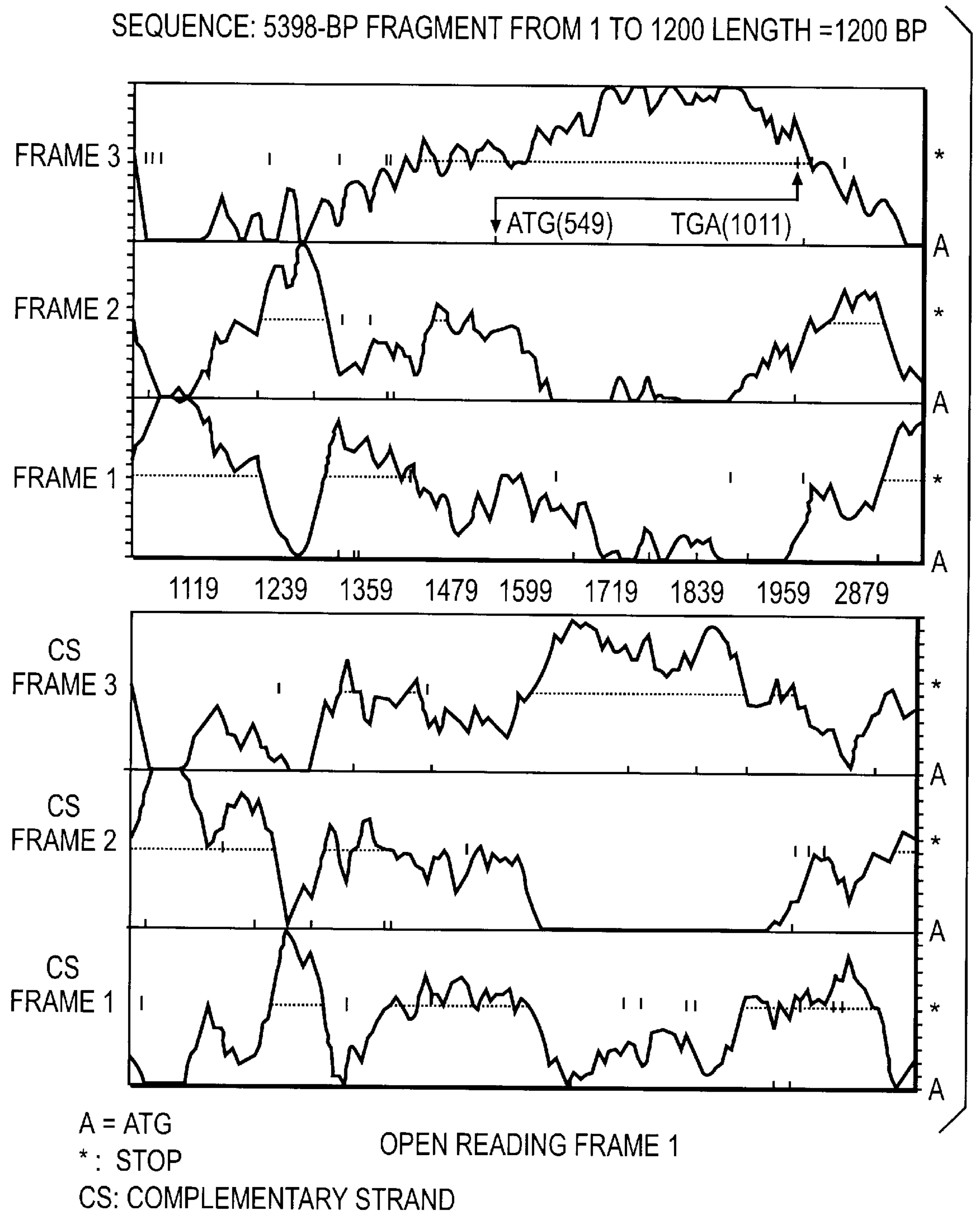
Figure 9B:
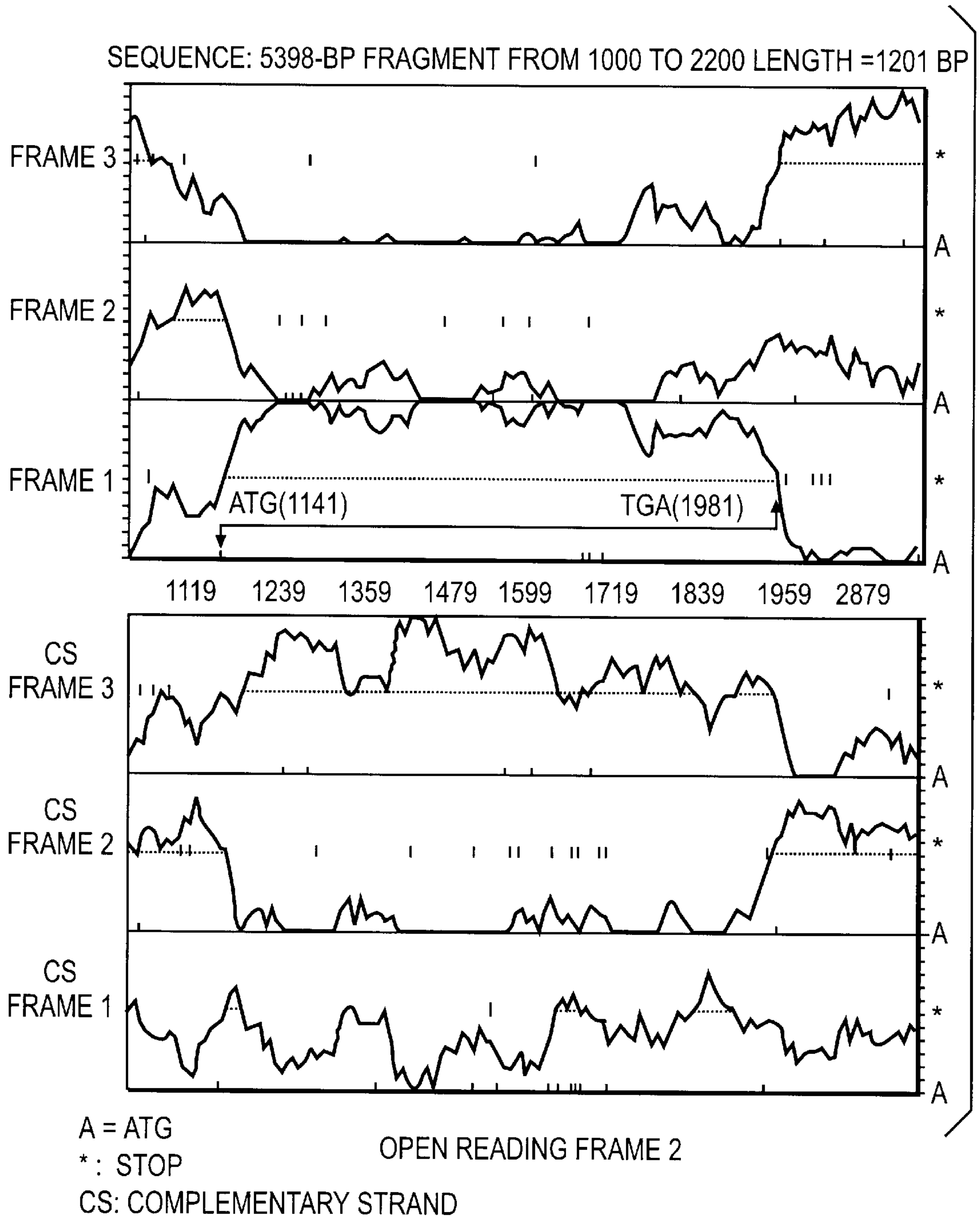
Figure 9C:
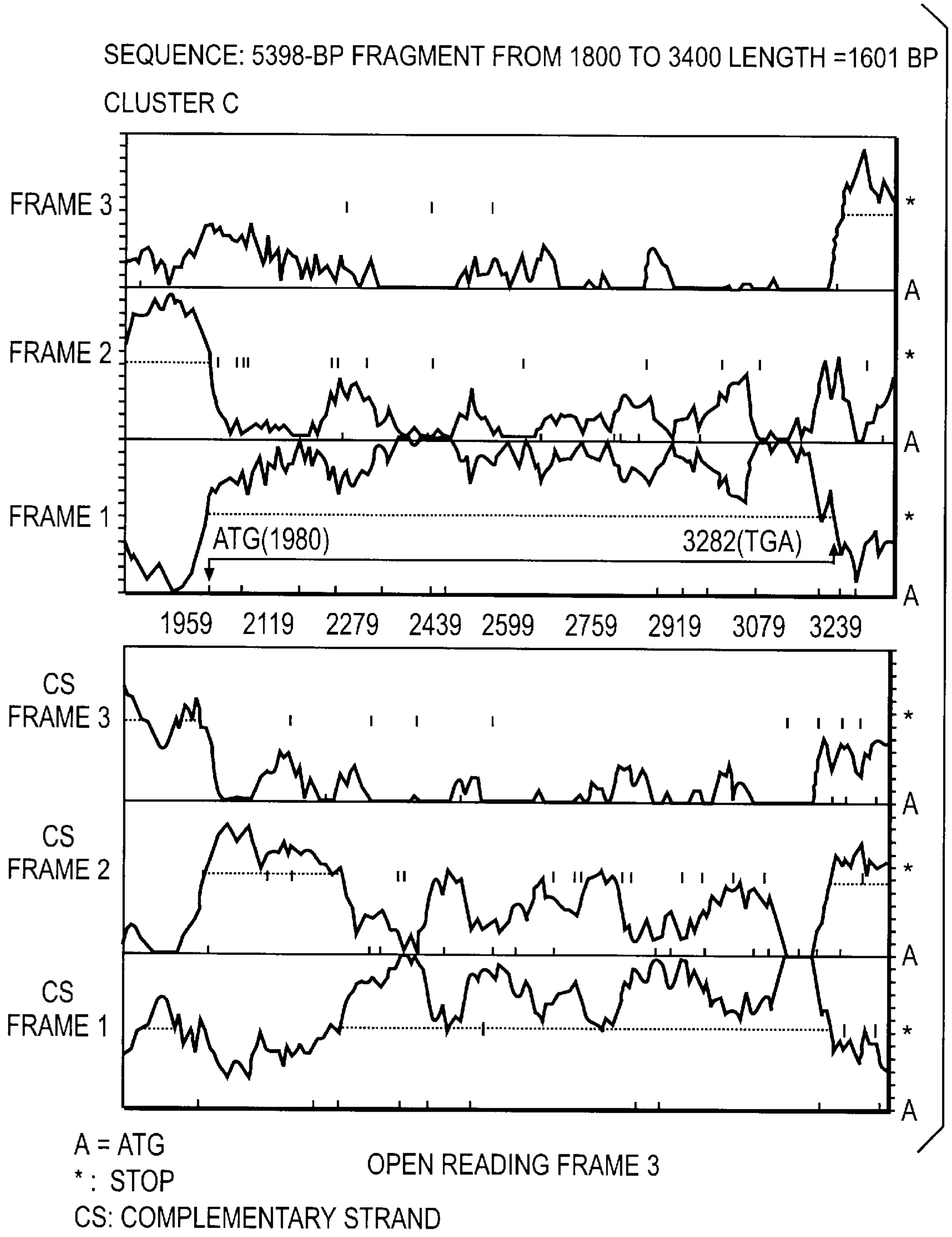
Figure 9D:
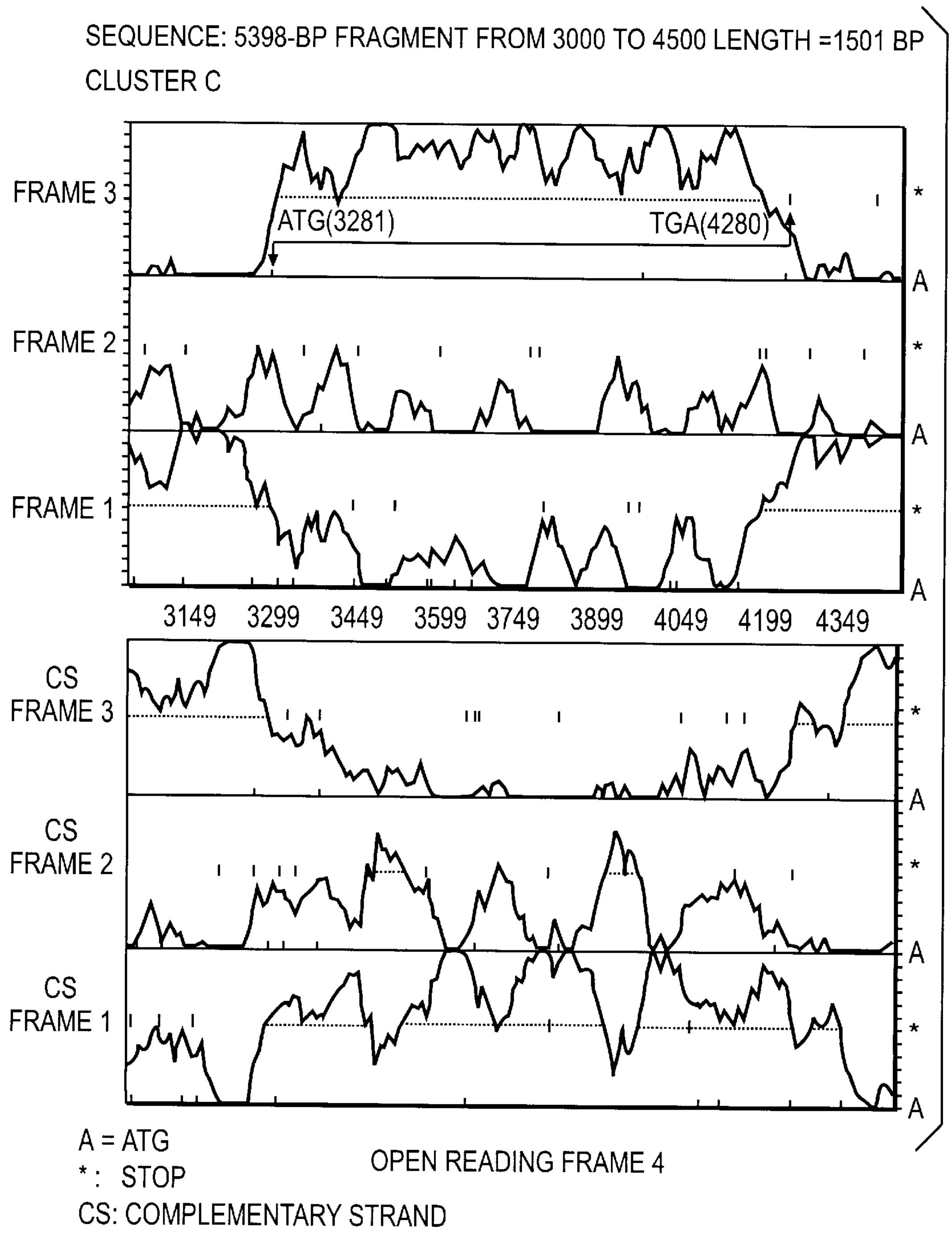
Figure 9E:
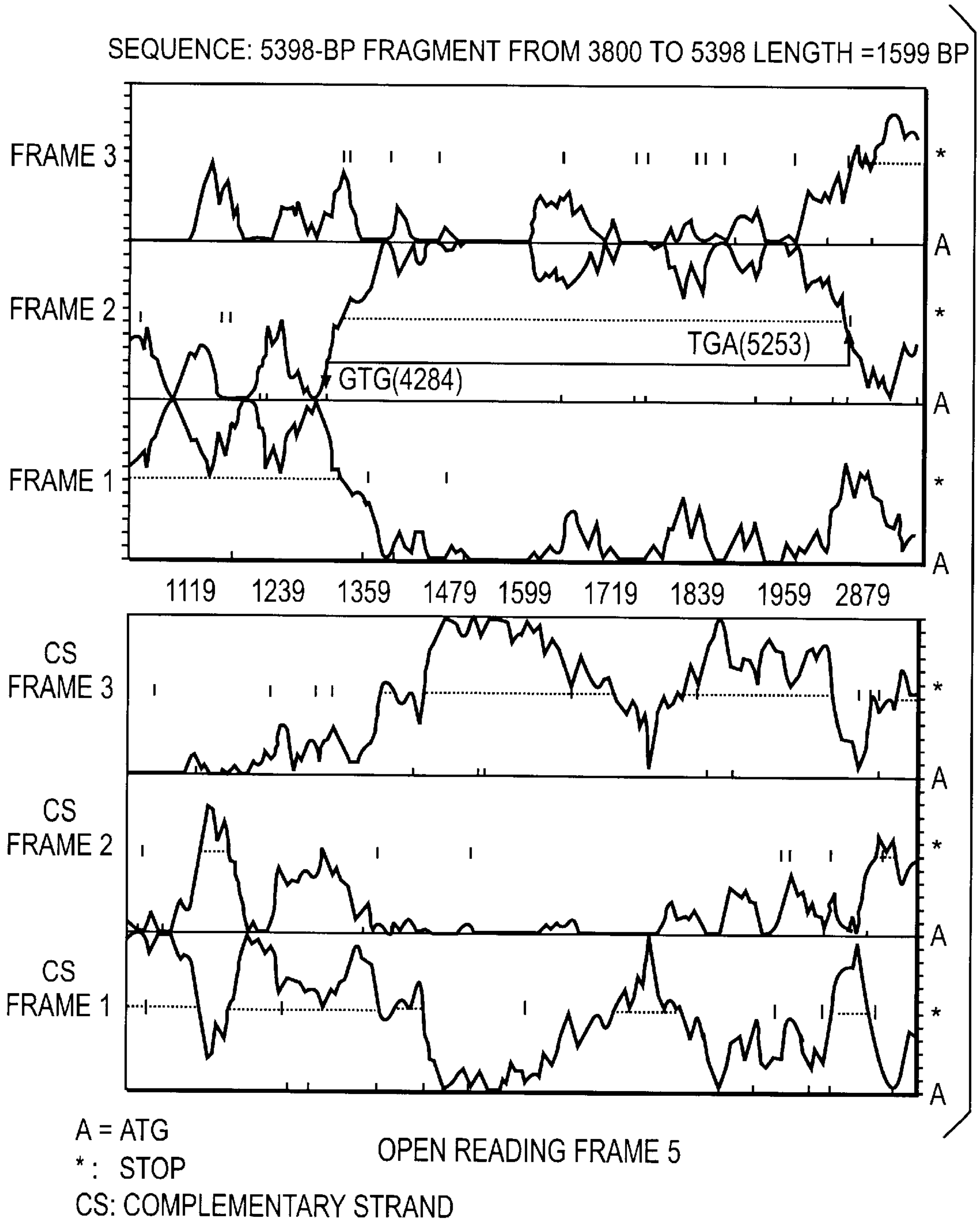
Figure 10A:
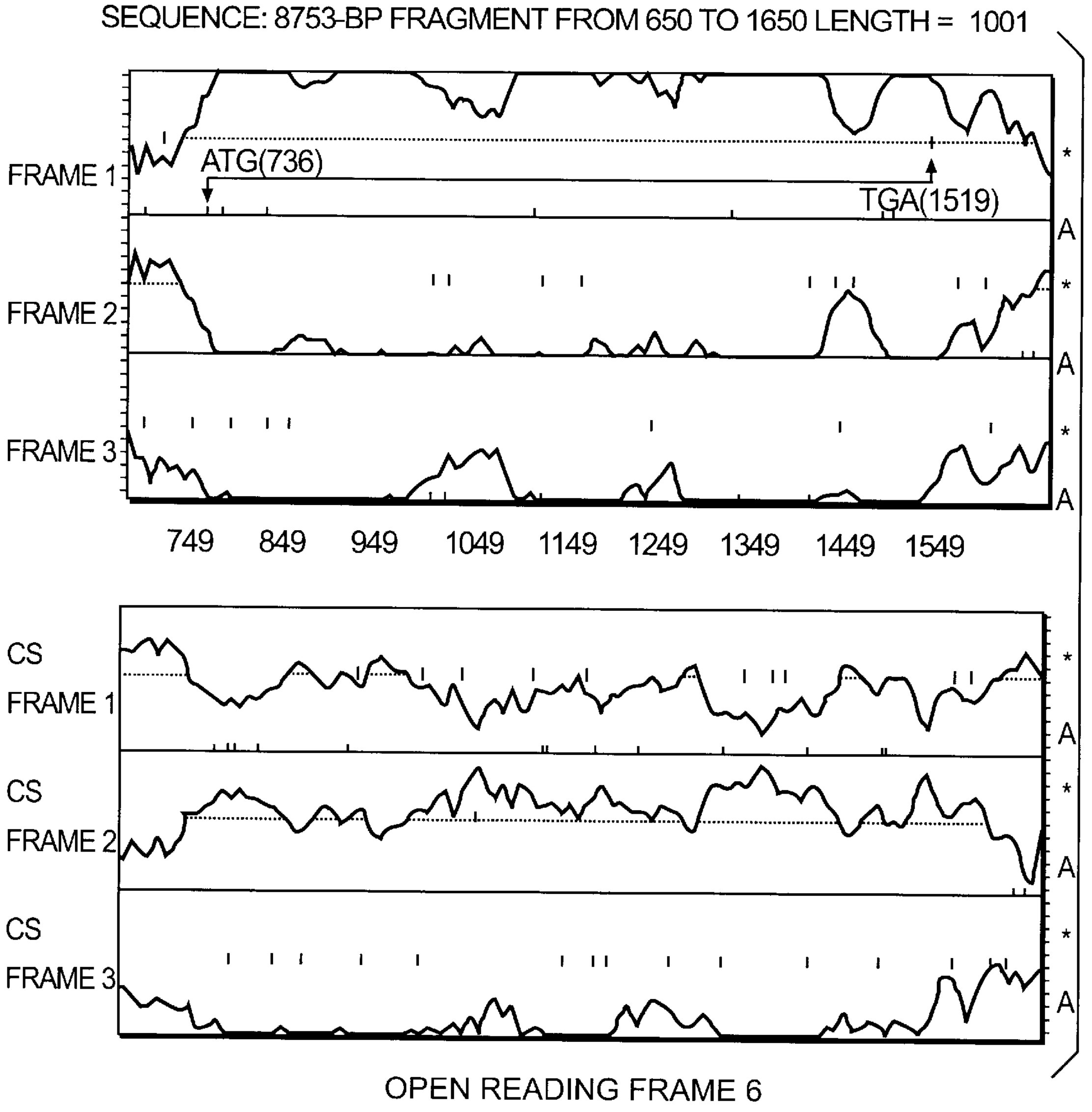
Figure 10B:
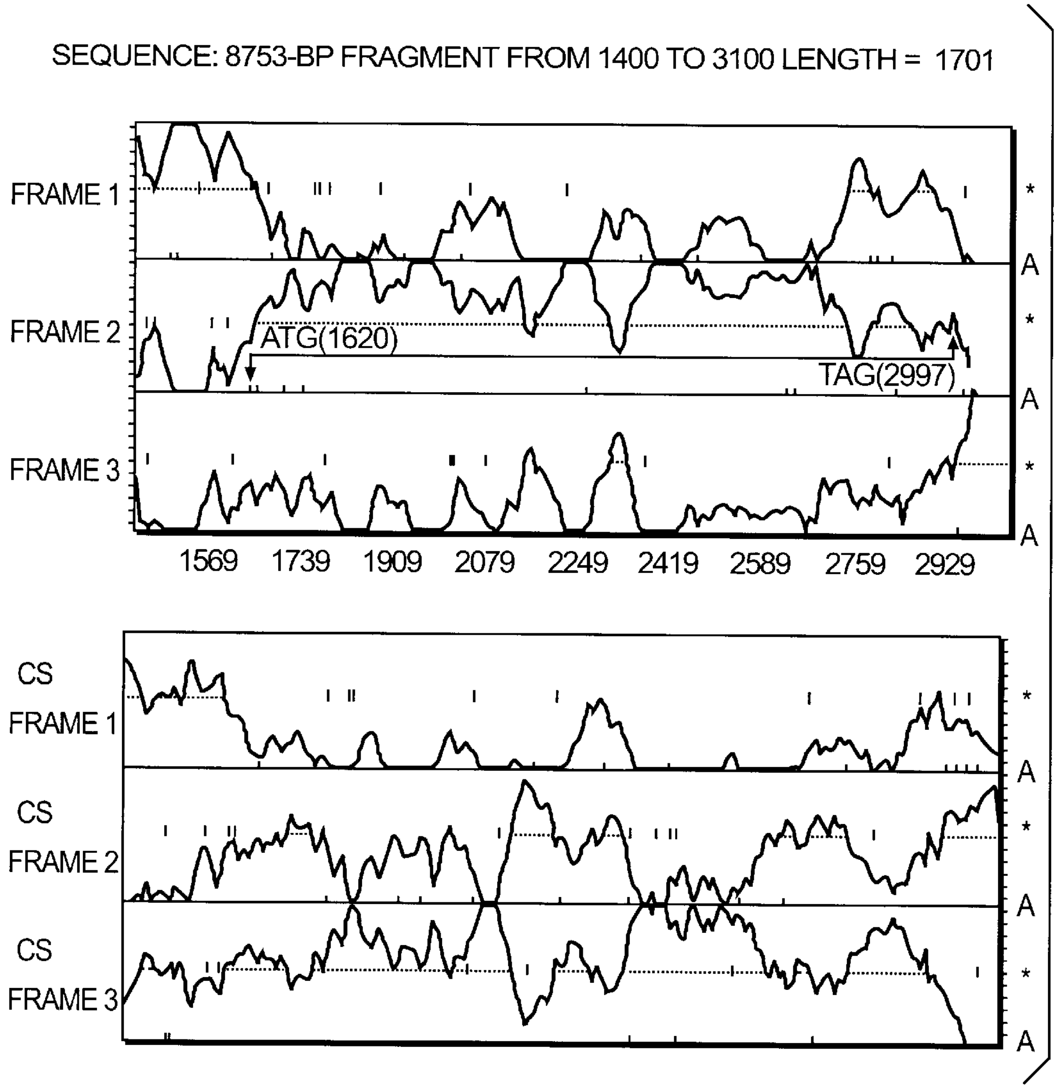
Figure 10C:
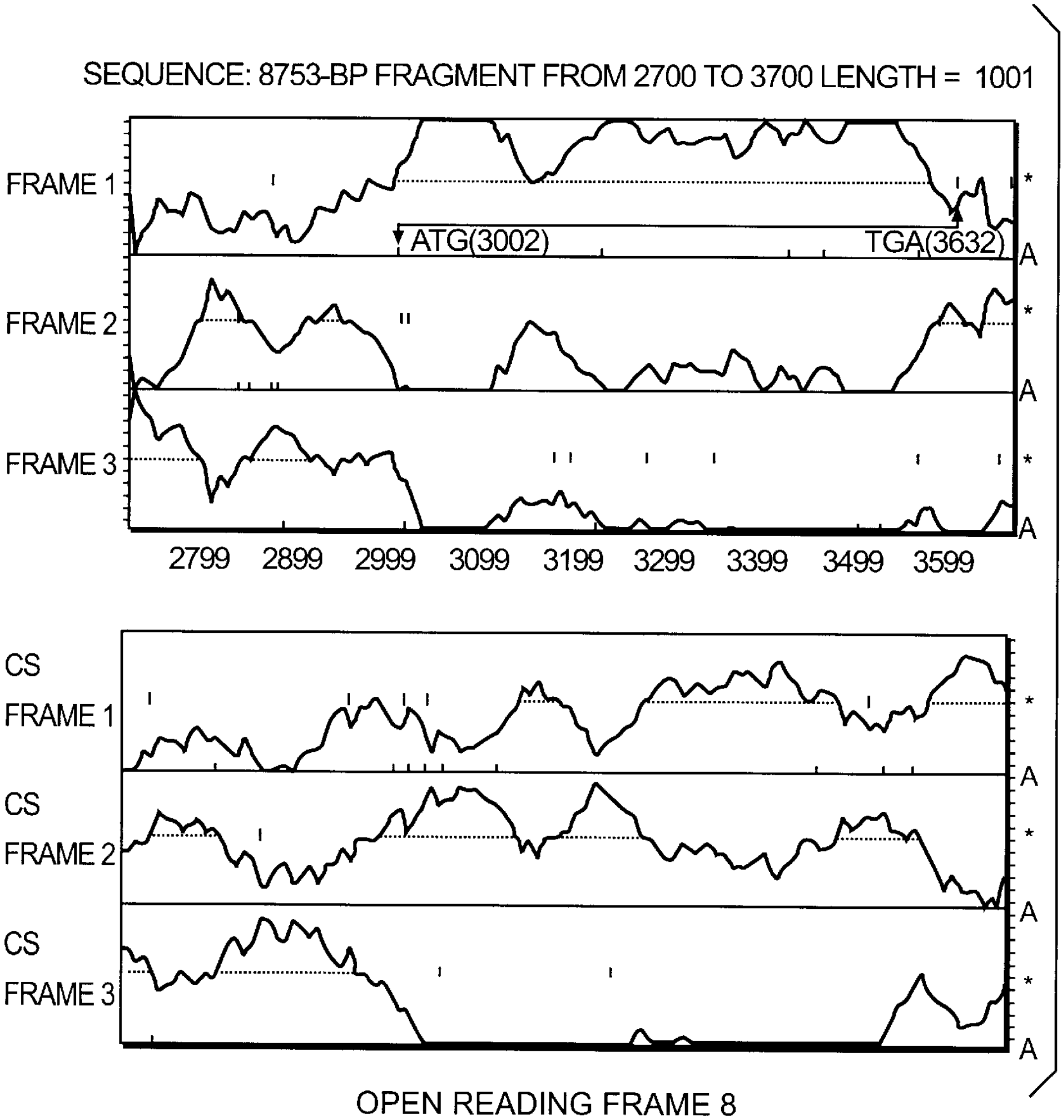
Figure 10D:
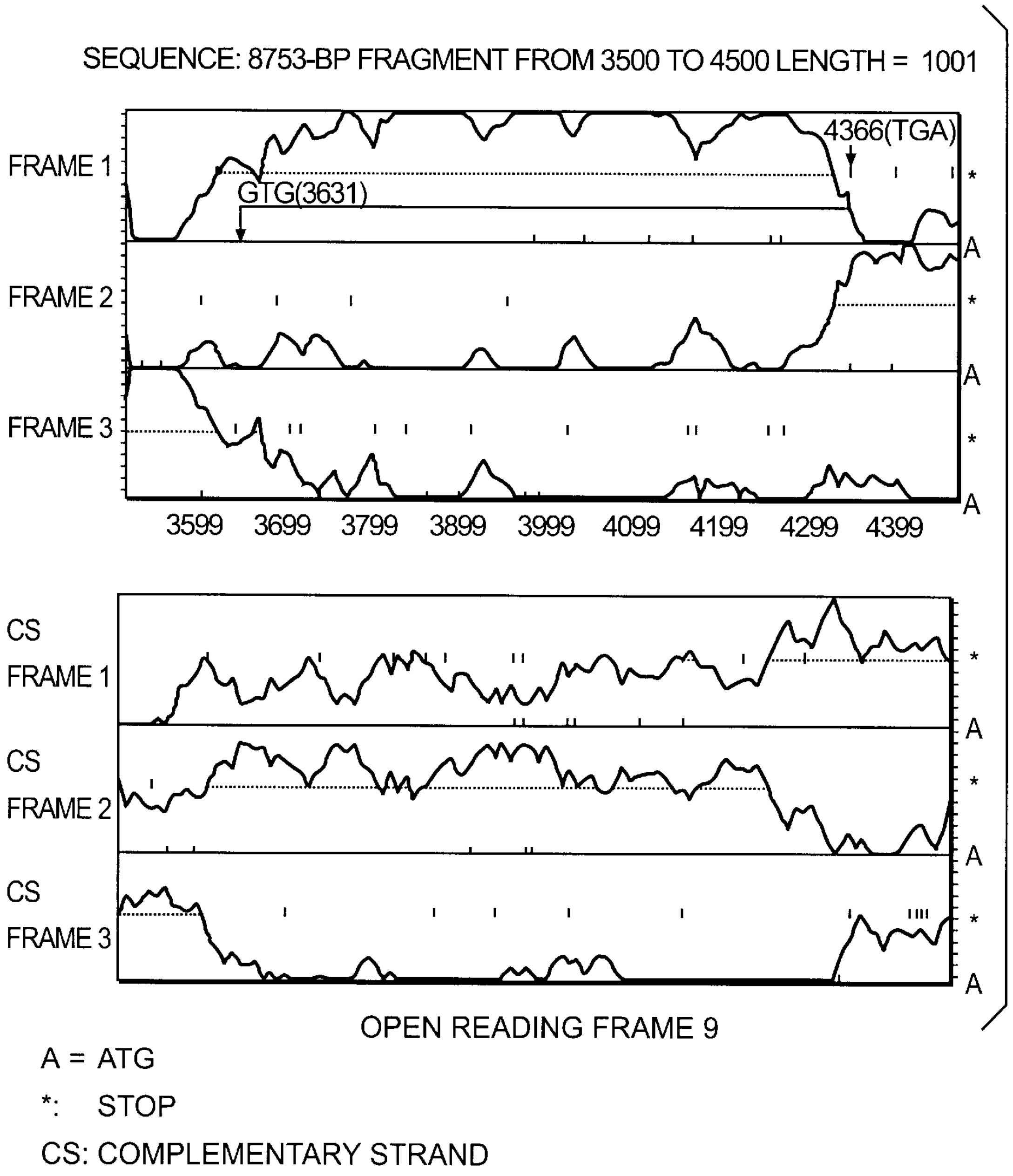
Figure 10E:
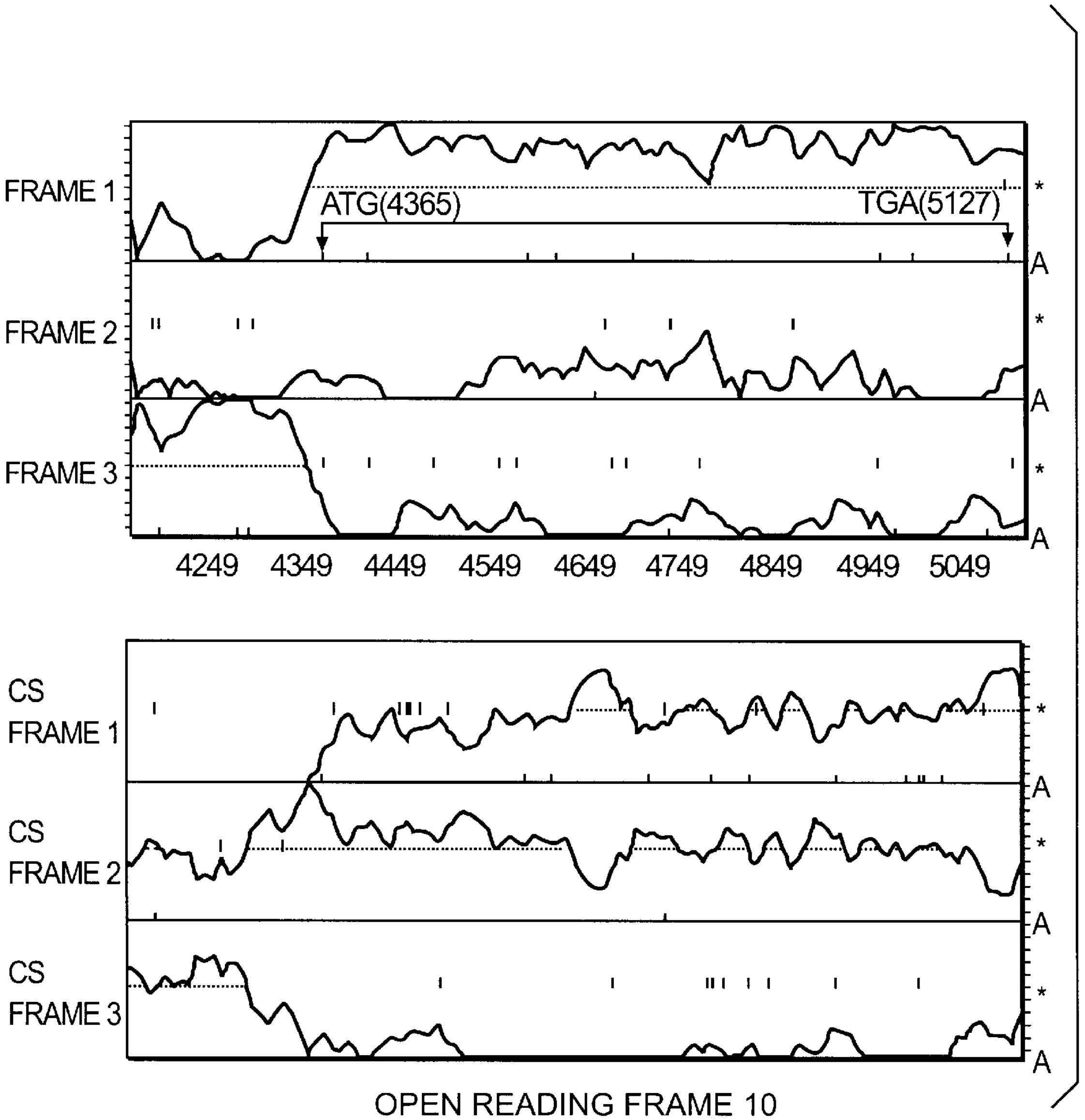
Figure 10F:
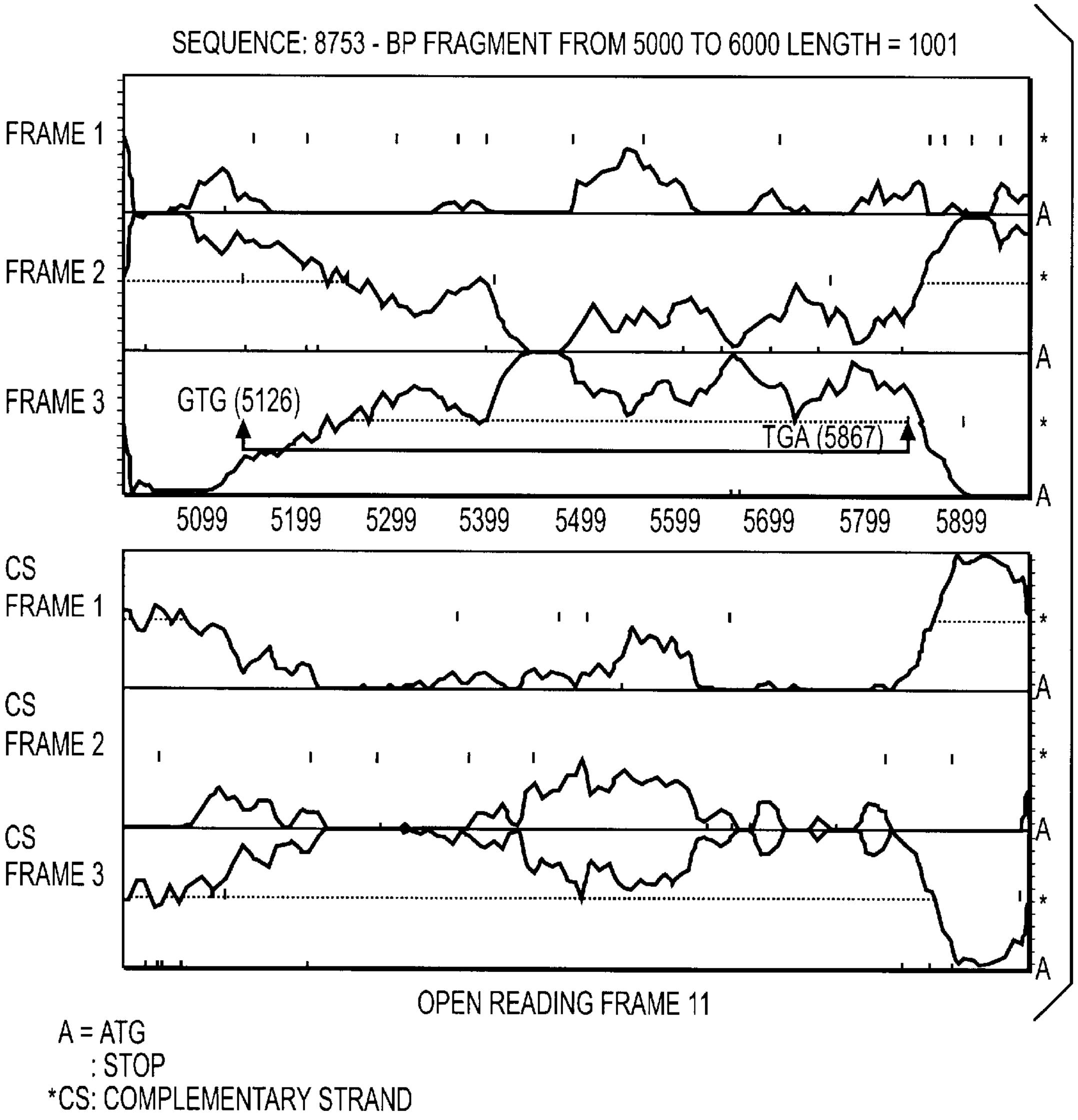
Figure 10G:
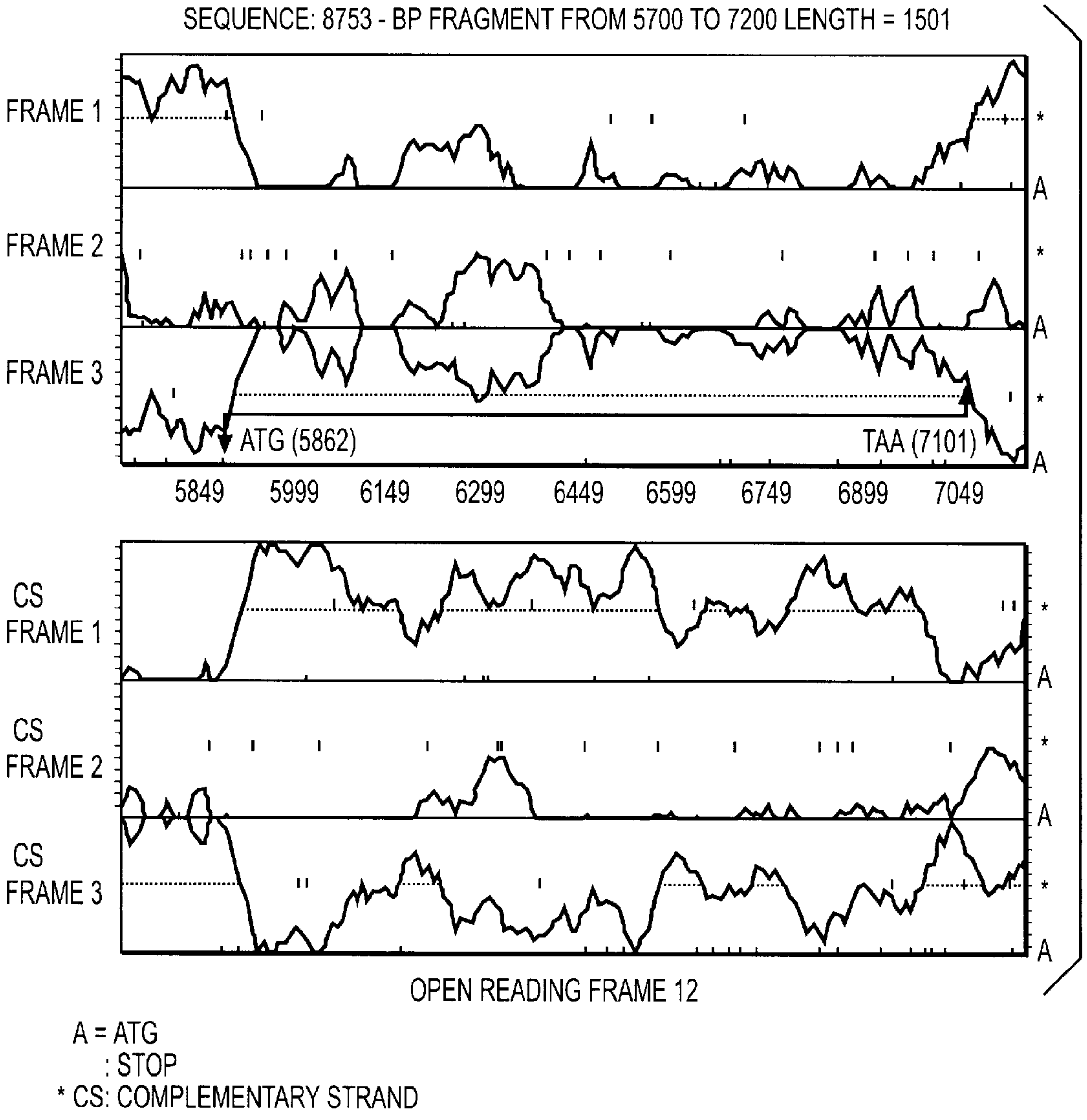
Figure 10H:
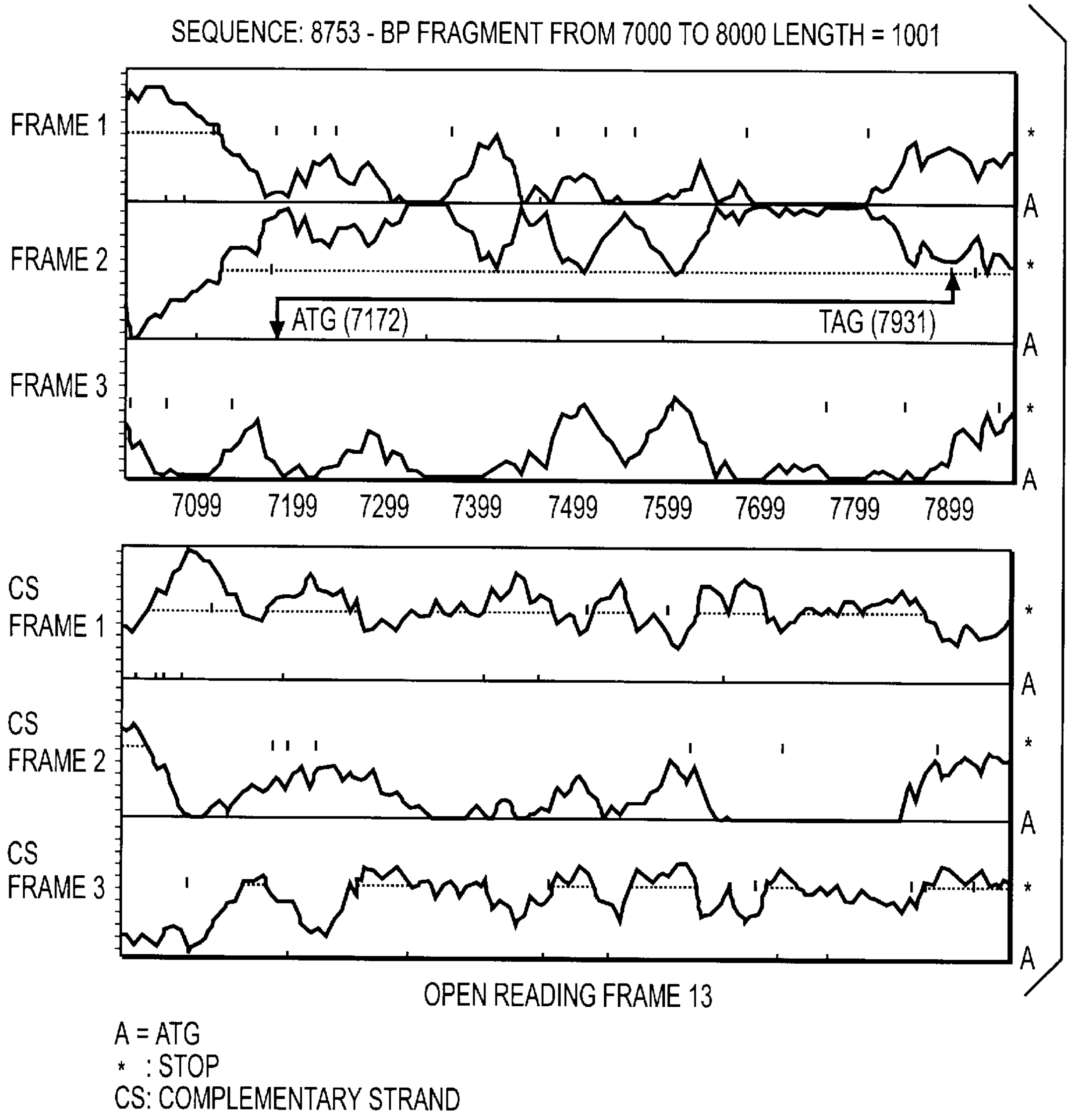

6.1.5. Identification of the COBU Protein Encoded by the cobU Gene a) Assay of Nicotinate-nucleotide:dimethylbenzimidazole phosphoribosyltransferase activity (FIG. 5, reaction 5). This example illustrates the assay of an enzymatic activity directly linked to the pathway of biosynthesis of cobalamins. The enzyme in question is nicotinate-nucleotide:dimethylbenzimidazole phosphoribosyltransferase (NN:DMBI PRT) (EC 2.4.2.21). The fractions containing NN:DMBI PRT activity (approximately 5 units) are incubated at 30° C. for 8 min in 0.1 M glycine-NaOH buffer pH 9.7 (500 $\mu$l) in the presence of 1 mM NaMN (nicotinic acid mononucleotide) and 10 $\mu$M DMBI. The reaction is then stopped by heating to 80° C. for 10 min, the reaction mixture is diluted with water (4 volumes) and this solution (100 $\mu$l) is injected onto a 15-cm Nucleosil 5-C8 HPLC column eluted with a 0.1 M potassium phosphate pH 2.9/acetonitrile (93:7) mixture at a flow rate of 1 ml/min. The $\alpha$-ribazole 5'-phosphate is detected and quantified by fluorimetry (excitation: 260 nm; emission >370 nm). The unit of enzymatic activity is defined as the quantity of enzyme necessary for generating 1 nmol of $\alpha$-ribazole 5'-phosphate per hour under these conditions.

b) Purification of *Pseudomonas denitrificans* NN:DMBI PRT activity. This experiment illustrates how a *P. denitrificans* protein participating in the pathway of biosynthesis of cobalamins may be purified. Using the assay described in Example 6.1.5.a), the purification of *Pseudomonas denitrificans* NN:DMBI PRT is carried out as described below. In a typical purification experiment, wet cells (10 g) of strain SC510 Rif$^r$, into which plasmid pXL1490B has been introduced as described above, are used. Plasmid pXL1490B is described in FIG. 38; this plasmid was obtained by cloning the 3.85-kb BamHI-SstI-SstI fragment of pXL519 (see FIG. 38). This plasmid hence carries the cobU and cobV genes of *P. denitrificans*. The cells, cultured in PS4 medium supplemented with lividomycin, as described previously, are harvested after 96 hours of culture in PS4 medium. They are resuspended in 1.0M Tris-HCl buffer pH 7.2 (25 ml) and sonicated for 15 min at 4° C. The crude extract is then recovered by centrifugation for 1 h at 50,000 g, and thereafter passed through a DEAE-Trisacryl M (IBF, France) column equilibrated with the same buffer. 10% of the eluate (120 mg of proteins) is fractionated on a mono Q HR 10/10 column using a KCl gradient (0 to 0.6 M). The active fractions are pooled and concentrated to 2 ml by ultrafiltration, and then, after mixing with 30 mM Tris-HCl buffer pH 7.2 (one volume), the sample is fractionated a second time on a Mono Q HR 5/5 column as before. The active fractions are pooled, and the sample is then brought to a molarity of 1 M using ammonium sulphate and chromatographed on a Phenyl-Superose HR 5/5 column eluted with a decreasing ammonium sulphate gradient (1 M to 0 M). The fractions containing the desired activity are pooled, concentrated by ultrafiltration and chromatographed on a Bio-Sil 250 gel permeation column eluted with 20 mM sodium phosphate/50 mM sodium sulphate pH 6.8.

After this step, the enzyme is more than 95% pure. It shows no contaminant protein in SDS-PAGE. This purity is confirmed by the uniqueness of the $NH_2$-terminal sequence. Its molecular weight in this technique is 35,000. The different steps of purification of the NN:DMBI PRT are given in the table below.

TABLE

Purification of *P. denitrificans* NN:DMBI PRT

| Purification Step | Vol (ml) | Proteins (mg) | Sp. activity (u/mg of proteins | Yield | Purification factor[1] |
|---|---|---|---|---|---|
| Crude extract | 6.0 | 120 | 2650 | — | — |
| MonoQ 10/10 | 6.0 | 12.7 | 13515 | 51.3 | 5.1 |
| MonoQ 5/5 | 3.0 | 6.19 | 20140 | 39.2 | 7.6 |
| Phenyl-Superose | 1.5 | 2.60 | 35510 | 29.0 | 13.4 |
| Bio-Sil 250 | 1.2 | 1.92 | 39750 | 24.0 | 15.0 |

c) $NH_2$-terminal sequence of *P. denitrificans* NN:DMBI PRT and identification of the *Pseudomonas denitrificans* structural gene coding for this activity. The $NH_2$-terminal sequence of *Pseudomonas denitrificans* NN:DMBI PRT, purified as described in Example 6.1.5b), was carried out according to the technique described above. The first 15 residues were identified:

1 2 3 4 5 6 7 8 9 10 11 12 13 14 15

Ser Ala Ser Gly Leu Pro Phe Asp Asp Phe Arg Glu Leu Leu Arg (amino acids 2–16 of SEQ ID NO: 38)

The $NH_2$-terminal sequence of the COBU protein (FIG. 41) corresponds to this sequence except that, in the sequence presented in FIG. 41, a methionine precedes the first amino acid of the peptide sequence determined by direct sequencing. It follows from this that the amino-terminal methionine is definitely excised in vivo by methionine aminopeptidase (Ben Bassat and Bauer, 1987). The molecular weight of the purified N-transglycosidase, estimated by 12.5% SDS-PAGE electrophoresis, is 35,000. The COBU protein has a molecular weight deduced from its sequence of 34,642 (FIG. 41). The correspondences between the $NH_2$-terminal sequences and the molecular weights clearly indicate that the COBU protein corresponds to NN:DMBI PRT. The cobU gene is the NN:DMBI PRT structural gene.

d) Specificity of NN:DBI PRT for DBI. This example illustrates how a study of the specificity of *P. denitrificans* NN:DMBI PRT enables *P. denitrificans* to be made to biosynthesise various cobamides, using the catalytic properties of *P. denitrificans* NN:DMBI PRT to perform the synthesis of the nucleotide base in question.

The enzyme substrate for synthesising cobalamines is 5,6-dimethylbenzimidazole. Benzimidazole and 5-methylbenzimidazole, respectively, are substrates for the reaction with reaction rates of 157% and 92%, respectively, compared to the natural substrate (5,6-dimethylbenzimidazole), the NaMN concentration being fixed at 2 mM. The specificity of *P. denitrificans* NN:DMBI PRT is hence low for substrates containing a benzimidazole ring-system. It is hence possible to use *P. denitrificans* strain SC510 Rif$^r$ (Cameron et al., 1989), and to culture it in PS4 medium in which 5,6-dimethylbenzimidazole is replaced by benzimidazole or 5-dimethylbenzimidazole, respectively, in order to make the bacterium synthesise Co$\alpha$-(benzimidazolyl)-Co$\beta$-cyanocobamide or Co$\alpha$-(5-methylbenzimidazolyl)-Co$\beta$-cyanocobamide, respectively. There is no doubt that other cobamides could be synthesised in this way.

6.1.6. Identification of the COBV Protein Encoded by the cobV Gene

This example illustrates how the assay of an activity of the pathway of biosynthesis of coenzyme $B_{12}$ in *P. denitrificans*, and then the partial purification of this activity, can enable the structural gene for this enzyme to be identified in *P. denitrificans*.

a) Assay of GDP-cobinamide: α-ribazole-5'-phosphate cobinamidephosphotransferase (or cobalamin-5'-phosphate synthase) activity. This example illustrates the assay of an activity directly linked to the pathway of biosynthesis of cobalamines. The enzyme in question is cobalamin-5'-phosphate synthase. The fractions containing the activity (approximately 5 to 10 units) are incubated in darkness at 30° C. in 0.3 Tris-HCl buffer pH 9.0 (500 $\mu$l) in the presence of 1 mM EDTA, 12.5 mM $MgCl_2$, 50 $\mu$M α-ribazole 5'-phosphate and 20 $\mu$M GDP-cobinamide [in 5'-deoxy-5'-adenosyl (Ado) or coenzyme form]. After 15 min of incubation, 20 mM potassium cyanide (500 $\mu$l) is added and the solution is heated to 80° C. for 10 min. After centrifugation to remove the precipitated matter, the vitamin $B_{12}$ 5'-phosphate present in the supernatant is assayed as described in Example 9. One unit of cobalamin-5'-phosphate synthase is defined as the quantity of enzyme necessary for generating 1 nmol of cobalamine 5'-phosphate per h under the conditions described above.

Ado-GDP-cobinamide is obtained by incubation of Ado-cobinamide phosphate (Blanche et al., 1989) with a SC510 $Rif^r$ pXL623 extract under the conditions of assay of cobinamidephosphate guanylyltransferase (see 6.1.11.b). The α-ribazole and α-ribazole 5'-phosphate are isolated from SC510 $Rif^r$ cultures and purified by HPLC under the assay conditions described in Example 6.1.5a).

b) Partial Purification of Cobalamin-5'-phosphate Synthase

This experiment illustrates how a *P. denitrificans* enzymatic activity participating in the pathway of biosynthesis of cobalamines of *P. denitrificans* can be partially purified. Using the assay described above, the purification of cobalamin 5'-phosphate synthase is carried out. For this purpose, in a typical purification experiment, wet cells (10 g) of strain SC510 $Rif^r$, into which plasmid pXL1490B has been introduced as described previously, are used. Plasmid pXL1490B is described in FIG. 38: this plasmid corresponds to the 3.85-kb SstI-SstI-BamHI fragment cloned into PKT230. This plasmid carries the *P. denitrificans* cobU and cobV genes. The presence of this plasmid in *P. denitrificans* SC510 $Rif^r$ leads to an amplification of the cobalamin-5'-phosphate synthase activity by a factor of approximately 100; it is hence probable that the insert carried by plasmid pXL1490B contains the structural gene for this enzyme; hence this gene can be only cobU or cobV. The SC510 $Rif^r$ pXL1490B cells are obtained by culture in PS4 medium supplemented with lividomycin, as described above. The cells are centrifuged and then resuspended in 0.1 M Tris-HCl (pH 8.3)/1 mM EDTA buffer (buffer A) (25 ml) and sonicated for 15 min at 4° C. The crude extract is then recovered by centrifugation for 1 h at 50,000 g and passed through a Sephadex G-25 column equilibrated with buffer A. The protein fraction is recovered and injected in 300-$\mu$l fractions (7.5 mg of proteins) onto a Superose 12 HR 10/30 column eluted in buffer A. The excluded fraction is recovered, mixed with an equal volume of buffer A/1.0 M ammonium sulphate and chromatographed on a Phenyl-Superose HR 5/5 column. The proteins are eluted with a decreasing ammonium sulphate gradient (0.5 M to 0 M) in buffer A, followed by a plateau at 0 M ammonium sulphate with the object of eluting the cobalamin-5'-phosphate synthase activity. The partial purification of this enzyme is described in the table below, on the basis of 75 mg of proteins introduced at the start in the purification process.

TABLE

Partial purification of *P. denitrificans* cobalamin-5'-phosphate synthase

| Purification step | Vol (ml) | Proteins (mg) | Sp. activity (u/mg of proteins) | Yield | Purification factor[1] |
|---|---|---|---|---|---|
| Crude extract | 3.0 | 75 | 325 | — | — |
| Superose 12HR | 50.0 | 2.9 | 6,810 | 81 | 21 |
| Phenyl-Superose | 4.5 | 0.35 | 17,850 | 26 | 55 |

c) Specificity of cobalamin-5'-phosphate synthase. The Km for (Ado)GDP-cobinamide is 0.9 $\mu$m. However, the enzyme possesses the same affinity and a virtually identical reaction rate for the (CN, aq) form of the substrate. The Km of the enzyme for α-ribazole 5'-phosphate is approximately 2.7 $\mu$M. In addition, the purest preparations of cobalamine-5'-phosphate synthase catalyse the reaction of Ado-GDP-cobinamide with α-ribazole to give coenzyme $B_{12}$ and, under these conditions, no accumulation of cobalamin 5'-phosphate is observed. The Km of the enzyme for α-ribazole is 7.8 $\mu$M. Intracellular α-ribazole 5'-phosphate and α-ribazole concentrations of 30 and 700 $\mu$M, respectively, were measured by HPLC during the production of cobalamins by SC510 $Rif^r$ in PS4 medium under the culture conditions described in Example 6.1.5a). This shows that coenzyme $B_{12}$ may be generated directly from Ado-GDP-cobinamide by cobalamin-5'-phosphate synthase without the participation of a cobalamin 5'-phosphatase.

The absence of accumulation or the presence of traces of cobalamin 5'-phosphate in the *P. dinitrificans* SC510 $Rif^r$ cultures confirms that coenzyme $B_{12}$ is produced by the direct reaction of Ado-GDP-cobinamide with α-ribazole in vivo.

This direct reaction has already been observed and described in vitro in *Propionibacterium shermanii* (Ronzio et al., 1967; Renz, 1968). As the cobalamin-5'-phosphate synthase structural gene can be only cobU or cobV, since the amplication in *P. denitrificans* of a fragment carrying these two *P. denitrificans* cob genes leads to an increase in cobalamin-5'-phosphate synthase activity by a factor of 100, and since the cobU gene is the NN:DMBI PRT structural gene, cobV is hence the cobalamin-5'-phosphate synthase structural gene.

6.1.7. Identification of the COBK Protein Encoded by the cobK Gene a) Assay of Precorrin-6x Reductase Activity.

This example illustrates the assay of a novel enzymatic activity directly linked to the pathway biosynthesis of cobalamins. The enzyme in question is precorrin-6x reductase.

The fractions containing precorrin-6x reductase activity (approximately 0.05 unit, U) are incubated at 30° C. for 60 min in 0.1 M Tris-HCl buffer pH 7.7 (250 $\mu$l) in the presence of 1 mM EDTA, 500 $\mu$M NADPH, 25 $\mu$M [methyl-$^3$H]SAM (80 $\mu$Ci/$\mu$mol), 4 $\mu$M precorrin-6x (Thibaut et al., 1990) and partially purified dihydroprecorrin-6x methylase (0.5 U) (see preparation below). The reaction is then stopped by heating to 80° C. for 5 min and, after centrifugation at 5000×g for 5 min, the supernatant is injected onto a DEAE-Sephadex column (containing 200 $\mu$l of gel). The column is then washed extensively with the Tris-HCl buffer, and the compounds bound are eluted with 1 M HCl (4 ml). The radio activity in this eluent is counted by liquid scintillation counting. The unit of enzymatic activity is defined as the quantity of enzyme necessary for reducing 1 nmol of precorrin-6x per h under these conditions.

Dihydroprecorrin-6x methylase is partially purified from a crude extract of SC510 Rif$^r$ pXL253 on a Mono Q HR 5/5 (Pharmacia) anion exchange column. The column is eluted with a linear gradient of 0 to 0.4 M KCl in 0.1 M Tris-HCl buffer pH 7.7. The enzymatic activity is eluted at 0.35 M KCl. This activity is detected and quantified by means of the precorrin-6x reductase activity test defined above (in the presence of precorrin-6x reductase (0.5 U) in the incubation medium). After the Mono Q step, the fractions containing dihydroprecorrin-6x methylase activity are completely devoid of precorrin-6x reductase activity. The unit of methylase activity is defined as the quantity of enzyme necessary for transferring 1 nmol of methyl groups to dihydroprecorrin-6x per h under the conditions described above.

b) Purification of Precorrin-6x Reductase Activity

Using the assay described above, the purification of *Pseudomonas denitrificans* precorrin-6x reductase is carried out as described below.

In a typical purification experiment, wet cells (100 g) of strain SC510 Rif$^r$, into which plasmid pXL253 (plasmid pKT230 into which the 8.7-kb fragment has been cloned at the EcoRI site, FIG. 13) has been introduced, are suspended in 0.1 M Tris-HCl pH 7.7/1 mM EDTA buffer (buffer A) (200 ml) and sonicated for 15 min at 4° C. The crude extract is then recovered by centrifugation at 1 h at 50,000×g and passed in three portions through a Sephadex G-25 column equilibrated with buffer A. The three fractions excluded from the gel are pooled and adjusted to 1 l with buffer A. The proteins precipitating at between 25 and 40% ammonium sulphate saturation are collected by centrifugation and resuspended in buffer A (50 ml), and this solution is desalted through a Sephadex G-25 column equilibrated with buffer B (25 mM Tris-HCl/500 pM DTT/15% glycerol). The protein solution is then injected at 2.5 ml/min onto a Q Sepharose Fast Flow (Pharmacia) column equilibrated with buffer B, and the proteins are eluted with a buffer B/0.2 M KCl mixture. This fraction is desalted on a Sephadex G-25 column equilibrated with buffer C (50 mM Tris-HCl/500 $\mu$M DTT/15% glycerol). The protein solution is then fractionated (100 mg of proteins at each chromatographic run) on a Mono Q HR 10/10 (Pharmacia) column using a gradient of 0 to 0.4 M KCl in buffer C, and the fraction containing the activity is thereafter chromatographed on a Phenyl-Superose HR 10/10 (Pharmacia) column in a linear decreasing ammonium sulphate gradient (1 to 0 M). The active fraction is desalted and the precorrin-6x reductase is repurified on a Mono Q HR 5/5 column. It is eluted in 50 mM Tris-HCl pH 8.1/500 $\mu$M DTT/15% glycerol buffer with a gradient of 0 to 0.2 M KCl. To complete the purification, the protein is finally chromatographed on a Bio-Sil 250 (Bio-Rad) column eluted with 20 mM potassium phosphate/50 mM sodium sulphate pH 6.8/500 $\mu$M DTT/15% glycerol. After this step, the enzyme is more than 95% pure. It shows no contaminant protein in SDS-PAGE, the proteins being visualised with silver nitrate. This degree of purity is confirmed by the uniqueness of the $NH_2$-terminal sequence. Its molecular weight in this technique is 31,000. The different steps of purification of precorrin-6x reductase with their purification factor and their yield, are given in the table below.

TABLE

Purification of precorrin-6x reductase

| Purification step | Vol (ml) | Proteins (mg) | Sp.activity (u/mg of proteins) | Yield | Purification factor[1] |
|---|---|---|---|---|---|
| Crude extract | 270 | 9600 | 0.535 | — | — |
| A.S. 25 40% | 100 | 4160 | 1.14 | 92 | 2.1 |
| Q Sepharose | 150 | 1044 | 3.64 | 74 | 6.8 |
| Mono Q 10/10 | 55 | 67 | 24.5 | 32 | 46 |
| Phenyl-Superose | 10 | 2.2 | 325 | 14 | 607 |
| Mono Q 5/5 | 2.5 | 0.082 | 5750 | 9.2 | 10750 |
| Bio-sil 250 | 1.0 | 0.055 | 7650 | 8.2 | 14300 |

c) $NH_2$-terminal Sequence and Partial Internal Sequences of *Pseudomonas denitrificans* Precorrin-6x Reductase and Identification of the *Pseudomonas denitrificans* Structural Gene Coding for This Activity The $NH_2$-terminal sequence of *Pseudomonas denitrificans* precorrin-6x reductase, purified as described above, was determined as described before. Six residues were identified:

Ala-Gly-Ser-Leu-Phe-Asp (amino acids 2–7 of SEQ ID NO: 24)

Similarly, after tryptic digestion and separation of the fragments by HPLC on a C-18 reversed-phase column, three internal sequences were obtained:

Ile-Gly-Gly-Phe-Gly-Gly-Ala-Asp-Gly-Leu (amino acids 60–69 of SEQ ID NO: 24)

Arg-Pro-Glu-Trp-Val-Pro-Leu-Pro-Gly-Asp-Arg (amino acids 112–182 of SEQ ID NO: 24)

Val-Phe-Leu-Ala-Ile-Gly (amino acids 143–148 of SEQ ID NO: 24)

The $NH_2$-terminal sequence of the COBK protein (FIG. 16) corresponds exactly to the $NH_2$-terminal sequence of precorrin-6x reductase except that, in the sequence presented in FIG. 16, a methionine precedes the peptide sequence determined by direct sequencing. It follows from this that the amino-terminal methionine is definitely excised in vivo by methionine aminopeptidase (Ben Bassat and Bauer, 1987). Similarly, the three internal sequences correspond to the three sequences 60 to 69, 112 to 122 and 143 to 148 of the COBK protein. The molecular weight of the purified precorrin-6x reductase is estimated by SDS-PAGE electrophoresis at 31,000. The COBK protein has a molecular weight deduced from its sequence of 28,000 (FIG. 16). The correspondences between the internal $NH_2$-terminal sequences and the molecular weights indicate clearly that the COBK protein corresponds to precorrin-6x reductase. The cobK gene is the precorrin-6x reductase structural gene.

d) Reaction Catalysed by Precorrin-6x Reductase

The enzymatic reaction of reduction of precorrin-6x is strictly NADPH-dependant in *P. denitrificans*. NADPH cannot be replaced by NADH. When the purified enzyme (or an active fraction during purification, or even a crude enzyme extract) is incubated under the conditions of the assay of activity, but in the absence of SAM and of dihydroprecorrin-6x methylase, the product of the reaction can then be purified by HPLC in the system described for the purification of precorrin-6x (see Example 6.1.4.d). After desalting and esterification (4% methanolic sulphuric acid, 20° C., 24 h, argon atmosphere), the corresponding ester has a mass m/z=1008. The product of the reaction catalysed by precorrin-6x reductase is hence dihydroprecorrin-6x, also known as precorrin-6y.

6.1.8. Identification of the COBQ Protein Encoded by the cobQ Gene a) Assay of Cobyric Acid Synthase Activity This example illustrates the assay of an enzymatic activity of the pathway of biosynthesis of cobalamins which has never been described hitherto. The enzyme in question is cobyric acid synthase. This enzyme catalyses the amidation of the peripheral carboxylic acid functions at positions b, d, e and g on the corrin ring-system (see FIG. 19). The $NH_2$-group donor is L-glutamine, and each amidation reaction is accompanied by the consumption of one ATP molecule.

The fraction to be assayed is incubated in darkness at 30° C. for 60 min in 0.1 M Tris hydrochloride buffer pH 7.5 (250 $\mu$l) containing 1 mM DTT, 1 mM EDTA, 1 mM ATP, 2.5 mM $MgCl_2$, 1 mM glutamine and 10 $\mu$M Ado-cobyrinic acid di- or pentaamide. The reaction is stopped by adding 0.1 M aqueous potassium cyanide solution (25 $\mu$l). After heating to 80° C. for 10 min and centrifugation at 3000×g for 10 min, the compounds formed, present in the supernatant, are analysed by HPLC. The unit of activity is defined as the quantity of enzyme necessary for generating 1 nmol of amide functions per h under these conditions.

5'-Deoxy-5'-adenosyl(Ado)-cobyrinic acid diamide and pentaamide are isolated from cultures of strain SC510 in PS4 medium, using the method the principle of which is described in Example 9.

b) Purification of Cobyric Acid Synthase

Using the assay described in Example 6.1.8a), purification of *Pseudomonas denitrificans* cobyric acid synthase is carried out as described below.

In a typical purification experiment, wet SC510 Rif[r] cells (6 g), into which strain plasmid pXL618 (see Example 4.5.2) has been introduced, are sonicated in 0.1 M Tris-HCl pH 7.7, 1 mM DTT, 1 mM EDTA buffer (15 ml). After centrifugation (50,000×g for 1 h), the extract is brought to 20% of glycerol (vol/vol). 10 mM Tris-HCl, 1 mM DTT, 20% glycerol buffer (24 ml) are added to the crude extract (8.5 ml; 203.5 mg of proteins). The solution is injected onto Mono Q HR 10/10 (Pharmacia) at 2 ml/min, equilibrated with 50 mM Tris-HCl pH 7.7, 1 mM DTT, 20% glycerol buffer. The proteins are eluted with a linear gradient of 0.5 M NaCl and the active fractions are pooled and brought to 1 mM EDTA. The solution is brought to 0.85 M with respect to ammonium sulphate and injected onto a Phenyl-Superose HR 5/5 (Pharmacia) column equilibrated in Tris-HCl pH 7.7, 1 mM DTT, 0.85 M ammonium sulphate buffer, and the proteins are eluted with a linear decreasing gradient of 0.85 M to 0 M ammonium sulphate. The fractions are immediately brought to 20% of glycerol. The active fraction is concentrated to 2.5 ml by ultrafiltration and chromatographed on a PD 10 (Pharmacia) column equilibrated and eluted with 50 mM Tris-HCl pH 8.3, 1 mM DTT, 20% glycerol (vol/vol) buffer. The protein fraction is collected and injected onto a mono Q HR 5/5 column equilibrated with the same buffer, and the proteins are eluted with a linear gradient of 0.5 M NaCl. Gel permeation chromatography on Bio-Sil 250 (Bio-Rad) gel in 50 mM Tris-HCl pH 7.5, 1 mM DTT, 20% glycerol, 0.1 M NaCl buffer medium finally enables a protein which is more than 97% pure to be obtained. It shows no contaminant protein in SDS-PAGE. This purity is confirmed by the uniqueness of the $NH_2$-terminal sequence. Its molecular weight in this technique is 57,000. The different steps of purification of cobyric acid synthase with their purification factor and their yield are given in the table below.

TABLE

Purification of cobyric acid synthase

| Purification step | Vol (ml) | Proteins (mg) | Sp. activity U/mg a b A B | Yield[a] | Purification factor[1] |
|---|---|---|---|---|---|
| Crude extract | 8.5 | 203 | 114/118 | — | — |
| Mono Q 10/10 | 8.0 | 35.5 | 388/425 | 60 | 3.4 |
| Phenyl-Superose | 8.0 | 3.23 | 1988/2021 | 28 | 17 |
| Mono Q 5/5 | 1.0 | 1.20 | 4549/4085 | 24 | 40 |
| Bio-Sil 250 | 0.75 | 0.88 | 4992/N.D. | 19 | 44 |

[a]with Ado-cobyrinic acid a,c-diamide as substrate
b with Ado-cobyrinic acid pentaamide as substrate
ND = Not Determined The very high degree of purity of the purified protein, together with the constancy of the ratio of the activities of amidation of cobyrinic acid diamide and pentaamide throughout the process of purification of the protein (see table above), indicate unambiguously that one and the same protein is responsible for the four activities of amidation of the corrin ring-system at positions b, d, e and g.

c) $NH_2$-Terminal Sequence of *Pseudomonas denitrificans* Cobyric Acid Synthase and Identification of the *Pseudomonas denitrificans* Structural Gene Coding for This Activity The $NH_2$-terminal sequence of *Pseudomonas denitrificans* cobyric acid synthase was determined as described above. Sixteen residues were identified:

Thr-Arg-Arg-Ile-Met-Leu-Gln-Gly-Thr-Gly-Ser-Asp-Val-Gly-Lys-Ser (amino acids 2–17 of SEQ ID NO: 43)

The $NH_2$-terminal sequence of the COBQ protein (FIG. 47) corresponds exactly to this sequence except that, in the sequence presented in FIG. 47, a methionine precedes the peptide sequence determined by direct sequencing. It follows from this that the amino-terminal methionine is definitely excised in vivo by methionine aminopeptidase (Ben Bassat and Bauer, 1987). The molecular weight of the purified cobyric acid synthase is estimated by SDS-PAGE electrophoresis at 57,000. The COBQ protein has a molecular weight deduced from its sequence of 52,000 (FIG. 47). The correspondences between the $NH_2$-terminal sequences and the molecular weights indicate clearly that the COBQ protein corresponds to cobyric acid synthase. The cobQ gene is the cobyric acid synthase structural gene.

6.1.9. Identification of the COBO Protein Encoded by the cobO Gene a) Assay of cob(I)Alamin Adenosyltransferase (EC 2.5.1.17) Activity This example illustrates the assay of an enzymatic activity directly linked to the pathway of biosynthesis of cobalamins. The enzyme in question is cob(I)alamin adenosyltransferase (EC 2.5.1.17). This enzyme was demonstrated in bacterial cells (Ohta et al., 1976, Brady et al., 1962) and animal cells (Fenton et al., 1978). It was purified from *Clostridium tetanomorphum* (Vitols et al., 1966).

The fractions containing cob(I)alamin adenosyltransferase activity (approximately 26 units) are incubated anaerobically at 30° C. for 15 min protected from light in 0.2 M Tris-HCl buffer pH 8.0 (1 ml) in the presence of 5 mM DTT, 400 $\mu$M [8-$^4$C)-ATP (2.5 $\mu$Ci/$\mu$mol), 800 $\mu$M $MnCl_2$, 50 $\mu$M hydroxocobalamin or diaquacobinamide and $KBH_4$ (3 mg). The reaction is then stopped by heating to 80° C. for 10 min and, after centrifugation at 15000×g for 5 min, the supernatant (200 $\mu$l) is analysed by HPLC (Gimsing et al., 1986, JacobSen et al., 1986).

The unit of enzymatic activity is defined as the quantity of enzyme necessary for generating 1 nmol of adenosylcorrinoid per min under these conditions.

b) Purification of cob(I)Alamin Adenosyltransferase Activity

Using the assay described in Example 6.1.9a), the purification of *Pseudomonas denitrificans* cob(I)alamin adenosyltransferase is carried out as described below.

In a typical purification experiment, wet cells (10 g) of strain SC510 Rif$^r$ in which the cobO gene has been amplified are suspended in 0.2 M Tris-HCl buffer pH 8.0 (20 ml) and sonicated for 40 min at 4° C. The crude extract is then recovered by centrifugation for 1 h at 50,000×g and desalted on PD10 (Pharmacia) columns equilibrated with 50 mM Tris-HCl pH 8.0, 5 mM DTT buffer (buffer A). The protein solution is then fractionated (280 mg of proteins at each chromatographic run) on a Mono Q HR 10/10 (Pharmacia) column using a gradient of 0 to 0.5 M KCl in buffer A, and the fractions containing the activity are then pooled, concentrated by ultrafiltration and chromatographed on a Phenyl-Superose HR 10/10 (Pharmacia) column in a linear decreasing ammonium sulphate gradient (1.7 to 0 M), the column being equilibrated in 0.1 M Tris-HCl pH 8.0, 5 mM DTT buffer. To complete the purification, the protein is finally chromatographed, after concentration by ultrafiltration, on a Bio-Sil 250 (Bio-Rad) column eluted with 50 mM Tris-HCl pH 7.5, 0.1 M NaCl, 5 mM DTT buffer.

After this step, the enzyme is more than 95% pure. It does not show any contaminant protein in SDS-PAGE. Its molecular weight in this technique is 28,000. This degree of purity is confirmed by the uniqueness of the $NH_2$-terminal sequence. The different steps of purification of cob(I)alamin adenosyltransferase, with their purification factor and their yield, are given in the table below for the following two substrates: diaquacobinamide (a) and hydroxocobalamin (b). These results demonstrate the absence of specificity of this enzyme for the nature of the corrinoid substrate. Moreover, all corrinoids of the biosynthetic pathway between cobyrinic acid diamide and $B_{12}$ have been isolated (Blanche et al., unpublished results) in their native form, and have proved to be in coenzyme form. This demonstrates that the natural substrate of cob(I)alamin adenosyltransferase is cobyrinic acid a,c-diamide.

TABLE

Purification of cob(I)alamin adenosyltransferase

| Purification step | Vol (ml) | Proteins (mg) | Sp. activity U/mg a b A B | Yield[a] | Purification factor[1] |
|---|---|---|---|---|---|
| Crude extract[c] | 100 | 1400 | 5.4/3.4 | — | — |
| Mono Q 10/10 | 90 | 140 | 34.9/14.1 | 65 | 6.5 |
| Phenyl-Superose | 30 | 15.9 | 84.5/49.5 | 18 | 16 |
| Bio-Sil 250 | 6.5 | 2.9 | 182.4/88.7 | 7.0 | 34 |

[c]after desalting on PD10 c) $NH_2$-Terminal Sequence of *Pseudomonas denitrificans* cob(I)Alamin Adenosyltransferase and Identification of the *Pseudomonas denitrificans* Structural Gene Coding for This Activity.

The $NH_2$-terminal sequence of *Pseudomonas denitrificans* cob(I)alamin adenosyltransferase, purified as described in Example 6.1.9b), was determined as described above. 13 residues were identified:

Ser-Asp-Glu-Thr-?-Val-Gly-Gly-Glu-Ala-Pro-Ala-Lys-Lys (amino acids 2–5 of SEQ ID NO: 51 and amino acids of SEQ ID NO: 51)

The $NH_2$-terminal sequence of the COBO protein (FIG. 47) corresponds exactly to the $NH_2$-terminal sequence of cob(I)alamin adenosyltransferase except that, in the sequence presented in FIG. 47, a methionine precedes the peptide sequence determined by direct sequencing. It follows from this that the amino-terminal methionine is definitely excised in vivo by methionine aminopeptidase (Ben Bassat and Bauer, 1987). The molecular weight of the purified cob(I)alamin adenosyltransferase is estimated by SDS-PAGE electrophoresis at 28,000. The COBO protein has a molecular weight deduced from its sequence of 24,000 (FIG. 47). The correspondences between $NH_2$-terminal sequences and the molecular weights indicate clearly that the COBO protein corresponds to cob(I)alamin adenosyltransferase. The cobO gene is the cob(I)alamin adenosyltransferase structural gene.

6.1.10. Identification of the COBN Protein Encoded by the cobN Gene a) Demonstration of the Activity of Conversion of Hydrogenobyrinic Acid a,c-Diamide to Cobyrinic Acid a,c-Diamide This example illustrates the demonstration of an enzymatic activity directly linked to the pathway of biosynthesis of cobalamins which has never been described hitherto. The activity in question is that of conversion of hydrogenobyrinic acid a,c-diamide to cobyrinic acid a,c-diamide.

This activity is demonstrated, inter alia, by the following typical experiment. A crude extract of strain SC510 Rif$^r$ is obtained by sonication of wet cells (10 g) in 0.2 M Tris-HCl buffer pH 8.0 (20 ml), followed by removal of the cell debris by centrifugation for 1 h at 50,000×g. Proteins (1000 mg) of this extract are incubated for 1 h at 30° C. with carbon-14-labelled hydrogenobyrinic acid diamide (32 nmol; 50 $\mu$Ci/$\mu$mol) in 0.2 M Tris-HCl buffer pH 8.0 (40 ml) containing 7 mM ATP and 200 $\mu$M $CoCl_2$. The reaction is stopped by adding 1 M $KH_2PO_4$ (7.5 ml) and 0.3 M KCN (6 ml), followed by heating for 10 min at 80° C. After centrifugation at 15000×g for 50 min, HPLC analysis of the supernatant shows: (1) the formation during the incubation of cobyrinic acid a,c-diamide (19.2 nmol) having the same specific radioactivity as the starting hydrogenobyrinic acid a,c-diamide, and (2) the disappearance of a corresponding quantity of the latter. To confirm that the product is indeed cobyrinic acid a,c-diamide, the product is purified by HPLC and then esterified in methanol containing 5% of sulphuric acid (18 h, 20° C.). The authenticity of the cobyrinic acid a,c-diamide pentamethyl-ester produced is demonstrated by TLC (relative to a reference sample) and mass spectrometry. It should be noted that, under similar incubation conditions in which the radioactive labelling is introduced, not into the hydrogenobyrinic acid a,c-diamide, but into the cobalt (using cobalt-57), cobalt-57-labelled cobyrinic acid a,c-diamide is biosynthesised and the same conclusions could be drawn.

Carbon-14-labelled hydrogenobyrinic acid a,c-diamide is obtained in the following manner: hydrogenobyrinic acid is biosynthesised in vitro using [methyl-$^{14}$C]SAM, then converted to hydrogenobyrinic acid a,c-diamide and purified by HPLC as described in Example 6.1.2.

This study demonstrates that the insertion of cobalt takes place at hydrogenobyrinic acid a,c-diamide level in *P. denitrificans*. Under the conditions described, hydrogenobyrinic acid is not a substrate for enzymatic chelation with cobalt.

b) Assay and Purification of a Protein of Strain SC510 Rif$^r$ Involved in the Conversion of Hydrogenobyrinic Acid a,c-Diamide to Cobyrinic Acid a,c-Diamide The fraction to be assayed (0.5 to 2 units) is incubated for 60 min at 30° C. with crude extract (50 $\mu$l) of strain SC510 Rif$^r$ obtained as described above, 7 mM ATP, 200 $\mu$M $CoCl_2$, and 7 μM carbon-14-labelled hydrogenobyrinic acid a,c-diamide (50 μCi/μmol) in 0.1 M Tris-HCl buffer pH 8.0 (400 μl). The reaction is stopped by adding 1 M $KH_2PO_4$ (75 μl) and 0.3 M KCN (60 μl), followed by heating for 10 min at 80° C. After centrifugation at 15000×g for 15 min, the supernatant is analysed by HPLC in order to quantify the cobyrinic acid a,c-diamide formed (see Example 9). The unit of enzymatic activity is defined as the quantity of enzyme necessary for generating 1 nmol of cobyrinic acid a,c-diamide per h under these conditions. Under these conditions, it is apparent that extracts of strain SC510 $Rif^r$ into which plasmid pXL1909 has been introduced (see Example 4.5.2) possess an activity between 20 and 50 times as high as extracts of strain SC510 $Rif^r$. It is on this basis that a protein which is alone responsible for this amplication of activity is purified.

In a typical purification experiment, wet cells (10 g) of strain SC510 $Rif^r$, into which plasmid pXL1909 has been introduced, are suspended in 0.2 M Tris-HCl buffer pH 8.0 (20 ml) and sonicated for 30 min at 4° C. The crude extract is then recovered by centrifugation for 1 h at 50,000×g and desalted on PD10 (Pharmacia) columns equilibrated with 0.1 M Tris-HCl buffer pH 8.0 (buffer A). The protein solution is then fractionated (213 mg of proteins at each chromatographic run) on a Mono Q HR 10/10 (Pharmacia) column using a gradient of 0 to 0.5 M KCl in buffer A, and the fractions containing the activity are then pooled, concentrated by ultrafiltration, desalted on PD10 (Pharmacia) columns equilibrated with 0.1 M Tris-HCl buffer pH 7.2 (buffer B) and chromatographed on a Mono Q HR 10/10 (Pharmacia) column using a gradient of 0 to 0.5 M KCl in buffer B. The fractions containing the activity are pooled, concentrated by ultrafiltration, desalted on PD10 (Pharmacia) columns equilibrated with buffer B and chromatographed on a Mono Q HR 5/5 (Pharmacia) column using a gradient of 0 to 0.5 M KCl in buffer B. To complete the purification, the protein is finally chromatographed on a Bio-Sil 250 (Bio-Rad) column eluted with 20 mM potassium phosphate/50 mM sodium sulphate pH 6.8.

After this step, the enzyme is more than 95 t pure. It does not show any contaminant protein in SDS-PAGE. Its molecular weight in this technique is 135,000. This degree of purity is confirmed by the uniqueness of the $NH_2$-terminal sequence. The different steps of purification of the protein of strain SC510 $Rif^r$ involved in the conversion of hydrogenobyrinic acid a,c-diamide to cobyrinic acid a,c-diamide, with their purification factor and their yield, are given in the table below.

TABLE

Purification of a protein of strain SC510 $Rif^r$ involved in the conversion of hydrogenobyrinic acid a,c-diamide cobyrinic acid a,c-diamide

| Purification step | Vol (ml) | Proteins (mg) | Sp. activity (u/mg of proteins) | Yield | Purification factor[1] |
|---|---|---|---|---|---|
| Crude extract | 31.5 | 1278 | 0.23 | — | — |
| Mono Q 10/10 | 44 | 79.2 | 2.4 | 64 | 10 |
| Mono Q 10/10 | 21 | 33.6 | 6.8 | 78 | 30 |
| Mono Q 5/5 | 3 | 6.6 | 16.0 | 36 | 70 |
| Bio-Sil 250 | 1.8 | 5.9 | 16.3 | 33 | 71 |

c) $NH_2$-Terminal Sequence of the *Pseudomonas denitrificans* Protein Involved in the Conversion of Hydrogenobyrinic Acid a,c-Diamide to Cobyrinic Acid a,c-Diamide, and Identification of the *Pseudomonas denitrificans* Structural Gene Coding for This Activity The $NH_2$-terminal sequence of this protein, purified as described in Example 6.1.10b), was determined as described above. Six residues were identified:

His-Leu-Leu-Leu-Ala-Gln (amino acids 2–7 of SEQ ID NO: 49)

The $NH_2$-terminal sequence of the COBN protein (FIG. 47) corresponds exactly to the $NH_2$-terminal sequence of the purified protein except that, in the sequence presented in FIG. 47, a methionine precedes the peptide sequence determined by direct sequencing. It follows from this that the amino-terminal methionine is definitely excised in vivo by methionine aminopeptidase (Ben Bassat and Bauer, 1987). The molecular weight of the purified protein is estimated by SDS-PAGE electrophoresis at 135,000. The COBN protein has a molecular weight deduced from its sequence of 138,000 (FIG. 47). The correspondences between the $NH_2$-terminal sequences and the molecular weights indicated clearly that the COBN protein corresponds to the protein involved in the conversion of hydrogenobyrinic acid a,c-diamide to cobyrinic acid a,c-diamide. The cobN gene is hence the structural gene for this protein.

6.1.11. Identification of the COBP Protein Encoded by the cobP Gene a) Assay of Cobinamide Kinase Activity This example illustrates the assay of an enzymatic activity of the pathway of biosynthesis of cobalamins which has never been studied hitherto. The activity in question is that of cobinamide kinase. It catalyses the ATP-dependent phosphorylation of the hydroxyl group of the (R)-1-amino-2-propanol residue of Ado-cobinamide to generate cobinamide phosphate.

The fraction to be assayed is incubated in darkness at 30° C. for 60 min in 0.1 M Tris-HCl buffer pH 8.8 (500 μl) containing 1 mM EDTA, 1 mM ATP, 2.5 mM $MgCl_2$ 16 μM Ado-cobinamide (Blanche et al., 1989). The reaction is stopped by adding 20 mM aqueous potassium cyanide solution (500 μl). After heating to 80° C. for 10 min and centrifugation at 5,000×g for 10 min, the cobinamide phosphate formed, present in the supernatant, is assayed by HPLC (see Example 9) using the following simplified linear gradient: 25% to 30% of B in A in the course of 15 min, then 30% to 100% of B in the course of 12 min, and 3 min at 100% of B.

The unit of activity is defined as the quantity of enzyme necessary for generating 1 nmol of cobinamide phosphate from cobinamide per h under these conditions.

b) Assay of Cobinamidephosphate Guanylyltransferase Activity

This example illustrates the assay of an enzymatic activity of the pathway of biosynthesis of cobalamins which has never been studied hitherto. The activity in question is that of cobalamidephosphate guanylyltransferase. It catalyses the addition of the GMP portion of a GTP molecule to Ado-cobinamide phosphate, thereby generating one molecule of GDP-cobinamide and liberating one molecule of pyrophosphate.

This activity is assayed under the same conditions as cobinamide kinase, except that Ado-cobinamide phosphate (16 μM) (Blanche et al., 1989) and GTP (2 mM) replace Ado-cobinamide and ATP, respectively, during the incubation.

The unit of activity is defined as the quantity of enzyme necessary for generating 1 nmol of GDP-cobinamide from cobinamide phosphate per h under these conditions.

c) Purification of Cobinamide Kinase

Using the assay described in Example 6.1.11a), the purification of *Pseudomonas denitrificans* kinase is carried as described below.

In a typical purification experiment, wet SC510 Rif$^r$ cells (5 g), into which strain plasmid pXL623 has been introduced (see Example 4.5.2) are sonicated in 0.1 M Tris buffer pH 7.6 (buffer A) (20 ml). After centrifugation (50,000×g for 1 h) and dialysis for 4 h against buffer A, the retentate (4.5 ml) is injected onto Mono Q HR 10/10 (Pharmacia) equilibrated with buffer A. The proteins are eluted with a linear gradient of 0.4 M NaCl, and the pooled active fractions are passed through a PD-10 (Pharmacia) column equilibrated in 30 mM Tris-HCl/5 mM potassium phosphate/5 $\mu$M calcium chloride pH 7.6 (buffer B). The protein solution is fractionated on a Bio-Gel HPHT (Bio-Rad) column equilibrated in buffer B and eluted with a gradient of 5 to 350 mM potassium phosphate. The active fractions are pooled and brought to 500 mM with respect to ammonium sulphate, and then fractionated on a Phenyl-Superose HR 5/5 (Pharmacia) column eluted with a decreasing ammonium sulphate gradient. The fraction containing the activity is finally repurified on a Mono Q HR 5/5 column in Tris-HCl at pH 7.3. After this step, the protein is more than 97% pure. It shows no contaminant protein in SDS-PAGE. This purity is confirmed by the uniqueness of the $NH_2$-terminal sequence. Its molecular weight in this technique is 20,000. The different steps of purification of cobinamide kinase, with their purification factor and their yield, are given in FIG. 55.

The fractions containing cobinamide kinase activity also possess cobinamidephosphate guanylyltransferase activity. Moreover, as shown by the results presented in the table above, the ratio of these two activities remains constant in the fractions throughout the purification. Lastly, the purified protein possesses a very high degree of purity, exceeding 97%. These results collectively hence indicate unambiguously that one and the same protein is responsible for both successive activities, namely cobinamide kinase and cobinamidephosphate guanylyltransferase of the pathway of biosynthesis of cobalamins in *Pseudomonas denitrificans.* d) $NH_2$-Terminal Sequence of *Pseudomonas denitrificans* Cobinamide Kinase/Cobinamidephosphate Gunaylyltransferase, and Identification of the *Pseudomonas denitrificans* Structural Gene Coding for This Activity The $NH_2$-terminal sequence of *Pseudomonas denitrificans* cobinamide kinase/cobinamidephosphate guanylyltransferase was determined as described above. Ten residues were identified:

Ser-Ser-Leu-Ser-Ala-Gly-Pro-Val-Leu-Val (amino acids 2–11 of SEQ ID NO: 45)

The $NH_2$-terminal sequence of the COBP protein (FIG. 47) corresponds exactly to this sequence except that, in the sequence presented in FIG. 47, a methionine precedes the peptide sequence determined by direct sequencing. It follows from this that the amino terminal methionine is definitely excised in vivo by methionine aminopeptidase (Ben Bassat and Bauer, 1987). The molecular weight of the purified cobinamide kinase/cobinamidephosphate guanylyltransferase is estimated by SDS-PAGE electrophoresis at 20,000. The COBP protein has a molecular weight deduced from its sequence of 19,500 (FIG. 47). The correspondences between the $NH_2$-terminal sequences and the molecular weights indicate clearly that the COBP protein corresponds to cobinamide kinase/cobinamidephosphate guanylyltransferase. The cobP gene is the cobinamide kinase/cobinamidephosphate guanylyltransferase structural gene.

6.2—Determination of the Properties of COB Proteins by Measurement of Accumulated Biosynthesis Intermediates This example illustrates how it is possible to assign an enzymatic activity to a COB protein of *Pseudomonas denitrificans*. This activity is assigned on the basis of data obtained relating to accumulated biosynthesis intermediates in the Cob mutant or mutants blocked in the step in question. In effect, if a mutant accumulates a biosynthesis intermediate, it is very probable that this mutant is blocked in the step which has the intermediate in question as its substrate.

6.2.1. Properties of the COBC and COBD Proteins

The Cob mutants G643 (*Agrobacterium tumefaciens*) and G572 (*Pseudomonas putida*) already described in Examples 1 and 4 are blocked in the step corresponding to the COBC protein. In effect, these two mutants are not complemented by the inactivating insertions of transposons Tn5 which occur in the cobC gene. The two strains G643 and G572, as well as the unmutated parent strains (C58-C9 Rif$^r$ and KT 2440 Rif$^r$ (Cameron et al., 1989)], were cultured in PS4' medium for *A. tumefaciens* and PS4" medium for *P. putida* (PS4' and PS4" correspond to PS4 medium containing 100-fold and 1000-fold, respectively, less cobalt than PS4 described above) for 3 days as described above. $^{57}CoCl_2$ was added to the cultures (2.5 $\mu$Ci/0.1 Am for a 25-ml culture). The intracellular corrinoids were isolated in their native form and identified by their HPLC behaviour. The parent strains do not accumulate corrinoids other than coenzyme $B_{12}$. The two mutants G643 and G572 accumulate adenosylated cobyric acid in respective proportions of 11% and 6%. These % proportions are calculated relative to the level of coenzyme $B_{12}$ synthesised by the parent strain. Apart from cobyric acid, mutant G643 accumulates cobyrinic acid pentaamide in a proportion of 2%; cobyrinic acid pentaamide is the intermediate which precedes cobyric acid. A study of these mutants brings out the fact that they are blocked after cobyric acid. All these Cob mutants are blocked either between uro'gen III and cobinamide, or between cobinamide and the cobalamins. The mutants G643 and G572 are blocked between uro'gen III and cobinamide. Now, if these mutants are blocked before cobinamide, and both accumulate cobyric acid, the proteins for which they code can participate only in the enzymatic step (referred to as cobinamide synthase) which catalyses the amidation of cobyric acid with an aminopropanol residue to give cobinamide; they can also possibly participate in the synthesis of the substrate of the reaction which provides aminopropanol, if not aminopropanol itself. The cobC gene codes for a protein which is either cobinamide synthase or one of its subunits.

The Cob mutant G634 of *Agrobacterium tumefaciens* which is blocked in the step corresponding to the cobD gene was analysed in the same manner. This mutant is not complemented by the inactivating insertions in the cobD gene (Example 4.1). The only intracellular corrinoid found in this mutant is adenosylated cobyric acid. Like the above mutants, this mutant codes for a protein participating in the conversion of cobyric acid to cobinamide, or else possibly in the synthesis of the other substrate of the reaction.

These two different genes (cobC and cobD) code for two proteins which participate in the same step.

6.2.2. Properties of the COBF to COBM Proteins

The *Agrobacterium tumefaciens* mutants already described were studied, the study described in Example 4.2 having shown in which genes each of these mutants is blocked. They are the following mutants: G612 (cobF), G615 (cobG), G616 (cobH), G613 (cobI), G611 (cobJ), G620 (cobK), G638 (cobL) and G609 (cobM); we have shown in brackets the *Pseudomonas denitrificans* gene responsible for the complementation of these mutants (Example 5), which hence corresponds to the gene mutated in this mutant. These mutants were cultured in PS4 medium as described above with labelled cobalt. After four days' incubation, the mutants were analysed for their intracellular content of corrinoids and decobaltocorrinoids (see Examples 6.1.2 and 9).

TABLE

Intermediates accumulated by *Agrobacterium tumefaciens* mutants blocked in the genes of the 8.7-kb fragment of *Pseudomonas denitrificans*

| Strain | Intracellular decobalto-corrinoids in %[1] HBA | HBAM | HBAD | Intracellular corrinoids as % of cobalamins | Mutated gene |
|---|---|---|---|---|---|
| C58-C9* | 100 | 100 | 100 | coenzyme $B_{12}$100 | — |
| G612 | <5 | <5 | 64 | cobinamide 2.2<br>coenzyme $B_{12}$34 | cobF |
| G615 | <5 | <5 | 84 | coenzyme $B_{12}$17 | cobG |
| G616 | 35 | <10 | <10 | coenzyme $B_{12}$13 | cobH |
| G613 | <5 | <5 | 57 | coenzyme $B_{12}$ < 1 | cobI |
| G611 | <5 | <5 | 65 | coenzyme $B_{12}$ < 1 | cobJ |
| G620 | 12 | <5 | <10 | coenzyme $B_{12}$ < 1 | cobK |
| G638 | <5 | <5 | 47 | coenzyme $B_{12}$ < 1 | cobL |
| G609 | <5 | <5 | 33 | coenzyme $B_{12}$ < 1 | cobM |

HBA: hydrogenobyrinic acid
HBAM: hydrogenobyrinic acid monoamide
HBAD: hydrogenobyrinic acid diamide
*in fact, this is strain C58-C9 $Rif^rNal^r$ already described (Cameron et al., 1989)
[1]the values are expressed as % of the same intermediates accumulated in the unmutated parent strain C58-C9 $Rif^rNal^r$.

These results show that none of the mutants accumulate any corrinoid (with the exception of the mutant inactivated in the cobF gene, G612, which, for its part, accumulates cobinamide but at a low level equivalent to 2.2% of the cobalamins synthesised by the unmutated strain). However, some mutants (G612, G615 and G616) have levels of cobalamins which represent more than 10% of the cobalamin level of the parent strain. It is probable that all these mutants are blocked at least before cobyrinic acid diamide. All the mutants accumulate hydrogenobyrinic acid and hydrogenobyrinic acid diamide in smaller quantities than the unmutated strain; they are hence very probably blocked before hydrogenobyrinic acid. It may be concluded that all the cobF to cobG genes code for proteins which participate before hydrogenobyrinic acid. Mutant G613 is known to be mutated in the cobI gene which codes for $SP_2MT$, participating well before hydrogenobyrinic acid. For this mutant, the results of the present example relating to the accumulation of intermediates are in complete agreement with the step inactivated in this mutant, namely, this mutant accumulates no intermediate after hydrogenobyrinic acid at a level higher than that observed with the unmutated strain. This result is, for the cobF, cobJ, cobL and cobM genes, consistent with those of Example 6.4, where it proposed that these genes code for proteins which catalyse SAM-dependent transfers of methyl and hence which participate before hydrogenobyrinic acid. With the exception of cobI, which is the $SP_2MT$ structural gene, these genes participate after precorrin-3. In effect, since they are neither the structural genes for SUMT nor for $SP_2MT$, they inevitably participate later, that is to say after precorrin-3 (all the cob genes described in the present invention participate between uro'gen III and the cobalamins). These cobF to cobH and cobJ to cobM genes code for enzymes which participate between precorrin-3 and hydrogenobyrinic acid.

6.2.3. Properties of the COBS and COBT Proteins

The mutant G2035 described in Examples 1 and 4.3 is blocked in the step corresponding to the COBS protein. The mutant G2037 described in Example 1 is blocked in this step corresponding to the COBT protein. These strains, as well as the parent strain (*Agrobacterium tumefaciens* C58C9$Rif^r$), are cultured in PS4' medium (this is PS4 medium in which the cobalt chloride concentration is 100-fold lower than in PS4 medium) in the presence of radioactive cobalt $^{57}CoCl_2$ for 3 days, and their intracellular content of decobaltocorrinoids is analysed, as is the corrinoid content, as already described above (see Example 6.2.2). The strains G2035 and G2037 do not accumulate corrinoids, and large concentrations (greater than those observed with the parent strain) of hydrogenobyrinic acid and hydrogenobyrinic acid mono- and diamide are present only with strain G2035. This mutant is probably blocked in a step located after hydrogenobyrinic acid diamide and before cobyrinic acid diamide. Consequently, the cobS gene is considered to code for one of the enzymes involved in the conversion of hydrogenobyrinic acid diamide to cobyrinic acid diamide; this protein may hence participate either in the insertion of cobalt, or in the reduction of the cobalt of unadenosylated cobyrinic acid a,c-diamide. In contrast, the mutant G2037 is considered to be blocked in a step located upstream of hydrogenobyrinic acid. The cobT gene is considered to code for a protein involved in an enzymatic step upstream of hydrogenobyrinic acid and downstream of precorrin-3 (other structural genes coding for enzymes involved downstream of precorrin-3 have already been identified). Another possibility for the COBT protein is that it participates, as proposed in Example. 5, as a cobalt-binding protein and/or as a protein which interacts with other protein(s) via its acidic portion.

6.2.4. Properties of the COBV Protein

The mutants G2039 and G2040 described in Examples 1 and 4.4 are blocked in the step corresponding to the COBV protein. These strains, as well as the parent strain, are cultured in PS4' medium for 3 days in the presence of radioactive cobalt $^{57}CoCl_2$, and their intracellular content of decobaltocorrinoids is then analysed and the corrinoid content is determined as described in Example 9. Strains G2039 and G2040 accumulate cobyric acid, cobinamide, cobinamide phosphate and GDP-cobinamide. These mutants are probably blocked in an enzymatic step downstream of GDP-cobinamide. The cobV gene is considered to code for an enzyme involved in the conversion of GDP-cobinamide to cobalamin, see FIG. 5. This result is in complete agreement with the cobalamin-5'-phosphate synthase activity of the COBV protein which possesses Ado-GDP-cobinamide as a substrate.

6.3—Determination of the Activity of COB Proteins by Studies of Affinity for SAM This example illustrates how it is possible, using COB proteins purified from *Pseudomonas denitrificans*, to demonstrate in vitro a SAM-binding activity. If a COB protein possesses such an activity, it means that this COB protein is a methyltransferase of the pathway, and that it participates in one of the transfers of the eight methyl groups which occur between the uro'gen III and cobyrinic acid.

6.3.1. Test of Affinity for SAM on a Purified Protein

The test is based on the principle according to which methyl transferases of the pathway of biosynthesis of cobalamins definitely have an SAM-binding site. This site must be demonstrated by a higher affinity of SAM than for any protein which does not specifically bind SAM. After incubation of the protein under study in the presence of an excess of radioactive SAM, the latter is separated from the free SAM by gel permeation chromatography. The radioactivity appearing in the fraction having the molecular weight of the protein corresponds to the SAM bound during the incubation. The chromatography is performed at 2° C. in order to limit to the maximum the release of bound SAM during the separation.

The protein (approximately 10 μg) is incubated for 10 minutes at 30° C. in 0.1 M Tris-HCl pH 7.7 (200 μl) with [methyl-$^3$H]SAM (5 nmol; 1 μCi). After incubation, a portion (100 μl) of the mixture is immediately injected onto a TSK-125 (Bio-Rad) column eluted at 1 ml/minute with the 50 mM sodium sulphate/20 mM sodium dihydrogen phosphate mixture, pH 6.8, recommended by the distributor of this column. 0.5-ml fractions are collected and subjected to liquid scintillation counting. The retention times of the protein and the SAM are obtained directly from the recording of the absorbance of the eluate at 280 nm.

6.3.2. In vitro Study of the Binding of SAM to the COBA and COBF Proteins of *Pseudomonas denitrificans* a) Purification of the COBF and COBA Proteins

The COBF protein of *Pseudomonas denitrificans* is purified as described below. In a typical purification experiment, wet cells (5 g) of strain SC150 Rif$^r$ into which plasmid pXL1546 has been introduced (see Ex. 7.3), obtained after culturing in PS4 medium, are resuspended in 0.1 M Tris-HCl pH 7.7 (30 ml) and sonicated for 15 minutes at 4° C. The crude extract is then recovered by centrifugation for 1 hour at 50,000 g, and the supernatant is passed through a DEAE-Sephadex column (1 ml of gel) to remove the tetrapyrrole compounds present. Proteins (10 mg; 0.7 ml) of this extract are then injected onto a MonoQ HR 5/5 column equilibrated with the same buffer. The proteins are eluted with a linear KCl gradient (0 to 0.25 M). The COBF protein is eluted with 0.20 M KCl. It is diluted twofold with 0.1 M Tris-HCl pH 7.7 and purified a second time on a MonoQ HR 5/5. SDS-PAGE electrophoresis with visualisation with Coomassie blue is used to reveal the protein. This technique shows, moreover, that COBF is approximately 95% pure after this purification step. The $NH_2$-terminal sequence of the purified protein was determined as described above. Two $NH_2$-terminal sequences appear at the same time in each degradation cycle; they are the following sequences, in the proportions indicated:

Sequence 1 (abundance 34%)

1 2 3 4 5 6 7 8 9 10 11

Ala Glu Ala Gly Met Arg Lys Ile Leu Ile Ile (amino acids 2–12 of SEQ ID NO: 14)

Sequence 2 (abundance 66%)

1 2 3 4 5 6 7 8 9 10 11

Met Arg Lys Ile Leu Ile Ile Gly Ile Gly Ser (amino acids 6–16 of SEQ ID NO: 14)

Sequence 1 corresponds to the $NH_2$-terminal sequence of the COBF protein which is given in FIG. 16, except that the amino-terminal methionine is excised according to rules already stated (Hirel et al., 1989) by methionine aminopeptidase (Ben Bassat and Bauer, 1989). Sequence 2, present in the larger amount, corresponds to the same protein but having its translation initiation apparently done not at the translation initiation ATG codon we had assumed, but at that located 5 codons downstream on the coding frame (FIG. 16). In effect, the amino acids of this sequence are exactly those which are found in the sequence of the COBF protein starting from the second methionine (amino acid No. 6) of this sequence (FIG. 16). In this case, the amino-terminal methionine is not excised, which confirms the rules already stated (Hirel et al., 1989). In strain SC510 Rif$^r$ carrying plasmid pXL1546, there are two translation initiations, on the one hand that corresponding to the methionine codon positioned at the correct distance, in our construction, from the Shine-Dalgarno sequence, and on the other hand that which is carried out at the second methionine codon occurring in the sequence of the cobF gene presented in FIG. 16. It emerges from this that the COBF protein proably begins not at the methionine indicated in FIG. 16, but at that occurring 5 amino acids further on.

At all events, this result shows that the COBF protein is, indeed, the one expressed, and that the latter is expressed in a form elongated by 4 amino acids. During purification, both protein forms are purified. In this example, the mixture of these two purified proteins is referred to by us as purified COBF protein.

The COBA protein of *Pseudomonas denitrificans* is purified as described above (Blanche et al., 1989).

b) Binding of SAM

The binding of SAM to these two proteins is studied as described above in Example 6.3 a). Bovine serum albumin and the purified COBH protein are used as negative controls. For the COBA and COBF proteins, a peak of radioactivity is observed at emergence from the TSK-125 column at the emergence time of these proteins (FIG. 20). In this test, the COBI protein displays the same property of binding of SAM. In contrast, there are no such peaks of radioactivity with BSA and the COBH protein. This test demonstrates the in vitro binding of SAM to the COBA, COBI and COBF proteins. These results show that COBA, COBI and COBF are SAM methyltransferases. This result is in complete agreement with the COBA and COBI activities, since they are the SUMT and the SP?MT, respectively, of *Pseudomonas denitrificans*. The COBF protein is hence probably an SAM methyltransferase of the pathway of biosynthesis of cobalamins. This test confirms that COBF is a methyltransferase.

6.4—Determination of the Activity of COB Proteins by Sequence Homology Studies This example illustrates how it is possible to find the COB proteins which are SAM methyl-transferases of the pathway of biosynthesis of cobalamins by comparisons between the sequences of various COB proteins of *Pseudomonas denitrificans*.

The COBI and COBA proteins are both SAM methyltransferases of the biosynthetic pathway. These two proteins were compared according to the programme of Kanehisa, 1984. This comparison brings out three regions of strong homology (FIG. 21). In each of these regions, there is more than 45% strict homology between the two proteins. Three regions of strong homology between COBA and CYSG are also presented (FIG. 22); they are the same regions of COBA which display a strong homology with COBI. These regions of strong homologies between COBA, CYSG and COBI display homology with other COB proteins. The proteins in question are COBF, COBJ, COBL and COBM (FIG. 23). As regards the region 1, the COBF, COBL and COBM proteins display significant homologies with respect to all the Genpro proteins, Genpro being a Genbank (version 59) protein extraction augmented by putative coding portions larger than 200 amino acids, according to the programme of Kanehisa (1984). As regards the region 2, the COBJ, COBL and COBM proteins display significant homologies with respect to all the Genpro (version 59) proteins. As regards the third region of homology, COBJ, COBL and COBM display significant homologies with respect to all the Genpro (version 59) proteins. The sequence comparisons hence enable it to be demonstrated that four proteins, COBF, COBJ, COBL and COBM, display significant homologies with the conserved regions of the sequences of three types of methyltransferases, COBA, COBI and COBF. The COBG, COBH and COBK proteins do not display significant homologies with the conserved regions of the methylases. The COBF protein displays a significant homology with the other proteins only in the region 1. These homologies must probably correspond to the fact that all these proteins are methyltransferases. This result ties up with the biological data described for COBF, relating to the capacity possessed by this protein for binding SAM in vitro (Example 6.3). These homologies on the one hand enable it to be confirmed that COF is an SAM methyltransferase of the pathway of biosynthesis of cobalamins, and on the other hand demonstrate that COBJ, COBL and COBM could be SAM methyltransferases of the pathway of biosynthesis of cobalamins. These results also show the homology existing between the COB proteins of *P. denitrificans* and the isofunctional proteins of other microorganisms.

EXAMPLE 6(B)

Purification and Cloning of the *Methanobacterium ivanovii* SUMT Structural Gene This example illustrates how it is possible to obtain, in other microorganisms, COB enzymes and cob genes corresponding to those identified in *P. denitrificans.*

6(B).1. Purification of *Methanobacterium ivanovii* SUMT

This example describes the purification of *Methanobacterium ivanovii* SUMT and a study of its catalytic properties.

*Methanobacterium ivanovii* strain DSM2611 is cultured as described (Souillard et al., 1988). Wet cells (12 g) are obtained. The latter are resuspended in 0.1 M Tris-HCl buffer pH 7.6 (80 ml) containing 5 mM DTT and 1 mM EDTA, and sonicated for 1 h 30 min at 4° C. and then centrifuged for 1 h at 50,000 g. Free tetrapyrrole compounds are then cleared from the extract by passage through a small DEAE-Sephadex A25 column set up in the same buffer. The proteins precipitating at between 55 and 75% ammonium sulphate saturation are solubilised in a 0.1 M Tris-HCl pH 7.5, 0.5 mM DTT, 1.7 M ammonium sulphate buffer and injected onto a Phenyl-Superose HR 10/10 (Pharmacia France/SA) column eluted with a decreasing gradient (1.7 M to 0 M with respect to ammonium sulphate). The active fractions are passed through a Sephadex G-25 column equilibrated with 0.1 M Tris-HCl pH 7.5, 0.5 mM DTT, 25% glycerol buffer (buffer A), then injected onto a Mono Q HR 5/5 (Pharmacia France SA) column equilibrated with buffer A and eluted with a KCl gradient of 0 to 0.3 M; this step is repeated a second time under the same conditions. Gel permeation chromatography of the active fraction of the preceding step on Bio-Sil TSK-250 (BioRad France SA) enables a protein which is homogeneous in SDS-PAGE and in RP-HPLC (C-18 pBondapak) to be obtained. The different steps of purification, with their yield, as well as their purification factor, are described in the table below.

As shown in this table, the total purification factor is more than 4,500. Some properties of the pure enzyme have been studied according to methods already described (Blanche et al., 1989). This enzyme does indeed have SUMT activity, i.e. it does indeed catalyse the SAM-dependant transfer of two methyl groups at C-2 and at C-7 of uro'gen III. The molecular weight of the enzyme estimated by gel permeation is 60,000+/−1,500, while by SDS-PAGE it is 29,000, which shows clearly that it is a homodimeric enzyme. Under conditions already described (Blanche et al., 1989), the enzyme has a Km for uro'gen III of 52 +/−8 nM. In addition, this enzyme does not show inhibition by substrate at concentrations below 20 μM, whereas *Pseudomonas denitrificans* SUMT shows an inhibition by uro'gen III at a concentration above 2 μM (Blanche et al., 1989).

TABLE

Purification of *M. ivanovii* SUMT

| Purification step | Vol (ml) | Proteins (mg) | Sp. activity (u/mg of proteins) | Yield | Purification factor[1] |
|---|---|---|---|---|---|
| Crude extract | 92 | 731 | 0.337 | — | — |
| 55–75% AS | 7.1 | 153 | 1.215 | 76 | 3.6 |
| Phenyl-Superose | 9.5 | 8.34 | 15.35 | 52 | 46 |
| Mono Q 5/5 | 1.0 | 0.262 | 422 | 43 | 1252 |
| Bio-Sil TSK | 1.0 | 0.061 | 1537 | 38 | 4561 |

[1]calculated from the specific activity of proteins.

The Vmax of *M. ivanovii* SUMT was determined. It is 1537 U/mg of proteins. This value is greater than that found for *P. denitrificans* SUMT, already determined under optimal conditions for the reaction (taking account of its inhibition by uro'gen III), 489 U/mg of proteins (Blanche et al., 1989).

6(B).2. Cloning of the *M. ivanovii* SUMT Structural Gene in *E. coli*

6(B).2.1. Cloning of a fragment internal to the *M. ivanovii* SUMT structural gene. For this purpose, the procedure is as follows: 200 picomols of *M. ivanovii* SUMT are used for the $NH_2$-terminal sequencing of the protein as described above. In addition, a peptide fragment obtained by tryptic digestion of the protein is likewise subjected to a sequencing of its $NH_2$-terminal portion. The sequences obtained are presented in FIG. 48. The sense and antisense oligonucleotides 946, 923 and 947, respectively (see FIG. 48) are synthesised as described above; these oligonucleotides contain a restriction site at their 5' end, which is either EcoRI for the sense oligonucleotides or HindIII for the antisense oligonucleotide. These oligonucleotides are used for an enzymatic DNA amplification experiment (Saiki et al., 1988) as shown diagrammatically in FIG. 48.B.

*M. ivanovii* genomic DNA is prepared in the following manner: *M. ivanovii* (DSM 2611) cells (0.4 g) are washed with 0.15 M NaCl solution. The cells are then incubated in a 25% sucrose, 50 mM Tris-HCl pH 8, lysozyme (40 mg) solution (4 ml), and thereafter for 2 to 3 h at 50° C. after the addition of proteinase K (40 mg) and a 0.2% SDS, 0.1 M EDTA pH 8 solution (5 ml). The DNA is then extracted with phenol/chloroform (50%/50%) twice and then twice with chloroform, and thereafter precipitated with isopropanol and taken up in TNE (10 mM Tris-HCl pH 8, 1 mM EDTA, 100 mM NaCl) (3 ml).

Enzymatic amplification of *M. ivanovii* DNA is performed according to the protocol of Saiki et al., 1988, in a volume of 0.1 ml with *M. ivanovii* genomic DNA (600 ng), using the primers 946 and 947 (reaction 1) or 923 and 947 (reaction 2). The buffer used for this reaction is 1 mM $MgCl_2$, 50 mM KC1, 0.001% gelatin and each dNTP at a concentration of 0.2 mM; for each amplification reaction, 10 mg of each oligonucleotide are used, as well as Taq DNA polymerase (2.5 units) (Cetus Corporation). Amplification is carried out over 30 cycles in the Perkin-Elmer Cetus DNA Amplication system; during each cycle, the DNA is denatured for 1 min at 95° C., the oligonucleotide primers are hybridysed with single-stranded DNA for 2 min at 38° C. and the newly formed strands are polymerised for 3 min at 72° C. The amplification products are then extracted with chloroform and thereafter undergo ethanol precipitation; they can then be visualised after migration on acrylamide gel, and thereafter be digested with restriction enzymes such as EcoRI and HindIII.

In the case of reaction 1, two fragments are observed: at 615 bp as well as at 240 bp. As regards reaction 2, two fragments are also observed: at 630 and 170 bp. The whole of the product of an enzymatic amplification reaction between the oligonucleotides 946-947 is separated by migration on acrylamide gel; the 615-bp fragment is purified as described above. This fragment is then digested with EcoRI and HindIII in order to make the ends of the fragment cohesive. This fragment is then ligated with the DNA of the replicative form of phage M13mp19. The ligation is transformed into *E. coli* TG1. Six recombinant clones containing a 615-bp insert are analysed by sequencing with the universal primer-20 (Pharmacia SA, France). As shown in FIG. 49, when the single-standed DNA of the recombinant phages which contain 615-bp insert is sequenced, there must be observed, downstream of the EcoRI site, a non-degenerate sequence corresponding to that of the oligonucleotide 946 followed, in the same frame, by a sequence coding for the amino acids LITLKAVNVLK?ADVVL (Amino acid fragment 15–31 of SEQ. ID. NO: 54) (? means that, at this position, the residue could not be determined); this sequence corresponds to that which, in the $NH_2$-terminal sequence of SUMT, follows the amino acids corresponding to the oligonucleotide 946 (see FIG. 48). For two clones, there was actually observed, after the EcoRI site, a sequence able to code for the $NH_2$-terminal region of *Methanobacterium ivanovii* SUMT, this sequence beginning with the arrangement Pro-Gly-Asp-Pro-Glu-Leu (Amino acids 10–15 of SEQ. ID. NO: 54) which are the amino acids encoded by a sequence containing the oligonucleotide 946. This observation shows that these two recombinant replicative forms contain an insert which corresponds to a fragment internal to the *Methanobacterium ivanovii* SUMT structural gene. The replicative form carrying this fragment internal to the *M. ivanovii* structural gene is referred to as pGlo.

6(B).2.2. Cloning of the *Methanobacterium ivanovii* SUMT Structural Gene

*Methanobacterium ivanovii* genomic DNA is digested with several restriction enzymes (single or double digestions). After digestion, the fragments are separated by agarose gel electrophoresis and are then transferred onto a nylon membrane as described above. After denaturation of the fragments thus transferred and prehybridisation, a hybridisation is performed with the replicative form pG10as a $^{32}$P-labelled probe, as described above. It is thus found that a 3.2-kb fragment emanating from an EcoRI-BglII digestion of *Methanobacterium ivanovii* hybridises with the probe (see FIG. 50). Genomic DNA (40 pg) of *M. ivanovii* are then digested with EcoRI and BglII and thereafter separated by migration on agarose gel. The fragments having a size of between 3 and 3.5 kb are electroeluted as described above. The fragments thus purified are ligated with the vector pBKS+(Stratagene Cloning Systems, La Jolla) digested with BamHI-EcoRI. The ligation is transformed into *E. coli* DH5α (Gibco BRL). The transformants are selected on LB medium supplemented with ampicillin and X-gal. 800 white colonies are subcultured on filters; after growth and then lysis of the bacteria, a colony hybridisation is performed according to the technique of Grunstein and Hogness (1975). The probe used is the replicative form pG10labelled with $^{32}$p. A single positive clone after this hybridisation test with the probe is found. The plasmid DNA of this clone is referred to as pXL1809 (see FIG. 56). A digestion of this DNA with EcoRI-XbaI enables a 3.2-kb insert to be visualised, as expected. Plasmid pXL1809 is sequenced on both strands by the technique of Chen and Seeburg (1985). A sequence of 955 bases is obtained (FIG. 51). An analysis of the open reading frames leads us to identify an open reading frame from base 34 (ATG) to base 729 (TGA). This open reading frame codes for a protein whose sequence is presented in FIG. 52. This protein has a molecular weight of 24,900 (see FIG. 53), which is close to the molecular weight of the protein purified from *M. ivanovii*. The $NH_2$-terminal sequence of this protein is exactly that determined for purified *M. ivanovii* SUMT (see FIG. 48 and FIG. 52). These observations establish unambiguously that the cloned and sequenced gene is indeed the *M. ivanovii* SUMT structural gene. Since this activity is assumed to participate in the biosynthesis of corrinoids in all bacteria, this gene is designated corA gene, and the protein encoded by this same gene CORA protein. The hydrophobicity profile of the CORA protein of *M. ivanovii*, produced from the programme of Hopp and Woods (1981), shows that it is, as expected, a hydrophilic protein, as presented in FIG. 54. The CORA protein of *M. ivanovii* shows a degree of strict homology of more than 40% with respect to COBA of *P. denitrificans* (FIG. 53). This homology extends over practically the whole of both proteins, since it relates to residues 3 to 227 of CORA of *M. ivanovii* and residues 17 to 251 of COBA of *P. denitrificans*. This homology reflects the structural homologies existing between two proteins that catalyse the same reaction. The regions which are most highly conserved between CORA and COBA of *P. denitrificans* are the same ones as are conserved between COBA of *P. denitrificans* and CYSG of *E. coli* (FIG. 22).

EXAMPLE 7

Expression of COB Proteins

7.1—Expression in *Pseudomonas denitrificans*

This example illustrates that the amplification of a structural gene for a COB protein of *Pseudomonas denitrificans* in *Pseudomonas denitrificans* leads to amplification of the activity of the COB protein.

7.1.1—Expression of the COBA Protein

Plasmid pXL557 corresponds to plasmid pXL59 into which the 2.4-kb BglII-EcoRV fragment (at positions 80 and 2394, respectively, in the sequence of FIG. 7) of the 5.4-kb fragment has been cloned. This fragment contains the cobA and cobE genes.

Plasmid pXL545 contains only the cobE gene. Its construction has been described in Example 4.1.

These two plasmids were introduced by conjugative transfer into SC510 Rif$^r$. Strains SC510 Rif$^r$, SC510 Rif$^r$ pXL59, SC510 Rif$^r$ pXL557 and SC510 Rif$^r$ pXL545 were cultured in PS4 medium. At 4 days, culturing was stopped and the SUMT activities were assayed according to a standard protocol already described (F. Blanche et al., 1989). The activities are given below.

TABLE

SUMT activity of SC510 Rif$^r$ and of some of its derivatives

| Strain | SUMT assayed nmol/h/mg of protein |
|---|---|
| SC510 Rif$^r$ | 0.05 |
| SC510 Rif$^r$ pXL59 | 0.04 |
| SC510 Rif$^r$ pXL557 | 2.10 |
| SC510 Rif$^r$ pXL545 | 0.05 |

It emerges clearly from these results that only plasmid pXL557 brings about a marked increase in SUMT activity (a factor of 50) in SC510 Rif$^r$. This increase results from the amplification of cobA and not of cobE, since plasmid pXL545, which permits the amplification of only cobE, does not produce an increase in SUMT activity. This result confirms that cobA is the structural gene for SUMT of *Pseudomonas denitrificans*. This result shows that it is possible to obtain an amplification of the SUMT activity in *Pseudomonas denitrificans* by amplification of the structural gene for SUMT of *Pseudomonas denitrificans*.

7.1.2—Expression of the COBI Protein

A fragment originating from the 8.7-kb DNA fragment containing the structural gene for $SP_2MT$ (cobI) is cloned into a plasmid having a broad host range in Gram-negative bacteria, and this plasmid is then introduced by conjugation into *Pseudomonas denitrificans* SC510 $Rif^r$. The S-adenosyl-L-methionine:precorrin-2 methyltransferase activity of the strain is then measured relative to that of the strain carrying the vector.

The 1.9-kb BamHI-BamHI-SstI-SstI fragment containing the cobH and cobI genes is purified from the 8.7-kb fragment. XbaI and EcoRI linkers are placed at the BamHI and SstI ends, respectively, after the latter have been filled in with bacteriophage T4 DNA polymerase. The fragment is then inserted between the XbaI and EcoRI sites of the broad host range plasmid pXL59. It carries kanamycin resistance. The plasmid thereby obtained is designated pXL1148 (FIG. 24).

Separately, a related plasmid was constructed: the 1.5-kb BamHI-BamHI-SstI fragment containing only the whole cobH gene and the 5' portion of the cobI gene was purified from the 8.7-kb fragment. XbaI and EcoRI linkers were added at the BamHI and SstI sites, respectively, after the latter had been filled in or digested with phage T4 DNA polymerase. This fragment was then inserted between the EcoRI and XbaI sites of pXL59 to give plasmid pXL1149. Plasmids pXL1148 and pXL1149 differ only in the presence in pXL1148 of the 0.3-kb SstI-SstI fragment which contains the 3' end of the cobI gene. pXL1148 possesses the whole structural gene for cobI, in contrast to pXL1149. Both plasmids contain the cobH gene.

These two plasmids were introduced by conjugation into SC510 $Rif^r$. Strains SC510 $Rif^r$, SC510 $Rif^r$ pXL59, SC510 $Rif^r$ pXL1148 and SC510 $Rif^r$ pXL1149 are cultured in PS4 medium. After 4 days of culture, the cells are harvested and the $SP_2MT$ activities are assayed as described in Example 6.1.3 a).

The result of these assays is given below, with the $SP_2MT$ activities defined as in Example 6.1.3 a).

TABLE $SP_2MT$ activities of various strains derived from *Pseudomonas denitrificans*

| Strain | $SP_2MT$ activity[1] in % |
|---|---|
| SC510 $Rif^r$ | <5 |
| SC510 $Rif^r$ PXL59 | <5 |
| SC510 $Rif^r$ PXL1148 | 75 |
| SC510 $Rif^r$ pXL1149 | <5 |

[1]per 500 μg of crude extract introduced in the test.

The activity is expressed in % as defined in Example 6.1.3 a).

Only plasmid pXL1148 brings about a substantial increase in $SP_2MT$ activity. In contrast, plasmid pXL1149 does not give results different from those observed with the controls SC510 $Rif^r$ and SC510 $Rif^r$ pXL59. pXL1148 is the only plasmid to contain the cobI gene, and it is the only one to amplify $SP_2MT$ activity; this result confirms that the structural gene for $SP_2MT$ of *Pseudomonas denitrificans* is the cobI gene. Furthermore, if the total proteins of these different strains are separated by electrophoresis under denaturing conditions (SDS-PAGE with 10% of acrylamide), the presence of a band which corresponds to a protein having a molecular weight of 25,000 is observed specifically in the case of pXL1148 (FIG. 25). The molecular weight of this protein corresponds to that of the COBI protein. Plasmid pXL1148 enables overproduction of the COBI protein to be obtained in *Pseudomonas denitrificans*.

7.1.3—Expression of COBF

The expression is obtained by positioning the Ptrp promoter of *E. coli* and the ribosome-binding site of the cII gene of bacteriophage lambda upstream of the cobF gene. The expression thereby obtained is much higher than that observed by simple gene amplification using the same multicopy plasmid.

The 2-kb EcoRI-BamHI-BamHI fragment of pXL1496 (Example 7.2.1 below) is purified (FIG. 26). This fragment contains the Ptrp promoter of *E. coli* and the ribosome-binding site of the cII gene of bacteriophage lambda upstream of the cobF gene. Dowstream of the cobF gene, there is the terminator of the rrnB operon of *E. coli*. This fragment is cloned at the EcoRI-BamHI sites of plasmid pKT230 to give pXL1546 (FIG. 26). pKT230 is a plasmid of the incompatibility group Q which replicates in almost all Gram-negative bacteria (Bagdasarian et al., 1981); this plasmid carries kanamycin resistance. Plasmid pXL1546 and pKT230 are introduced by conjugation into SC510 $Rif^r$. Strains Sc510 $Rif^r$, SC510 $Rif^r$ pKT230 and SC510 $Rif^r$ pXL1546 are cultured in PS4 medium as described above. After four days of culture, the total proteins of the different strains are analysed in 10% SDS-PAGE. As shown in FIG. 27, a protein of molecular weight 32,000 which is overexpressed is observed in the extract of SC510 $Rif^r$ pXL1546; this protein comigrates with the protein which is overexpressed by *E. coli* B pXL1496 (Example 7.2.1 below). Furthermore, this protein is specifically expressed in strain SC510 $Rif^r$ containing pXL1546, where it represents at least 20% of the total proteins. In contrast, this protein is not observed in the total proteins of strains SC510 $Rif^r$ and SC510$Rif^r$ pKT230. This overexpressed protein is hence the COBF protein.

7.1.4—Expression of COBH

This example describes the amplification of a DNA fragment of *Pseudomonas denitrificans* containing the cobH gene. The protein which is encoded by this gene is purified; it is the COBH protein. Plasmid pXL1149, described in Example 7.1.2, contains in the DNA insert originating from the 8.7-kb fragment only the whole cobH gene. In SC510 $Rif^r$, this plasmid, in contrast to the vector, brings about the overexpression of a protein of molecular weight 22,000 (FIG. 25).

7.1.5—Expression of COBV

This example describes the amplification of cobalamin-5'-phosphate synthase activity by a plasmid carrying only cobV (pXL699, see FIG. 38). The cobalamin-5'-phosphate synthase activity is amplified in SC877 $Rif^r$ by plasmid pXL699 by a factor of 50 relative to the same strain with the vector pXL435, pXL1303, pXL1324 or pKT230. This plasmid contains in its insert only the whole of cobV plus the 5'-terminal portions of ORF18 and of cobU. In such a strain (SC877$Rif^r$ pXL699), the COBV protein is definitely overexpressed; this overexpression is by a factor of 50 relative to the expression of strain SC877$Rif^r$.

7.1.6—Expression of the CORA Protein

The 1.5-kb EcoRI-BamHI-BamHI fragment of pXL1832 (see Example 7.2.4), containing the Ptrp promotor and then the RBS cII of bacteriophage λ, the *M. ivanovii* SUMT structural gene and the terminator region of the rrnB operon of *E. coli*, is cloned at the EcoRI-BamHI sites of pKT230 (Bagdasarian et al., 1981). In this manner, plasmid pXL1841 is obtained (see FIG. 56). This plasmid is mobilised in *P.*

*denitrificans* SC510 $Rif^r$ as described above. A transconjugant is studied in greater detail. This strain is cultured in PS4 medium, and the SUMT activity of the bacterial extracts is assayed at the same time as that of the control strain SC510 $Rif^r$ pXL435 (Cameron et al., 1989). The activities of these strains are presented below.

| Strain | SUMT specific activity in pmol/h/mg of proteins |
|---|---|
| SC510 $Rif^r$pXL435 | 50–100 |
| SC510 $Rif^r$pXL1841 | 1700 |

This result shows clearly that there is expression of the SUMT activity of *M. ivanovii* in *P. denitrificans* as a result of plasmid pXL1841, since the SUMT activity of strain SC510 $Rif^r$ pXL1841 is markedly greater than that of SC510 $Rif^r$ pXL435.

7.2—Expression in *E. coli*

This example illustrates how a COB protein of *Pseudomonas denitrificans* can be overproduced in *E. coli.*

7.2.1—Expression of COBF

The 2250-bp EcoRI-XhoI fragment of the 8.7-kb EcoRI fragment (at the respective positions. 0 and 2250 in the sequence presented in FIG. 8) was cloned into phage M13mp19 (Norrander et al., 1983) between the EcoRI and SalI sites. The plasmid thereby constructed is designated pXL1405. An NdeI site was introduced by directed mutagenesis so that the last three bases (ATG) of this restriction site constitute the translation initiation site of the cobF gene. This amounts to modifying the three bases which precede the ATG of the cobF gene, GAA (the G is at position 733 in the sequence presented in FIG. 8), to CAT. The NdeI-SphI-SphI fragment (FIG. 26) containing the cobF gene is then purified; this 1.5-kb fragment is then cloned between the NdeI-SphI sites of plasmid pXL694 (Denèfle et al., 1987). The plasmid thereby constructed is designated pXL1496 (FIG. 26). Signals for regulation of genetic expression in *E. coli* are present in the 120-bp EcoRI-NdeI fragment (which originates from pXL694) which precedes the cobF gene. These signals consist of the [−40+1] region of the Ptrp promoter of *E. coli*, and then of 73 bp which contain the ribosome-binding site of the cII gene of bacteriophage λ (Denèfle et al., 1987). Downstream of the cobF gene, there are the terminators of the rrnB operon of *E. coli* (in the HindIII-BamHI fragment). Plasmid pXL1496 was introduced by transformation into the *E. coli* strain (Monod and Wollman, 1947). Expression of the cobF gene was studied as already described (Denèfle et al., 1987) under conditions where the Ptrp promoter is either repressed (in the presence of tryptophan) or not repressed (absence of tryptophan). The medium in which the expression was carried out is M9 minimum medium (Miller, 1972) supplemented with 0.4% of glucose, 0.4% of casamino acids, 10 mM thiamine and 40 μg/ml of tryptophan in the case where it is desired to repress the Ptrp promoter. *E. coli* strain B pXL1496 was cultured at 37° C. in the medium described above with ampicillin (100 μg). As shown in FIG. 28, the absence of tryptophan brings about the expression of a protein of molecular weight 32,000. In effect, in the extract of total proteins of *E. coli* B pXL1496 analysed in SDS-PAGE (FIG. 28), a protein of molecular weight 32,000 D which represents between 1 and 4% of the total proteins is clearly observed. This protein is present in markedly smaller quantities in the extract of the total proteins of *E. coli* B pXL1496 cultured under the same conditions but in the presence of tryptophan. The molecular weight of the protein which is expressed under these conditions is close to the molecular weight of the COBF protein deduced from the amino acid sequence of the protein, which is 28,927 (FIG. 16). The protein which is thus expressed in *E. coli* is the COBF protein.

7.2.2—Expression of COBT

Overproduction is obtained by fusing the lac promotor and the first three codons of lacZ of *E. coli* to the 5' end of the cob gene.

The EcoRI site located at position 2624 in the sequence presented in FIG. 32 of the 4.8-kb fragment contains the fourth codon of the cobT gene. The 3.5-kb EcoRI-XbaI fragment of pXL837 (see FIG. 36) is cloned at the EcoRI and XbaI sites of pTZ18R or pTZ19R (Pharmacia) to generate pXL1874 or pXL1875, respectively; these two plasmids differ in the orientation of the truncated cobT gene with respect to the promoter of the lactose operon of *E. coli* (Plac). Plac is upstream of cobT in pXL1874 while the opposite is true in pXL1875. Cloning of the EcoRI-XbaI fragment of pXL837 at the EcoRI-XbaI sites of pTZ18R enables a protein fusion to be carried out between the first 4 amino acids of *E. coli* β-galactosidase and the cobT gene from its $4^{th}$ codon. Expression of this lacZ' 'cobT gene is under the control of the expression signals of lacZ. Plasmids pXL1874, pXL1875 and pTZ18R are introduced by transformation into *E. coli* strain BL21. Expression of the cobT gene is studied as already described (Maniatis et al., 1989).

Figure 42A:
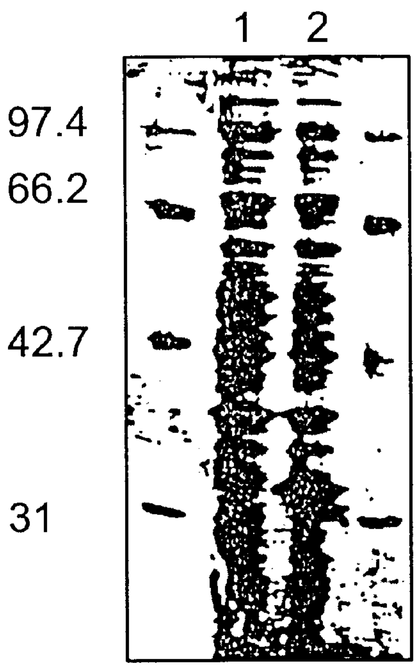
Figure 42B:
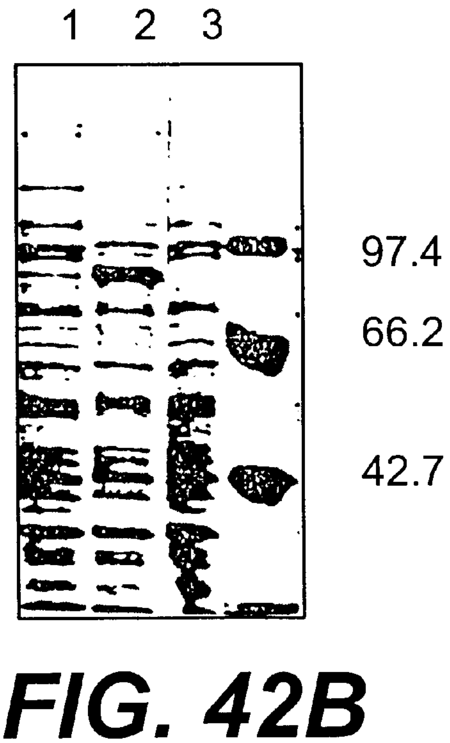
Figure 45A:
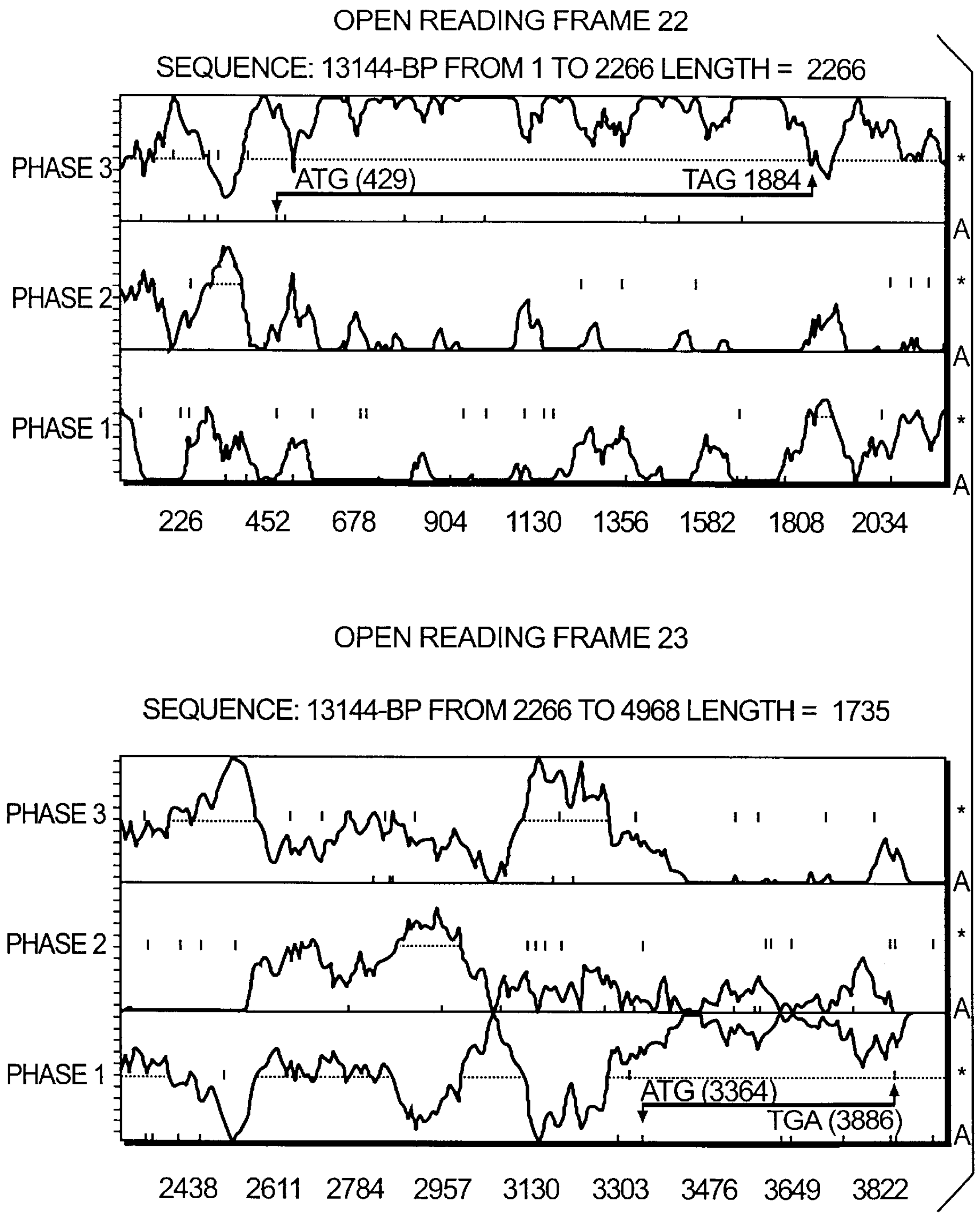
Figure 45B:
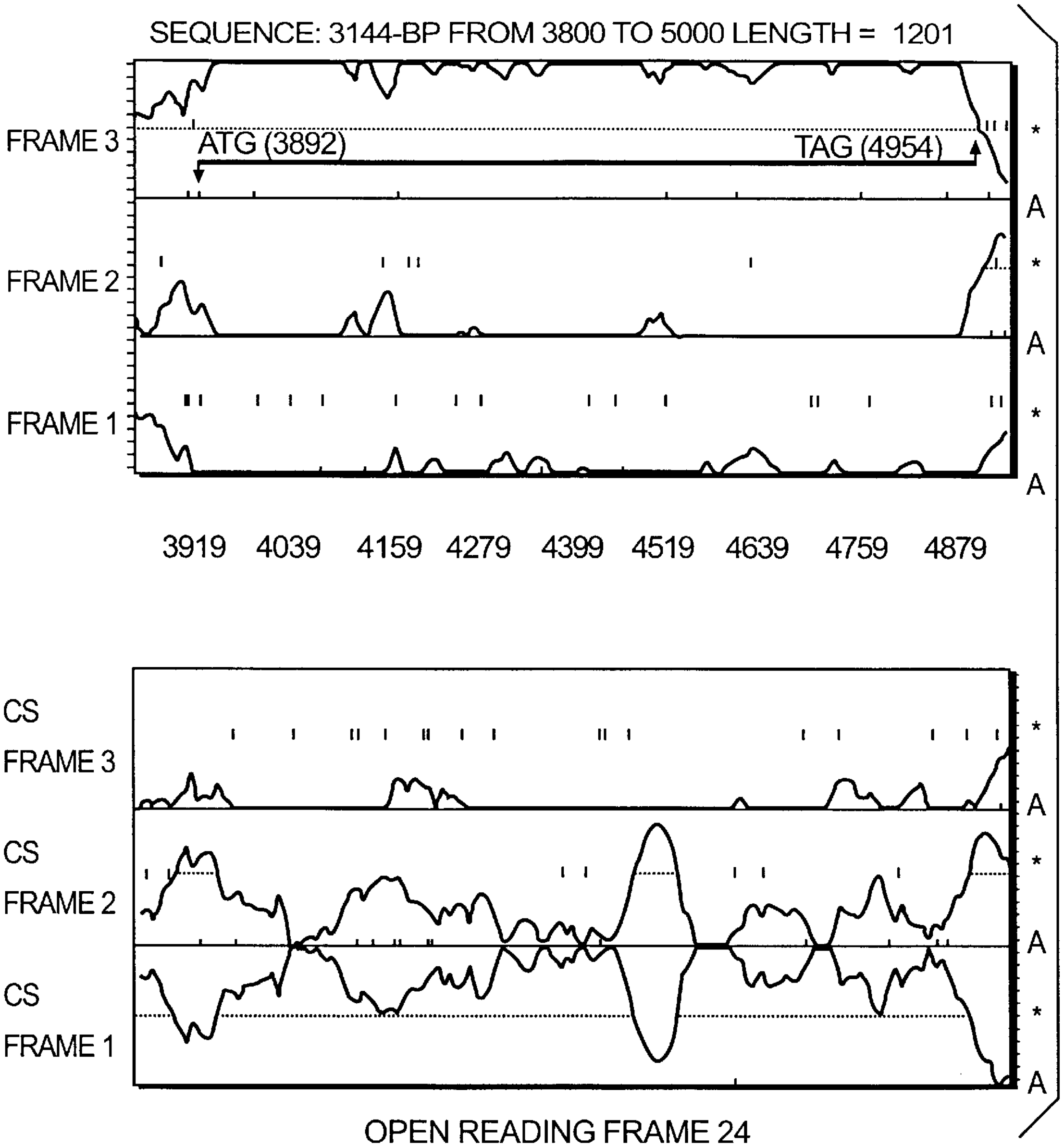
Figure 45C:
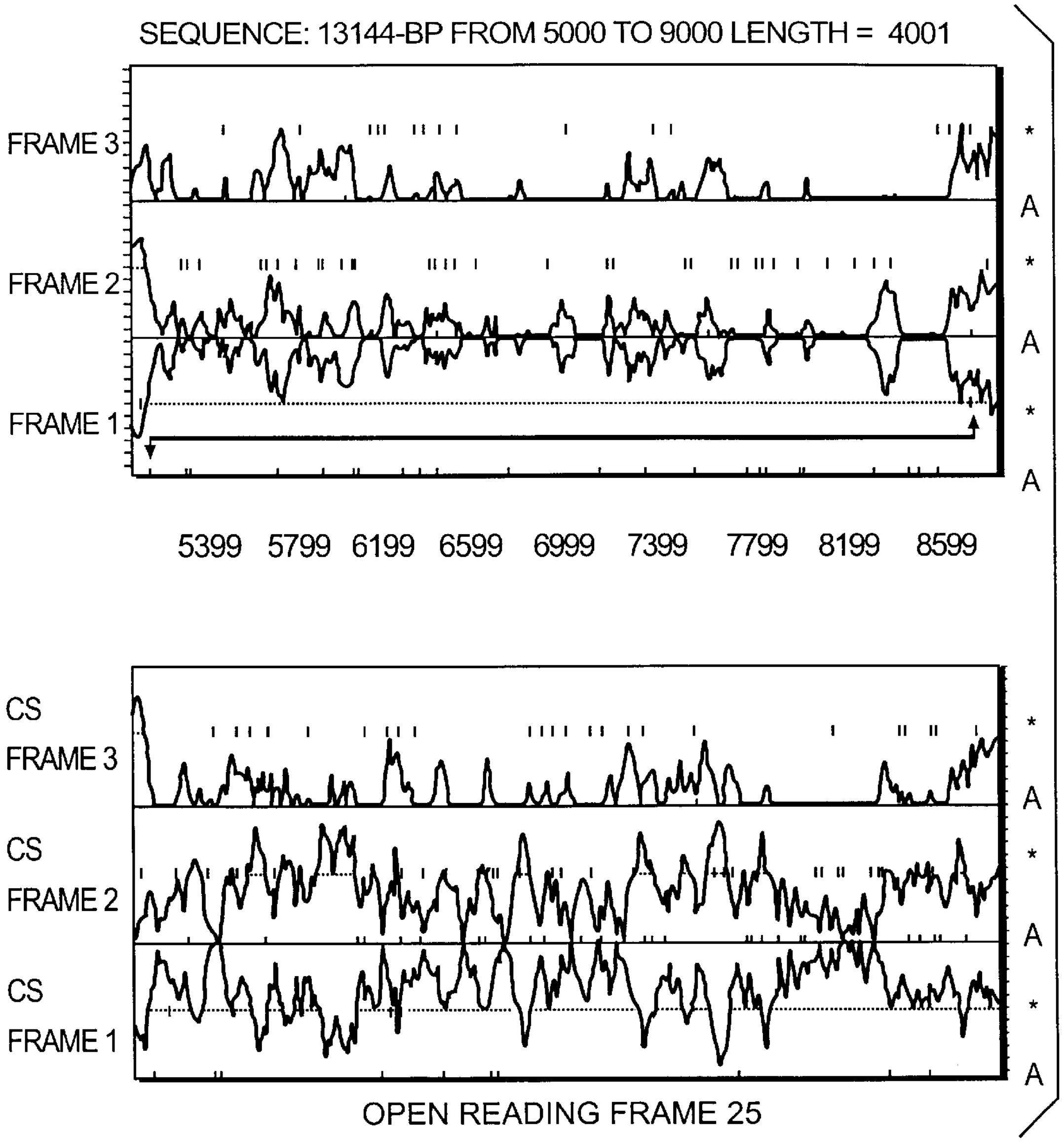
Figure 45D:
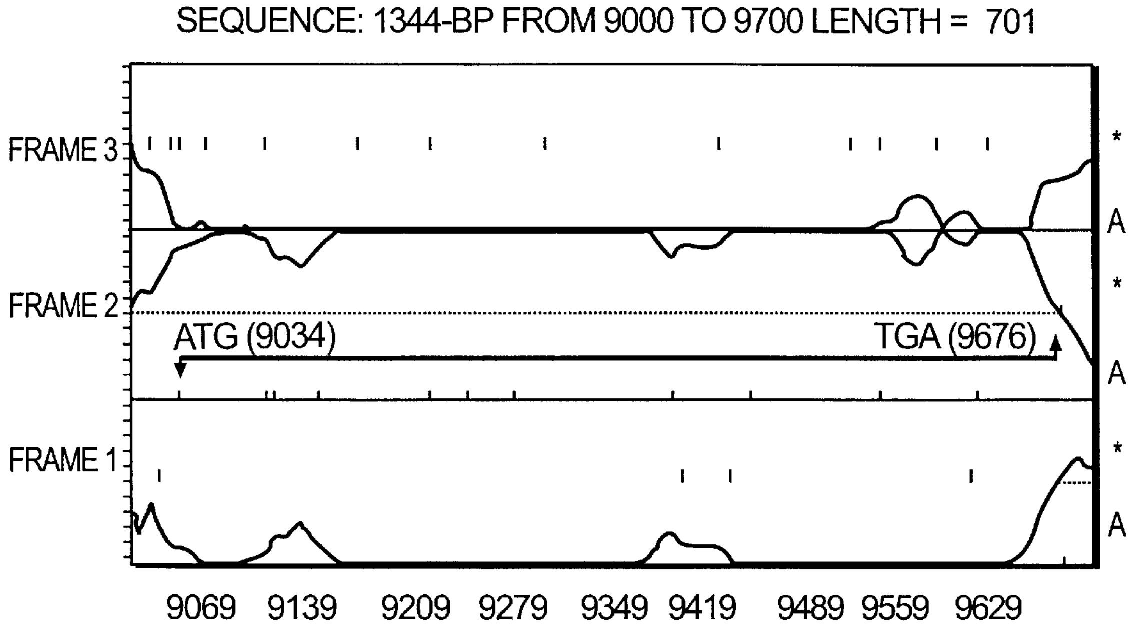
Figure 45E:
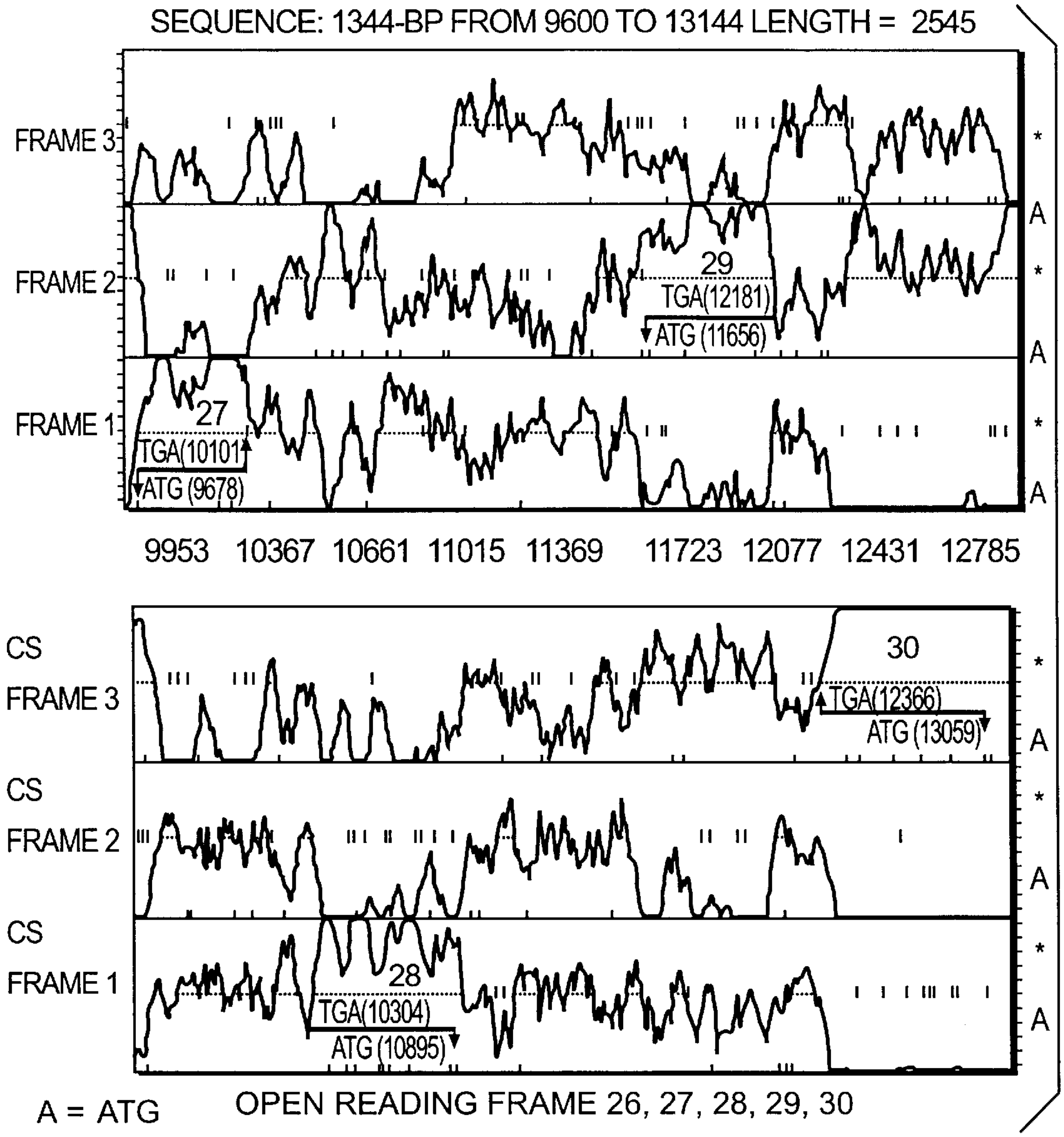

As shown in FIG. 42B, a protein of molecular weight 72,000 is expressed only with pXL1874 and represents, in the extract of total proteins of BL21, pXL1874 analysed in SDS-PAGE, 1 to 4% of the total proteins. The molecular weight of the protein which is expressed under these conditions is close to the molecular weight of the COBT protein deduced from the amino acid sequence, which is 70,335, in FIG. 40. This experiment shows clearly that, from the EcoRI site located in the fourth codon of the cobT gene, an open reading frame compatible with that found for the cobT gene can be expressed.

7.2.3—Expression of a Truncated COBS Protein

A BamHI site is located at the 45th codon of the COBS gene. The 1.2-kb BamHI-BamHI fragment containing the 3' portion of the cobS gene and sequences downstream of this gene is excised from pXL843 and cloned at the BamHI site of plasmid pET-3b (Rosenberg et al., 1987) to generate pXL1937. The BamHI fragment is oriented in such a way that the truncated portion of the cobS gene is fused, in frame, with the first 12 codons of the major capsid protein of bacteriophage T7 or gene 10 (Rosenberg et al., 1987). This hydbrid gene is under the control of the 010 promotor of bacteriophage T7. Plasmid pXL1937 and also pET-3b are introduced by transformation into *E. coli* BL21 pLysS (W. Studier, personal communication). After reisolation on selective medium, both strains are cultured in L liquid medium to an OD at 610 nm of 1; at this stage, the medium is adjusted to an IPTG (isopropyl β-thiogalactoside) concentration of 1 mM in order to induce expression of the polymerase of bacteriophage T7 (Rosenberg et al., 1987). The culture is then incubated for 3 h at 37° C. and bacterial lysates are thereafter prepared. The total proteins of the bacteria thus cultured are separated by PAGE under denaturing conditions. As seen in FIG. 42A, there is specifically overexpression of a 33,000 protein with the culture BL21 pLysS pXL1937. This molecular weight is entirely compatible with the expected molecular weight for the fusion protein (33 kD). This experiment shows clearly that, from the BamHI site located at the 45th codon of the cobS gene, an open reading frame compatible with that found for the cobS gene can be overexpressed.

7.2.4. Expression of the CORA Protein

The following oligonucleotides were synthesised as described above:

```
oligonucleotide 1277
5' GGC CGA ATT CAT ATG GTA GTT TAT TTA 3' (SEQ.ID.NO:59)
       -------- 1   2   3   4   5    (1 to 5 first 5
       EcoRI ____________        codons of M. ivanovii
       NdeI                                          SUMT)

oligonucleotide 1278
          5' GGC CGA GCT CTA TTA CAT AAT T/3' (SEQ.ID.NO:60)
                 ________==============
                  SstI
```

(=sequence appearing in FIG. 51, positions 926 to 915, in the strand complementary to the coding strand) oligonucleotide 1277 possesses the recognition sequences for the restriction enzymes EcoRI and NdeI. The last three bases of the NdeI site (ATG), which corresponds to a translation initiation codon, are directly followed by codons 2 to 5 of the *M. ivanovii* SUMT structural gene as appear in the sequence presented in FIG. 52. The oligonucleotide 1278 contains the recognition sequence for SstI, followed directly by the sequence TATTACATAATT which corresponds to a sequence present in the 955-bp fragment containing the corA gene presented in FIG. 51; this sequence occurs at position 926 to 915 (see FIG. 51) in the strand complementary to the strand coding of the CORA protein. The two oligonucleotides 1277 and 1278 hence contain sequences in their 3' portion corresponding, respectively, to the coding strand of the corA gene and to the complementary strand downstream of this gene. These two oligonucleotides may be used to carry out an enzymatic amplification experiment with plasmid pXL1809 as template. This experiment makes it possible to obtain a 910-bp fragment containing the corA gene of *M. ivanovii* possessing an NdeI site at the ATG of the corA gene, and an SstI site at the other end of the fragment after the end of the corA gene. Enzymatic amplification is carried out as described above for the enzymatic amplification performed on the genomic DNA of *M. ivanovii*, except that the template consists of DNA (10 ng) of plasmid pXL1809; the temperatures used are the same, but only 20 amplification cycles are carried out. As described above, the amplification products are digested with NdeI and SstI before being separated by migration on agarose gel. As expected, a fragment 910 bp in size is indeed visualised. This fragment is purified as already described. This fragment is cloned at the NdeI and SstI sites of pXL694 (Denèfle et al., 1987). The resulting plasmid, designated pXL1832, is described in FIG. 56. In this plasmid, in the same way as described in Example 7.2, the *M. ivanovii* SUMT structural gene is preceded by the ribosome binding site of the cII gene of bacteriophage λ. Upstream of this RBS there is the Ptrp promotor. Plasmid pXL832 is introduced into *E. coli* B5548, which is an *E. coli* strain carrying the mutation cysG44 (Cossart and Sanzey, 1982) by transformation. The SUMT activities of the strains *E. coli* B5548 pUC13 and *E. coli* B5548 pXL1832 are assayed on extracts obtained from cells cultured in LB medium supplemented with ampicillin. The assay of SUMT activity is carried out as already described (Blanche et al., 1989). The results of this assay are given below.

| Strain | SUMT specific activity in pmol/h/mg of proteins |
|---|---|
| *E. coli* B5548 pUC13 | 5.9 |
| *E. coli* B5548 pXL1832 | 310 |

The results presented in the table above show clearly that there is expression of a SUMT activity in *E. coli* strain B5548 when the latter contains a plasmid pXL1832 which expresses *M. ivanovii* SUMT. The *M. ivanovii* SUMT can hence be expressed in *E. coli.*

EXAMPLE 8

Amplification of the Production of Cobalamins by Recombinant DNA Techniques

8.1—Amplification in *P. denitrificans*

This example illustrates how an improvement in the production of cobalamins is obtained in *Pseudomonas denitrificans* SC510 $Rif^r$ by amplification of cob genes of *Pseudomonas denitrificans* SC510.

8.1.1 Improvement in the Production of Cobalamins in *Pseudomonas denitrificans* by Removal of a Limiting Step in the Biosynthesis of Cobalamins This example illustrates how the productivity of cobalamins in *Pseudomonas denitrificans* strains may be improved by amplification of cob genes of *Pseudomonas denitrificans*. This improvement results from the removal of a limiting step of the biosynthetic pathway.

Plasmid pXL367 is described in Example 4.2 (FIG. 13). This plasmid corresponds to pRK290 (Ditta et al., 1981) into which the 8.7-kb EcoRI fragment has been inserted. This plasmid pXL367 effects an improvement in the biosynthesis of cobalamins in strain SC510 $Rif^r$. Strains SC510 $Rif^r$, SC510 $Rif^r$ pRK290 and SC510 $Rif^r$ pXL367 are cultured in an Erlenmeyer in PS4 medium according to the conditions described in the experimemntal protocols. An improvement in the production titre due to the presence of plasmid pXL367 is observed. In effect, strain SC510 $Rif^r$ pXL367 produces 30% more cobalamins than strains SC510 $Rif^r$ and SC510 $Rif^r$ pRK290. This improvement is not due to the amplification of unspecified genes of *Pseudomonas denitrificans*, but to the specific amplification of the genes carried by the 8.7-kb EcoRI fragment. In effect, plasmid pXL723 described in FIG. 11 gives no improvement, and the same production titre is observed with this plasmid as with strains SC510 $Rif^r$ and SC510 $Rif^r$ pRK290.

8.1.2 Improvement in the Production of Coenzyme $B_{12}$ in *Pseudomonas denitrificans* by Removal of Two Limiting Steps in the Biosynthesis of Cobalamins This example illustrates how the productivity of cobalamins in strains of *Pseudomonas denitrificans* may be improved by amplification of cob genes of *Pseudomonas denitrificans*. This improvement results from the removal of two limiting steps of the biosynthetic pathway.

The 2.4-kb ClaI-Eco RV fragment derived from the 5.4-kb fragment (containing the cobA and cobE genes) is cocloned with the 8.7-kb EcORI fragment into the broad host range plasmid pXL203. The plasmid thereby constructed is referred to as pXL525 (FIG. 29). This plasmid is introduced into SC510 $Rif^r$ by conjugation. Strain SC510 $Rif^r$ pXL525 produces 20% more cobalamins than SC510 $Rif^r$ pXL367. Amplification of the cobA and cobE genes enables a further limiting step in SC510 $Rif^r$ in the biosynthesis of cobalamins to be removed. *Pseudomonas denitrificans* strain SC510 $Rif^r$ is improved in the present example by the successive removal of two limiting steps. This example shows that the removal of two limiting steps in the biosynthesis of cobalamins can lead to further improvements in production.

8.2—Improvement in the Productivity of Cobalamins in *Agrobacterium tumefaciens*

This example illustrates the improvement in the production of cobalamins in a strain productive of cobalamins by amplification of the cob genes of *Pseudomonas denitrificans* SC510.

The strain used is a strain of a Gram-negative bacterium; it is a strain of *Agrobacterium tumefaciens.*

The plasmids described in Examples 4.2 and 8.1, pXL367 and pXL525, as well as the vector pRK290 (Ditta et al., 1981) and plasmid pXL368 (FIG. 29), are introduced by conjugative transfer into *Agrobacterium tumefaciens* strain C58-C9 $Rif^r$ (Cameron et al., 1989). Strains C58-C9 $Rif^r$, C58-C9 $Rif^r$ pRK290, C58-C9 $Rif^r$ pXL367, C58-C9 $Rif^r$ pXL368 and C58-C9 $Rif^r$ pXL525 are cultured in PS4 medium at 30° C. as described above. The cobalamins produced are assayed as described above. The production titres are given in the table below.

TABLE

Titres of vitamin $B_{12}$ produced by different recombinant strains of *Agrobacterium tumefaciens*

| Strain | Vitamin $B_{12}$ in mg/l |
|---|---|
| C58-C9 $Rif^r$ | 0.4 |
| C58-C9 $Rif^r$ pRK290 | 0.4 |
| C58-C9 $Rif^r$ pXL367 | 0.8 |
| C58-C9 $Rif^r$ pXL368 | 0.8 |
| C58-C9 $Rif^r$ pXL525 | 1.2 |

As is clearly apparent in the above table, the production of cobalamins is improved in the *Agrobacterium tumefaciens* strain used. Two different plasmids improve the production of cobalamins in the *Agrobacterium tumefaciens* strain used: pXL367 and pXL368. These plasmids contain the 8.7-kb EcoRI fragment (cobF to cobM genes) and the 2.4-kb ClaI-EcoRV fragment (cobE and cobA gene), respectively. Separately, they improve the production of cobalamins by *Agrobacterium tumefaciens* C58-C9 $Rif^r$ by a factor of 2; this result shows that it is possible to improve the production of cobalamins by a strain of *Agrobacterium tumefaciens* by amplifying fragments carrying cob genes of *Pseudomonas denitrificans*. In the present case, it is possible to speak of heterologous improvment, that is to say improvement of the production of cobalamins by one strain by means of the amplification of cob genes of another strain.

The improvements in production of cobalamins provided by the different *Pseudomonas denitrificans* fragments containing cob genes are capable of cumulation, i.e., by putting into the same plasmid the two fragments which are separately cloned into pXL367 and pXL368, additive improvements are observed, in the sense that plasmid pXL525 provides in *Agrobacterium tumefaciens* C58-C9 $Rif^r$ an improvement in the production greater than that provided by each of the fragments cloned separately into the same vector.

8.3—Improvement in the Productivity of Cobalamins in *Rhizobium meliloti*

This example describes the improvement in the production of cobalamins by another strain productive of cobalamins.

The plasmid described in Example 8.2, pXL368, as well as the vector pRK290 (Ditta et al., 1981), are introduced by conjugative transfer into Rhizobium meliloti strain 102F34 $Rif^r$ (Leong et al., 1982). The transconjugants, namely 102F34 $Rif^r$, 102F34 $Rif^r$ pRK290 and 102F34 $Rif^r$ pXL368, are cultured in PS4 medium at 30° C. as described above. The cobalamins produced are assayed as described above. The production titres are given in the table below.

TABLE

Titres of cobalamins produced by different recombinant strains of *Rhizobium meliloti*

| Strain | Vitamin $B_{12}$ in mg/l |
|---|---|
| 102F34 $Rif^r$ | 0.4 |
| 102F34 $Rif^r$ pRK290 | 0.4 |
| 102F34 $Rif^r$ pXL368 | 0.8 |

As is clearly apparent in the above table, the production of cobalamins is improved in the Rhizobium meliloti strain used. Plasmid pXL368 improves the production of cobalamins by the Rhizobium meliloti strain used. This plasmid contains the 2.4-kb ClaI-EcoRV fragment (cobA and cobE genes); it improves the production of cobalamins by Rhizobium meliloti 102F34 $Rif^r$ by a factor of 2. This result shows that it is possible to improve the production of cobalamins by a strain of Rhizobium meliloti by amplifying fragments carrying cob genes of *Pseudomonas denitrificans*. In the present case, it is possible to speak of heterologous improvement, that is to say improvement of the production of cobalamins by one strain by means of the amplification of cob genes of another strain.

EXAMPLE 9

Assay of Corrinoids and Decobaltocorrinoids in Musts and Cells of Strains Productive of Corrinoids This example illustrates how it is possible to identify and assay the different corrinoids and decobaltocorrinoids produced by different strains productive of cobalamins. This assay makes it possible, inter alia, to assay coenzyme $B_{12}$.

The musts (or the cells alone) are cyanide-treated as already described (Renz, 1971). After centrifugation, an aliquot of the supernatant is passed through a DEAE-Sephadex column which is then washed with 0.1 M phosphate buffer. The collected fractions are combined and desalted on a Sep-Pak C-18 (Waters) cartridge. After evaporation and resuspension in water (100 $\mu l$ to 1 ml depending on the quantity of corrinoids present), the corrinoids are identified and assayed by HPLC on a Nucleosil C-18 column (Macherey-Nagel). The column is eluted at 1 ml/min with an acetonitrile gradient (from 0% to 100%) in 0.1 M potassium phosphate buffer containing 10 mM KCN.

The corrinoids are visualised by UV detection at 371 nm and/or by specific detection of $^{57}Co$ (if culturing has been performed in the presence of $^{57}CoCl_2$) using a Berthold LB 505 detector. They are hence identified by comparison of their retention times with standards. Similarly, the "metal-free corrinoids" (hydrogenobyrinic acid, hydrogenobyrinic acid monoamide and hydrogenobyrinic acid diamide) are visualised by UV detection at 330 nm. By this technique, the following intermediates are separated: cobyrinic acid, cobyrinic acid monoamide, cobyrinic acid diamide, cobyrinic acid triamide, cobyrinic acid tetraamide, cobyrinic acid pentaamide, cobyric acid, cobinamide, cobinamide phosphate, GDP-cobinamide, $B_{12}$ phosphate and vitamin $B_{12}$. The adenosylated forms of these products are also separated and assayed by this technique. For this purpose, the initial step of the cyanide treatment is cut out and the HPLC column is eluted with buffer devoid of KCN. FIG. 31 gives the retention times of different standards separated by this system and identified at emergence from the column by UV absorbance.

A sample of strain SC510 $Rif^r$ was deposited on Jan. 30th, 1990 at the Centraal Bureau voor Schimmelcultures at Baarn (Netherlands), where it was registered under reference CBS 103.90.

BIBLIOGRAPHIC REFERENCES

Ausubel F. M., Brent R., Kinston R. E., Moore D. D., Smith J. A.,. Seidman J. G. and K. Struhl, 1987. Current protocols in molecular biology 1987–1988. John Wiley and Sons, New York.

Bagdasarian, M., R. Lurz, B. Rückert, F. C. Franklin, M. M. Bagdasarian, J. Frey, and K. Timmis, 1981. Specific-purpose plasmid cloning vectors. II. Broad host range, high copy number, RSF1010-derived vectors, and a host vector system for gene cloning in Pseudomonas. Gene 16:237–247.

Barrère G., Geneste B., and Sabatier A., 1981. Fabrication de la vitamine B12: l'amélioration d'un procédé (Manufacture of vitamin B12: improvement of a process). Pour la Science, 49, 56–64.

Battersby A. R., Fookes C. J. R., Matcham G. W. J., and MacDonald E., 1980. Biosynthesis of the pigments of life: formation of the macrocycle. Nature, 285, 17–21.

Battersby, A. R., and E. MacDonald, 1982. Biosynthesis of the corrin macrocycle. p. 107–144. In D. Dolphin (ed.), B12, vol. 1. John Wiley & Sons, Inc., New York.

Beck., W. S. 1982. Biological and medical aspects of vitamin B12. p. 1–30. In D. Dolphin (ed.), B12, vol. 1. John Wiley & Sons, Inc., New York.

Ben Bassat A., and K. Bauer. 1987. Amino-terminal processing of proteins. Nature, 326:315.

Blanche F., L. Debussche, D. Thibaut, J. Crouzet and B. Cameron. 1989. Purification and Characterisation of S-Adenosyl-L-Methionine:Uroporphyrinogen III methyltransferase from *Pseudomonas denitrificans*. J. Bacteriol., 171:4222–4231.

Brey R. N., Banner C. D. B., and Wolf J. B., 1986. Cloning of Multiple Genes Involved with Cobalamin (Vitamin B12) Biosynthesis in *Bacillus megaterium. J. Bacteriol.,* 167, 623–630.

Cameron B., K. Briggs, S. Pridmore, G. Brefort and J. Crouzet, 1989. Cloning and analysis of genes involved in coenzyme B12 biosynthesis in *Pseudomonas denitrificans*. J. Bacteriol, 171, 547–557.

Casadaban, M. J., A. Martinez-Arias, S. T. Shapira and J. Chou. 1983. β-galactosidase gene fusion for analysing gene expression in *Escherichia coli* and Yeast. Methods Enzymol. 100, 293–308.

De Bruijn F. J. and J. R. Lupski, 1984. The use of transposon Tn5 mutagenesis in the rapid generation of correlated physical and genetic maps of DNA segments cloned into multicopy plasmids—a review. Gene, 27, 131–149.

De Graff, J., J. H. Crosa, F. Heffron, and S. Falkow. 1978. Replication of the nonconjugative plasmid RSF1010 in *Escherichia coli* K-12. J. Bacteriol. 146, 117–122.

Denèfle P., S. Kovarik, J.-D. Guiton, T. Cartwright and J.-F. Mayaux. 1987. Chemical synthesis of a gene coding for human angiogenin, its expression in *Escherichia coli* and conversion of the product into its active form. Gene, 56, 61–70.

Ditta G., Schmidhauser T., Yakobson E., Lu P., Liang X.-W., Finlay D. R., Guiney D. and D. R. Helinski, 1985. Plasmids related to the broad host range vector pRK290, useful for gene cloning and for monitoring gene expression. Plasmid, 13, 149–154.

Ditta, G., S. Stanfield, D. Corbin, and D. R. Helinski, 1980. Broad host range DNA cloning system for Gram-negative bacteria: Construction of a gene library of Rhizobium meliloti. Proc. Natl. Acad. Sci. USA 77, 7347–7351.

Escalante-Semerena J. C. and J. R. Roth, 1987.

Regulation of the cobalamin biosynthetic operons in *Salmonella typhimurium*. J. Bacteriol, 169, 225–2258.

Florent, J. 1986. Vitamins. p115–158. In H.-J. Rehm and G. Reed (ed.), Biotechnology, vol. 4, VCH Verlagsgesellschaft mbH, Weinheim.

Friedmann H. C. and L. M. Cagen, 1970. Microbial biosynthesis of B12-like compounds. Ann. Rev. Microbiol., 24, 159–208.

Friedmann H. C., 1968. Vitamin B12 biosynthesis. J. Biol. Chem., 243, 2065–2075.

Friedmann H. C., 1975. Biosynthesis of corrinoids. In Babior B. M., Cobalamin, 75–110, John Wiley and Sons, New York.

Henikoff S. 1984. Unidirectional digestion with exonuclease III creates targeted breakpoints for DNA sequencing. Gene, 28, 351–359.

Hirel Ph-H, J.-M. Schmitter, P. Dessen and S. Blanquet. 1989. Extent of N-terminal methionine excision within *E. coli* proteins is governed by the side chain of the penultimate aminoacids. Proc. Natl. Acad. USA, in press.

Hopp T. P. and K. R. Woods, 1981. Prediction of protein antigenic determinants from amino acids sequences. Proc. Natl. Acad. Sci. USA, 78, 3824–3828.

Huennekens F. M., Vitols K. S., Fujii K. and JacobSen D. W., 1982. Biosynthesis of cobalamin coenzyme. In Dolphin D., B12, vol. 1, 145–167, John Wiley & Sons, New York.

Irion R. and Ljungdahl L. G., 1965. Isolation of factor IIIm coenzyme and cobyric acid coenzyme plus other B12 factors from *Clostridium thermoaceticum*. Biochemistry, 4, 2780–2790.

Jeter R. M., Olivera B. M. and Roth J. R., 1984. *Salmonella typhimurium* synthesises cobalamin (vitamin B12) de novo under anaerobic growth conditions. J. Bacteriol., 159, 206–213.

Jeter, R. M. and J. R. Roth, 1987. Cobalamin (Vitamin B12) Biosynthetic Genes of *Salmonella tyohimurium*. J. Bacteriol. 169, 3189–3198.

Jorgensen R. A., Rothstein S. J. and Reznikoff W. R., 1979. A restriction enzyme cleavage map of Tn5 and location of a region encoding neomycin resistance. Molec. Gen. Genet., 177, 65–62.

Kanangara C. G., S. P. Gough, P. Bruyant, J. K. Hoober, A. Kahn and D. von Wettstein, 1988. $tRNA^{Glu}$ as a cofactor in d-aminolevulinate biosynthesis: steps that regulate chlorophyll synthesis. Trends in Biochem. Sci., 139–143.

Kanehisa M. 1984. Use of statistical criteria for screening potential homologies in nucleic acids sequences. Nucleic Acids Res., 12:203–215.

Kieny M. P., R. Lathe and J. P. Lecocq. 1983. New versatile cloning vectors based on bacteriophage M13. Gene, 26, 91–99.

Krzycki J. and J. G. Zeikus. Quantification of corrinoids in methanogenic bacteria. 1980. Curr. Microbiol., 3, 243–245.

L. Skatrud, A. J. Tietz, T. D. Ingolia, C. A. Cantwell, D. L. Fisher, J. L. Chapman and S. W. Queener. 1989. Use of recombinant DNA to improve production of L. Skatrud, A. J. Tietz, T. D. Ingolia, C. A. Cantwell, D. L. Fisher, J. L. Chapman and S. W. Queener. 1989. Use of recombinant DNA to improve production of cephalosporin C by *Cephalosporium acremonium*. Bio/Technology, 1989, 7, 477–485.

Laemli U. K., 1970. Cleavage of structura proteins during the assembly of the head of bacteriophage T4. Nature, 227, 680–685.

Leong S. A., Ditta G. S., Helinski D. R., 1982. Haem Biosynthesis in Rhizobium. Identification of a cloned gene coding for d-aminolevulinic acid synthetase from *Rhizobium meliloti*. J. Biol. Chem., 257, 8724–8730.

Macdonald H. and J. Cole. Molecular cloning and functional analysis of the cysG and nirB genes of *E. coli* K12, Two closely-linked genes required for NADH-dependent reductase activity. Submitted to publication.

Maniatis, T., E. F. Fritsch, and J. Sambrook, 1982. Molecular cloning: a laboratory manual. Cold Spring Harbor Laboratory, Cold Spring Harbor, N.Y.

Mazumder T. K., N. Nishio, M. Hayashi and S. Nagai, 1987. Production of corrinoids including vitamin by *Methanosarcina barkeri*. 1986. Biotechnol. Letters, 12, 843:848.

Mazumder T. K., N. Nishio, S. Fukazaki and S. Nagai. 1987. Production of Extracellular vitamin B12 compounds from methanol by *Methanosarcina barkeri*. Appl. Microbiol. Biotechnol., 26, 511–516.

Miller, J. H. 1972. Experiment in molecular genetics. Cold Spring Harbor Laboratory, Cold Spring Harbor, N.Y.

Monod J. and E. Wollman. 1947. Inhibition de la croissance et de l'adaptation enzymatique chez les bactèries infectees par le bacteriophage (Inhibition of growth and of enzymatic adaptation in bacteria infected with bacteriophage). Ann. Inst. Pasteur, 73, 937–956.

Murphy M. J., Siegel L. M, Kamin H. and Rosenthal D., 1973. Identification of a new class of haem prosthetic group: an iron-tetrahydroporphyrin (isobacteriochlorin type) with eight carboxylic acid groups. J. Biol. Chem., 248, 2801–2814.

Murphy M. J., Siegel L. M., 1973. The basis for a new type of porphyrin-related prosthetic group common to both assimilatory and dissimilatory sulfite reductases. J. Biol. Chem., 248, 6911–6919.

Nexo E. and Olesen H., 1982. Intrinsic factor, transcobalamin and haptocorrin. In Dolphin D., B12, 57–85, John Wiley & Sons, New York.

Normark S., S. Bergtröm, T. Edlund, T. Grundström, B. Jaurin, F. Lindberg and O. Olsson. 1983. Overlapping genes. Ann. Rev. Genet., 17, 499–525.

Norrander J., T. Kempe and J. Messing. 1983. Construction of improved M13 vectors using oligode-oxynucleotide-directed mutagenesis. Gene 26, 101–106. Noyes R., 1970. Vitamin B12 manufacture, 145–182, Noyes developpement S.A., Park Ridge, N.J., USA.

Prentki P. and H. M. Krisch. 1984. In vitro insertional mutagenesis with a selectable DNA fragment. Gene, 29, 303–313.

Renz P. 1970. Some intermediates in the biosynthesis of vitamin $B_{12}$. Methods in Enzymol., 18, 82–92.

Rigby P. W. J., Dieckmann M., Rhodes C., Berg P., 1977. Labeling deoxyribonucleic acid to high specific activity in vitro by nick translation with DNA polymerase I. J. Mol. Biol., 113, 237.

Roof D. M. and J. R. Roth. 1988. Ethanolamine utilization in *Salmonella typhimurium*. J. Bacteriol., 170, 3855–3863.

Sanger F., S. Nicklen and A. R. Coulson. 1977. DNA sequencing with chain-terminating inhibitors. Proc. Natl. Acad. Sci., 74, 5463–5468.

Saunders G., Tuite M. F. and Holt G., 1986. Fungal cloning vectors. Trends Biotechnol., 4, 93–98.

Scherer P., Höllriegel V., Krug C., Bokel M. and Renz P., 1984. On the biosynthesis of 5-hydroxybenzimidazolylcobamide (vitamin B12-factor III) in *Methanosarcina barkeri*. Arch. Microbiol., 138, 354–359.

Schneider Z. and Friedmann H., 1972. Studies on enzymatic dephosphorylation of vitamin B12 5'-phosphate. Arch. Biochem. Biophys., 152, 488–495.

Scott A. I., N. E. Mackenzie, P. J. Santander, P. E. Fagerness, G. Muller, E. Schneider, R. Seldmeier and G. Worner, 1984. Biosynthesis of vitamin B12-Timing of the methylation steps between uro'gen III and cobyrinic acid. Bioorg. Chem. 12:356–352.

Southern E., 1975. Detection of specific sequences among DNA fragments separated by gel electrophoresis. J. Mol.Biol., 98, 503–517.

Stachel S. E., G. An, C. Flores and E. W. Nester, 1985. a Tn3lacZ transposon for the random generation of β-galactosidase gene fusions: application to the analysis of gene expression in Agrobacterium. Embo J., 4, 891–898.

Staden R. and A. D. McLachlan, 1982. Codon preference and its use in identifying protein coding regions in long DNA sequences. Nucleic Acid Res., 10, 141–156.

Stupperich E., I.Steiner and H. J. Eisinger, 1987. Substitution of Coα-(5-Hydroxybenzimidazolyl)Cobamide (Factor III) by vitamin B12 in *Methanobacterium thermoautotrophicum*. J. Bacteriol., 169:3076–3081.

Taylor J. W., J. Ott and F. Eckstein, 1985. The rapid generation of oligonucleotide-directed mutations at high frequency using phophorothioate-modified DNA. Nucl. Acid Res., 13, 8764–8765.

Viera J. and Messing J., 1982. The pUC plasmids, an M13mp7-derived system for insertion mutagenesis and sequencing with synthetic universal primers. Gene, 19, 259–268.

Wein-Hsiung L., L. Chi-Cheng and W. Chung-I. 1985. Evolution of DNA sequences. p 1–94. In R. J. MacIntyre (ed.), Molecular Evolutionary genetics. Plenum Press, New York and London.

Latta, M., M. Philit, I. Maury, F. Soubrier, P. Denèfle and J.-F. Mayaux. 1990. Tryptophan promoter derivatives on multicopy plasmids: a comparative analysis of the expression potentials en *Escherichia coli*. DNA Cell Biol., 9, 129–137.

Mayaux, J.-F., E. Cerbelaud, F. Soubrier, D. Faucher and D. Pètrè. 1990. Purification, cloning and primary structure of an enantio-selective amidase from Brevibacterium sp. R312. Structural evidence for a genetic coupling with nitrile-hydratase. 1990. J. Bacteriol., 172, 6764–6773.

Belyaev, S. S., R. Wolkin, W. R. Kenealy, M. J. De Niro, M. J. Epstein and J. G. Zeikus. 1983. Methanogenic bacteria from Bondyuzhskoe oil field: general characterization and analysis of stable-carbon isotopic fractionation. Appl. Environ. Microbiol., 45, 691–697.

Saiki, R. K., D. H. Gelfand, S. Stoffel, S. Scharf, R. Higuchi, G. T. Horn, K. B. Mullis and H. A. Erlich. 1988. Primer-directed enzymatic amplification of DNA with a thermostable DNA polymerase. Science, 239, 487–491.

Souillard, N., M. Magot, O. Possot and L. Sibold. 1988. Nucleotide sequence of regions homologous to NifH (nitrogenase Fe protein) from the nitrogen fixing archaebacteria *Methanococcus thermolithotrophicum* and *Methanobacterium ivanovi*: evolutionary implications. J. Mol. Evol., 2, 65–76.

Chen, E. L. and P. H. Seeburg. 1985. Supercoil sequencing: a fast and simple method for sequencing plasmid DNA. DNA, 4, 165–170.

Saiki R. K., D. H. Gelfand, S. Stoffel, S. J. Scharf, R. Higuchi, G. T. Horn, K. B. Mullis and H. Erlich. 1988. Primer-directed enzymatic amplification of DNA with a thermostable DNA polymerase. Science, 239, 487–491.

Grunstein M., Hogness D., 1975. Colony hybridisation: a method for the isolation of cloned DNAs that contains a specific gene. Proc. Natl. Acad. Sci. USA, 72, 3961–3971.

Cossart, P. and B. Gicquel-Sanzey. 1982. Cloning and sequence of the crp gene of *Escherichia coli* K 12. Nucleic Accid Res., 10, 1363–1378.

Viera, J. and J. Messing, 1987. Production of single stranded plasmid DNA. Meth. Enzymol., 153, 3–11.

Barbieri P. G., Boretti A., Di Marco A., Migliacci A., and Spalla C. 1962. Further observations on the biosynthesis of vitamin B12 in *Nocardia rugosa*. Biochim. Biophys. Acta., 57, 599–600.

Renz P. 1968. Reaktionfolge der enzymatischen synthese von vitamin B12 aus cobInamid bei *Propionibacterium shermanii*. Z. Physiol. Chem., 349, 979–981.

Ronzio R. A., and Barker H. A. 1967. Enzimic synthesis of guanosine diphosphate cobInamide by extracts of propionic acid bacteria. Biochemistry, 6, 2244–2354.

Thibaut D., Debussche L., and Blanche F. 1990. Biosynthesis of vitamin B12: Isolation of precorrin-6x, a metal-free precursor of the corrin macrocycle retaining five S-adenosylmethionine-derived peripheral methyl groups. Proc. Natl. Acad. Sci., 87, 8795–8799.

Ohta H., and Beck W. S. 1976. Studies of the ribosome-associated vitamin B12s adenosylating enzyme of *Lactobacillus leichmannii*. Arch. Biochem. Biophys., 174, 713–725.

Brady R. O., Castanera E. C., and Barker H. A. 1962. The enzymatic synthesis of cobamide coenzymes. J. Biol. Chem., 237, 2325–2332.

Fenton W. A., and Rosenberg L. E. 1978. Mitochondrial metabolism of hydroxocobalamin: synthesis of adenosylcobalamin by intact rat liver mitochondria. Arch. Biochem. Biophys., 189, 441–447.

Vitols E., Walker G. A., and Huennekens F. M. 1966. Enzymatic conversIon of vitamin B12s to a cobamide coenzyme, α-(5,6-dimethyl-benzimidazolyl) deoxyadenosylcobamide (Adenosyl-B12). J. Biol. Chem. 241, 1455–1461.

Gimsing P., and Beck W. S. 1986. Determination of cobalamins in biological material. Methods Enzymol., 123, 3–14.

JacobSen W. J., Green R., and Brown K. L. 1986. Analysis of cobalamin coenzymes and other corrinoids by high-performance liquid chromatography. Methods

What is claimed is:

1. A method for increasing the production of cobalamins, cobamides, cobalamin precursors, or cobamide precursors, wherein said method comprises:

a) introducing a plasmid comprising a DNA sequence selected from the group consisting of the cobA, cobB, cobC, cobD, cobE, cobF, cobG, cobH, cobI, cobJ, cobK, cobL, cobM, cobN, cobO, cobP, cobQ, cobS, cobT, cobU, cobV, cobW, and cobX genes of *P. denitrificans* and homologs of said genes resulting from the degeneracy of the genetic code into a microorganism capable of producing cobalamins or cobamides;

b) culturing said microorganism under conditions suitable for the synthesis of cobalamins, cobamides, cobalamin precursors, or cobamide precursors, wherein said culture conditions are also suitable for expression of said DNA; and c) recovering the cobalamins, cobamides, cobalamin precursors, or cobamide precursors produced.

2. The method of claim 1, wherein said recovery step comprises:

a) solubilization;

b) conversion to a cyanoform; and c) purification.

3. The method of claim 1, wherein said cobalamin is coenzyme $B_{12}$.

4. The method of claim 1, wherein said cobalamin precursor or cobamide precursor is selected from the group consisting of decobaltocorrinoids and corrinoids.

5. A method for increasing the production of cobalamins, cobamides, cobalamin precursors, or cobamide precursors, wherein said method comprises:

a) introducing a DNA selected from the group consisting of the cobA, cobB, cobC, cobD, cobE, cobF, cobG, cobH, cobI, cobJ, cobK, cobL, cobM, cobN, cobO, cobP, cobQ, cobS, cobT, cobU, cobV, cobW, and cobX genes of *P. denitrificans* and homologs of said genes resulting from the degeneracy of the genetic code into a microorganism capable of producing cobalamins or cobamides;

b) culturing said microorganism under conditions suitable for the synthesis of cobalamins, cobamides, cobalamin precursors, or cobamide precursors, wherein said culture conditions are also suitable for expression of said DNA; and c) recovering the cobalamins, cobamides, cobalamin precursors, or cobamide precursors produced.

6. The method of claim 5, wherein said recovery step comprises:

a) solubilization;

b) conversion to a cyanoform; and c) purification.

7. The method of claim 5, wherein said cobalamin is coenzyme $B_{12}$.

8. The method of claim 5, wherein said cobalamin precursor or cobamide precursor is selected from the group consisting of decobaltocorrinoids and corrinoids.

9. The method of claim 1 or 5 wherein said microorganism is *P. denitrificans* strain SC510 RifR.

10. A method for increasing the industrial production of cobalamins, cobamides, cobalamin precursors, or cobamide precursors, wherein said method comprises: a) introducing at least one plasmid comprising a DNA sequence selected from the group consisting of cobA, cobB, cobC, cobD, cobE, cobF, cobG, cobH, cobI, cobJ, cobK, cobL, cobM, cobN, cobO, cobP, cobQ, cobS, cobT, cobU, cobV, cobW, and cobX genes of *P. denitrificans* and homologs of said genes resulting from the degeneracy of the genetic code into a microorganism producing cobalamins or cobamides;

b) culturing said microorganism under conditions suitable for the synthesis of cobalamins, cobamides, cobalamin precursors, or cobamide precursors, wherein industrial production comprises culture conditions suitable for expression of said DNA and suitable for production of at least 100 grams of cells; and c) recovering the cobalamins, cobamides, cobalamin precursors, or cobamide precursors produced, wherein the industrial production of cobalamins, cobamides, cobalamin precursors, or cobamide precursors by said microorganism is increased by the introduction of said plasmid.

11. The method of claim 10, wherein said host cell is selected from *Pseudomonas denitrificans, Rhizobium meliloti*, and *Agrobacterium tumefaciens.*

12. The method of claim 11, wherein said microorganism is *P. denitrificans* strain SC510 RifR.

13. The method of any one of claims 10–12, wherein said cobalamin is coenzyme $B_{12}$.

14. The method of claim 10, wherein said cobalamin precursor or cobamide precursor is selected from the group consisting of decobaltocorrinoids and corrinoids.

15. The method of claim 10, wherein said at least one plasmid comprises the cobF, cobG, cobH, cobI, cobJ, cobK, cobL, and cobM genes of *P. denitrificans* or homologs of said genes resulting from the degeneracy of the genetic code.

16. The method of claim 15, wherein said host cell is selected from *Pseudomonas denitrificans, Rhizobium meliloti*, and *Agrobacterium tumefaciens.*

17. The method of claim 16, wherein said microorganism is *P. denitrificans* strain SC510 RifR.

18. The method of any one of claims 15–17, wherein said cobalamin is coenzyme $B_{12}$.

19. The method of claim 15, wherein said cobalamin precursor or cobamide precursor is selected from the group consisting of decobaltocorrinoids and corrinoids.

20. The method of claim 15, wherein said at least one plasmid further comprises the cobA and cobE genes of *P. denitrificans* or homologs of said genes resulting from the degeneracy of the genetic code.

21. The method of claim 20, wherein said host cell is selected from *Pseudomonas denitrificans, Rhizobium meliloti*, and *Agrobacterium tumefaciens.*

22. The method of claim 21, wherein said microorganism is *P. denitrificans* strain SC510 RifR.

23. The method of claim any one of claims 20–22, wherein said cobalamin is coenzyme $B_{12}$.

24. The method of claim 20, wherein said cobalamin precursor or cobamide precursor is selected from the group consisting of decobaltocorrinoids and corrinoids.

25. The method of claim 10, wherein said at least one plasmid further comprises the cobA and cobE genes of *P. denitrificans* or homologs of said genes resulting from the degeneracy of the genetic code.

26. The method of claim 25, wherein said host cell is selected from *Pseudomonas denitrificans, Rhizobium melloti*, and *Agrobacterium tumefaciens.*

27. The method of claim 26, wherein said microorganism is *P. denitrificans* strain SC510 RifR.

28. The method of any one of claims 25–27, wherein said cobalamin is coenzyme $B_{12}$.

29. The method of claim 25, wherein said cobalamin precursor or cobamide precursor is selected from the group consisting of decobaltocorrinoids and corrinoids.

30. A method for increasing the industrial production of cobalamins, cobamides, cobalamin precursors, or cobamide precursors, wherein said method comprises:

a) introducing at least one plasmid comprising a DNA sequence selected from the group consisting of cobA, cobB, cobC, cobD, cobE, cobF, cobG, cobH, cobI, cobJ, cobK, cobL, cobM, cobN, cobO, cobP, cobQ, cobS, cobT, cobU, cobV, cobW, and cobX genes of *P. denitrificans* and homologs of said genes resulting from the degeneracy of the genetic code into a microorganism capable of producing cobalamins or cobamides;

b) culturing said microorganism under conditions suitable for the synthesis of cobalamins, cobamides, cobalamin precursors, or cobamide precursors, wherein industrial production comprises culture conditions suitable for expression of said DNA and suitable for production of at least 100 grams of cells; and c) recovering the cobalamins, cobamides, cobalamin precursors, or cobamide precursors produced, wherein the industrial production of cobalamins, cobamides, cobalamin precursors, or cobamide precursors by said microorganism is increased by the introduction of said plasmid.

31. The method of claim 30, wherein said host cell is selected from *Pseudomonas denitrificans, Rhizobium meliloti*, and *Agrobacterium tumefaciens.*

32. The method of claim 31, wherein said microorganism is *P. denitrificans* strain SC510 RifR.

33. The method of any one of claims 30–32, wherein said cobalamin is coenzyme $B_{12}$.

34. The method of claim 30, wherein said cobalamin precursor or cobamide precursor is selected from the group consisting of decobaltocorrinoids and corrinoids.

35. The method of claim 30, wherein said at least one plasmid comprises the cobF, cobG, cobH, cobI, cobJ, cobK, cobL, and cobM genes of *P. denitrificans* or homologs of said genes resulting from the degeneracy of the genetic code.

36. The method of claim 35, wherein said host cell is selected from *Pseudomonas denitrificans, Rhizobium meliloti*, and *Agrobacterium tumefaciens.*

37. The method of claim 36, wherein said microorganism is *P. denitrificans* strain SC510 RifR.

38. The method of any one of claims 35–37, wherein said cobalamin is coenzyme $B_{12}$.

39. The method of claim 35, wherein said cobalamin precursor or cobamide precursor is selected from the group consisting of decobaltoconrinoids and corrinoids.

40. The method of claim 35, wherein said at least one plasmid further comprises the cobA and cobE genes of *P. denitrificans* or homologs of said genes resulting from the degeneracy of the genetic code.

41. The method of claim 40, wherein said host cell is selected from *Pseudomonas denitrificans, Rhizobium meliloti*, and *Agrobacterium tumefaciens.*

42. The method of claim 41, wherein said microorganism is *P. denitrificans* strain SC510 RifR.

43. The method of claim any one of claims 40–42, wherein said cobalamin is coenzyme $B_{12}$.

44. The method of claim 40, wherein said cobalamin precursor or cobamide precursor is selected from the group consisting of decobaltocorrinoids and corrinoids.

45. The method of claim 30, wherein said at least one plasmid further comprises the cobA and cobE genes of *P. denitrificans* or homologs of said genes resulting from the degeneracy of the genetic code.

46. The method of claim 45, wherein said host cell is selected from *Pseudomonas denitrificans, Rhizobium meliloti*, and *Agrobacterium tumefaciens.*

47. The method of claim 46, wherein said microorganism is *P. denitrificans* strain SC510 RifR.

48. The method of any one of claims 45–49, wherein said cobalamin is coenzyme $B_{12}$.

49. The method of claim 45, wherein said cobalamin precursor or cobamide precursor is selected from the group consisting of decobaltocorrinoids and corrinoids.

50. The method of any one of claims 10–12, 14–17, 19–22, 24–27, 30–32, 34–37, 39–42, 44–47, and 49, wherein said recovery step comprises:

a) solubilization;

b) conversion to a cyanoform; and c) purification.

51. The method of claim 13, wherein said recovery step comprises:

a) solubilization;

b) conversion to a cyanoform; and c) purification.

52. The method of claim 18, wherein said recovery step comprises:

a) solubilization;

b) conversion to a cyanoform; and c) purification.

53. The method of claim 23, wherein said recovery step comprises:

a) solubilization;

b) conversion to a cyanoform; and c) purification.

54. The method of claim 28, wherein said recovery step comprises:

a) solubilization;

b) conversion to a cyanoform; and c) purification.

55. The method of claim 33, wherein said recovery step comprises:

a) solubilization;

b) conversion to a cyanoform; and c) purification.

56. The method of claim 38, wherein said recovery step comprises:

a) solubilization;

b) conversion to a cyanoform; and c) purification.

57. The method of claim 43, wherein said recovery step comprises:

a) solubilization;

b) conversion to a cyanoform; and c) purification.

58. The method of claim 48, wherein said recovery step comprises:

a) solubilization;

b) conversion to a cyanoform; and c) purification.

* * * * *

UNITED STATES PATENT AND TRADEMARK OFFICE

CERTIFICATE OF CORRECTION

PATENT NO. : 6,656,709 B1
DATED : December 2, 2003
INVENTOR(S) : Francis Blanche et al.

It is certified that error appears in the above-identified patent and that said Letters Patent is hereby corrected as shown below:

Title page,
Item [57], ABSTRACT,
Lines 1-2, "cobalamines" should read -- cobalamins --.

Column 221,
Line 55, delete "claim" (first occurrence).
Line 65, "melloti," should read -- meliloti, --.

Column 222,
Line 50, "decobaltoconrinoids" should read -- decobaltocorrinoids --.
Line 59, delete "claim" (first occurrence).

Column 223,
Line 6, "claims 45-49," should read -- claims 45-47, --.

Signed and Sealed this

First Day of June, 2004

JON W. DUDAS
*Acting Director of the United States Patent and Trademark Office*